US007737283B2

(12) United States Patent
Flynn et al.

(10) Patent No.: US 7,737,283 B2
(45) Date of Patent: Jun. 15, 2010

(54) ANTI-INFLAMMATORY MEDICAMENTS

(75) Inventors: Daniel L. Flynn, Lawrence, KS (US); Peter A. Petillo, Arlington, MA (US)

(73) Assignee: Deciphera Pharmaceuticals, LLC, Lawrence, KS (US)

( * ) Notice: Subject to any disclaimer, the term of this patent is extended or adjusted under 35 U.S.C. 154(b) by 534 days.

(21) Appl. No.: 11/450,849

(22) Filed: Jun. 9, 2006

(65) Prior Publication Data
US 2009/0075986 A1    Mar. 19, 2009

Related U.S. Application Data

(63) Continuation of application No. 10/886,329, filed on Jul. 6, 2004, now Pat. No. 7,202,257, which is a continuation-in-part of application No. 10/746,460, filed on Dec. 24, 2003, now Pat. No. 7,144,911.

(60) Provisional application No. 60/437,487, filed on Dec. 31, 2002, provisional application No. 60/437,403, filed on Dec. 31, 2002, provisional application No. 60/437,415, filed on Dec. 31, 2002, provisional application No. 60/437,304, filed on Dec. 31, 2002, provisional application No. 60/463,804, filed on Apr. 18, 2003.

(51) Int. Cl.
C07D 285/10 (2006.01)
C07D 233/00 (2006.01)
A61K 31/41 (2006.01)
A61K 31/415 (2006.01)
C12N 9/96 (2006.01)

(52) U.S. Cl. .............. 548/135; 548/134; 548/300.1; 548/311.1; 548/315.7; 514/361; 514/362; 514/385; 514/386; 435/188

(58) Field of Classification Search .............. 548/134, 548/135, 300.1, 311.1, 315.7; 514/361, 362, 514/385, 386; 435/188
See application file for complete search history.

(56) References Cited

U.S. PATENT DOCUMENTS

| 3,818,024 | A  | 6/1974 | Krenzer |
| 3,939,122 | A  | 2/1976 | Merten et al. |
| 4,093,624 | A  | 6/1978 | Revankar et al. |
| 4,296,237 | A  | 10/1981 | Cragoe, Jr. |
| 4,432,992 | A  | 2/1984 | Cragoe, Jr. et al. |
| 4,816,454 | A  | 3/1989 | Zoller et al. |
| 5,103,014 | A  | 4/1992 | Musser et al. |
| 5,162,360 | A  | 11/1992 | Creswell et al. |
| 5,319,099 | A  | 6/1994 | Kamata et al. |
| 5,494,925 | A  | 2/1996 | Court et al. |
| 5,621,010 | A  | 4/1997 | Sueda et al. |
| 5,721,231 | A  | 2/1998 | Moriwaki et al. |
| 5,811,456 | A  | 9/1998 | Seman et al. |
| 6,020,357 | A  | 2/2000 | Pinto et al. |
| 6,080,763 | A  | 6/2000 | Regan et al. |
| 6,197,599 | B1 | 3/2001 | Chin et al. |
| 6,235,786 | B1 | 5/2001 | Dai et al. |
| 6,294,573 | B1 | 9/2001 | Curtin et al. |
| 6,319,921 | B1 | 11/2001 | Cirillo et al. |
| 6,410,254 | B1 | 6/2002 | Finer et al. |
| 6,500,628 | B1 | 12/2002 | Robison |
| 6,525,046 | B1 | 2/2003 | Cirillo et al. |
| 6,645,990 | B2 | 11/2003 | Askew et al. |
| 7,135,550 | B2 | 11/2006 | Come et al. |
| 7,144,911 | B2 | 12/2006 | Flynn et al. |
| 7,202,257 | B2 | 4/2007 | Flynn et al. |
| 7,211,575 | B2 | 5/2007 | Moss et al. |
| 7,342,037 | B2 | 3/2008 | Flynn et al. |
| 7,531,566 | B2 | 5/2009 | Flynn et al. |
| 2001/0008898 | A1 | 7/2001 | Tomiyama et al. |
| 2002/0058678 | A1 | 5/2002 | Cirillo et al. |
| 2003/0060455 | A1 | 3/2003 | Moss et al. |
| 2003/0181411 | A1 | 9/2003 | Bosch et al. |
| 2003/0186221 | A1 | 10/2003 | Lockhart et al. |
| 2004/0043388 | A1 | 3/2004 | Come et al. |
| 2004/0171075 | A1 | 9/2004 | Flynn et al. |
| 2004/0180906 | A1 | 9/2004 | Flynn et al. |
| 2005/0288286 | A1 | 12/2005 | Flynn et al. |
| 2007/0078121 | A1 | 4/2007 | Flynn et al. |
| 2007/0191336 | A1 | 8/2007 | Flynn et al. |
| 2008/0045531 | A1 | 2/2008 | Flynn et al. |

(Continued)

FOREIGN PATENT DOCUMENTS

CN           1333767 A         1/2002

(Continued)

OTHER PUBLICATIONS

Investigation of the relationship between the inhibitory activity of glycolic acid oxidase (GAO) and its chemical structure: electron-topological approach; Y. Guzel; Journal of Molecular Structure 366 (1996) 131-137.
Protein kinase inhibitors: emerging pharmacophores 1997-2000; Jacques Dumas; Exp. Opin. Ther. Patent (2001) 11(3); p. 405-429.
Inhibition of p38 MAP kinase by utilizing a novel allosteric binding site; Pargellis, Tong, Churchill, Cirillo, Gilmore, Graham, Grob, Hickey, Moss, Pav and John Regan; Nature Structural Biology; vol. 9, No. 4, Apr. 2002; p. 268-272.
Structural Mechanism for STI-571 Inhibition of Abelson Tyrosine Kinase; Schindler, Bornmann, Pellicena, Miller, Clarkson, Kuriyan; Science Magazine; Sep. 15, 2000; vol. 289; p. 1938-1942.
Synthesis of Novel Uracil-5-Sulphonamide Derivatives of Possible Biological Activity; Nofal, Gadalla, Fathalla and Karnel; Egypt J. Chem. 33; No. 4, p. 375-380 (1990).

(Continued)

Primary Examiner—Kamal A Saeed
Assistant Examiner—Samantha L Shterengarts
(74) Attorney, Agent, or Firm—Wilmer Cutler Pickering Hale and Dorr LLP

(57) ABSTRACT

Novel compounds and methods of using those compounds for the treatment of inflammatory conditions are provided. In a preferred embodiment, modulation of the activation state of p38 kinase protein comprises the step of contacting the kinase protein with the novel compounds.

10 Claims, 8 Drawing Sheets

U.S. PATENT DOCUMENTS

| | | |
|---|---|---|
| 2008/0045706 A1 | 2/2008 | Flynn et al. |
| 2008/0113967 A1 | 5/2008 | Flynn et al. |
| 2008/0132506 A1 | 6/2008 | Flynn et al. |
| 2008/0187978 A1 | 8/2008 | Flynn et al. |
| 2008/0220497 A1 | 9/2008 | Flynn et al. |
| 2008/0248487 A1 | 10/2008 | Flynn et al. |
| 2008/0248548 A1 | 10/2008 | Flynn et al. |
| 2009/0069310 A1 | 3/2009 | Flynn et al. |
| 2009/0075986 A1 | 3/2009 | Flynn et al. |
| 2009/0105230 A1 | 4/2009 | Flynn et al. |
| 2009/0137021 A1 | 5/2009 | Flynn et al. |

FOREIGN PATENT DOCUMENTS

| | | |
|---|---|---|
| DE | 1115350 | 5/1968 |
| DE | 2156343 | 5/1972 |
| DE | 2341064 | 3/1974 |
| DE | 3406329 A1 | 8/1985 |
| DE | 4302702 A1 | 8/1994 |
| DE | 4337847 A1 | 5/1995 |
| DE | 4343831 A1 | 6/1995 |
| DE | 4414840 A1 | 11/1995 |
| EP | 0021228 A1 | 6/1980 |
| EP | 0021228 B1 | 6/1980 |
| EP | 0025232 A1 | 9/1980 |
| EP | 0025232 B1 | 9/1980 |
| EP | 0031796 A2 | 7/1981 |
| EP | 0031796 B1 | 7/1981 |
| EP | 0 692 483 A | 1/1996 |
| EP | 0739884 A2 | 4/1996 |
| EP | 0739884 B1 | 4/1996 |
| EP | 0867435 A1 | 3/1998 |
| EP | 0867435 B1 | 3/1998 |
| EP | 0956855 A1 | 4/1998 |
| EP | 0956855 B1 | 4/1998 |
| EP | 0927555 A1 | 12/1998 |
| EP | 1281399 A2 | 7/2002 |
| FR | 2337554 | 8/1977 |
| FR | 2396549 | 2/1979 |
| GB | 971307 | 3/1961 |
| GB | 1127875 | 3/1967 |
| GB | 1115350 | 5/1968 |
| GB | 2220206 | 1/1990 |
| JP | 59-15247 | 1/1984 |
| JP | 59-177557 | 10/1994 |
| JP | 9-221476 | 8/1997 |
| JP | 10-7804 | 1/1998 |
| JP | 11-209350 | 8/1999 |
| JP | 2000-275886 | 10/2000 |
| JP | 2001-2687 | 1/2001 |
| WO | WO9119708 | 12/1991 |
| WO | WO9208693 | 5/1992 |
| WO | WO9424095 | 10/1994 |
| WO | WO9515954 | 6/1995 |
| WO | WO9534540 | 12/1995 |
| WO | WO9616046 | 5/1996 |
| WO | WO9616046 A2 | 5/1996 |
| WO | WO9616046 A3 | 5/1996 |
| WO | WO9619477 | 6/1996 |
| WO | WO9734900 | 9/1997 |
| WO | WO9822103 | 5/1998 |
| WO | WO-98/52558 A | 11/1998 |
| WO | WO9915164 | 4/1999 |
| WO | WO-99/23091 | 5/1999 |
| WO | WO9923093 | 5/1999 |
| WO | WO-99/32106 A | 7/1999 |
| WO | WO-99/32110 | 7/1999 |
| WO | WO-99/32110 A | 7/1999 |
| WO | WO-99/32111 A | 7/1999 |
| WO | WO-99/32455 A | 7/1999 |
| WO | WO9959959 | 11/1999 |
| WO | WO0002851 | 1/2000 |
| WO | WO0006550 | 1/2000 |
| WO | WO0007980 | 2/2000 |
| WO | WO0018738 | 4/2000 |
| WO | WO0021927 | 4/2000 |
| WO | WO-00/43384 | 7/2000 |
| WO | WO0041698 | 7/2000 |
| WO | WO0043384 | 7/2000 |
| WO | WO0059506 | 10/2000 |
| WO | WO-00/55139 A2 | 11/2000 |
| WO | WO0112621 | 2/2001 |
| WO | WO0114372 A2 | 3/2001 |
| WO | WO0114372 A3 | 3/2001 |
| WO | WO0174771 | 10/2001 |
| WO | WO0196298 | 12/2001 |
| WO | WO-02/14311 A2 | 2/2002 |
| WO | WO0214291 | 2/2002 |
| WO | WO0228835 | 4/2002 |
| WO | WO-02/34727 | 5/2002 |
| WO | WO0234727 A2 | 5/2002 |
| WO | WO0234727 A3 | 5/2002 |
| WO | WO0240458 | 5/2002 |
| WO | WO02060869 | 8/2002 |
| WO | WO02060876 | 8/2002 |
| WO | WO-02/070662 | 9/2002 |
| WO | WO03000189 | 1/2003 |
| WO | WO03005999 | 1/2003 |
| WO | WO03053368 | 7/2003 |
| WO | WO03059373 | 7/2003 |
| WO | WO03068223 | 8/2003 |
| WO | WO03072577 | 9/2003 |
| WO | WO-03/084539 A2 | 10/2003 |
| WO | WO-2004/056783 | 7/2004 |
| WO | WO-2004/060306 | 7/2004 |
| WO | WO2004/060306 | 7/2004 |
| WO | WO-2004/061084 | 7/2004 |
| WO | WO2004113352 | 12/2004 |
| WO | WO2005110994 | 11/2005 |
| WO | WO-2006/014290 | 2/2006 |
| WO | WO-2006/071940 | 7/2006 |
| WO | WO-2006/081034 | 8/2006 |
| WO | WO-2007/008917 | 1/2007 |

OTHER PUBLICATIONS

The Stereochemistry of Oxidation at Sulfur Oxidation of 2-Thiabicyclo[2.2.1]Heptane; Johnson, Diefenbach, Keiser and Sharp; vol. 25, p. 5649 to 5633; Pergamon Press 1969.

TPAP: Tetra-n-propylammonium Perruthenate, A Mild and Convenient Oxidant for Alcohols; Griffith and Ley; Aldrichimica Acta, vol. 23, No. 1, 1990; pp. 13-19.

Aminolysis and Polymerization of 3-(p-Toluenesulfonoxy) Hydantoin; Zvilichovsky and Zucker; Israel Journal of Chemistry; Vo. 7, 1969, p. 547-554.

Palladium-catalyzed amination of arly halides and sulfonates; Yang and Buchwald; Journal of Organometallic Chemistry 576 (1999) pp. 125-146.

A General, Efficient, and Inexpensive Catalyst System for the Coupling of Aryl Iodides and Thiols; Kwong and Buchwald; Organic Letters 2002; vol. 4, No. 20, pp. 3517-3520.

Novel Solution Phase Strategy for the Synthesis of Chemical Libraries Containing Small Organic Molecules; Cheng, Comer, Williams, Myers, and Boger; J. Am. Chem. Soc. 1996, 118, pp. 2567-2573.

A Useful 12-I-5 Triacetoxyperiodiane (the Des-Martin Periodiane) for the Selective Oxidation of Primary or Secondary Alcohols and a Variety of Related 12-I-5 Species; Dess and Martin; J. Am. Chem. Soc. 1991, 113, pp. 7277-7287.

Proton-Transfer Chemistry of Urazoles and Related Imides, Amides, and Diacyl Hydrazides; Bausch, David, Dobrowolski, Guadalupe-Fasano, Gostowski, Selmarten, Prasad, Vaughn and Wang; J. Org. Chem. 1991, 56, pp. 5643-5651.

A General Synthesis of 4-Substituted 1,1-Dioxo-1,2,5-thiadiazolidin-3-ones Derived from a-Amino Acids; Muller and DuBois; J. Org. Chem. 1989, 54, pp. 4471-4473.

The Reaction of S-Methiodide Derivatives of Activated Thioureas with Hydroxylic Compounds. A Novel Synthesis of Mercaptans; Klayman, Shine, and Bower; J. Org. Chem., vol. 37, No. 10, 1972; pp. 1532-1537.

Efficient Solid-Phase Synthesis of Sulfahydantoins; Tremblay, Voyer, Boujabi and Dewynter; J. Comb. Chem. 2002, 4, pp. 429-435.

Identification of Novel Inhibitors of BCR-ABL Tyrosine Kinase via Virtual Screening; Peng, Huang, Qi, Xie, Xu, Wang and Yang; Bioorganic & Medicinal Chemistry Letters 13 (2003) 3693-3699.

Implications of Protein Flexibility for Drug Discovery; Simon J. Teague; astrazeneca.com; Reviews.

The Conformational Plasticity of Protein Kinases; Huse and Kuriyan; Cell, vol. 109, pp. 275-282; May 3, 2002.

Discovery of a Novel Family of CDK Inhibitors with the Program LIDAEUS: Structural Basis for Ligand-Induced Disordering of the Activation Loop; Wu, McNae, Kontopidis, McClue, McInnes, Stewart, Wang, Zheleva, Marriage, Lane, Taylor, Fischer, and Walkinshaw; Structure, vol. 11, pp. 399-410; Apr. 2003.

Molecular Recognition with Convergent Functional Groups. 6. Synthetic and Structural Studies with a Model Receptor for Nucleic Acid Components; Askew, Ballester, Buhr, Jeong, Jones, Parris, Williams and Rebek, Jr.; J. Am. Chem. Soc. 1989, 111, pp. 1082-1090.

Pyrazole Urea-Based Inhibitors of p38 MAP Kinase: From Lead Compound to Clinical Candidate; Regan, Breitfelder, Cirillo, Gilmore, Graham, Hickey, Klaus, Madwed, Moriak, Moss, Pargellis, Pav, Proto, Swinamer, Tong, and Torcellini; J. Med. Chem. 2002, 45, pp. 2994-3008.

The Sequence of the Human Genome; J. Craig Venter, et al; Science Magazine; Feb. 16, 2001; vol. 291; pp. 1304-1351 (including Erratum/post date Jun. 8, 2001), 1 pg.

Initial sequencing and analysis of the human genome; Nature/vol. 409; Feb. 15, 2001; pp. 860-921.

Copper-Catalyzed Coupling of Aryl Iodides with Aliphatic Alcohols; Wolter, Nordmann, Job, and Buchwald; Organic Letters 2002; vol. 4, No. 6, pp. 973-976.

First Non-ATP Competitive Glycogen Synthase Kinase 3 (GSK-3) Inhibitors: Thiadizolidinones (TDZD) as Potential Drugs for the Treatment of Alzheimer's Disease; Martinez, Alonso, Castro, Perez, and Moreno; J. Med. Chem. 2002, 45, pp. 1292-1299.

On the preparation of 1-aryl-2-heteroaryl- and 2-aryl-1-heteroaryl-pyrroles as useful building blocks for biologically interesting heterocycles; Almerico, Montalbano, Diana, Barraja, Lauria, Cirrincione and Dattolo; Dipartimento Farmacochimico, Tossicologico e Biologico, Palermo, Italy; pp. 129-142.

QSAR and Molecular Modelling for a Series of Isomeric X-Sulfanilamido-1-phenylpyrazoles; Koch, Seydel, Gasco, Tironi, and Fruttero; Quant. Struct. Act. Relat. 12, pp. 373-382 (1993).

Disposition of 1-[3-Aminomethyl) phenyl]-N-[3-fluoro-2'-methylsulfonyl)-[1,1'-biphenyl]-4-yl]-3-(trifluomethyl)-1$H$-pyrazole-5-carboxamide (DPC 423) by Novel Metabolic Pathways. Characterization of Unusual Metabolites by Liquid Chromatography/Mass Spectrometry and NMR; Mutlib, Shockcor, Chen, Espina, Pinto, Orwat, Prakash, and Gan; Chem. Res. Toxicol. 2002, 15, pp. 48-62.

P450-Mediated Metabolism of 1-[3-(Aminomethyl)phenyl]-N-[3-fluoro-2'-(methylsulfonyl)-[1,1'-biphenyl]-4-yl]-3(trifluoromethyl)-1$H$-pyrazole-5-carboxamide (DPC 423) and Its Analogues to Aldoximes. Characterization of Glutathione Conjugates of Postulated Intermediates Derived from Aloximes; Mutlib, Chen, Espina, Shockcor, Prakash, and Gan; Chem. Res. Toxicol. 2002, 15, pp. 63-75.

Synthesis and Characterization of Conjugated Mono- and Dithiol Oligomers and Characterization of Their Self-Assembled Monolayers; Boer, Meng, Perepichka, Zheng, Frank, Chabal, and Bao; Langmuir 2003, 19, pp. 4272-4284; 2003 American Chemical Society.

An evaluation of the effect of light stabilisers on the exterior durability of polyester powder coatings for the architectural market; Johnson, Parducci and Nascovilli; Surface Coatings International 1999 (3); pp. 134-141.

Synthesis and Spectral-Luminescence Properties of Hetarylethylene Derivatives of 2,5-Diphenyloxazole and 2,5-Diphenyl-1,3,4-Oxadizole; Krasovitskii, Egorova, Afanasiadi, Lysova, Polyakov and Tsukerman; 1982 Plenum Publishing Corporation; pp. 461-465.

The Difluoromethylensulfonic Acid Group as a Monoanionic Phosphate Surrogate for Obtaining PTP1B Inhibitors; Leung, Grzyb, Lee, Meyer, Hum, Jia, Liu, and Tyalor; Bioorganic & Medicinal Chemistry 10 (2002) pp. 2309-2323.

Abnormal Diels-Alder Reaction of 5-Alkoxythiazoles with Highly Reactive Dienophiles; 4-Phenyl-3$H$-1,2,4-triazole-3,5(4$H$)-dione, Diethyl Azodicarboxylate, and Diethyl Oxomalonate; Shi, Ibata, Suga, and Matsumoto; Bull. Chem. Soc. Jpn., 65, pp. 3315-3321 (1992).

Telomere Shortening and Growth Inhibition of Human Cancer Cells by Novel Synthetic Telomerase Inhibitors MST-312, MST-295, and MST-199; Seimiya, Oh-hara, Suzuki, Naasani, Shimazaki, Tsuchiya, and Tsuruo; Molecular Cancer Therapeutics; vol. 1, Jul. 2002, pp. 657-665.

The Synthesis of some Substituted Biphenyl-4-carboxylic Acids, 4-Biphenylylacetic Acids, and 4-Aminobiphenyls; Byron, Gray, and Wilson; J. Chem. Soc. (1966); pp. 840-845.

Synthesis of a Sulfahydantoin Library; Albericio, Bryman, Garcia, Michelotti, Nicolas, and Tice; J. Comb. Chem. 2001, 3, pp. 290-300.

Novel Chromophoric Heterocycles Based on Maleimide and Naphthoquinone; Katritzky, Fan, Li, and Bayyuk; J. Heterocyclic Chem., 26, (1989) pp. 885-892.

Nitrofuryl Heterocyclics 1; Closier and Islip; Journal of Medicinal Chemistry, 1970, vol. 13, No. 4; pp. 638-640.

Discovery of Novel Mesangial Cell Proliferation Inhibitors Using a Three-Dimensional Database Searching Method; Kurogi, Miyata, Okamura, Hashimoto, Tsutsumi, Nasu, and Moriyasu; J. Med. Chem. 2001, 44, pp. 2304-2307.

Nitrofuryl Heterocyclics 3; Islip and Johnson; Journal of Medicinal Chemistry, 1973, vol. 16, No. 11; pp. 1308-1310.

Inhibitors of Glycolic Acid Oxidase. 4-Substituted 3-Hydroxy-1$H$-pyrrole-2,5-dione Derivatives; Rooney, Randall, Streeter, Ziegler, Cragoe, Schwam, Michelson, Williams, Eichler, Duggan, Ulm, and Noll; J. Med. Chem. 1983, 26, pp. 700-714.

Organic Phosphorus Compounds. 2. Synthesis and Coronary Vasodilator Activity of (Benzothizolylbenzyl) phosphonate Derivatives; Yoshino, Kohno, Morita, and Tsukamoto; J. Med. Chem. 1989, 32, pp. 1528-1532.

Additions and Corrections; Journal Of Medicinal Chemistry; 1989, vol. 32, No. 12, p. 2583.

Inhibitors of Acyl-CoA: Cholesterol o-Acyltransferase. 17. Structure-Activity Relationships of Several Series of Compounds Derived from n-Chlorosulfonyl Isocyanate; Picard, O'Brien, Sliskovic, Anderson, Bousley, Hamelehle, Krause, and Stanfield; J. Med. Chem. 1996, 39, pp. 1243-1252.

Convergent Functional Groups: Synthetic and Structural Studies; Rebek, Jr., Marshall, Wolak, Parris, Killoran, Askew, Nemeth, and Islam; J. Am. Chem. Soc. 1985, 107, pp. 7476-7481.

Laser-Jet Delayed Trapping: Electron-Transfer Trapping of the Photoenol from 2-Methylbenzophenone; Wilson, Hannemann, Heineman, and Kirchoff; J. Am. Chem. Soc. 1987, 109, pp. 4743-4745.

Molecular Recognition in the Solid Waste State: Controlled Assembly of Hydrogen-Bonded Molecular Sheets; Garcia-Tellado, Geib, Goswami, and Hamilton; J. Am. Chem. Soc. 1991, 113, pp. 9265-9269.

Theoretical Study of a Molecular Resonant Tunneling Diode; Seminario, Zacarias, and Tour; J. Am. Chem. Soc. 2000, 122, pp. 3015-3020.

A New Synthesis of Purines; Yoneda, Matsumoto, and Higuchi; J.C.S. Chem. Comm., 1974; p. 551.

Alkyl- and Arylthiation of Uracil and Indole; Kentaro Anzai; J. Heterocyclic Chem., 16, (1979) p. 567-569.

Synthesis of 8-Substituted 5-Deazaflavins; Link, van der Plas, and Muller; J. Heterocyclic Chem., 22, (1985) pp. 841-848.

Irreversible Enzyme Inhibitors. 188. Inhibition of Mammalian Thymidine Phsphorylase; Baker and Kelley; Journal of Medicinal Chemistry, 1971, vol. 14, No. 9; pp. 612-616.

Correlation Analysis of Baker's Studies on Enzyme Inhibition. 2. Chyotrypsin, Trypsin, Thymidine Phosphorylase, Uridine Phosphorylase, Thymidylate Synthetase, Cytosine Nucleoside Deaminase, Dihodrofolate reductase, Malate Dehydrogenase, Glutamate Dehydrogenase, Lactate Dehydrogenase, and Glyceraldehyde-phosphate Dehydrogenase; Yoshimoto and Hansch; Journal of Medicinal Chemistry, 1976, vol. 19, No. 1; pp. 71-98.

Synthesis and Pharmacological Evaluation of New Pyrazolidine-3,5-diones as $AT_1$ Angiotensin II Receptor Antagonists; Bourdonnec, Meulon, Yous, Goossens, Houssin, and Henichart; J. Med. Chem. 2000, 43, pp. 2685-2697.

Convergent Functional Groups. 2. Structure and Selectivity in Olefin Epoxidation with Peracids; Rebek, Jr.; Marshall, McManis, and Wolak/ J. Org. Chem. 1986, 51, pp. 1649-1653.

A Convenient Synthesis of Perfluoroalkylated and Fluorinated-Aryl Nitrogen Bases by Electrochemically Induced $S_{RN}1$ Substitution; Medebielle, Oturan, Pinson, and Saveant; J. Org. Chem. 1996, 61, pp. 1331-1340.

Coenzyme Models, Part 45. [1] Synthesis of Atropisomeric Flavins and their Novel Redox-induced Racemisation; Shinkai, Nakao, Kuwahara, Miyamoto, Yamaguchi, and Manabe; J. Chem. Soc. Perkin Trans. (1988).

Inhibition of Nucleoside Transport by Protein Kinase Inhibitors; Huang, Wang, Cogut, Mitchell, and Graves; The Journal of Pharmacology and Experimental Therapeutics; vol. 304, No. 2; pp. 753-760.

Relative Reactivities of the Chlorine Atoms of 2,2', 4-Trichloro-4', 5-Dipyrimidinyl in its Reaction with Piperidine; Mikhaleva, Naumenko, and Mamaev; 1979 Plenum Publishing Corporation; pp. 671-676.

Solid phase synthesis of benzamidine and butylamine-derived hydantoin libraries; Kim, Koh, Lee, and Ro; Molecular Diversity 3; 1998, pp. 129-132.

Synthesis of sequentially controlled isomeric, wholly aromatic polyketones composed of 2-trifluoromethylbiphenylene and 2.2'-dimethoxybiphenylene units; Yonezawa, Nakamura, and Maeyama; Reactive & Functional Polymers 52 (2002) pp. 19-30.

Solubility of Polytherm in the System $HNO_{-3}-H_2-O-(C_4H_9-O)PO(C_4H_9)_2$; Nikolaev, Dyadin, and Yakovlev; Institute of Inorganic Chemistry, Siberian Division of the Academy of Sciences USSR, Translated from Doklady Akademii Nauk SSSR, vol. 160, No. 4, pp. 841-844, Feb. 1968, Original Article submitted Aug. 31, 1964; pp. 135-138.

Condensation Reaction of Ethyl (4-Uracil)-Acetate with Ethyl Orthoformate; Nantaka-Namirski, and Wojciechowski; ACTA Polon. Pharm. XXVII, No. 5, 1971; pp. 455-463.

Inhibition of endogenous oxalate production: biochemical consideration of the roles of glycollate oxidase and lactate dehydrogenase; Bais, Rofe, and Conyers; Clinical Science (1989) 76, pp. 303-309.

1-(4 Substituted-thiazol-2-yl)hydantoins as Anti-inflammatory and CNS-Active Agents; Satsangi, Zaidi, and Misra; Pharmazie 38 (1983) H.5; pp. 341-342.

Addition of 4-Ethoxyimidazoles to Dimethyl Acetylenedicarboxylate and Transformation of the Adducts to Pyrimidian-5-yl Acetates[1]; Furyua, Omura and Furukawa; Chem. Pharm. Bull. 36(5) (1998) pp. 1669-1675.

New Anti-mycobacterial Hydantoins; Zaidi, Satsangi,Mohd, Agarwal, and Tiwari; Pharmazie 35, H. 12 (1980) pp. 755-766.

Molecular arrangement and electrical conduction of self-assembled monolayers made from terphenyl thiols; Ishida, Mizutani, Azehara, Miyake, Aya, Sasaki, and Tokumoto; Surface Science 514 (2002) pp. 187-193.

Depropargylation under palladium-copper catalysis: synthesis of diaryl sulfides; Kundu and Nandi; Tetrahedron 57 (2001); 2001 Elsevier Science Ltd., pp. 5885-5895.

A New Convenient Synthesis of 5-Aryl Uracils Using SRN1 Aromatic Nucleophilic Substitution; Medebielle, Oturan, Pinson and Saveant; Tetrahedron Letters, vol. 34, No. 21, pp. 3409-3412.

o-Bromophenylzinc Compound: A Readily Available and Efficient Synthetic Equivalent of o-Phenylene 1-Anion 2-Cation; Okano, Amano, and Takagi; Tetrahedron Letters 39 (1998)pp. 3001-3004.

Synthesis of thiol substituted oligoanilines for molecular device candidates; Flatt and Tour; Tetrahedron Letters 44 (2003) pp. 6699-6702.

Consecutive cross-coupling of o-phenylenedizinc compound with acyl and/or aryl halides in the presence of Pd(0)-tris(2,4,6-trimethoxyphenyl)phosphine; Saiga, Hossain, and Takagi; Tetrahedron Letters 41 (2000) pp. 4629-4632.

Synthesis of 2,5'-Bipyrimidines from Substituted 5-Cyanopyrimidines; 1988 Plenum Publishing Corporation; pp. 303-307.

Antimicrobial activities of 2-arylthio-N-alkylmaleimides; Igarashi and Watanabe; Journal of Industrial Microbiology, 9 (1992), pp. 91-96.

Synthesis of New Uracil-5-Sulfonamide Derivatives and Immuno-Stimulatory Effect of a Chemically Modified Hemolymph of *Biomphalaria alexandrina* on *Schistosoma mansoni* Infected Mice; Fathalla, Haiba, and Maghraby; Arch Pharm Res vol. 26, No. 5, pp. 358-366 (2003).

Synthesis of New Pyrazolo[1,5-a]pyrimidine Derivative Using 5-Aminouracil and Ketene Dithioacetal; O. A. Fathalla; Arch Pharm Res vol. 22, No. 6, (1999); pp. 571-574.

Synthesis of Some New Uracil—5—Sulphonamide-p-Phenyl Derivatives and Their Effect on *Biomphalaria alexandrina* Snails Nucleoproteins; Fathalla, Gad, and Maghraby; Bull. N.R.C. Egypt, 25, No. 4 (2000) pp. 341-363.

Characterization of pp60[c-src] Tyrosine Kinase Activities Using a Continuous Assay: Autoactivation of the Enzyme Is an Intermolecular Autophosphorylation Process; Baker, Kassel, Weigl, Huang, Luther, and Knight; Biochemistry 1995, 34, 14843-14851.

c-Abul Has High Intrinsic Tyrosine Kinase Activity That is Stimulated by Mutation of the Src Hoology 3 Domain and by Autophosphorylation at Two Distinct Regulatory Tyrosines; Brasher and Van Etten; The Journal of Biological Chemistry; vol. 275, No. 45, Issue of Nov. 10, pp. 35631-35637, 2000.

A New Practical One-Pot Access to Sulfonimidates; Leca, Fensterbank, Lacote and Malacria; Organic Letters, 2002, vol. 4, No. 23; pp. 4093-4095.

Treatment of Rheumatoid Arthritis with Methotrexate Alone, Sulfasalazine and Hydroxychloroquine, or a Combination of All Three Medications, O'Dell, J. et al., New. Eng. J. Med., vol. 334(20), pp. 1287-1291 (May 1996) at p. 1287, col. 1, lines 6-9.

Structure-Activity Relationships of the p38a MAP Knase Inhibitor 1-(5-tert-Butyl-2-p-tolyl-2H-pyrazol-3-yl)-3-[4-(2-morpholin-7-yl-ethoxy)naphthalen-1-yl]urea (BIRB 796), Regan et al., J. Med. Chem., vol. 46, pp. 4676-4686 (2003).

Mallakpour, S.E. and Butler, G.B., "Uncatalyzed Polymerization of Bistriazolinediones with Electron-Rich Aromatic Compounds via Electrophilic Aromatic Substitution," Journal of Polymer Science, Part A: Polymer Chemistry, vol. 27(1), pp. 217-235 (1989).

Kern, et al., "Synthese von Makromolekeln einheitlicher GroBe. II. Mitt.[1], Synthese neuer Diol-oligo-urethane nach dem Duplikationsverfahren," Die Makromolekulare Chemie, Received 24 Mai1955, pp. 89-107, German only; no English translation.

Tominaga et al., "General Model for Estimation of the Inhibition of Protein Kinases Using Monte Carlo Simulations," J. Med. Chem. (2004), 47(10), 2534-2549.

U.S. Appl. No. 11/721,026, Flynn et al.

U.S. Appl. No. 12/268,997, Flynn et al.

"NHLBI LBC Computational Biophysics Scetion", CHARMM Documentation Index, http://www.lobos.nih.qov/Charmm/chmdoc.html, printed Mar. 4, 2005 (1 page).

"Trilateral Project WM4—Comparative Studies in New Technologies: Report on Comparative Study on Protein 3-Dimensional Structure Related Claims—Annex 3: Comments of the USPTO", Vienna, Austria, Nov. 4-8, pp. 58-79 (2002).

Benvenuti, et al., "Crystallization of Soluble Proteins in Vapor Diffusion for X-Ray Crystallography", Nature Protocols, 2(7):1633-1651 (2007).

Bosca, et al., "Circular Dichroism Analysis of Ligand-Induced Conformational Changes in Protein Kinase C", Biochem J., 290:827-832 (1993).

Boschelli, "4-Anilino-3-quinolinecarbonitriles: An Emerging Class of Kinase Inhibitors", Current Topics in Medicinal Chemistry, 2:1051-1063 (2002).

Boyer, "Small Molecule Inhibitors of KDR (VEGFR-2) Kinase: An Overview of Structure Activity Relationships", Current Topics in Medicinal Chemisty, 2:973-1000 (2002).

Brady, et al., "Fast Prediction and Visualization of Protein Binding Pockets with PASS". Journal of Computer-Aided Molecular Design, 14:383-401 (2000).

Bullock, et al., "Prospects for Kinase Activity Modulators in the Treatment of Diabetes and Diabetic Complications", Current Topics in Medicinal Chemistry, 2:915-938 (2002).

Cardillo, et al., "Sulle 1,2-difenil-3.5-dichetopirazolidine", Gazz. Chico., Ital., 9:973-985 (1966)—Italian Language.

Chen, et al., "Biochemical Evidence for the Autophosphorylation and Transphosphorylation of Transforming Growth Factor β Receptor Kinases", Proc. Natl. Acad. Sci. USA, 92:1565-1569 (1995).

Chu, et al., "Using Affinity Capillary Electrophoresis to Determine Binding Stoichiometries of Protein-Ligand Interactions", Biochemistry, 33:10616-10621 (1994).

Cirillo, et al., "The Non-Dairyl Heterocycle Classes of p38 MAP Kinase Inhibitors", Current Topics in Medicinal Chemistry, 2:1021-1035 (2002).

Cockerill, et al., "Small Molecule Inhibitors of the Class 1 Receptor Tyrosine Kinase Family", Current Topics in Medicinal Chemistry, 2:1001-1010 (2002).

Colton, et al., "Affinity Capillary Electrophoresis: A Physical-Organic Tool for Studying Interactions in Biomolecular Recognition", Electrophoresis, 19:367-382 (1998).

Cross, et al., "Inhibition of Glycogen Synthase Kinase-3 by Insulin Mediated by Protein Kinase B", Nature, 378:785-789 (1995).

Cudney, "Preface: Protein Crystallization and Dumb Luck", The Rigaku Journal, 16(1):1-7 (1999).

Dajani, et al., "Crystal Structur of Glycogen Synthase Kinas 3β : Structural Basis for Phosphate-Primed Substrate Specificity and Autoinhibition", Cell, 105:721-732 (2001).

Dajani, et al., "Structural Basis for Recruitment of Glycogen Synthase Kinase 3β to the Axin-APC Scaffold Comples", EMBO, 22(3):494-501 (2003).

Davis, et al., "Iterative Size-Exclusion Chromatography Coupled with Liquid Chromatographic Mass Spectrometry to Enrich and Identify Tight-Binding Ligands from Complex Mixtures", Tetrahedron, 55:11653-11667 (1999).

Deng, et al., "Expression, Characterization, and Crystallization of the Pyrophosphate-Dependent Phosphofructo-1-Kinase of Borrelia Burgdorferi", Archives of Biochemistry and Biophysics, 371(2):326-331 (1999).

Dumas, "Preface", Current Topics in Medicinal Chemistry (2002) (1 Page).

Dumas, et al., "Discovery of a New Class of p38 Kinase Inhibitors", Bioorganic & Medicinal Chemistry Letters, 10:2047-2050 (2000).

Ewing, "Critical Evaluation of Search Algorithms for Automated Molecular Docking and Database Screening", Journal of Computational Chemistry, 18(9):1175-1189 (1997).

Farooqui, et al., "Interactions Between Neural Membrane Glycerophospholipid and Sphingolipid Mediators: A Recipe for Neural Cell Survival or Suicide", Journal of Neuroscience Research, 85:1834-1850 (2007).

Frame, et al., "A Common Phosphate Binding Site Explains the Unique Substrate Specificity of GSK3 and Its Inactivation by Phosphorylation", Molecular Cell, 7:1321-1327 (2001).

Greene, et al., "Chapter 7: Protection for the Amino Group", in Protective Groups in Organic Synthesis, Third Edition, pp. 494-653 (1999).

Haar, et al., "Structure of GSK3β Reveals a Primed Phosphorylation Mechanism", Nature Structural Biology, 8(7):593-596 (2001).

Haesslein, et al., "Recent Advances in Cyclin-Dependent Kinase Inhibition. Purine-Based Derivatives as Anti-Cancer Agents. Roles and Perspectives for the Future", Current Topics in Medicinal Chemistry, 2:1037-1050 (2002).

Heegaard, et al., "Affinity Capillary Electrophoresis: Important Application Areas and Some Recent Developments", Journal of Chromatography B, 715:29-54 (1998).

Honda, et al., "Determination of the Association Constant of Monovalent Mode Protein-Sugar Interaction by Capillary Zone Electrophoresis", Journal of Chromatography, 597:377-382 (1992).

Hu, et al., "Capillary Electrophoresis for the Analysis of Biopolymers", Anal., Chem., 74:2833-2850 (2002).

Hubbard, "Crystal Structure of the Activated Insulin Receptor Tyrosine Kinase in Complex with Peptide Substrate and ATP Analog", EMBO, 16(18):5573-5581 (1997).

Hubbard, et al., "Crystal Structure of the Tyrosine Kinase Domain of the Human Insulin Receptor", Nature, 374:746-754 (1994).

Hughes, et al., "Modulation of the Glycogen Synthase Kinase-3 Family by Tyrosine Phosphorylation", EMBO, 12(2):803-808 (1993).

Huse, et al., "Crystal Structure of the Cytoplasmic Domain of the Type I TGFβ Receptor in Complex with FKBP12", Cell, 96:425-436 (1999).

Huse, et al., "The TGFβ Receptor Activation Process: An Inhibitor- to Substrate-Binding Switch", Molecular Cell, 8:671-682 (2001).

International Human Genome Sequencing Consortium, "Initial Sequencing and Analysis of the Human Genome", Nature, 409:860-921 (2001).

Jackson, et al., "N-Terminal Mutations Activate the Leukemogenic Potential of the Myristoylated form of c-abl", EMBO, 8(2):449-456 (1989).

Jackson, et al., "Pyridinylimidazole Based p38 MAP Kinase Inhibitors", Current Topics in Medicinal Chemistry, 2:1011-1020 (2002).

Jiang, et al., ""Soft Docking": Matching of Molecular Surface Cubes", J. Mol. Biol., 219:79-102 (1991).

Johnson, "Circular Dichroism Spectroscopy and The Vacuum Ultraviolet Region", Ann. Rev. Phys. Chem., 29:93-114 (1978).

Johnson, "Protein Secondary Structure and Circular Dichroism: A Practical Guide", Proteins: Structure, Function, and Genetics, 7:205-214 (1990).

Kleywegt, et al., "Detection, Delineation, Measurement and Display of Cavities in Macromolecular Structures", Acta Cryst, D50:178-185 (1994).

Kuhn, et al., "The Genesis of High-Throughput Structure-Based Drug Discovery using Protein Crystallography", Analytical Techniques, Current Opinion in Chemical Biology, 6:704-710 (2002).

Kumar, et al., "P38 Map Kinases: Key Signalling Molecules as Therapeutic Targets for Inflammatory Diseases", Nature Reviews Drug Discovery, 2:717-726 (2003).

Kundrot, "Which Strategy for a Protein Crystallization Project", CMLS, Cell. Mol. Life Sci., 61:525-536 (2004).

Laskowski, "SURFNET: A Program for Visualizing Molecular Surfaces, Cavities, and Intermolecular Interactions", Journal of Molecular Graphics, 13:323-330 (1995).

Lesort, et al., "Insulin Transiently Increases Tau Phosphorylation: Involvement of Glycogen Synthase Kinase-3β and Fyn Tyrosine Kinase", Journal of Neurochemistry, 72(2):576-584 (1999).

Ll, et al., "Targeting Serine/Threonine Protein Kinase B/Akt and Cell-cycle Checkpoint Kinases for Treating Cancer", Current Topics in Medicinal Chemistry, 2:939-971 (2002).

Lipinski , et al., "Experimental and Computational Approaches to Estimate Solubility and Permeability in Drug Discovery and Development Settings", Advanced Drug Delivery Reviews, 23:3-25 (1997).

March's Advanced Organic Chemistry: Reactions, Mechanisms, and Structure, Fifth Edition, Smith and March Editors, Wiley-Interscience Publication (2001) (4 pages).

Mattsson, et al., "Six X-Linked Agammaglobulinemia-Causing Missense Mutations in the Src Homology 2 Domain of Bruton's Tyrosine Kinase: Phosphotyrosine-Binding and Circular Dichroism Analysis", Journal of Immunology, pp. 4170-4177 (2000).

McPherson, "Current Approaches to Macromolecular Crystallization", Eur. J. Biochem, 189:1-23 (1990).

Morris, et al., "Automated Docking of Flexible Ligands to Macromolecules", AutoDock Website, www.scripps.edu/mb/olson/doc/autodock/, printed Mar. 3, 2005 (3 pages).

Morris, et al., "Automated Docking Using a Lamarckian Genetic Algorithm and an Empirical Binding Free Energy Function", Journal of Computational Chemistry , 19(14):1639-1662 (1998).

Murayama, et al., "JNK (c-Jun $NH_2$ Terminal Kinase) and p38 During Ischemia Reperfusion Injury in the Small Intestine" Transplantation, 81(9):1325-1330 (2006).

Nagar, et al., "Crystal Structures of the Kinase Domain of c-Abl in Complex with the Small Molecule Inhibitors PD173955 and Imatinib (STI-571)", Cancer Research, 62:4236-4243 (2002).

Nagar, et al., "Structural Basis for the Autoinhibition of c-Abl Tyrosine Kinase", Cell, 112:859-871 (2003).

O'Neill, "Targeting Signal Transduction as a Strategy to Treat Inflammatory Diseases", Nature Review Drug Discovery, Published Online Jun. 9, 2006, www.nature.com/reviews/drugdisc (15 pages).

Okishio, et al., "Differential Ligand Recognition by the Src and Phosphatidylinositol 3-Kinase Src Homology 3 Domains: Circular Dichroism and Ultraviolet Resonance Raman Studies", Biochemistry, 42:208-216 (2003).

Okishio, et al., "Identification of Tyrosine Residues Involved in Ligand Recognition by the Phosphatidylinositol 3-Kinase Src Homology 3 Domain: Circular Dichroism and UV Resonance Raman Studies", Biochemistry, 40:15797-15804 (2001).

Okishio, et al., "Role of the Conserved Acidic Residue Asp21 in the Structure of Phosphatidylinositol 3-Kinase Src Homolgy 3 Domain: Circular Dichroism and Nuclear Magnetic Resonance Studies", Biochemistry 40:119-129 (2001).

Parang, et al., "Mechanism-based Design of a Protein Kinase Inhibitor", Nature Structural Biology, 8(1):37-41 (2001).

Pearlman, et al., "Assisted Model Building with Energy Refinement", Amber Home Page, amber.scripts.edu (9 pages).

Raimbault, et al., "Effects of pH and KCl on the Conformations of Creatine Kinase from Rabbit Muscle", Eur. J. Biochem., 234:570-578 (1995).

Reed, et al., "Circular Dichroic Evidence for an Ordered Sequence Ligand/Binding Site Interactions in the Catalytic Reaction of the cAMP-Dependent Protein Kinase", Biochemistry, 24:2967-2973 (1985).

Roux, et al., "ERK and p38 MAPK-Activated Protein Kinases: a Family of Protein Kinases with Diverse Biological Functions", Microbiology and Molecular Biology Reviews, 68(2):320-344 (2004).

Shah, et al., "Circular Dichroic Studies of Protein Kinase C and its Interactions with Calcium and Lipid Vesicles", Biochimica et Biophysica Acta, 1119:19-26 (1992).

Shiozaki, et al., "Impaired Differentiation of Endocrine and Exocrine Cells of the Pancreas in Transgenic Mouse Expressing the Truncated Type II Activin Receptor", Biochimica et Biophysica Acta, 1450:1-11 (1999).

Stout, et al., "High-Throughput Structural Biology in Drug Discovery: Protein Kinases", Current Pharmaceutical Design, 10:1069-1082 (2004).

Sugden, et al., ""Stress-Responsive" Mitogen-Activated Protein Kinases (c-Jun N-Terminal Kinases and p38 Mitogen-Activated Protein Kinases) in the Myocardium", Circulation Research—Journal of the American Heart Association, 83:345-352 (1998).

Tanis, et al., "Two Distinct Phosphorylation Pathways Have Additive Effects on Abl Family Kinase Activation", Molecular and Cellular Biology, 23(11):3884-3896 (2003).

Waetzig, et al., "Review Article: Mitogen-Activated Protein Kinases in Chronic Intestinal Inflammation—Targeting Ancient Pathways to Treat Modern Diseases", Aliment Pharmacol Ther, 18:17-32 (2003).

Wan, et al., "Mechanism of Activation of the RAF-ERK Signaling Pathway by Oncogenic Mutations of B-RAF", Cell, 116:855-867 (2004).

Welker, et al., "Glucocorticoid-Induced Modulation of Cytokine Secretion from Normal and Leukemic Human Myelomonocytic Cells", Int. Arch. Allergy Immunol, 109:110-115 (1996).

Wilson, et al., "The Structural Basis for the Specificity of Pyridinylimidazole Inhibitors of p38 MAP Kinase", Chemistry & Biology, 4(6):423-431 (1997).

Wrana, et al., "Mechanism of Activation of the TGF-β Receptor", Nature, 370:341-347 (1994).

Yang, et al., "Molecular Mechanism for the Regulation of Protein Kinase B/Akt by Hydrophobic Motif Phosphorylation", Molecular Cell, 9:1227-1240 (2002).

Zinner, et al., "Zur Weiteren Kenntnis Bicyclischer 3.5-Dioxopyrazolidine", Die Pharmazie, 25(5):309-312 (1970).

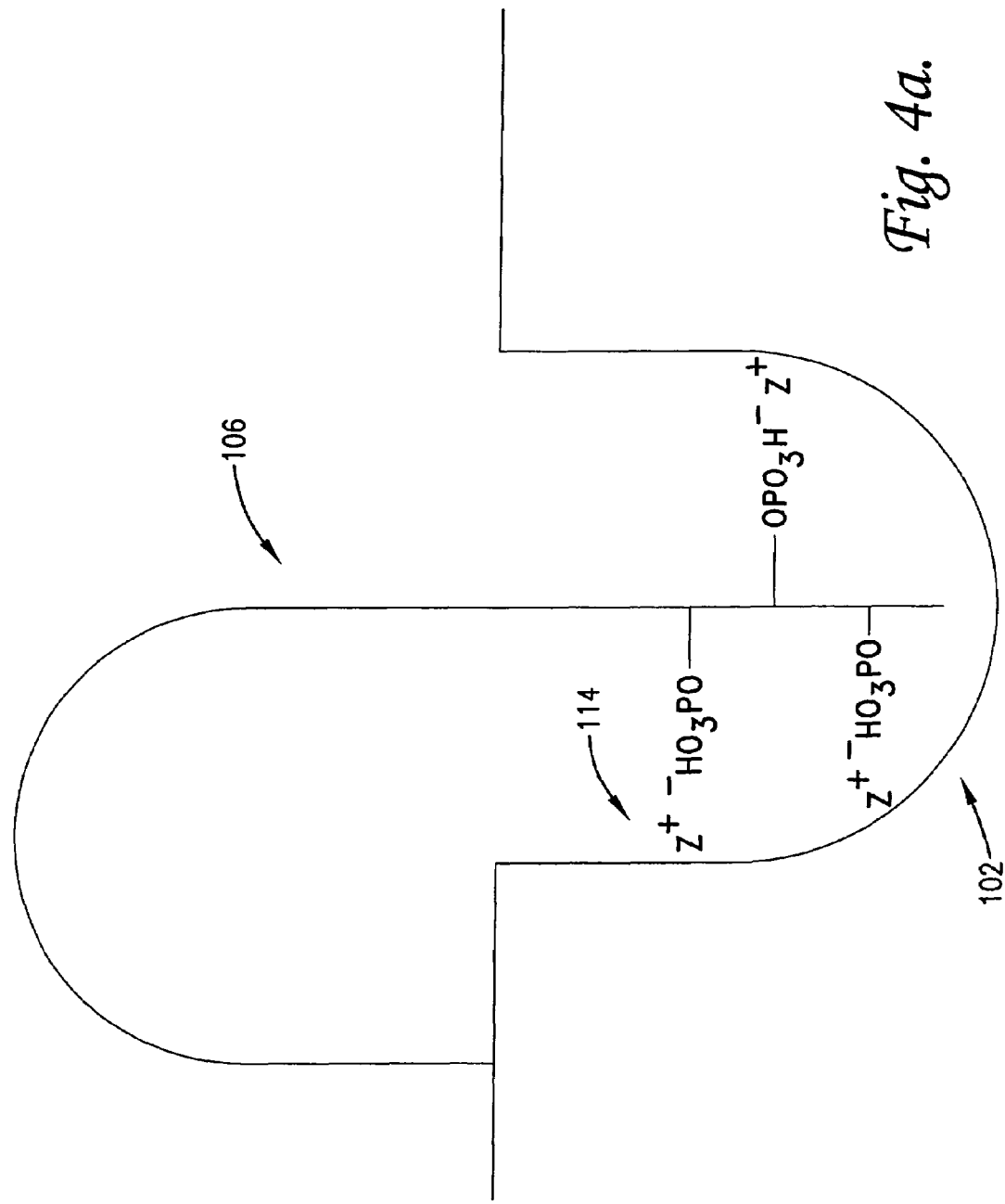

SEQUENCE LISTING

<160> NUMBER OF SEQ ID NOS: 7

<210> SEQ ID NO 1
<211> LENGTH: 360
<212> TYPE: PRT
<213> ORGANISM: Homo sapiens

<400> SEQUENCE: 1

```
Met Ser Gln Glu Arg Pro Thr Phe Tyr Arg Gln Glu Leu Asn Lys Thr
1               5                   10                  15

Ile Trp Glu Val Pro Glu Arg Tyr Gln Asn Leu Ser Pro Val Gly Ser
            20                  25                  30

Gly Ala Tyr Gly Ser Val Cys Ala Ala Phe Asp Thr Lys Thr Gly Leu
        35                  40                  45

Arg Val Ala Val Lys Lys Leu Ser Arg Pro Phe Gln Ser Ile Ile His
    50                  55                  60

Ala Lys Arg Thr Tyr Arg Glu Leu Arg Leu Leu Lys His Met Lys His
65                  70                  75                  80

Glu Asn Val Ile Gly Leu Leu Asp Val Phe Thr Pro Ala Arg Ser Leu
                85                  90                  95

Glu Glu Phe Asn Asp Val Tyr Leu Val Thr His Leu Met Gly Ala Asp
            100                 105                 110

Leu Asn Asn Ile Val Lys Cys Gln Lys Leu Thr Asp Asp His Val Gln
        115                 120                 125

Phe Leu Ile Tyr Gln Ile Leu Arg Gly Leu Lys Tyr Ile His Ser Ala
    130                 135                 140

Asp Ile Ile His Arg Asp Leu Lys Pro Ser Asn Leu Ala Val Asn Glu
145                 150                 155                 160

Asp Cys Glu Leu Lys Ile Leu Asp Phe Gly Leu Ala Arg His Thr Asp
                165                 170                 175

Asp Glu Met Thr Gly Tyr Val Ala Thr Arg Trp Tyr Arg Ala Pro Glu
            180                 185                 190

Ile Met Leu Asn Trp Met His Tyr Asn Gln Thr Val Asp Ile Trp Ser
        195                 200                 205

Val Gly Cys Ile Met Ala Glu Leu Leu Thr Gly Arg Thr Leu Phe Pro
    210                 215                 220

Gly Thr Asp His Ile Asp Gln Leu Lys Leu Ile Leu Arg Leu Val Gly
225                 230                 235                 240
```

```
Thr Pro Gly Ala Glu Leu Leu Lys Lys Ile Ser Ser Glu Ser Ala Arg
                245                 250                 255

Asn Tyr Ile Gln Ser Leu Thr Gln Met Pro Lys Met Asn Phe Ala Asn
            260                 265                 270

Val Phe Ile Gly Ala Asn Pro Leu Ala Val Asp Leu Leu Glu Lys Met
        275                 280                 285

Leu Val Leu Asp Ser Asp Lys Arg Ile Thr Ala Ala Gln Ala Leu Ala
    290                 295                 300

His Ala Tyr Phe Ala Gln Tyr His Asp Pro Asp Asp Glu Pro Val Ala
305                 310                 315                 320

Asp Pro Tyr Asp Gln Ser Phe Glu Ser Arg Asp Leu Leu Ile Asp Glu
                325                 330                 335

Trp Lys Ser Leu Thr Tyr Asp Glu Val Ile Ser Phe Val Pro Pro Pro
            340                 345                 350

Leu Asp Gln Glu Glu Met Glu Ser
        355                 360

<210> SEQ ID NO 2
<211> LENGTH: 17
<212> TYPE: PRT
<213> ORGANISM: Homo sapiens
<220> FEATURE:
<221> NAME/KEY: MISC_FEATURE
<222> LOCATION: (2)..(16)
<223> OTHER INFORMATION: X is any amino acid

<400> SEQUENCE: 2

Ile Ile His Xaa Lys Arg Xaa Xaa Arg Glu Xaa Xaa Leu Leu Xaa Xaa
1               5                   10                  15

Met

<210> SEQ ID NO 3
<211> LENGTH: 6
<212> TYPE: PRT
<213> ORGANISM: Homo sapiens

<400> SEQUENCE: 3

Asp Ile Ile His Arg Asp
1               5

<210> SEQ ID NO 4
<211> LENGTH: 10
<212> TYPE: PRT
<213> ORGANISM: Homo sapiens

<400> SEQUENCE: 4

Asp Phe Gly Leu Ala Arg His Thr Asp Asp
1               5                   10

<210> SEQ ID NO 5
<211> LENGTH: 12
<212> TYPE: PRT
<213> ORGANISM: Homo sapiens

<400> SEQUENCE: 5

Glu Met Thr Gly Tyr Val Ala Thr Arg Trp Tyr Arg
1               5                   10

<210> SEQ ID NO 6
<211> LENGTH: 4
<212> TYPE: PRT
```

```
<213> ORGANISM: Homo sapiens

<400> SEQUENCE: 6

Trp Met His Tyr
1

<210> SEQ ID NO 7
<211> LENGTH: 4
<212> TYPE: PRT
<213> ORGANISM: Homo sapiens

<400> SEQUENCE: 7

Tyr Gly Ser Val
1
```

ANTI-INFLAMMATORY MEDICAMENTS

RELATED APPLICATIONS

This application is a continuation of U.S. patent application Ser. No. 10/886,329, filed Jul. 6, 2004, now U.S. Pat. No. 7,202,257, which is a continuation-in-part of application Ser. No. 10/746,460 filed Dec. 24, 2003, now U.S. Pat. No. 7,144,911, which claims the benefit of U.S. Provisional Applications Ser. No. 60/437,487, filed Dec. 31, 2002, Ser. No. 60/437,403, filed Dec. 31, 2002, Ser. No. 60/437,415, filed Dec. 31, 2002, Ser. No. 60/437,304, filed Dec. 31, 2002, and Ser. No. 60/463,804 filed Apr. 18, 2003. These prior applications are incorporated by reference herein.

The following application contains a sequence listing in computer readable format (CRF), submitted as a text file entitled "34477C~1.TXT," created on Jul. 2, 2004,as 5KB. The content of the CRF is hereby incorporated by reference.

BACKGROUND OF THE INVENTION

1. Field of the Invention

The present invention relates to novel compounds and methods of using those compounds to treat anti-inflammatory diseases.

2. Description of the Prior Art

Basic research has recently provided the life sciences community with an unprecedented volume of information on the human genetic code and the proteins that are produced by it. In 2001, the complete sequence of the human genome was reported (Lander, E. S. et al. Initial sequencing and analysis of the human genome. *Nature* (2001) 409:860; Venter, J. C. et al. The sequence of the human genome. *Science* (2001) 291: 1304). Increasingly, the global research community is now classifying the 50,000+ proteins that are encoded by this genetic sequence, and more importantly, it is attempting to identify those proteins that are causative of major, undertreated human diseases.

Despite the wealth of information that the human genome and its proteins are providing, particularly in the area of conformational control of protein function, the methodology and strategy by which the pharmaceutical industry sets about to develop small molecule therapeutics has not significantly advanced beyond using native protein active sites for binding to small molecule therapeutic agents. These native active sites are normally used by proteins to perform essential cellular functions by binding to and processing natural substrates or transducing signals from natural ligands. Because these native pockets are used broadly by many other proteins within protein families, drugs which interact with them are often plagued by lack of selectivity and, as a consequence, insufficient therapeutic windows to achieve maximum efficacy. Side effects and toxicities are revealed in such small molecules, either during preclinical discovery, clinical trials, or later in the marketplace. Side effects and toxicities continue to be a major reason for the high attrition rate seen within the drug development process. For the kinase protein family of proteins, interactions at these native active sites have been recently reviewed: see J. Dumas, Protein Kinase Inhibitors: Emerging Pharmacophores 1997-2001, *Expert Opinion on Therapeutic Patents* (2001) 11: 405-429; J. Dumas, Editor, New challenges in Protein Kinase Inhibition, in *Current Topics in Medicinal Chemistry* (2002) 2: issue 9.

It is known that proteins are flexible, and this flexibility has been reported and utilized with the discovery of the small molecules which bind to alternative, flexible active sites with proteins. For review of this topic, see Teague, *Nature Reviews/Drug Discovery*, Vol. 2, pp. 527-541 (2003). See also, Wu et al., *Structure*, Vol. 11, pp. 399-410 (2003). However these reports focus on small molecules which bind only to proteins at the protein natural active sites. Peng et al., *Bio. Organic and Medicinal Chemistry Ltrs.*, Vol. 13, pp. 3693-3699 (2003), and Schindler, et al., *Science*, Vol. 289, p. 1938 (2000) describe inhibitors of abl kinase. These inhibitors are identified in WO Publication No. 2002/034727. This class of inhibitors binds to the ATP active site while also binding in a mode that induces movement of the kinase catalytic loop. Pargellis et al., *Nature Structural Biology*, Vol. 9, p. 268 (2002) reported inhibitors p38 alpha-kinase also disclosed in WO Publication No. 00/43384 and Regan et al., *J. Medicinal Chemistry*, Vol. 45, pp. 2994-3008 (2002). This class of inhibitors also interacts with the kinase at the ATP active site involving a concomitant movement of the kinase activation loop.

More recently, it has been disclosed that kinases utilize activation loops and kinase domain regulatory pockets to control their state of catalytic activity. This has been recently reviewed (see, e.g., M. Huse and J. Kuriyan, *Cell* (2002) 109:275).

SUMMARY OF THE INVENTION

The present invention is broadly concerned with new compounds for use in treating anti-inflammatory conditions and methods of treating such conditions. In more detail, the inventive compounds have the formula (IA)

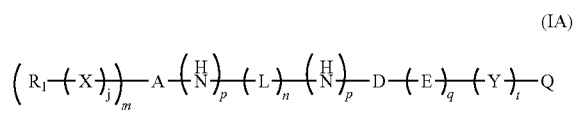

wherein:
  $R^1$ is selected from the group consisting of aryls (preferably $C_6$-$C_{18}$, and more preferably $C_6$-$C_{12}$) and heteroaryls;
  each X and Y is individually selected from the group consisting of —O—, —S—, —$NR_6$—, —$NR_6SO_2$—, —$NR_6CO$—, alkynyls (preferably $C_1$-$C_{18}$, and more preferably $C_1$-$C_{12}$), alkenyls (preferably $C_1$-$C_{18}$, and more preferably $C_1$-$C_{12}$), alkylenes (preferably $C_1$-$C_{18}$, and more preferably $C_1$-$C_{12}$), —O(CH$_2$)$_h$—, and —NR$_6$(CH$_2$)$_h$—, where each h is individually selected from the group consisting of 1, 2, 3, or 4, and where for each of alkylenes (preferably $C_1$-$C_{18}$, and more preferably $C_1$-$C_{12}$), —O(CH$_2$)$_h$—, and —NR$_6$(CH$_2$)$_h$—, one of the methylene groups present therein may be optionally double-bonded to a side-chain oxo group except that where —O(CH$_2$)$_h$— the introduction of the side-chain oxo group does not form an ester moiety;
  A is selected from the group consisting of aromatic (preferably $C_6$-$C_{18}$, and more preferably $C_6$-$C_{12}$), monocycloheterocyclic, and bicycloheterocyclic rings;
  D is phenyl or a five- or six-membered heterocyclic ring selected from the group consisting of pyrazolyl, pyrrolyl, imidazolyl, oxazolyl, thiazolyl, furyl, oxadiazolyl, thiadiazolyl, thienyl, pyridyl, and pyrimidyl;
  E is selected from the group consisting of phenyl, pyridinyl, and pyrimidinyl;
  L is selected from the group consisting of —C(O)— and —S(O)$_2$—;
  j is 0 or 1;
  m is 0 or 1;

n is 0 or 1;
p is 0 or 1;
q is 0 or 1;
t is 0 or 1;
Q is selected from the group consisting of
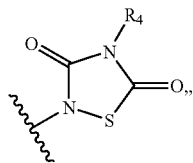
Q-1
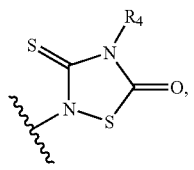
Q-2
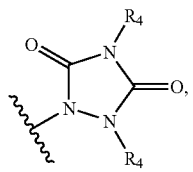
Q-3
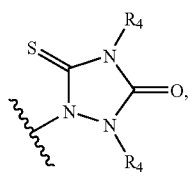
Q-4
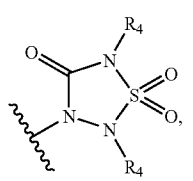
Q-5
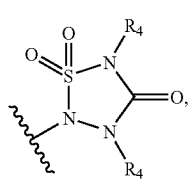
Q-6
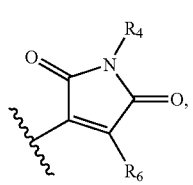
Q-7
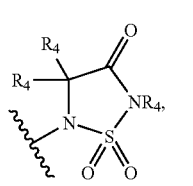
Q-8
-continued
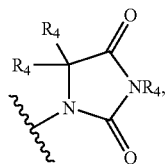
Q-9
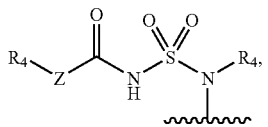
Q-10
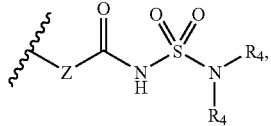
Q-11
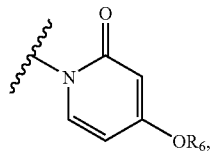
Q-12
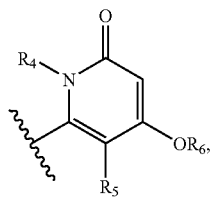
Q-13
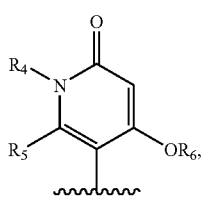
Q-14
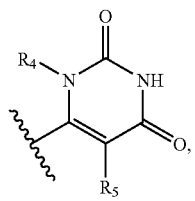
Q-15
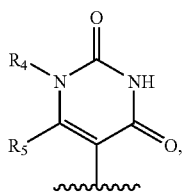
Q-16
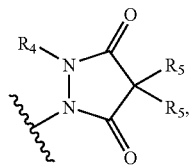
Q-17

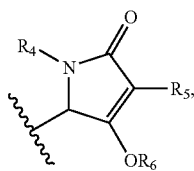
Q-18
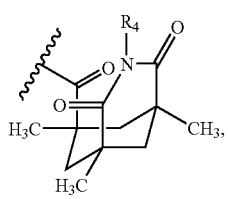
Q-19
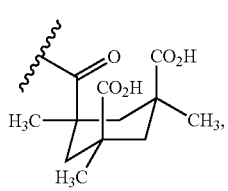
Q-20
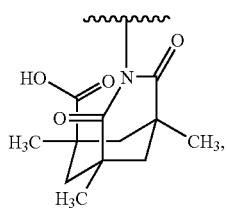
Q-21
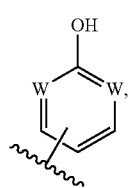
Q-22
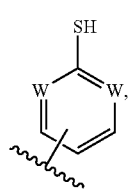
Q-23
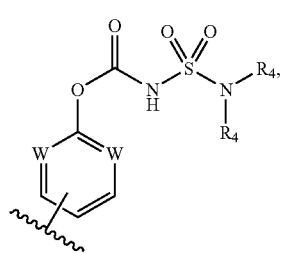
Q-24
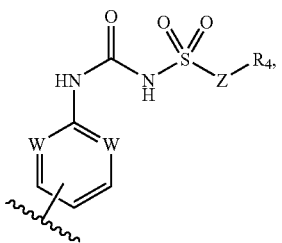
Q-25
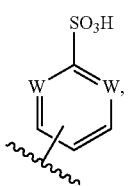
Q-26
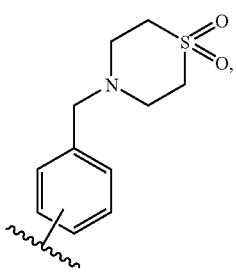
Q-27
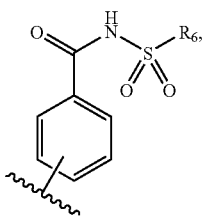
Q-28
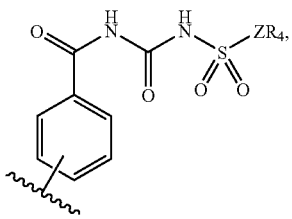
Q-29
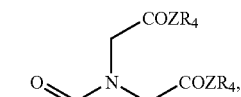
Q-30
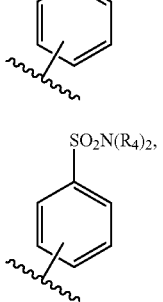
Q-31

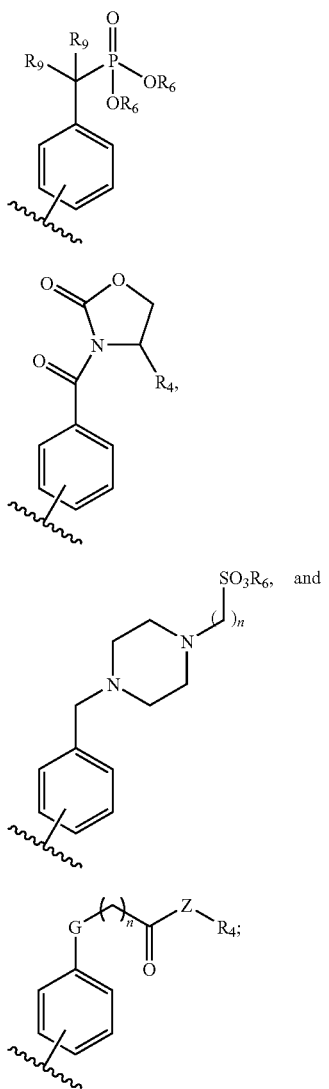

each $R_4$ group is individually selected from the group consisting of —H, alkyls (preferably $C_1$-$C_{18}$, and more preferably $C_1$-$C_{12}$), aminoalkyls (preferably $C_1$-$C_{18}$, and more preferably $C_1$-$C_{12}$), alkoxyalkyls (preferably $C_1$-$C_{18}$, and more preferably $C_1$-$C_{12}$), aryls (preferably $C_6$-$C_{18}$, and more preferably $C_6$-$C_{12}$), aralkyls (preferably $C_6$-$C_{18}$, and more preferably $C_6$-$C_{12}$ and preferably $C_1$-$C_{18}$, and more preferably $C_1$-$C_{12}$), heterocyclyls, and heterocyclylalkyls except when the $R_4$ substituent places a heteroatom on an alpha-carbon directly attached to a ring nitrogen on Q;

when two $R_4$ groups are bonded with the same atom, the two $R_4$ groups optionally form an alicyclic or heterocyclic 4-7 membered ring;

each $R_5$ is individually selected from the group consisting of —H, alkyls (preferably $C_1$-$C_{18}$, and more preferably $C_1$-$C_{12}$), aryls (preferably $C_6$-$C_{18}$, and more preferably $C_6$-$C_{12}$), heterocyclyls, alkylaminos (preferably $C_1$-$C_{18}$, and more preferably $C_1$-$C_{12}$), arylaminos (preferably $C_6$-$C_{18}$, and more preferably $C_6$-$C_{12}$), cycloalkylaminos (preferably $C_1$-$C_{18}$, and more preferably $C_1$-$C_{12}$), heterocyclylaminos, hydroxys, alkoxys (preferably $C_1$-$C_{18}$, and more preferably $C_1$-$C_{12}$), aryloxys (preferably $C_6$-$C_{18}$, and more preferably $C_6$-$C_{12}$), alkylthios (preferably $C_1$-$C_{18}$, and more preferably $C_1$-$C_{12}$), arylthios (preferably $C_6$-$C_{18}$, and more preferably $C_6$-$C_{12}$), cyanos, halogens, perfluoroalkyls (preferably $C_1$-$C_{18}$, and more preferably $C_1$-$C_{12}$), alkylcarbonyls (preferably $C_1$-$C_{18}$, and more preferably $C_1$-$C_{12}$), and nitros;

each $R_6$ is individually selected from the group consisting of —H, alkyls (preferably $C_1$-$C_{18}$, and more preferably $C_1$-$C_{12}$), allyls, and β-trimethylsilylethyl;

each $R_8$ is individually selected from the group consisting of alkyls (preferably $C_1$-$C_{18}$, and more preferably $C_1$-$C_{12}$), phenyl, naphthyl, aralkyls (wherein the aryl is preferably $C_6$-$C_{18}$, and more preferably $C_6$-$C_{12}$, and wherein alkyl is preferably $C_1$-$C_{18}$, and more preferably $C_1$-$C_{12}$), heterocyclyls, and heterocyclylalkyls (wherein the alkyl is preferably $C_1$-$C_{18}$, and more preferably $C_1$-$C_{12}$);

each $R_9$ group is individually selected from the group consisting of —H, —F, and alkyls (preferably $C_1$-$C_{18}$, and more preferably $C_1$-$C_{12}$), wherein when two $R_9$ groups are geminal alkyl groups, said geminal alkyl groups may be cyclized to form a 3-6 membered ring;

G is alkylene (preferably $C_1$-$C_8$, and more preferably $C_1$-$C_4$), $N(R_6)$, O;

each Z is individually selected from the group consisting of —O— and —$N(R_4)$—; and each ring of formula (IA) optionally includes one or more of $R_7$, where $R_7$ is a noninterfering substituent individually selected from the group consisting of —H, alkyls (preferably $C_1$-$C_{18}$, and more preferably $C_1$-$C_{12}$), aryls (preferably $C_6$-$C_{18}$, and more preferably $C_6$-$C_{12}$), heterocyclyls, alkylaminos (preferably $C_1$-$C_{18}$, and more preferably $C_1$-$C_{12}$), arylaminos (preferably $C_6$-$C_{18}$, and more preferably $C_6$-$C_{12}$), cycloalkylaminos (preferably $C_1$-$C_{18}$, and more preferably $C_1$-$C_{12}$), heterocyclylaminos, hydroxys, alkoxys (preferably $C_1$-$C_{18}$, and more preferably $C_1$-$C_{12}$), aryloxys (preferably $C_6$-$C_{18}$, and more preferably $C_6$-$C_{12}$), alkylthios (preferably $C_1$-$C_{18}$, and more preferably $C_1$-$C_{12}$), arthylthios, cyanos, halogens, nitrilos, nitros, alkylsulfinyls (preferably $C_1$-$C_{18}$, and more preferably $C_1$-$C_{12}$), alkylsulfonyls (preferably $C_1$-$C_{18}$, and more preferably $C_1$-$C_{12}$), aminosulfonyls, and perfluoroalkyls (preferably $C_1$-$C_{18}$, and more preferably $C_1$-$C_{12}$).

In one preferred embodiment, the compound has the structure of formula (I) except that:

when Q is Q-3 or Q-4, then the compound of formula (I) is not

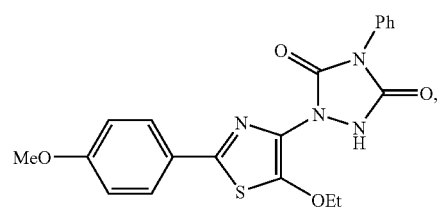

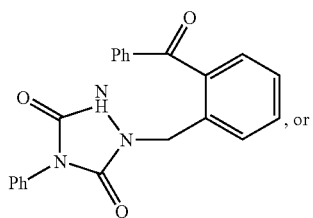, or

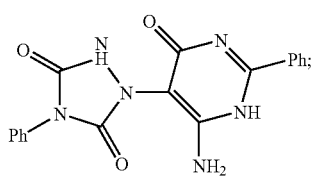

when Q is Q-7, q is 0, and $R_5$ and D are phenyl, then A is not phenyl, oxazolyl, pyridyl, pyrimidyl, pyrazolyl, or imidazolyl;

when Q is Q-7, $R_5$ is —OH, Y is —O—, —S—, or —CO—, m is 0, n is 0, p is 0, and A is phenyl, pyridyl, or thiazolyl, then D is not thienyl, thiazolyl, or phenyl;

when Q is Q-7, $R_5$ is —OH, m is 0, n is 0, p is 0, t is 0, and A is phenyl, pyridyl, or thiazolyl, then D is not thienyl, thiazolyl, or phenyl;

when Q is Q-7, then the compound of formula (I) is not

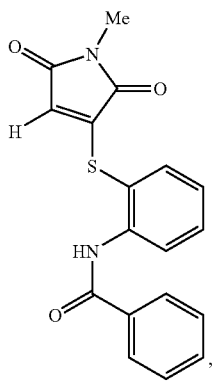, 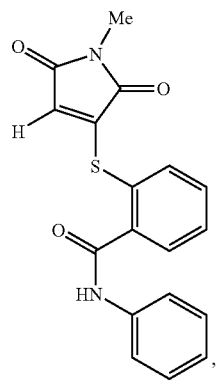,

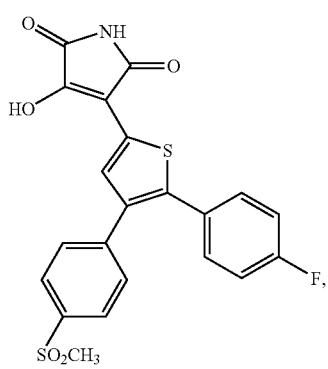

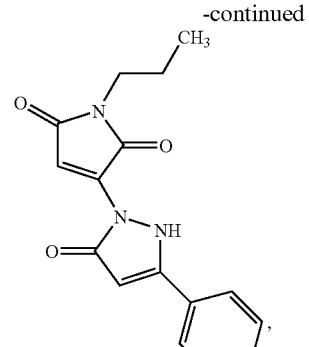,

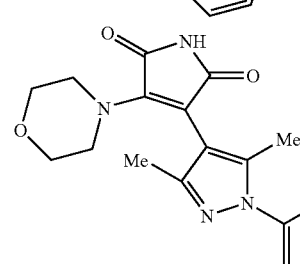;

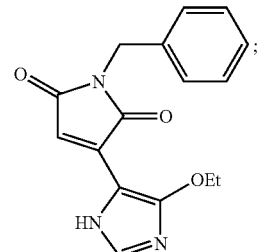

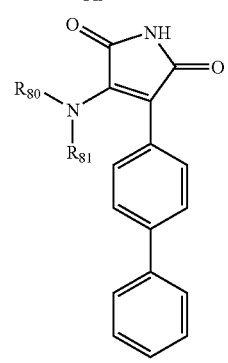 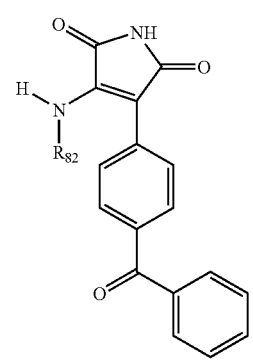

R80 is H, Me
R81 is substituted phenyl

R82 is substituted phenyl when Q is Q-8, then Y is not —CH$_2$O—;
when Q is Q-8, the compound of formula (I) is not

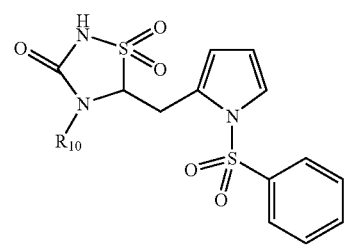 or

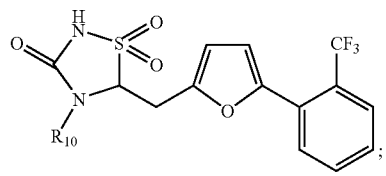

R10 = alkyl, aryl, arylalkoxyalkyl, or arylalkyls when Q is Q-9, then the compound of formula (I) is not

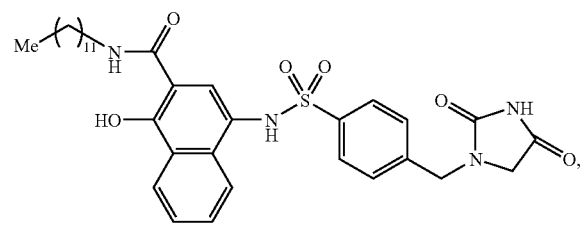

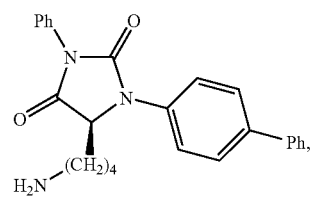

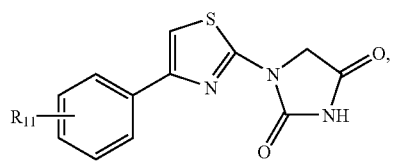

R11 = H, alkyl, alkoxy, nitro, halogen

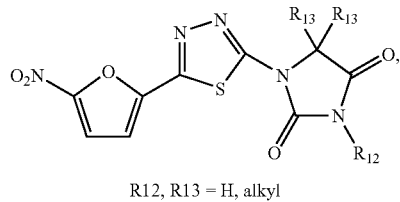

R12, R13 = H, alkyl

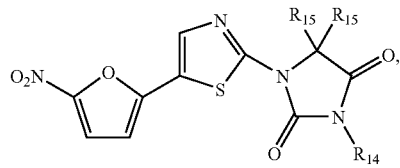

R14 = H, alkyl, allyl, propargyl
R15 = H, alkyl,

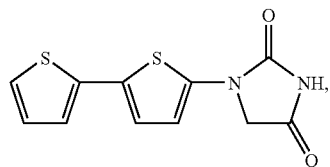

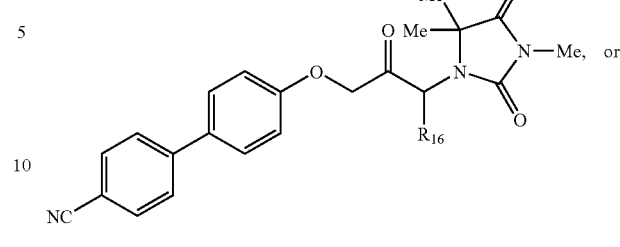

R16 = H, methyl

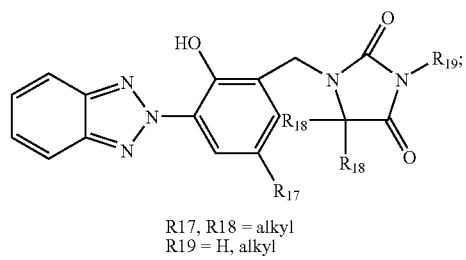

R17, R18 = alkyl
R19 = H, alkyl when Q is Q-10, t is 0, and E is phenyl, then any $R_7$ on E is not an o-alkoxy;

when Q is Q-10, then the compound of formula (I) is not

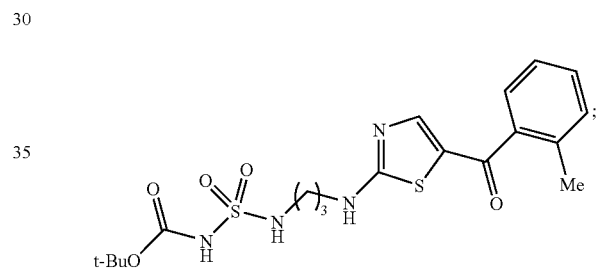

when Q is Q-11, t is 0, and E is phenyl, then any $R_7$ on E is not an o-alkoxy;

when Q is Q-11, then the compound of formula (I) is not

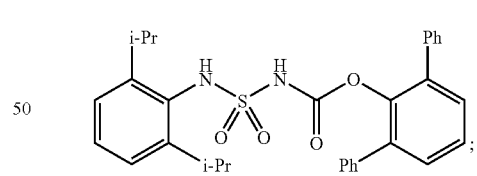

when Q is Q-15, then the compound of formula (I) is not

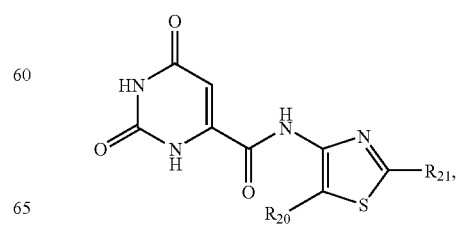

-continued

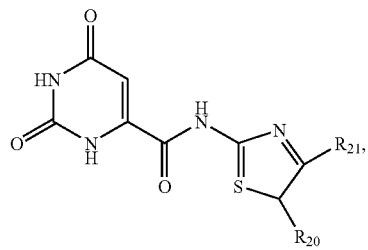

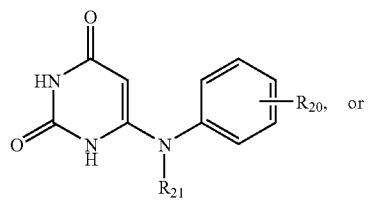

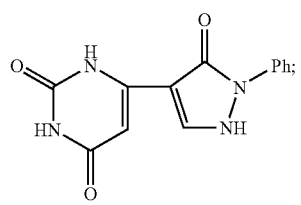

R$_{20}$ = substituted phenyl, R$_{21}$ = H, alkyl when Q is Q-16 and Y is —NH—, then

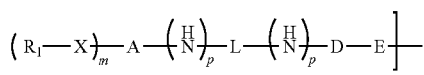

of formula (I) is not biphenyl;
when Q is Q-16 and Y is —S—, then

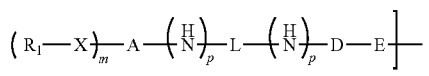

of formula (I) is not phenylsulfonylaminophenyl or phenylcarbonylaminophenyl;
when Q is Q-16 and Y is —SO$_2$NH—, then the compound of formula (I) is not

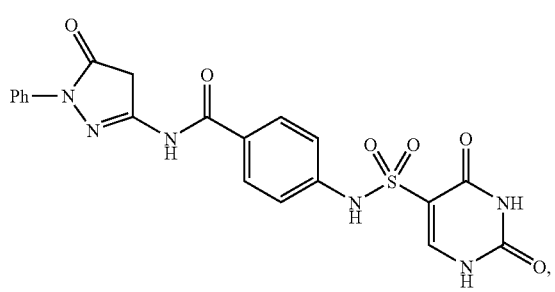

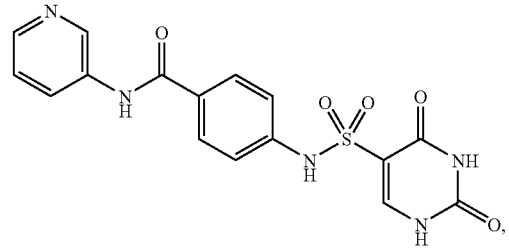

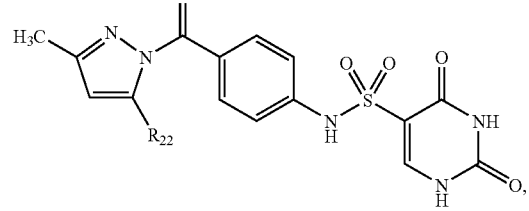

R$_{22}$ = Me, OH

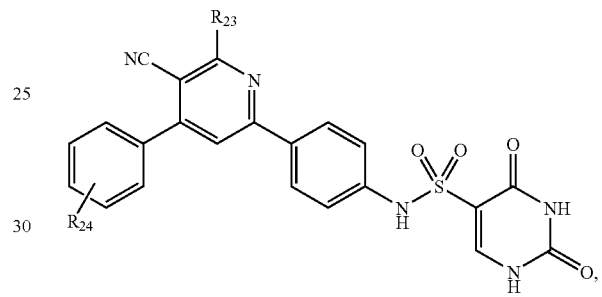

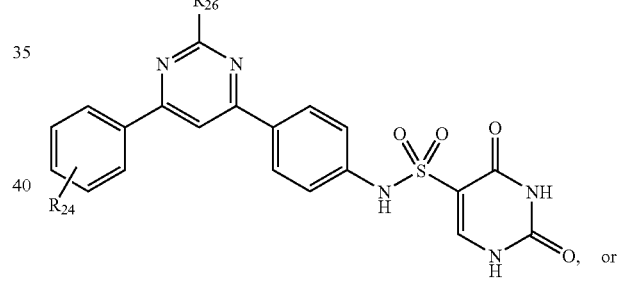

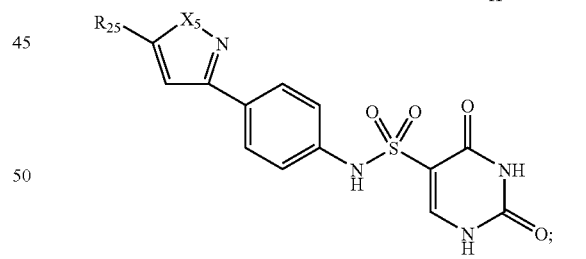

R$_{23}$ = OH, SH, NH2
R$_{24}$ = hydrogen or one or more methoxy, hydroxy, fluoro, chloro, nitro, dimethylamino, or furanyl
R$_{25}$ = substituted phenyl, furanyl
R$_{26}$ = OH or Cl
X$_5$ = O, NH;

when Q is Q-16 and Y is —CONH—, then

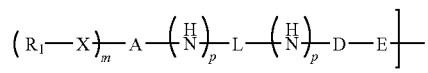

of formula (I) is not imidazophenyl;

when Q is Q-16 and Y is —CONH—, then the compound of formula (I) is not

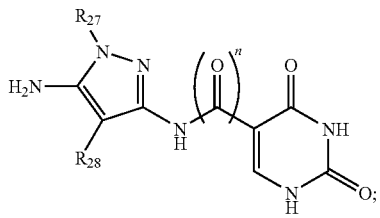

R27 = substituted phenyl, pyridylcarbonyl
R28 = CN, methoxycarbonyl
n = 0 or 1 when Q is Q-16 and t is 0, then

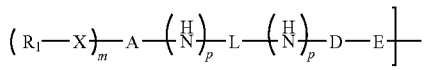

of formula (I) is not phenylcarbonylphenyl, pyrimidophenyl, phenylpyrimidyt, pyrimidyl, or N-pyrolyl;
when Q is Q-17, then the compound of formula (I) is not

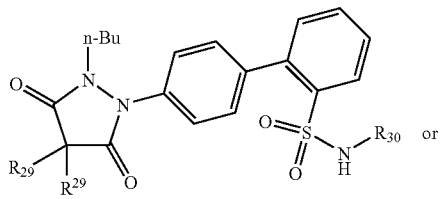

R29 = alkyl
R30 = H, t-Bu, benzoyl

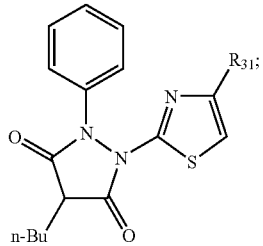

R31 = substituted phenyl when Q is Q-21, then the compound of formula (I) is not

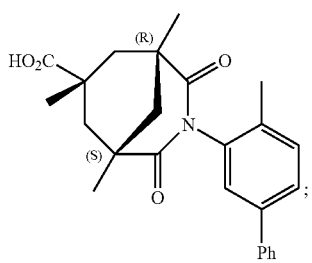

when Q is Q-22, then the compound of formula (I) is selected from the group consisting of

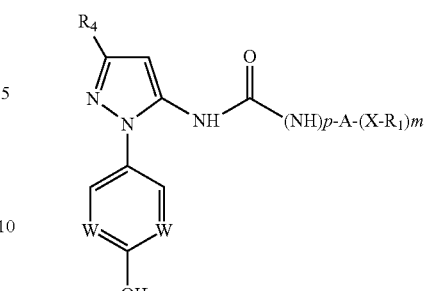

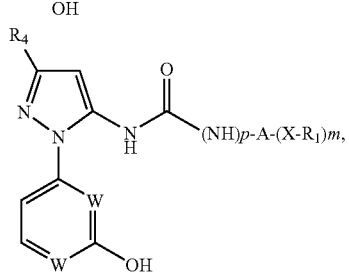

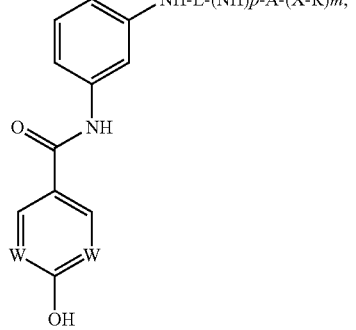

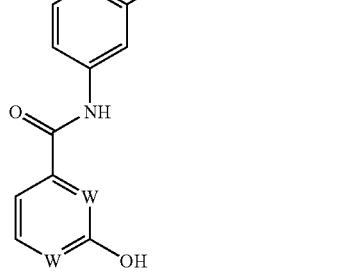

when Q is Q-22 and q is 0, then the compound of formula (I) is selected from the group consisting of

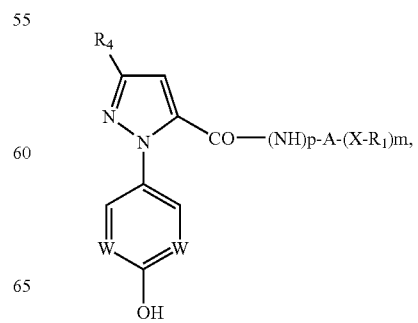

-continued
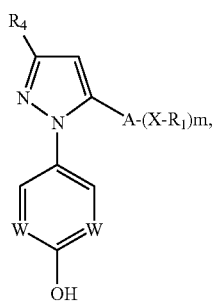
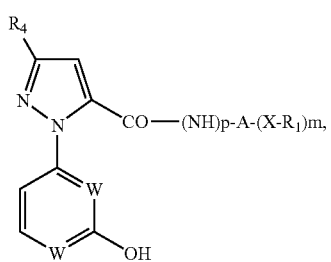
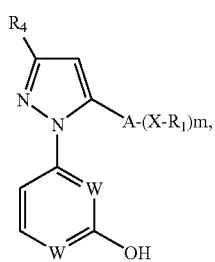
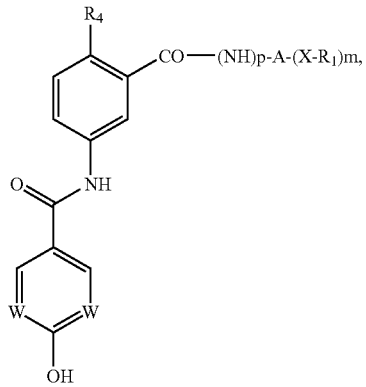
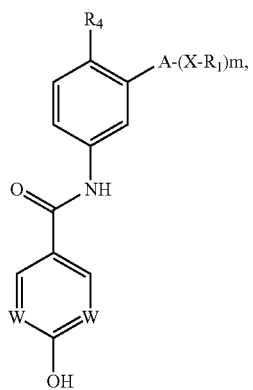
-continued
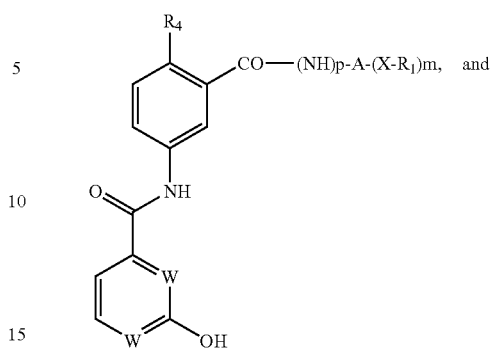
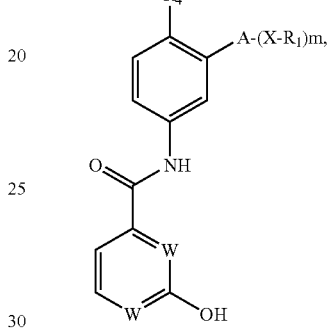
but excluding
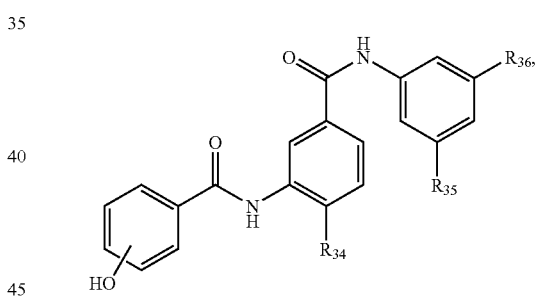
meta or para-
R34 = Me, Cl
R35 = -N(Me)2, morpholino
R36 = H, F
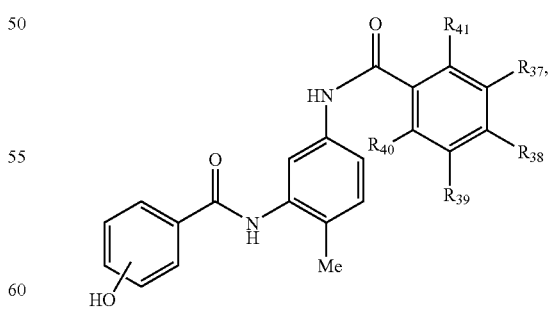
meta or para-
R37 = N(Me)2, morpholino, OMe, OH, H
R38 = H, CN, OMe, OH, benzyloxy, phenyl, nitro
R39 = H, OH
R40 = H, F
R41 = H, Cl -continued
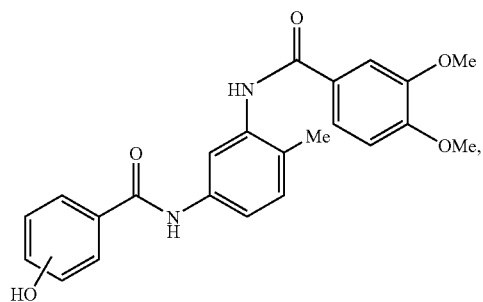
meta or para-
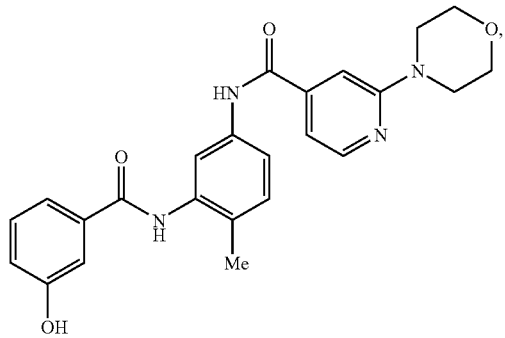
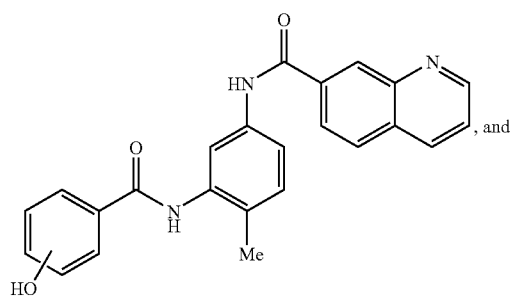
, and
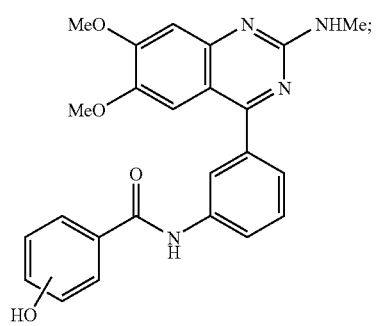
meta or para-
when Q is Q-23, then the compound of formula (I) is not
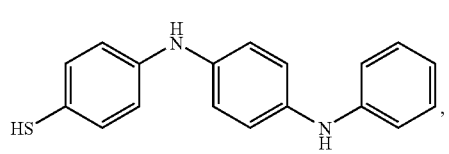
-continued
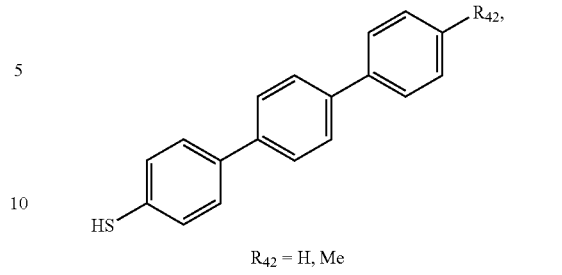
$R_{42}$ = H, Me
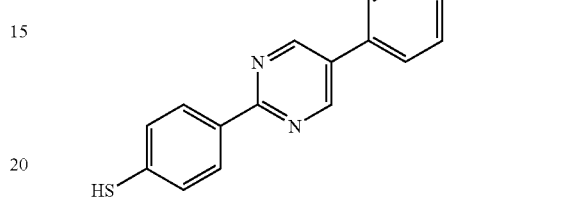
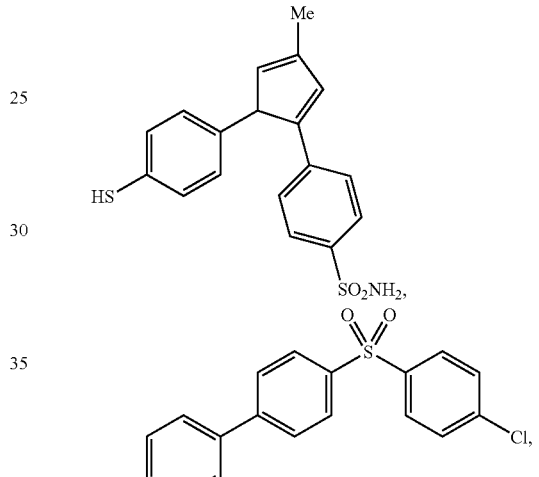
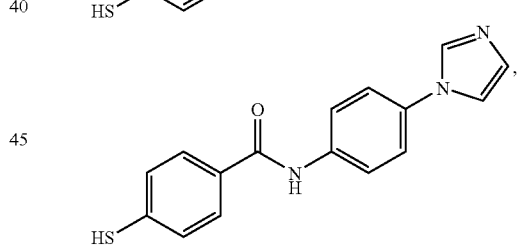
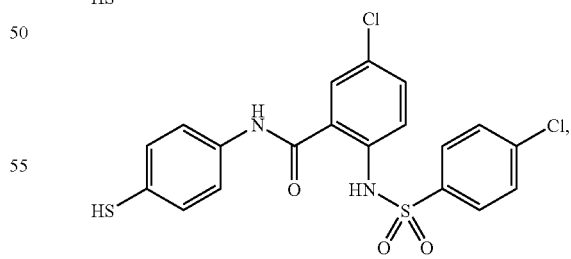
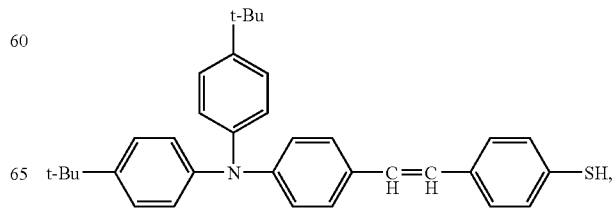

-continued
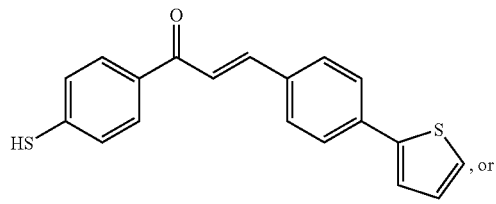, or
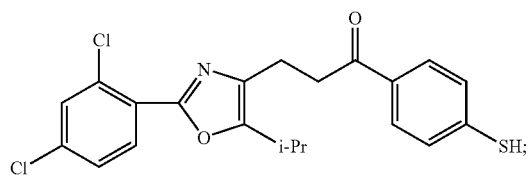
when Q is Q-24, Q-25, Q-26, or Q-31, then the compound of formula (I) is selected from the group consisting of
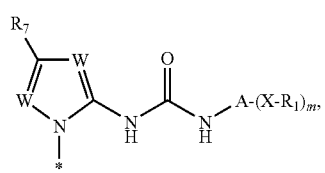
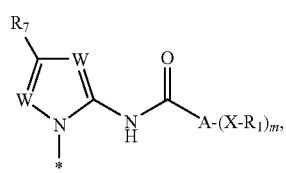
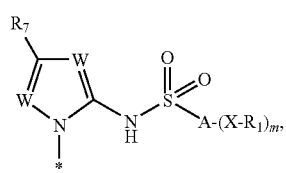
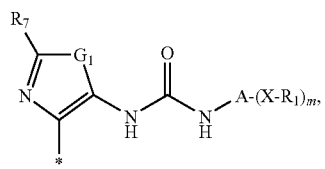
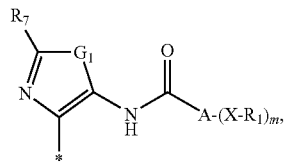
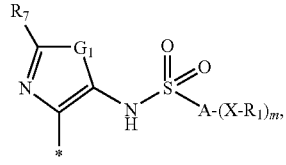
-continued
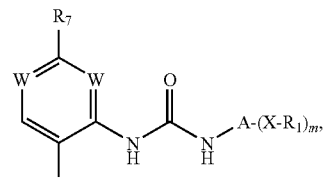
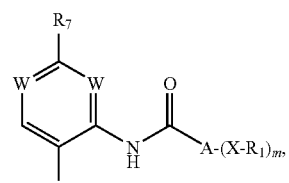
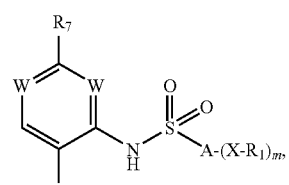
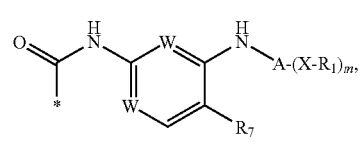
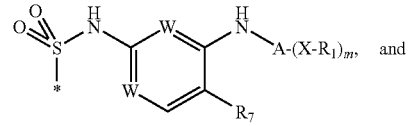 and
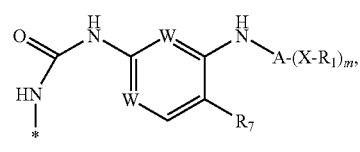
wherein each W is individually selected from the group consisting of —CH— and —N—;
each $G_1$ is individually selected from the group consisting of —O—, —S—, and —N($R_4$)—; and
* denotes the point of attachment to Q-24, Q-25, Q-26, or Q-31 as follows:
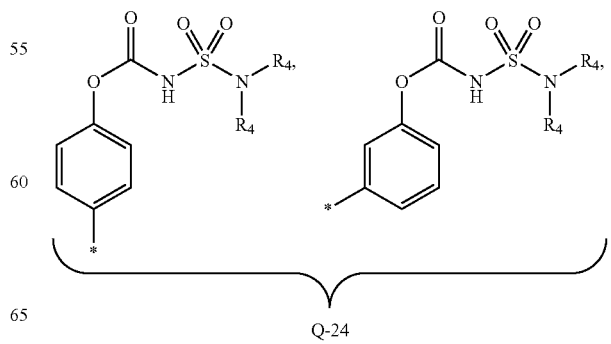

-continued

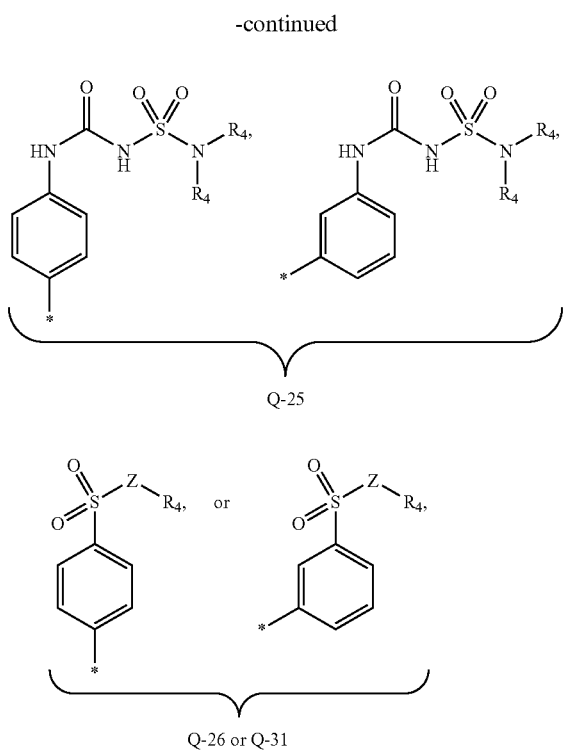

Q-25

Q-26 or Q-31 wherein each Z is individually selected from the group consisting of —O— and —N(R$_4$)—;

when Q is Q-31, then the compound of formula (I) is not

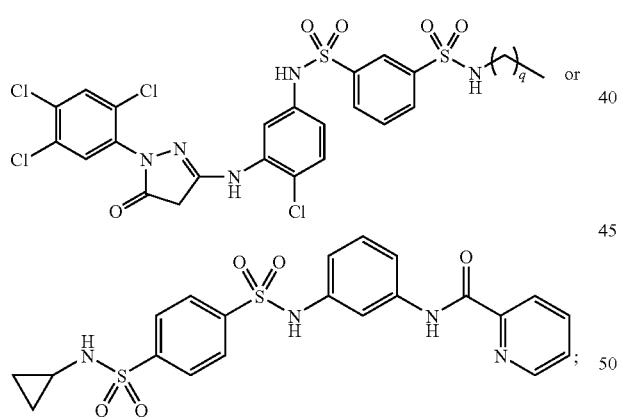

when Q is Q-28 or Q-29 and t is 0, then the compound of formula (I) is not

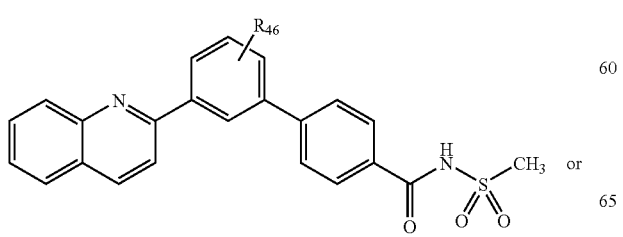

-continued

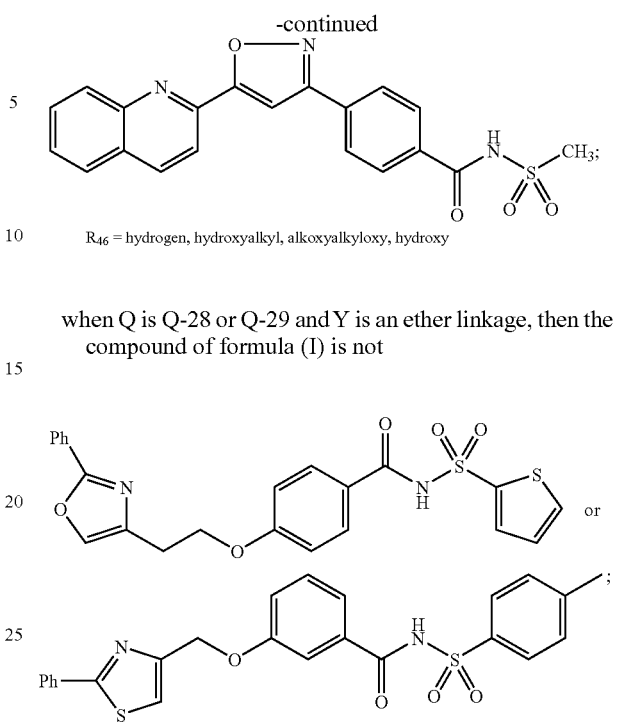

R$_{46}$ = hydrogen, hydroxyalkyl, alkoxyalkyloxy, hydroxy when Q is Q-28 or Q-29 and Y is an ether linkage, then the compound of formula (I) is not when Q is Q-28 or Q-29 and Y is —CONH—, then the compound of formula (I) is not when Q is Q-32, then $$(R_1\!-\!X)_{\!m}\!-\!A\!-\!(\!\underset{N}{\overset{H}{|}}\!)_{\!p}\!-\!L\!-\!(\!\underset{N}{\overset{H}{|}}\!)_{\!p}\!-\!D\!-\!E\!-\!Y\,]$$

is not biphenyl, benzoxazolylphenyl, pyridylphenyl or bipyridyl;

when Q is Q-32, Y is —CONH—, q is 0, m is 0, and $$-[(\!\underset{N}{\overset{H}{|}}\!)_{\!p}\!-\!L\!-\!(\!\underset{N}{\overset{H}{|}}\!)_{\!p}]-$$

of formula (I) is —CONH—, then A is not phenyl;
when Q is Q-32, q is 0, m is 0, and $$-[(\!\underset{N}{\overset{H}{|}}\!)_{\!p}\!-\!L\!-\!(\!\underset{N}{\overset{H}{|}}\!)_{\!p}]-$$

is —CONH—, then the compound of formula (I) is not

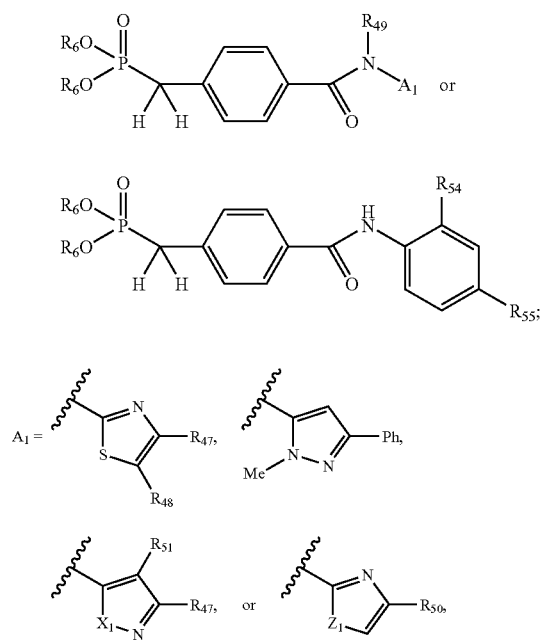

R47 = alkyl, substituted phenyl, thienyl, phenacetyl naphthyl
R48 = H, alkyl, Br, substituted phenyl, benzoyl, phenylsulfonyl
R49 = H, alkyl, phenyl
R50 = substituted phenyl
R54 = benzoyl, phenylalkylaminocarbonyl, substituted phenylaminocarbonyl H, Br
R55 = Cl, Br, SPh, benzoyl, phenylsulfonyl
R51 = H, phenylsulfonyl, phenyl, benzyl
R6 = Et, i-Pr
R53 = substituted phenyl, substituted benzyl
X1 = O, N-Ph, N-alkyl, N-carbamoyl
Z1 = N(R50), O when Q is Q-32, D is thiazolyl, q is 0, t is 0, p is 0, n is 0, and m is 0, then A is not phenyl or 2-pyridone;
when Q is Q-32, D is oxazolyl or isoxazolyl, q is 0, t is 0, p is 0, n is 0, and m is 0, then A is not phenyl;
when Q is Q-32, D is pyrimidyl q is 0, t is 0, p is 0, n is 0, and m is 0, then A is not phenyl;
when Q is Q-32 and Y is an ether linkage, then

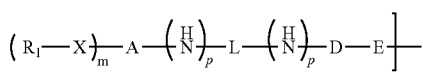

of formula (I) is not biphenyl or phenyloxazolyl;
when Q is Q-32 and Y is —CH═CH—, then

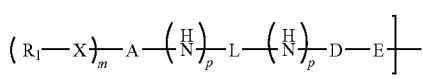

of formula (I) is not phenylaminophenyl;

when Q is Q-32, then the compound of formula (I) is not

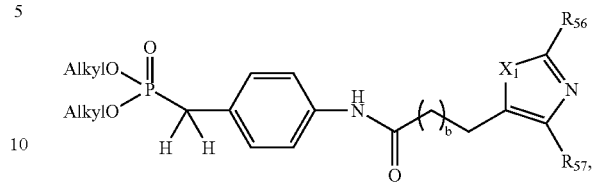

b = 0-1
X1 = O, S
R56 = H, CF3, Cl, imidazolyl, amino, morpholino, phenylthio, cycloalkyl, benzyl, phenyl, phenoxy, thienyl, substituted alkyl, pyridylthio, pyrimidyl, benzylamino, N-benimidazolyl, pyridylcarbonylamino, ureido, N-thiourea, substituted alkanoylamino, phenylsulfonyl, substituted benzoyl, phenylalkenoyl, furanoyl, thienoyl, pyridinoyl,
R57 = substituted phenyl, substituted biphenyl

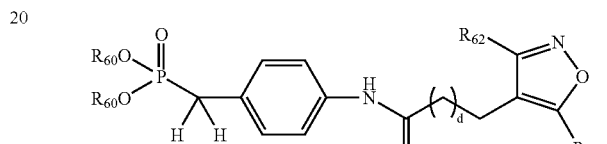

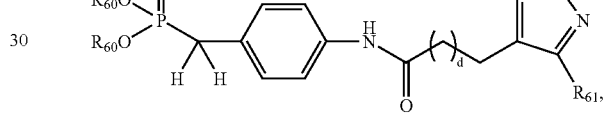

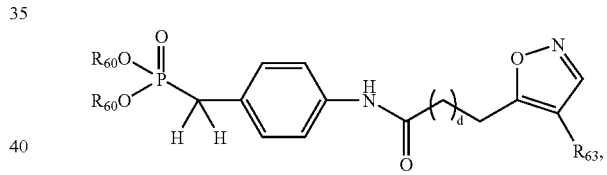

R58 = substituted alkylaminocarbonyl, phenylaminocarbonyl
R59 = H, Cl

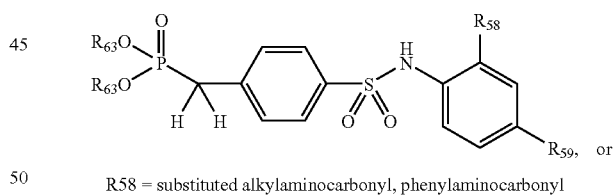

d = 0-2
R60 = H, alkyl
R61 = substituted phenyl, thienyl, Br
R62 = H, alkyl, phenyl
R63 = substituted phenyl when Q is Q-35 as shown

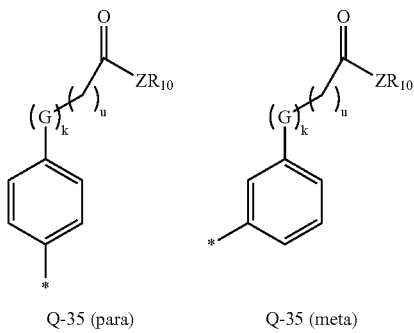
Q-35 (para)   Q-35 (meta)
wherein G is selected from the group consisting of —O—, —S—, —NR$_4$—, and —CH$_2$—, k is 0 or 1, and u is 1, 2, 3, or 4, then
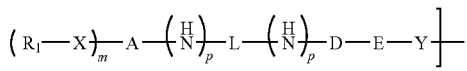
is selected from the group-consisting of
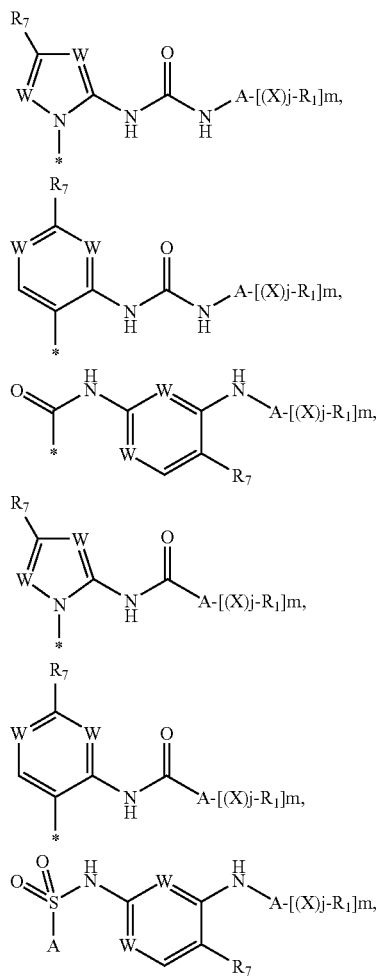
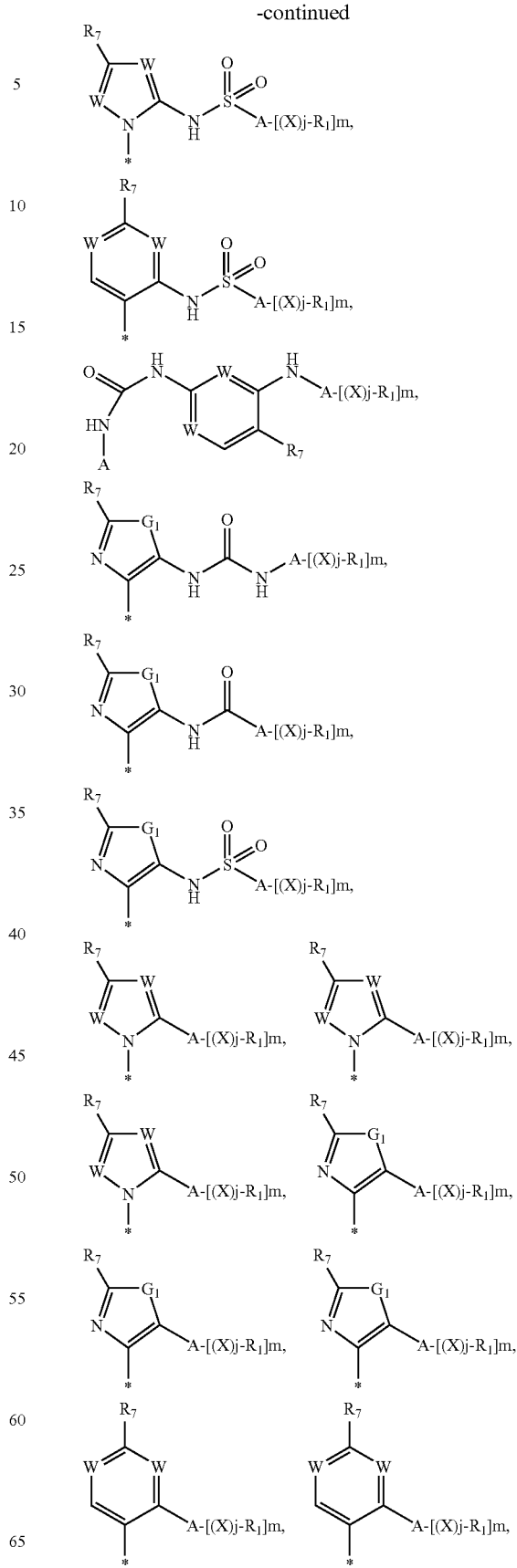

-continued
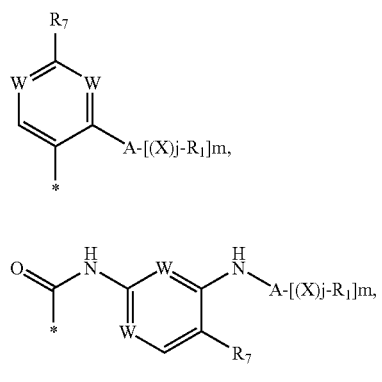
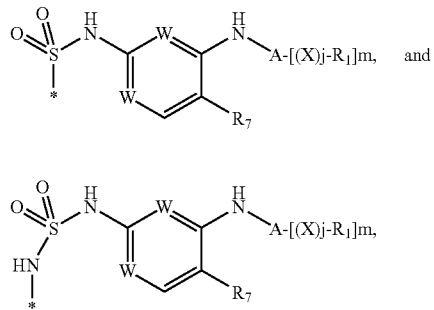
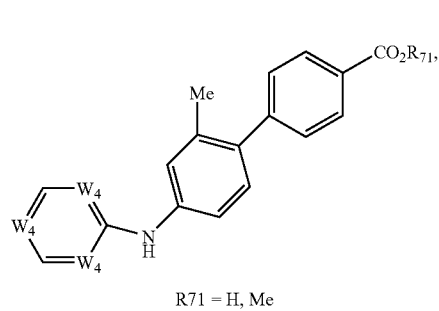
except that the compound of formula (I) is not
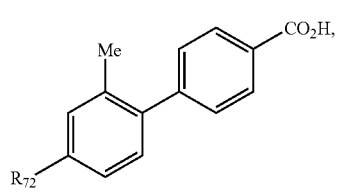
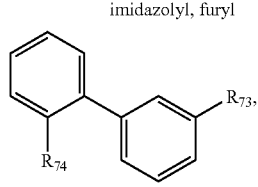
28.1 R73 = —OCH2CO2H
R74 = oxazolyl, imidazolyl
28.2 R73 = CO2Me
R74 = chlorophenyl
-continued
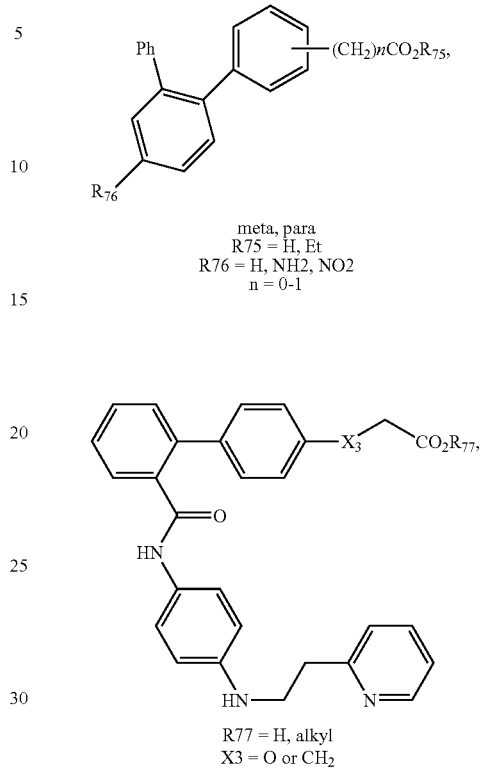
meta, para
R75 = H, Et
R76 = H, NH2, NO2
n = 0-1
R77 = H, alkyl
X3 = O or CH2
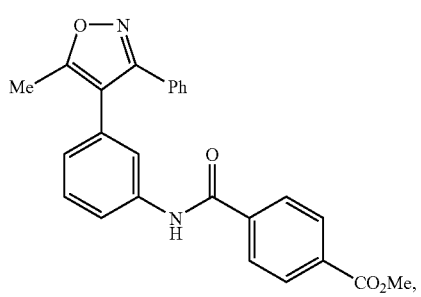
meta, para
R78 = H, alkyl

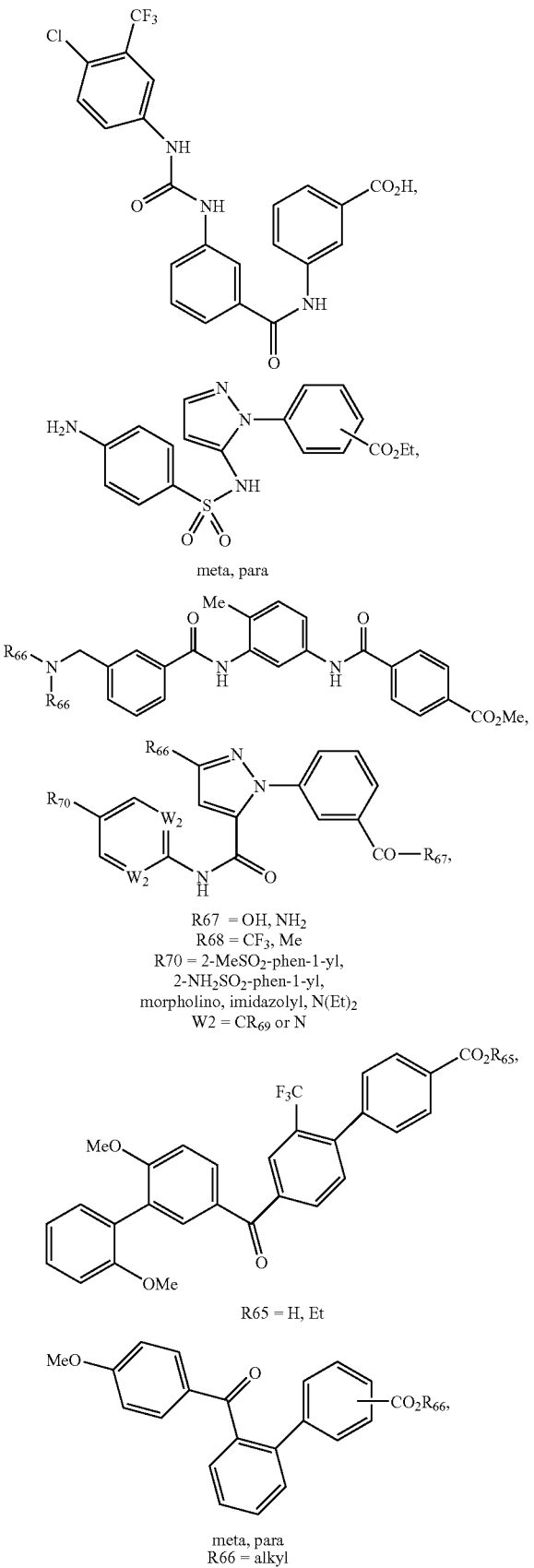
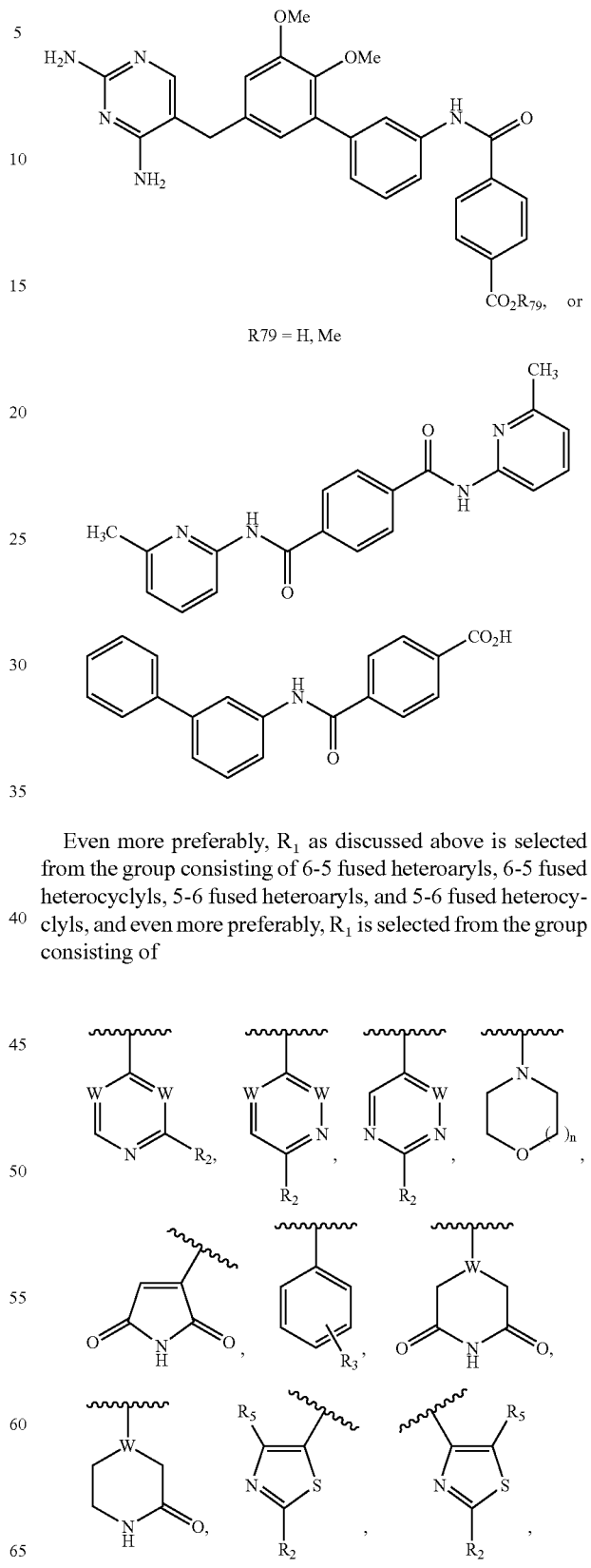
R79 = H, Me
Even more preferably, $R_1$ as discussed above is selected from the group consisting of 6-5 fused heteroaryls, 6-5 fused heterocyclyls, 5-6 fused heteroaryls, and 5-6 fused heterocyclyls, and even more preferably, $R_1$ is selected from the group consisting of -continued

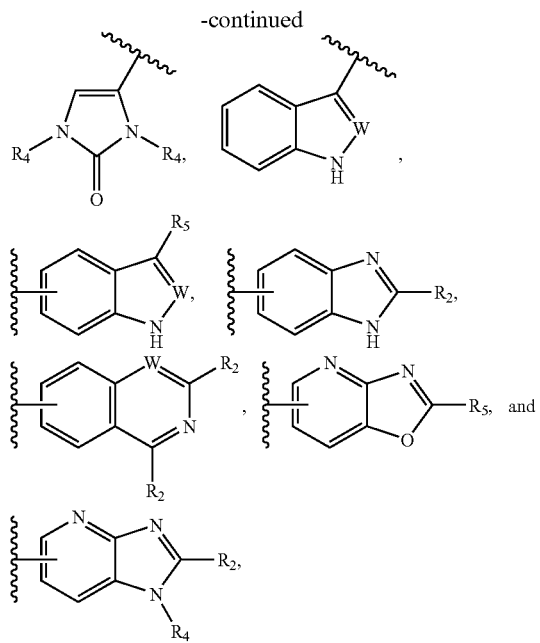

each R$_2$ is individually selected from the group consisting of —H, alkyls (preferably C$_1$-C$_{18}$, and more preferably C$_1$-C$_{12}$), aminos, alkylaminos (preferably C$_1$-C$_{18}$, and more preferably C$_1$-C$_{12}$), arylaminos (preferably C$_6$-C$_{18}$, and more preferably C$_6$-C$_{12}$), cycloalkylaminos (preferably C$_1$-C$_{18}$, and more preferably C$_1$-C$_{12}$), heterocyclylaminos, halogens, alkoxys (preferably C$_1$-C$_{18}$, and more preferably C$_1$-C$_{12}$), and hydroxys; and each R$_3$ is individually selected from the group consisting of —H, alkyls (preferably C$_1$-C$_{18}$, and more preferably C$_1$-C$_{12}$), alkylaminos (preferably C$_1$-C$_{18}$, and more preferably C$_1$-C$_{12}$), arylaminos (preferably C$_6$-C$_{18}$, and more preferably C$_6$-C$_{12}$), cycloalkylaminos (preferably C$_1$-C$_{18}$, and more preferably C$_1$-C$_{12}$), heterocyclylaminos, alkoxys (preferably C$_1$-C$_{18}$, and more preferably C$_1$-C$_{12}$), hydroxys, cyanos, halogens, perfluoroalkyls (preferably C$_1$-C$_{18}$, and more preferably C$_1$-C$_{12}$), alkylsulfinyls (preferably C$_1$-C$_{18}$, and more preferably C$_1$-C$_{12}$), alkylsulfonyls (preferably C$_1$-C$_{18}$, and more preferably C$_1$-C$_{12}$), R$_4$NHSO$_2$—, and —NHSO$_2$R$_4$.

Finally, in another preferred embodiment, wherein A is selected from the group consisting of aromatic, monocycloheterocyclic, and bicycloheterocyclic rings; and most preferably phenyl, naphthyl, pyridyl, pyrimidyl, thienyl, furyl, pyrrolyl, thiazolyl, isothiazolyl, oxaxolyl, isoxazolyl, imidazolyl, oxadiazolyl, thiadiazolyl, indolyl, indazolyl, benzimidazolyl, benzotriazolyl, isoquinolyl, quinolyl, benzothiazolyl, benzofuranyl, benzothienyl, pyrazolylpyrimidinyl, imidazopyrimidinyl, purinyl, and

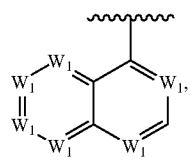

where each W$_1$ is individually selected from the group consisting of —CH— and —N—.

An additional class of compounds useful in the invention have the formula $$A\text{-}T\text{-}(L)_n\text{-}(NH)_p\text{-}D\text{-}(E)_q\text{-}(Y)_t\text{-}Q \quad (IB)$$

wherein:

Y is selected from the group consisting of —O—, —S—, —NR$_6$—, —NR$_6$SO$_2$—, —NR$_6$CO—, alkynyls (preferably C$_1$-C$_{18}$, and more preferably C$_1$-C$_{12}$), alkenyls (preferably C$_1$-C$_{18}$, and more preferably C$_1$-C$_{12}$), alkylenes (preferably C$_1$-C$_{18}$, and more preferably C$_1$-C$_{12}$), —O(CH$_2$)$_h$—, and —NR$_6$(CH$_2$)$_h$—, where each h is individually selected from the group consisting of 1, 2, 3, or 4, and where for each of alkylenes (preferably C$_1$-C$_{18}$, and more preferably C$_1$-C$_{12}$), —O(CH$_2$)$_h$—, and —NR$_6$(CH$_2$)$_h$—, one of the methylene groups present therein may be optionally double-bonded to a side-chain oxo group except that where —O(CH$_2$)$_h$— the introduction of the side-chain oxo group does not form an ester moiety;

A is selected from the group consisting of aromatic (preferably C$_6$-C$_{18}$, and more preferably C$_6$-C$_{12}$), monocycloheterocyclic, and bicycloheterocyclic rings; and most preferably phenyl, naphthyl, pyridyl, pyrimidyl, thienyl, furyl, pyrrolyl, thiazolyl, isothiazolyl, oxaxolyl, isoxazolyl, imidazolyl, oxadiazolyl, thiadiazolyl, indolyl, indazolyl, benzimidazolyl, benzotriazolyl, isoquinolyl, quinolyl, benzothiazolyl, benzofuranyl, benzothienyl, pyrazolylpyrimidinyl, imidazopyrimidinyl, purinyl, and

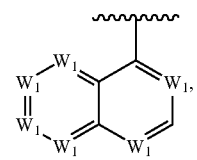

where each W1 is individually selected form the group consisting of —CH— and —N—.

D is phenyl or a five- or six-membered heterocyclic ring selected from the group consisting of pyrazolyl, pyrrolyl, imidazolyl, oxazolyl, thiazolyl, furyl, oxadiazolyl, thiadiazolyl, thienyl, pyridyl, and pyrimidyl;

E is selected from the group consisting of phenyl, pyridinyl, and pyrimidinyl;

L is selected from the group consisting of —C(O)— and —S(O)$_2$—;

T is NR$_6$, O, alkylene (preferably C$_1$-C$_{12}$, more preferably C$_1$-C$_4$), —O(CH$_2$)$_h$—, or —NR$_6$(CH$_2$)$_h$—, where each h is individually selected from the group consisting of 1, 2, 3, or 4, or T is absent wherein A is directly bonded to -(L)$_n$(NH)$_p$-D-(E)$_q$-(Y)$_t$, -Q;

n is 0 or 1;

p is 0 or 1;

q is 0 or 1;

t is 0 or 1;

v is 1, 2, or 3;

x is 1 or 2;

Q is selected from the group consisting of formulae Q$_{36}$-Q$_{59}$, inclusive;

each R$_4$ group is individually selected from the group consisting of —H, alkyls (preferably C$_1$-C$_{18}$, and more preferably C$_1$-C$_{12}$), aminoalkyls (preferably C$_1$-C$_{18}$, and more preferably C$_1$-C$_{12}$), alkoxyalkyls (preferably C$_1$-C$_{18}$, and more preferably C$_1$-C$_{12}$), aryls (preferably C$_6$-C$_{18}$, and more preferably C$_6$-C$_{12}$), aralkyls (preferably $C_6$-$C_{18}$, and more preferably $C_6$-$C_{12}$ and preferably $C_1$-$C_{18}$, and more preferably $C_1$-$C_{12}$), heterocyclyls, and heterocyclylalkyls except when the $R_4$ substituent places a heteroatom on an alpha-carbon directly attached to a ring nitrogen on Q;

when two $R_4$ groups are bonded with the same atom, the two $R_4$ groups optionally form an alicyclic or heterocyclic 4-7 membered ring;

each $R_6$ is individually selected from the group consisting of —H, alkyls (preferably $C_1$-$C_{18}$, and more preferably $C_1$-$C_{12}$), allyls, and B-trimethylsilylethyl;

each $R_8$ is individually selected from the group consisting of alkyls (preferably $C_1$-$C_{18}$, and more preferably $C_1$-$C_{12}$), phenyl, naphthyl, aralkyls (wherein the aryl is preferably $C_6$-$C_{18}$, and more preferably $C_6$-$C_{12}$), wherein alkyl is preferably $C_1$-$C_{18}$, and more preferably $C_1$-$C_{12}$), heterocyclyls, and heterocyclylalkyls (wherein the alkyl is preferably $C_1$-$C_{18}$, and more preferably $C_1$-$C_{12}$);

each $R_9$ group is individually selected from the group consisting of —H, —F, and alkyls (preferably $C_1$-$C_{18}$, and more preferably $C_1$-$C_{12}$), wherein when two $R_9$ groups are geminal alkyl groups, said geminal alkyl groups may be cyclized to form a 3-6 membered ring;

each $R_9$ group is individually selected from the group consisting of —F, and alkyls (preferably $C_1$-$C_{18}$, and more preferably $C_1$-$C_{12}$), wherein when two $R_9$ groups are geminal alkyl groups, said geminal alkyl groups may be cyclized to form a 3-6 membered ring;

each $R_{10}$ is alkyl or perfluoroalkyl;

G is alkylene (preferably $C_1$-$C_8$, and more preferably $C_1$-$C_4$), $N(R_6)$, O;

each Z is individually selected from the group consisting of —O— and —$N(R_4)$—; and each ring of formula (I) optionally includes one or more of $R_{7'}$, where $R_{7'}$ is a substituent individually selected from the group consisting of —H, alkyls (preferably $C_1$-$C_{18}$, and more preferably $C_1$-$C_{12}$), aryls (preferably $C_6$-$C_{18}$, and more preferably $C_6$-$C_{12}$), heterocyclyls, alkylaminos (preferably $C_1$-$C_{18}$, and more preferably $C_1$-$C_{12}$), arylaminos (preferably $C_6$-$C_{18}$, and more preferably $C_6$-$C_{12}$), cycloalkylaminos (preferably $C_1$-$C_{18}$, and more preferably $C_1$-$C_{12}$), heterocyclylaminos, hydroxys, alkoxys (preferably $C_1$-$C_{18}$, and more preferably $C_1$-$C_{12}$), perfluoroalkoxys (preferably $C_1$-$C_8$, more preferably $C_1$-$C_4$), aryloxys (preferably $C_6$-$C_{18}$, and more preferably $C_6$-$C_{12}$), alkylthios (preferably $C_1$-$C_{18}$, and more preferably $C_1$-$C_{12}$), arthylthios, cyanos, halogens, nitrilos, nitros, alkylsulfinyls (preferably $C_1$-$C_{18}$, and more preferably $C_1$-$C_{12}$), alkylsulfonyls (preferably $C_1$-$C_{18}$, and more preferably $C_1$-$C_{12}$), aminosulfonyls, perfluoroalkyls (preferably $C_1$-$C_{18}$, and more preferably $C_1$-$C_{12}$); aminooxaloylamino; alkylaminooxaloylamino; dialkylaminooxaloylamino; morpholinooxaloylamino; piperazinooxaloylamino; alkoxycarbonylamino; heterocyclyloxycarbonylamino; heterocyclylalkyloxycarbonylamino; heterocyclylcarbonylamino; heterocyclylalkylcarbonylamino; aminoalkyloxycarbonylamino; alkylaminoalkyloxycarbonylamino; or dialkylaminoalkyloxycarbonylamino.

In a preferred embodiment, A as described above is selected from the group consisting of phenyl, naphthyl, pyridyl, pyrimidyl, thienyl, furyl, pyrrolyl, pyrazolyl, thiazolyl, thiadiazolyl, oxazolyl, oxadiazolyl, imidazolyl, indolyl, indazolyl, benzimidazolyl, benzotriazolyl, isoquinolyl, quinolyl, benzothiazolyl, benzofuranyl, benzothienyl, pyrazolylpyrimidinyl, imidazopyrimidinyl, purinyl, and where each $W_1$ is individually selected from the group consisting of —CH— and —N—.

Q groups Q-36 through Q-59 are set forth below. In an additionally preferred embodiment, Q is taken from Q-37, Q-39, Q-41, Q-42, Q-43, Q-44, Q-47, Q-48, Q-54, and Q-57; in a more preferred embodiment, Q is taken from Q-39, Q-41, Q-42, Q-43, Q-44, Q-47, Q-48, and Q-54.

Q-36

Q-37

Q-38

Q-39

Q-40

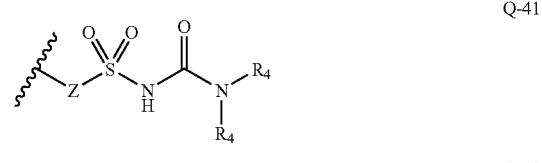

Q-41

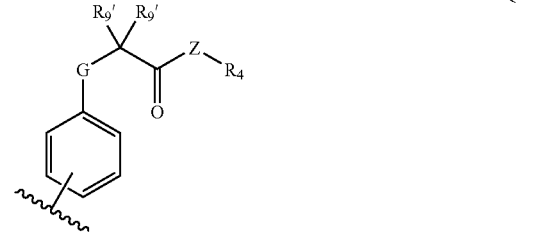

Q-42

Q-43 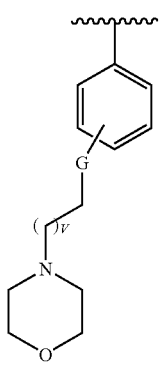
Q-44 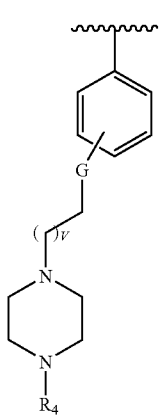
Q-45 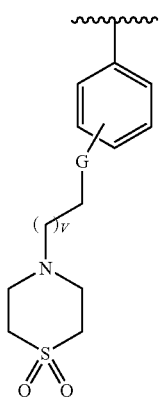
Q-46 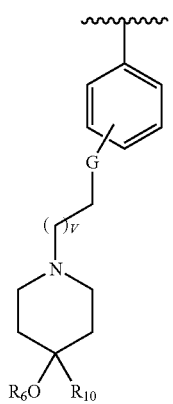
Q-47 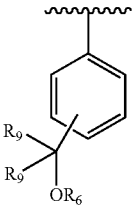
Q-48 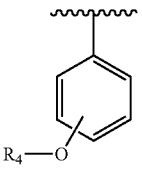
Q-49 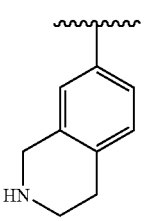
Q-50 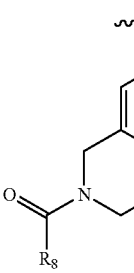
Q-51 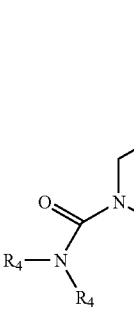
Q-52 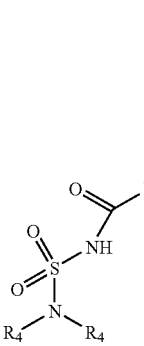

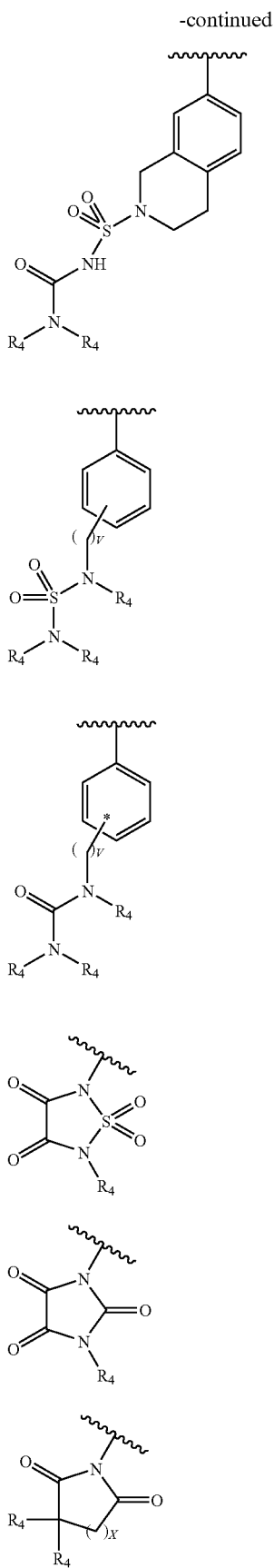

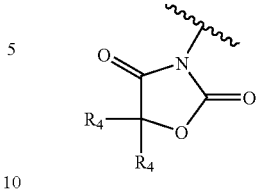

With respect to the method of using the novel compounds, the activation state of a kinase is determined by the interaction of switch control ligands and complemental switch control pockets. One conformation of the kinase may result from the switch control ligand's interaction with a particular switch control pocket while another conformation may result from the ligand's interaction with a different switch control pocket. Generally interaction of the ligand with one pocket, such as the "on" pocket, results in the kinase assuming an active conformation wherein the kinase is biologically active. Similarly, an inactive conformation (wherein the kinase is not biologically active) is assumed when the ligand interacts with another of the switch control pockets, such as the "off" pocket. The switch control pocket can be selected from the group consisting of simple, composite and combined switch control pockets. Interaction between the switch control ligand and the switch control pockets is dynamic and therefore, the ligand is not always interacting with a switch control pocket. In some instances, the ligand is not in a switch control pocket (such as occurs when the protein is changing from an active conformation to an inactive conformation). In other instances, such as when the ligand is interacting with the environment surrounding the protein in order to determine with which switch control pocket to interact, the ligand is not in a switch control pocket. Interaction of the ligand with particular switch control pockets is controlled in part by the charge status of the amino acid residues of the switch control ligand. When the ligand is in a neutral charge state, it interacts with one of the switch control pockets and when it is in a charged state, it interacts with the other of the switch control pockets. For example, the switch control ligand may have a plurality of OH groups and be in a neutral charge state. This neutral charge state results in a ligand that is more likely to interact with one of the switch control pockets through hydrogen boding between the OH groups and selected residues of the pocket, thereby resulting in whichever protein conformation results from that interaction. However, if the OH groups of the switch control ligand become charged through phosphorylation or some other means, the propensity of the ligand to interact with the other of the switch control pockets will increase and the ligand will interact with this other switch control pocket through complementary covalent binding between the negatively or positively charged residues of the pocket and ligand. This will result in the protein assuming the opposite conformation assumed when the ligand was in a neutral charge state and interacting with the other switch control pocket.

Of course, the conformation of the protein determines the activation state of the protein and can therefore play a role in protein-related diseases, processes, and conditions. For example, if a metabolic process requires a biologically active protein but the protein's switch control ligand remains in the switch control pocket (i.e. the "off" pocket) that results in a biologically inactive protein, that metabolic process cannot occur at a normal rate. Similarly, if a disease is exacerbated by a biologically active protein and the protein's switch control ligand remains in the switch control pocket (i.e. the "on" pocket) that results in the biologically active protein conformation, the disease condition will be worsened. Accordingly, as demonstrated by the present invention, selective modulation of the switch control pocket and switch control ligand by the selective administration of a molecule will play an important role in the treatment and control of protein-related diseases, processes, and conditions.

One aspect of the invention provides a method of modulating the activation state of a kinase, preferably p38 α-kinase and including both the consensus wild type sequence and disease polymorphs thereof. The activation state is generally selected from an upregulated or downregulated state. The method generally comprises the step of contacting the kinase with a molecule having the general formula (I). When such contact occurs, the molecule will bind to a particular switch control pocket and the switch control ligand will have a greater propensity to interact with the other of the switch control pockets (i.e., the unoccupied one) and a lesser propensity to interact with the occupied switch control pocket. As a result, the protein will have a greater propensity to assume either an active or inactive conformation (and consequently be upregulated or downregulated), depending upon which of the switch control pockets is occupied by the molecule. Thus, contacting the kinase with a molecule modulates that protein's activation state. The molecule can act as an antagonist or an agonist of either switch control pocket. The contact between the molecule and the kinase preferably occurs at a region of a switch control pocket of the kinase and more preferably in an interlobe oxyanion pocket of the kinase. In some instances, the contact between the molecule and the pocket also results in the alteration of the conformation of other adjacent sites and pockets, such as an ATP active site. Such an alteration can also effect regulation and modulation of the active state of the protein. Preferably, the region of the switch control pocket of the kinase comprises an amino acid residue sequence operable for binding to the Formula I molecule. Such binding can occur between the molecule and a specific region of the switch control pocket with preferred regions including the α-C helix, the α-D helix, the catalytic loop, the activation loop, and the C-terminal residues or C-lobe residues (all residues located downstream (toward the C-end) from the Activation loop), the glycine rich loop, and combinations thereof. When the binding region is the α-C helix, one preferred binding sequence in this helix is the sequence IIHXKRXXREXXLLXXM, (SEQ ID NO. 2). When the binding region is the catalytic loop, one preferred binding sequence in this loop is DIIHRD (SEQ ID NO. 3). When the binding region is the activation loop, one preferred binding sequence in this loop is a sequence selected from the group consisting of DFGLARHTDD (SEQ ID NO.4), EMTGYVATRWYR (SEQ ID NO. 5), and combinations thereof. When the binding region is in the C-lobe residues, one preferred binding sequence is WMHY (SEQ ID NO. 6). When the binding region is in the glycine rich loop one preferred binding sequence is YGSV (SEQ ID NO. 7). When a biologically inactive protein conformation is desired, molecules which interact with the switch control pocket that normally results in a biologically active protein conformation (when interacting with the switch control ligand) will be selected. Similarly, when a biologically active protein conformation is desired, molecules which interact with the switch control pocket that normally results in a biologically inactive protein conformation (when interacting with the switch control ligand) will be selected. Thus, the propensity of the protein to assume a desired conformation will be modulated by administration of the molecule. In preferred forms, the molecule will be administered to an individual undergoing treatment for a condition selected from the group consisting of human inflammation, rheumatoid arthritis, rheumatoid spondylitis, ostero-arthritis, asthma, gouty arthritis, sepsis, septic shock, endotoxic shock, Gram-negative sepsis, toxic shock syndrome, adult respiratory distress syndrome, stroke, reperfusion injury, neural trauma, neural ischemia, psoriasis, restenosis, chronic pulmonary inflammatory disease, bone resorptive diseases, graft-versus-host reaction, Chron's disease, ulcerative colitis, inflammatory bowel disease, pyresis, and combinations thereof. In such forms, it will be desired to select molecules that interact with the switch control pocket that generally leads to a biologically active protein conformation so that the protein will have the propensity to assume the biologically inactive form and thereby alleviate the condition. It is contemplated that the molecules of the present invention will be administrable in any conventional form including oral, parenteral, inhalation, and subcutaneous. It is preferred for the administration to be in the oral form. Preferred molecules include the preferred compounds of formula (I), as discussed above.

Another aspect of the present invention provides a method of treating an inflammatory condition of an individual comprising the step of administering a molecule having the general formula (I) to the individual. Such conditions are often the result of an overproduction of the biologically active form of a protein, including kinases. The administering step generally includes the step of causing said molecule to contact a kinase involved with the inflammatory process, preferably p38 α-kinase. When the contact is between the molecule and a kinase, the contact preferably occurs in an interlobe oxyanion pocket of the kinase that includes an amino acid residue sequence operable for binding to the Formula I molecule. Preferred binding regions of the interlobe oxyanion pocket include the α-C helix region, the α-D helix region, the catalytic loop, the activation loop, the C-terminal residues, the glycine rich loop residues, and combinations thereof. When the binding region is the α-C helix, one preferred binding sequence in this helix is the sequence IIHXKRXXREXXLLXXM, (SEQ ID NO. 2). When the binding region is the catalytic loop, one preferred binding sequence in this loop is DIIHRD (SEQ ID NO. 3). When the binding region is the activation loop, one preferred binding sequence in this loop is a sequence selected from the group consisting of DFGLARHTDD (SEQ ID NO.4), EMTGYVATRWYR (SEQ ID NO. 5), and combinations thereof. Such a method permits treatment of the condition by virtue of the modulation of the activation state of a kinase by contacting the kinase with a molecule that associates with the switch control pocket that normally leads to a biologically active form of the kinase when interacting with the switch control ligand. Because the ligand cannot easily interact with the switch control pocket associated with or occupied by the molecule, the ligand tends to interact with the switch control pocket leading to the biologically inactive form of the protein, with the attendant result of a decrease in the amount of biologically active protein. Preferably, the inflammatory condition is selected from the group consisting of human inflammation, rheumatoid arthritis, rheumatoid spondylitis, ostero-arthritis, asthma, gouty arthritis, sepsis, septic shock, endotoxic shock, Gram-negative sepsis, toxic shock syndrome, adult respiratory distress syndrome, stroke, reperfusion injury, neural trauma, neural ischemia, psoriasis, restenosis, chronic pulmonary inflammatory disease, bone resorptive diseases, graft-versus-host reaction, Chron's disease, ulcerative colitis, inflammatory bowel disease, pyresis, and combinations thereof. As with the other methods of the invention, the molecules may be administered in any conventional form, with any convention excipients or ingredients. However, it is preferred to administer the molecule in an oral dosage form. Preferred molecules are again selected from the group consisting of the preferred formula (I) compounds discussed above.

BRIEF DESCRIPTION OF THE DRAWINGS

FIG. 4a is an enlarged schematic view illustrating a representative binding between the phosphorylated residues of the switch control ligand 106, and complementary residues Z+ from the on switch control pocket 102;

DETAILED DESCRIPTION OF THE PREFERRED EMBODIMENTS

Figure 1:
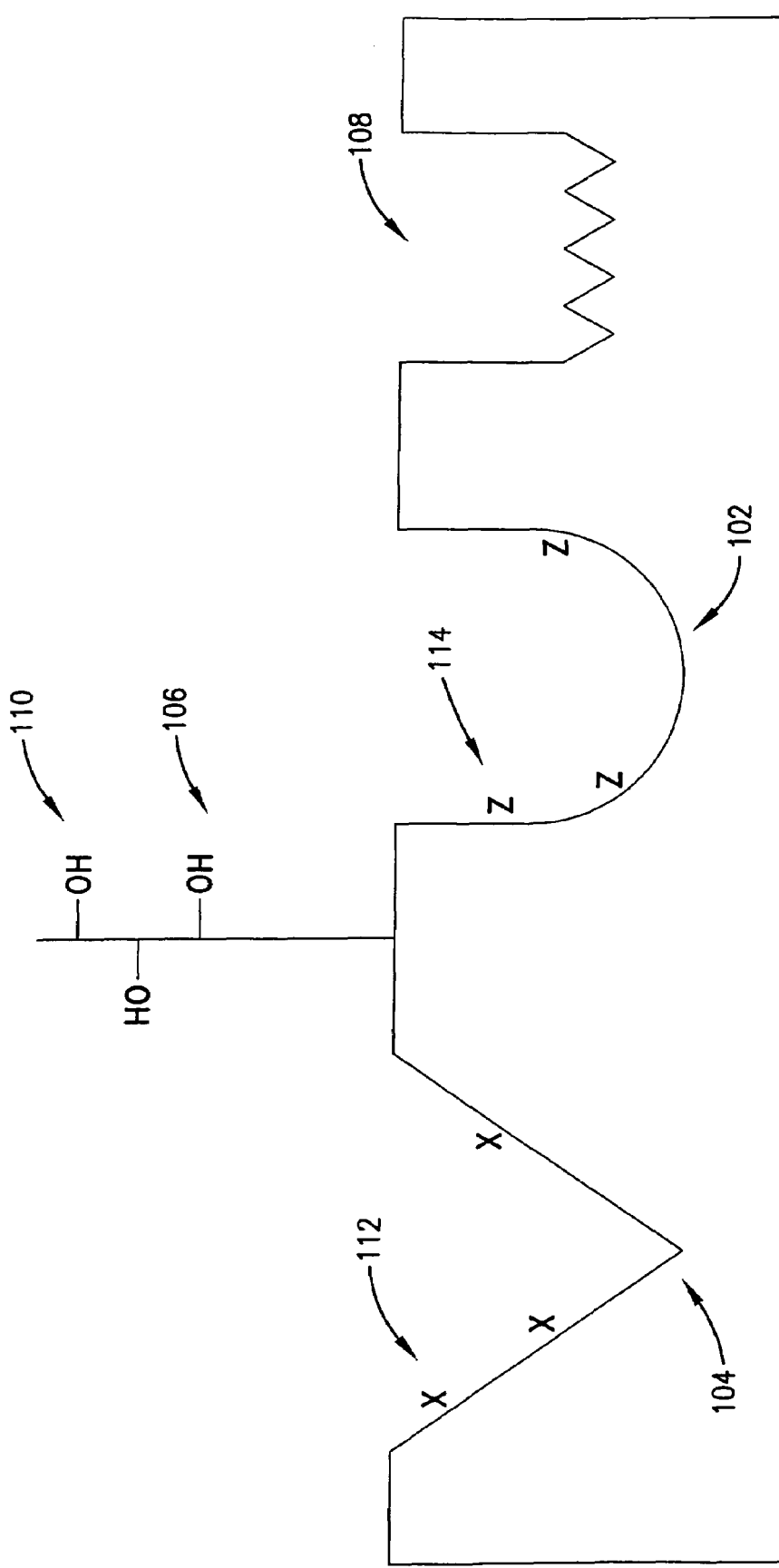
FIG. 1 is a schematic representation of a naturally occurring mammalian protein in accordance with the invention including "on" and "off" switch control pockets 102 and 104, respectively, a transiently modifiable switch control ligand 106, and an active ATP site 108.

The present invention provides a way of rationally developing new small molecule modulators which interact with naturally occurring proteins (e.g., mammalian, and especially human proteins) in order to modulate the activity of the proteins. Novel protein-small molecule adducts are also provided. The invention preferably makes use of naturally occurring proteins having a conformational property whereby the proteins change their conformations in vivo with a corresponding change in protein activity. For example, a given enzyme protein in one conformation may be biologically upregulated, while in another conformation, the same protein may be biologically downregulated. The invention preferably makes use of one mechanism of conformation change utilized by naturally occurring proteins, through the interaction of what are termed "switch control ligands" and "switch control pockets" within the protein.

As used herein, "switch control ligand" means a region or domain within a naturally occurring protein and having one or more amino acid residues therein which are transiently modified in vivo between individual states by biochemical modification, typically phosphorylation, sulfation, acylation or oxidation. Similarly, "switch control pocket" means a plurality of contiguous or non-contiguous amino acid residues within a naturally occurring protein and comprising residues capable of binding in vivo with transiently modified residues of a switch control ligand in one of the individual states thereof in order to induce or restrict the conformation of the protein and thereby modulate the biological activity of the protein, and/or which is capable of binding with a non-naturally occurring switch control modulator molecule to induce or restrict a protein conformation and thereby modulate the biological activity of the protein.

A protein-modulator adduct in accordance with the invention comprises a naturally occurring protein having a switch control pocket with a non-naturally occurring molecule bound to the protein at the region of said switch control pocket, said molecule serving to at least partially regulate the biological activity of said protein by inducing or restricting the conformation of the protein. Preferably, the protein also has a corresponding switch control ligand, the ligand interacting in vivo with the pocket to regulate the conformation and biological activity of the protein such that the protein will assume a first conformation and a first biological activity upon the ligand-pocket interaction, and will assume a second, different conformation and biological activity in the absence of the ligand-pocket interaction.

The nature of the switch control ligand/switch control pocket interaction may be understood from a consideration of schematic FIGS. 1-4. Specifically, in FIG. 1, a protein 100 is illustrated in schematic form to include an "on" switch control pocket 102, and "off" switch control pocket 104, and a switch control ligand 106. In addition, the schematically depicted protein also includes an ATP active site 108. In the exemplary protein of FIG. 1, the ligand 106 has three amino acid residues with side chain OH groups 110. The off pocket 104 contains corresponding X residues 112 and the on pocket 102 has Z residues 114. In the exemplary instance, the protein 100 will change its conformation depending upon the charge status of the OH groups 110 on ligand 106, i.e., when the OH groups are unmodified, a neutral charge is presented, but when these groups are phosphorylated a negative charge is presented.

Figure 2:
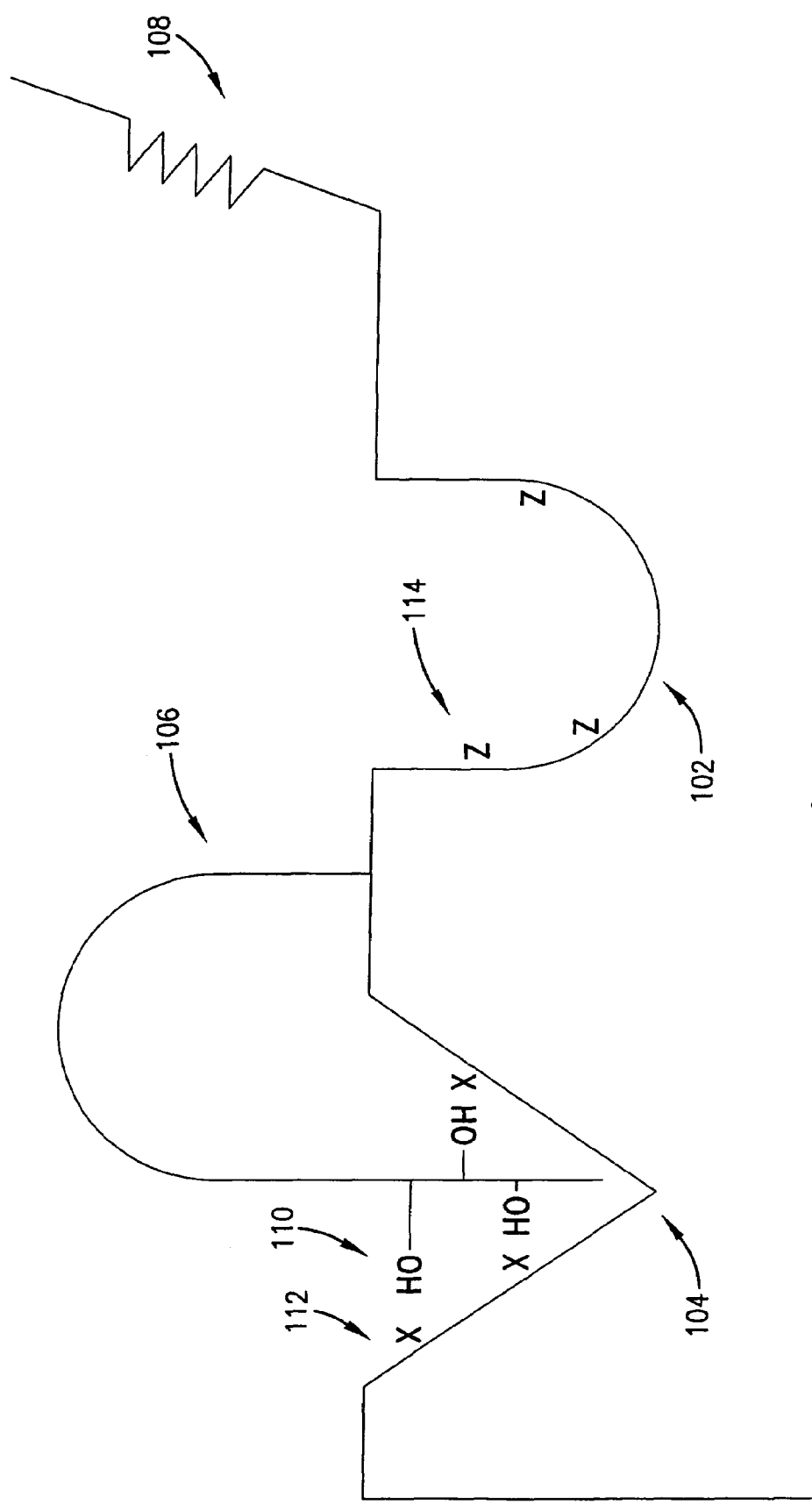
FIG. 2 is a schematic representation of the protein of FIG. 1, wherein the switch control ligand 106 is illustrated in a binding relationship with the off switch control pocket 104, thereby causing the protein to assume a first biologically downregulated conformation.
Figure 3:
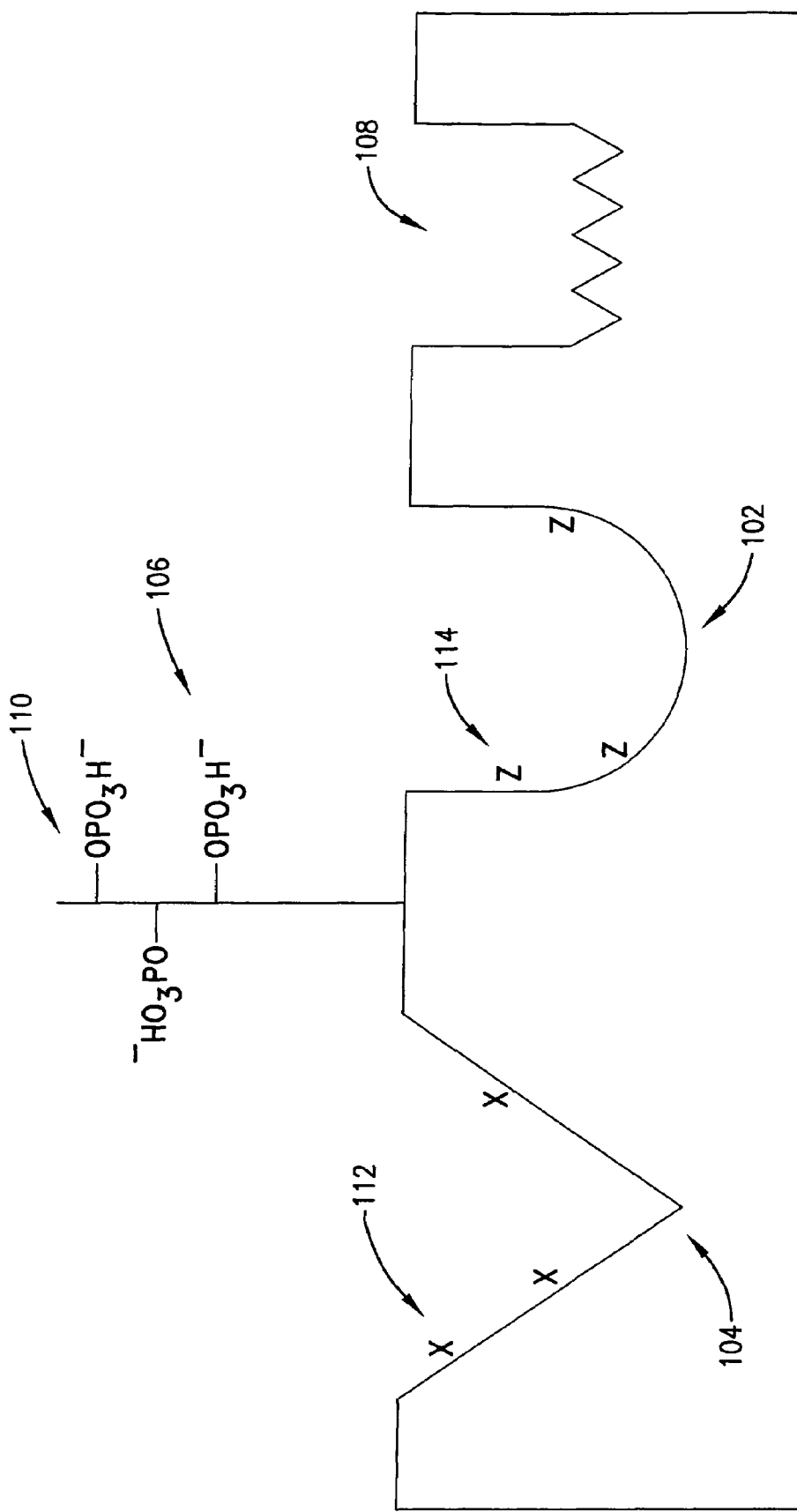
FIG. 3 is a view similar to that of FIG. 1, but illustrating the switch control ligand 106 in its charged-modified condition wherein the OH groups 110 of certain amino acid residues have been phosphorylated.
Figure 4:
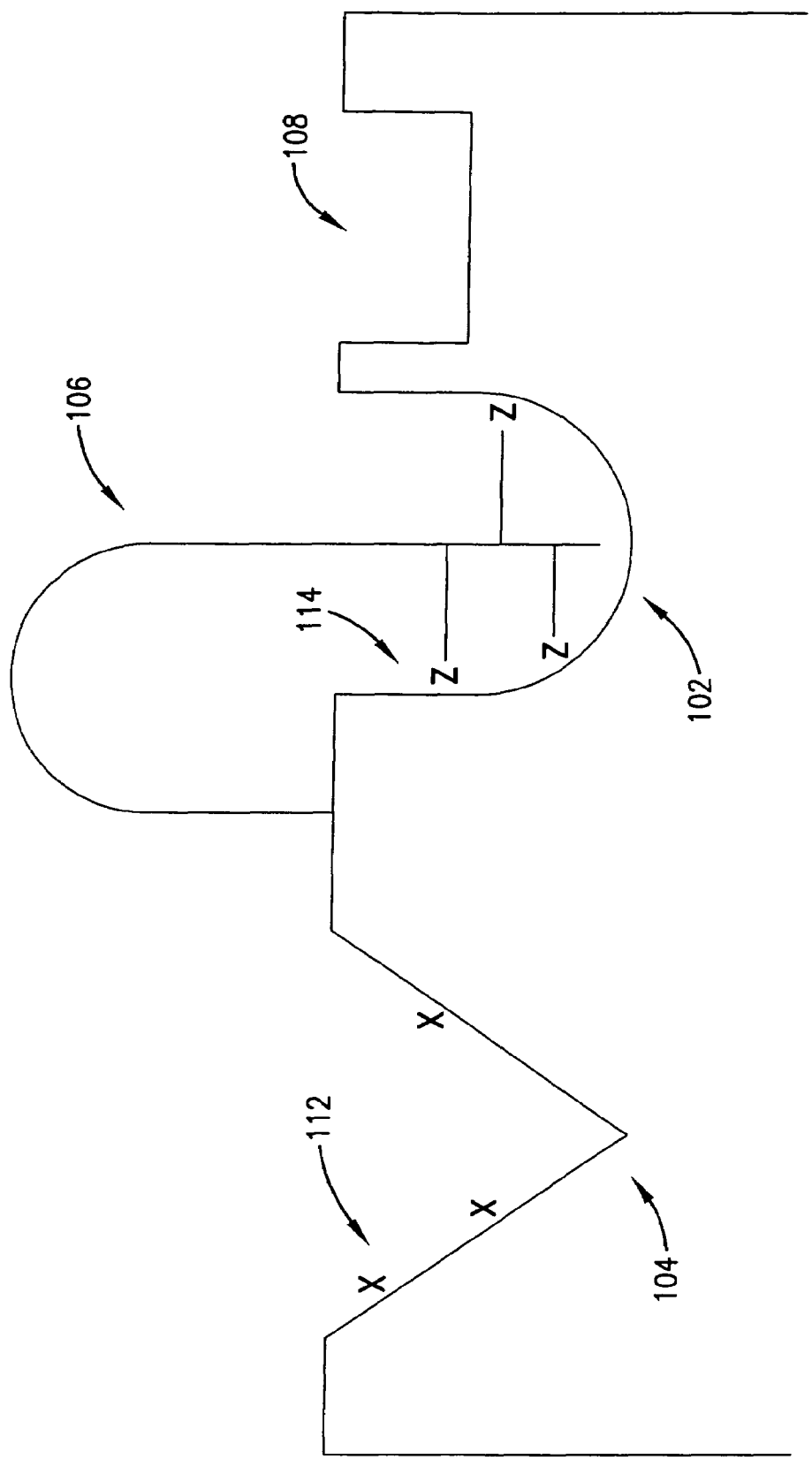
FIG. 4 is a view similar to that of FIG. 2, but depicting the protein wherein the phosphorylated switch control ligand 106 is in a binding relationship with the on switch control pocket 102, thereby causing the protein to assume a second biologically-active conformation different than the first conformation of FIG. 2.
Figure 5:
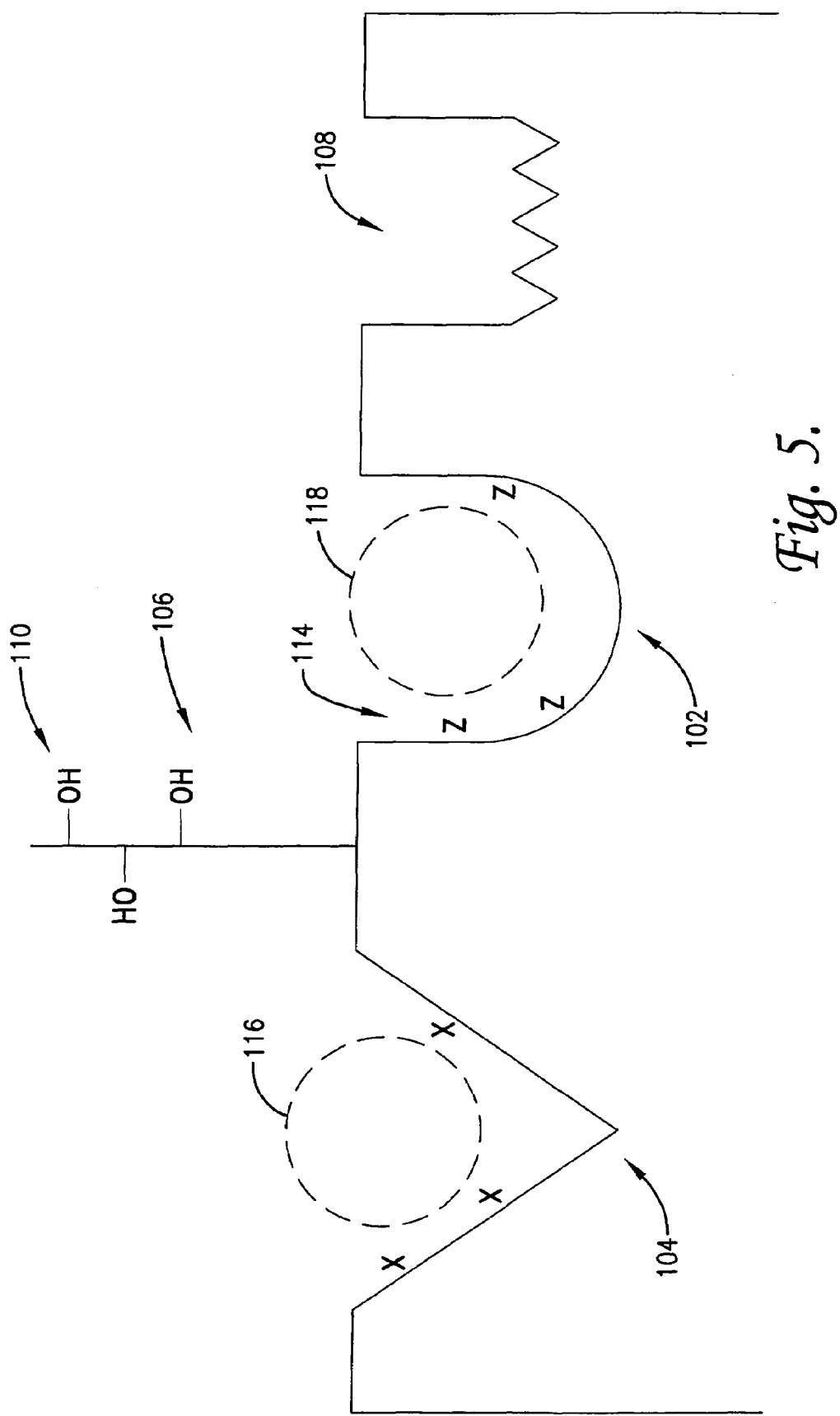
FIG. 5 is a view similar to that of FIG. 1, but illustrating in schematic form possible small molecule compounds 116 and 118 in a binding relationship with the off and on switch control pockets 104 and 102, respectively.

The functionality of the pockets 102, 104 and ligand 106 can be understood from a consideration of FIGS. 2-4. In FIG. 2, the ligand 106 is shown operatively interacted with the off pocket 104 such that the OH groups 110 interact with the X residues 112 forming a part of the pocket 104. Such interaction is primarily by virtue of hydrogen bonding between the OH groups 110 and the residues 112. As seen, this ligand/pocket interaction causes the protein 100 to assume a conformation different from that seen in FIG. 1 and corresponding to the off or biologically downregulated conformation of the protein.

FIG. 3 illustrates the situation where the ligand 106 has shifted from the off pocket interaction conformation of FIG. 2 and the OH groups 110 have been phosphorylated, giving a negative charge to the ligand. In this condition, the ligand has a strong propensity to interact with on pocket 102, to thereby change the protein conformation to the on or biologically upregulated state (FIG. 4). FIG. 4a illustrates that the phosphorylated groups on the ligand 106 are attracted to positively charged residues 114 to achieve an ionic-like stabilizing bond. Note that in the on conformation of FIG. 4, the protein conformation is different than the off conformation of FIG. 2, and that the ATP active site is available and the protein is functional as a kinase enzyme.

Figure 6:
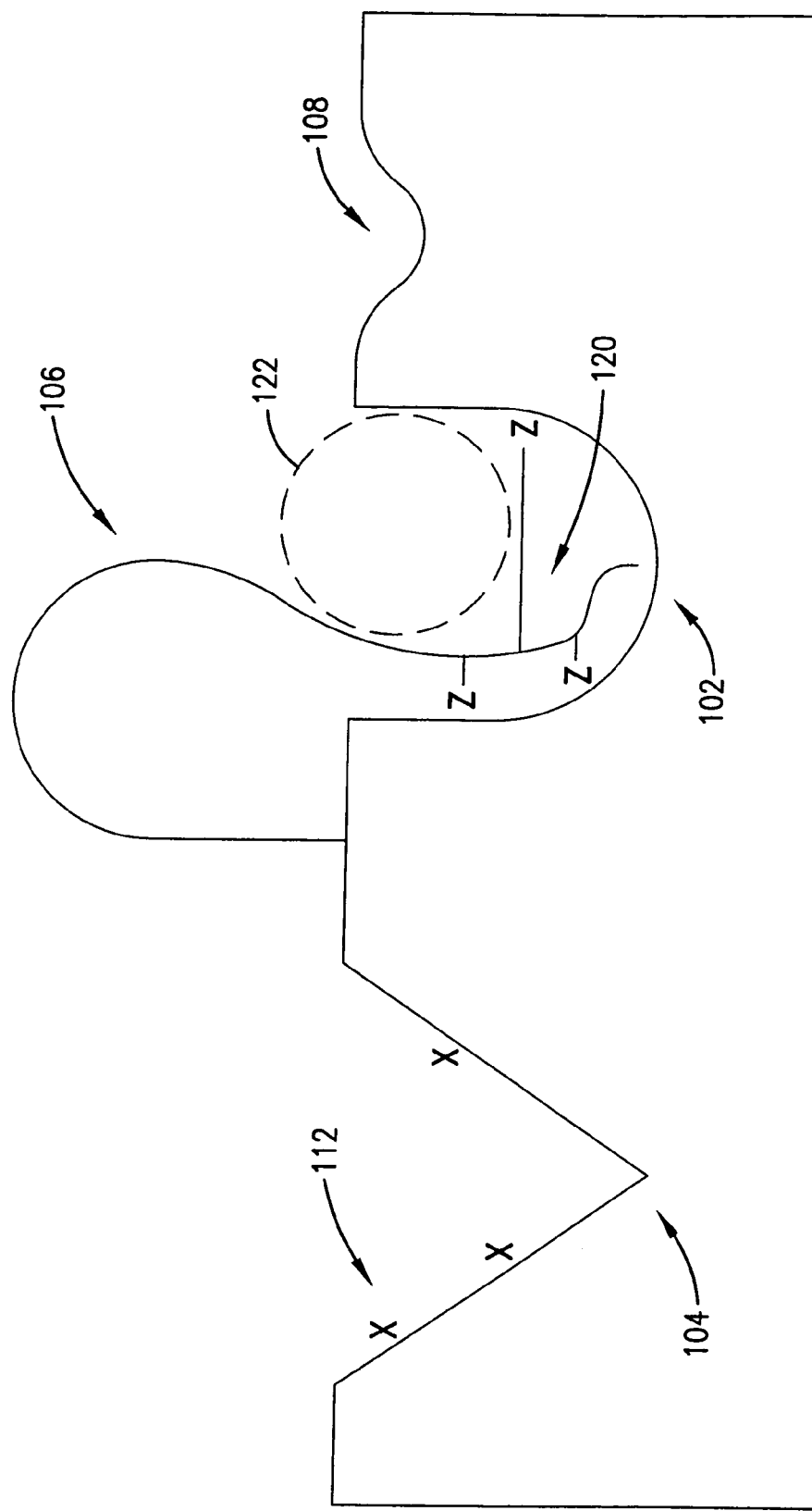
FIG. 6 is a schematic view of the protein in a situation where a composite switch control pocket 120 is formed with portions of the switch control ligand 106 and the on switch control pocket 102, and with a small molecule 122 in binding relationship with the composite pocket.

FIGS. 1-4 illustrate a simple situation where the protein exhibits discrete pockets 102 and 104 and ligand 106. However, in many cases a more complex switch control pocket pattern is observed. FIG. 6 illustrates a situation where an appropriate pocket for small molecule interaction is formed from amino acid residues taken both from ligand 106 and, for example, from pocket 102. This is termed a "composite switch control pocket" made up of residues from both the ligand 106 and a pocket, and is referred to by the numeral 120. A small molecule 122 is illustrated which interacts with the pocket 120 for protein modulation purposes.

Figure 7:
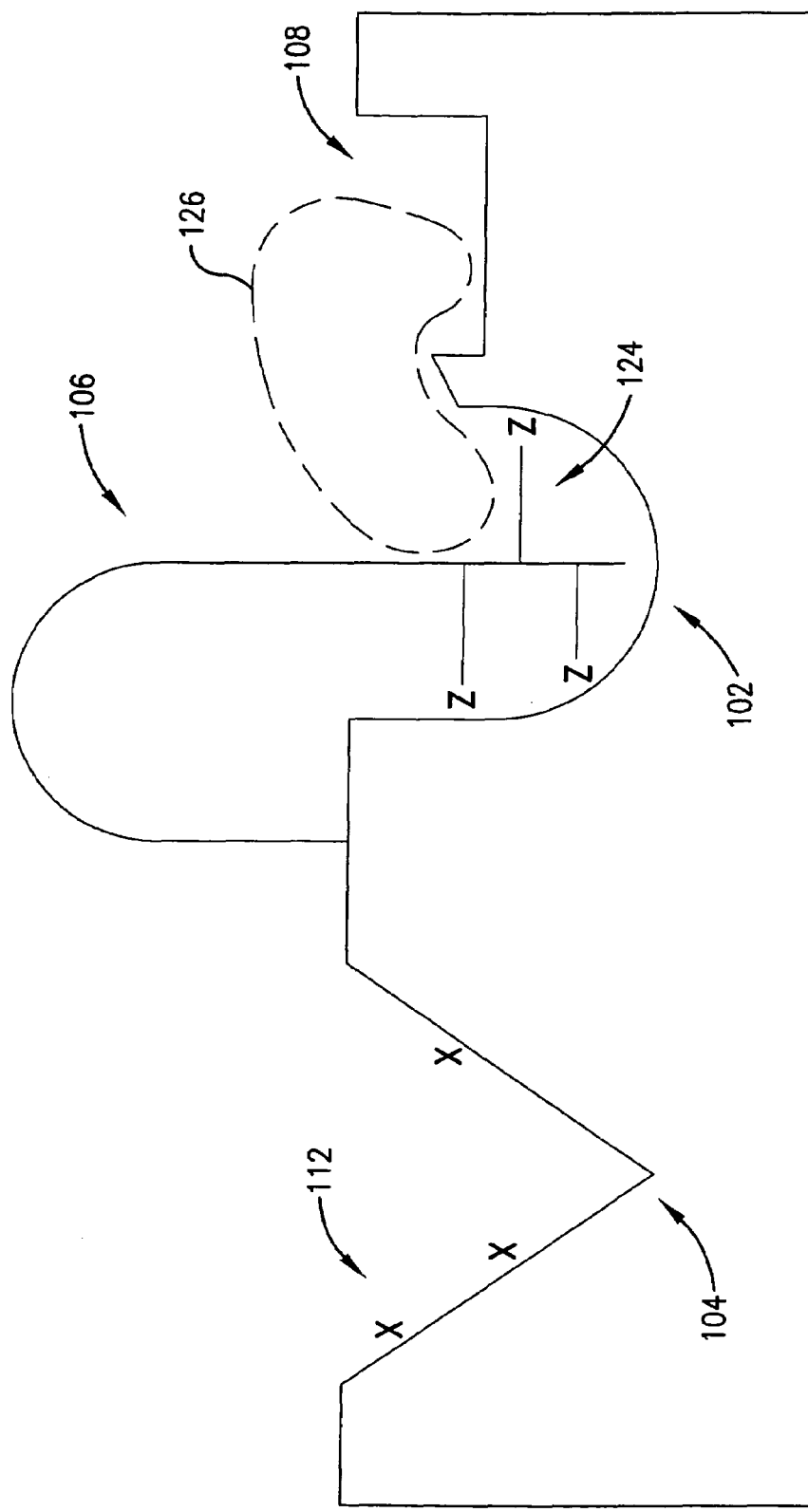
FIG. 7 is a schematic view of the protein in a situation where a combined switch control pocket 124 is formed with portions of the on switch control pocket 102, the switch control ligand sequence 106, and the active ATP site 108, and with a small molecule 126 in binding relationship with the combined switch control pocket.

Another more complex switch pocket is depicted in FIG. 7 wherein the pocket includes residues from on pocket 102, and ATP site 108 to create what is termed a "combined switch control pocket." Such a combined pocket is referred to as numeral 124 and may also include residues from ligand 106. An appropriate small molecule 126 is illustrated with pocket 124 for protein modulation purposes.

It will thus be appreciated that while in the simple pocket situation of FIGS. 1-4, the small molecule will interact with the simple pocket 102 or 104, in the more complex situations of FIGS. 6 and 7 the interactive pockets are in the regions of the pockets 120 or 124. Thus, broadly the small molecules interact "at the region" of the respective switch control pocket.

Materials and Methods

General Synthesis of Compounds

In the synthetic schemes of this section, q is 0 or 1. When q=0, the substituent is replaced by a synthetically non-interfering group $R_7$.

Compounds of Formula I wherein Q is taken from Q-1 or Q-2 and Y is alkylene are prepared according to the synthetic route shown in Scheme 1.1. Reaction of isothiocyanate 1 with chlorine, followed by addition of isocyanate 2 affords 3-oxo-thiadiazolium salt 3. Quenching of the reaction with air affords compounds of Formula I-4. Alternatively, reaction of isothiocyanate 1 with isothiocyanate 5 under the reaction conditions gives rise to compounds of Formula I-7. See A. Martinez et al, *Journal of Medicinal Chemistry* (2002) 45:1292.

Intermediates 1, 2 and 5 are commercially available or prepared according to Scheme 1.2. Reaction of amine 8 with phosgene or a phosgene equivalent affords isocyanate 2. Similarly, reaction of amine 8 with thiophosgene affords isothiocyanate 5. Amine 8 is prepared by palladium(0)-catalyzed amination of 9, wherein M is a group capable of oxidative insertion into palladium(0), according to methodology reported by S. Buchwald. See M. Wolter et al, *Organic Letters* (2002) 4:973; B. H. Yang and S. Buchwald, *Journal of Organometallic Chemistry* (1999) 576(1-2):125. In this reaction sequence, P is a suitable amine protecting group. Use of and removal of amine protecting groups is accomplished by methodology reported in the literature (Protective Groups in Organic Synthesis, Peter G. M. Wutts, Theodora Greene (Editors) 3rd edition (April 1999) Wiley, John & Sons, Incorporated; ISBN: 0471160199). Starting compounds 9 are commercially available or readily prepared by one of ordinary skill in the art: See March's Advanced Organic Chemistry: Reactions, Mechanisms, and Structure, Michael B. Smith & Jerry March (Editors) 5th edition (January 2001) Wiley John & Sons; ISBN: 0471585890.

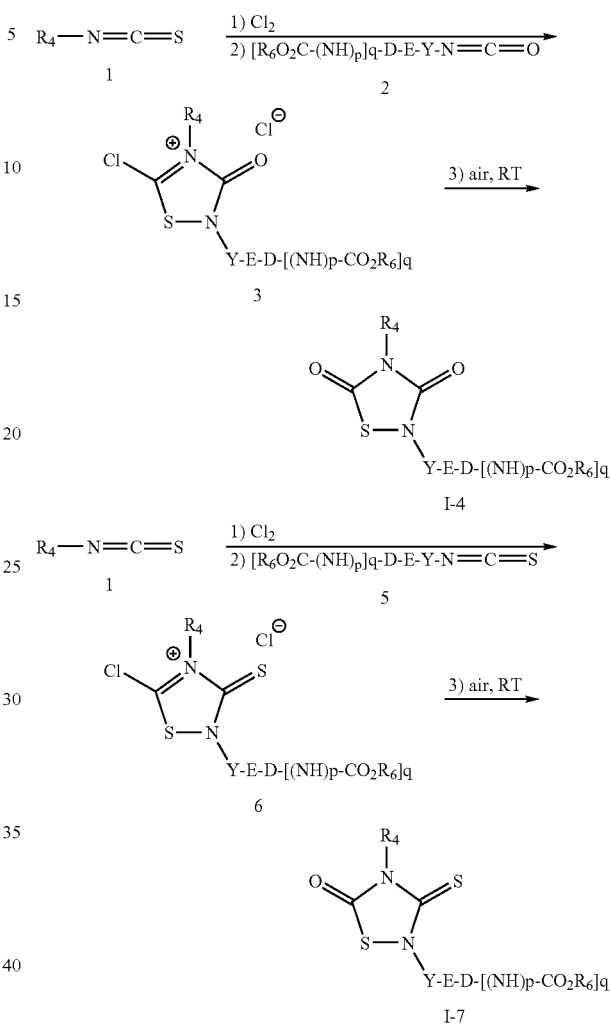

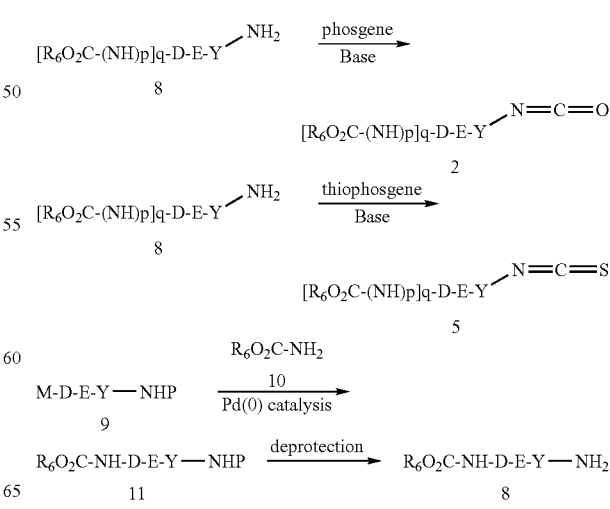

Compounds of Formula I wherein Q is taken from Q1 or Q-2 and Y is alkylene are also available via the synthetic route shown in Scheme 1.3. Reaction of amine 8 with isocyanate or isothiocyanate 2a yields the urea/thiourea 8a which can be cyclized by the addition of chlorocarbonyl sulfenyl chloride. See GB1115350 and U.S. Pat. No. 3,818,024, Revankar et. al U.S. Pat. No. 4,093,624, and Klayman et. al *JOC* 1972, 37(10), 1532 for further details. Where $R_4$ is a readily removable protecting group (e.g. R=3,4-d-methoxybenzyl amine), the action of mild, acidic deprotection conditions such as CAN or TFA will reveal the parent ring system of I-4 (X=O) and I-7 (X=S).

Scheme 1.3

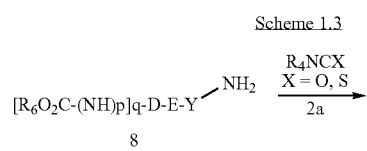

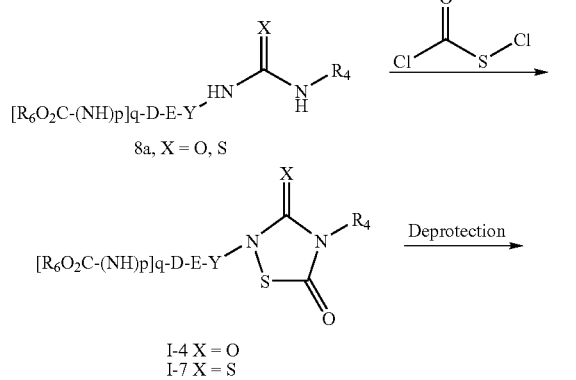

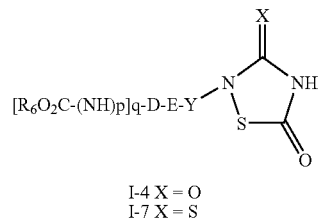

I-7 is also available as shown in Scheme 1.4. Condensation of isocyanate or isothiocyanate 2a with amine $R_5NH_2$ yields urea/thiourea 2b, which, when reacted with chlorocarbonyl sulfenyl chloride according to GB 1115350 and U.S. Pat. No. 3,818,024 yields 2c. Where $R_4$ is a readily removable protecting group (e.g. R=3,4-d-methoxybenzyl amine), the action of mild, acidic deprotection conditions such as CAN or TFA will reveal the parent ring system of 2d. Reaction of 2d with NaH in DMF, and displacement wherein M is a suitable leaving group such as chloride, bromide or iodide yields I-4 (X=O) and I-7 (X=S).

Scheme 1.4

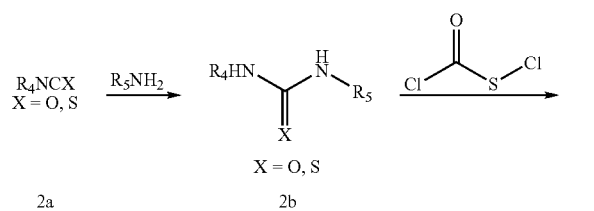

-continued

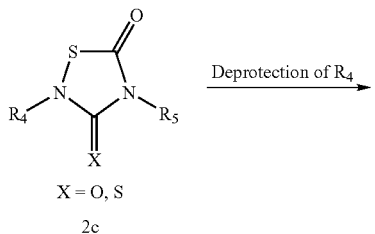

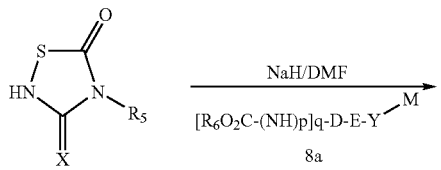

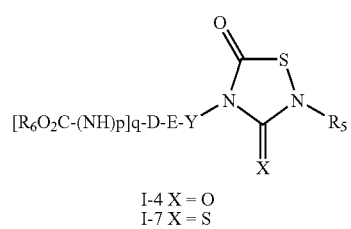

Compounds of Formula I wherein Q is taken from Q-1' or Q-2' and Y is alkylene are available via the synthetic route shown in Scheme 1.3. Condensation of isocyanate or isothiocyanate 2a with ammonia yields urea/thiourea 2e, which, when reacted with chlorocarbonyl sulfenyl chloride according to GB1115350 and U.S. Pat. No. 3,818,024 yields 2f. Reaction of 2f with NaH in DMF, and displacement wherein M is a suitable leaving group such as chloride, bromide or iodide yields I-4' (X=O) and I-7' (X=S).

Scheme 1.5

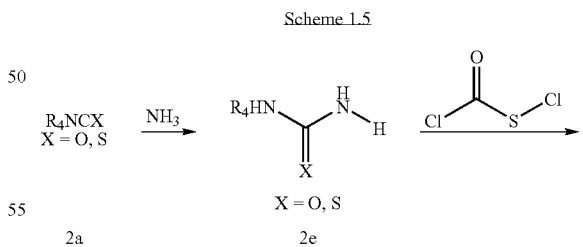

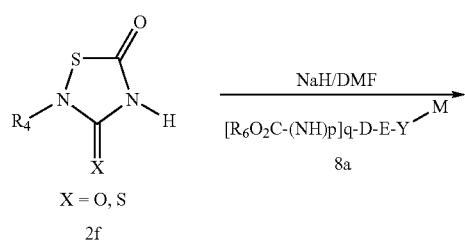

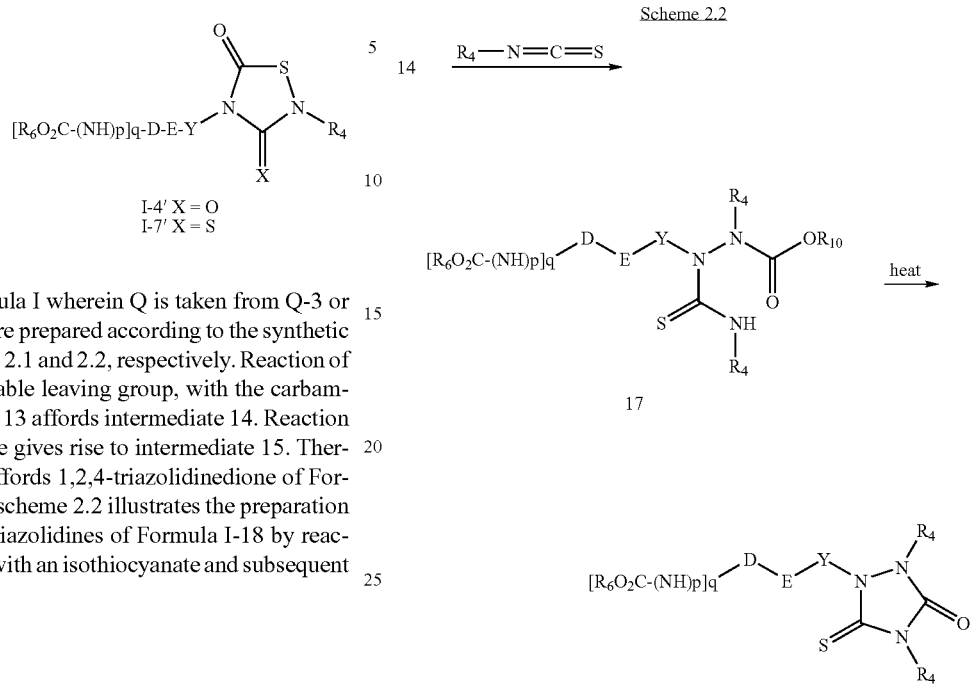

Compounds of Formula I wherein Q is taken from Q-3 or Q-4 and Y is alkylene, are prepared according to the synthetic route shown in Schemes 2.1 and 2.2, respectively. Reaction of 12, wherein M is a suitable leaving group, with the carbamate-protected hydrazine 13 affords intermediate 14. Reaction of 14 with an isocyanate gives rise to intermediate 15. Thermal cyclization of 15 affords 1,2,4-triazolidinedione of Formula I-16. By analogy, scheme 2.2 illustrates the preparation of 3-thio-5-oxo-1,2,4-triazolidines of Formula I-18 by reaction of intermediate 14 with an isothiocyanate and subsequent thermal cyclization.

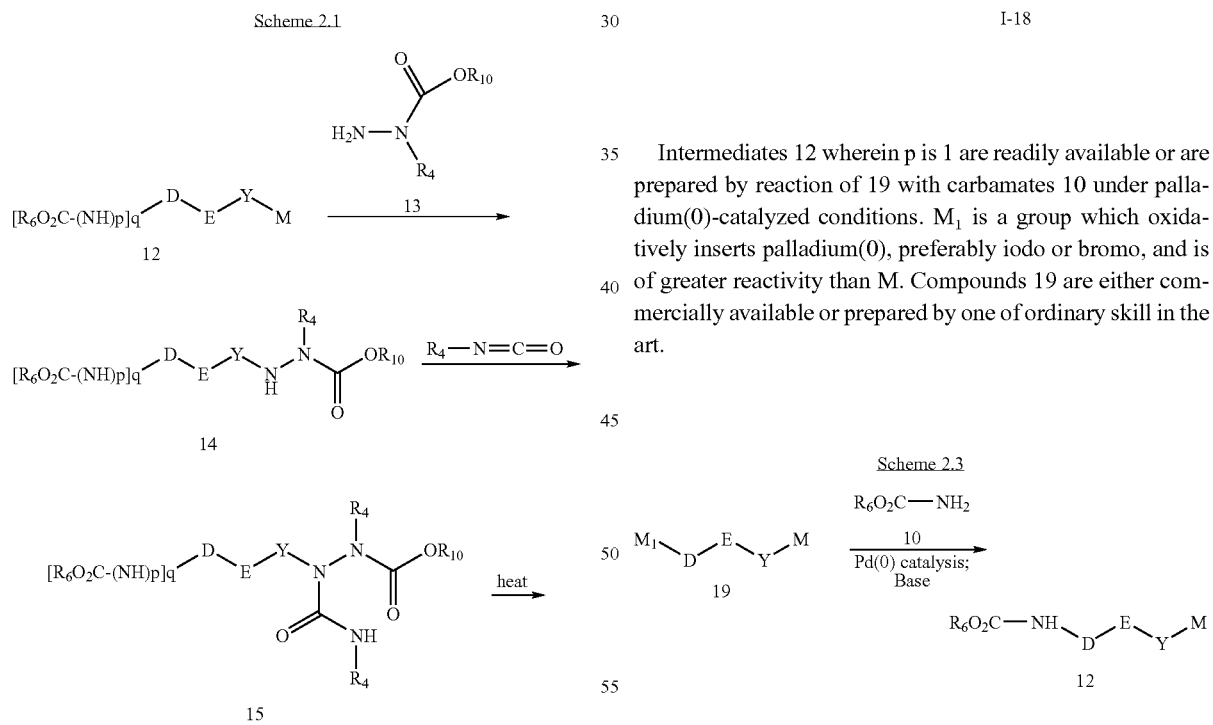

Intermediates 12 wherein p is 1 are readily available or are prepared by reaction of 19 with carbamates 10 under palladium(0)-catalyzed conditions. $M_1$ is a group which oxidatively inserts palladium(0), preferably iodo or bromo, and is of greater reactivity than M. Compounds 19 are either commercially available or prepared by one of ordinary skill in the art.

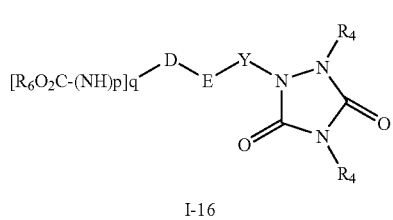

Compounds of Formula I wherein D is taken from Q-3 or Q-4 and Y is alkylene, are also prepared according to the synthetic route shown in Scheme 2.4. Oxidation of amine $R_4NH_2$ to the corresponding hydrazine, condensation with ethyl chloroformate subsequent heating yields 1,2,4-triazolidinedione 15a. After the action of NaH in DMF, displacement wherein M is a suitable leaving group such as chloride, bromide or iodide yields I-16 (X=O) and I-18 (X=S).

Scheme 2.4

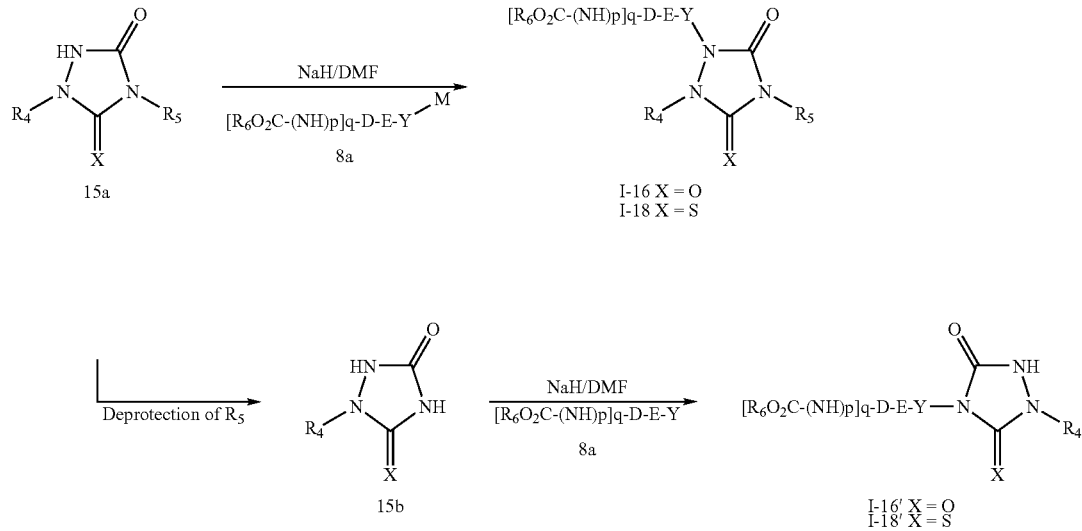

Compounds of Formula I wherein D is taken from D-3' or D-4' and Y is alkylene, are also prepared according to the synthetic route shown in Scheme 2.4. When $R_5$ is a readily removable protecting group (e.g. R=3,4-d-methoxybenzyl amine), the action of mild, acidic deprotection conditions such as CAN or TFA on 15a will reveal 1,2,4-triazolidinedione 15b. After deprotonation of 15b by NaH in DMF, displacement wherein M is a suitable leaving group such as chloride, bromide or iodide yields I-16' (X=O) and I-18' (X=S).

Compounds of Formula I wherein Q is taken from Q-5 or Q-6 and Y is alkylene are prepared according to the synthetic route shown in Scheme 3. Reaction of hydrazine 20 with chlorosulfonylisocyanate and base, such as triethylamine, gives rise to a mixture of intermediates 21A and 21B which are not isolated but undergo cyclization in situ to afford compounds of Formulae I-22A and I-22B. Compounds I-22A and I-22B are separated by chromatography or fractional crystallization. Optionally, compounds I-22A and I-22B can undergo Mitsunobu reaction with alcohols $R_4OH$ to give compounds of Formulae I-23A and I-23B. Compounds 20 are prepared by acid-catalyzed deprotection of t-butyl carbamates of structure 14, wherein $R_{10}$ is t-butyl.

Scheme 3

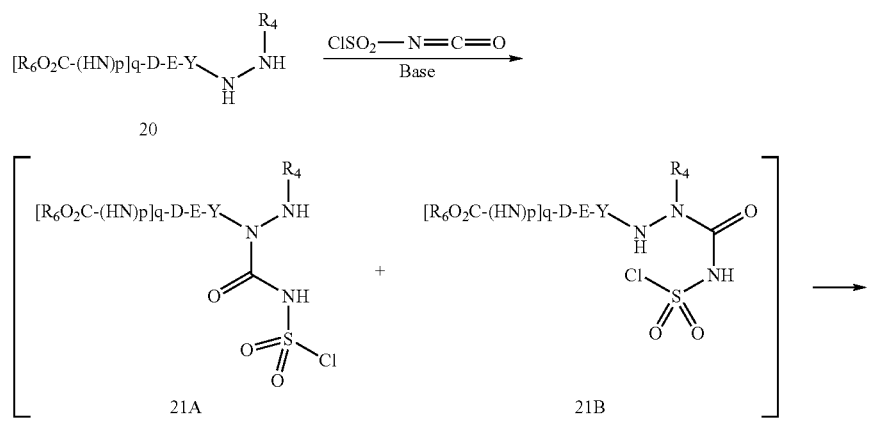

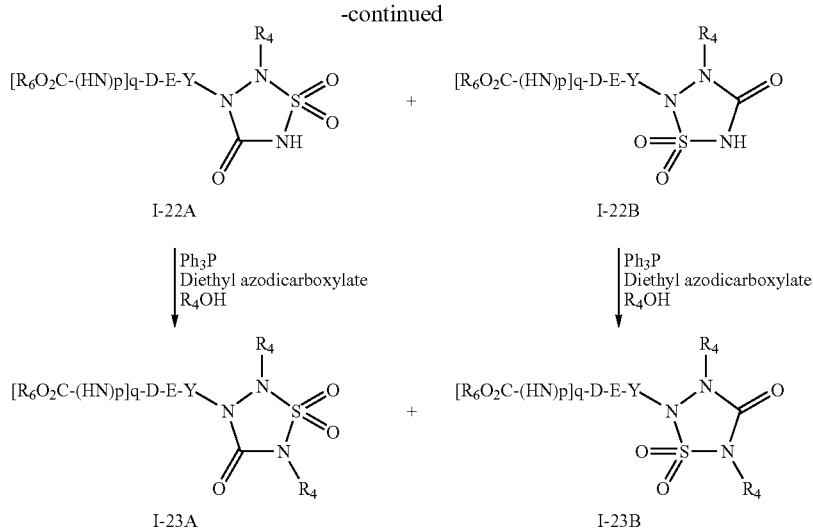

Compounds of Formula I wherein Q is Q-7 and Y is alkylene are prepared as shown in Scheme 4. Reaction of amine 8 with maleimide 24, wherein M is a suitable leaving group, affords compounds of Formula I-25. Reaction of compound 26, wherein M is a group which can oxidatively insert Pd(0), can participate in a Heck reaction with maleimide 27, affording compounds of Formula I-28. Maleimides 24 and 27 are commercially available or prepared by one of ordinary skill in the art.

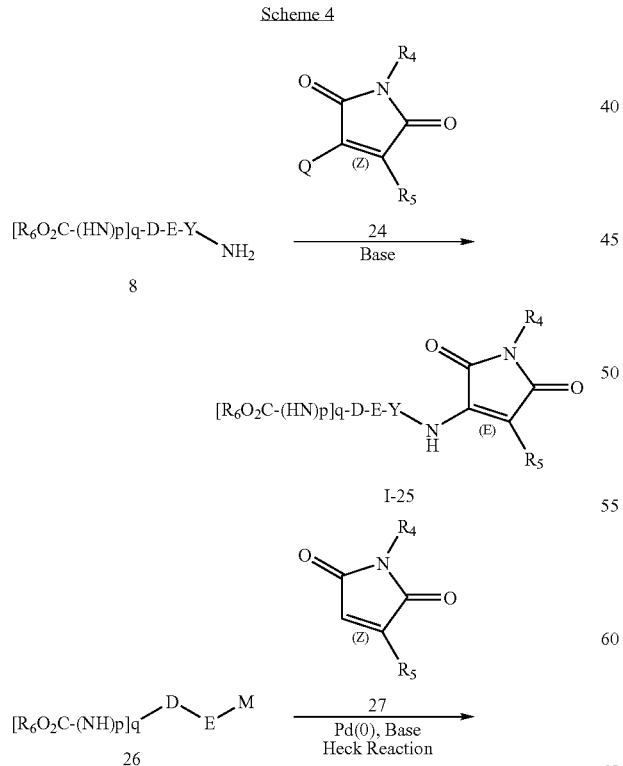

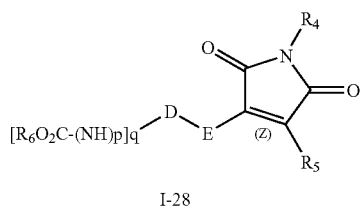

Compounds of Formula I wherein Q is Q-8 and Y is alkylene are prepared as shown in Scheme 5, according to methods reported by M. Tremblay et al, *Journal of Combinatorial Chemistry* (2002) 4:429. Reaction of polymer-bound activated ester 29 (polymer linkage is oxime activated-ester) with chlorosulfonylisocyante and t-butanol affords N—BOC sulfonylurea 30. Subjection of 30 to the Mitsunobu reaction with $R_4OH$ gives rise to 31. BOC-group removal with acid, preferably trifluoroacetic acid, and then treatment with base, preferably triethylamine, provides the desired sulfahydantoin I-32. Optionally, intermediate 30 is treated with acid, preferably trifluoroacetic acid, to afford the N-unsubstituted sulfahydantoin I-33.

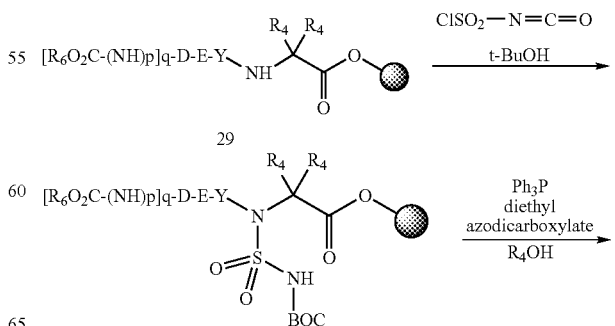

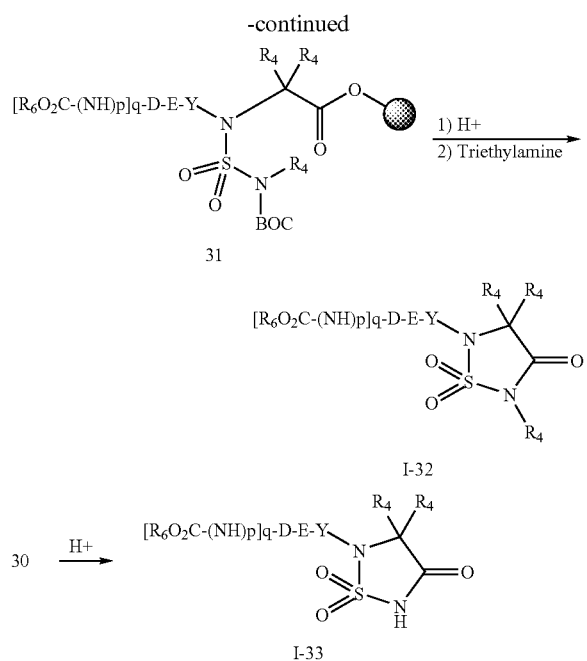

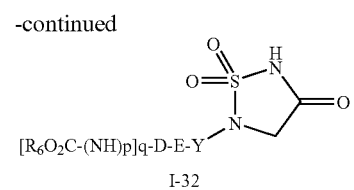

Compounds of Formula I wherein Q is taken from Q-8', are prepared according to the synthetic route shown in Scheme 5.2. Formation of 31c by the method of Muller and DuBois *JOC* 1989, 54, 4471 and its deprotonation with NaH/DMF or NaH/DMF and subsequently alkylation wherein M is a suitable leaving group such as chloride, bromide or iodide yields I-32'. Alternatively, I-32' is also available as shown in Scheme 5.3. Mitsunobu reaction of boc-sulfamide amino ethyl ester with alcohol 8b (made by methods analogous to that for amine 8) yields 31c, which after Boc removal with 2N HCl in dioxane is cyclized by the action of NaH on 31d results in I-32'.

Compounds of Formula I wherein Q is Q-8 and Y is alkylene are also prepared as shown in Scheme 5a. Amine 8 is condensed with the glyoxal hemiester to yield 31a. Reaction of chlorosulphonyl isocyanate first with benzyl alcohol then 31a yields 31b, which after heating yields I-32.

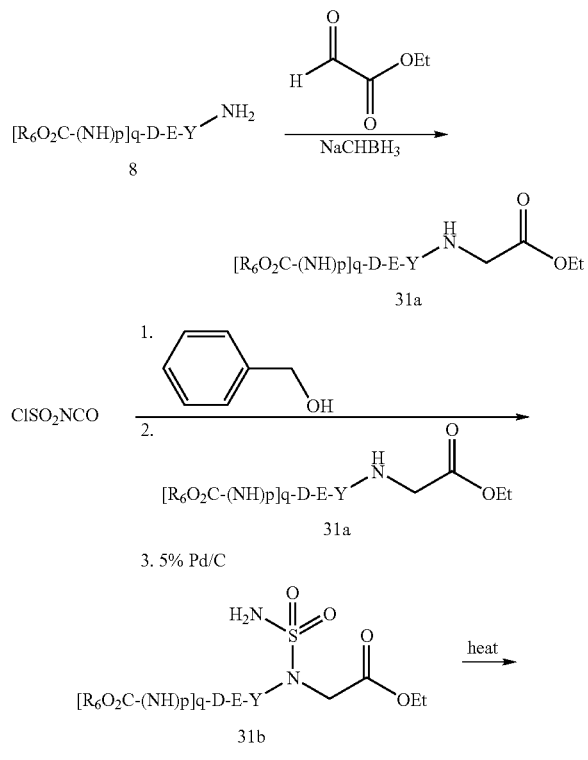

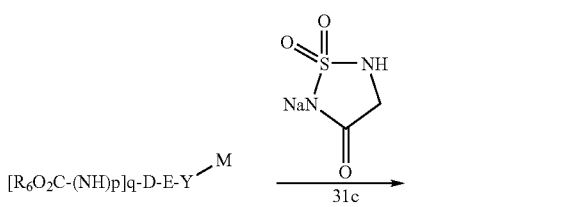

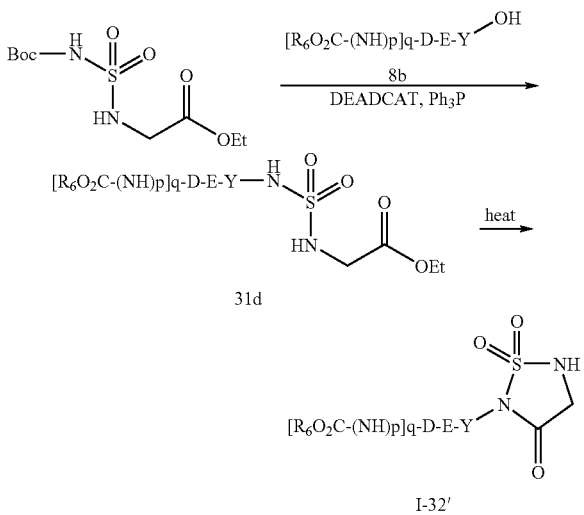

Compounds of Formula I wherein Q is Q-9 and Y is alkylene are prepared as shown in Scheme 6. Reaction of polymer-bound amino acid ester 34 with an isocyanate affords intermediate urea 35. Treatment of 35 with base, preferably pyridine or triethylamine, with optional heating, gives rise to compounds of Formula I-36.

Compounds of Formula I wherein Q is taken from Q-9', are prepared according to the synthetic route shown in Scheme 6.2. Formation of 35c by the method described in JP10007804A2 and Zvilichovsky and Zucker, Israel Journal of Chemistry, 1969, 7(4), 547-54 and its deprotonation with NaH/DMF or NaH/DMF and its subsequent displacement of M, wherein M is a suitable leaving group such as chloride, bromide or iodide, yields I-36'.

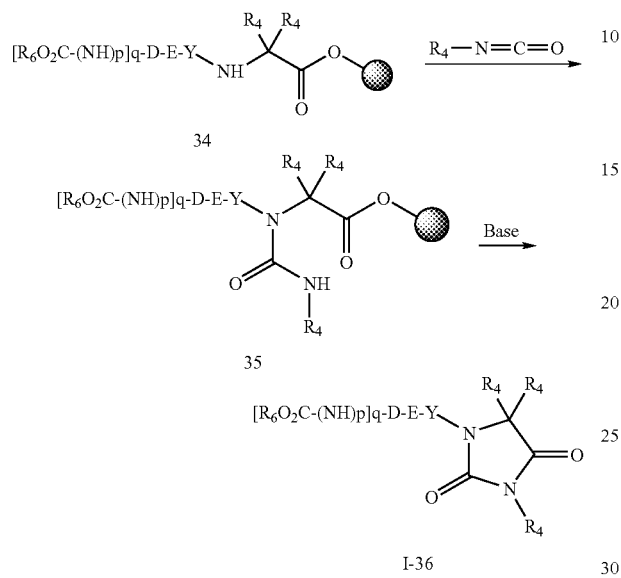

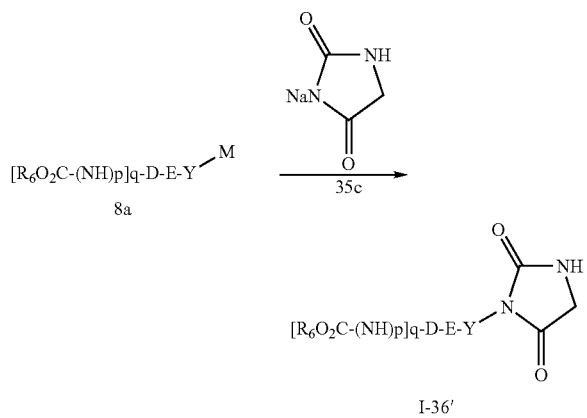

Compounds of Formula I wherein Q is Q-9 and Y is alkylene are also prepared as shown in Scheme 6.1. Reaction of aldehyde 8c under reductive amination conditions with the t-butyl ester of glycine yields 35a. Isocyanate 2a is condensed with p-nitrophenol (or the corresponding $R_4NH_2$ amine is condensed with p-nitrophenyl chloroformate) to yield the carbamic acid p-nitrophenyl ester, which when reacted with deprotonated 35a and yields the urea that when deprotected with acid yields 35b. Formula I-36 is directly available from 35b by the action of NaH and heat.

Compounds of Formula I wherein Q is Q-10 or Q-11, and Y is alkylene are prepared as shown in Schemes 7.1 and 7.2, respectively. Treatment of alcohol 37 (Z=O) or amine 37 (Z=NH) with chlorosulfonylisocyanate affords intermediate carbamate or urea of structure 38. Treatment of 38 with an amine of structure $HN(R_4)_2$ and base, preferably triethylamine or pyridine, gives sulfonylureas of Formula I-39. Reaction of chlorosulonylisocyanate with an alcohol (Z=O) or amine (Z=NR_4) 40 affords intermediate 41. Treatment of 41 with an amine 8 and base, preferably triethylamine or pyridine, gives sulfonylureas of Formula I-42.

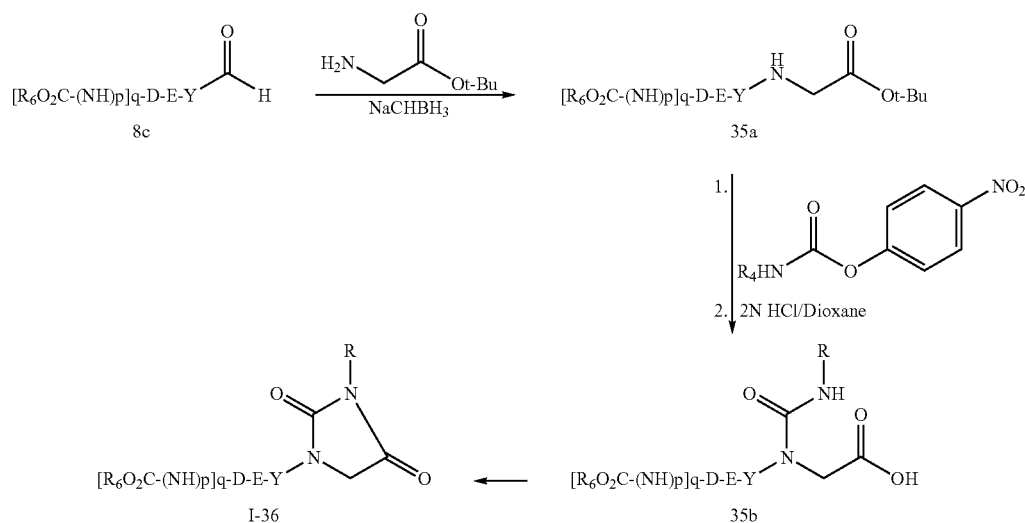

Scheme 7.1

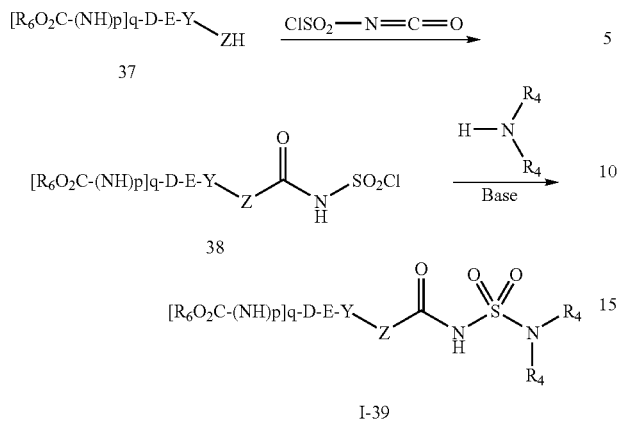

Scheme 7.2

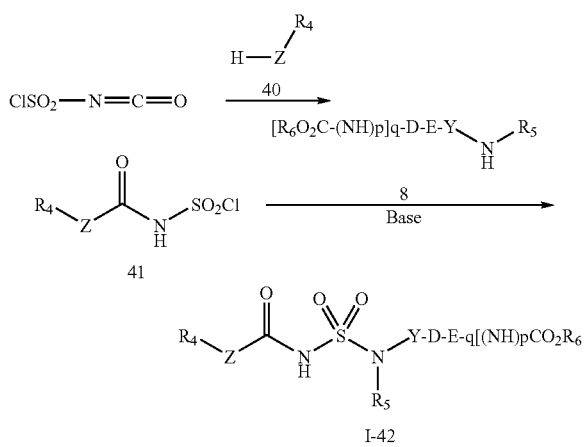

Scheme 8

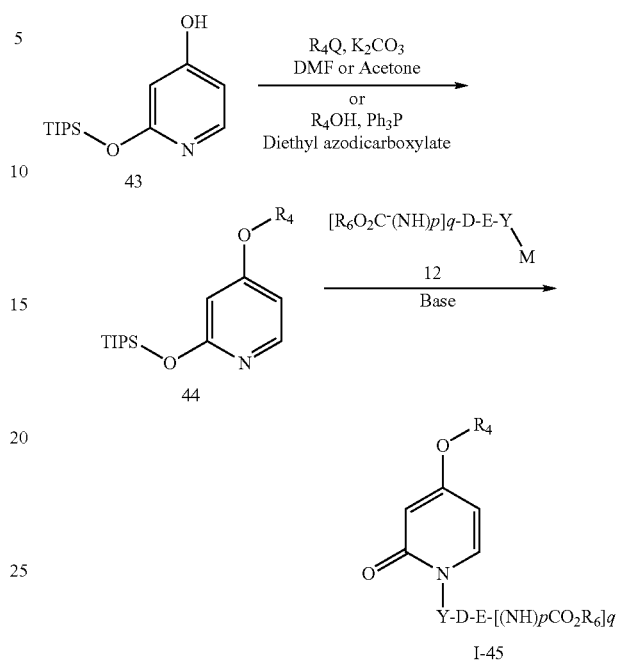

Compounds of Formula I wherein Q is taken from Q-12 are prepared according to the synthetic route shown in Scheme 8. Alkylation of pyridine 43, wherein TIPS is tri-isopropylsilyl, under standard conditions ($K_2CO_3$, DMF, $R_4$—I or Mitsunobu conditions employing $R_4$—OH) yields pyridine derivative 44 which is reacted with compound 12, wherein M is a suitable leaving group, to afford pyridones of formula I-45.

Compounds of Formula I wherein Q is taken from Q-13 are prepared according to the synthetic route shown in Scheme 9. Starting from readily available pyridine 46, alkylation under standard conditions ($K_2CO_3$, DMF, $R_4$—I or Mitsunobu conditions employing $R_4$—OH) yields pyridine derivative 47. N-alkylation with $K_2CO_3$, DMF, $R_4$—I affords pyridones of formula 48. Intermediate 48 is partitioned to undergo a Heck reaction, giving I-49; a Buchwald amination reaction, giving I-51; or a Buchwald Cu(I) catalyzed O-arylation reaction, to give I-52. The Heck reaction product I-49 may be optionally hydrogenated to afford the saturated compound I-50. Wherein the phenyl ether $R_4$ group is methyl, compounds of formula I-49, I-50, I-51, or 1-52 are treated with boron tribromide or lithium chloride to afford compounds of Formula I-53, wherein $R_4$ is hydrogen.

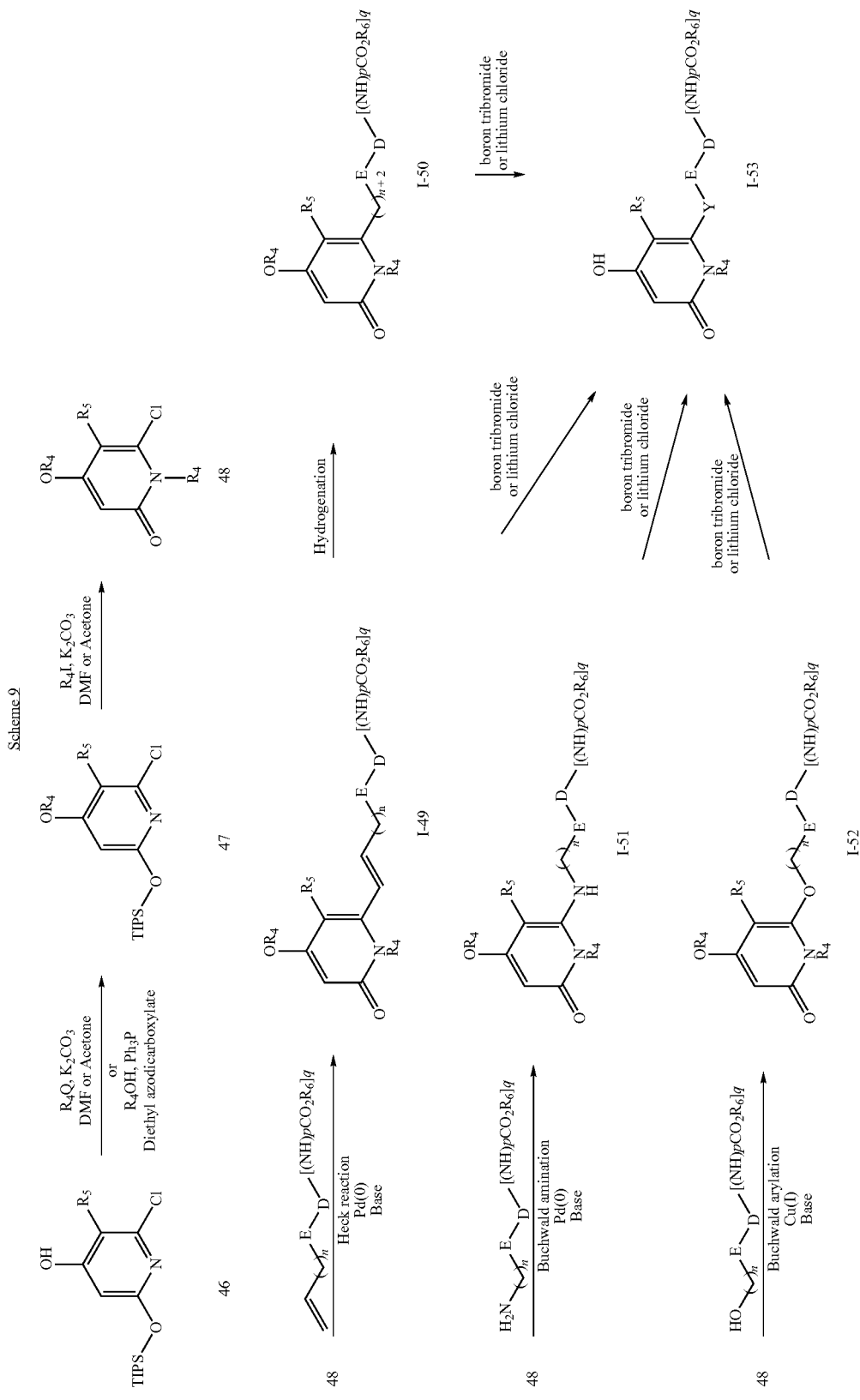

Compounds of Formula I wherein Q is taken from Q-14 are prepared according to the synthetic route shown in Scheme 10. Starting from readily available pyridine 54, alkylation under standard conditions ($K_2CO_3$, DMF, $R_4$—I or Mitsunobu conditions employing $R_4$—OH) yields pyridine derivative 55. N-alkylation with $K_2CO_3$, DMF, $R_4$—I affords pyridones of formula 56. Intermediate 56, wherein M is a suitable leaving group, preferably bromine or chlorine, is partitioned to undergo a Heck reaction, giving I-57; a Buchwald amination reaction, giving I-59; or a Buchwald Cu(I) catalyzed O-arylation reaction, to give I-60. The Heck reaction product I-57 may be optionally hydrogenated to afford the saturated compound I-58. Wherein $R_4$ is methyl, compounds of formula I-57, I-58, I-59, or I-60 are treated with boron tribromide or lithium chloride to afford compounds of Formula I-61, wherein $R_4$ is hydrogen.

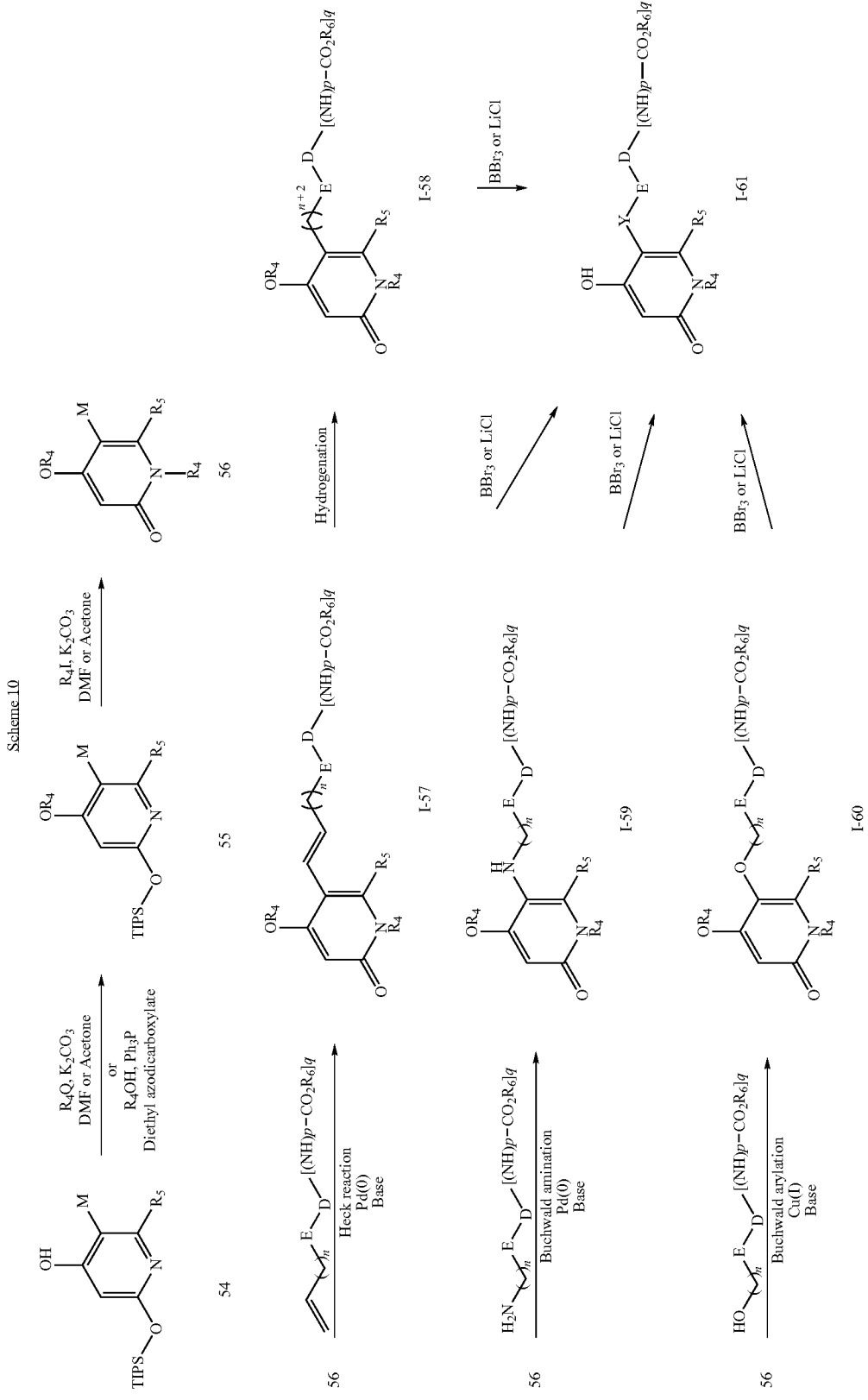

Compounds of Formula I wherein Q is taken from Q-15 are prepared according to the synthetic routes shown in Schemes 11 and 12. Starting esters 62 are available from the corresponding secoacids via TBS-ether and ester formation under standard conditions. Reaction of protected secoester 62 with Meerwin's salt produces the vinyl ether 63 as a pair of regioisomers. Alternatively, reaction of 62 with dimethylamine affords the vinylogous carbamate 64. Formation of the dihydropyrimidinedione 66 proceeds by condensation with urea 65 with azeotropic removal of dimethylamine or methanol. Dihydropyrimidinedione 66 may optionally be further substituted by Mitsunobu reaction with alcohols $R_4OH$ to give rise to compounds 67.

Scheme 12 illustrates the further synthetic elaboration of intermediates 67. Removal of the silyl protecting group (TBS) is accomplished by treatment of 67 with flouride (tetra-n-butylammonium fluoride or cesium flouride) to give primary alcohols 68. Reaction of 68 with isocyanates 2 gives rise to compounds of Formula I-69. Alternatively, reaction of 68 with $[R_6O_2C(NH)p]q$-D-E-M, wherein M is a suitable leaving group, affords compounds of Formula I-70. Oxidation of 68 using the Dess-Martin periodinane (D. Dess, J. Martin, *J. Am. Chem. Soc.* (1991) 113:7277) or tetra-n-alkyl peruthenate (W. Griffith, S. Ley, *Aldrichimica Acta* (1990) 23:13) gives the aldehydes 71. Reductive amination of 71 with amines 8 gives rise to compounds of Formula I-72. Alternatively, aldehydes 71 may be reacted with ammonium acetate under reductive alkylation conditions to give rise to the primary amine 73. Reaction of 73 with isocyanates 2 affords compounds of Formula I-74.

Scheme 11

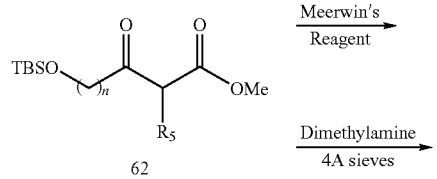

-continued

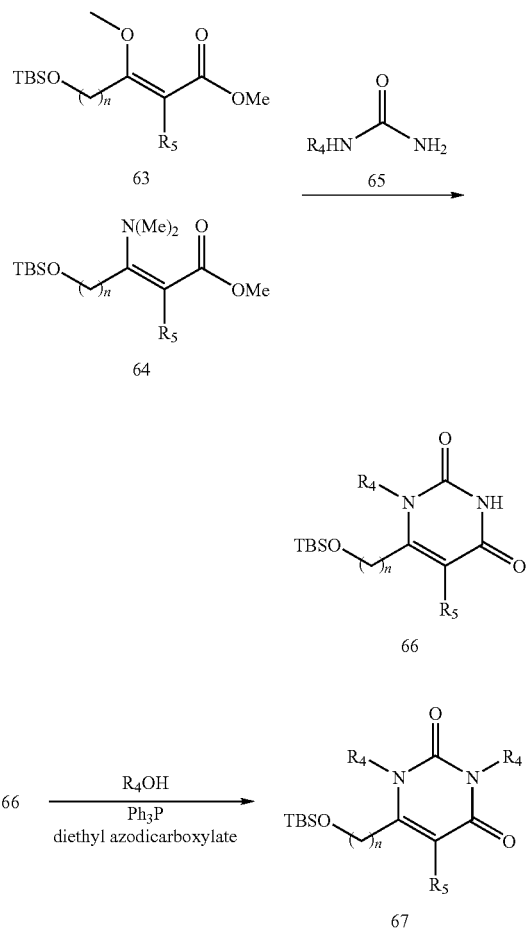

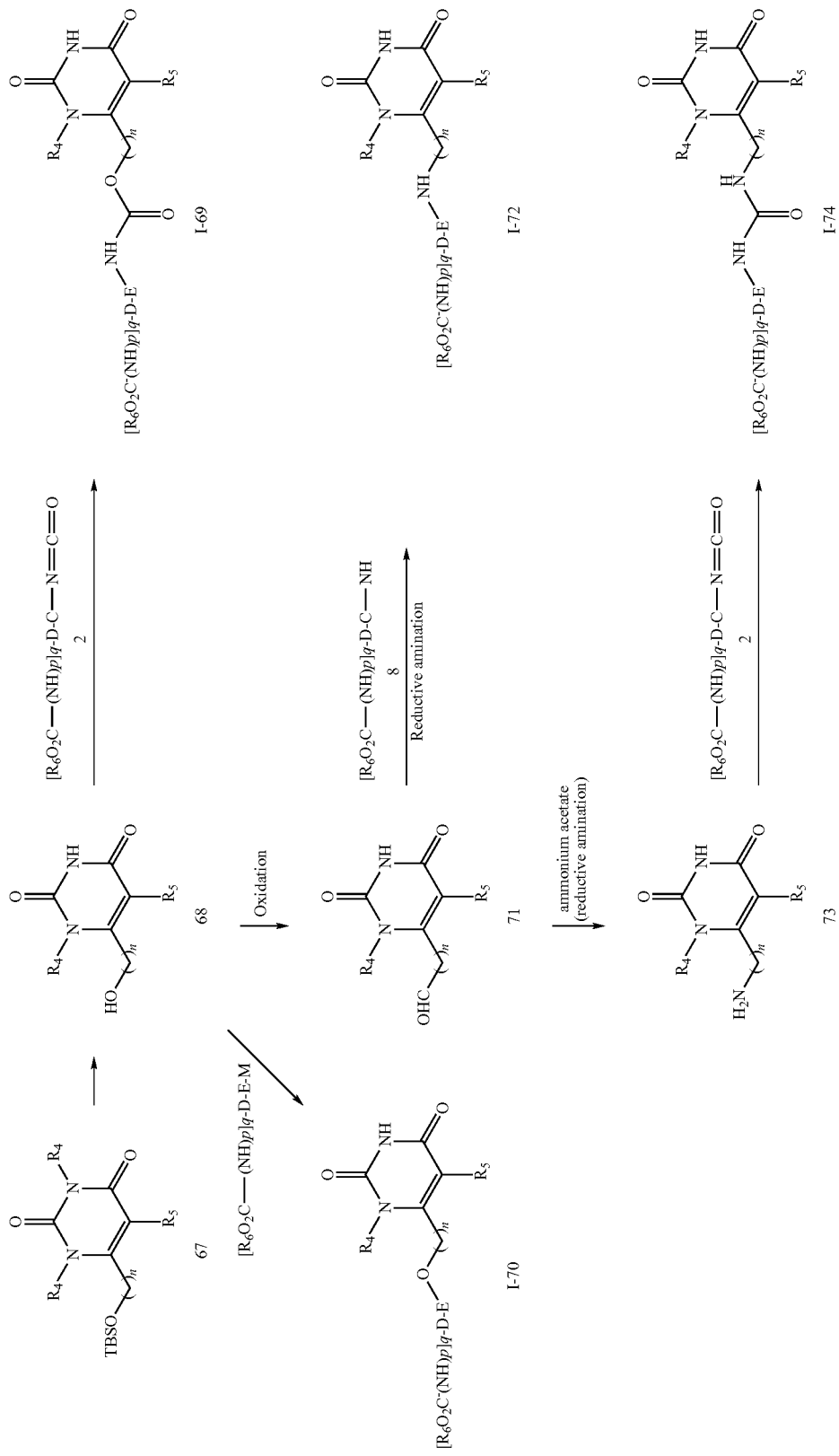

Compounds of Formula I wherein Q is taken from Q-16 are prepared according to the synthetic routes shown in Schemes 13 and 14. Starting esters 75 are available from the corresponding secoacids via TBS-ether and ester formation under standard conditions. Reaction of protected secoester 75 with Meerwin's salt produces the vinyl ether 76 as a pair of regioisomers. Alternatively, reaction of 75 with dimethylamine affords the vinylogous carbamate 77. Formation of the dihydropyrimidinedione 78 proceeds by condensation with urea 65 with azeotropic removal of dimethylamine or methanol. Dihydropyrimidinedione 78 may optionally be further substituted by Mitsunobu reaction with alcohols $R_4OH$ to give rise to compounds 79. Compounds of Formulae I-81, I-82, I-84, and I-86 are prepared as shown in Scheme 14 by analogy to the sequence previously described in Scheme 12.

Scheme 13

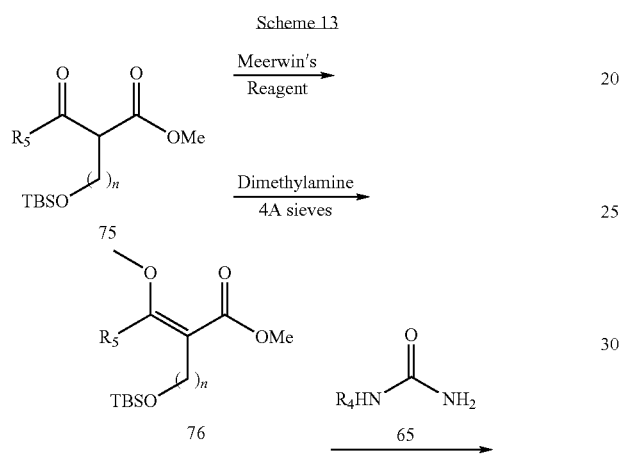

-continued

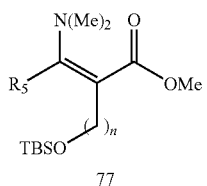

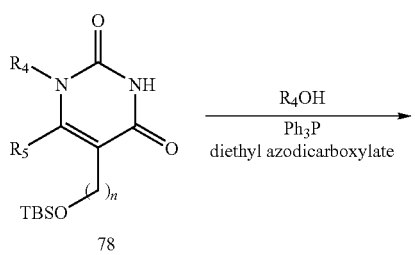

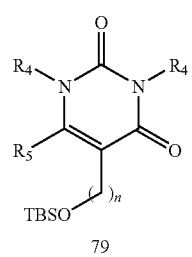

Scheme 14

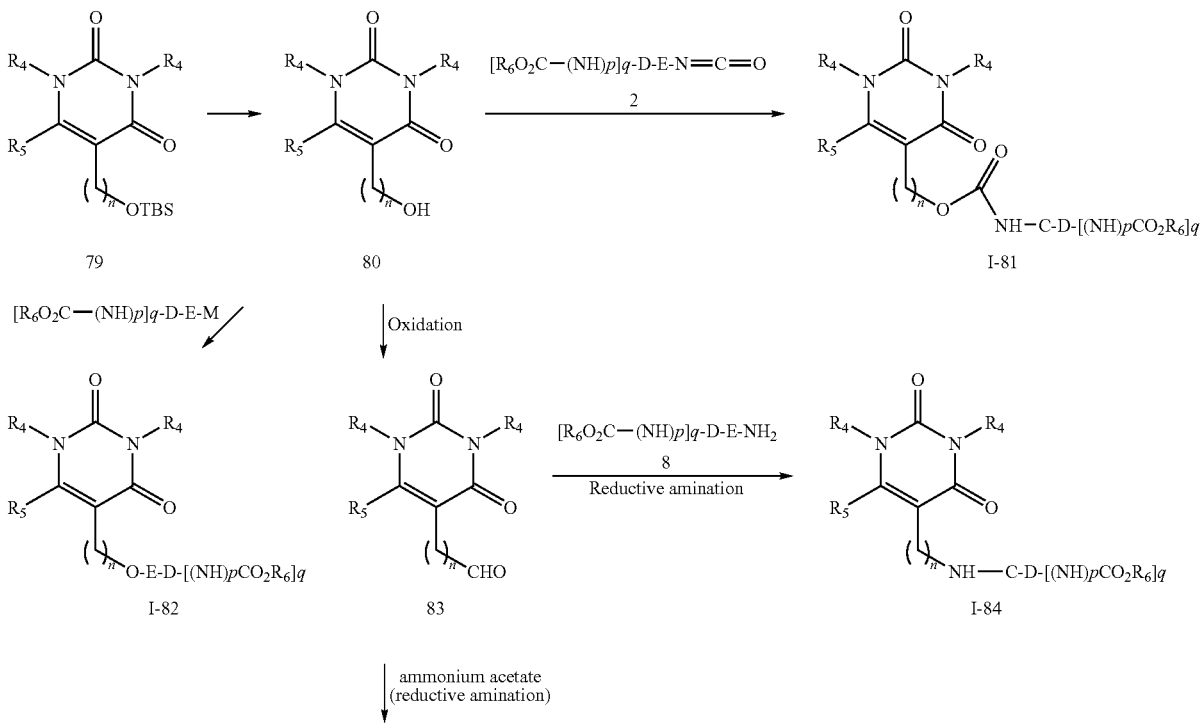

-continued

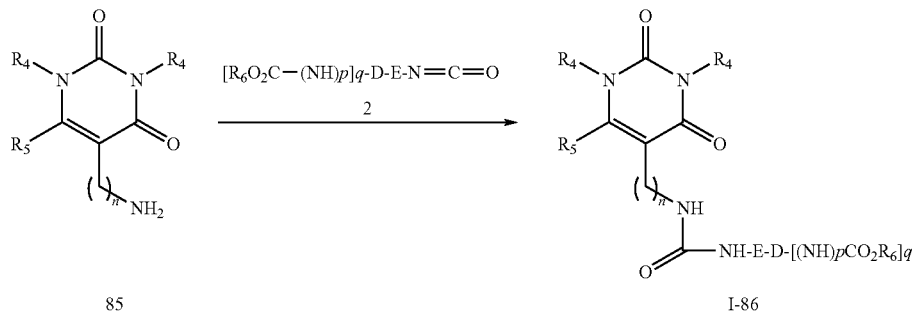

Alkyl acetoacetates 87 are commercially available and are directly converted into the esters 88 as shown in Scheme 15. Treatment of 87 with NaHMDS in THF, followed by quench with formaldehyde and TBSCl (n=1) or Q-(CH2)$_n$—OTBS (n=2-4), gives rise to compounds 88.

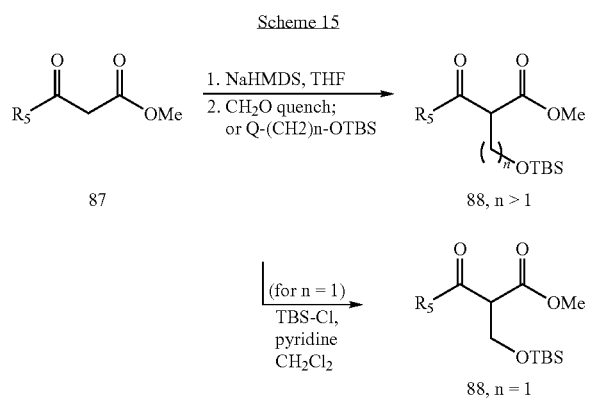

Compounds of Formula I wherein Q is taken from Q-17 are prepared according to the synthetic routes shown in Schemes 16.1 and 16.2, and starts with the BOC-protected hydrazine 13, which is converted to the 1,2-disubstituted hydrazine 89 by a reductive alkylation with a glyoxal derivative mediated by sodium cyanoborohydride and acidic workup. Condensation of 89 with diethyl malonate in benzene under reflux yields the heterocycle 90. Oxidation with $N_2O_4$ in benzene (see Cardillo, Merlini and Boeri *Gazz. Chim. Ital.*, (1966) 9:8) to the nitromalonohydrazide 91 and further treatment with $P_2O_5$ in benzene (see: Cardillo, G. et al, *Gazz. Chim. Ital.* (1966) 9:973-985) yields the tricarbonyl 92. Alternatively, treatment of 90 with Brederick's reagent (t-BuOCH(N(Me$_2$)$_2$, gives rise to 93 which is subjected to ozonolysis, with a DMS and methanol workup, to afford the protected tricarbonyl 92. Compound 92 is readily deprotected by the action of CsF in THF to yield the primary alcohol 94. Alcohol 94 is optionally converted into the primary amine 95 by a sequence involving tosylate formation, azide displacement, and hydrogenation.

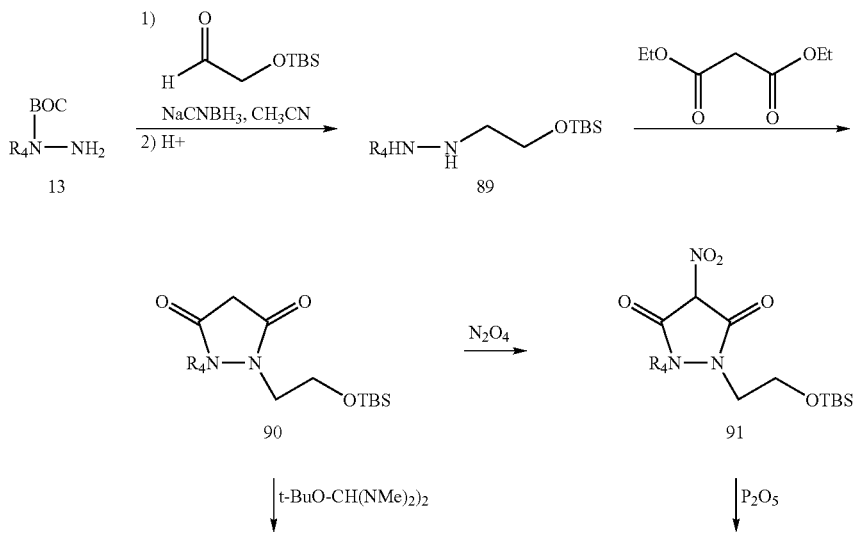

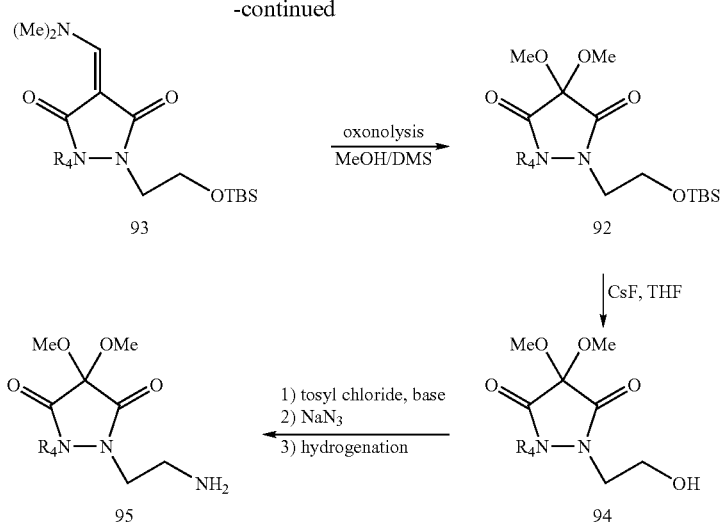

Reaction of 94 with (hetero)aryl halide 26, wherein M is iodo, bromo, or chloro, under copper(I) catalysis affords compounds I-96. Optional deprotection of the di-methyl ketal with aqueous acid gives rise to compounds of Formula I-98. By analogy, reaction of amine 95 with 26 under palladium(0) catalysis affords compounds of Formula I-97. Optional deprotection of the di-methyl ketal with aqueous acid gives rise to compounds of Formula I-99.

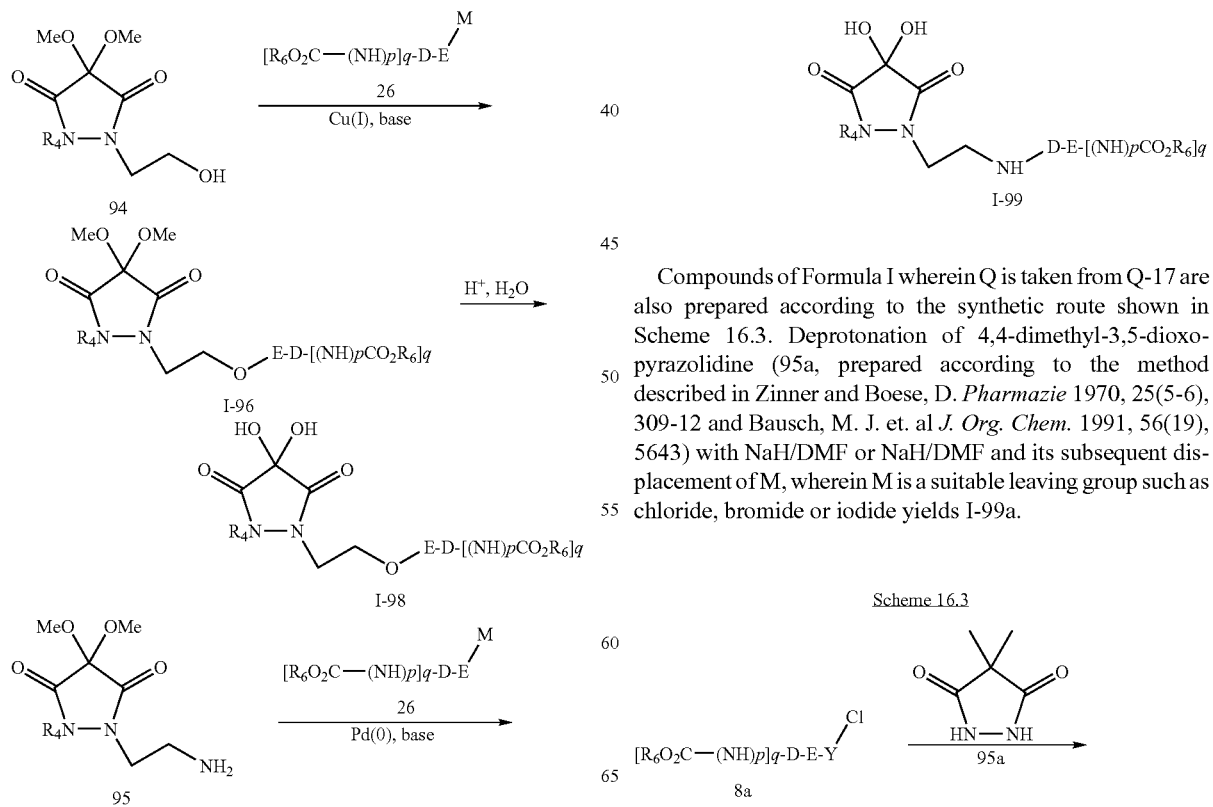

Compounds of Formula I wherein Q is taken from Q-17 are also prepared according to the synthetic route shown in Scheme 16.3. Deprotonation of 4,4-dimethyl-3,5-dioxo-pyrazolidine (95a, prepared according to the method described in Zinner and Boese, D. *Pharmazie* 1970, 25(5-6), 309-12 and Bausch, M. J. et. al *J. Org. Chem.* 1991, 56(19), 5643) with NaH/DMF or NaH/DMF and its subsequent displacement of M, wherein M is a suitable leaving group such as chloride, bromide or iodide yields I-99a.

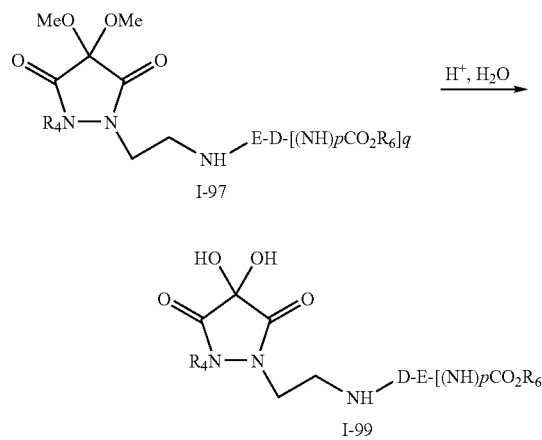

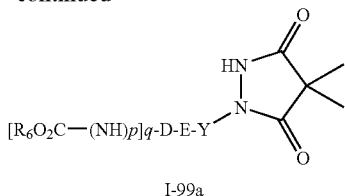

I-99a

Compounds of Formula I wherein Q is taken from Q-18 are prepared as shown in Schemes 17.1 and 17.2. Aminoesters 100 are subjected to reductive alkylation conditions to give rise to intermediates 101. Condensation of amines 101 with carboxylic acids using an acid activating reagent such as dicyclohexylcarbodiimide (DCC)/hydroxybenzotriazole (HOBt) affords intermediate amides 102. Cyclization of amides 102 to tetramic acids 104 is mediated by Amberlyst A-26 hydroxide resin after trapping of the in situ generated alkoxide 103 and submitting 103 to an acetic acid-mediated resin-release.

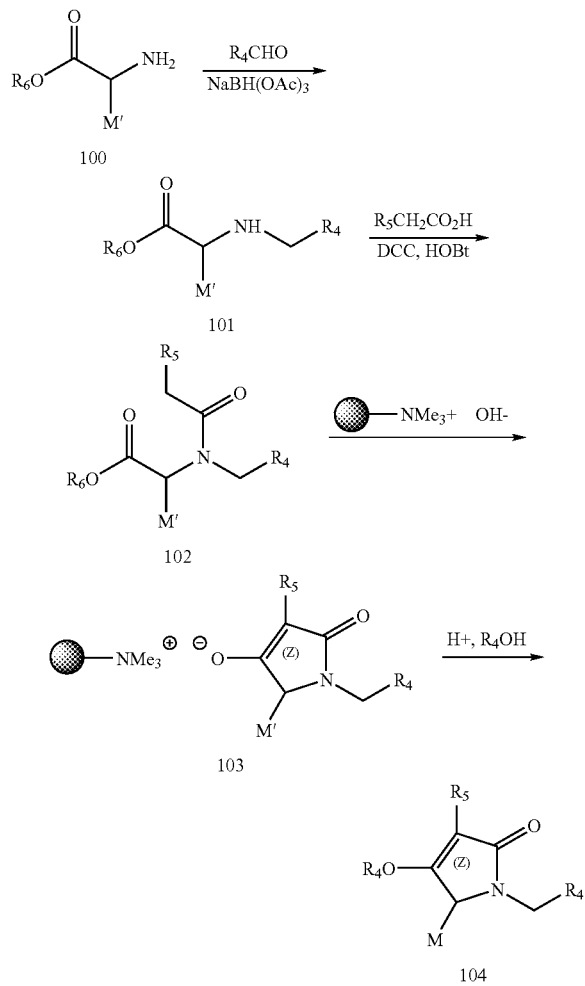

Scheme 17.2 illustrates the synthetic sequences for converting intermediates 104 to compounds of Formula I. Reaction of alcohol 104.1 with aryl or heteroaryl halide 26 (Q=halogen) under copper(I) catalysis gives rise to compounds of Formula I-105.1. Reaction of amines 104.2 and 104.3 with 26 under Buchwald palladium(0) catalyzed amination conditions affords compounds of Formulae I-105.2 and I-105.3. Reaction of acetylene 104.4 with 26 under Sonogashira coupling conditions affords compounds of Formula I-105.4. Compounds I-105.4 may optionally be reduced to the corresponding saturated analogs I-105.5 by standard hydrogenation.

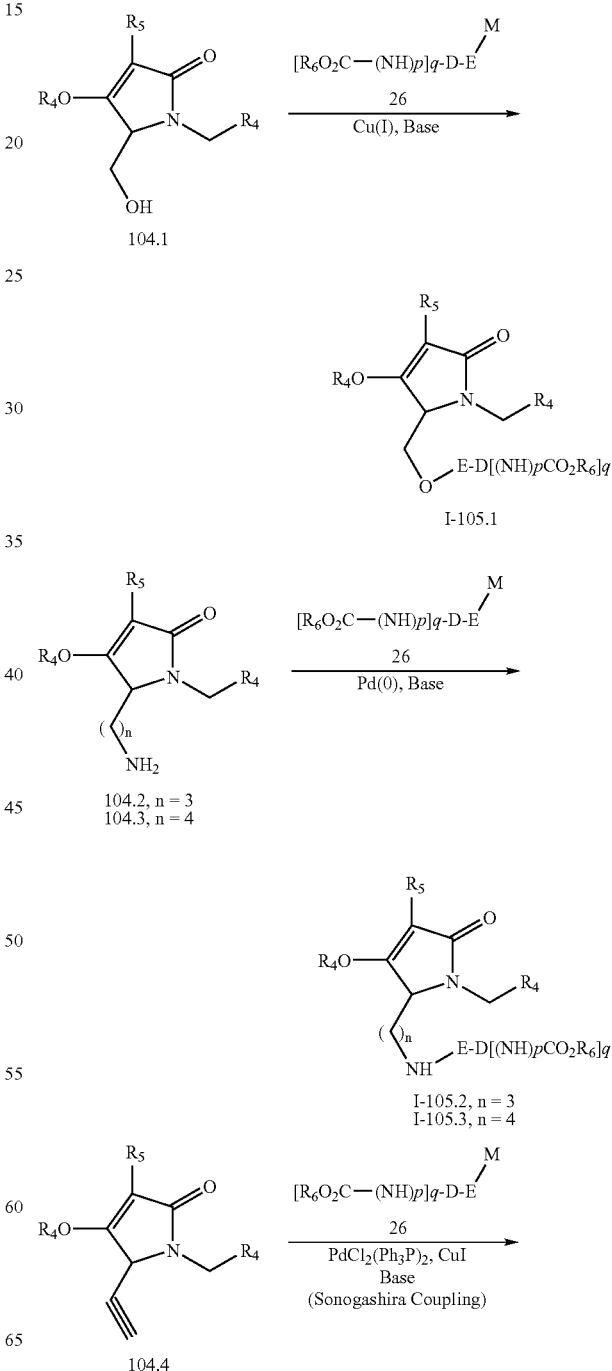

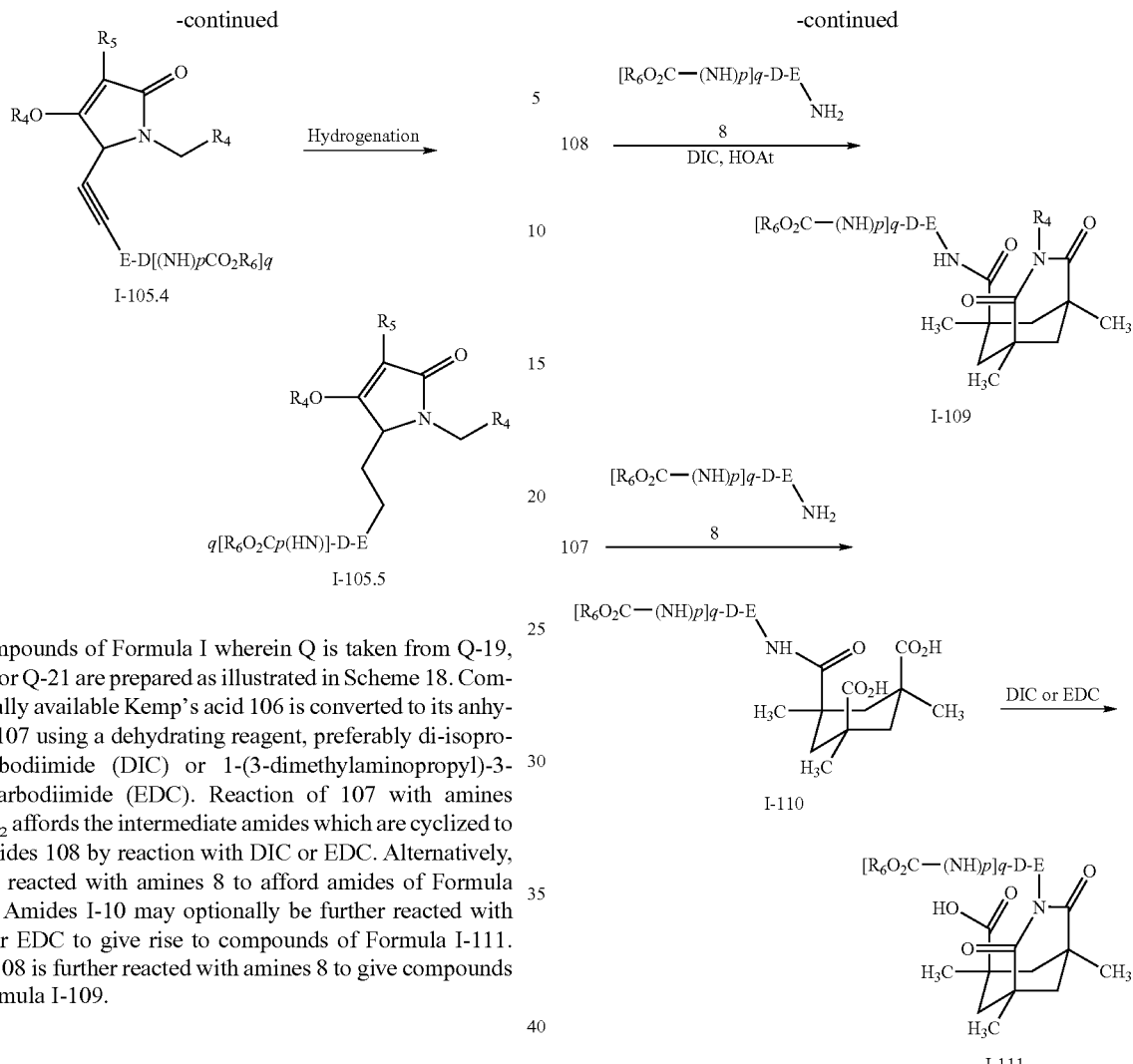

Compounds of Formula I wherein Q is taken from Q-19, Q-20, or Q-21 are prepared as illustrated in Scheme 18. Commercially available Kemp's acid 106 is converted to its anhydride 107 using a dehydrating reagent, preferably di-isopropylcarbodiimide (DIC) or 1-(3-dimethylaminopropyl)-3-ethylcarbodiimide (EDC). Reaction of 107 with amines $R_4NH_2$ affords the intermediate amides which are cyclized to the imides 108 by reaction with DIC or EDC. Alternatively, 107 is reacted with amines 8 to afford amides of Formula I-110. Amides I-10 may optionally be further reacted with DIC or EDC to give rise to compounds of Formula I-111. Acid 108 is further reacted with amines 8 to give compounds of Formula I-109.

Scheme 18

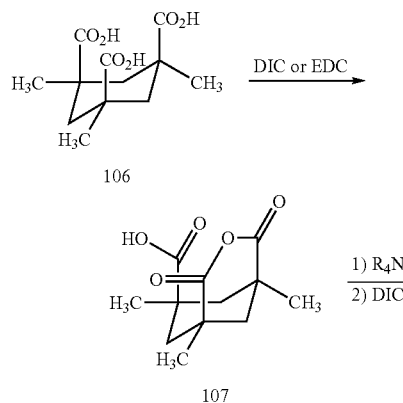

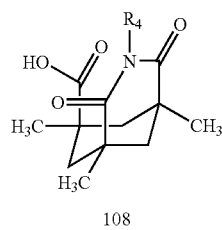

Compounds of Formula I wherein Q is taken from Q-22 or Q-23 are prepared as shown in Schemes 19.1 through 19.3. Preparation of intermediates 113 and 114 are prepared as shown in Scheme 19.1 from di-halo(hetero)aryls 112, wherein $M_2$ is a more robust leaving group than $M_1$. Reaction of 112 with amines 37 (Z=NH) either thermally in the presence of base or by palladium(0) catalysis in the presence of base and phosphine ligand affords compounds 113. Alternatively, reaction of 112 with alcohols 37 (X=O) either thermally in the presence of base or by copper(I) catalysis in the presence of base affords compounds 114.

Scheme 19.1

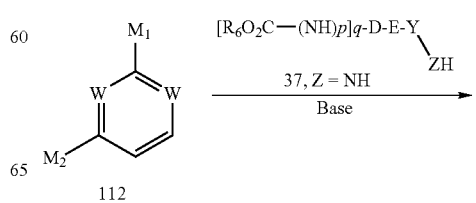

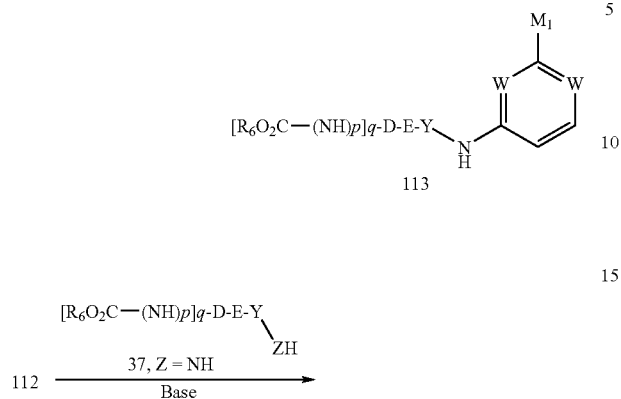

Scheme 19.2 illustrates the conversion of intermediates 113 into compounds of Formula I-115, I-118, or 117. Treatment of 113 with aqueous copper oxide or an alkaline hydroxide affords compounds of Formula I-115. Alternatively, treatment of 113 with t-butylmercaptan under copper(I) catalysis in the presence of ethylene glycol and potassium carbonate gives rise to 116 (see F. Y. Kwong and S. L. Buchwald, *Organic Letters* (2002) 4:3517. Treatment of the t-butyl sulfide 116 with acid affords the desired thiols of Formula I-118. Alternatively, 113 may be treated with excess ammonia under pressurized conditions to afford compound 117.

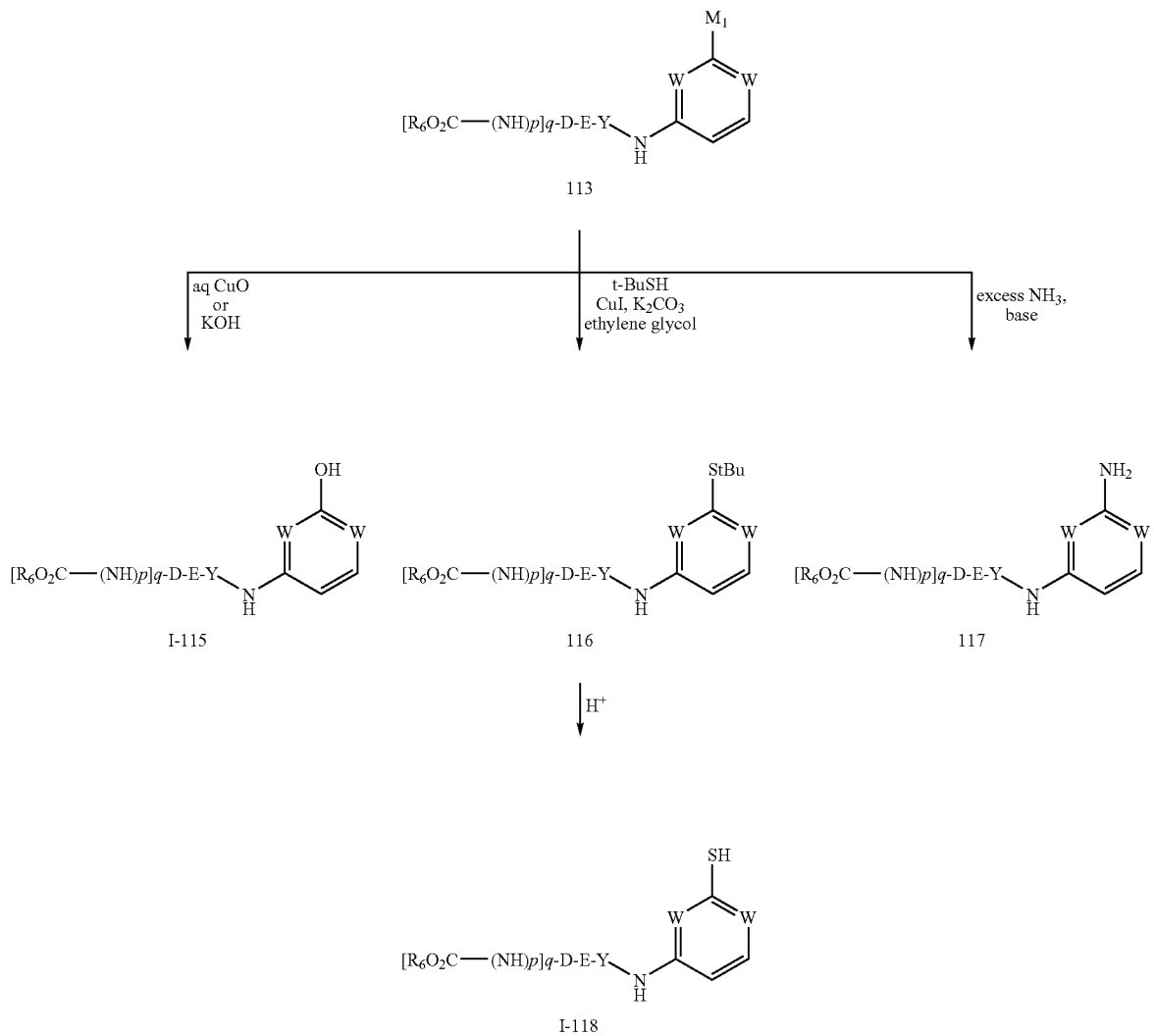

Scheme 19.3 illustrates the conversion of intermediate 114 into compounds of Formula I-119, I-122, and 121, by analogy to the sequence described in Scheme 19.2.

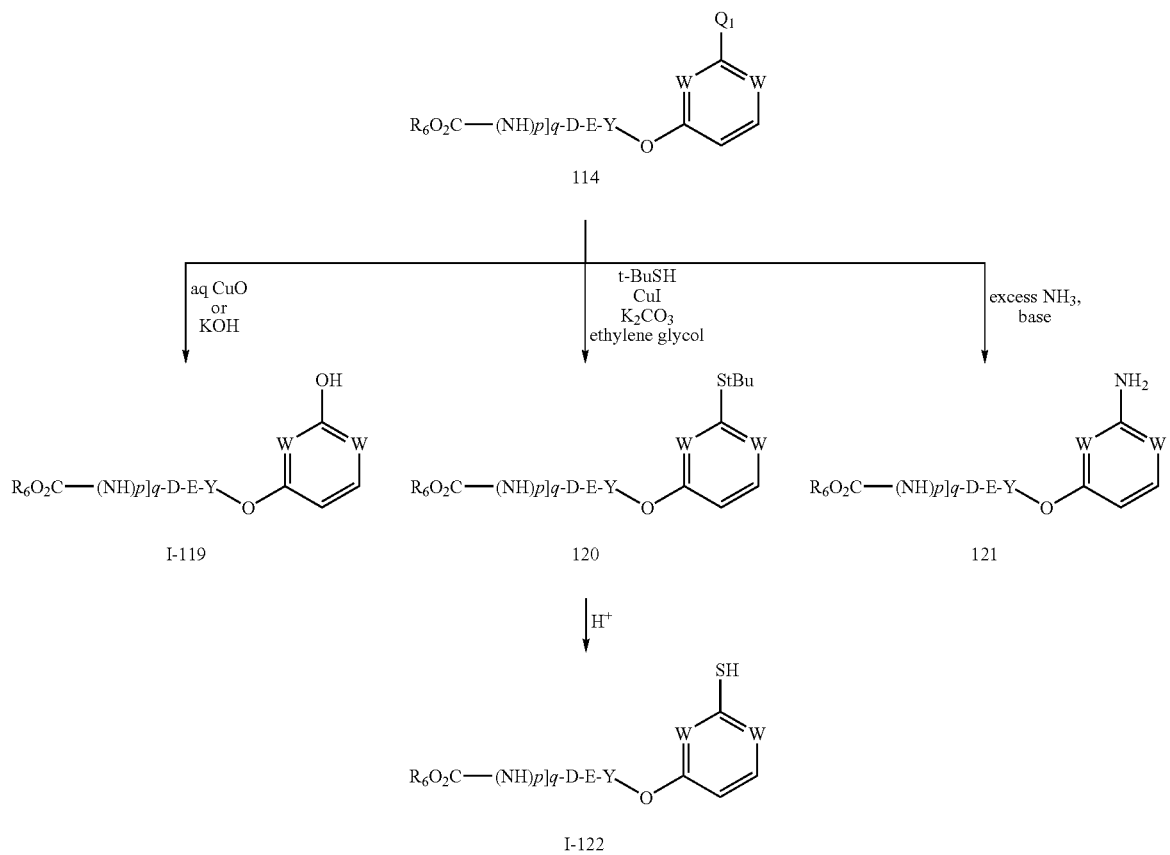

Compounds of Formula I wherein q is taken from Q-24, Q-25, or Q-26 are prepared as shown in Scheme 20. Reaction of compounds I-115 or I-119 with chlorosulfonylisocyanate, followed by in situ reaction with amines $HN(R_4)_2$ gives rise to compounds of Formulae I-123 or I-124. Reaction of compounds I-118 or I-122 with a peracid, preferably peracetic acid or trifluoroperacetic acid, affords compounds of Formula I-125 or I-126. Reaction of compounds 117 or 121 with chlorosulfonylisocyanate, followed by in situ reaction with amines $HN(R_4)_2$ or alcohols $R_4OH$, affords compounds of Formulae I-127, I-128, I-129, or I-130.

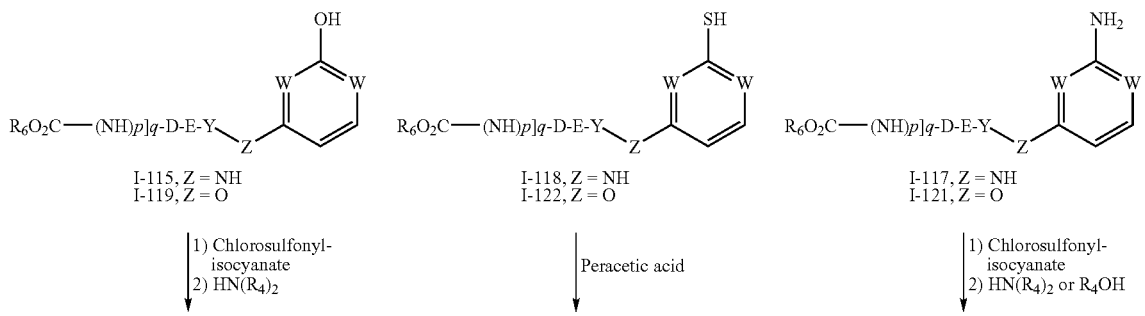

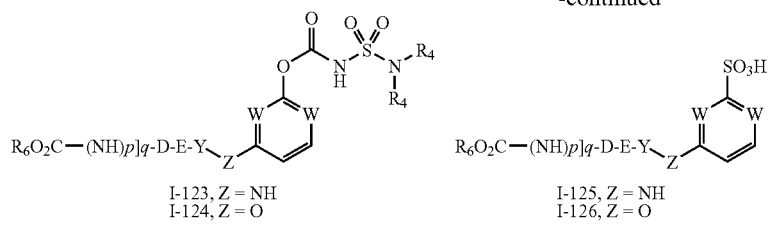

I-123, Z = NH
I-124, Z = O

I-125, Z = NH
I-126, Z = O

I-127, Z = NH
I-128, Z = O

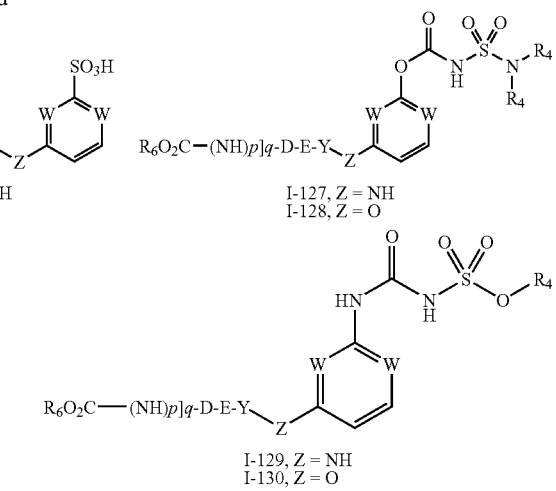

I-129, Z = NH
I-130, Z = O

Compounds of Formula I wherein Q is taken from Q-27 are prepared as illustrated in Scheme 21. Reductive alkylation of thiomorpholine with aldehydes 131 affords benzylic amines 132, which are then subjected to peracid oxidation to give rise to the thiomorpholine sulfones 133 (see C. R. Johnson et al, *Tetrahedron* (1969) 25: 5649). Intermediates 133 are reacted with amines 8 (Z=NH$_2$) under Buchwald palladium-catalyzed amination conditions to give rise to compounds of Formula I-134. Alternatively, compounds 133 are reacted with alcohols 8 (Z=OH) under Buchwald copper(I) catalyzed conditions to afford compounds of Formula I-135. Alternatively, intermediates 133 are reacted with alkenes under palladium(0)-catalyzed Heck reaction conditions to give compounds of Formula I-136. Compounds I-136 are optionally reduced to the corresponding saturated analogs I-137 by standard hydrogenation conditions or by the action of diimide.

Scheme 21

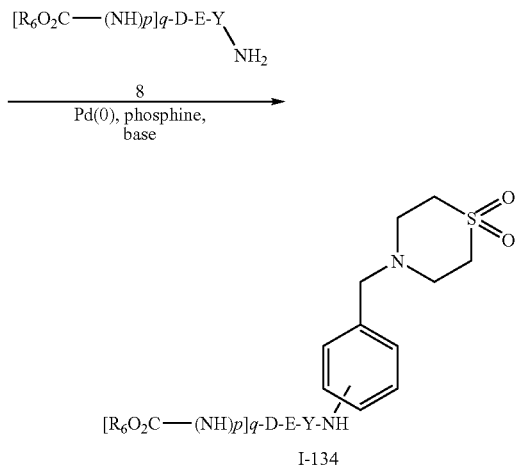

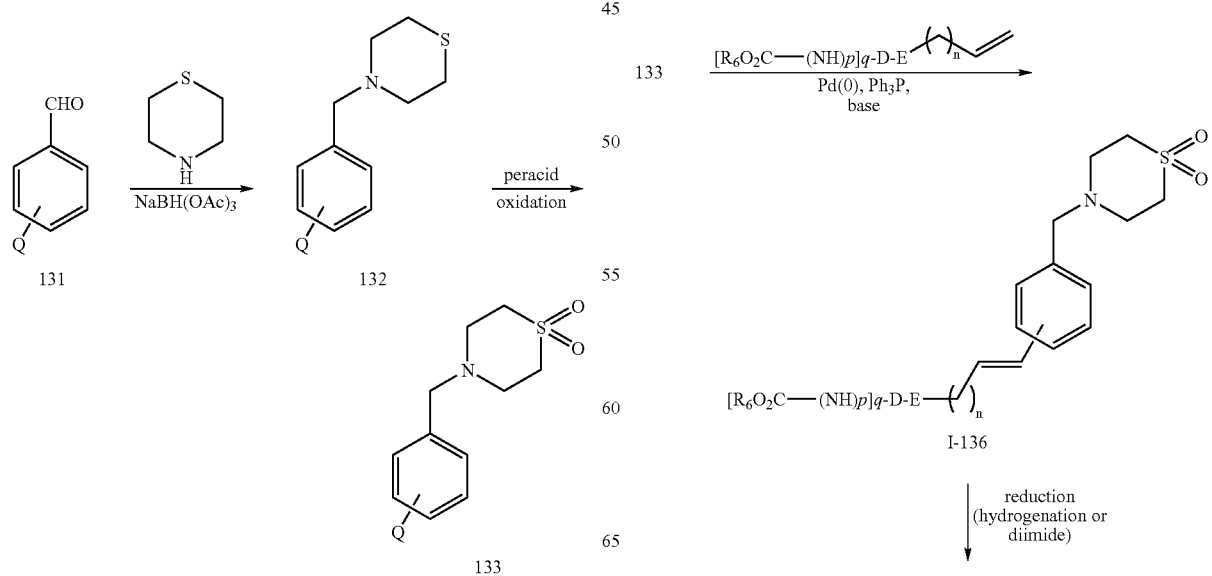

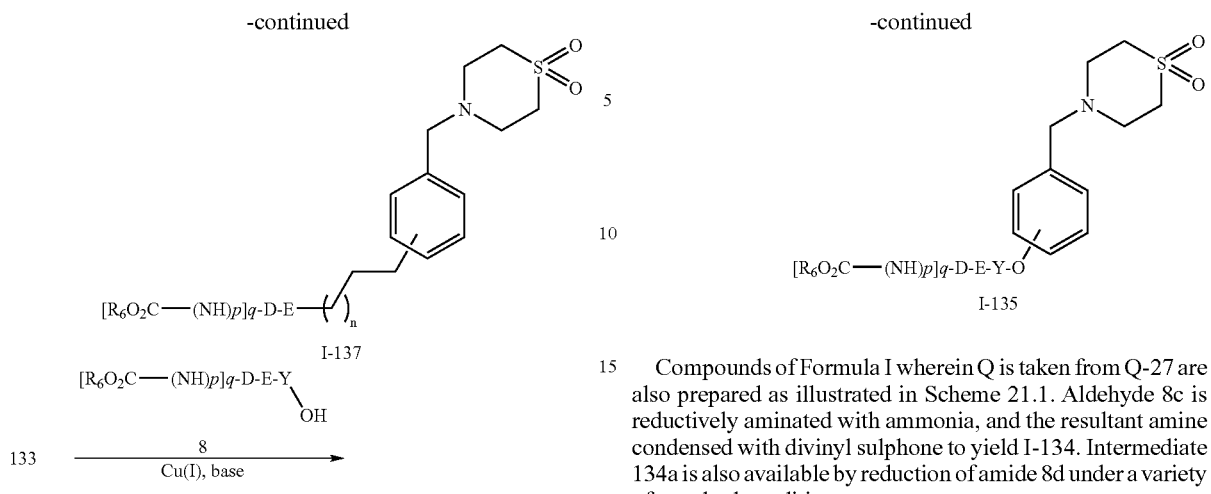

Compounds of Formula I wherein Q is taken from Q-27 are also prepared as illustrated in Scheme 21.1. Aldehyde 8c is reductively aminated with ammonia, and the resultant amine condensed with divinyl sulphone to yield I-134. Intermediate 134a is also available by reduction of amide 8d under a variety of standard conditions.

Scheme 21.1

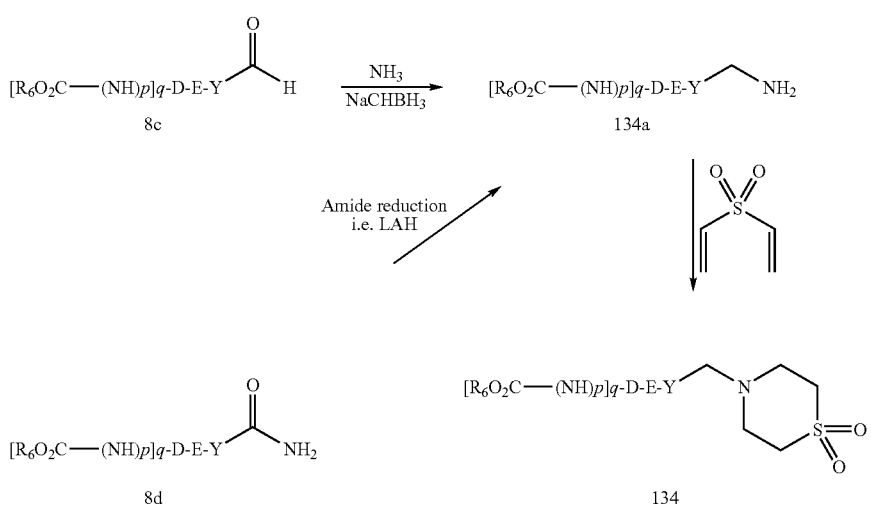

More generally, amines 134c are available via the reduction of amides 134b as shown in Scheme 21.2. The morpholine amide analogues 134d and morpholine analogues 134e are also available as shown in Scheme 21.2.

Scheme 21.2

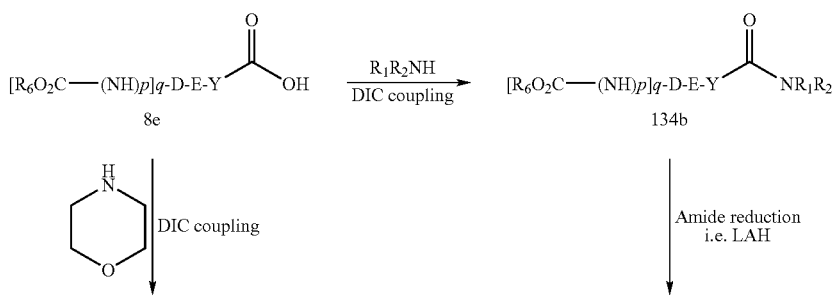

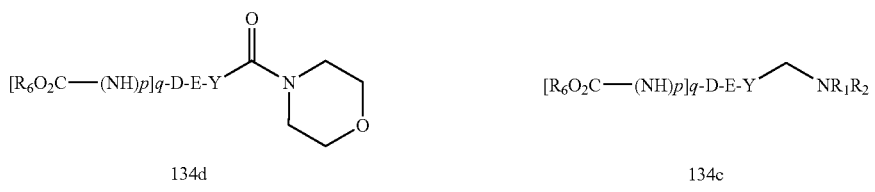

134d      134c

Amide reduction
i.e. LAH

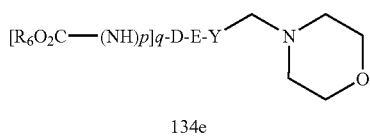

134e

Compounds of Formula I wherein Q is taken from Q-28 or Q-29 are prepared according to the sequences illustrated in Scheme 22. Readily available amides 138 are reacted with chlorosulfonylisocyanate to give intermediates 140, which are reacted in situ with amines $HN(R_4)_2$ or alcohols $R_4OH$ to afford compounds of Formulae I-141 or I-142, respectively. Alternatively, amides 138 are reacted with sulfonylchlorides to give compounds of Formula I-139.

Scheme 22

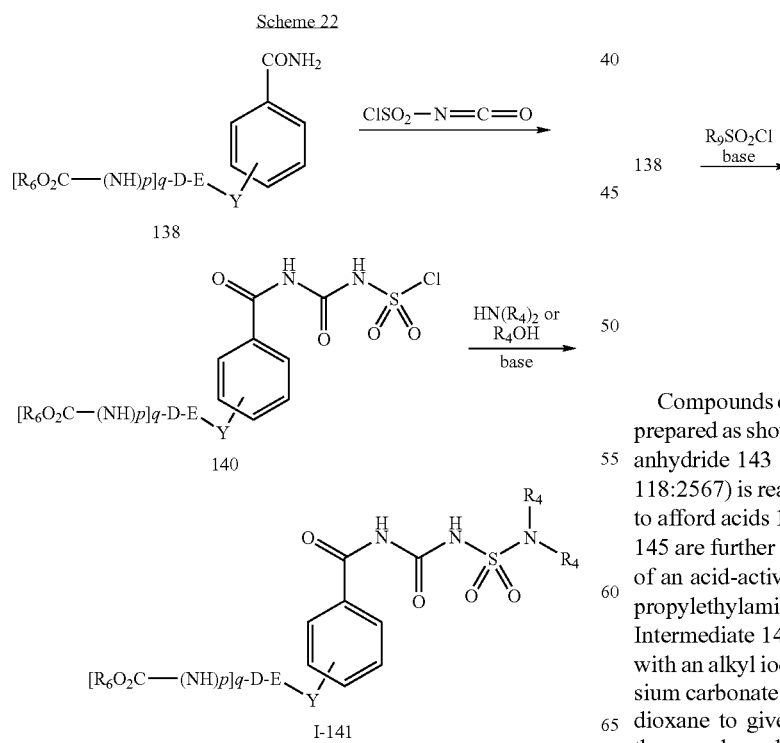

-continued

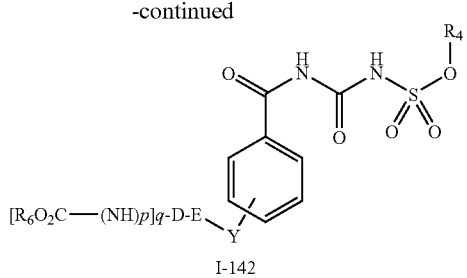

I-142

I-139

Compounds of Formula I wherein Q is taken from Q-30 are prepared as shown in Scheme 23. Readily available N—BOC anhydride 143 (see S. Chen et al, *J. Am. Chem. Soc.* (1996) 118:2567) is reacted with amines $HN(R_4)_2$ or alcohols $R_6OH$ to afford acids 144 or 145, respectively. Intermediates 144 or 145 are further reacted with amines $HN(R_4)_2$ in the presence of an acid-activating reagent, preferably PyBOP and di-isopropylethylamine, to give diamides 146 or ester-amides 147. Intermediate 145 is converted to the diesters 148 by reaction with an alkyl iodide in the presence of base, preferably potassium carbonate. Intermediates 146-148 are treated with HCl/dioxane to give the secondary amines 149-151, which are then condensed with acids 152 in the presence of PyBOP and di-isopropylethylamine to give compounds of Formula I-153.

Scheme 23

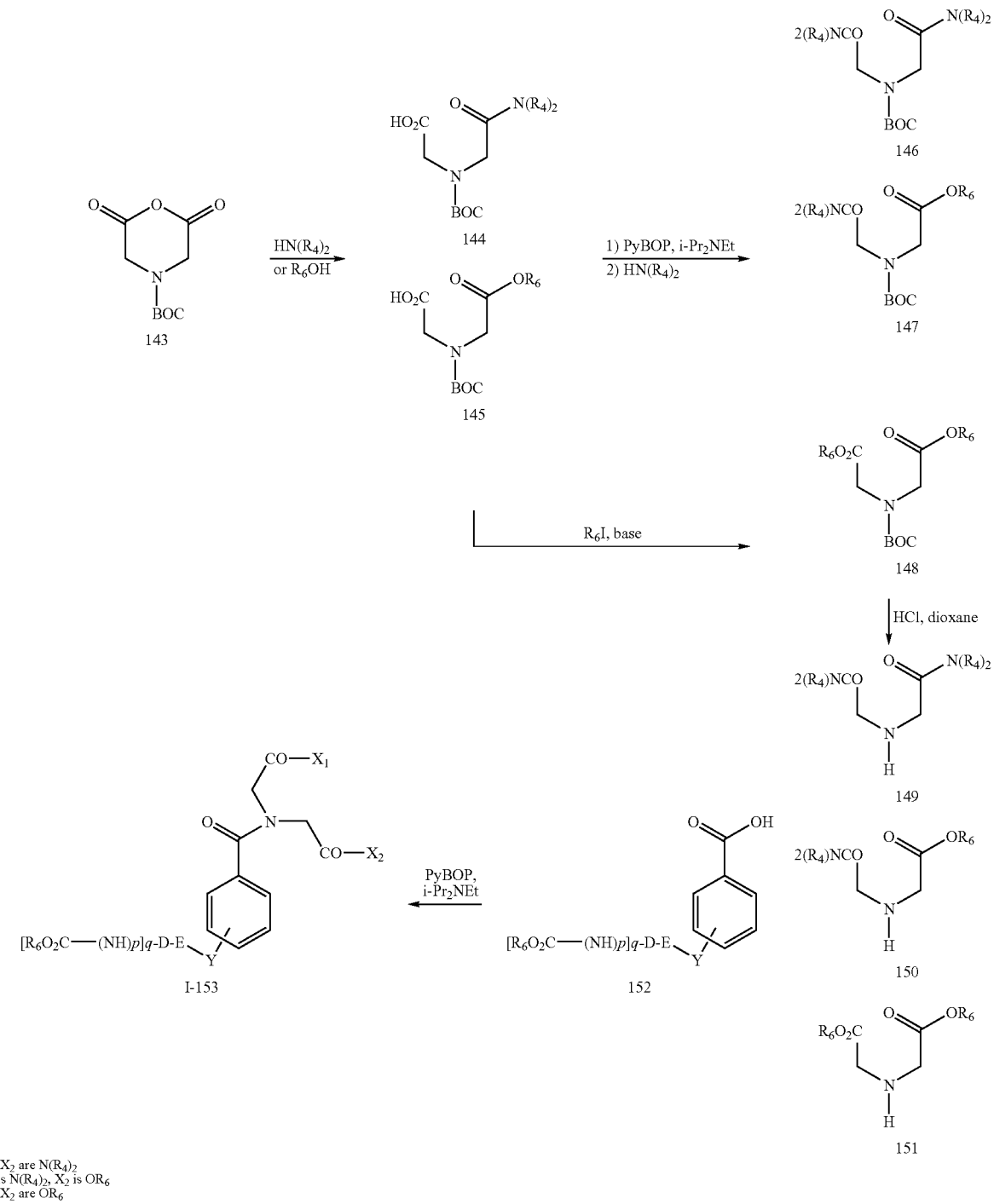

X₁, X₂ are N(R₄)₂
X₁ is N(R₄)₂, X₂ is OR₆
X₁, X₂ are OR₆

Compounds of Formula I wherein Q is taken from Q-31 or Q-32 are prepared according to the sequences illustrated in Scheme 24. Treatment of readily available sulfenamides 154 with amines 37 (Z=NH), alcohols 37 (Z=O), or alkenes 37 (Z=—CH=CH₂), gives rise to compounds of Formula I-155. Treatment of sulfenamides I-155 with iodosobenzene in the presence of alcohols R₆OH gives rise to the sulfonimidates of Formula I-157 (see D. Leca et al, *Organic Letters* (2002) 4:4093). Alternatively, compounds I-155 (Z=—CH=CH) may be optionally reduced to the saturated analogs I-156 (Z=CH₂—CH₂—), which are converted to the corresponding sulfonimidates I-157.

Treatment of readily available sulfonylchlorides 154.1 with amines HN(R₄)₂ and base gives rise to compounds of Formula I-154.2.

Scheme 24

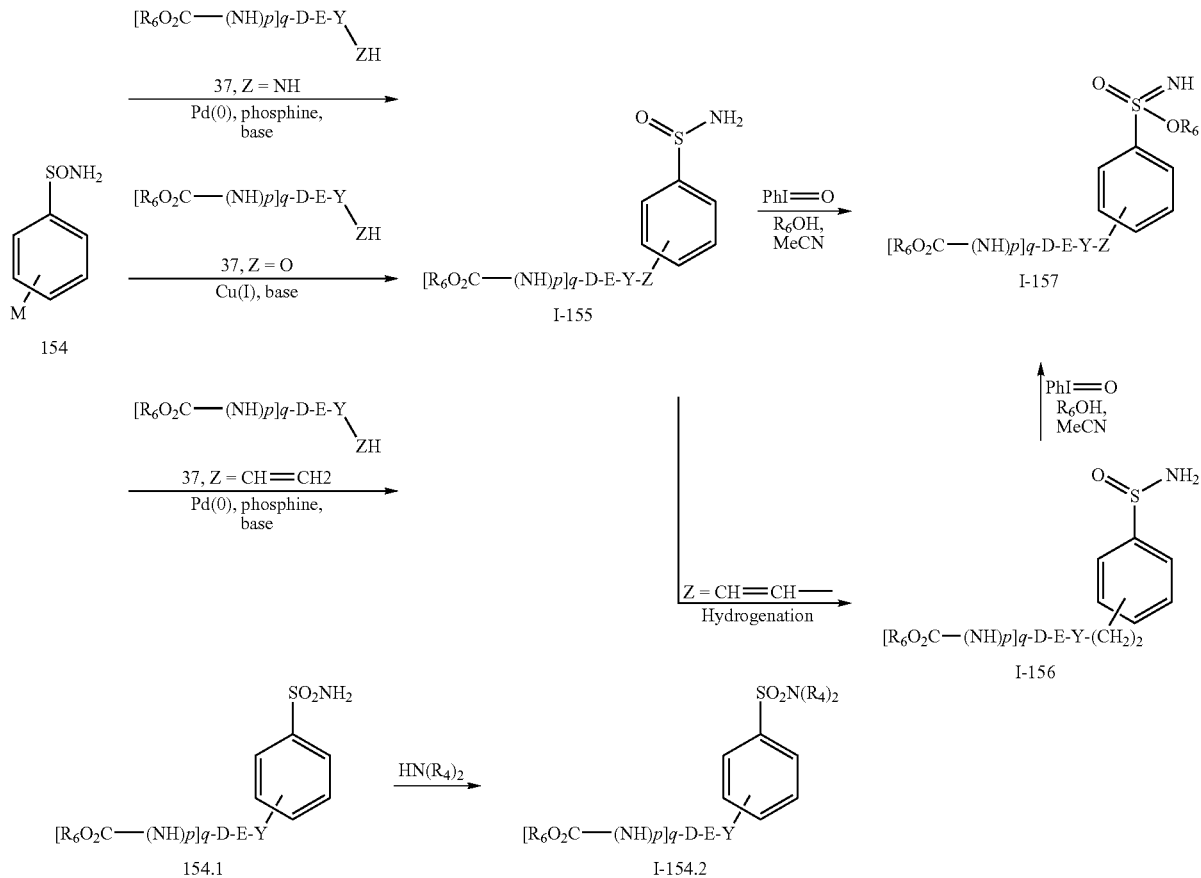

Compounds of Formula I wherein Q is taken from Q-33 are prepared as shown in Scheme 25. Readily available nitriles 158 are reacted with amines 37 (Z=NH), alcohols 37 (Z=O), or alkenes 37 (Z=―CH=CH₂) to afford compounds of Formula I-159. Compounds I-159 (wherein Z=CH=CH―) are optionally reduced to their saturated analogs I-160 by standard catalytic hydrogenation conditions. Treatment of compounds I-159 or I-160 with a metal azide (preferably sodium azide or zinc azide) gives rise to tetrazoles of Formula I-161.

Scheme 25

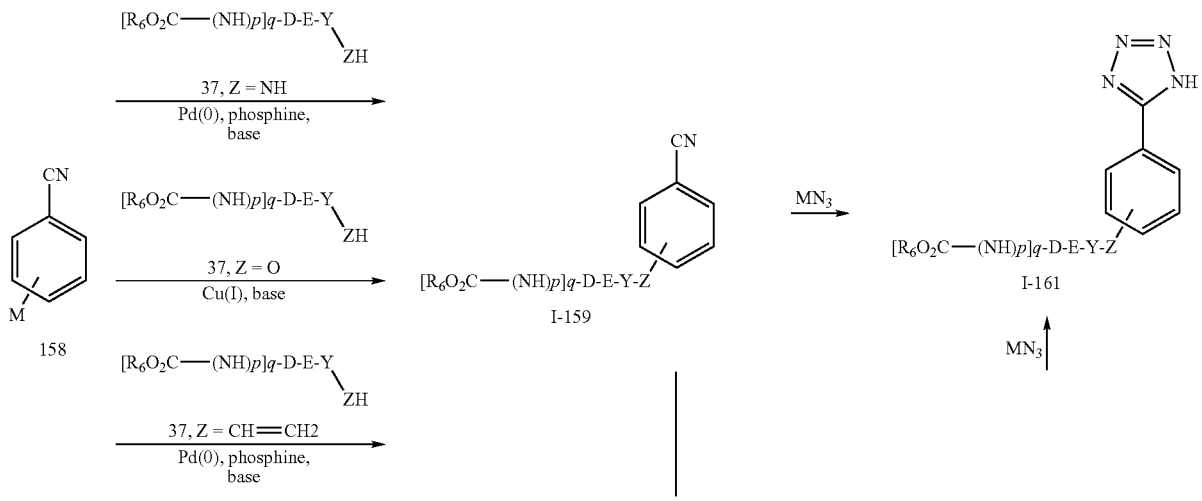

-continued

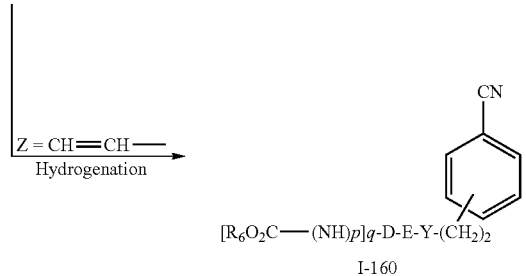

I-160

Compounds of Formula I wherein Q is taken from Q-34 are prepared as shown in Scheme 26. Readily available esters 162 are reacted with amines 37 (Z=NH), alcohols 37 (Z=O), or alkenes 37 (Z=—CH=CH$_2$) to afford compounds of Formula I-163. Compounds I-163 (wherein Z is —CH=CH—) are optionally converted to the saturated analogs I-164 by standard hydrogenation conditions. Compounds I-163 or I-164 are converted to the desired phosphonates I-165 by an Arbuzov reaction sequence involving reduction of the esters to benzylic alcohols, conversion of the alcohols to the benzylic bromides, and treatment of the bromides with a trialkylphosphite. Optionally, phosphonates I-165 are converted to the flourinated analogs I-166 by treatment with diethylaminosulfur trifluoride (DAST).

Scheme 26

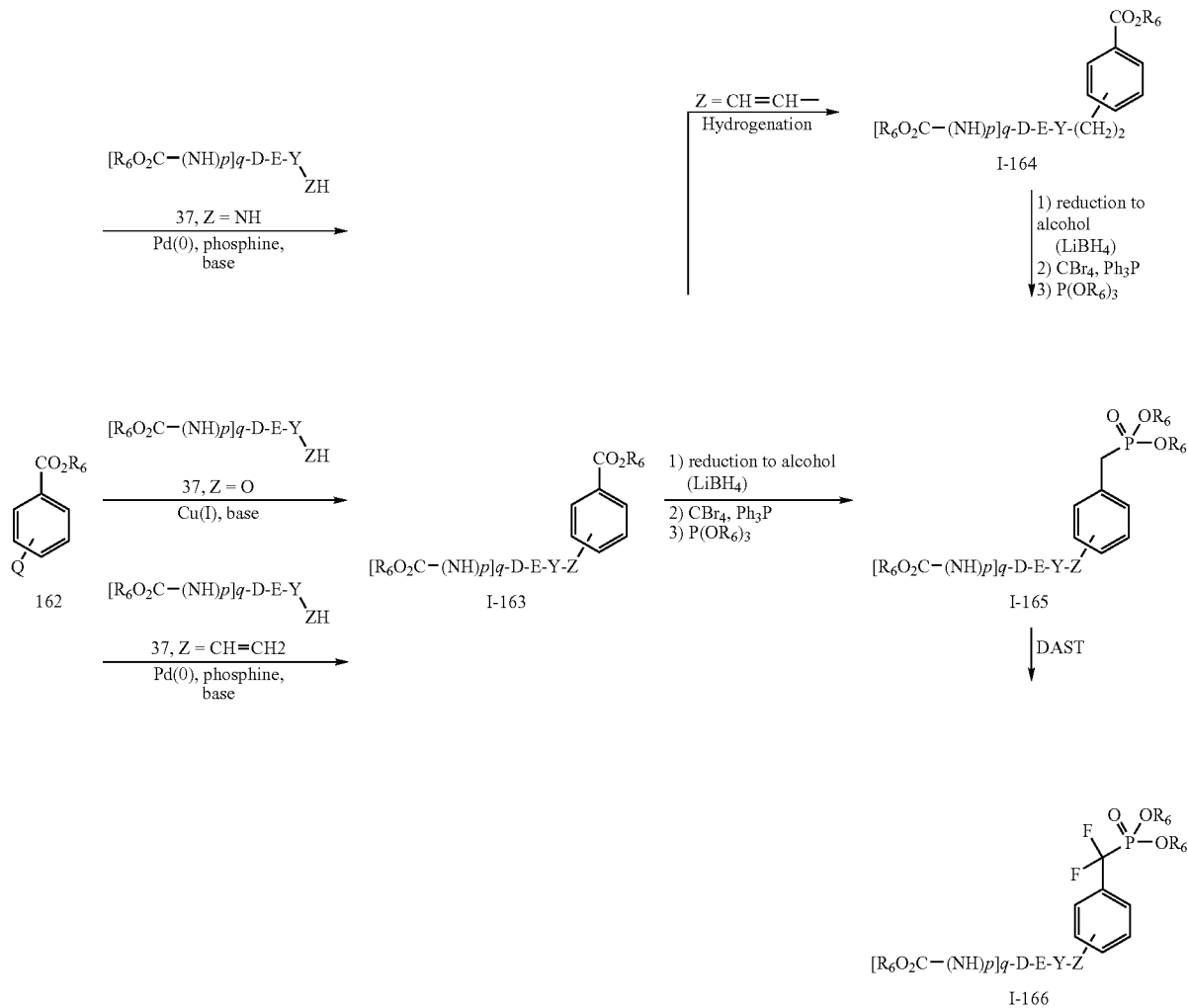

Compounds of Formula I wherein Q is taken from Q-35 are prepared according to Scheme 27. Readily available acid chlorides 167 are reacted with oxazolidones in the presence of base to afford the N-acyl oxazolidinones 168. Intermediate 168 are reacted with amines 37 (Z=NH), alcohols 37 (Z=O), or alkenes 37 (Z=—CH=CH$_2$) to afford the N-acyl oxazolidinones of Formula I-169. Compounds I-169 (wherein Z is —CH=CH—) are optionally converted to the saturated analogs I-170 under standard hydrogenation conditions.

Compounds of Formula I wherein Q is taken from Q-36 are prepared as illustrated in Schemes 28.1 and 28.2. Reductive alkylation of the t-butylsulfide substituted piperazines with the readily available aldehydes 131 gives rise to the benzylic piperazines 171. Intermediates 171 are reacted with amines 37 (Z=NH), alcohols 37 (Z=O), or alkenes 37 (Z=—CH=CH$_2$) to give compounds 172, 173, or 174, respectively. Optionally, intermediates 174 are converted to the saturated analogs 175 under standard hydrogenation conditions.

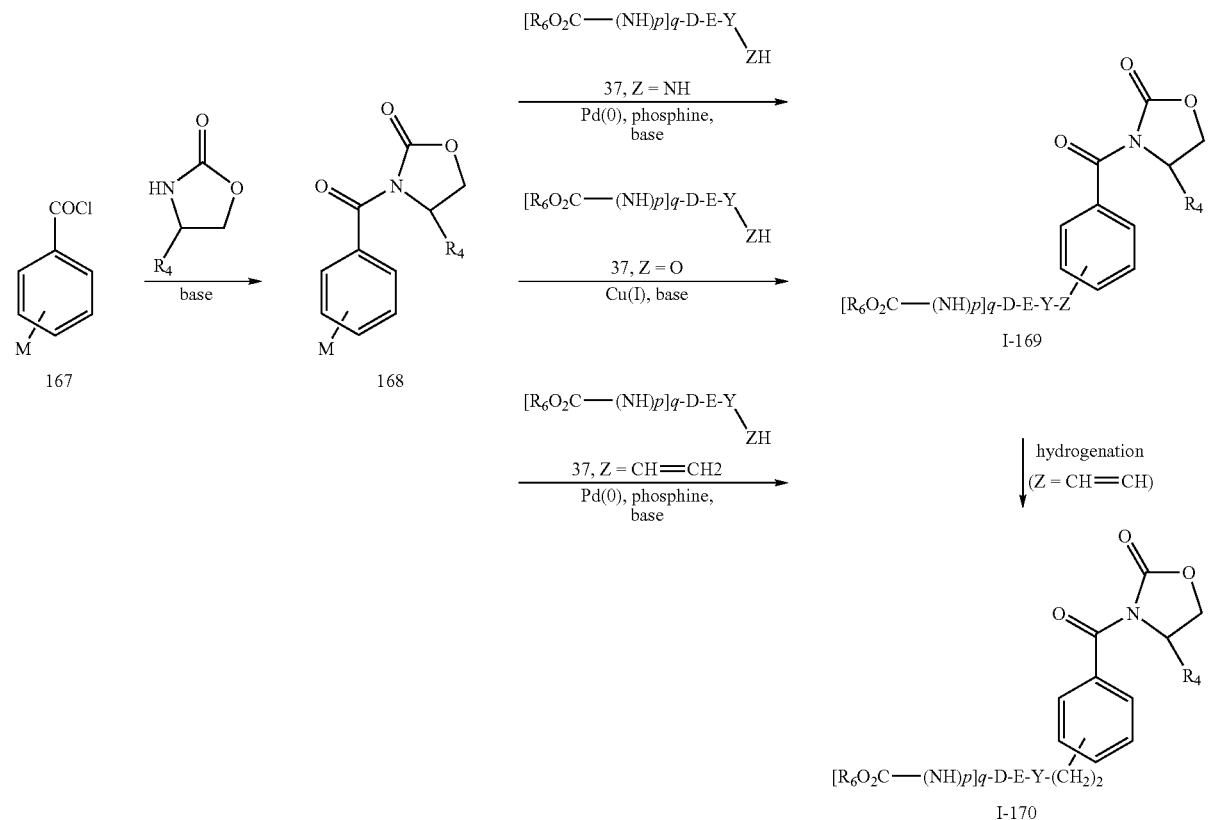

Compounds of Formula I wherein Q is taken from Q-35 are also prepared as illustrated in Scheme 27.1. Intermediate 8a, wherein M is a suitable leaving group such as chloride, bromide or iodide, is refluxed with triethyl phosphite and the resulting phosphoryl intermediate saponified under mild conditions to yield I-165.

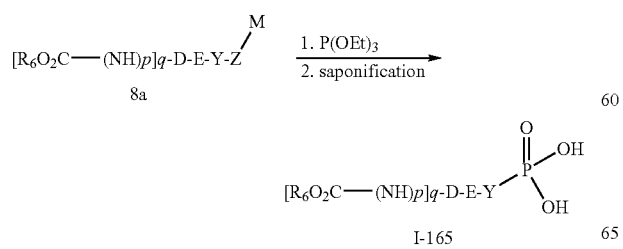

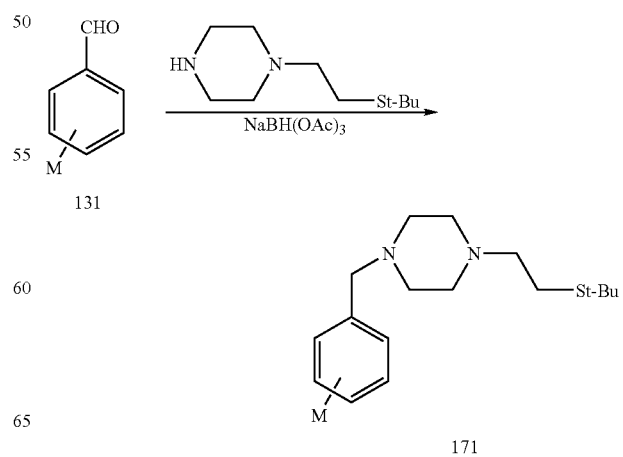

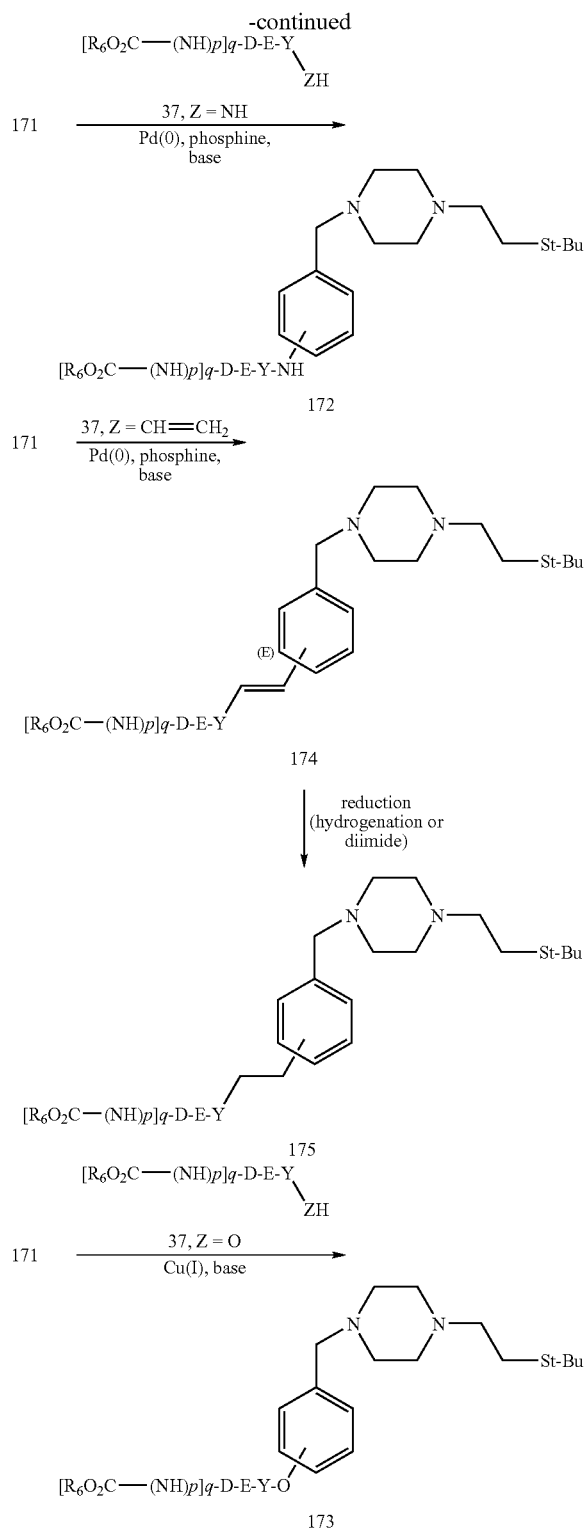

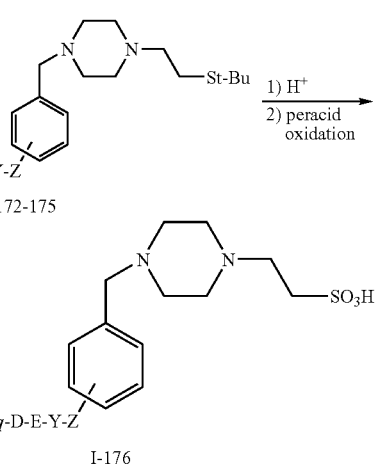

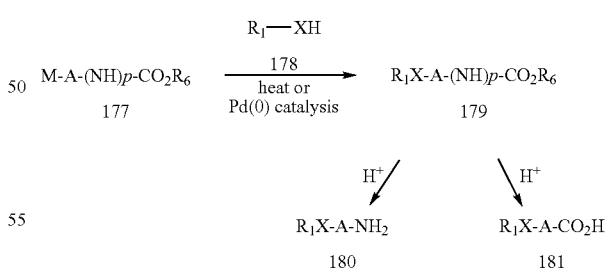

Scheme 28.2 illustrates the conversion of intermediate t-butylsulfides 172-175 to the sulfonic acids, employing a two step process involving acid-catalyzed deprotection of the t-butyl sulfide to the corresponding mercaptans, and subsequent peracid oxidation (preferably with peracetic acid or trifluoroperacetic acid) of the mercaptans to the desired sulfonic acids of Formula I-176.

In some instances a hybrid p38-alpha kinase inhibitor is prepared which also contains an ATP-pocket binding moiety or an allosteric pocket binding moiety $R_1$—X-A. The synthesis of functionalized intermediates of formula $R_1$—X-A are accomplished as shown in Scheme 29. Readily available intermediates 177, which contain a group M capable of oxidative addition to palladium(0), are reacted with amines 178 (X=NH) under Buchwald Pd(0) amination conditions to afford 179. Alternatively amines or alcohols 178 (X=NH or O) are reacted thermally with 177 in the presence of base under nuclear aromatic substitution reaction conditions to afford 179. Alternatively, alcohols 178 (X=O) are reacted with 177 under Buchwald copper(I)-catalyzed conditions to afford 179. In cases where p=1, the carbamate of 179 is removed, preferably under acidic conditions when $R_6$ is t-butyl, to afford amines 180. In cases where p=0, the esters 179 are converted to the acids 181 preferably under acidic conditions when $R_6$ is t-butyl.

Another sequence for preparing amines 180 is illustrated in Scheme 30. Reaction of amines or alcohols 178 with nitro (hetero)arenes 182 wherein M is a leaving group, preferably M is fluoride, or M is a group capable of oxidative insertion into palladium(0), preferably M is bromo, chloro, or iodo, gives intermediates 183. Reduction of the nitro group under standard hydrogenation conditions or treatment with a reducing metal, such as stannous chloride, gives amines 180.

Scheme 30

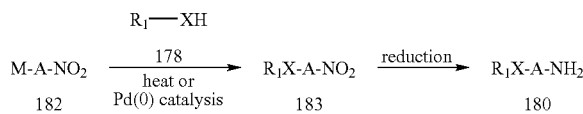

In instances when hybrid p38-alpha kinase inhibitors are prepared, compounds of Formula I-184 wherein q is 1 may be converted to amines I-185 (p=1) or acids I-186 (p=0) by analogy to the conditions described in Scheme 29. Compounds of Formula I-184 are prepared as illustrated in previous schemes 1.1, 2.1, 2.2, 3, 4, 5, 6, 7.1, 7.2, 8, 9, 10, 12, 14, 16.2, 17.2, 18, 19.1, 19.2, 19.3, 20, 21, 22, 23, 24, 25, 26, 27, or 28.2.

Scheme 31

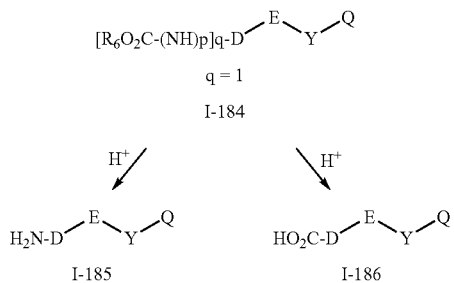

Compounds I-184 are taken from schemes 1.1, 2.1, 2.2, 3, 4, 5, 6, 7.1, 7.2, 8, 9, 10, 12, 14, 16.2, 17.2, 18, 19.1, 19.2, 19.3, 20, 21, 22, 23, 24, 25, 26, 27, 28.2

The preparation of inhibitors of Formula I which contain an amide linkage —CO—NH— connecting the oxyanion pocket binding moieties and $R_1$—X-A moieties are shown in Scheme 32. Treatment of acids 181 with an activating agent, preferably PyBOP in the presence of di-isopropylethylamine, and amines 1-185 gives compounds of Formula I. Alternatively, retroamides of Formula I are formed by treatment of acids I-186 with PyBOP in the presence of di-iso-propylethylamine and amines 180.

Scheme 32

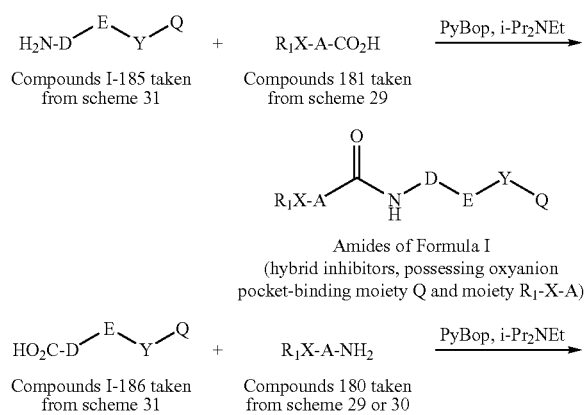

-continued

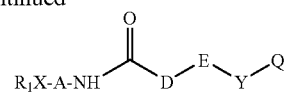

RetroamideFormula I
(hybrid inhibitors, possessing oxyanion pocket-binding moiety Q and moiety $R_1$-X-A)

The preparation of inhibitors of Formula I which contain an urea linkage NH—CO—NH— connecting the oxyanion pocket binding moieties and the $R_1$—X-A moieties are shown in Scheme 33. Treatment of amines 1-185 with p-nitrophenyl chloroformate and base affords carbamates 187. Reaction of 187 with amines 180 gives ureas of Formula I.

Scheme 33

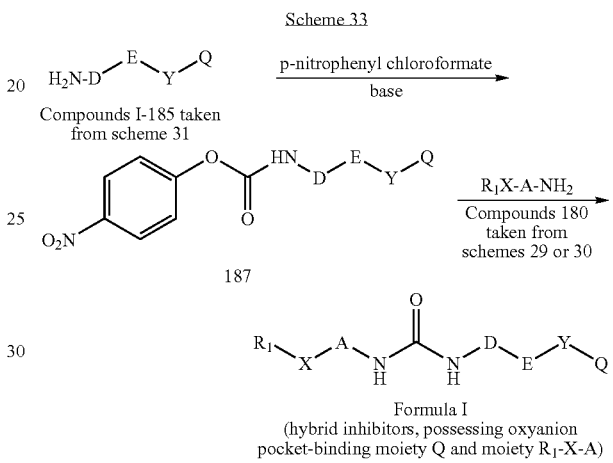

Formula I
(hybrid inhibitors, possessing oxyanion pocket-binding moiety Q and moiety $R_1$-X-A)

Alternatively, inhibitors of Formula I which contain an urea linkage NH—CO—NH— connecting the oxyanion pocket binding moieties and the $R_1$—X-A moieties are prepared as shown in Scheme 33. Treatment of amines 180 with p-nitrophenyl chloroformate and base affords carbamates 188. Reaction of 188 with amines I-185 gives ureas of Formula I.

Scheme 34

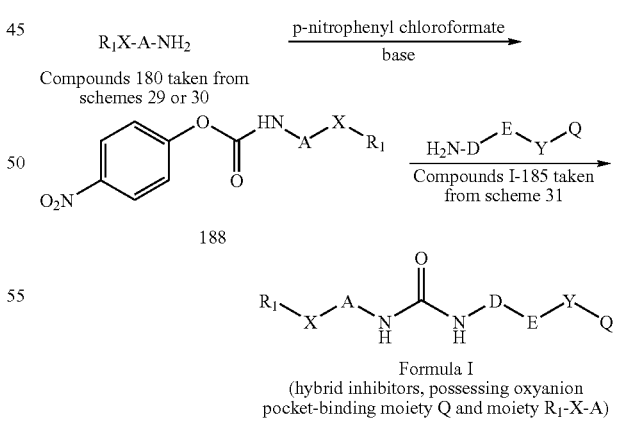

Formula I
(hybrid inhibitors, possessing oxyanion pocket-binding moiety Q and moiety $R_1$-X-A)

The preparation of inhibitors of Formula I.B can be generally accomplished starting from a variety of readily available beta-ketonitriles 189, wherein $R_{40}$ is alkyl, phenyl, or perfluoroalkyl. As illustrated in Scheme 35, reaction of 189 with an alcohol $R_4OH$, preferably methanol or ethanol, under anhydrous acidic conditions, preferably anhydrous HCl, leads to the formation of imidates 190. Reaction of 190 with acyl chlorides, isocyanates, para-nitrophenylcarbamates, or substituted chloroformates in the presence of a base, preferably pyridine, triethylamine, di-iso-propylethylamine, Barton's base, or an alkali metal carbonate, affords key intermediates 191 and 192 as a mixture of tautomers, wherein T is alkylene, NH, O, or when T is absent, then the carbonyl side chain and A are connected by a direct bond.

tively, the reaction sequence initiating from 190 and yielding 194 may take place in a one-pot procedure, without isolation of the intermediate 191/192 mixture.

In a further modification, the reaction sequence initiating from 190 and yielding 194 may take place in a parallel array format, wherein phase-trafficking reagents, including scavenging reagents, are utilized to allow purification and isola- Scheme 35

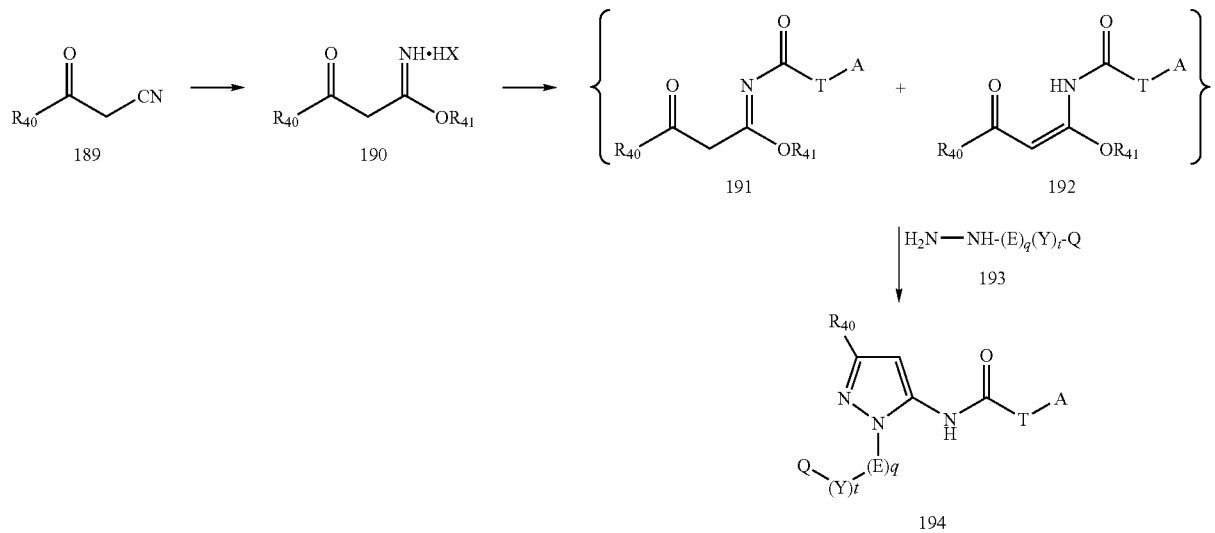

The mixture of tautomers 191/192 are not separated from each other, but are reacted as a mixture with a substituted hydrazine 193, wherein the Q moiety is optionally protected by a protecting group that diminishes its reactivity with the 191/192 mixture. This cyclodehydration reaction is performed in the presence of base, acid catalysis, or under neutral conditions optionally in the presence of a dehydrating agent to afford the desired pyrazoles 194. Preferable reaction solvents include dichloromethane, ethyl acetate, acetonitrile, or an alcoholic solvent taken from methanol, ethanol, or 2-propanol.

The reaction sequence initiating from 190 and yielding 194 may take place as two separate reactions, wherein the tautomeric mixture 191/192 is isolated, and then in a second reaction step this 191/192 mixture is reacted with a substituted hydrazine 193 to afford the desired pyrazoles 194. Alternation of intermediates and products. Scheme 36 illustrates this modification. Excess imidate 190 is reacted with a limiting amount of electrophile in the presence of a polymer-supported base 195 to afford the acylated imidates 191/192 as a mixture of tautomers. The crude mixture of 191/192 is optionally purified by incubation with a polymer-supported electrophile 196, preferably a polymer-supported isocyanate or acid chloride. Reaction of 196 with any remaining imidate 190 sequesters this imidate as polymer-supported 197. Filtration gives purified 191/192. In the second step, purified acylated imidates 191/192 are reacted with the substituted hydrazines 193 to afford desired crude products 194. A polymer-supported hydrazine 198 is optionally utilized to scavenge any remaining 191/192 from solution phase as derivatized 199. Filtration gives rise to purified desired pyrazoles 194.

Scheme 36

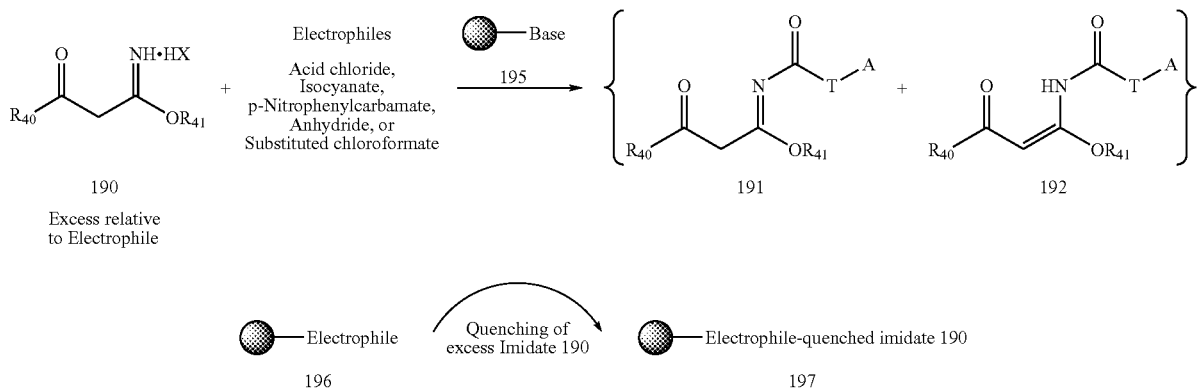

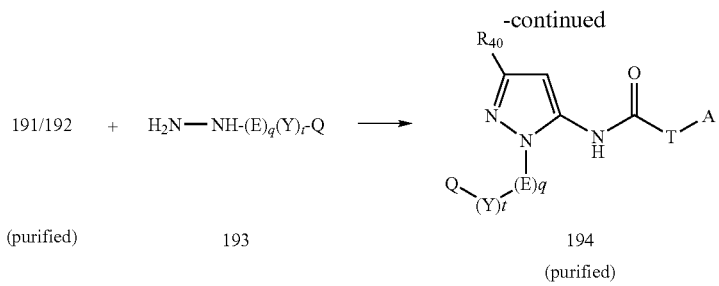

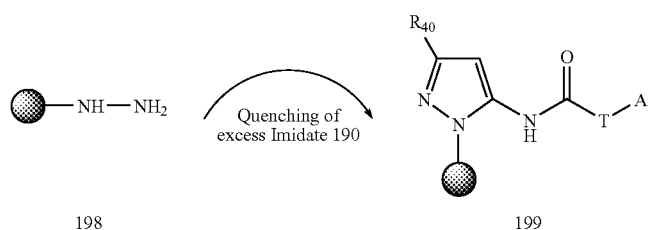

Scheme 37 illustrates the preparation of compounds wherein Q is Q-40. Readily available amine 200, wherein P is a suitable amine-protecting group or a group convertible to an amine group, is reacted with p-nitrophenyl chloroformate to give rise to carbamate 201. Intermediate 201 is reacted with a substituted amino acid ester with a suitable base to afford urea 202. Further treatment with base results in cyclization to afford hydantoin 203. The protecting group P is removed to afford the key amine-containing intermediate 204. Alternatively, if P is a nitro group, then 203 is converted to 204 under reducing conditions such as iron/HCl, tin(II) chloride, or catalytic hydrogenation. Amine 204 is converted to 205A by reaction with an isocyanate; 204 is converted to amide 205B by reaction with an acid chloride, acid anhydride, or a suitable activated carboxylic acid in the presence of a suitable base; 204 is converted to carbamate 205C by reaction with a substituted alkyl or aryl chloroformate in the presence of a suitable base.

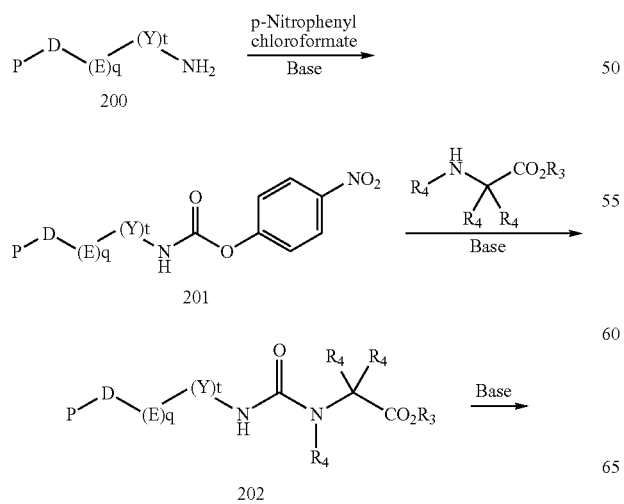

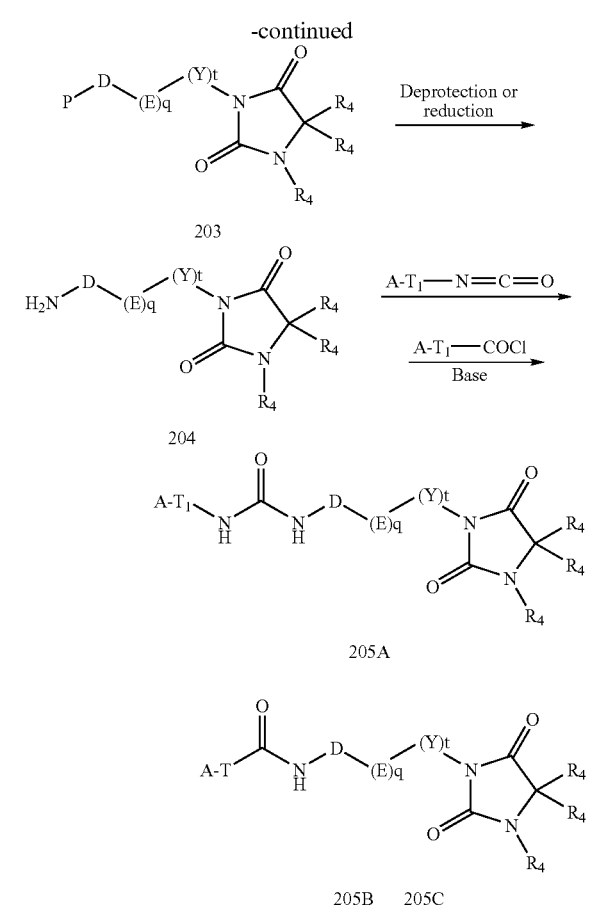

Scheme 38 illustrates the synthesis of key substituted hydrazine 210. This hydrazine can be converted into compounds of formula I.B using the methods previously outlined in Schemes 35 and 36. The nitrophenyl substituted amine 206 is reacted with p-nitrophenyl chloroformate to give rise to carbamate 207. Reaction of 207 with a suitable amino acid ester affords urea 208, which is cyclized under basic conditions to give hydantoin 209. Reduction of the nitro group of 209, diazotization of the resulting amine, and reduction of the diazonium salt affords key hydrazine 210.

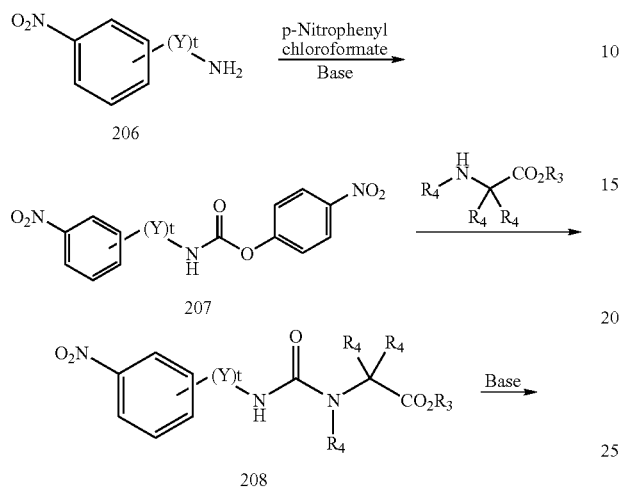

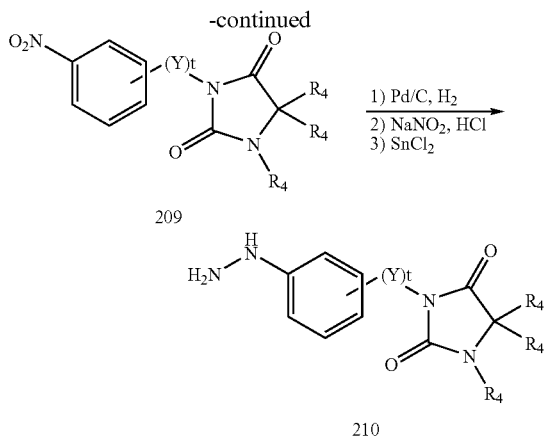

Scheme 39 illustrates the synthesis of key substituted hydrazines 213 and 216, utilized to prepare compounds of formula I.B wherein Q is Q-42 and G is oxygen. Nitrophenol 211 is reacted with an alpha-hydroxy acid, wherein $R_{42}$ is H or alkyl and $R_{43}$ is alkyl, under Mitsunobu reaction conditions to give 212; alternatively 211 is reacted under basic conditions with a carboxylic acid ester containing a displaceable $Q_x$ group to afford 212. Conversion of 212 to the hydrazine 213 is accomplished by standard procedures as described above.

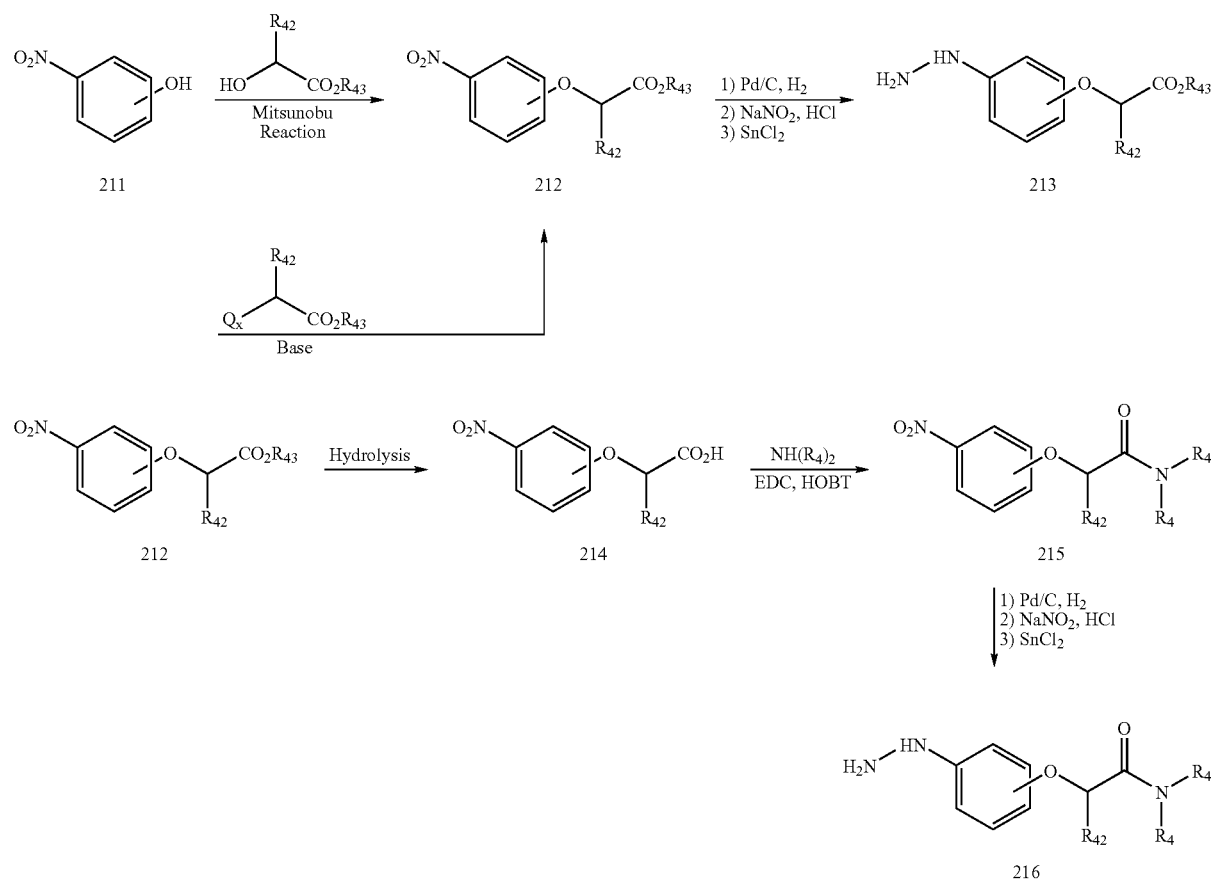

Alternatively, the ester group of 212 is hydrolyzed to afford carboxylic acid 214, which is reacted with an amine NH(R$_4$)$_2$ in the presence of a coupling reagent, preferably EDC/HOBT, to give amide 215. Conversion of 215 to the substituted hydrazine 216 is accomplished by standard procedures. Hydrazines 213 and 216 can be converted into compounds of formula I.B using the methods previously outlined in Schemes 35 and 36.

Scheme 40 illustrates the synthesis of key substituted hydrazines 219 and 222, utilized to prepare compounds of formula I.B wherein Q is Q-42 and G is methylene. Nitrophenyl bromide 217 is reacted with an alpha-beta unsaturated ester using Pd(0) catalyzed Heck reaction conditions, to afford ester 218. This intermediate is converted to the substituted hydrazine 219 by standard procedures involving concomitant reduction of the alpha-beta unsaturated bond. Alternatively, ester 218 is hydrolyzed to the carboxylic acid 220, which is reacted with an amine NH(R$_4$)$_2$ in the presence of a coupling reagent, preferably EDC/HOBT, to give amide 221. Conversion of 221 to the substituted hydrazine 222 is accomplished by standard procedures. Hydrazines 219 and 222 can be converted into compounds of formula I.B using the methods previously outlined in Schemes 35 and 36.

-continued

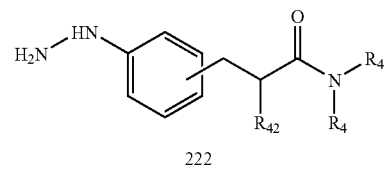

222

Scheme 41 illustrates an alternative synthesis of key substituted hydrazines 225 and 228, utilized to prepare compounds of formula I.B wherein Q is Q-42, G is methylene, and one or both of R$_{42}$ are carbon-containing substituents. Nitrobenzyl acetate 223 is reacted with a substituted silylketene acetal to afford ester 224. This intermediate is converted to the substituted hydrazine 225 by standard procedures. Alternatively, ester 223 is hydrolyzed to the carboxylic acid 226, which is reacted with an amine NH(R$_4$)$_2$ in the presence of a coupling reagent, preferably EDC/HOBT, to give amide 227. Conversion of 227 to the substituted hydrazine 228 is accomplished by standard procedures. Hydrazines 225 and 228 can be converted into compounds of formula I.B using the methods previously outlined in Schemes 35 and 36.

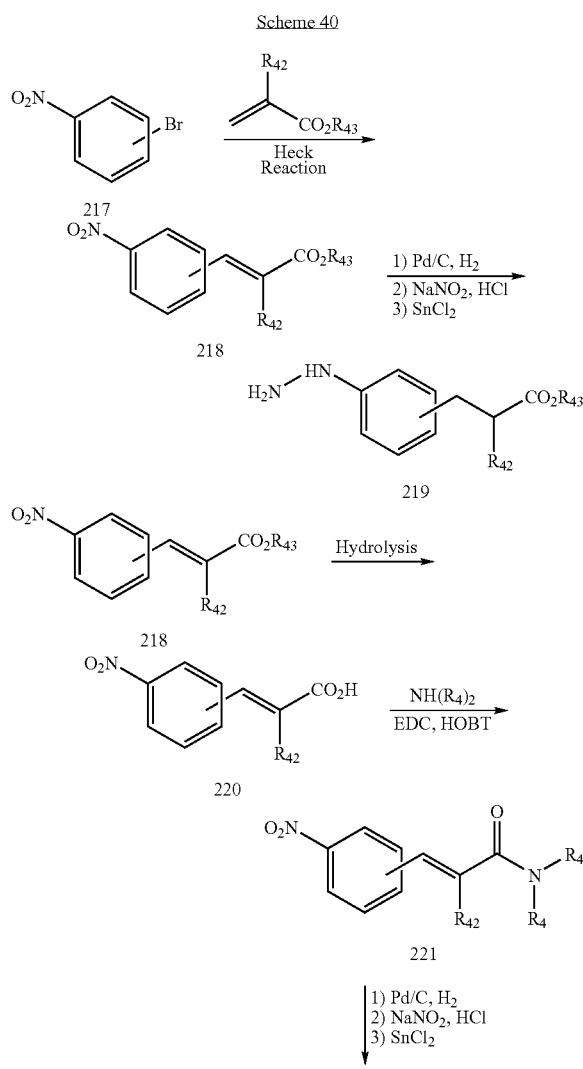

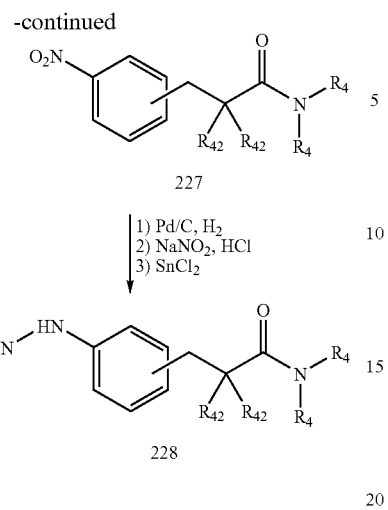

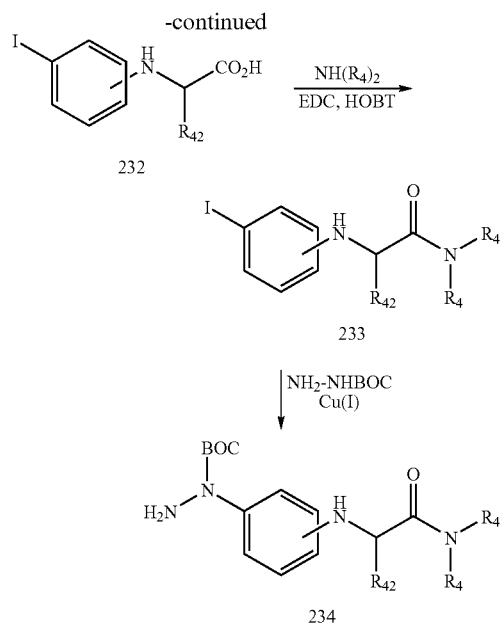

Scheme 42 illustrates an alternative synthesis of key substituted hydrazines 231 and 234, utilized to prepare compounds of formula I.B wherein Q is Q-42 and G is NH. Iodoaniline 229 is reacted with an alpha-keto ester under reductive amination conditions, preferably sodium triacetoxyborohydride, to afford ester 230. This intermediate is converted to the substituted hydrazine 231 by Cu(I)-catalyzed reaction with N—BOC hydrazine. Alternatively, ester 231 is hydrolyzed to the carboxylic acid 232, which is reacted with an amine $NH(R_4)_2$ in the presence of a coupling reagent, preferably EDC/HOBT, to give amide 233. Conversion of 233 to the substituted hydrazine 234 is accomplished by Cu(I)-catalyzed reaction with N—BOC hydrazine. Hydrazines 231 and 234 can be converted into compounds of formula I.B using the methods previously outlined in Schemes 35 and 36, after acid-catalyzed removal of the hydrazine N—BOC protecting group, preferably with trifluoroacetic acid or HCl-dioxane.

Scheme 43 illustrates an alternative synthesis of key substituted hydrazine 239, utilized to prepare compounds of formula I.B wherein Q is Q-42, G is oxygen, and X is taken from piperidinyl, piperazinyl, thiomorphorlino sulfone, or 4-hydroxypiperinyl. Iodophenol 235 is reacted with an alpha-hydroxy acid under Mitsunobu reaction conditions to give 236; alternatively 235 is reacted under basic conditions with a carboxylic acid ester containing a displaceable $Q_x$ group to afford 236. Ester 236 is hydrolyzed to the carboxylic acid 237, which is reacted with an amine X—H in the presence of a coupling reagent, preferably EDC/HOBT, to give amide 238. Conversion of 238 to the substituted hydrazine 239 is accomplished by Cu(I)-catalyzed reaction with N—BOC hydrazine. Hydrazine 239 can be converted into compounds of formula I.B using the methods previously outlined in Schemes 35 and 36, after acid-catalyzed removal of the hydrazine N—BOC protecting group, preferably with trifluoroacetic acid or HCl-dioxane.

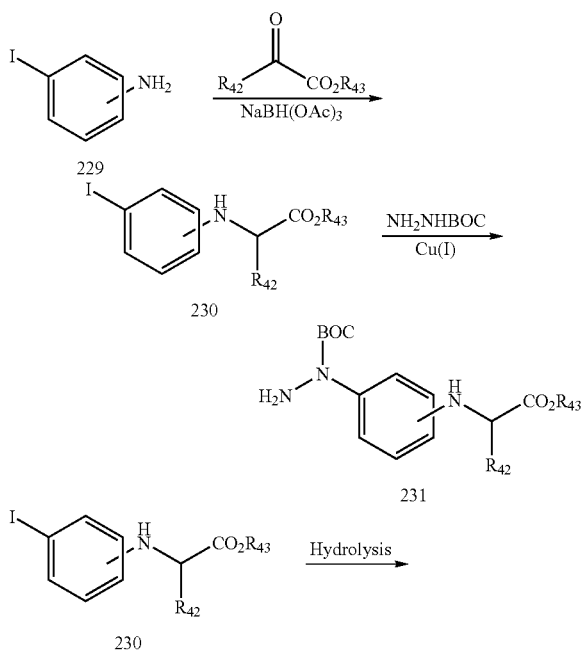

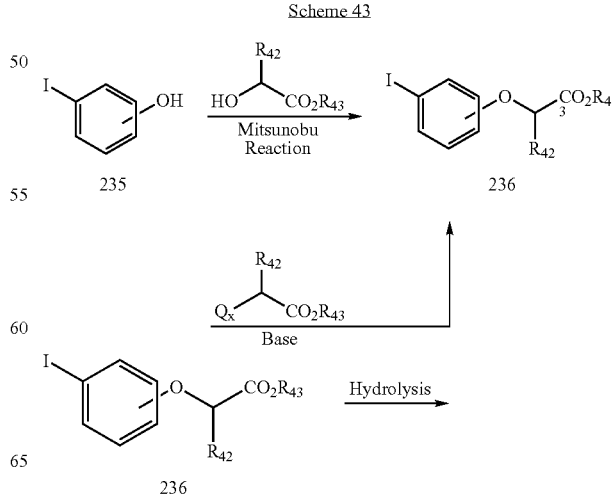

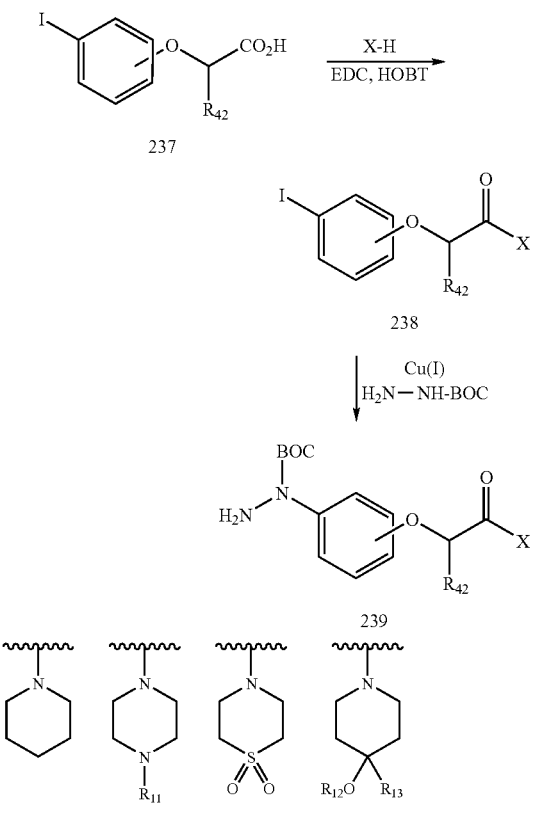

Scheme 44 illustrates an alternative synthesis of key substituted hydrazine 241, utilized to prepare compounds of formula I.B wherein Q is Q-42, G is NH, and X is taken from piperidinyl, piperazinyl, thiomorphorlino sulfone, or 4-hydroxypiperinyl. Carboxylic acid 237 is reacted with an amine X—H in the presence of a coupling reagent, preferably EDC/HOBT, to give amide 240. Conversion of 240 to the substituted hydrazine 241 is accomplished by Cu(I)-catalyzed reaction with N—BOC hydrazine. Hydrazine 241 can be converted into compounds of formula I.B using the methods previously outlined in Schemes 35 and 36, after acid-catalyzed removal of the hydrazine N—BOC protecting group, preferably with trifluoroacetic acid or HCl-dioxane.

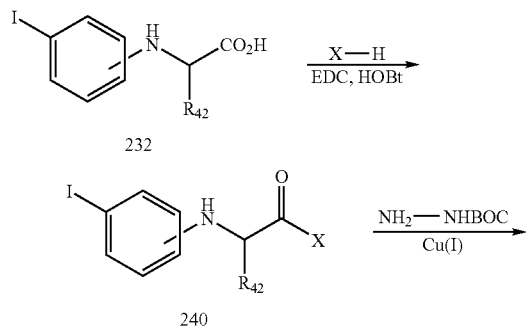

Scheme 45 illustrates an alternative synthesis of key substituted hydrazine 246, utilized to prepare compounds of formula I.B wherein Q is Q-42, G is methylene, and X is taken from piperidinyl, piperazinyl, thiomorphorlino sulfone, or 4-hydroxypiperinyl. Iodobenzyl acetate 242 is reacted with a substituted silylketene acetal to afford ester 243. Ester 243 is hydrolyzed to the carboxylic acid 244, which is reacted with an amine X—H in the presence of a coupling reagent, preferably EDC/HOBT, to give amide 245. Conversion of 245 to the substituted hydrazine 246 is accomplished by Cu(I)-catalyzed reaction with N—BOC hydrazine. Hydrazine 246 can be converted into compounds of formula I.B using the methods previously outlined in Schemes 35 and 36, after acid-catalyzed removal of the hydrazine N—BOC protecting group, preferably with trifluoroacetic acid or HCl-dioxane.

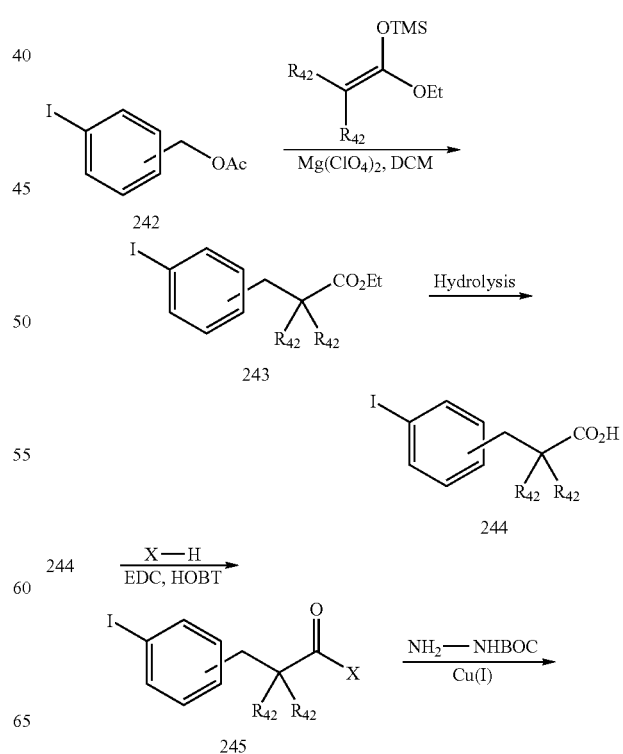

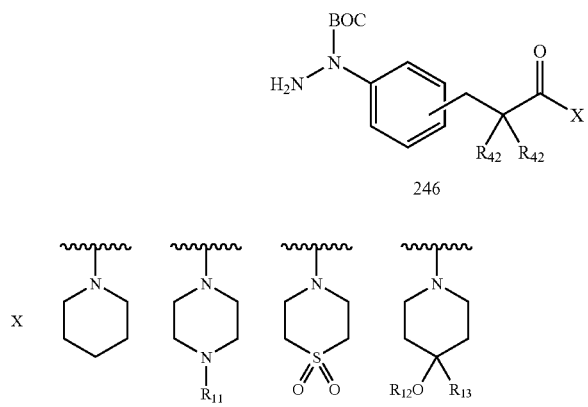

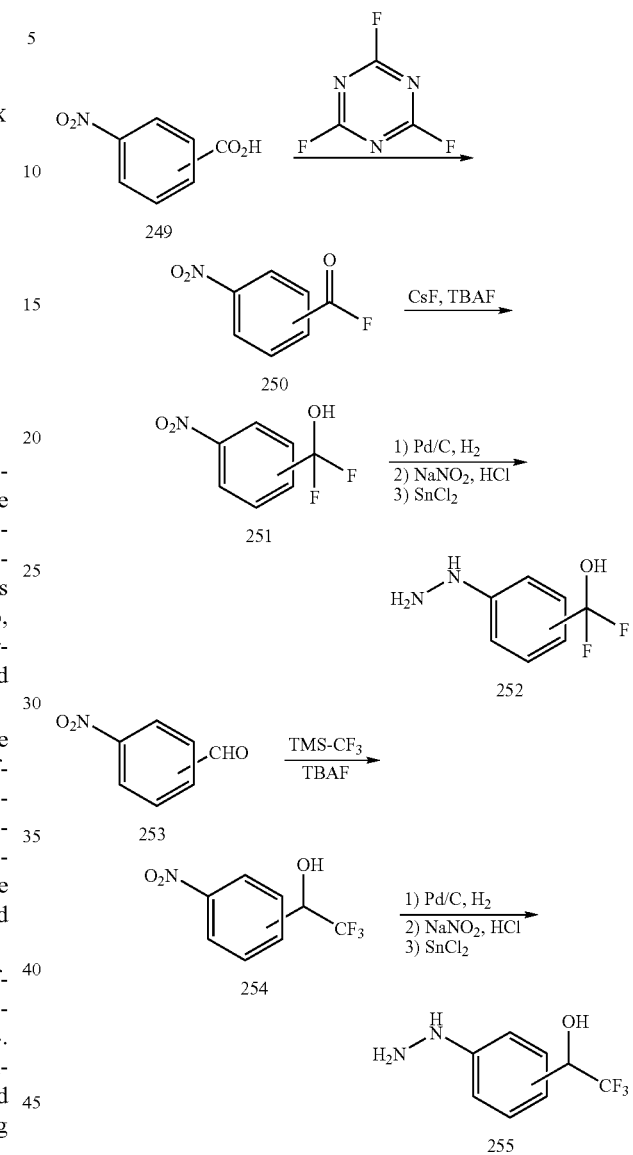

Scheme 46 illustrates an alternative synthesis of key substituted hydrazines 248, 252, and 255; utilized to prepare compounds of formula I.B wherein Q is Q-47 or Q-48. Nitrophenol 211 is reacted with a substituted alcohol under Mitsunobu reaction conditions to afford 247; alternatively 211 is alkylated with $R_4$-$Q_x$, wherein $Q_x$ is a suitable leaving group, under basic reaction conditions, to give rise to 247. Conversion of 247 to the substituted hydrazine 248 is accomplished under standard conditions.

The nitrobenzoic acid 249 is converted to the acid fluoride 250 by reaction with a fluorinating reagent, preferably trifluorotriazine. Treatment of acid fluoride 250 with a nucleophilic fluoride source, preferably cesium fluoride and tetra-n-butylammonium fluoride, affords the alpha-alpha-difluorosubstituted carbinol 251. Conversion of 251 to the substituted hydrazine 252 is accomplished under standard conditions.

Nitrobenzaldehyde 253 is reacted with trimethylsilyltrifluoromethane (TMS-$CF_3$) and tetra-n-butylammonium fluoride to give rise to trifluoromethyl-substituted carbinol 254. Conversion of 254 to the substituted hydrazine 255 is accomplished under standard conditions. Hydrazines 248, 252, and 255 can be converted into compounds of formula I.B using the methods previously outlined in Schemes 35 and 36.

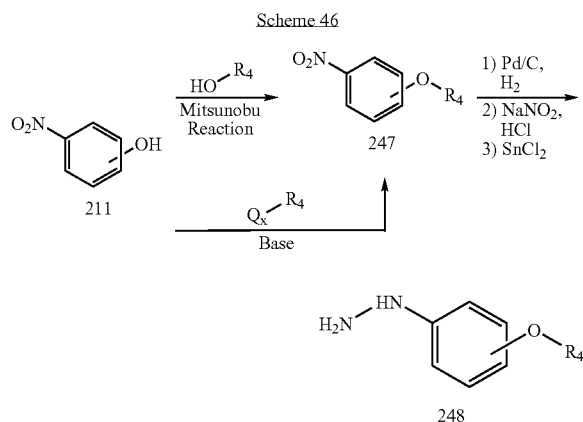

Scheme 47 illustrates the preparation of compounds of formula I.B wherein Q is Q-59. p-Nitrophenylcarbamate 201 is reacted with a substituted alpha-hydroxy ester with a suitable base to afford carbamate 256. Further treatment with base results in cyclization to afford oxazolidinedione 257. The protecting group P is removed to afford the key amine-containing intermediate 258; alternatively, if P is a nitro group, then 257 is converted to 258 under reducing conditions such as iron/HCl, tin(II) chloride, or catalytic hydrogenation. Amine 258 is converted to 259A by reaction with an isocyanate wherein T1 is alkylene or a direct bond connecting A and the carbonyl moiety; 258 is converted to amide 259B by reaction with an acid chloride, acid anhydride, or a suitable activated carboxylic acid in the presence of a suitable base; 258 is converted to carbamate 259C by reaction with a substituted alkyl or aryl chloroformate in the presence of a suitable base.

117

Scheme 47

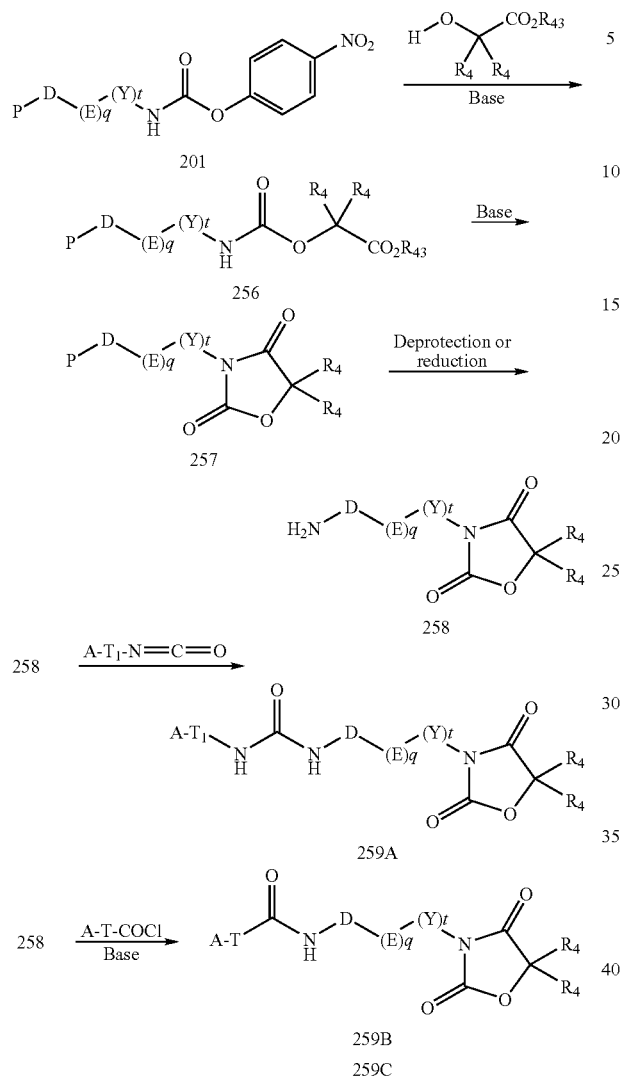

Scheme 48 illustrates an alternative approach to the preparation of compounds of formula I.B wherein Q is Q-59. Amine 260 is reacted with p-nitrophenylchloroformate under basic conditions to give rise to carbamate 261. This intermediate is reacted with an alpha-hydroxy ester in the presence of base to afford carbamate 262. Further treatment with base converts 262 into the oxazolidinedione 263. Conversion of 263 to the substituted hydrazine 264 is accomplished by standard procedures. Hydrazine 264 can be converted into compounds of formula I.B using the methods previously outlined in Schemes 35 and 36.

Scheme 48

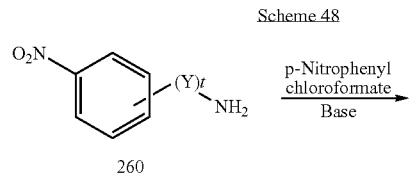

118

-continued

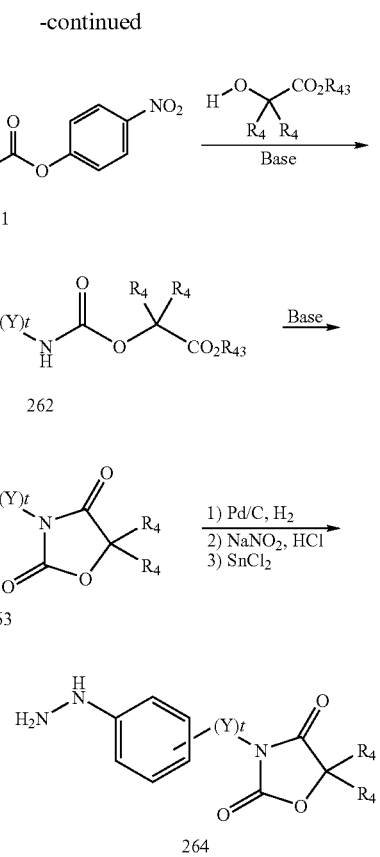

Scheme 49 illustrates the approach to the preparation of compounds of formula I.B wherein Q is Q-57. Amine 265 is reacted with p-methoxybenzylisocyanate under standard conditions to give rise to urea 266. This intermediate is reacted with an oxalyl chloride in the presence of base to afford trione 267. Conversion of 267 to the substituted hydrazine 268 and removal of the p-methoxybenzyl protecting group is accomplished by standard procedures. Hydrazine 264 can be converted into compounds of formula I.B using the methods previously outlined in Schemes 35 and 36.

Scheme 49

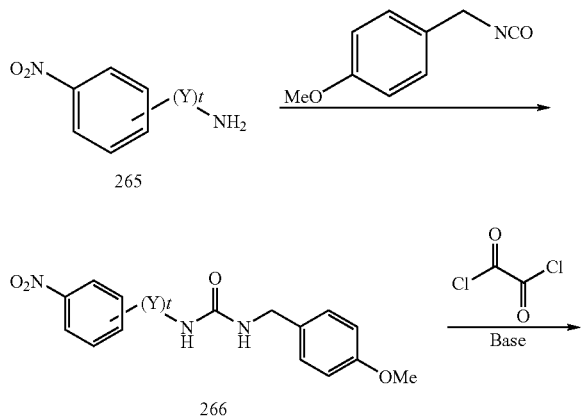

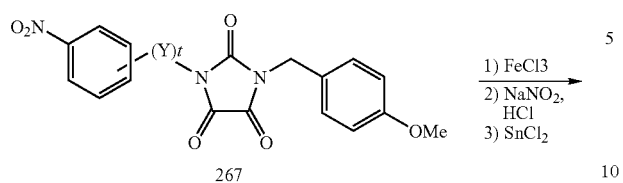

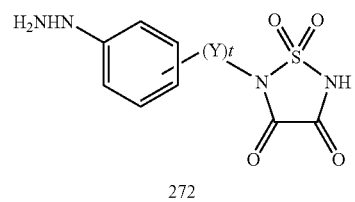

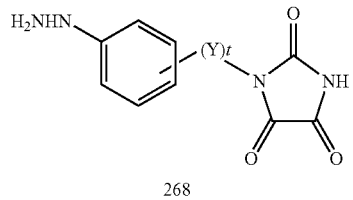

Scheme 51 illustrates an approach to the preparation of compounds of formula I.B wherein Q is Q-58. Amine 273 is reacted with a cyclic anhydride e.g. succinic anhydride in the presence of base under standard conditions to give rise to imide 274. Conversion of 274 to the substituted hydrazine 275 is accomplished by standard procedures. Hydrazine 275 can be converted into compounds of formula I.B using the methods previously outlined in Schemes 35 and 36.

Scheme 50 illustrates an approach to the preparation of compounds of formula I.B wherein Q is Q-56. Amine 269 is reacted with p-methoxybenzylsulfonylchloride under standard conditions to give rise to sulfonylurea 270. This intermediate is reacted with an oxalyl chloride in the presence of base to afford the cyclic sulfonyl urea 271. Conversion of 271 to the substituted hydrazine 272 and removal of the p-methoxybenzyl protecting group is accomplished by standard procedures. Hydrazine 272 can be converted into compounds of formula I.B using the methods previously outlined in Schemes 35 and 36.

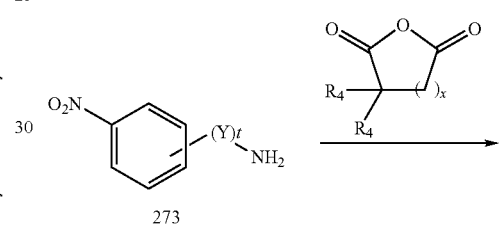

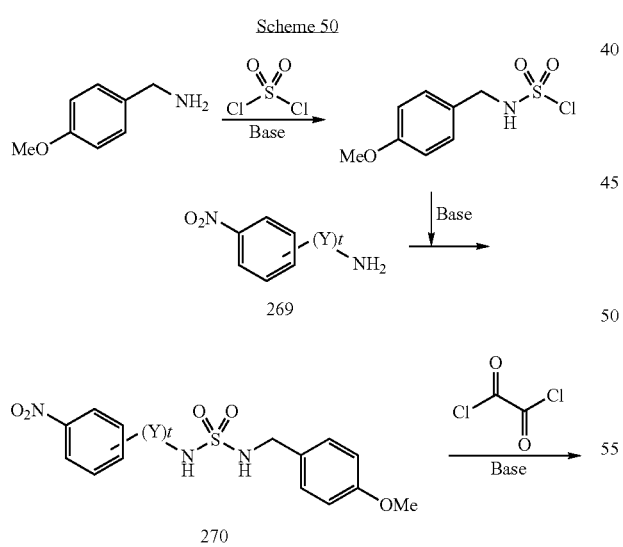

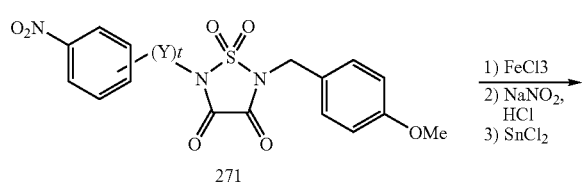

Scheme 52 illustrates an approach to the preparation of compounds of formula I.B wherein Q is Q-54 or Q-55. Carboxylic acid 276 is converted to protected amine 279 under standard conditions, which can be subsequently converted to hydrazine 280 by standard procedures. Hydrazine 280 can be converted into compounds of formula I.B using the methods previously outlined in Schemes 35 and 36 to yield protected amine 283 which is readily deprotected to yield amine 284. Reaction of amine 284 with CDI and amine $(R_4)_2NH$ yields 285 (Q=Q-54). Reaction of amine 284 with the indicated sulfamoylchloride derivative yields 286 (Q=Q-55).

Scheme 52

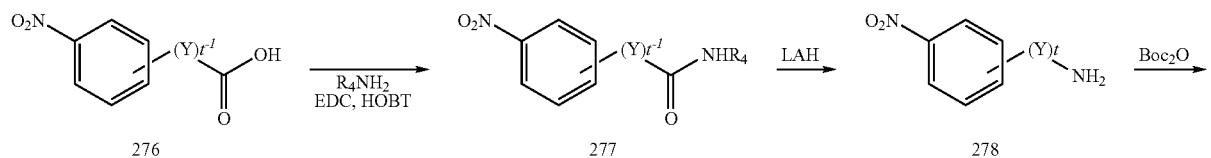

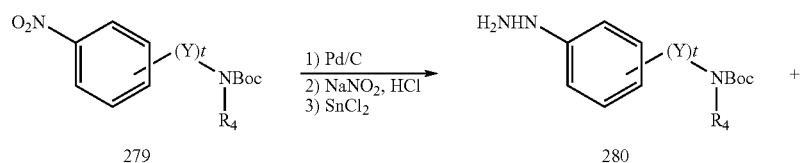

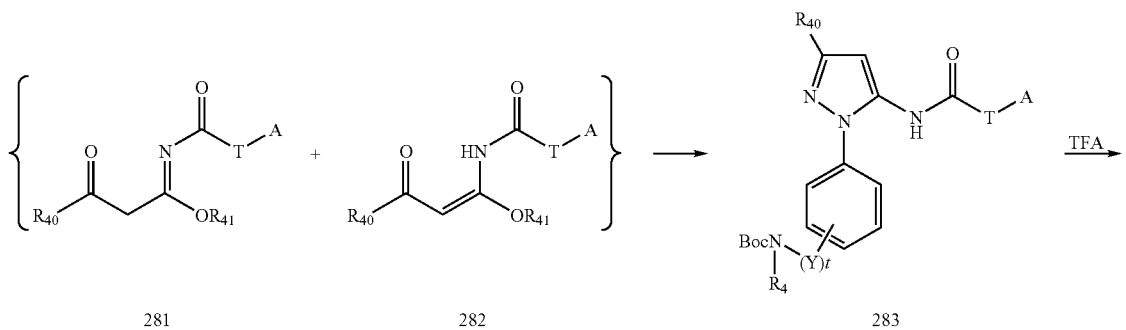

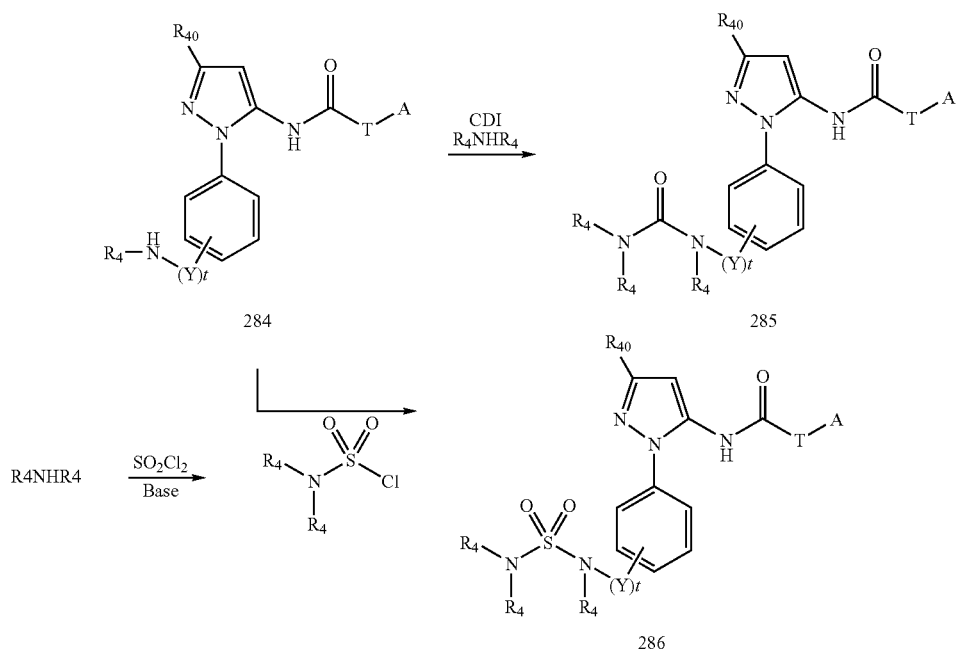

Scheme 53 illustrates an approach to the preparation of compounds of formula I.B wherein Q is Q-49, Q-50 or Q-51. Protected amine 287 (available by several literature procedures) is converted to deprotected hydrazine 288 is accomplished by standard procedures. Hydrazine 288 (Q=Q-49) can be converted into compounds of formula I.B using the methods previously outlined in Schemes 35 and 36. Amine 287 can be deprotected by TFA to yield amine 289 which can be subsequently converted amide 290. Amide 290 is converted to hydrazine 291 (Q=Q-50) by standard procedures, which can be subsequently converted into compounds of formula I.B using the methods previously outlined in Schemes 35 and 36. Alternatively, amine 289 can be reacted with CDI and amine $(R_4)_2NH$ to yield urea 292 (Q=Q-51). Urea 292 is converted to hydrazine 293 (Q=Q-51) by standard procedures, which can be subsequently converted into compounds of formula I.B using the methods previously outlined in Schemes 35 and 36.

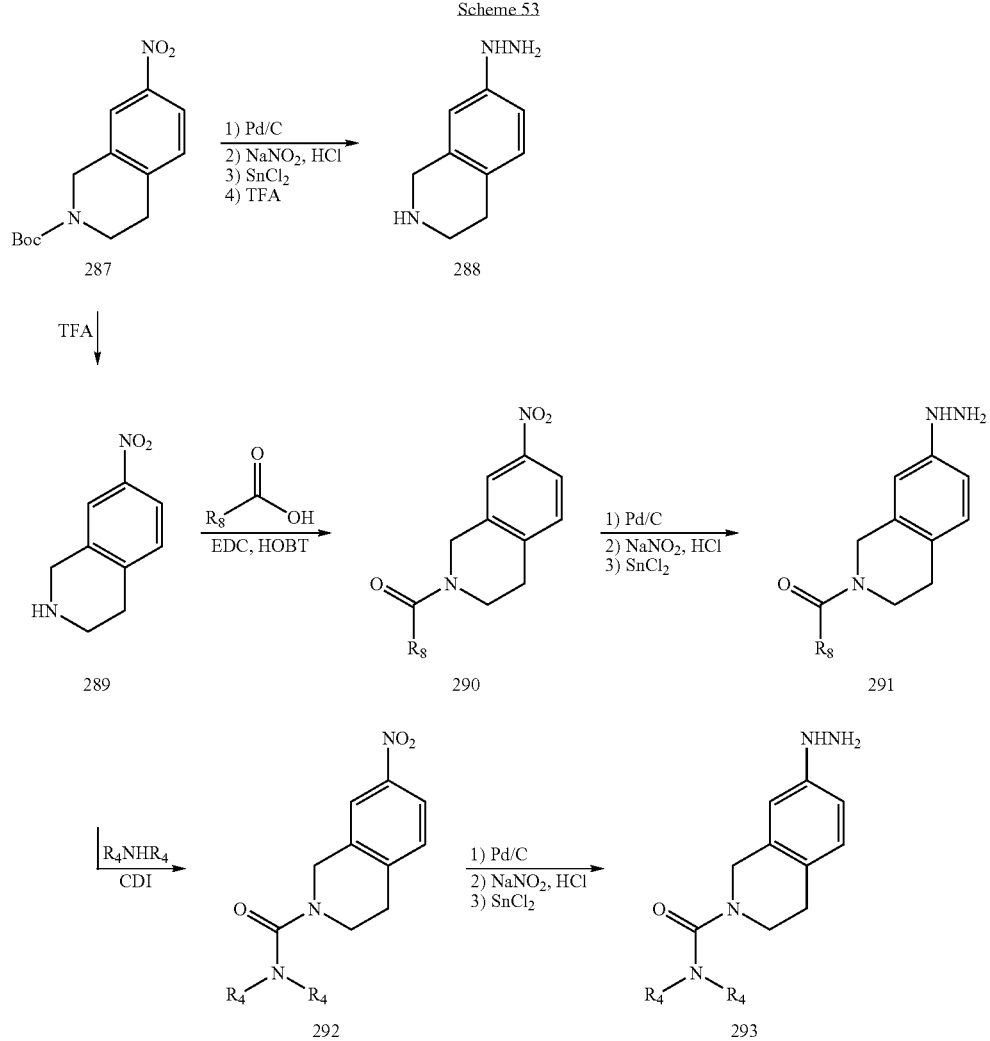

Scheme 54 illustrates an approach to the preparation of compounds of formula I.B wherein Q is Q-52 and Q-53. Protected amine 294 (available by several literature procedures) is converted to protected hydrazine 295 is accomplished by standard procedures. Hydrazine 295 (Q=Q-49) can be converted into compounds of formula I.B to yield protected amine 298 which is readily deprotected to yield amine 299. Reaction of amine 299 with chlorosulfonylisocyanate followed by amine $(R_4)_2NH$ yields 300 (Q=Q-52). Alternatively, reaction of chlorosulfonylisocyanate and amine $(R_4)_2NH$ followed by amine 299 yields 301 (Q=Q-53).

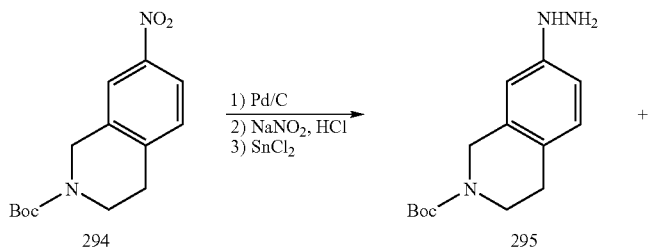

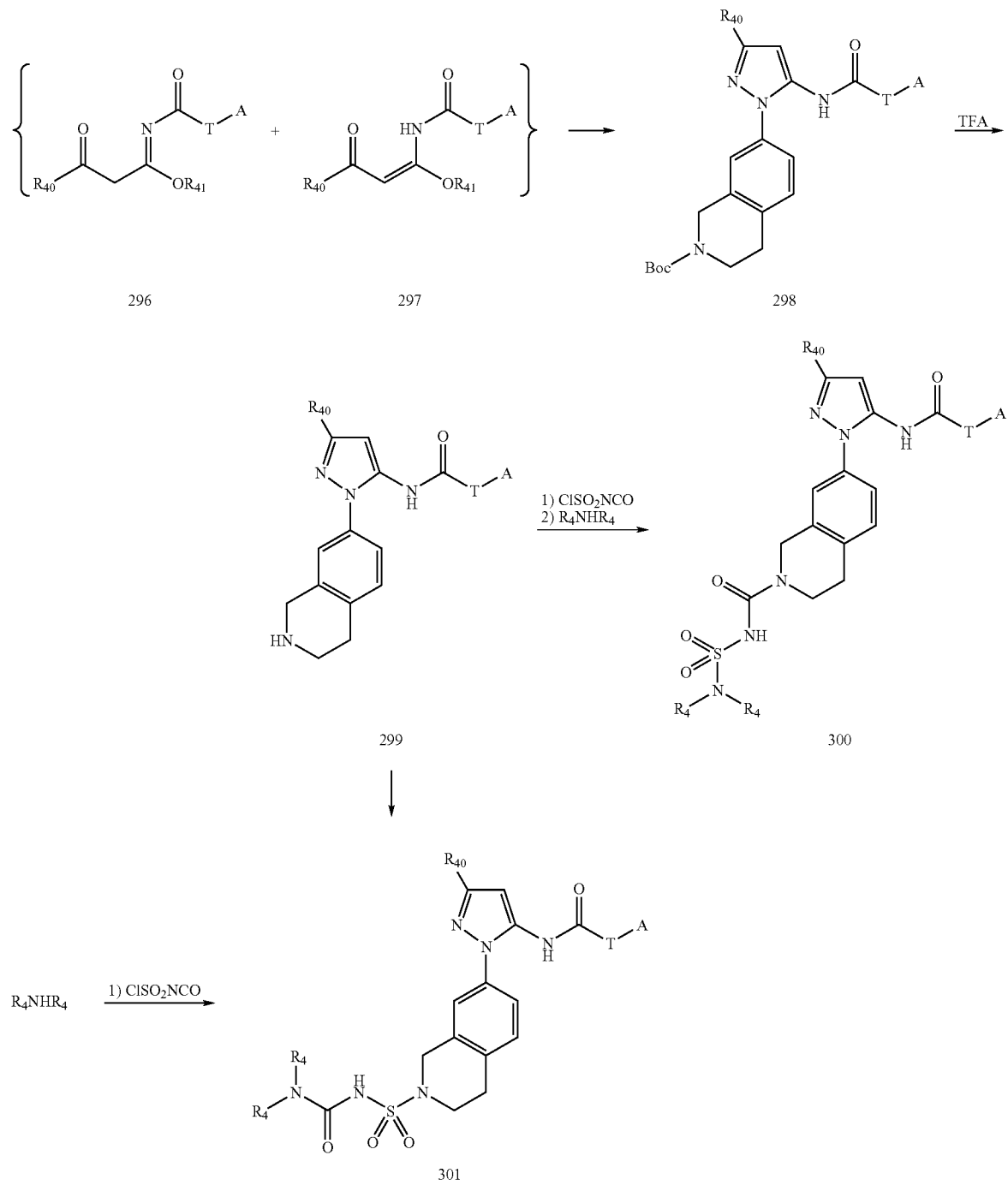

Scheme 55 illustrates an approach to the preparation of compounds of formula I.B wherein Q is Q-36. Amine 302 is reacted with CDI and amine $R_4NH_2$ to yield 303, which is reacted with chlorocarbonyl sulfenylchloride to yield thiadiazolidinedione 304. Conversion of 304 to the substituted hydrazine 305 is accomplished by standard procedures. Hydrazine 305 can be converted into compounds of formula I.B using the methods previously outlined in Schemes 35 and 36.

Scheme 55

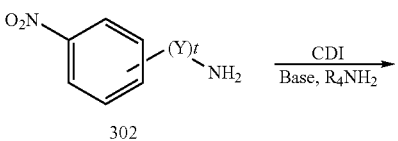

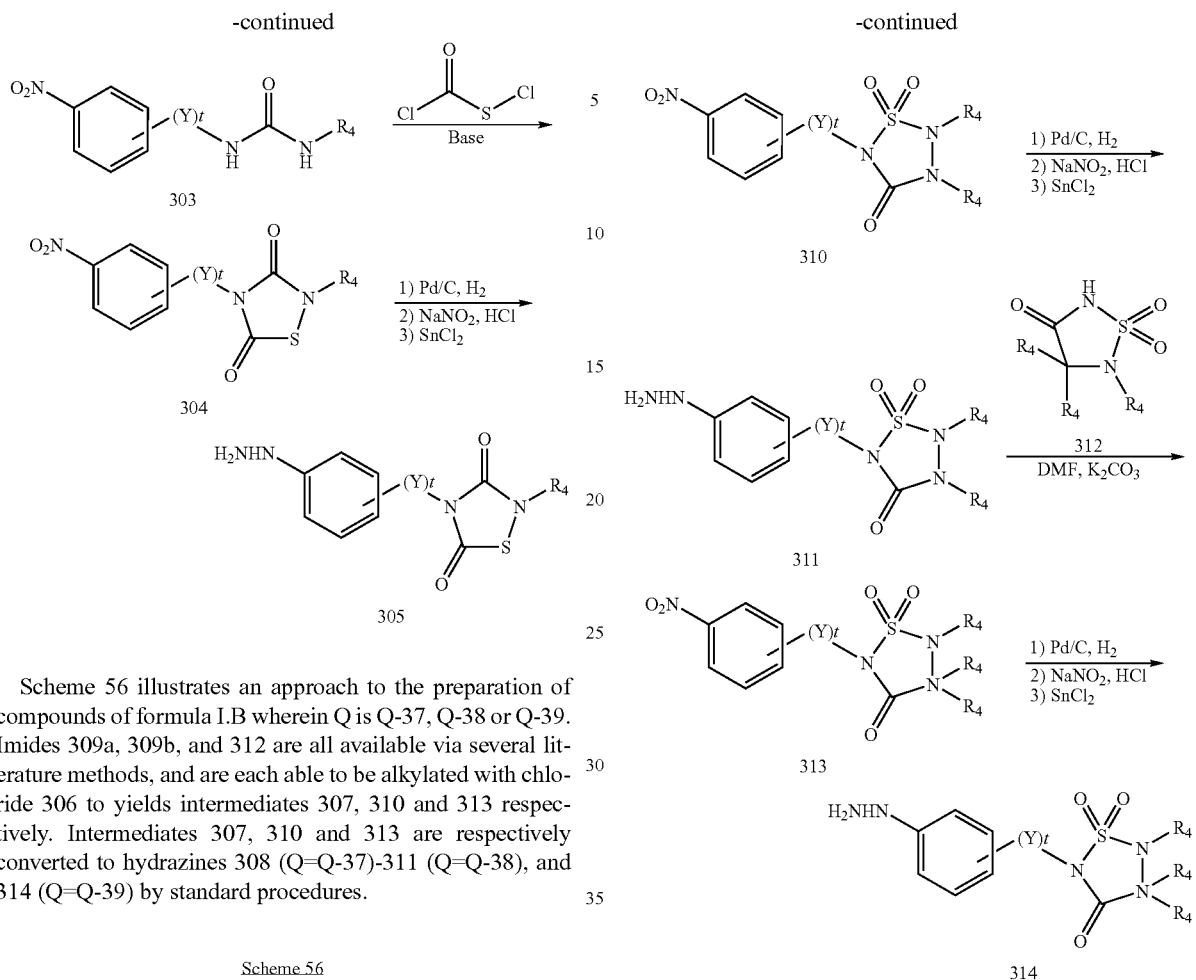

Scheme 56 illustrates an approach to the preparation of compounds of formula I.B wherein Q is Q-37, Q-38 or Q-39. Imides 309a, 309b, and 312 are all available via several literature methods, and are each able to be alkylated with chloride 306 to yields intermediates 307, 310 and 313 respectively. Intermediates 307, 310 and 313 are respectively converted to hydrazines 308 (Q=Q-37)-311 (Q=Q-38), and 314 (Q=Q-39) by standard procedures.

Scheme 56

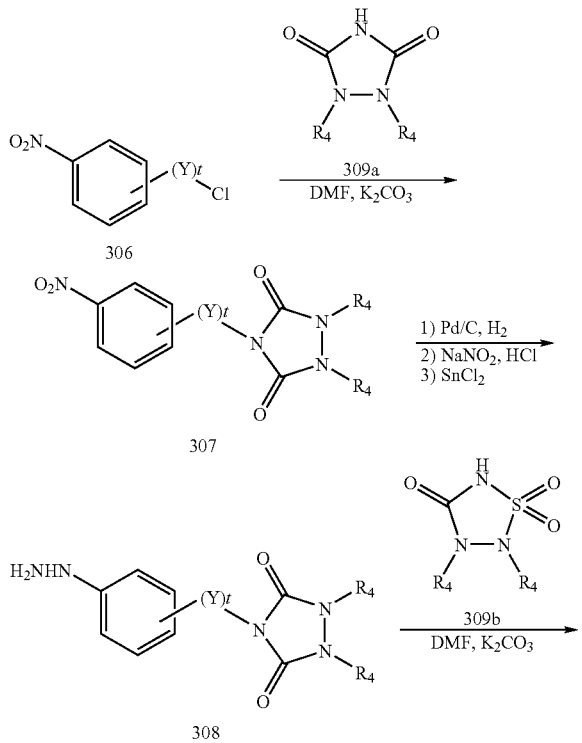

Scheme 57 illustrates an alternative preparation of compounds wherein Q is Q-37. Readily available amine 315, wherein P is a suitable amine-protecting group or a group convertible to an amine group, is reacted with $SO_2Cl_2$ to give rise to sulfonyl chloride 316. Intermediate 316 is reacted with a substituted amino acid ester with a suitable base to afford sulfonylurea-317. Further treatment with base results in cyclization to afford sulfohydantoin 318. The protecting group P is removed to afford the key amine-containing intermediate 319. Alternatively, if P is a nitro group, then 318 is converted to 319 under reducing conditions such as iron/HCl, tin(II) chloride, or catalytic hydrogenation. Amine 319 is converted to 320A by reaction with an isocyanate; 319 is converted to amide 320B by reaction with an acid chloride, acid anhydride, or a suitable activated carboxylic acid in the presence of a suitable base; 319 is converted to carbamate 320C by reaction with a substituted alkyl or aryl chloroformate in the presence of a suitable base.

Scheme 57

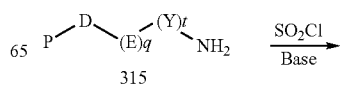

-continued

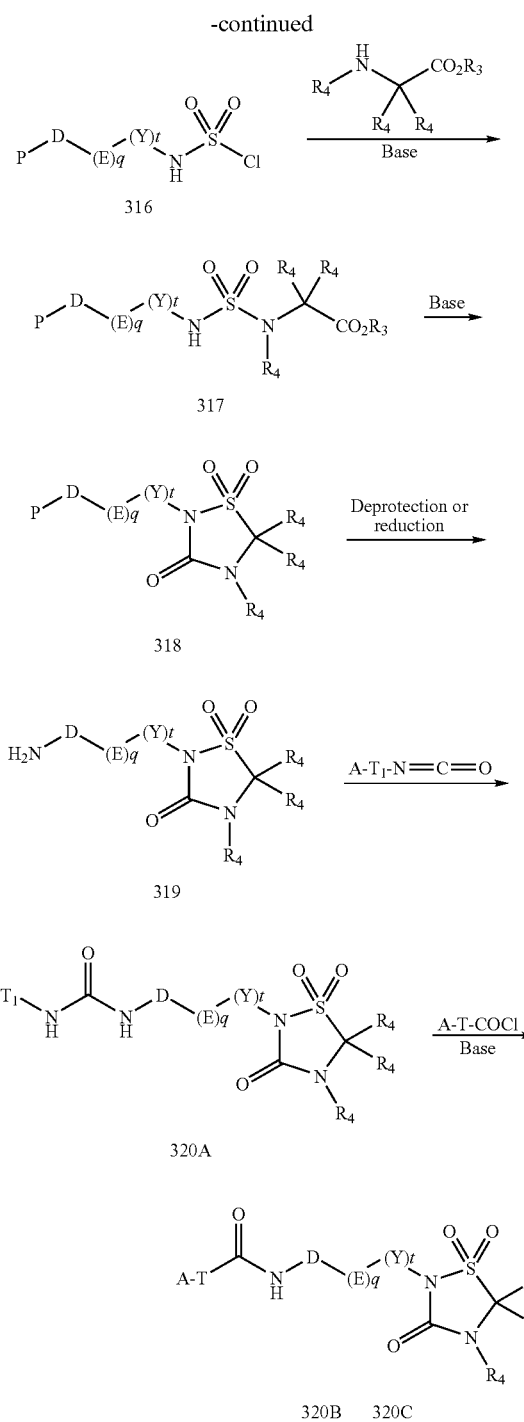

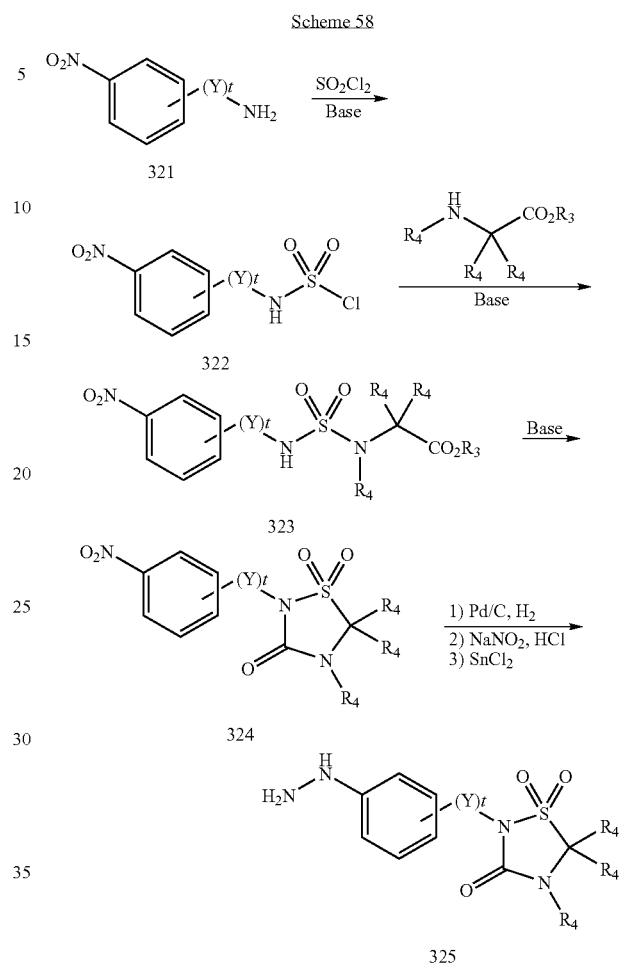

Scheme 58 illustrates an alternative synthesis of key substituted hydrazine 325 of compounds wherein Q is Q-37. This hydrazine can be converted into compounds of formula I.B using the methods previously outlined in Schemes 35 and 36. The amine 321 is reacted with $SO_2Cl_2$ to give rise to sulfonyl chloride 322. Reaction of 322 with a suitable amino acid ester affords sulfonylurea 323, which is cyclized under basic conditions to give sulfohydantoin 324. Reduction of the nitro group of 324, diazotization of the resulting amine, and reduction of the diazonium salt affords key hydrazine 325.

Scheme 59 illustrates an alternative preparation of compounds wherein Q is Q-38. Readily available amine 326, wherein P is a suitable amine-protecting group or a group convertible to an amine group, is reacted with $SO_2Cl_2$ to give rise to sulfonyl chloride 327. Intermediate 327 is reacted with a substituted hydrazide ester with a suitable base to afford sulfonylurea 328. Further treatment with base results in cyclization to afford sulfotriazaolinedione 329. The protecting group P is removed to afford the key amine-containing intermediate 330. Alternatively, if P is a nitro group, then 329 is converted to 330 under reducing conditions such as iron/HCl, tin(II) chloride, or catalytic hydrogenation. Amine 330 is converted to 331A by reaction with an isocyanate; 330 is converted to amide 331B by reaction with an acid chloride, acid anhydride, or a suitable activated carboxylic acid in the presence of a suitable base; 330 is converted to carbamate 331C by reaction with a substituted alkyl or aryl chloroformate in the presence of a suitable base.

Scheme 59

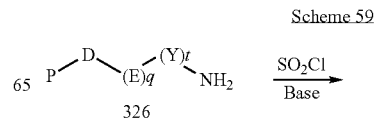

-continued

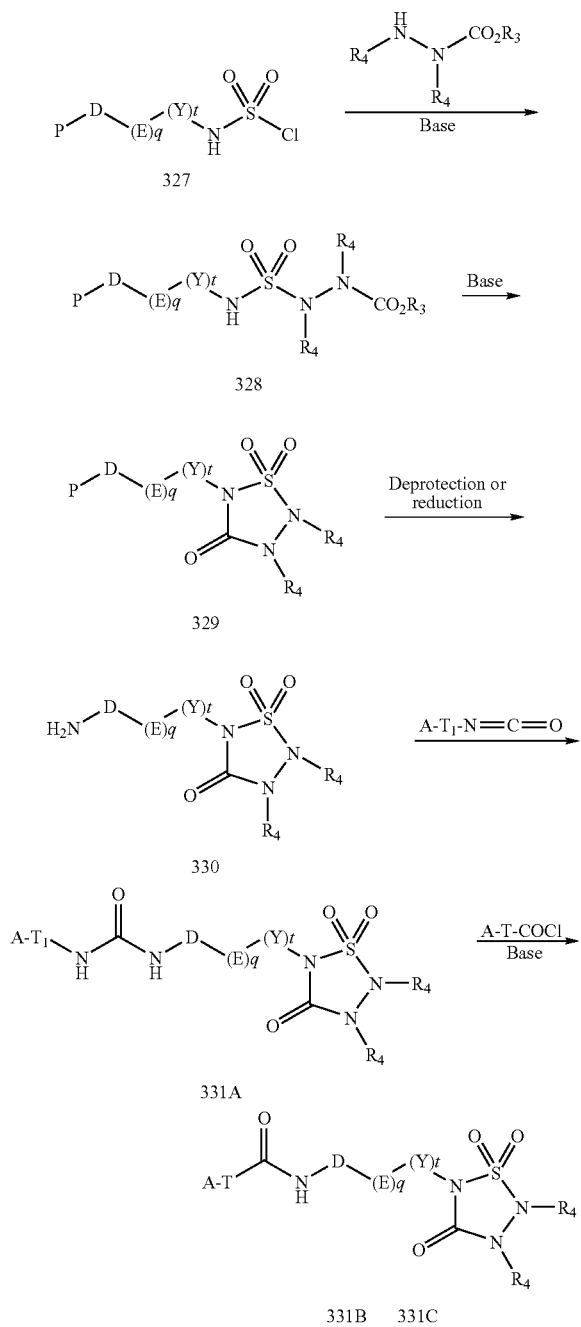

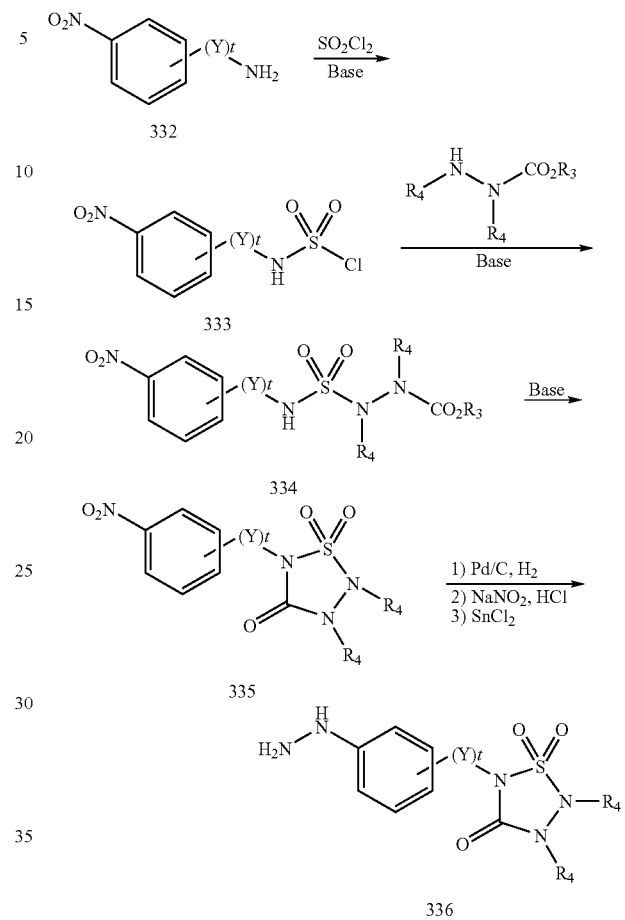

Scheme 60 illustrates an alternative synthesis of key substituted hydrazine 336 of compounds wherein Q is Q-38. This hydrazine can be converted into compounds of formula I.B using the methods previously outlined in Schemes 35 and 36. The amine 332 is reacted with $SO_2Cl_2$ to give rise to sulfonyl chloride 333. Reaction of 333 with a ubstituted hydrazide ester affords sulfonylurea 334, which is cyclized under basic conditions to give sulfotriazaolinedione 335. Reduction of the nitro group of 335, diazotization of the resulting amine, and reduction of the diazonium salt affords key hydrazine 336.

Scheme 61 illustrates the preparation of compounds wherein Q is Q-39. Readily available amine 337, wherein P is a suitable amine-protecting group or a group convertible to an amine group, is reacted with p-nitrophenyl chloroformate to give rise to carbamate 338. Intermediate 338 is reacted with a substituted amino acid ester with a suitable base to afford urea 339. Further treatment with base results in cyclization to afford triazolinedione 340. The protecting group P is removed to afford the key amine-containing intermediate 341. Alternatively, if P is a nitro group, then 340 is converted to 341 under reducing conditions such as iron/HCl, tin(II) chloride, or catalytic hydrogenation. Amine 341 is converted to 342A by reaction with an isocyanate; 341 is converted to amide 342B by reaction with an acid chloride, acid anhydride, or a suitable activated carboxylic acid in the presence of a suitable base; 341 is converted to carbamate 342C by reaction with a substituted alkyl or aryl chloroformate in the presence of a suitable base.

Scheme 61

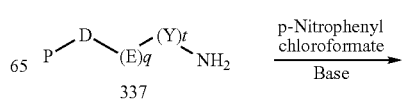

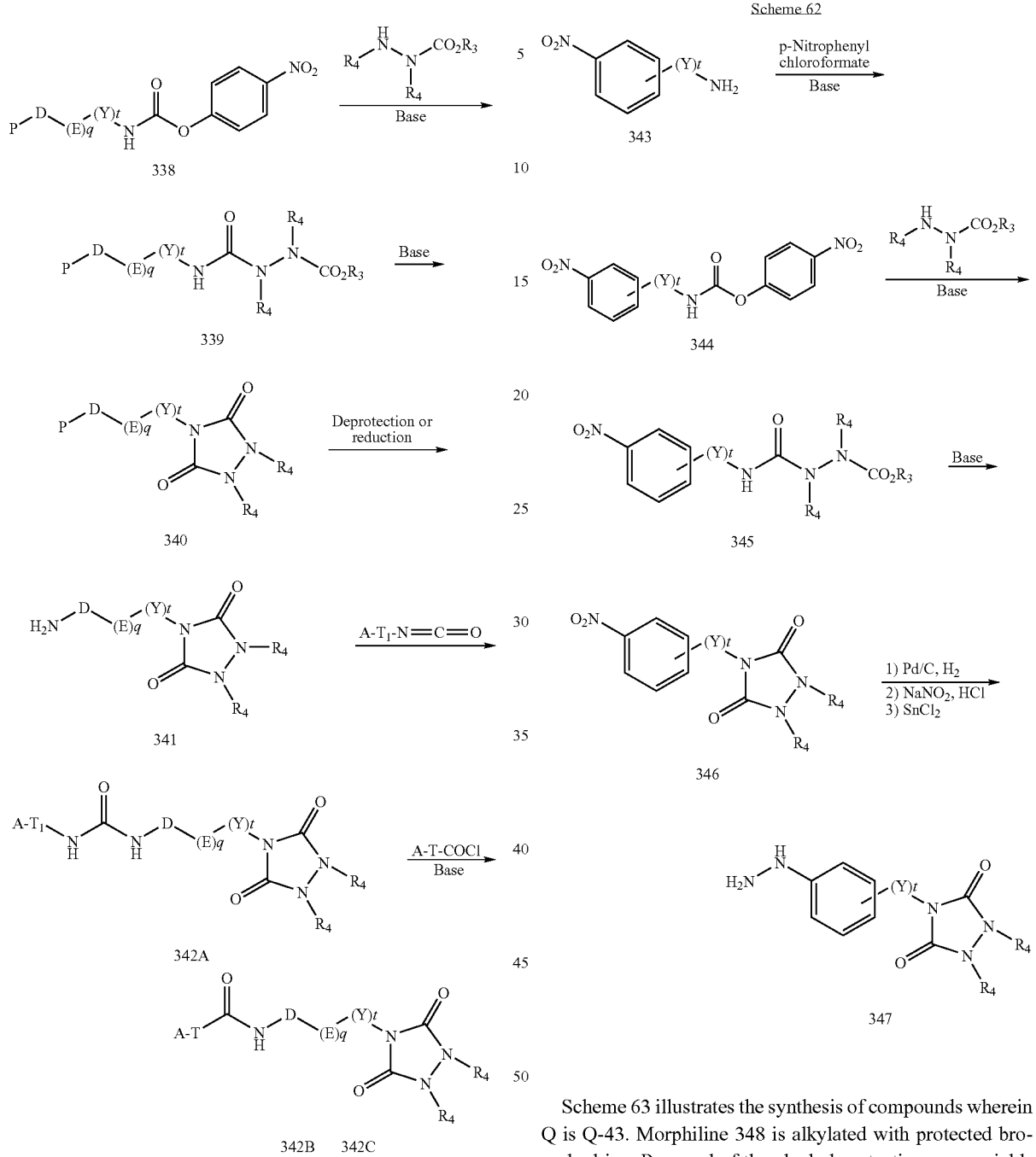

Scheme 62 illustrates an alternative synthesis of key substituted hydrazine 347 of compounds wherein Q is Q-39. This hydrazine can be converted into compounds of formula I.B using the methods previously outlined in Schemes 35 and 36. The nitrophenyl substituted amine 343 is reacted with p-nitrophenyl chloroformate to give rise to carbamate 344. Reaction of 344 with a suitable amino acid ester affords urea 345, which is cyclized under basic conditions to give triazolinedione 346. Reduction of the nitro group of 346, diazotization of the resulting amine, and reduction of the diazonium salt affords key hydrazine 347.

Scheme 63 illustrates the synthesis of compounds wherein Q is Q-43. Morphiline 348 is alkylated with protected bromohydrine. Removal of the alcohol protecting group yields intermediate 349, which can be oxidized to aldehyde 350. When G=NH, iodoaniline 351 is reacted with 350 under reductive amination conditions, preferably sodium triacetoxyborohydride, to afford intermediate 352. This intermediate is converted to the substituted hydrazine 353 by Cu(I)-catalyzed reaction with N—BOC hydrazine. When G=O, iodophenol 355 is either alkylated with 354 or reacted under Mitsunobu conditions with alcohol 349 to yield intermediate 356. This intermediate is converted to the substituted hydrazine 353 by Cu(I)-catalyzed reaction with N—BOC hydrazine.

Scheme 63

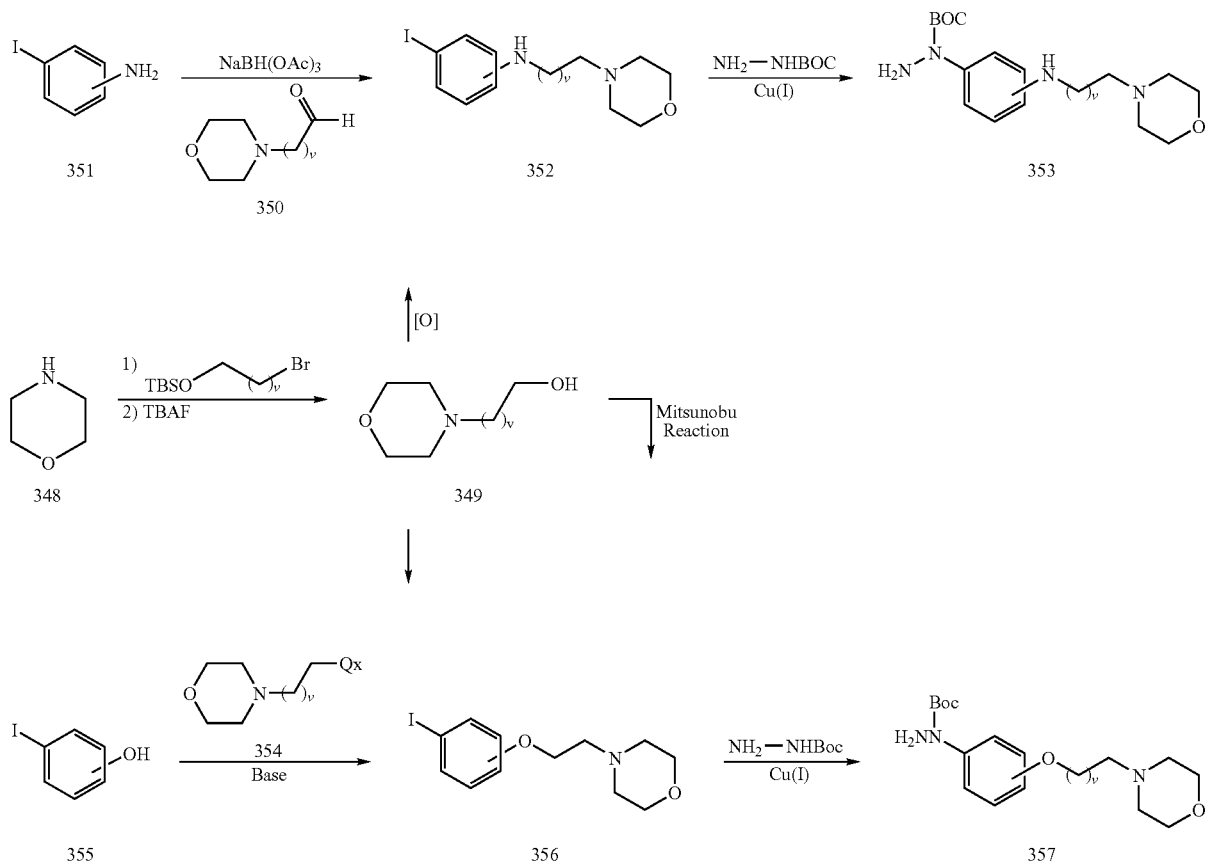

Scheme 64 illustrates the synthesis of compounds wherein Q is Q-43, G=CH$_2$. Nitroacid 358 (readily available by anyone with normal skills in the art) is reacted with morphiline to yield amide 359, which upon reduction to the amine and conversion of the nitro group under standard conditions results in hydrazine 360. This hydrazine can be converted into compounds of formula I.B using the methods previously outlined in Schemes 35 and 36.

Scheme 64

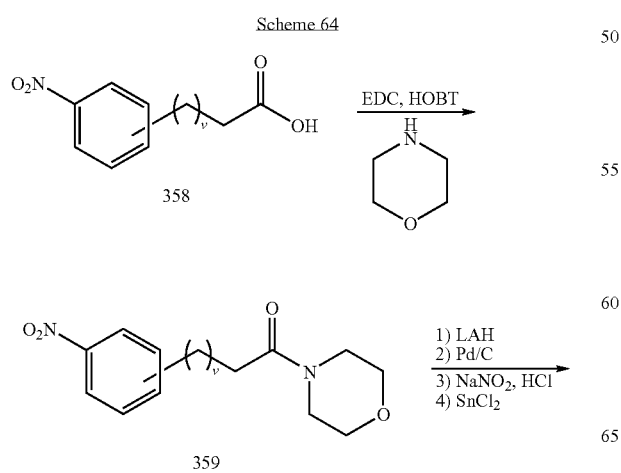

-continued

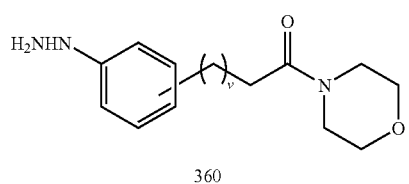

360

Scheme 65 illustrates the synthesis of compounds wherein Q is Q-44. N-methyl piperazine 361 is alkylated with protected bromohydrine. Removal of the alcohol protecting group yields intermediate 362, which can be oxidized to aldehyde 363. When G=NH, iodoaniline 364 is reacted with 363 under reductive amination conditions, preferably sodium triacetoxyborohydride, to afford intermediate 365. This intermediate is converted to the substituted hydrazine 366 by Cu(I)-catalyzed reaction with N—BOC hydrazine. When G=O, iodophenol 368 is either alkylated with 367 or reacted under Mitsunobu conditions with alcohol 362 to yield intermediate 369. This intermediate is converted to the substituted hydrazine 370 by Cu(I)-catalyzed reaction with N—BOC hydrazine.

Scheme 65

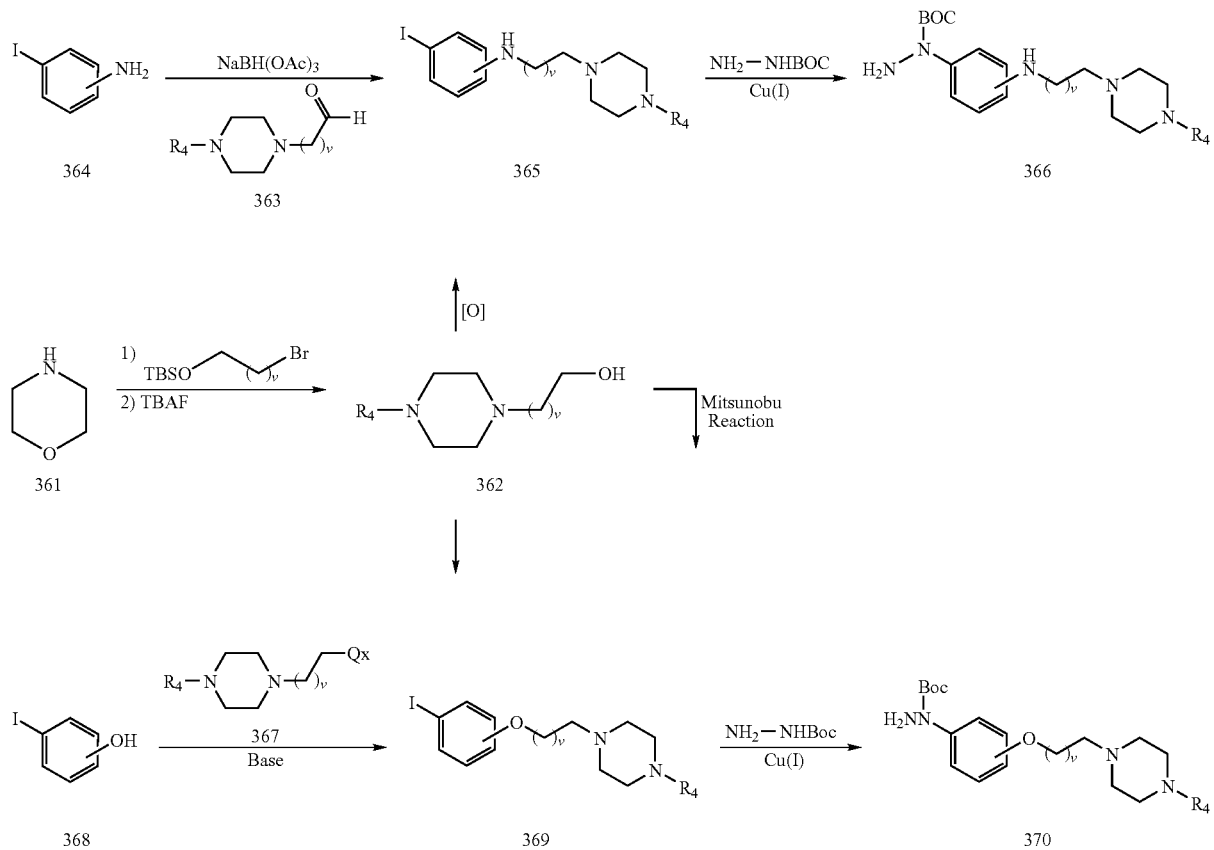

Scheme 66 illustrates the synthesis of compounds wherein Q is Q-44, G=CH$_2$. Nitroacid 371 (readily available by anyone with normal skills in the art) is reacted with N-methyl piperazine to yield amide 372, which upon reduction to the amine and conversion of the nitro group under standard conditions results in hydrazine 373. This hydrazine can be converted into compounds of formula I.B using the methods previously outlined in Schemes 35 and 36.

Scheme 66

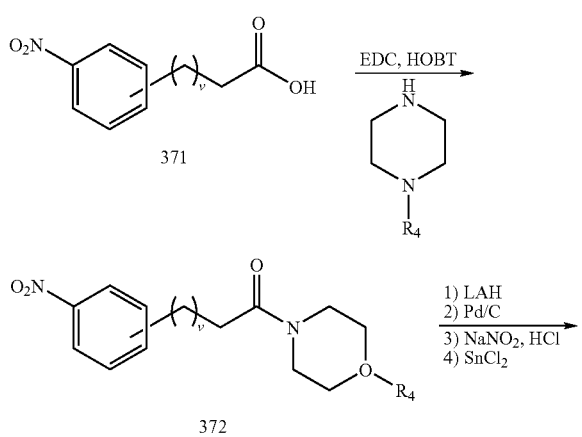

-continued

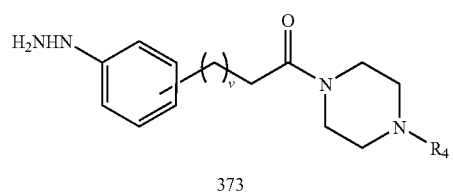

Scheme 67 illustrates the synthesis of compounds wherein Q is Q-45. Thiomorpholine sulphone 374 is alkylated with protected bromohydrine. Removal of the alcohol protecting group yields intermediate 375, which can be oxidized to aldehyde 376. When G=NH, iodoaniline 377 is reacted with 376 under reductive amination conditions, preferably sodium triacetoxyborohydride, to afford intermediate 378. This intermediate is converted to the substituted hydrazine 379 by Cu(I)-catalyzed reaction with N—BOC hydrazine. When G=O, iodophenol 380 is either alkylated with 381 or reacted under Mitsunobu conditions with alcohol 375 to yield intermediate 382. This intermediate is converted to the substituted hydrazine 383 by Cu(I)-catalyzed reaction with N—BOC hydrazine.

Scheme 67

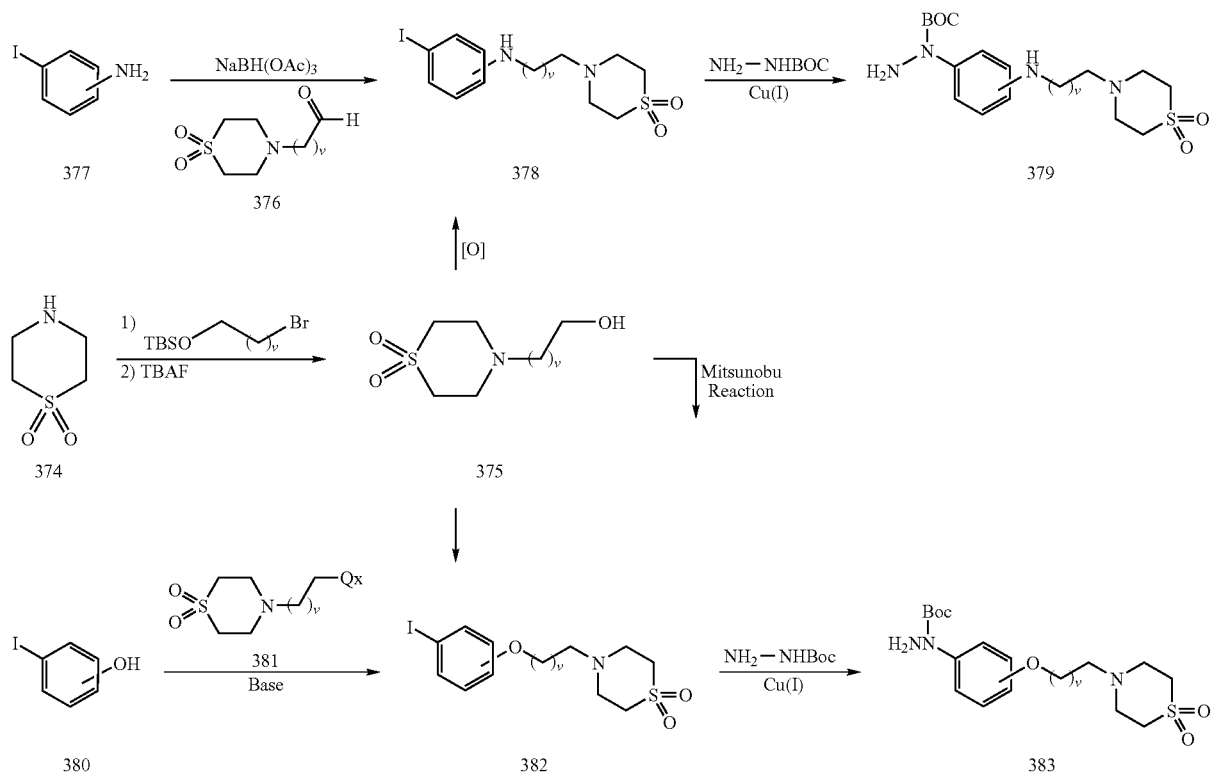

Scheme 68 illustrates the synthesis of compounds wherein Q is Q-44, G=CH$_2$. Nitroacid 384 (readily available by anyone with normal skills in the art) is reacted with thiomorpholine sulphone to yield amide 385, which upon reduction to the amine and conversion of the nitro group under standard conditions results in hydrazine 386. This hydrazine can be converted into compounds of formula I.B using the methods previously outlined in Schemes 35 and 36.

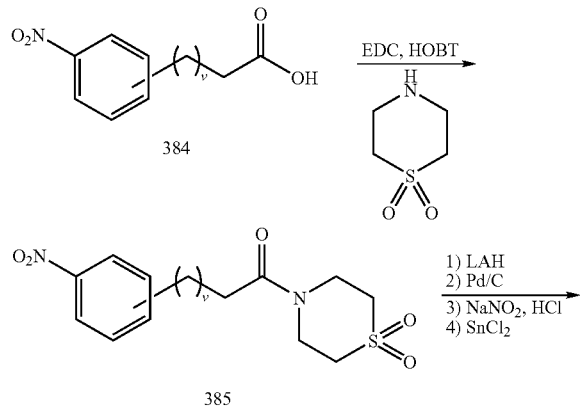

-continued

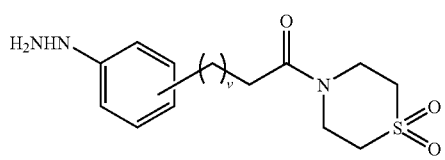

Scheme 69 illustrates the synthesis of compounds wherein Q is Q-46. Piperadine derivative 387 is alkylated with protected bromohydrine. Removal of the alcohol protecting group yields intermediate 388, which can be oxidized to aldehyde 389. When G=NH, iodoaniline 390 is reacted with 389 under reductive amination conditions, preferably sodium triacetoxyborohydride, to afford intermediate 391. This intermediate is converted to the substituted hydrazine 392 by Cu(I)-catalyzed reaction with N—BOC hydrazine. When G=O, iodophenol 393 is either alkylated with 396 or reacted under Mitsunobu conditions with alcohol 388 to yield intermediate 394. This intermediate is converted to the substituted hydrazine 395 by Cu(I)-catalyzed reaction with N—BOC hydrazine.

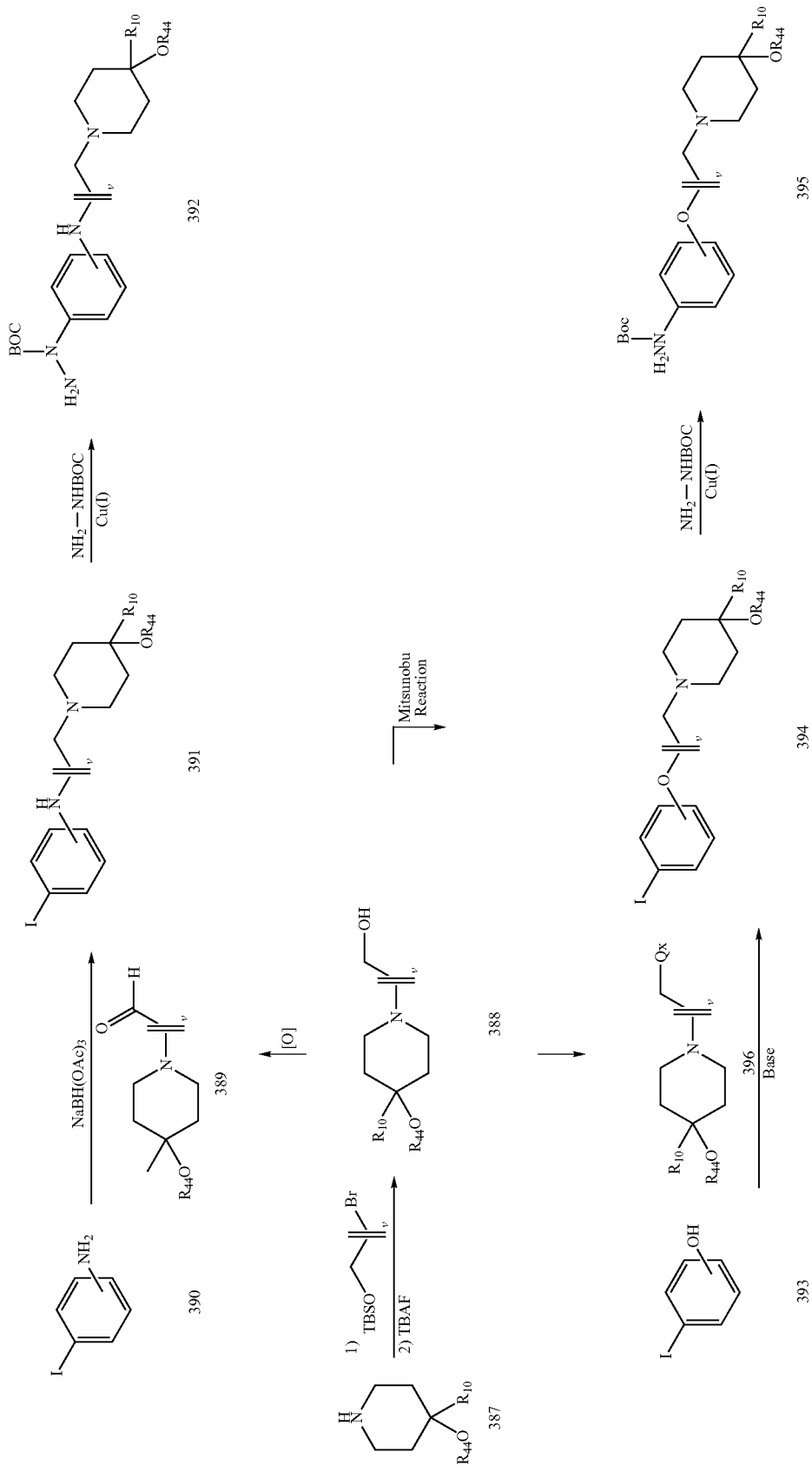

Scheme 70 illustrates the synthesis of compounds wherein Q is Q-44, G=CH$_2$. Nitroacid 397 (readily available by anyone with normal skills in the art) is reacted with thiomorpholine sulphone to yield amide 398, which upon reduction to the amine and conversion of the nitro group under standard conditions results in hydrazine 399. This hydrazine can be converted into compounds of formula I.B using the methods previously outlined in Schemes 35 and 36.

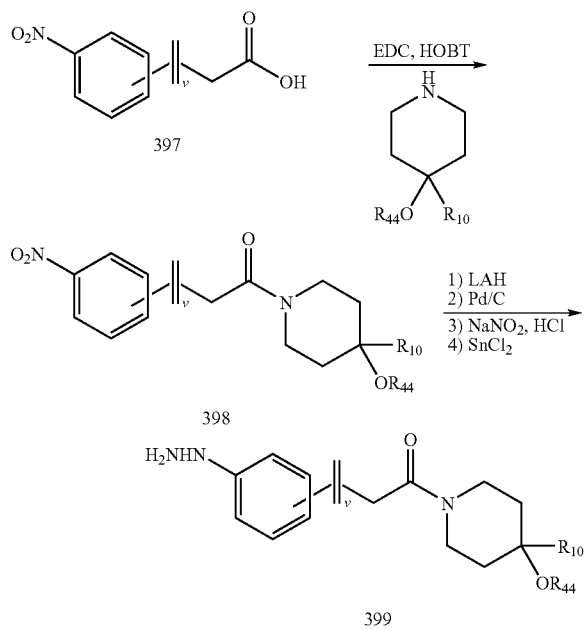

Scheme 70

Affinity and Biological Assessment of P38-Alpha Kinase Inhibitors

A fluorescence binding assay is used to detect binding of inhibitors of Formula I with unphosphorylated p38-alpha kinase as previously described: see J. Regan et al, *Journal of Medicinal Chemistry* (2002) 45:2994.

1. P38 MAP Kinase Binding Assay

The binding affinities of small molecule modulators for p38 MAP kinase were determined using a competition assay with SKF 86002 as a fluorescent probe, modified based on published methods (C. Pargellis, et al Nature Structural Biology (2002) 9, 268-272. J. Regan, et al J. Med. Chem. (2002) 45, 2994-3008). Briefly, SKF 86002, a potent inhibitor of p38 kinase (K$_d$=180 nM), displays an emission fluorescence around 420 nm when excitated at 340 nm upon its binding to the kinase. Thus, the binding affinity of an inhibitor for p38 kinase can be measured by its ability to decrease the fluorescence from SKF 86002. The assay was performed in a 384 plate (Greiner uclear 384 plate) on a Polarstar Optima plate reader (BMG). Typically, the reaction mixture contained 1 µM SKF 86002, 80 nM p38 kinase and various concentrations of an inhibitor in 20 mM Bis-Tris Propane buffer, pH 7, containing 0.15% (w/v) n-octylglucoside and 2 mM EDTA in a final volume of 65 µl. The reaction was initiated by addition of the enzyme. The plate was incubated at room temperature (~25° C.) for 2 hours before reading at emission of 420 nm and excitation at 340 nm. By comparison of rfu (relative fluorescence unit) values with that of a control (in the absence of an inhibitor), the percentage of inhibition at each concentration of the inhibitor was calculated. IC$_{50}$ value for the inhibitor was calculated from the % inhibition values obtained at a range of concentrations of the inhibitor using Prism. When time-dependent inhibition was assessed, the plate was read at multiple reaction times such as 0.5, 1, 2, 3, 4 and 6 hours. The IC$_{50}$ values were calculated at the each time point. An inhibition was assigned as time-dependent if the IC$_{50}$ values decrease with the reaction time (more than two-fold in four hours). This is illustrated below in Table 1.

TABLE 1

| Example # | IC50, nM | Time-dependent |
|---|---|---|
| 1 | 292 | Yes |
| 2 | 997 | No |
| 2 | 317 | No |
| 3 | 231 | Yes |
| 4 | 57 | Yes |
| 5 | 1107 | No |
| 6 | 238 | Yes |
| 7 | 80 | Yes |
| 8 | 66 | Yes |
| 9 | 859 | No |
| 10 | 2800 | No |
| 11 | 2153 | No |
| 12 | ~10000 | No |
| 13 | 384 | Yes |
| 15 | 949 | No |
| 19 | ~10000 | No |
| 21 | 48 | Yes |
| 22 | 666 | No |
| 25 | 151 | Yes |
| 26 | 68 | Yes |
| 29 | 45 | Yes |
| 30 | 87 | Yes |
| 31 | 50 | Yes |
| 32 | 113 | Yes |
| 37 | 497 | No |
| 38 | 508 | No |
| 41 | 75 | Yes |
| 42 | 373 | No |
| 43 | 642 | No |
| 45 | 1855 | No |
| 46 | 1741 | No |
| 47 | 2458 | No |
| 48 | 3300 | No |
| 57 | 239 | Yes |

IC50 values obtained at 2 hours reaction time

P-38 Alpha Kinase Assay (Spectrophometric Assay)

Activity of phosphorylated p-38 kinase was determined by following the production of ADP from the kinase reaction through coupling with the pyruvate kinase/lactate dehydrogenase system (e.g., Schindler, et al. Science (2000) 289, 1938-1942). In this assay, the oxidation of NADH was continuously measured spectrophometrically. The reaction mixture (100 µl) contained phospho p-38 alpha kinase (3.3 nM. Panvera), peptide substrate (IPTSPITTTYFFFKKK-OH, 0.2 mM), ATP (0.3 mM), MgCl$_2$ (10 mM), pyruvate kinase (8 units. Sigma), lactate dehydrogenase (13 units. Sigma), phosphoenol pyruvate (1 mM), and NADH (0.28 mM) in 65 mM Tris buffer, pH 7.5, containing 3.5% DMSO and 150 uM n-Dodecyl-B-D-maltopyranoside. The reaction was initiated by adding ATP. The absorption at 340 nm was monitored continuously for up to 4 hours at 30° C. on Polarstar Optima plate reader (BMG). The kinase activity (reaction rate) was calculated from the slope at the time frame from 1.5 h to 2 h. Under these conditions, a turn over number (k$_{cat}$) of ~1 s$^{-1}$ was obtained. The reaction rates calculated from different time frames such as 0.5 min to 0.5 h, 0.5 h to 1 h, 1.5 h to 2 h or 2.5 h to 3 h were generally constant.

For inhibition determinations, test compounds were incubated with the reaction mixture for ~5 min before adding ATP to start the reaction. Percentage of inhibition was obtained by comparison of reaction rate with that of a control well containing no test compound. $IC_{50}$ values were calculated from a series of % inhibition values determined at a range of concentrations of each inhibitor using Prism to process the data and fit inhibition curves. Generally, the rates obtained at the time frame of 1.5 h to 2 h were used for these calculations. In assessing whether inhibition of a test compound was time-dependent (i.e., greater inhibition with a longer incubation time), the values of % inhibition and/or IC50 values obtained from other time frames were also calculated for the inhibitor. The biological activity for compounds of the present invention in the spectrophotometric assay are illustrated in Tables 2 and 3.

TABLE 2

| Example # | IC50, uM | % inhibition @ concentration, uM |
|---|---|---|
| 1 | 0.067 | |
| 2 | 0.29 | |
| 3 | 0.019 | |
| 4 | 0.609 | |
| 5 | 0.514 | |
| 6 | 0.155 | |
| 7 | 0.165 | |
| 9 | 0.355 | |
| 10 | | 83% @ 10 |
| 11 | 0.953 | |
| 12 | | 70% @ 10 |
| 13 | 0.269 | |
| 14 | 0.096 | |
| 15 | 0.53 | |
| 17 | | 40% @ 10 |
| 18 | | 60% @ 10 |
| 21 | 0.171 | |
| 22 | 0.445 | |
| 25 | 0.055 | |
| 26 | 0.19 | |
| 29 | 0.011 | |
| 30 | 0.251 | |
| 31 | 0.056 | |
| 32 | 0.307 | |
| 38 | 0.51 | |
| 39 | 0.012 | |
| 40 | 0.055 | |
| 41 | 0.013 | |
| 42 | 0.425 | |
| 43 | 7.5 | |
| 45 | 0.48 | |
| 46 | 1 | |
| 47 | 0.295 | |
| 48 | 2 | |
| 49 | 0.071 | |
| 51 | 0.033 | |
| 52 | 0.416 | |
| 53 | 0.109 | |
| 54 | | 68% @ 1.0 |
| 55 | 0.74 | |
| 57 | 0.782 | |
| 58 | 0.172 | |
| 59 | 0.709 | |
| 60 | 0.264 | |
| D | 0.179 | |
| F | 0.437 | |

TABLE 3

| Example # | IC50, uM | % Inhibition @ concentration, uM |
|---|---|---|
| 145 | 1.3 | |
| 146 | | 9% @ 10 |
| 147 | | 27% @ 10 |
| 150 | | 53% @ 10 |
| 154 | | 21% @ 10 |
| 155 | | 58% @ 10 |
| 160 | 0.044 | |
| 161 | 0.1 | |
| 162 | 0.65 | |
| 163 | 0.464 | |
| 196 | 0.028 | |
| 197 | 0.243 | |
| 198 | 0.137 | |
| 199 | 0.684 | |
| 200 | | 73% @ 1.0 |
| 201 | 0.029 | |
| 202 | 1.9 | |
| 203 | 0.328 | |
| 204 | 0.008 | |
| 206 | 0.013 | |
| 207 | 0.033 | |
| 209 | 0.354 | |
| 234 | 11 | |
| 284 | 1.95 | |
| 285 | 0.102 | |
| 286 | 0.079 | |
| 287 | 0.041 | |
| 288 | 0.104 | |
| 289 | 1.3 | |
| 291 | 5.1 | |
| 294 | 2.1 | |
| 295 | 1.2 | |
| 296 | 0.284 | |
| 297 | 0.34 | |
| 298 | 0.025 | |
| 299 | 2.3 | |
| 300 | 0.251 | |
| 301 | 0.63 | |
| 302 | 0.077 | |

Human Peripheral Blood Mononuclear Leukocyte Cell Assay.

Human peripheral blood mononuclear leukocytes are challenged with 25 ng/mL lipopolysaccharide (LPS) in the absence or presence of Test Compound and incubated for 16 hours as described by Welker P. et al, *International Archives Allergy and Immunology* (1996) 109: 110. The quantity of LPS-induced tumor necrosis factor-alpha (TNF-alpha) cytokine release is measured by a commercially available Enzyme-Linked Immunosorbent Assay (ELISA) kit. Test compounds are evaluated for their ability to inhibit TNF-alpha release. Table 2 records $IC_{50}$ values for inhibition of TNF-alpha release by Test Compounds of the present invention, wherein the $IC_{50}$ value, in micromolar concentration, represents the concentration of Test Compound resulting in a 50% inhibition of TNF-alpha release from human peripheral blood mononuclear leukocytes as compared to control experiments containing no Test Compound. Test compounds evaluated are illustrated in Table 4.

TABLE 4

| Example Number | IC50, uM |
|---|---|
| 3 | 6.1 |
| 13 | 6.32 |
| 21 | 3.4 |
| 29 | 2.68 |
| 31 | 4.52 |
| 60 | 2.34 |
| 296 | 3.49 |
| 300 | 4.78 |
| 302 | 5.45 |

EXAMPLES

The following examples set forth preferred methods in accordance with the invention. It is to be understood, however, that these examples are provided by way of illustration and nothing therein should be taken as a limitation upon the overall scope of the invention.

[Boc-sulfamide]aminoester (Reagent AA), 1,5,7-trimethyl-2,4-dioxo-3-aza-bicyclo[3.3.1]nonane-7-carboxylic acid (Reagent BB), and Kemp acid anhydride (Reagent CC) was prepared according to literature procedures. See Askew et. al *J. Am. Chem. Soc.* 1989, 111, 1082 for further details.

Example A

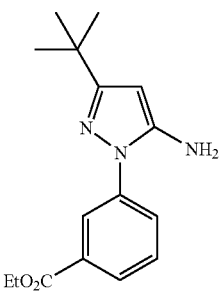

To a solution (200 mL) of m-amino benzoic acid (200 g, 1.46 mol) in concentrated HCl was added an aqueous solution (250 mL) of $NaNO_2$ (102 g, 1.46 mol) at 0° C. The reaction mixture was stirred for 1 h and a solution of $SnCl_2.2H_2O$ (662 g, 2.92 mol) in concentrated HCl (2L) was then added at 0° C., and the reaction stirred for an additional 2 h at RT. The precipitate was filtered and washed with ethanol and ether to yield 3-hydrazino-benzoic acid hydrochloride as a white solid.

The crude material from the previous reaction (200 g, 1.06 mol) and 4,4-dimethyl-3-oxo-pentanenitrile (146 g, 1.167 mol) in ethanol (2 L) were heated to reflux overnight. The reaction solution was evaporated in vacuum and the residue purified by column chromatography to yield ethyl 3-(3-tert-butyl-5-amino-1H-pyrazol-1-yl)benzoate (Example A, 116 g, 40%) as a white solid together with 3-(5-amino-3-tert-butyl-1H-pyrazol-1-yl)benzoic acid (93 g, 36%). $^1$H NMR (DMSO-$d_6$): 8.09 (s, 1H), 8.05 (brd, J=8.0 Hz, 1H), 7.87 (brd, J=8.0 Hz, 1H), 7.71 (t, J=8.0 Hz, 1H), 5.64 (s, 1H), 4.35 (q, J=7.2 Hz, 2H), 1.34 (t, J=7.2 Hz, 3H), 1.28 (s, 9H).

Example B

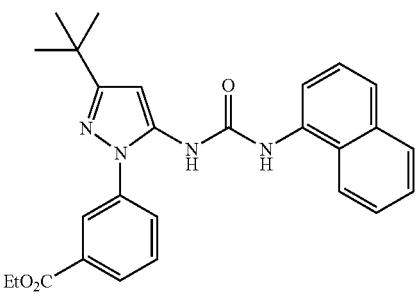

To a solution of 1-naphthyl isocyanate (9.42 g, 55.7 mmol) and pyridine (44 mL) in THF (100 mL) was added a solution of Example A (8.0 g, 27.9 mmol) in THF (200 mL) at 0° C. The mixture was stirred at RT for 1 h, heated until all solids were dissolved, stirred at RT for an additional 3 h and quenched with $H_2O$ (200 mL). The precipitate was filtered, washed with dilute HCl and $H_2O$, and dried in vacuum to yield ethyl 3-[3-t-butyl-5-(3-naphthalen-1-yl)ureido)-1H-pyrazol-1-yl]benzoate (12.0 g, 95%) as a white power. $^1$H NMR (DMSO-$d_6$): 9.00 (s, 1H), 8.83 (s, 1H), 8.25 7.42 (m, 11H), 6.42 (s, 1H), 4.30 (q, J=7.2 Hz, 2H), 1.26 (s, 9H), 1.06 (t, J=7.2 Hz, 3H); MS (ESI) m/z: 457.10 (M+H$^+$).

Example C

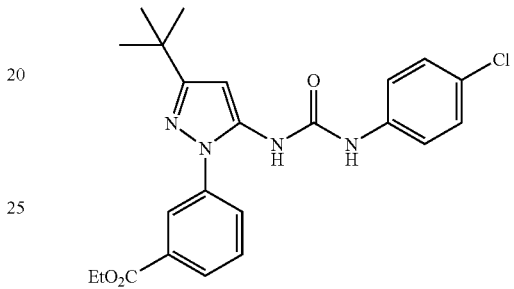

To a solution of Example A (10.7 g, 70.0 mmol) in a mixture of pyridine (56 mL) and THF (30 mL) was added a solution of 4-nitrophenyl 4-chlorophenylcarbamate (10 g, 34.8 mmol) in THF (150 mL) at 0° C. The mixture was stirred at RT for 1 h and heated until all solids were dissolved, and stirred at RT for an additional 3 h. $H_2O$ (200 mL) and $CH_2Cl_2$ (200 mL) were added, the aqueous phase separated and extracted with $CH_2Cl_2$ (2×100 mL). The combined organic layers were washed with 1N NaOH, and 0.1N HCl, saturated brine and dried over anhydrous $Na_2SO_4$. The solvent was removed in vacuum to yield ethyl 3-{3-tert-butyl-5-[3-(4-chlorophenyl)ureido]-1H-pyrazol-1-yl}benzoate (8.0 g, 52%). $^1$H NMR (DMSO-$d_6$): δ 9.11 (s, 1H), 8.47 (s, 1H), 8.06 (m, 1H), 7.93 (d, J=7.6 Hz, 1H), 7.81 (d, J=8.0 Hz, 1H), 7.65 (dd, J=8.0, 7.6 Hz, 1H), 7.43 (d, J=8.8 Hz, 2H), 7.30 (d, J=8.8 Hz, 2H), 6.34 (s, 1H), 4.30 (q, J=6.8 Hz, 2H), 1.27 (s, 9H), 1.25 (t, J=6.8 Hz, 3H); MS (ESI) m/z: 441 (M$^+$+H).

Example D

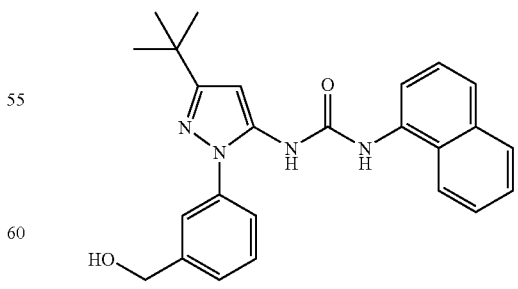

To a stirred solution of Example B (8.20 g, 18.0 mmol) in THF (500 mL) was added LiAlH$_4$ powder (2.66 g, 70.0 mmol) at −10° C. under $N_2$. The mixture was stirred for 2 h at RT and excess LiAlH$_4$ destroyed by slow addition of ice. The reaction mixture was acidified to pH=7 with dilute HCl, concentrated in vacuum and the residue extracted with EtOAc. The combined organic layers were concentrated in vacuum to yield 1-{3-tert-butyl-1-[3-(hydroxymethyl)phenyl]-1H-pyrazol-5-yl}-3-(naphthalen-1-yl)urea (7.40 g, 99%) as a white powder. $^1$H NMR (DMSO-$d_6$): 9.19 (s, 1H), 9.04 (s ~1H), 8.80 (s, 1H), 8.26-7.35 (m, 11H), 6.41 (s, 1H), 4.60 (s, 2H), 1.28 (s, 9H); MS (ESI) m/z: 415 (M+H$^+$).

Example E

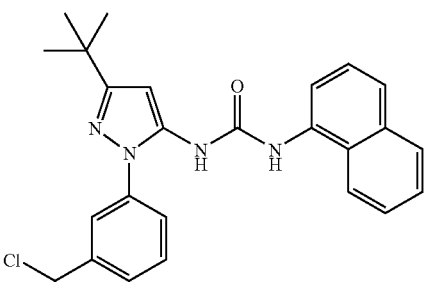

A solution of Example C (1.66 g, 4.0 mmol) and SOCl$_2$ (0.60 mL, 8.0 mmol) in CH$_3$Cl (100 mL) was refluxed for 3 h and concentrated in vacuum to yield 1-{3-tert-butyl-1-[3-chloromethyl)phenyl]-1H-pyrazol-5-yl}-3-(naphthalen-1-yl)urea (1.68 g, 97%) was obtained as white powder. $^1$H NMR (DMSO-d6): δ 9.26 (s, 1H), 9.15 (s, 1H), 8.42-7.41 (m, 11H), 6.40 (s, 1, H), 4.85 (s, 2H), 1.28 (s, 9H). MS (ESI) m/z: 433 (M+H$^+$).

Example F

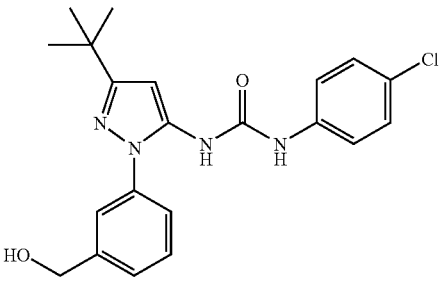

To a stirred solution of Example C (1.60 g, 3.63 mmol) in THF (200 mL) was added LiAlH$_4$ powder (413 mg, 10.9 mmol) at −10° C. under N$_2$. The mixture was stirred for 2 h and excess LiAlH$_4$ was quenched by adding ice. The solution was acidified to pH=7 with dilute HCl. Solvents were slowly removed and the solid was filtered and washed with EtOAc (200+100 mL). The filtrate was concentrated to yield 1-{3-tert-butyl-1-[3-hydroxymethyl)phenyl]-1H-pyrazol-5-yl}-3-(4-chlorophenyl)urea (1.40 g, 97%). $^1$H NMR (DMSO-$d_6$): δ 9.11 (s, 1H), 8.47 (s, 1H), 7.47-7.27 (m, 8H), 6.35 (s, 1H), 5.30 (t, J=5.6 Hz, 1H), 4.55 (d, J=5.6 Hz, 2H), 1.26 (s, 9H); MS (ESI) m/z: 399 (M+H$^+$).

Example G

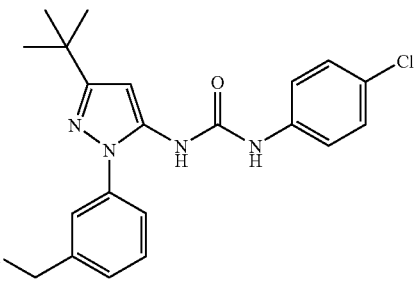

A solution of Example F (800 mg, 2.0 mmol) and SOCl$_2$ (0.30 mL, 4 mmol) in CHCl$_3$ (30 mL) was refluxed gently for 3 h. The solvent was evaporated in vacuum and the residue was taken up to in CH$_2$Cl$_2$ (2×20 mL). After removal of the solvent, 1-{3-tert-butyl-1-[3-(chloromethyl)phenyl]-1H-pyrazol-5-yl}-3-(4-chlorophenyl)urea (812 mg, 97%) was obtained as white powder. $^1$H NMR (DMSO-$d_6$): δ 9.57 (s, 1H), 8.75 (s, 1H), 7.63 (s, 1H), 7.50-7.26 (m, 7H), 6.35 (s, 1H), 4.83 (s, 2H), 1.27 (s, 9H); MS (ESI) m/z: 417 (M+H$^+$).

Example H

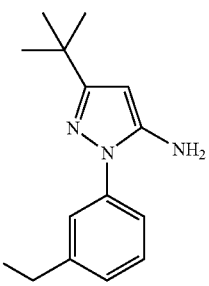

To a suspension of LiAlH$_4$ (5.28 g, 139.2 mmol) in THF (1000 mL) was added Example A (20.0 g, 69.6 mmol) in portions at 0° C. under N$_2$. The reaction mixture was stirred for 5 h, quenched with 1 N HCl at 0° C. and the precipitate was filtered, washed by EtOAc and the filtrate evaporated to yield [3-(5-amino-3-tert-butyl-1H-pyrazol-1-yl)phenyl]methanol (15.2 g, 89%). $^1$H NMR (DMSO-$d_6$): 7.49 (s, 1H), 7.37 (m, 2H), 7.19 (d, J=7.2 Hz, 1H), 5.35 (s, 1H), 5.25 (t, J=5.6 Hz, 1H), 5.14 (s, 2H), 4.53 (d, J=5.6 Hz, 2H), 1.19 (s, 9H); MS (ESI) m/z: 246.19 (M+H$^+$).

The crude material from the previous reaction (5.0 g, 20.4 mmol) was dissolved in dry THF (50 mL) and SOCl$_2$ (4.85 g, 40.8 mmol), stirred for 2 h at RT, concentrated in vacuo to yield 3-tert-butyl-1-(3-chloromethylphenyl)-1H-pyrazol-5-amine (5.4 g), which was added to N$_3$ (3.93 g, 60.5 mmol) in DMF (50 mL). The reaction mixture was heated at 30° C. for 2 h, poured into H$_2$O (50 mL), and extracted with CH$_2$Cl$_2$. The organic layers were combined, dried over MgSO$_4$, and concentrated in vacuo to yield crude 3-tert-butyl-1-[3-(azidomethyl)phenyl]-1H-pyrazol-5-amine (1.50 g, 5.55 mmol).

Example I

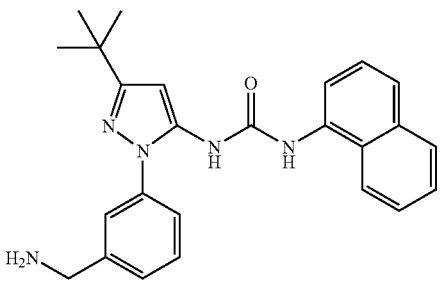

Example H was dissolved in dry THF (10 mL) and added a THF solution (10 mL) of 1-isocyano naphthalene (1.13 g, 6.66 mmol) and pyridine (5.27 g, 66.6 mmol) at RT. The reaction mixture was stirred for 3 h, quenched with H$_2$O (30 mL), the resulting precipitate filtered and washed with 1 N HCl and ether to yield 1-[2-(3-azidomethyl-phenyl)-5-t-butyl-2H-pyrazol-3-yl]-3-naphthalen-1-yl-urea (2.4 g, 98%) as a white solid.

The crude material from the previous reaction and Pd/C (0.4 g) in THF (30 mL) was hydrogenated under 1 atm at RT for 2 h. The catalyst was removed by filtration and the filtrate concentrated in vacuo to yield 1-{3-tert-butyl-1-[3-(amonomethyl)phenyl}-1H-pyrazol-5-yl)-3-(naphthalene-1-yl)urea (2.2 g, 96%) as a yellow solid. $^1$H NMR (DMSO-d$_6$): 9.02 (s, 1H), 7.91 (d, J=7.2 Hz, 1H), 7.89 (d, J=7.6 Hz, 2H), 7.67-7.33 (m, 9H), 6.40 (s, 1H), 3.81 (s, 2H), 1.27 (s, 9H); MS (ESI) m/z: 414 (M+H$^+$).

Example J

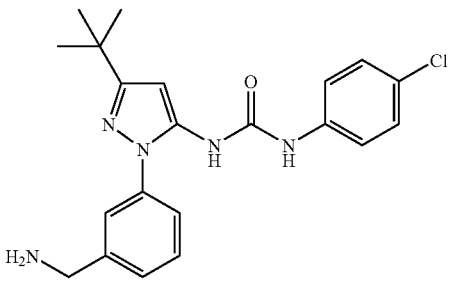

To a solution of Example H (1.50 g, 5.55 mmol) in dry THF (10 mL) was added a THF solution (10 mL) of 4-chlorophenyl isocyanate (1.02 g, 6.66 mmol) and pyridine (5.27 g, 66.6 mmol) at RT. The reaction mixture was stirred for 3 h and then H$_2$O (30 mL) was added. The precipitate was filtered and washed with 1N HCl and ether to give 1-{3-tert-butyl-1-[3-(amonomethyl)phenyl}-1H-pyrazol-5-yl)-3-(4-chlorophenyl)urea (2.28 g, 97%) as a white solid, which was used for next step without further purification. MS (ESI) m/z: 424 (M+H$^+$).

Example K

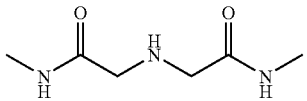

To a solution of benzyl amine (16.5 g, 154 mmol) and ethyl bromoacetate (51.5 g, 308 mmol) in ethanol (500 mL) was added K$_2$CO$_3$ (127.5 g, 924 mmol). The mixture was stirred at RT for 3 h, was filtered, washed with EtOH, concentrated in vacuo and chromatographed to yield N-(2-ethoxy-2-oxoethyl)-N-(phenylmethyl)-glycine ethyl ester (29 g, 67%). $^1$H NMR (CDCl$_3$): δ 7.39-7.23 (m, 5H), 4.16 (q, J=7.2 Hz, 4H), 3.91 (s, 2H), 3.54 (s, 4H), 1.26 (t, J=7.2 Hz, 6H); MS (ESI): m/e: 280 (M$^+$+H).

A solution of N-(2-ethoxy-2-oxoethyl)-N-(phenylmethyl)-glycine ethyl ester (7.70 g, 27.6 mmol) in methylamine alcohol solution (25-30%, 50 mL) was heated to 50° C. in a sealed tube for 3 h, cooled to RT and concentrated in vacuo to yield N-(2-methylamino-2-oxoethyl)-N-(phenylmethyl)-glycine methylamide in quantitative yield (7.63 g). $^1$H NMR (CDCl$_3$): δ 7.35-7.28 (m, 5H), 6.75 (br s, 2H), 3.71 (s, 2H), 3.20 (s, 4H), 2.81 (d, J=5.6 Hz, 6H); MS (ESI) m/e 250(M+H$^+$).

The mixture of N-(2-methylamino-2-oxoethyl)-N-(phenylmethyl)-glycine methylamide (3.09 g, 11.2 mmol) in MeOH (30 mL) was added 10% Pd/C (0.15 g). The mixture was stirred and heated to 40° C. under 40 psi H$_2$ for 10 h, filtered and concentrated in vacuo to yield N-(2-methylamino-2-oxoethyl)-glycine methylamide in quantitative yield (1.76 g). $^1$H NMR (CDCl$_3$): δ 6.95(br s, 2H), 3.23 (s, 4H), 2.79(d, J=6.0, 4.8 Hz), 2.25(br s 1H); MS (ESI) m/e 160(M+H$^+$)

Example 1

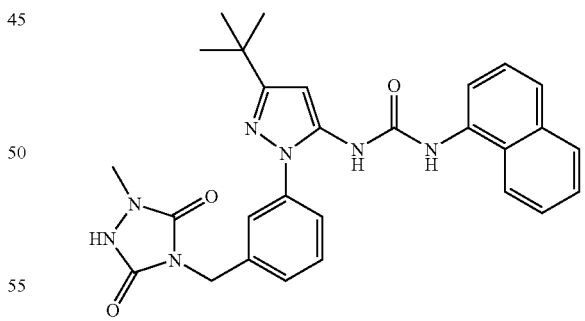

To a solution of 1-methyl-[1,2,4]triazolidine-3,5-dione (188 mg, 16.4 mmol) and sodium hydride (20 mg, 0.52 mmol) in DMSO (1 mL) was added Example E (86 mg, 0.2 mmol). The reaction was stirred at RT overnight, quenched with H$_2$O (10 mL), extracted with CH$_2$Cl$_2$, and the organic layer was separated, washed with brine, dried over Na$_2$SO$_4$ and concentrated in vacuo. The residue was purified by preparative HPLC to yield 1-(3-tert-butyl-1-{3-[(1-methyl-3,5-dioxo-1,2,4-triazolidin-4-yl)methyl]phenyl}-1H-pyrazol-5-yl)-3-

(naphthalene-1-yl)urea (Example 1, 14 mg). $^1$H NMR (CD$_3$OD): δ 7.88-7.86 (m, 2H), 7.71-7.68 (m, 2H), 7.58 (m, 2H), 7.60-7.42 (m, 5H), 6.49 (s, 1H), 4.85 (s, 1H), 1.34 (s, 9H), 1.27 (s, 6H); MS (ESI) m/z: 525 (M+H$^+$).

Example 2

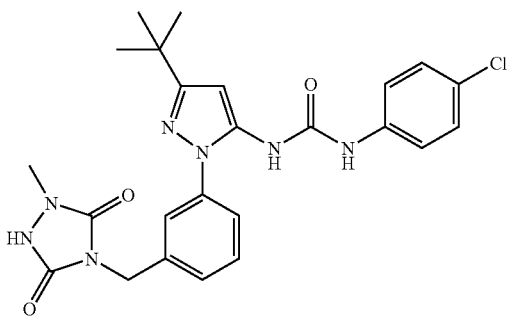

The title compound was synthesized in a manner analogous to Example 1, utilizing Example G to yield 1-(3-tert-butyl-1-{3-[(1-methyl-3,5-dioxo-1,2,4-triazolidin-4-yl)methyl]phenyl}-1H-pyrazol-5-yl)-3-(4-chlorophenyl)urea $^1$H NMR (CD$_3$OD): δ 7.2-7.5 (m, 7H), 6.40 (s 1H), 4.70 (s, 2H), 2.60 (d, J=14 Hz, 2H), 1.90 (m, 1H), 1.50 (m, 1H), 1.45 (s, 9H), 1.30 (m, 2H), 1.21 (s, 3H), 1.18 (s, 6H); MS (ESI) m/z: 620 (M+H$^+$).

Example 3

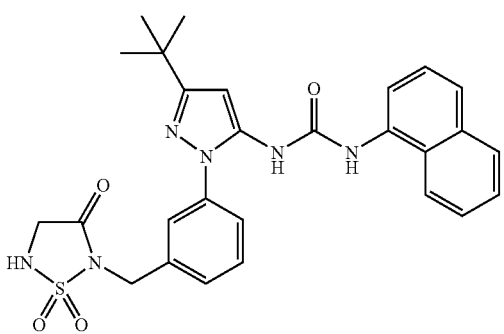

A mixture of compound 1,1-Dioxo-[1,2,5]thiadiazolidin-3-one (94 mg, 0.69 mmol) and NaH (5.5 mg, 0.23 mmol) in THF (2 mL) was stirred at −10° C. under N$_2$ for 1 h until all NaH was dissolved. Example E (100 mg, 0.23 mmol) was added and the reaction was allowed to stir at RT overnight, quenched with H$_2$O, and extracted with CH$_2$Cl$_2$. The combined organic layers were concentrated in vacuo and the residue was purified by preparative HPLC to yield 1-(3-tert-butyl-1-{[3-(1,1,3-trioxo-[1,2,5]thiadiazolidin-2-yl)methyl]phenyl}-1H-pyrazol-5-yl)-3-(naphthalen-1-yl)urea (18 mg) as a white powder. $^1$H NMR (CD$_3$OD): δ 7.71-7.44 (m, 11H), 6.45 (s, 1H), 4.83 (s, 2H), 4.00 (s, 2H), 1.30 (s, 9H). MS (ESI) m/z: 533.40 (M+H$^+$).

Example 4

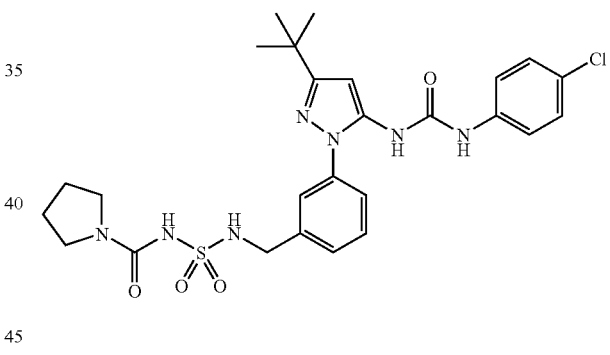

The title compound was obtained in a manner analogous to Example 3 utilizing Example G. to yield 1-(3-tert-butyl-1-{[3-(1,1,3-trioxo-[1,2,5]thiadiazolidin-2-yl)methyl]phenyl}-1H-pyrazol-5-yl)-3-(4-chlorophenyl)urea. $^1$H NMR (CD$_3$OD): δ 7.38-7.24 (m, 8H), 6.42 (s, 1H), 4.83 (s, 2H), 4.02 (s, 2H), 1.34 (s, 9H); MS (ESI) m/z: 517 (M+H$^+$).

Example 5

To a stirred solution of chlorosulfonyl isocyanate (19.8 μL, 0.227 mmol) in CH$_2$Cl$_2$ (0.5 mL) at 0° C. was added pyrrolidine (18.8 μL, 0.227 mmol) at such a rate that the reaction solution temperature did not rise above 5° C. After stirring for 1.5 h, a solution of Example J (97.3 mg, 0.25 mmol) and Et$_3$N (95 μL, 0.678 mmol) in CH$_2$Cl$_2$ (1.5 mL) was added at such a rate that the reaction temperature did not rise above 5° C. When the addition was completed, the reaction solution was warmed to RT and stirred overnight. The reaction mixture was poured into 10% HCl, extracted with CH$_2$Cl$_2$, the organic layer washed with saturated NaCl, dried over MgSO$_4$, and filtered. After removal of the solvents, the crude product was purified by preparative HPLC to yield 1-(3-tert-butyl-1-[[3-N-[[(1-pyrrolidinylcarbonyl)amino]sulphonyl]aminomethyl]phenyl]-1H-pyrazol-5-yl)-3-(4-chlorophenyl)urea. $^1$H NMR (CD$_3$OD): δ 7.61 (s, 1H), 7.43-7.47 (m, 3H), 7.23-7.25 (dd, J=6.8 Hz, 2H), 7.44 (dd, J=6.8 Hz, 2H), 6.52 (s, 1H), 4.05 (s, 2H), 3.02 (m, 4H), 1.75 (m, 4H), 1.34 (s, 9H); MS (ESI) m/z: 574.00 (M+H$^+$).

Example 6

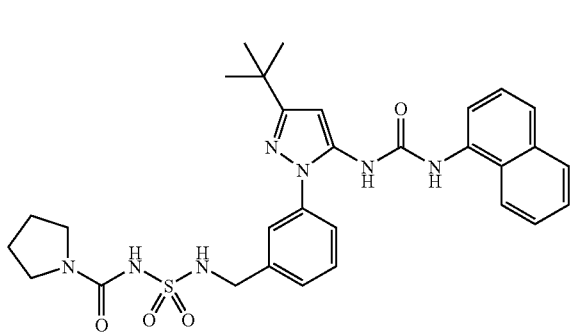

The title compound was made in a manner analogous to Example 5 utilizing Example I to yield 1-(3-tert-butyl-1-[[3-N-[[(1-pyrrolidinylcarbonyl)amino]sulphonyl]aminomethyl]-phenyl]-1H-pyrazol-5-yl)-3-(naphthalen-1-yl)urea.
¹HNMR (CDCl₃): δ 7.88 (m, 2H), 7.02-7.39 (m, 2H), 7.43-7.50 (m, 7H), 6.48 (s, 1H), 4.45 (s, 1H), 3.32-3.36 (m, 4H), 1.77-1.81 (m, 4H), 1.34 (s, 9H); MS (ESI) m/z: 590.03 (M+H⁺).

Example 7

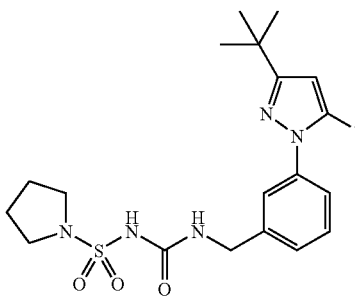

To a stirred solution of chlorosulfonyl isocyanate (19.8μΛ, 0.227μμολ)ινXH₂Xλ₂ (0.5μΛ) ατ 0° C., was added Example J (97.3 mg, 0.25 mmol) at such a rate that the reaction solution temperature did not rise above 5° C. After being stirred for 1.5 h, a solution of pyrrolidine (18.8 μL, 0.227 mmol) and Et₃N (95 μL, 0.678 mmol) in CH₂Cl₂ (1.5 mL) was added at such a rate that the reaction temperature did not rise above 5° C. When addition was completed, the reaction solution was warmed to RT and stirred overnight. The reaction mixture was poured into 10% HCl, extracted with CH₂Cl₂, the organic layer was washed with saturated NaCl, dried over Mg₂SO₄, and filtered. After removal of the solvents, the crude product was purified by preparative HPLC to yield 1-(3-tert-butyl-1-[[3-N-[[(1-pyrrolidinylsulphonyl)amino]carbonyl]aminomethyl]phenyl]-1H-pyrazol-5-yl)-3-(4-chlorophenyl)urea.
¹HNMR (CDCl₃): δ 7.38 (m, 1H), 7.36-7.42 (m, 3H), 7.23 (d, J=8.8 Hz, 2H), 7.40 (d, J=8.8 Hz, 2H), 6.43 (s, 1H), 4.59 (s, 1H), 4.43 (s, 2H), 1.81 (s, 2H), 1.33 (s, 9H); MS (ESI) m/z: 574.10 (M+H⁺).

Example 8

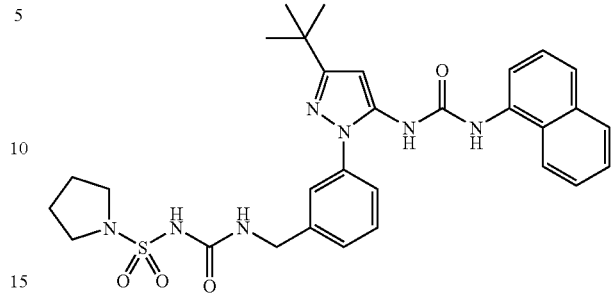

The title compound was made in a manner analogous to Example 7 utilizing Example I to yield 1-(3-tert-butyl-1-[[3-N-[[(1-pyrrolidinylsulphonyl)amino]carbonyl]aminomethyl]-phenyl]-1H-pyrazol-5-yl)-3-(naphthalen-1-yl)urea.
¹HNMR (CDCl₃): δ 7.88 (m, 2H), 7.02-7.39 (m, 2H), 7.43-7.50 (m, 7H), 6.48 (s, 1H), 4.45 (s, 1H), 3.32-3.36 (m, 4H), 1.77-1.81 (m, 4H), 1.34 (s, 9H); MS (ESI) m/z: 590.03 (M+H⁺).

Example 9

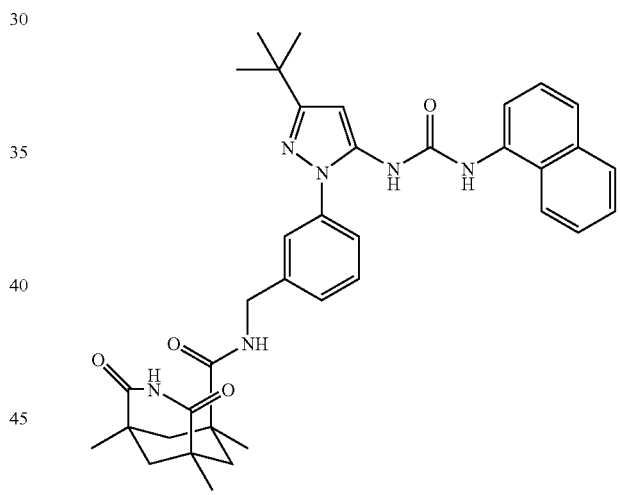

To a solution of Reagent BB (36 mg, 0.15 mmol), Example 1 (62 mg, 0.15 mmol), HOBt (40 mg, 0.4 mmol) and NMM (0.1 mL, 0.9 mmol) in DMF (10 mL) was added EDCI (58 mg, 0.3 mmol). After being stirred overnight, the mixture was poured into water (15 mL) and extracted with EtOAc (3 5 mL). The organic layers were combined, washed with brine, dried with Na₂SO₄, and concentrated in vacuo. The residue was purified by preparative TLC to yield 1,5,7-trimethyl-2,4-dioxo-3-azabicyclo[3.3.1]nonane-7-carboxylic acid 3-[3-t-butyl-5-(3-naphthalen-1-yl-ureido)-pyrazol-1-yl]benzylamide (22 mg). ¹H NMR (CDCl₃): δ 8.40 (s, 1H), 8.14 (d, J=8.0 Hz, 2H), 7.91 (s, 1H), 7.87 (s, 1H), 7.86 (d, J=7.2 Hz, 1H), 7.78 (d, J=7.6 Hz, 1H), 7.73 (d, J=8.4 Hz, 1H), 7.69 (d, J=8.4 Hz, 1H), 7.57-7.40 (m, 4H), 7.34 (d, J=7.6 Hz, 1H), 6.69 (s, 1H), 6.32 (t, J=5.6 Hz, 1H), 5.92 (brs, 1H), 4.31 (d, J=5.6 Hz, 2H), 2.37 (d, J=14.8 Hz, 2H), 1.80 (d, J=13.2 Hz, 1H), 1.35 (s, 9H), 1.21 (d, J=13.2 Hz, 1H), 1.15 (s, 3H), 1.12 (d, J=12.8 Hz, 2H), 1.04 (s, 6H); MS (ESI) m/z: 635 (M+H⁺).

Example 10

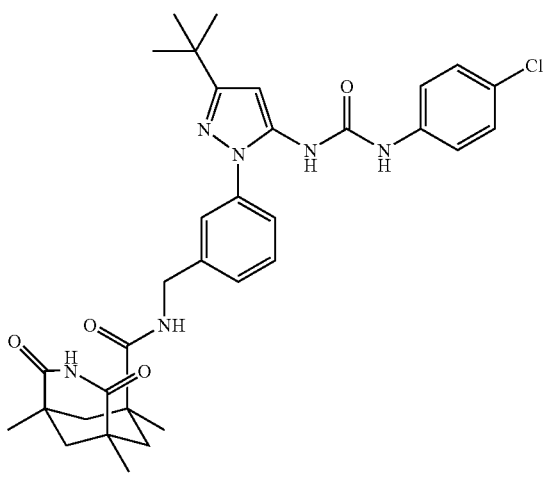

The title compound, was synthesized in a manner analogous to Example 9 utilizing Example J to yield 1,5,7-trimethyl-2,4-dioxo-3-aza-bicyclo[3.3.1]nonane-7-carboxylic acid 3-{3-t-butyl-5-[3-(4-chloro-phenyl)-ureido]-pyrazol-1-yl}benzylamide. $^1$H NMR (CDCl$_3$): δ 8.48 (s, 1H), 7.78 (s, 1H), 7.75 (d, J=8.0 Hz, 1H), 7.69 (s, 1H), 7.53 (t, J=8.0 Hz, 1H), 7.48 (d, J=8.8 Hz, 2H), 7.26 (m, 3H), 6.62 (s, 1H), 6.35 (t, J=6.0 Hz, 1H), 5.69 (brs, 1H), 4.26 (d, J=6.0 Hz, 2H), 2.48 (d, J=14.0 Hz, 2H), 1.87 (d, J=13.6 Hz, 1H), 1.35 (s, 9H), 1.25 (m, 6H), 1.15 (s, 6H); MS (ESI) m/z: 619 (M+H$^+$).

Example 11

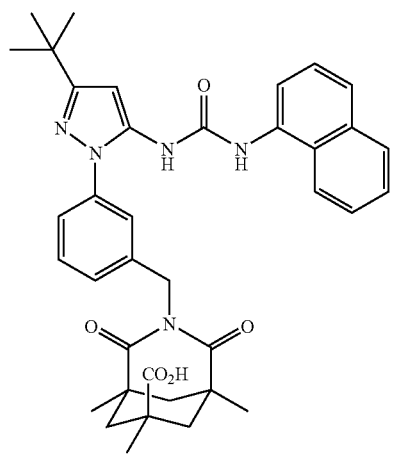

A mixture of Example I (41 mg, 0.1 mmol), Kemp acid anhydride (24 mg, 0.1 mmol) and Et$_3$N (100 mg, 1 mmol) in anhydrous CH$_2$Cl$_2$ (2 mL) were stirred overnight at RT, and concentrated in vacuo. Anhydrous benzene (20 mL) was added to the residue, the mixture was refluxed for 3 h, concentrated in vacuo and purified by preparative HPLC to yield 3-{3-[3-t-butyl-5-(3-naphthalen-1-yl-ureido)-pyrazol-1-yl]-benzyl}-1,5-di-methyl-2,4-dioxo-3-aza-bicyclo[3.3.1]nonane-7-carboxylic acid (8.8 mg, 14%). $^1$H NMR (CD$_3$OD): δ 7.3-7.4 (m, 2H), 7.20 (m, 2H), 7.4-7.6 (m, 7H), 6.50 (m, 1H), 4.80 (s, 2H), 2.60 (d, J=14 Hz, 2H), 1.90 (m, 1H), 1.40 (m, 1H), 1.30 (m, 2H), 1.20 (s, 3H), 1.15 (s, 6H); MS (ESI) m/z: 636 (M+H$^+$).

Example 12

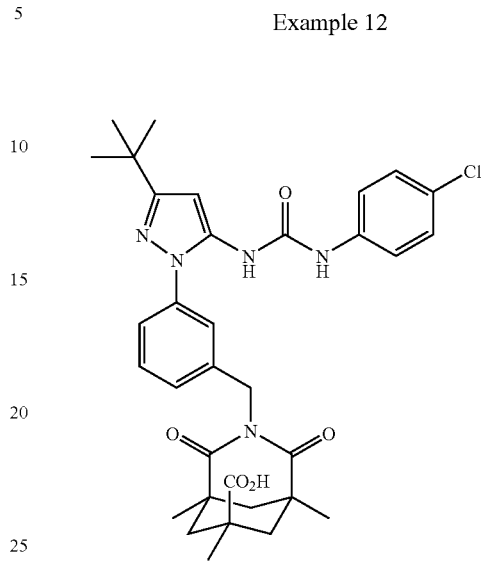

The title compound, was synthesized in a manner analogous to Example 11 utilizing Example J to yield 3-{3-[3-t-butyl-5-(3-naphthalen-1-yl-ureido)-pyrazol-1-yl]-benzyl}-1,5-dimethyl-2,4-dioxo-3-aza-bicyclo[3.3.1]nonane-7-carboxylic acid. $^1$H NMR (CD$_3$OD): δ 7.2-7.5 (m, 7H), 6.40 (s, 1H), 4.70 (s, 2H), 2.60 (d, J=14 Hz, 2H), 1.90 (m, 1H), 1.50 (m, 1H), 1.45 (s, 9H), 1.30 (m, 2H), 1.21 (s, 3H), 1.18 (s, 6H); MS (ESI) m/z: 620 (M+H$^+$).

Example 13

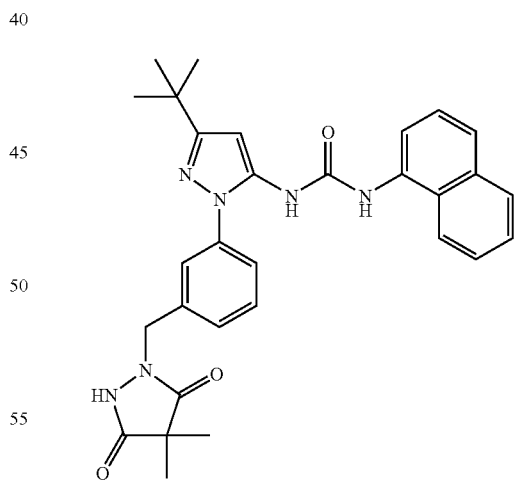

The title compound was synthesized in a manner analogous to Example 1 utilizing Example E and 4,4-dimethyl-3,5-dioxo-pyrazolidine to yield 1-(3-tert-butyl-1-{3-[(4,4-dimethyl-3,5-dioxopyrazolidin-1-yl)methyl]phenyl}-1H-pyrazol-5-yl)-3-(naphthalen-1-yl)urea. $^1$H NMR (CD$_3$OD): δ 7.88-7.86 (m, 2H), 7.71-7.68 (m, 2H), 7.58 (m, 2H), 7.60-7.42 (m, 5H), 6.49 (s, 1H), 4.85 (s, 1H), 1.34 (s, 9H), 1.27 (s, 6H); MS (ESI) m/z: 525 (M+H$^+$).

Example 14

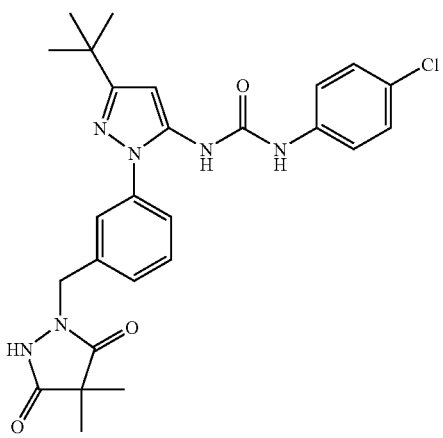

The title compound was synthesized in a manner analogous to Example 1 utilizing Example G and 4,4-dimethyl-3,5-dioxo-pyrazolidine to yield 1-(3-tert-butyl-1-{3-[(4,4-dimethyl-3,5-dioxopyrazolidin-1-yl)methyl]phenyl}-1H-pyrazol-5-yl)-3-(4-chlorophenyl)urea. $^1$H NMR (CD$_3$OD): δ 7.60-7.20 (m, 8H), 6.43 (s, 1H), 4.70 (s, 1H), 1.34 (s, 9H), 1.26 (s, 6H); MS (ESI) m/z: 509, 511 (M+H$^+$).

Example 15

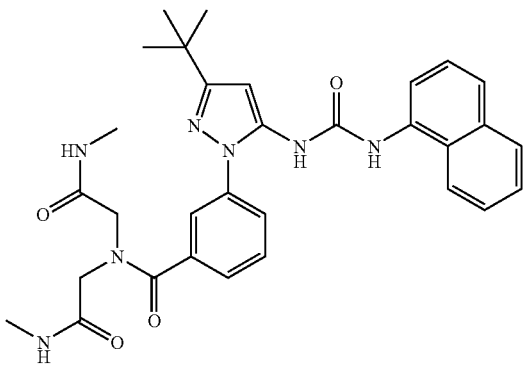

Example B was saponified with 2N LiOH in MeOH, and to the resulting acid (64.2 mg, 0.15 mmol) were added HOBt (30 mg, 0.225 mmol), Example K (24 mg, 0.15 mmol) and 4-methylmorpholine (60 mg, 0.60 mmol 4.0 equiv), DMF (3 mL) and EDCI (43 mg, 0.225 mmol). The reaction mixture was stirred at RT overnight and poured into H$_2$O (3 mL), and a white precipitate collected and further purified by preparative HPLC to yield 1-[1-(3-{bis[(methylcarbamoyl)methyl]carbamoyl}phenyl)-3-tert-butyl-1H-pyrazol-5-yl]-3-(naphthalen-1-yl)urea (40 mg). $^1$H NMR (CDCl$_3$): δ 8.45 (brs, 1H), 8.10 (d, J=7.6 Hz, 1H), 7.86-7.80 (m, 2H), 7.63-7.56 (m, 2H), 7.52 (s, 1H), 7.47-7.38 (m, 3H), 7.36-7.34 (m, 1H), 7.26 (s, 1H), 7.19-7.17 (m, 2H), 6.60 (s, 1H), 3.98 (s, 2H), 3.81 (s, 3H), 2.87 (s, 3H), 2.63 (s, 3H), 1.34 (s, 9H); MS (ESI) m/z: 570 (M+H$^+$).

Example 16

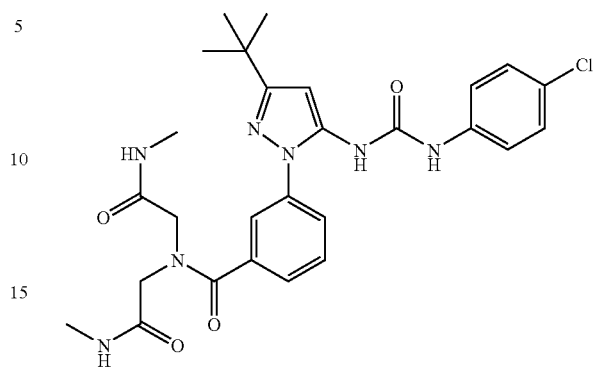

The title compound was synthesized in a manner analogous to Example 15 utilizing Example C (37 mg) and Example K to yield 1-[1-(3-{bis[(methylcarbamoyl)methyl]carbamoyl}phenyl)-3-tert-butyl-1H-pyrazol-5-yl]-3-(4-chlorophenyl)urea. $^1$H NMR (CD$_3$OD): δ 8.58 (brs, 1H), 8.39 (brs, 1H), 7.64-7.62 (m, 3H), 7.53-7.51 (m, 1H), 7.38 (d, J=9.2 Hz, 2H), 7.25 (d, J=8.8 Hz, 2H), 6.44 (s, 1H), 4.17 (s, 2H), 4.11 (s, 2H), 2.79 (s, 3H), 2.69 (s, 3H), 1.34-1.28 (m, 12H); MS (ESI) m/z: 554 (M+H$^+$).

Example 17

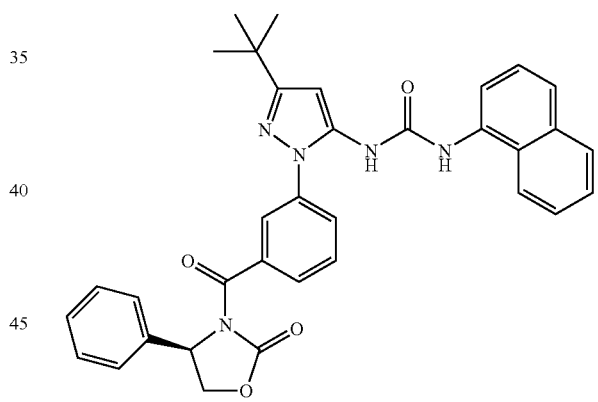

Example B was saponified with 2N LiOH in MeOH, and to the resulting acid (0.642 g, 1.5 mmol) in dry THF (25 mL) at −78° C. were added freshly distilled triethylamine (0.202 g, 2.0 mmol) and pivaloyl chloride (0.216 g, 1.80 mmol) with vigorous stirring. After stirring at −78° C. for 15 min and at 0° C. for 45 min, the mixture was again cooled to −78° C. and then transferred into the THF solution of lithium salt of D-4-phenyl-oxazolidin-2-one [*: The lithium salt of the oxazolidinone regeant was previously prepared by the slow addition of n-BuLi (2.50M in hexane, 1.20 mL, 3.0 mmol) into THF solution of D-4-phenyl-oxazoldin-2-one at −78° C.]. The reaction solution was stirred at −78° C. for 2 h and RT overnight, and then quenched with aq. ammonium chloride and extracted with dichloromethane (100 mL). The combined organic layers were dried (Na$_2$SO$_4$) and concentrated in vacuo. The residue was purified by preparative HPLC to yield D-1-{5-tert-butyl-2-[3-(2-oxo-4-phenyl-oxazolidinyl-3-carbonyl)phenyl]-2H-pyrazol-3-yl}-3-(naphthalen-1-yl)urea (207 mg, 24%). ¹HNMR (CDCl₃): δ 8.14-8.09 (m, 2H), 8.06 (s, 1H), 7.86-7.81 (m, 4H), 7.79 (s, 1H), 7.68-7.61 (m, 2H), 7.51-7.40 (m, 9H), 6.75 (s, 1H), 5.80 (t, J=9.2, 7.6 Hz, 1H), 4.89 (t, J=9.2 Hz, 1H), 4.42 (dd, J=9.2, 7.6 Hz, 1H), 1.37 (s, 9H); MS (ESI) m/z: 574 (M+H⁺).

Example 18

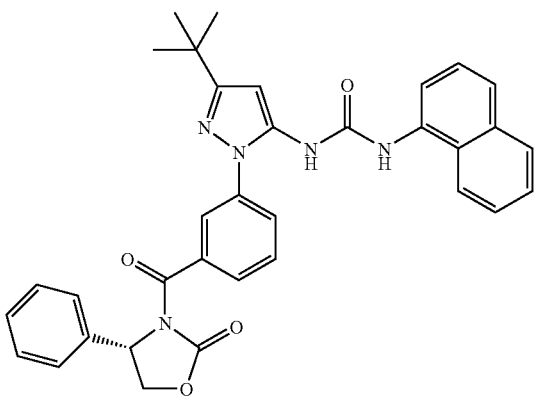

The title compound was synthesized in a manner analogous to Example 17 utilizing Example B and L-4-phenyl-oxazolidin-2-one to yield L-1-{5-tert-butyl-2-[3-(2-oxo-4-phenyl-oxazolidinyl-3-carbonyl)phenyl]-2H-pyrazol-3-yl}-3-(naphthalen-1-yl)urea ¹H NMR (CDCl₃): δ 8.14-8.09 (m, 2H), 8.06 (s, 1H), 7.86-7.81 (m, 4H), 7.79 (s, 1H), 7.68-7.61 (m, 2H), 7.51-7.40 (m, 9H), 6.75 (s, 1H), 5.80 (t, J=9.2, 7.6 Hz, 1H), 4.89 (t, J=9.2 Hz, 1H), 4.42 (dd, J=9.2, 7.6 Hz, 1H), 1.37 (s, 9H); MS (ESI) m/z: 574 (M+H⁺)

Example 19

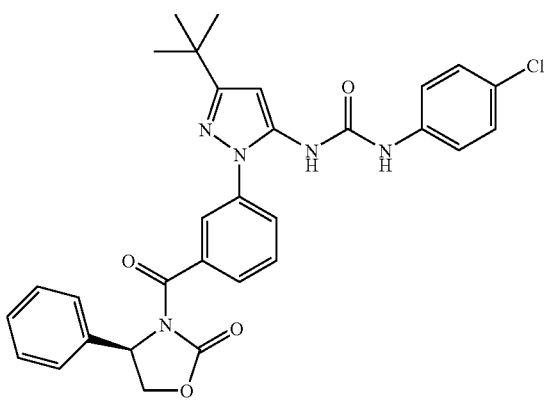

The title compound was synthesized in a manner analogous to Example 17 utilizing Example C and D-4-phenyl-oxazolidin-2-one to yield D-1-{5-tert-butyl-2-[3-(2-oxo-4-phenyl-oxazolidinyl-3-carbonyl)phenyl]-2H-pyrazol-3-yl}-3-(4-chlorophenyl)urea. ¹H NMR (CDCl₃): δ 7.91 (s, 1H), 7.85 (d, J=8.0 Hz, 1H), 7.79 (d, J=7.6 Hz, 1H), 7.71 (m, 1H), 7.65 (m, 1H), 7.49-7.40 (m, 8H), 7.26-7.24 (m, 2H), 6.68 (s, 1H), 5.77 (dd, J=8.8, 8.0 Hz, 1H), 4.96 (t, 8.8 Hz, 1H), 4.44 (dd, J=8.8, 8.0 Hz, 1H), 1.36 (s, 9H); MS (ESI) m/z: 558 (M+H⁺)

Example 20

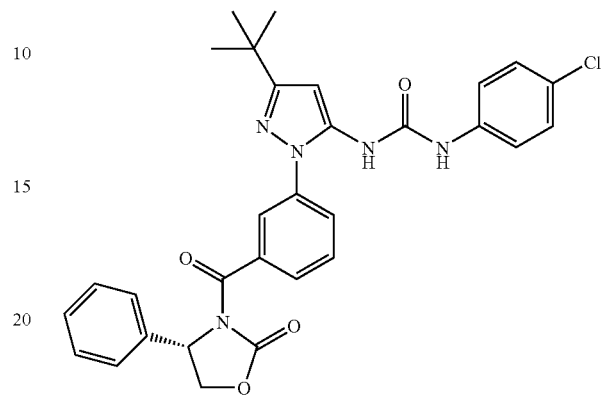

The title compound was synthesized in a manner analogous to Example 17 utilizing Example C and L-4-phenyl-oxazolidin-2-one to yield L-1-{5-tert-butyl-2-[3-(2-oxo-4-phenyl-oxazolidinyl-3-carbonyl)phenyl]-2H-pyrazol-3-yl}-3-(4-chlorophenyl)urea. ¹H NMR (CDCl₃): δ 7.91 (s, 1H), 7.85 (d, J=8.0 Hz, 1H), 7.79 (d, J=7.6 Hz, 1H), 7.71 (m, 1H), 7.65 (m, 1H), 7.49-7.40 (m, 8H), 7.26-7.24 (m, 2H), 6.68 (s, 1H), 5.77 (dd, J=8.8, 8.0 Hz, 1H), 4.96 (t, 8.8 Hz, 1H), 4.44 (dd, J 8.8, 8.0 Hz, 1H), 1.36 (s, 9H); MS (ESI) m/z: 558 (M+H⁺)

Example L

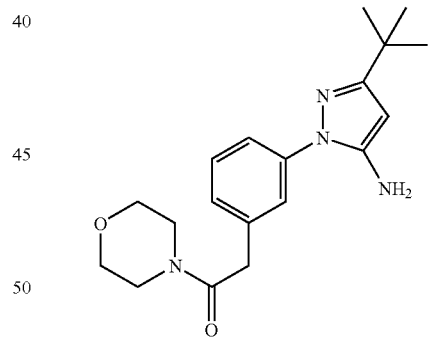

To a stirred suspension of (3-nitro-phenyl)-acetic acid (2 g) in CH₂Cl₂ (40 ml, with a catalytic amount of DMF) at 0° C. under N₂ was added oxalyl chloride (1.1 ml) drop wise. The reaction mixture was stirred for 40 min morpholine (2.5 g) was added. After stirring for 20 min, the reaction mixture was filtered. The filtrate was concentrated in vacuo to yield 1-morpholin-4-yl-2-(3-nitro-phenyl)-ethanone as a solid (2 g). A mixture of 1-morpholin-4-yl-2-(3-nitro-phenyl)-ethanone (2 g) and 10% Pd on activated carbon (0.2 g) in ethanol (30 ml) was hydrogenated at 30 psi for 3 h and filtered over Celite. Removal of the volatiles in vacuo provided 2-(3-amino-phenyl)-1-morpholin-4-yl-ethanone (1.7 g). A solution of 2-(3-amino-phenyl)-1-morpholin-4-yl-ethanone (1.7 g, 7.7 mmol) was dissolved in 6 N HCl (15 ml), cooled to 0° C., and vigorously stirred. Sodium nitrite (0.54 g) in water (8 ml) was added. After 30 min, tin (II) chloride dihydrate (10 g) in 6 N HCl (30 ml) was added. The reaction mixture was stirred at 0° C. for 3 h. The pH was adjusted to pH 14 with solid potassium hydroxide and extracted with EtOAc. The combined organic extracts were concentrated in vacuo provided 2-(3-hydrazinphenyl)-1-morpholin-4-yl-ethanone (1.5 g). 2-(3-Hydrazinophenyl)-1-morpholin-4-yl-ethanone (3 g) and 4,4-dimethyl-3-oxopentanenitrile (1.9 g, 15 mmol) in ethanol (60 ml) and 6 N HCl (1 ml) were refluxed for 1 h and cooled to RT. The reaction mixture was neutralized by adding solid sodium hydrogen carbonate. The slurry was filtered and removal of the volatiles in vacuo provided a residue that was extracted with ethyl acetate. The volatiles were removed in vacuo to provide 2-[3-(3-tert-butyl-5-amino-1H-pyrazol-1-yl)phenyl]-1-morpholinoethanone (4 g), which was used without further purification.

Example 21

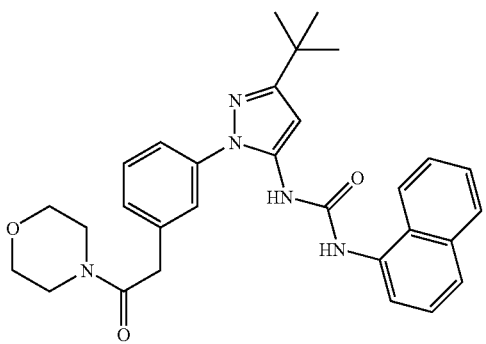

A mixture of Example L (0.2 g, 0.58 mmol) and 1-naphthylisocyanate (0.10 g, 0.6 mmol) in dry $CH_2Cl_2$ (4 ml) was stirred at RT under $N_2$ for 18 h. The solvent was removed in vacuo and the crude product was purified by column chromatography using ethyl acetate/hexane/$CH_2Cl_2$ (3/1/0.7) as the eluent (0.11 g, off-white solid) to yield 1-{3-tert-butyl-1-[3-(2-morpholino-2-oxoethyl)phenyl]-1H-pyrazol-5-yl}-3-(naphthalene-1-yl)urea. mp: 194-196; $^1$H NMR (200 MHz, DMSO-$d_6$): δ 9.07 (1H, s), 8.45 (s, 1H), 8.06-7.93 (m, 3H), 7.69-7.44 (m, 7H), 7.33-7.29 (d, 6.9 Hz, 1H), 6.44 (s, 1H), 3.85 (m, 2H), 3.54-3.45 (m, 8H), 1.31 (s, 9H); MS:

Example 22

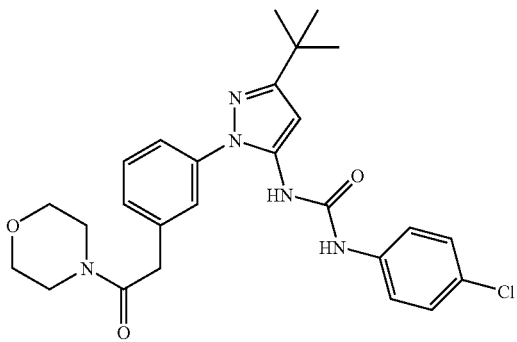

The title compound was synthesized in a manner analogous to Example 21 utilizing Example L (0.2 g, 0.58 mmol) and 4-chlorophenylisocyanate (0.09 g, 0.6 mmol) to yield 1-{3-tert-butyl-1-[3-(2-morpholino-2-oxoethyl)phenyl]-1H-pyrazol-5-yl}-3-(4-chlorophenyl)urea. mp: 100 104; $^1$H NMR (200 MHz, DMSO-$d_6$): δ 9.16 (s, 1H), 8.45 (s, 1H), 7.52-7.30 (m, 8H), 6.38 (s, 1H), 3.83 (m, 1H), 3.53-3.46 (m, 8H), 1.30 (s, 9H); MS:

Example 23

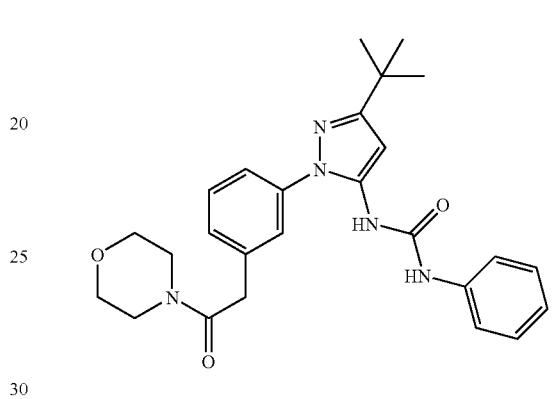

The title compound is synthesized in a manner analogous to Example 21 utilizing Example L (0.2 g, 0.58 mmol) and phenylisocyanate (0.09 g, 0.6 mmol) to yield 1-{3-tert-butyl-1-[3-(2-morpholino-2-oxoethyl)phenyl]-1H-pyrazol-5-yl}-3-phenylurea.

Example 24

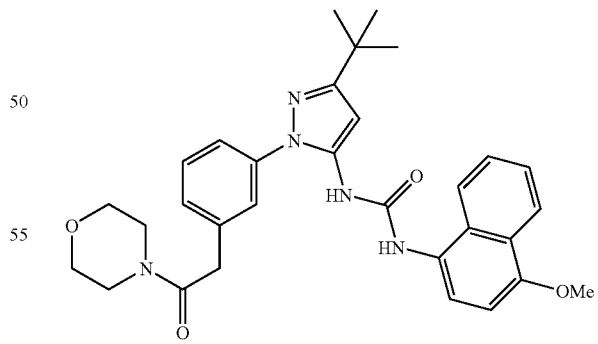

The title compound is synthesized in a manner analogous to Example 21 utilizing Example L (0.2 g, 0.58 mmol) and 1-isocyanato-4-methoxy-naphthalene to yield 1-{3-tert-butyl-1-[3-(2-morpholino-2-oxoethyl)phenyl]-1H-pyrazol-5-yl}-3-(1-methoxynaphthalen-4-yl)urea.

Example M

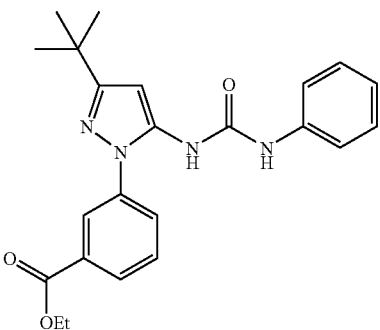

The title compound is synthesized in a manner analogous to Example C utilizing Example A and phenylisocyanate to yield ethyl 3-(3-tert-butyl-5-(3-phenylureido)-1H-pyrazol-1-yl)benzoate.

Example N

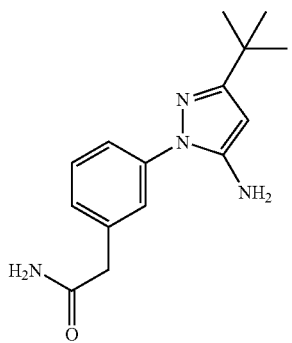

A solution of (3-nitrophenyl)acetic acid (23 g, 127 mmol) in methanol (250 ml) and a catalytic amount of concentrated in vacuo $H_2SO_4$ was heated to reflux for 18 h. The reaction mixture was concentrated in vacuo to a yellow oil. This was dissolved in methanol (250 ml) and stirred for 18 h in an ice bath, whereupon a slow flow of ammonia was charged into the solution. The volatiles were removed in vacuo. The residue was washed with diethyl ether and dried to afford 2-(3-nitrophenyl)acetamide (14 g, off-white solid). $^1$H NMR (CDCl$_3$): δ 8.1 (s, 1H), 8.0 (d, 1H), 7.7 (d, 1H), 7.5 (m, 1H), 7.1 (bd s, 1H), 6.2 (brs, 1H), 3.6 (s, 2H).

The crude material from the previous reaction (8 g) and 10% Pd on activated carbon (1 g) in ethanol (100 ml) was hydrogenated at 30 psi for 18 h and filtered over Celite. Removal of the volatiles in vacuo provided 2-(3-aminophenyl)acetamide (5.7 g). A solution of this material (7 g, 46.7 mmol) was dissolved in 6 N HCl (100 ml), cooled to 0° C., and vigorously stirred. Sodium nitrite (3.22 g, 46.7 mmol) in water (50 ml) was added. After 30 min, tin (II) chloride dihydrate (26 g) in 6 N HCl (100 ml) was added. The reaction mixture was stirred at 0° C. for 3 h. The pH was adjusted to pH 14 with 50% aqueous NaOH solution and extracted with ethyl acetate. The combined organic extracts were concentrated in vacuo provided 2-(3-hydrazinophenyl)acetamide.

The crude material from the previous reaction (ca. 15 mmol) and 4,4-dimethyl-3-oxopentanenitrile (1.85 g, 15 mmol) in ethanol (60 ml) and 6 N HCl (1.5 ml) was refluxed for 1 h and cooled to RT. The reaction mixture was neutralized by adding solid sodium hydrogen carbonate. The slurry was filtered and removal of the volatiles in vacuo provided a residue, which was extracted with ethyl acetate. The solvent was removed in vacuo to provide 2-[3-(3-tert-butyl-5-amino-1H-pyrazol-1-yl)phenyl]acetamide as a white solid (3.2 g), which was used without further purification.

Example 25

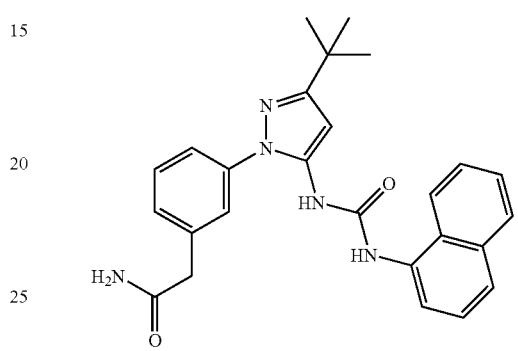

A mixture of Example N (2 g, 0.73 mmol) and 1-naphthylisocyanate (0.124 g, 0.73 mmol) in dry CH$_2$Cl$_2$ (4 ml) was stirred at RT under N$_2$ for 18 h. The solvent was removed in vacuo and the crude product was washed with ethyl acetate (8 ml) and dried in vacuo to yield 1-{3-tert-butyl-1-[3-(carbamoylmethyl)phenyl)-1H-pyrazol-5-yl}-3-(naphthalene-1-yl)urea as a white solid (0.22 g). mp: 230 (dec.); $^1$HNMR (200 MHz, DMSO-d$_6$): δ 9.12 (s, 1H), 8.92 (s, 1H), 8.32-8.08 (m, 3H), 7.94-7.44 (m, 8H), 6.44 (s, 1H), 3.51 (s, 2H), 1.31 (s, 9H); MS:

Example 26

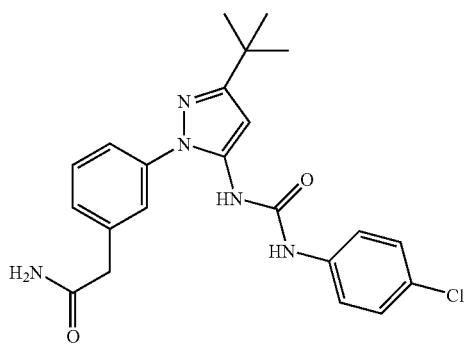

The title compound was synthesized in a manner analogous to Example 23 utilizing Example N (0.2 g, 0.73 mmol) and 4-chlorophenylisocyanate (0.112 g, 0.73 mmol) to yield 1-{3-tert-butyl-1-[3-(carbamoylmethyl)phenyl)-1H-pyrazol-5-yl}-3-(4-chlorophenyl)urea as a white solid (0.28 g). mp: 222 224. (dec.); $^1$H NMR (200 MHz, DMSO-d$_6$); δ 9.15 (s, 1H), 8.46 (s, 1H), 7.55-7.31 (m, 8H), 6.39 (s, 1H), 3.48 (s, 2H), 1.30 (s, 9H); MS:

Example O

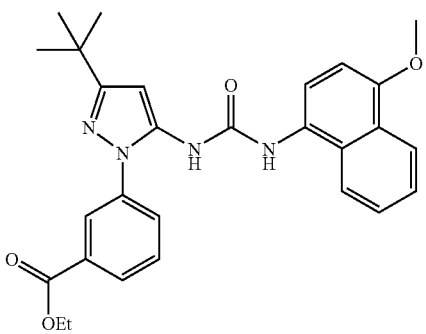

The title compound is synthesized in a manner analogous to Example C utilizing Example A and 1-isocyanato-4-methoxy-naphthaleneto yield ethyl 3-(3-tert-butyl-5-(3-(1-methoxynaphthalen-4-yl)ureido)-1H-pyrazol-1-yl)benzoate.

Example 27

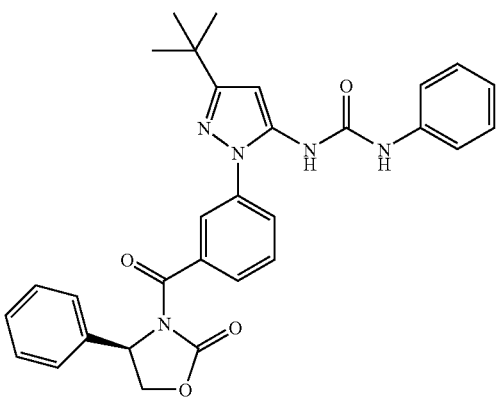

The title compound is synthesized in a manner analogous to Example 17 utilizing Example M and D-4-phenyl-oxazolidin-2-one to yield D-1-{5-tert-butyl-2-[3-(2-oxo-4-phenyl-oxazolidinyl-3-carbonyl)phenyl]-2H-pyrazol-3-yl}-3-phenylurea.

Example 28

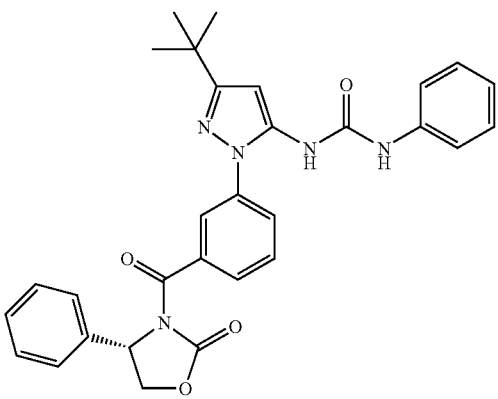

The title compound is synthesized in a manner analogous to Example 17 utilizing Example M and L-4-phenyl-oxazolidin-2-one to yield L-1-{5-tert-butyl-2-[3-(2-oxo-4-phenyl-oxazolidinyl-3-carbonyl)phenyl]-2H-pyrazol-3-yl}-3-phenylurea.

Example P

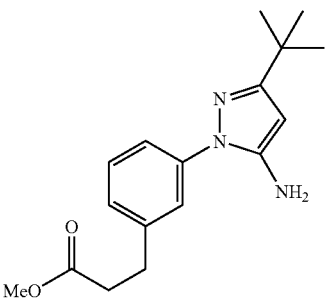

A mixture of 3-(3-amino-phenyl)-acrylic acid methyl ester (6 g) and 10% Pd on activated carbon (1 g) in ethanol (50 ml) was hydrogenated at 30 psi for 18 h and filtered over Celite. Removal of the volatiles in vacuo provided 3-(3-amino-phenyl)propionic acid methyl ester (6 g).

A vigorously stirred solution of the crude material from the previous reaction (5.7 g, 31.8 mmol) dissolved in 6 N HCl (35 ml) was cooled to 0° C., and sodium nitrite (2.2 g) in water (20 ml) was added. After 1 h, tin (II) chloride dihydrate (18 g) in 6 N HCl (35 ml) was added. And the mixture was stirred at 0° C. for 3 h. The pH was adjusted to pH 14 with solid KOH and extracted with EtOAc. The combined organic extracts were concentrated in vacuo provided methyl 3-(3-hydrazino-phenyl)propionate (1.7 g).

A stirred solution of the crude material from the previous reaction (1.7 g, 8.8 mmol) and 4,4-dimethyl-3-oxopentanenitrile (1.2 g, 9.7 mmol) in ethanol (30 ml) and 6 N HCl (2 ml) was refluxed for 18 h and cooled to RT. The volatiles were removed in vacuo and the residue dissolved in EtOAc and washed with 1 N aqueous NaOH. The organic layer was dried ($Na_2SO_4$) and concentrated in vacuo and the residue was purified by column chromatography using 30% ethyl acetate in hexane as the eluent to provide methyl 3-[3-(3-tert-butyl-5-amino-1H-pyrazol-1-yl)phenyl]propionate (3.2 g), which was used without further purification

Example 29

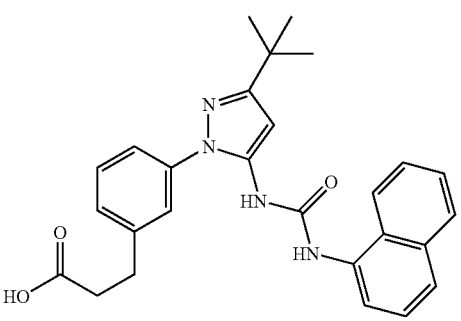

A mixture of Example P (0.35 g, 1.1 mmol) and 1-naphthylisocyanate (0.19 g, 1.05 mmol) in dry $CH_2Cl_2$ (5 ml) was stirred at RT under $N_2$ for 20 h. The solvent was removed in vacuo and the residue was stirred in a solution of THF (3 ml)/MeOH (2 ml)/water (1.5 ml) containing lithium hydroxide (0.1 g) for 3 h at RT, and subsequently diluted with EtOAc and dilute citric acid solution. The organic layer was dried ($Na_2SO_4$), and the volatiles removed in vacuo. The residue was purified by column chromatography using 3% methanol in $CH_2Cl_2$ as the eluent to yield 3-(3-{3-tert-butyl-5-[3-(naphthalen-1-yl)ureido]-1H-pyrazol-1-yl)phenylpropionic acid (0.22 g, brownish solid). mp: 105-107; $^1$H NMR (200 MHz, $CDCl_3$): δ 7.87-7.36 (m, 10H), 7.18-7.16 (m, 1H), 6.52 (s, 1H), 2.93 (t, J=6.9 Hz, 2H), 2.65 (t, J=7.1 Hz, 2H), 1.37 (s, 9H); MS Example 30

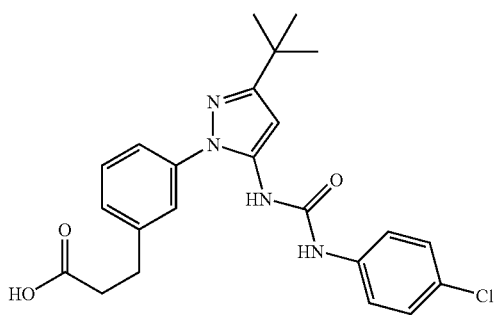

The title compound was synthesized in a manner analogous to Example 29 utilizing Example P (0.30 g, 0.95 mmol) and 4-chlorophenylisocyanate (0.146 g, 0.95 mmol) to yield 3-(3-{3-tert-butyl-5-[3-(4-chloropnehyl)ureido]-1H-pyrazol-1-yl)phenyl)propionic acid (0.05 g, white solid). mp: δ 87; $^1$H NMR (200 MHz, $CDCl_3$): δ 8.21 (s, 1H), 7.44-7.14 (m, 7H), 6.98 (s, 1H), 6.55 (s, 1H), 2.98 (t, J=5.2 Hz, 2H), 2.66 (t, J=5.6 Hz, 2H), 1.40 (s, 9H); MS Example Q

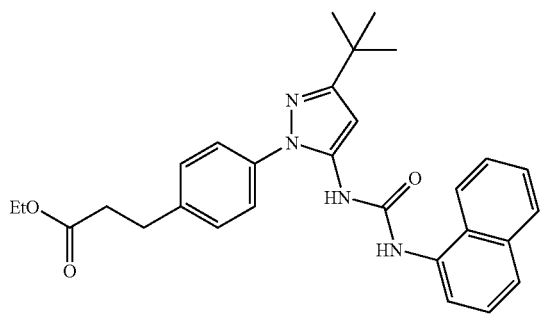

A mixture of ethyl 3-(4-aminophenyl)acrylate (1.5 g) and 10% Pd on activated carbon (0.3 g) in ethanol (20 ml) was hydrogenated at 30 psi for 18 h and filtered over Celite. Removal of the volatiles in vacuo provided ethyl 3-(4-aminophenyl)propionate (1.5 g).

A solution of the crude material from the previous reaction (1.5 g, 8.4 mmol) was dissolved in 6 N HCl (9 ml), cooled to 0° C., and vigorously stirred. Sodium nitrite (0.58 g) in water (7 ml) was added. After 1 h, tin (II) chloride dihydrate (5 g) in 6 N HCl (10 ml) was added. The reaction mixture was stirred at 0° C. for 3 h. The pH was adjusted to pH 14 with solid KOH and extracted with EtOAc. The combined organic extracts were concentrated in vacuo provided ethyl 3-(4-hydrazinophenyl)-propionate(1 g).

The crude material from the previous reaction (1 g, 8.8 mmol) and 4,4-dimethyl-3-oxopentanenitrile (0.7 g) in ethanol (8 ml) and 6 N HCl (1 ml) was refluxed for 18 h and cooled to RT. The volatiles were removed in vacuo. The residue was dissolved in ethyl acetate and washed with 1 N aqueous sodium hydroxide solution. The organic layer was dried ($Na_2SO_4$) and concentrated in vacuo. The residue was purified by column chromatography using 0.7% methanol in $CH_2Cl_2$ as the eluent to provide ethyl 3-{4-[3-tert-butyl-5-(3-(naphthalene-1-yl)ureido]-1H-pyrazol-1-yl}phenyl)propanoate (0.57 g).

Example 31

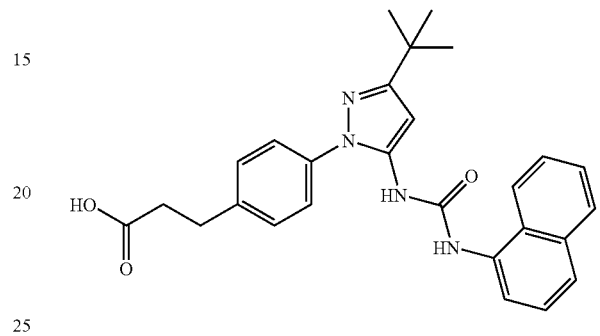

A mixture of Example Q (0.25 g, 0.8 mmol) and 1-naphthylisocyanate (0.13 g, 0.8 mmol) in dry $CH_2Cl_2$ (5 ml) was stirred at RT under $N_2$ for 20 h. The solvent was removed in vacuo and the residue was stirred in a solution of THF (3 ml)/MeOH (2 ml)/water (1.5 ml) containing lithium hydroxide (0.1 g) for 3 h at RT and diluted with EtOAc and diluted citric acid solution. The organic layer was dried ($Na_2SO_4$), and the volatiles removed in vacuo. The residue was purified by column chromatography using 4% methanol in $CH_2Cl_2$ as the eluent to yield 3-{4-[3-tert-butyl-5-(3-(naphthalene-1-yl)ureido]-1H-pyrazol-1-yl}phenyl)propanonic acid (0.18 g, off-white solid). mp: 120 122; $^1$H NMR (200 MHz, $CDCl_3$): δ 7.89-7.06 (m, 11H), 6.5 (s, 1H), 2.89 (m, 2H), 2.61 (m, 2H), 1.37 (s, 9H); MS Example 32

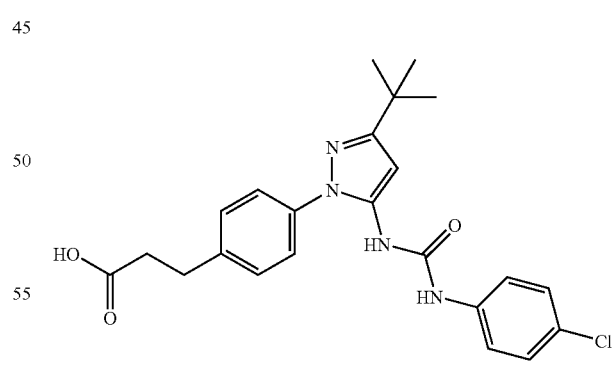

The title compound was synthesized in a manner analogous to Example 31 utilizing Example Q (0.16 g, 0.5 mmol) and 4-chlorophenylisocyanate (0.077 g, 0.5 mmol) to yield 3-{4-[3-tert-butyl-5-(3-(4-chlorphenyl)ureido]-1H-pyrazol-1-yl}phenyl)propanonic acid acid (0.16 g. off-white solid). mp: 112-114; $^1$H NMR (200 MHz, $CDCl_3$): δ 8.16 (s, 1H), 7.56 (s, 1H), 7.21 (s, 2H), 7.09 (s, 2H), 6.42 (s, 1H), 2.80 (m, 2H), 2.56 (m, 2H), 1.32 (s, 9H); MS

Example R

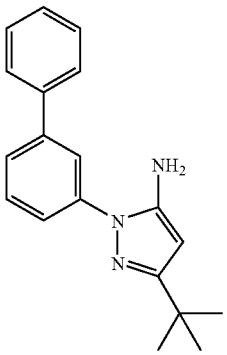

A 250 mL pressure vessel (ACE Glass Teflon screw cap) was charged with 3-nitrobiphenyl (20 g, 0.10 mol) dissolved in THF (~100 mL) and 10% Pd/C (3 g). The reaction vessel was charged with $H_2$ (g) and purged three times. The reaction was charged with 40 psi $H_2$ (g) and placed on a Parr shaker hydrogenation apparatus and allowed to shake overnight at RT. HPLC showed that the reaction was complete thus the reaction mixture was filtered through a bed of Celite and evaporated to yield the amine: 16.7 g (98% yield)

In a 250 mL Erlenmeyer flask with a magnetic stir bar, the crude material from the previous reaction (4.40 g, 0.026 mol) was added to 6 N HCl (40 mL) and cooled with an ice bath to ~0° C. A solution of $NaNO_2$ (2.11 g, 0.0306 mol, 1.18 eq.) in water (5 mL) was added drop wise. After 30 min, $SnCl_2 2H_2O$ (52.0 g, 0.23 mol, 8.86 eq.) in 6N HCl (100 mL) was added and the reaction mixture was allowed to stir for 3 h, then subsequently transferred to a 500 mL round bottom flask. To this, 4,4-dimethyl-3-oxopentanenitrile (3.25 g, 0.026 mol) and EtOH (100 ml) were added and the mixture refluxed for 4 h, concentrated in vacuo and the residue extracted with EtOAc (2×100 mL). The residue was purified by column chromatograph using hexane/EtOAc/$Et_3N$ (8:2:0.2) to yield 0.53 g of Example R. $^1H$ NMR ($CDCl_3$): δ 7.5 (m, 18H), 5.8 (s, 1H), 1.3 (s, 9H).

Example 33

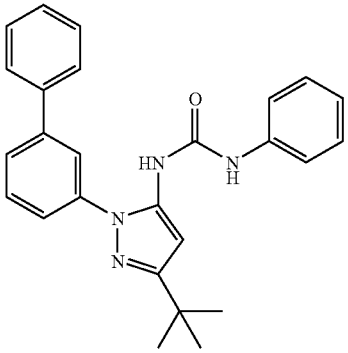

In a dry vial with a magnetic stir bar, Example R (0.145 g; 0.50 mmol) was dissolved in 2 mL $CH_2Cl_2$ (anhydrous) followed by the addition of phenylisocyanate (0.0544 mL; 0.50 mmol; 1 eq.). The reaction was kept under argon and stirred for 17 h. Evaporation of solvent gave a crystalline mass that was triturated with hexane/EtOAc (4:1) and filtered to yield 1-(3-tert-butyl-1-(3-phenylphenyl)-1H-pyrazol-5-yl)-3-phenylurea (0.185 g, 90%). HPLC purity: 96%; mp: 80 84; $^1H$ NMR ($CDCl_3$): δ 7.3 (m, 16H), 6.3 (s, 1H), 1.4 (s, 9H).

Example 34

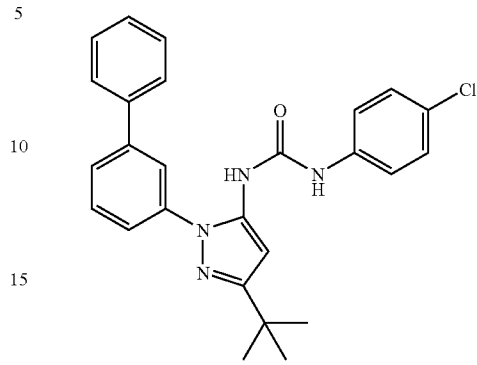

The title compound was synthesized in a manner analogous to Example 33 utilizing Example R (0.145 g; 0.50 mmol) and p-chlorophenylisocyanate (0.0768 g, 0.50 mmol, 1 eq.) to yield 1-(3-tert-butyl-1-(3-phenylphenyl)-1H-pyrazol-5-yl)-3-(4-chlorophenyl)urea (0.205 g, 92%). HPLC purity: 96.5%; mp: 134 136; $^1H$ NMR ($CDCl_3$): δ 7.5 (m, 14H), 7.0 (s, 1H), 6.6 (s, 1H), 6.4 (s, 1H), 1.4 (s, 9H).

Example S

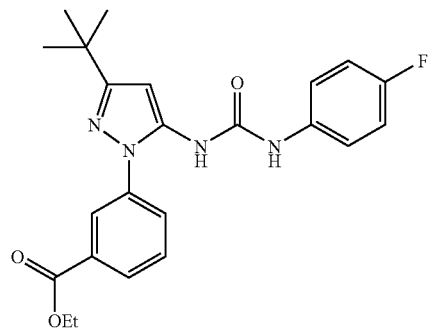

The title compound is synthesized in a manner analogous to Example C utilizing Example A and 4-fluorophenyl isocyanate yield ethyl 3-(3-tert-butyl-5-(3-(4-fluorophenyl)ureido)-1H-pyrazol-1-yl)benzoate.

Example 35

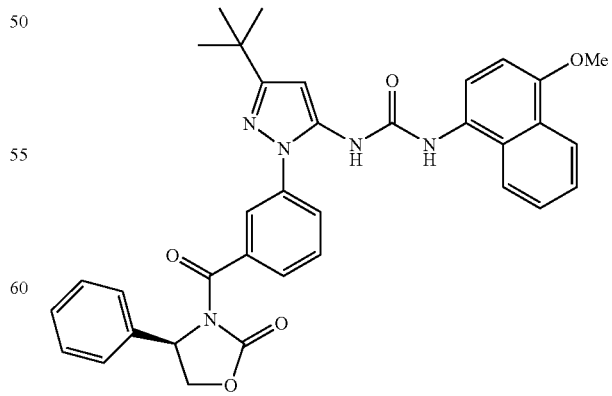

The title compound is synthesized in a manner analogous to Example 17 utilizing Example M and D-4-phenyl-oxazolidin-2-one to yield D-1-{5-tert-butyl-2-[3-(2-oxo-4-phenyl-oxazolidinyl-3-carbonyl)phenyl]-2H-pyrazol-3-yl}-3-(naphthalen-1-yl)urea.

Example 36

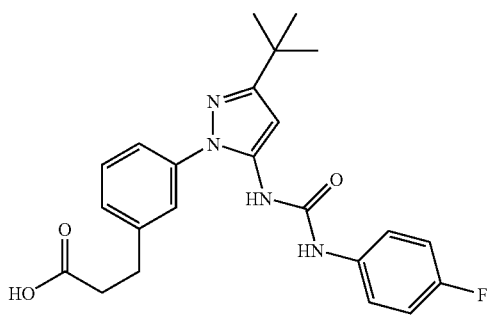

The title compound is synthesized in a manner analogous to Example 29 utilizing Example P (0.30 g, 0.95 mmol) and 4-fluorophenylisocyanate (0.146 g, 0.95 mmol) to yield 3-(3-(3-tert-butyl-5-(3-(4-fluorophenyl)ureido)-1H-pyrazol-1-yl)phenyl)propanoic acid.

Example T

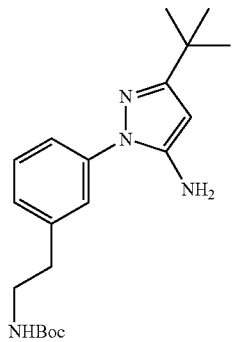

To a stirred solution of Example N (2 g, 7.35 mmol) in THF (6 ml) was added borane-methylsulfide (18 mmol). The mixture was heated to reflux for 90 min and cooled to RT, after which 6 N HCl was added and heated to reflux for 10 min. The mixture was basified with NaOH and extracted with EtOAc. The organic layer was dried ($Na_2SO_4$) filtered and concentrated in vacuo to yield 3-tert-butyl-1-[3-(2-aminoethyl)phenyl]-1H-pyrazol-5 amine (0.9 g).

A mixture of the crude material from the previous reaction (0.8 g, 3.1 mmol) and di-tert-butylcarbonate (0.7 g, 3.5 mmol) and catalytically amount of DMAP in dry $CH_2Cl_2$ (5 ml) was stirred at RT under N, for 18 h. The reaction mixture was concentrated in vacuo and the residue was purified by column chromatography using 1% methanol in $CH_2Cl_2$ as the eluent to yield tert-butyl 3-(3-tert-butyl-5-amino-1H-pyrazol-1-yl)phenylcarbamate (0.5 g).

Example 37

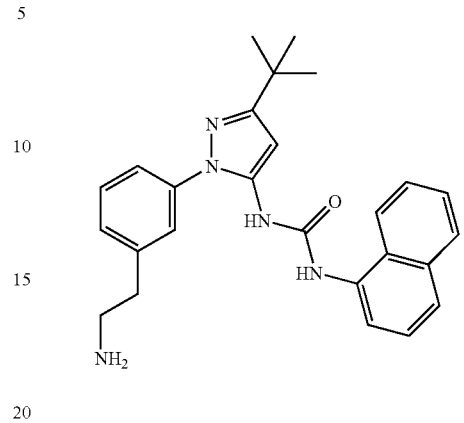

A mixture of Example T (0.26 g, 0.73 mmol) and 1-naphthylisocyanate (0.123 g, 0.73 mmol) in dry $CH_2Cl_2$ (5 ml) was stirred at RT under $N_2$ for 48 h. The solvent was removed in vacuo and the residue was purified by column chromatography using 1% methanol in $CH_2Cl_2$ as the eluent (0.15 g, off-white solid). The solid was then treated with TFA (0.2 ml) for 5 min and diluted with EtOAc. The organic layer was washed with saturated $NaHCO_3$ solution and brine, dried ($Na_2SO_4$), filtered and concentrated in vacuo to yield 1-{3-tert-butyl-1-[3-(2-Aminoethyl)phenyl]-1H-pyrazol-5-yl}-3-(naphthalen-1-yl)urea as a solid (80 mg). mp: 110-112; $^1$H NMR (200 MHz, DMSO-$d_6$): δ 9.09 (s, 1H), 8.90 (s, 1H), 8.01-7.34 (m, 11H), 6.43 (s, 1H), 3.11 (m, 2H), 2.96 (m, 2H), 1.29 (s, 9H); MS Example 38

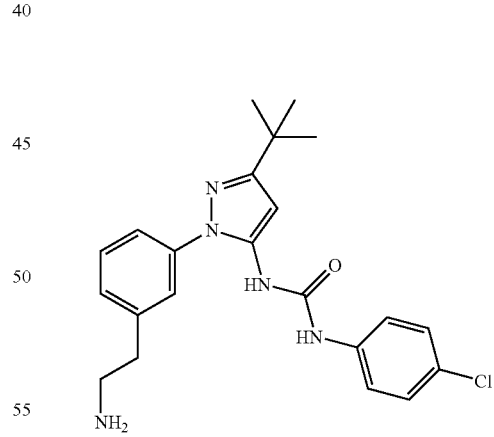

The title compound was synthesized in a manner analogous to Example 37 utilizing Example T (0.15 g, 0.42 mmol) and 4-chlorophenylisocyanate (0.065 g, 0.42 mmol) to yield 1-{3-tert-butyl-1-[3-(2-Aminoethyl)phenyl]-1H-pyrazol-5-yl}-3-(4-chlorophenyl)urea as an off-white solid (20 mg). mp:125-127; $^1$H NMR (200 MHz, CDCl$_3$): δ 8.81 (s, 1H), 8.66 (s, 1H), 7.36-7.13 (m, 8H), 6.54 (s, 1H), 3.15 (brs, 2H), 2.97 (brs, 2H), 1.32 (s, 9H); MS

Example U

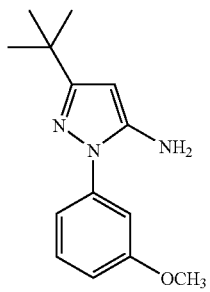

In a 250 mL Erlenmeyer flask with a magnetic stir bar, m-anisidine (9.84 g, 0.052 mol) was added to 6 N HCl (80 mL) and cooled with an ice bath to 0° C. A solution of NaNO$_2$ (4.22 g, 0.0612 mol, 1.18 eq.) in water (10 mL) was added drop wise. After 30 min, SnCl$_2$2H$_2$O (104.0 g, 0.46 mol, 8.86 eq.) in 6 N HCl (200 mL) was added and the reaction mixture was allowed to stir for 3 h., and then subsequently transferred to a 1000 mL round bottom flask. To this, 4,4-dimethyl-3-oxopentanenitrile (8.00 g, 0.064 mol) and EtOH (200 mL) were added and the mixture refluxed for 4 h, concentrated in vacuo and the residue recrystallized from CH$_2$Cl$_2$ to yield 3-tert-butyl-1-(3-methoxyphenyl)-1H-pyrazol-5-amine as the HCl salt (13.9 g).

The crude material from the previous reaction (4.65 g, 0.165 mol) was dissolved in 30 mL of CH$_2$Cl$_2$ with Et$_3$N (2.30 mL, 0.0165 mol, 1 eq.) and stirred for 30 min Extraction with water followed by drying of the organic phase with Na$_2$SO$_4$ and concentration in vacuo yielded a brown syrup that was the free base, 3-tert-butyl-1-(3-methoxyphenyl)-1H-pyrazol-5-amine (3.82 g, 94.5%), which was used without further purification.

Example 39

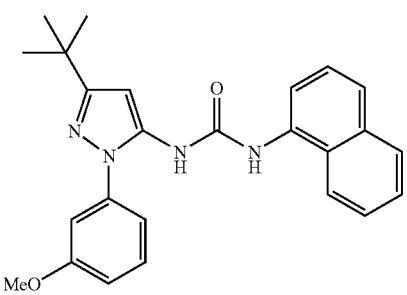

In a dry vial with a magnetic stir bar, Example U (2.62 g, 0.0107 mol) was dissolved in CH$_2$Cl$_2$ (5 mL, anhydrous) followed by the addition of 1-naphthylisocyanate (1.53 mL, 0.0107 mol, 1 eq.). The reaction was kept under Ar and stirred for 18 h. Evaporation of solvent followed by column chromatography with EtOAc/hexane/Et$_3$N (7:2:0.5) as the eluent yielded 1-[3-tert-butyl-1-(3-methoxyphenyl)-1H-pyrazol-5-yl]-3-(naphthalen-1-yl)urea (3.4 g, 77%). HPLC: 97%; mp: 78-80; $^1$H NMR (CDCl$_3$): δ 7.9-6.8 (m, 15H), 6.4 (s, 1H), 3.7 (s, 3H), 1.4 (s, 9H).

Example 40

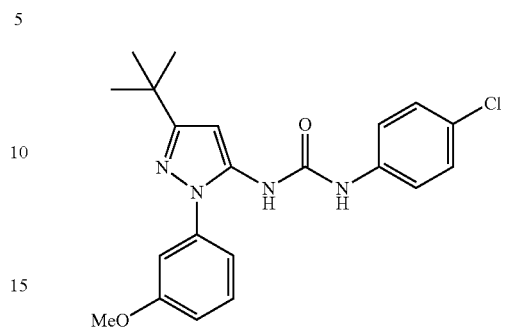

The title compound was synthesized in a manner analogous to Example 39 utilizing Example U (3.82 g; 0.0156 mol) and p-chlorophenylisocyanate (2.39 g, 0.0156 mol, 1 eq.), purified by trituration with hexane/EtOAc (4:1) and filtered to yield 1-[3-tert-butyl-1-(3-methoxyphenyl)-1H-pyrazol-5-yl]-3-(4-chlorophenyl)urea (6.1 g, 98%). HPLC purity: 95%; mp: 158-160; $^1$H NMR (CDCl$_3$): δ 7.7 (s, 1H); δ 7.2 6.8 (m, 8H), 6.4 (s, 11H), 3.7 (s, 3H), 1.3 (s, 9H).

Example 41

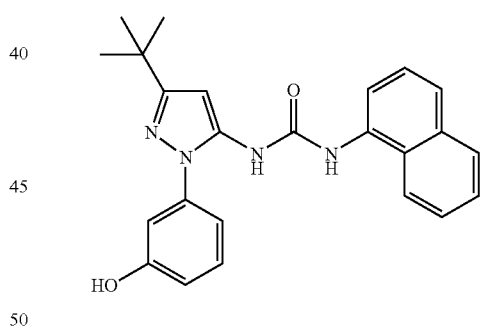

In a 100 ml round bottom flask equipped with a magnetic stir bar, Example 39 (2.07 g) was dissolved in CH$_2$Cl$_2$ (20 mL) and cooled to 0° C. with an ice bath. BBr$_3$ (1 M in CH$_2$Cl$_2$; 7.5 mL) was added slowly. The reaction mixture was allowed to warm warm to RT overnight. Additional BBr$_3$ (1 M in CH$_2$Cl$_2$, 2×1 mL, 9.5 mmol total added) was added and the reaction was quenched by the addition of MeOH. Evaporation of solvent led to a crystalline material that was chromatographed on silica gel (30 g) using CH$_2$Cl$_2$/MeOH (9.6:0.4) as the eluent to yield 1-[3-tert-butyl-1-(3-hydroxyphenyl)-1H-pyrazol-5-yl]-3-(naphthalene-1-yl)urea (0.40 g, 20%). $^1$H NMR (DMSO-d$_6$): δ 9.0 (s, 1H), 8.8 (s, 1H), 8.1-6.8 (m, 11H), 6.4 (s, 1H), 1.3 (s, 9H). MS (ESI) m/z: 401 (M+H$^+$).

Example 42

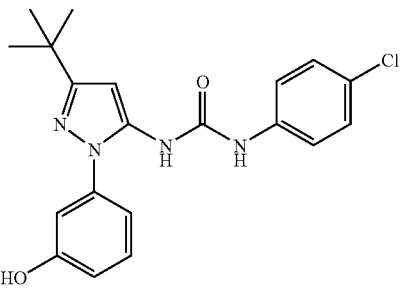

The title compound was synthesized in a manner analogous to Example 41 utilizing Example 40 (2.00 g, 5 mmol) that resulted in a crystalline material that was filtered and washed with MeOH to yield 1-[3-tert-butyl-1-(3-hydroxyphenyl)-1H-pyrazol-5-yl]-3-(4-chlorophenyl)urea (1.14 g, 60%). HPLC purity: 96%; mp: 214-216; $^1$H NMR (CDCl$_3$): δ 8.4 (s, 1H), 7.7 (s, 1H), 7.4-6.6 (m, 9H), 1.3 (s, 9H).

Example V

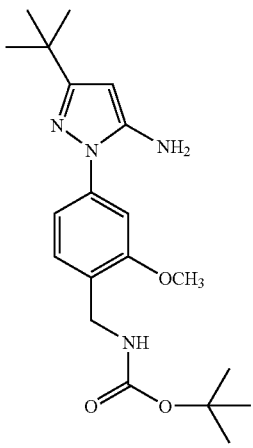

The starting material, 1-[4-(aminomethyl)phenyl]-3-tert-butyl-N-nitroso-1H-pyrazol-5-amine, was synthesized in a manner analogous to Example A utilizing 4-aminobenzamide and 4,4-dimethyl-3-oxopentanenitrile.

A 1 L four-necked round bottom flask was equipped with a stir bar, a source of dry Ar, a heating mantle, and a reflux condenser. The flask was flushed with Ar and charged with the crude material from the previous reaction (12 g, 46.5 mmol; 258.1 g/mol) and anhydrous THF (500 ml). This solution was treated cautiously with LiAlH$_4$ (2.65 g, 69.8 mmol) and the reaction was stirred overnight. The reaction was heated to reflux and additional LiAlH$_4$ was added complete (a total of 8.35 g added). The reaction was cooled to 0 and H$_2$O (8.4 ml), 15% NaOH (8.4 ml) and H$_2$O (24 ml) were added sequentially. The mixture was stirred for 2 h, the solids filtered through Celite, and washed extensively with THF, the solution was concentrated in vacuo to yield 1-(4-(aminomethyl-3-methoxy)phenyl)-3-tert-butyl-1H-pyrazol-5-amine (6.8 g) as an oil.

A 40 mL vial was equipped with a stir bar, a septum, and a source of Ar. The vial was charged with the crude material from the previous reaction (2 g, 8.2 mmol, 244.17 g/mol) and CHCl$_3$ (15 mL) were cooled to 0 under Ar and di-tert-butyl-carbonate (1.9 g, 9.0 mmol) dissolved in CHCl$_3$ (5 mL) was added drop wise over a 2 min period. The mixture was treated with 1N KOH (2 mL), added over a 2 h period. The resulting emulsion was broken with the addition of saturated NaCl solution, the layers were separated and the aqueous phase extracted with CH$_2$Cl$_2$ (2×1.5 ml). The combined organic phases were dried over Na$_2$SO$_4$, filtered, concentrated in vacuo to yield tert-butyl [4-(3-tert-butyl-5-amino-1H-pyrazol-1-yl)-2-methoxybenzylcarbamate (2.23 g, 79%) as a light yellow solid. $^1$H NMR (CDCl$_3$): δ 7.4 (m, 5H), 5.6 (s, 1H), 4.4 (d, 2H), 1.5 (s, 9H), 1.3 (s, 9H).

Example 43

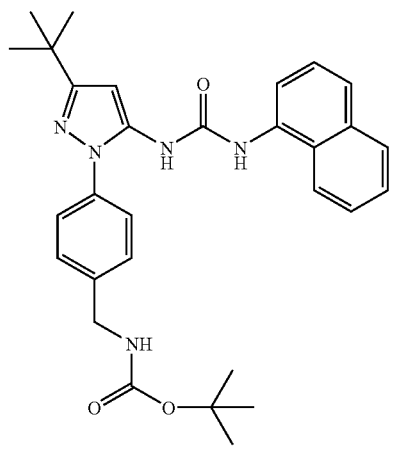

A 40 mL vial was equipped with a septum, a stir bar and a source of Ar, and charged with Example V (2 g, 5.81 mmol), flushed with Ar and dissolved in CHCl$_3$ (20 mL). The solution was treated with 2-naphthylisocyanate (984 mg, 5.81 mmol) in CHCl$_3$ (5 mL) and added over 1 min The reaction was stirred for 8 h, and additional 1-naphthylisocyanate (81 mg) was added and the reaction stirred overnight. The solid was filtered and washed with CH$_2$Cl$_2$ to yield tert-butyl 4-[3-tert-butyl-5-(3-naphthalen-1-yl)ureido)-1H-pyrazol-1-yl]benzylcarbamate (1.2 g). HPLC purity: 94.4%; $^1$H NMR (DMSO-d$_6$): δ 9.1 (s, 1H), 8.8 (s, 1H), 8.0 (m, 3H), 7.6 (m, 9H), 6.4 (s, 1H), 4.2 (d, 2H), 1.4 (s, 9H), 1.3 (s, 9H).

Example 44

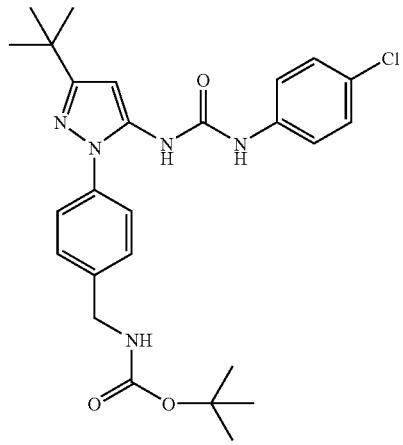

The title compound was synthesized in a manner analogous to Example 43 utilizing Example V (2.0 g, 5.81 mmol) and p-chlorophenylisocyanate (892 mg) to yield tert-butyl 4-[3-tert-butyl-5-(3-(4-chloropnehyl)ureido)-1H-pyrazol-1-yl]benzylcarbamate (1.5 g). HPLC purity: 97%; $^1$H NMR (DMSO-d$_6$): δ 9.2 (s, 1H), 8.4 (s, 1H), 7.4 (m, 8H), 6.4 (s, 1H), 4.2 (d, 2H), 1.4 (s, 9H), 1.3 (s, 9H).

Example 45

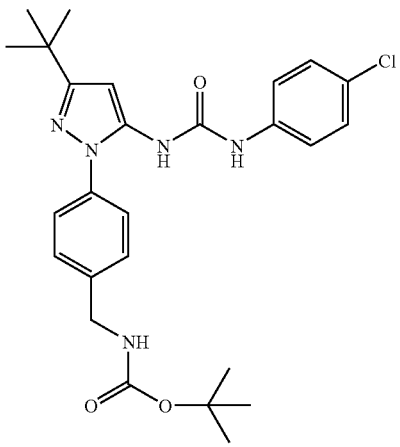

A 10 mL flask equipped with a stir bar was flushed with Ar and charged with Example 43 (770 mg, 1.5 mmol) and CH$_2$Cl$_2$ (1 ml) and 1:1 CH$_2$Cl$_2$:TFA (2.5 mL). After 1.5 h, reaction mixture was concentrated in vacuo, the residue was dissolved in EtOAc (15 mL), washed with saturated NaHCO$_3$ (10 mL) and saturated NaCl (10 mL). The organic layers was dried, filtered and concentrated in vacuo to yield 1-{3-tert-butyl-1-[4-(aminomethyl)phenyl]-1H-pyrazol-5-yl}-3-(naphthalen-1-yl)urea (710 mg). $^1$HNMR (DMSO-d$_6$): δ 7.4 (m, 11H), 6.4 (s, 1H), 3.7 (s, 2H), 1.3 (s, 9H).

Example 46

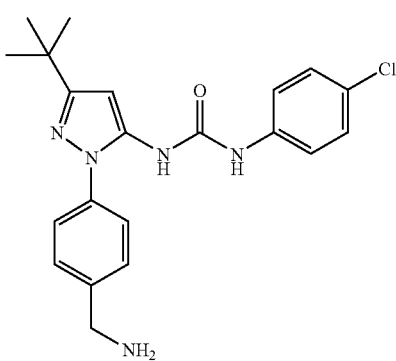

The title compound was synthesized in a manner analogous to Example 45 utilizing Example 44 (1.5 g, 1.5 mmol) to yield 1-{3-tert-butyl-1-[4-(aminomethyl)phenyl]-1H-pyrazol-5-yl}-3-(4-chlorophenyl)urea (1.0 g). HPLC purity: 93.6%; mp: 100-102; $^1$H NMR (CDCl$_3$): δ 8.6 (s, 1H), 7.3 (m, 8H), 6.3 (s, 1H), 3.7 (brs, 2H), 1.3 (s, 9H).

Example 47

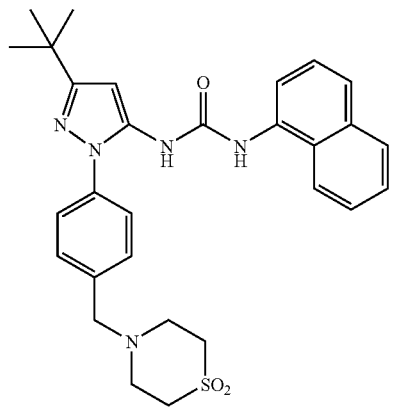

A 10 ml vial was charged with Example 45 (260 mg, 63 mmol) and absolute EtOH (3 mL) under Ar. Divinylsulfone (63 uL, 74 mg, 0.63 mmol) was added drop wise over 3 min and the reaction was stirred at RT for 1.5 h. and concentrated in vacuo to yield a yellow solid, which was purified via preparative TLC, developed in 5% MeOH:CH$_2$Cl$_2$. The predominant band was cut and eluted off the silica with 1:1 EtOAc:MeOH, filtered and concentrated in vacuo to yield 1-{3-tert-butyl-1-[4-(1,1-dioxothiomorpholin-4-yl)methylphenyl]-1H-pyrazol-5-yl}-3-(naphthalen-1-yl)urea (150 mg). HPLC purity: 96%; $^1$H NMR (DMSO-d$_6$): δ 9.1 (s, 1H), 9.0 (s, 1H), 7.9 (m, 3H), 7.5 (m, 8H), 6.4 (s, 1H), 3.1 (brs, 4H), 2.9 (brs, 4H), 1.3 (s, 9H).

Example 48

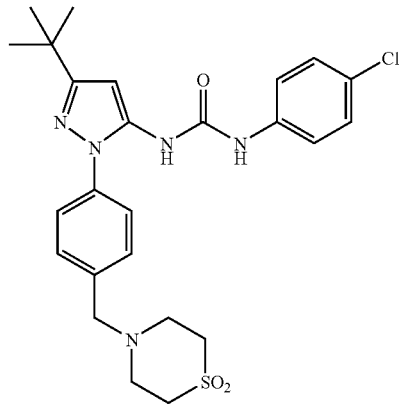

The title compound was synthesized in a manner analogous to Example 47 utilizing Example 46 (260 mg, 0.66 mmol) to yield 1-{3-tert-butyl-1-[4-(1,1-dioxothiomorpholin-4-yl)methylphenyl]-1H-pyrazol-5-yl}-3-(4-chlorophenyl)urea (180 mg). HPLC purity: 93%; mp: 136-138; $^1$H NMR (DMSO-d$_6$): δ 9.2 (s, 1H), 8.5 (s, 1H), 7.4 (m, 9H), 6.4 (s, 1H), 3.1 (brs, 4H), 3.0 (brs, 4H), 1.3 (s, 9H).

Example 49

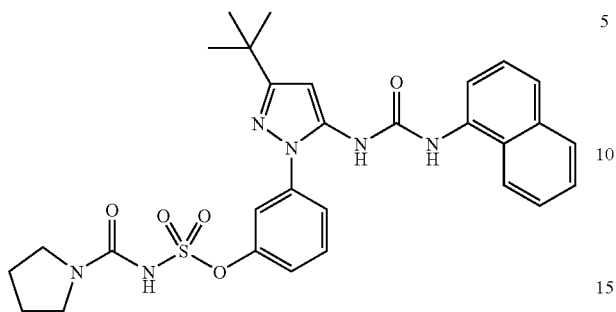

To a stirring solution of chlorosulfonyl isocyanate (0.35 g, 5 mmol) in $CH_2Cl_2$ (20 mL) at 0° C. was added pyrrolidine (0.18 g, 5 mmol) at such a rate that the reaction temperature did not rise above 5° C. After stirring for 2 h, a solution of Example 41 (1.10 g, 6.5 mmol) and triethylmine (0.46 g, 9 mmol) in $CH_2Cl_2$ (20 mL) was added. When the addition was complete, the mixture was allowed to warm to RT and stirred overnight. The reaction mixture was poured into 10% HCl (10 mL) saturated with NaCl, the organic layer was separated and the aqueous layer extracted with ether (20 mL). The combined organic layers were dried ($Na_2SO_4$) and concentrated in vacuo, purified by preparative HPLC to yield (pyrrolidine-1-carbonyl)sulfamic acid 3-[3-tert-butyl-5-(3-naphthalen-1-yl-ureido)-pyrazol-1-yl]phenyl ester (40 mg). $^1$H NMR ($CDCl_3$): δ 9.12 (brs, 1H), 8.61 (brs, 1H), 7.85-7.80 (m, 3H), 7.65 (d, J=8.0 Hz, 2H), 7.53-7.51 (m, 1H), 7.45-7.25 (m, 5H), 6.89 (s, 4H), 3.36-3.34 (brs, 1H), 3.14-3.13 (brs, 2H), 1.69 (brs, 2H), 1.62 (brs, 2H), 1.39 (s, 9H); MS (ESI) m/z: 577 ($M+H^+$).

Example 50

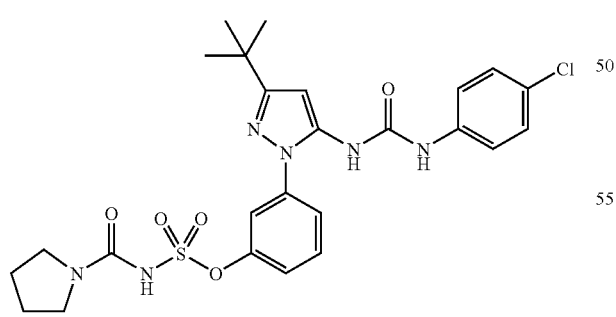

The title compound was synthesized in a manner analogous to Example 49 utilizing Example 42 to yield (pyrrolidine-1-carbonyl)sulfamic acid 3-[3-tert-butyl-5-(4-chlorophenyl-1-yl-ureido)pyrazol-1-yl]phenyl ester. MS (ESI) m/z: 561 ($M+H^+$).

Example W

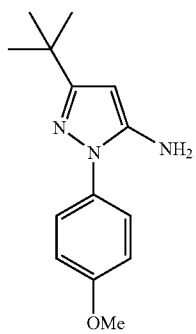

Solid 4-methoxyphenylhydrazine hydrochloride (25.3 g) was suspended in toluene (100 mL) and treated with triethylamine (20.2 g). The mixture was stirred at RT for 30 min and treated with pivaloylacetonitrile (18 g). The reaction was heated to reflux and stirred overnight. The hot mixture was filtered, the solids washed with hexane and dried in vacuo to afford 3-tert-butyl-1-(4-methoxyphenyl)-1H-pyrazol-5-amine (25 g, 70%). $^1$H NMR (DMSO-$d_6$): δ 7.5 (d, 2H), 7.0 (d, 1H), 6.4 (s, 11H), 6.1 (s, 2H), 3.9 (s, 34H), 1.3 (s, 9H).

Example 51

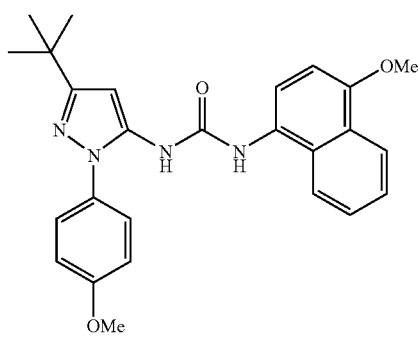

To a solution of 1-isocyanato-4-methoxy-naphthalene (996 mg) in anhydrous $CH_2Cl_2$ (20 mL) of was added Example W (1.23 g). The reaction solution was stirred for 3 h, the resulting white precipitate filtered, treated with 10% HCl and recrystallized from MeOH, and dried in vacuo to yield 1-[3-tert-butyl-1-(4-methoxyphenyl)-1H-pyrazol-5-yl]-3-(1-methoxynaphthalen-4-yl-urea as white crystals (900 mg, 40%). HPLC purity: 96%; mp: 143-144; $^1$H NMR (DMSO-$d_6$): δ 8.8 (s, 1H), 8.5 (s, 1H), 8.2 (d, 1H), 8.0 (d, 1H), 7.6 (m, 5H), 7.1 (d, 2H), 7.0 (d, 1H), 6.3 (s, 1H), 4.0 (s, 3H), 3.9 (s, 3H); 1.3 (s, 9H).

Example 52

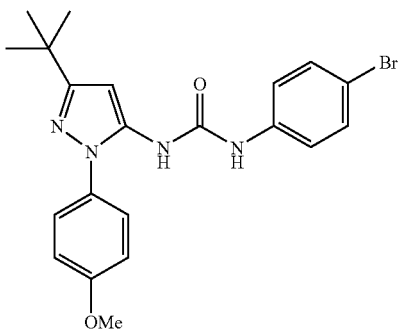

The title compound was synthesized in a manner analogous to Example 51 utilizing Example W and p-bromophenylisocyanate (990 mg) to yield 1-{3-tert-butyl-1-(4-methoxyphenyl)-1H-pyrazol-5-yl}-3-(4-bromophenyl)urea as off-white crystals (1.5 g, 68%). HPLC purity: 98%; mp: 200-201; $^1$H NMR (DMSO-$d_6$): δ 9.3 (s, 1H), 8.3 (s, 1H), 7.4 (m, 6H), 7.0 (d, 2H), 6.3 (s, 1H), 3.8 (s, 3H), 1.3 (s, 9H).

Example 53

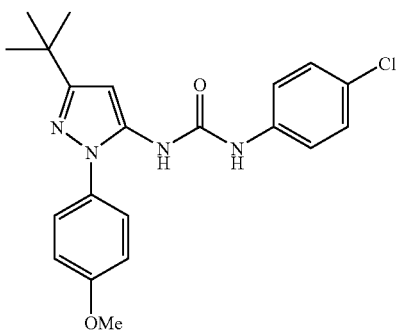

The title compound was synthesized in a manner analogous to Example 51 utilizing Example W and p-chlorophenylisocyanate (768 mg) into yield 1-{3-tert-butyl-1-(4-methoxyphenyl)-1H-pyrazol-5-yl}-3-(4-chlorophenyl)urea as white crystals (1.3 g, 65%). HPLC purity: 98%; mp: 209-210; $^1$H NMR (DMSO-$d_6$): δ 9.1 (s, 1H), 8.3 (s, 1H), 7.4 (m, 4H), 7.3 (d, 2H), 7.1 (d, 2H), 6.3 (s, 1H), 3.8 (s, 3H), 1.3 (s, 9H).

Example 54

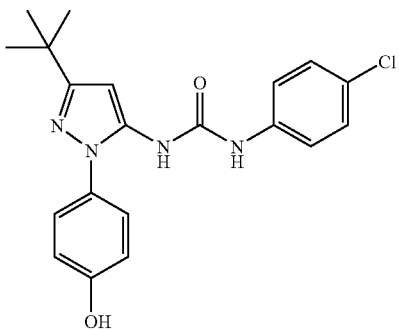

The title compound was synthesized in a manner analogous to Example 41 utilizing Example 53 (500 mg) to yield 1-{3-tert-butyl-1-(4-hydroxyphenyl)-1H-pyrazol-5-yl}-3-(4-chlorophenyl)urea as white crystals (300 mg, 62%). HPLC purity: 94%; mp: 144-145; $^1$H NMR (DMSO-$d_6$): δ 9.7 (s, 1H), 9.1 (s, 1H), 8.3 (s, 1H), 7.4 (d, 2H), 7.3 (m, 4H); 6.9 (d, 2H), 6.3 (s, 1H), 1.3 (s, 9H)

Example 55

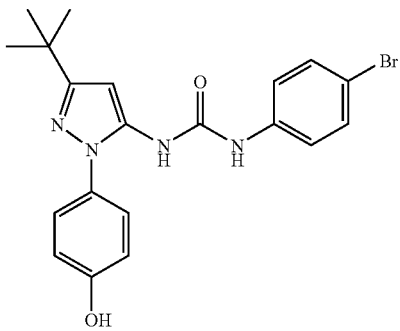

The title compound was synthesized in a manner analogous to Example 41 utilizing Example 52 (550 mg) to yield 1-{3-tert-butyl-1-(4-hydroxyphenyl)-1H-pyrazol-5-yl}-3-(4-bromophenyl)urea as a white crystalline solid (400 mg, 70%). HPLC purity: 93%; mp: 198 200; $^1$H NMR (DMSO-$d_6$): δ 9.7 (s, 1H), 9.2 (s, 1H), 8.3 (s, 1H), 7.4 (d, 4H), 7.2 (m, 2H), 6.9 (d, 2H), 6.3 (s, 1H), 1.3 (s, 9H).

Example X

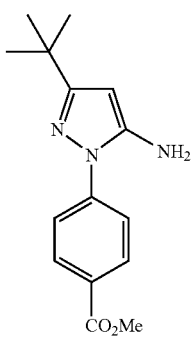

Methyl 4-(3-tert-butyl-5-amino-1H-pyrazol-1-yl)benzoate (3.67 mmol) was prepared from methyl 4-hydrazinobenzoate and pivaloylacetonitrile by the procedure of Regan, et al., *J. Med. Chem.*, 45, 2994 (2002).

Example 56

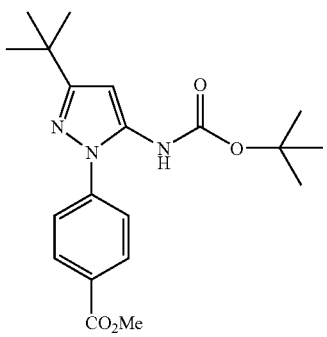

A 500 mL round bottom flask was equipped with a magnetic stir bar and an ice bath. The flask was charged with Example X (1 g) and this was dissolved in $CH_2Cl_2$ (100 mL). Saturated sodium bicarbonate (100 mL) was added and the mixture rapidly stirred, cooled in an ice bath and treated with diphosgene (1.45 g) and the heterogeneous mixture stirred for 1 h. The layers were separated and the $CH_2Cl_2$ layer treated with tert-butanol (1.07 g) and the solution stirred overnight at RT. The solution was washed with $H_2O$ (2×150 mL), dried ($Na_2SO_4$), filtered, concentrated in vacuo, and purified by flash chromatography using 1:2 ethyl acetate:hexane as the eluent to yield tert-butyl 1-(4-(methoxycarbonyl)phenyl)-3-tert-butyl-1H-pyrazol-5-ylcarbamate (100 mg) as an off-white solid. $^1$H NMR (DMSO-$d_6$): δ 9.2 (s, 1H), 8.1 (d, 2H), 7.7 (d, 2H), 6.3 (s, 1H), 3.3 (s, 3H), 1.3 (s, 18H).

Example 57

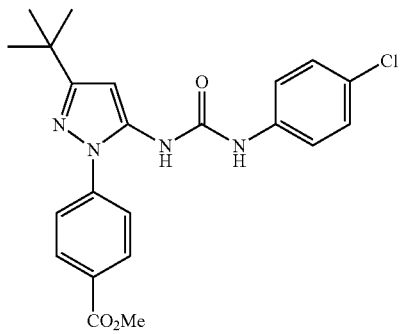

The title compound was synthesized in a manner analogous to Example 41 utilizing Example X (1.37 g) and p-chlorophenylisocyanate (768 mg) to yield methyl 4-{3-tert-butyl-5-[3-(4-chlorophenyl)ureido]-1H-pyrazol-1-yl}benzoate as white crystals (1.4 g 66%). HPLC purity: 98%; mp: 160-161; $^1$H NMR (DMSO-$d_6$): δ 9.2 (s, 1H), 8.6 (s, 1H), 8.1 (d, 2H), 7.8 (d, 2H), 7.5 (d, 2H), 7.3 (d, 2H), 6.4 (s, 1H), 3.9 (s, 3H), 1.3 (s, 9H).

Example 58

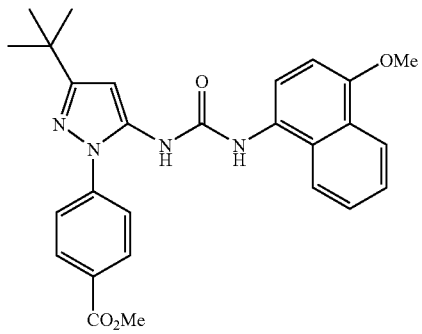

The title compound was synthesized in a manner analogous to Example 41 utilizing Example X (1.27 g) and 1-isocyanato-4-methoxy-naphthalene (996 mg) to yield methyl 4-{3-tert-butyl-5-[3-(1-methoxynaphthalen-4-yl)ureido]-1H-pyrazol-1-yl}benzoate as white crystals (845 mg, 36%). HPLC purity: 98%; mp: 278 280; $^1$H NMR (DMSO-$d_6$): δ 8.76 (s, 1H), 8.73 (s, 1H), 8.1 (m, 3H), 7.9 (d, 1H), 7.7 (d, 2H), 7.6 (m, 3H), 7.0 (d, 1H), 7.0 (d, 1H), 6.3 (s, 1H), 4.0 (s, 3H), 3.9 (s, 3H), 1.3 (s, 9H).

Example 59

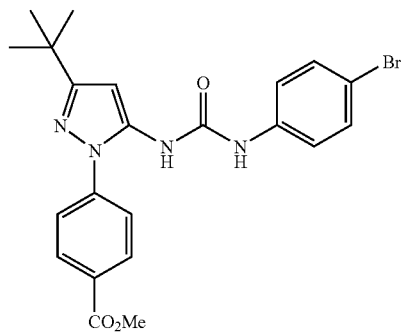

The title compound was synthesized in a manner analogous to Example 41 utilizing Example X (1.37 g) and p-bromophenylisocyanate (990 mg) to yield methyl 4-{3-tert-butyl-5-[3-(4-bromophenyl)ureido]-1H-pyrazol-1-yl}benzoate as white crystals (1.4 g, 59%). HPLC purity: 94%; mp: 270 272; $^1$H NMR (DMSO-$d_6$): δ 9.2 (s, 1H), 8.6 (s, 1H), 8.1 (d, 2H), 7.7 (d, 2H), 7.4 (d, 4H), 6.4 (s, 1H), 3.9 (s, 3H), 1.3 (s, 9H).

Example 60

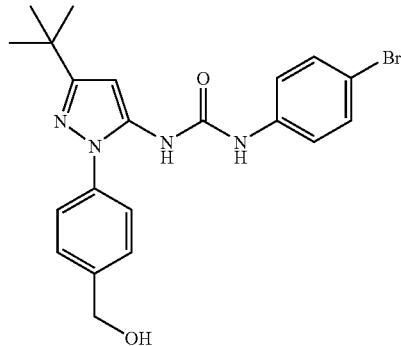

To a solution of Example 59 (700 mg) in 30 mL of toluene at −78° C., was added dropwise a solution of diisobutylaluminum hydride in toluene (1M in toluene, 7.5 mL) over 10 min. The reaction mixture was stirred for 30 min at −78° C., and then 30 min at 0° C. The reaction mixture was concentrated in vacuo to dryness and treated with $H_2O$. The solid was filtered and treated with acetonitrile. The solution was evaporated to dryness and the residue was dissolved in ethyl acetate, and precipitated by hexanes to afford yellow solid which was dried under vacuum to give 1-[3-tert-butyl-1-(4-hydroxymethyl)phenyl)-1H-pyrazol-5-yl]urea (400 mg, 61%). HPLC purity: 95%; $^1$H NMR (DMSO-$d_6$): δ 9.2 (s, 1H), 8.4 (s, 1H), 7.5 (m, 8H), 6.4 (s, 1H), 5.3 (t, 1H), 4.6 (d, 2H), 1.3 (s, 9H).

187
Example 1
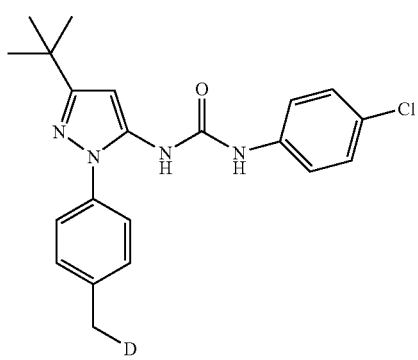
Example 2
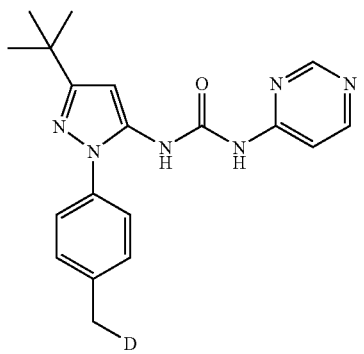
Example 3
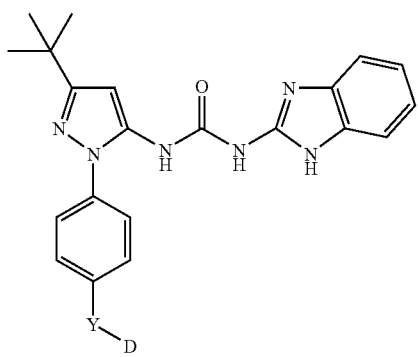
188
Example 4
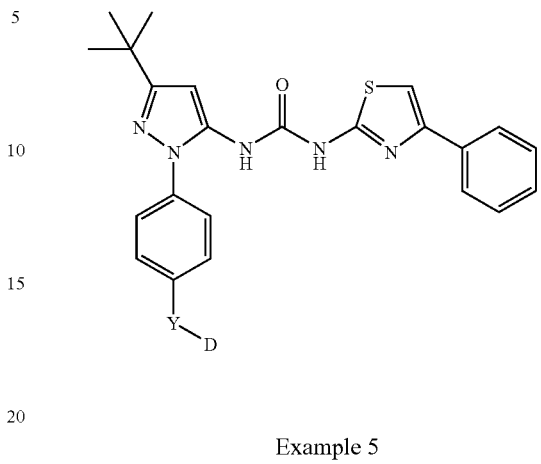
Example 5
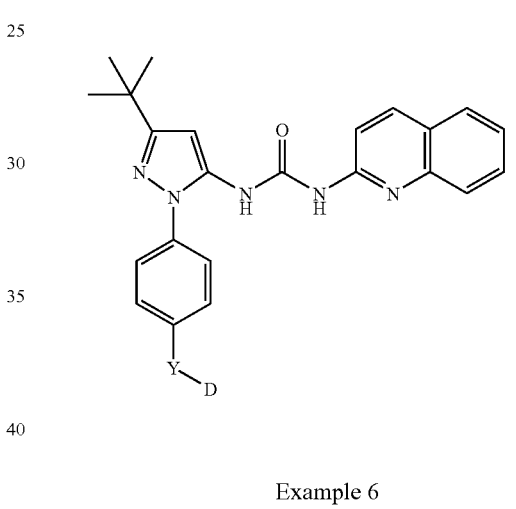
Example 6
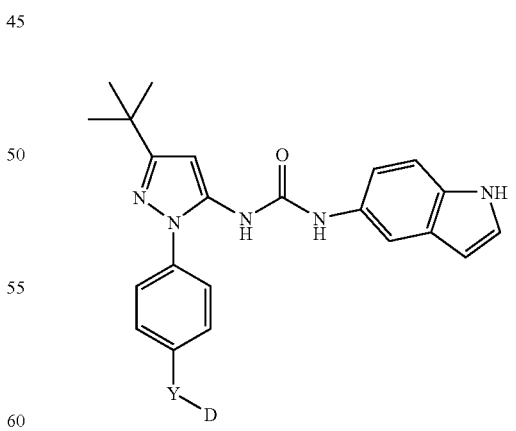
Wherein Y is O, S, NR6, —NR6SO2-, NR6CO—, alkylene, O—(CH2)n-, NR6-(CH2)n-, wherein one of the methylene units may be substituted with an oxo group, or Y is a direct bond; D is taken from the groups identified in Chart I:

Chart 1
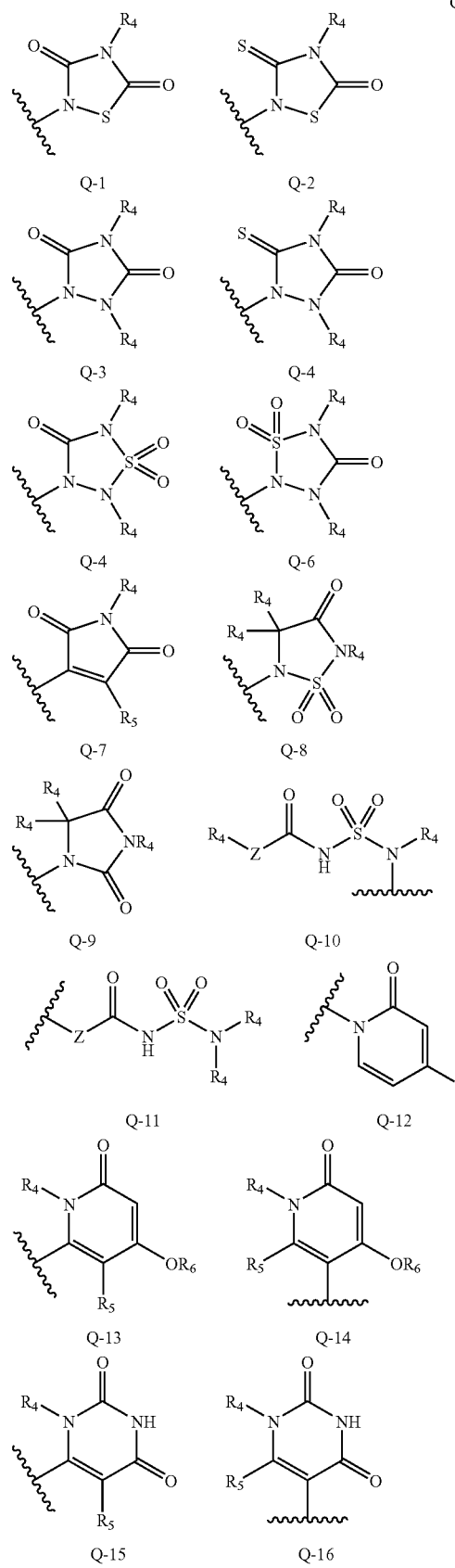
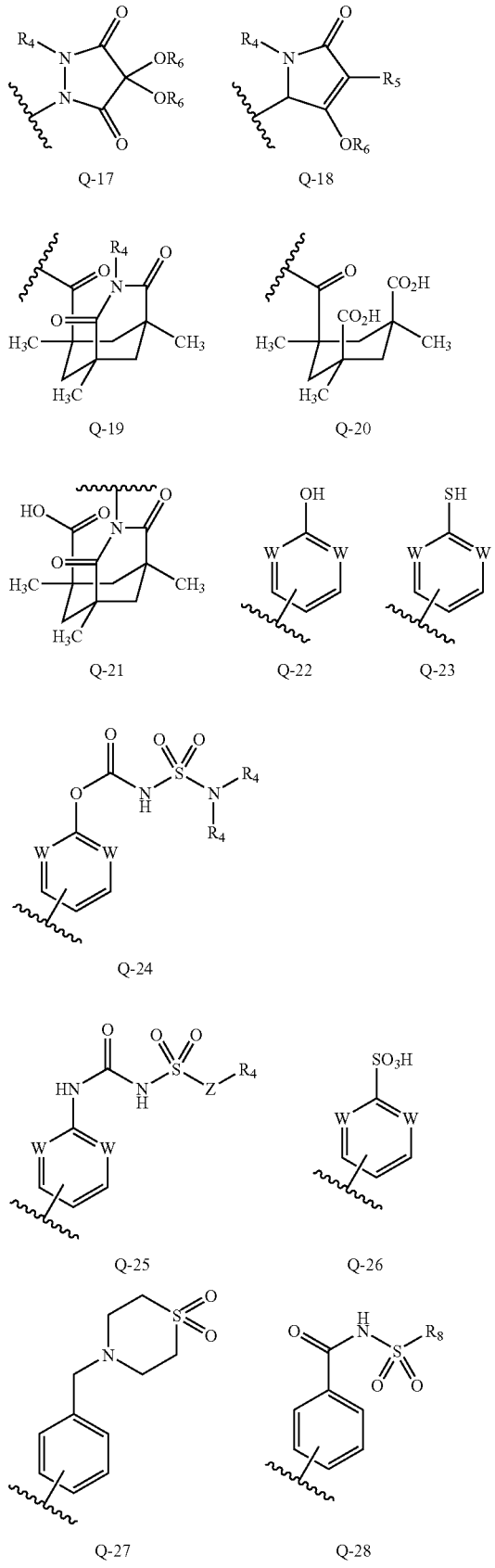

-continued
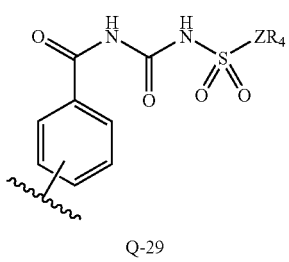
Q-29
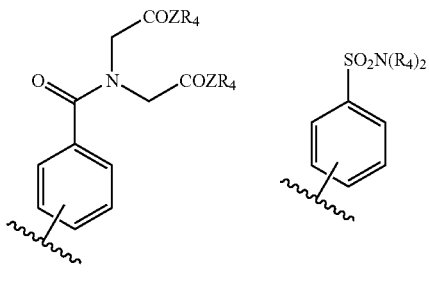
Q-30        Q-31
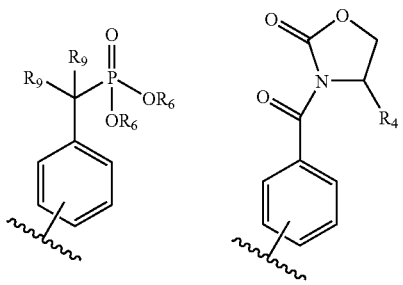
Q-32        Q-33
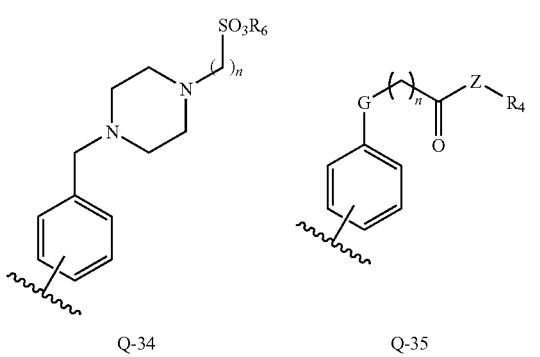
Q-34        Q-35
Example 7
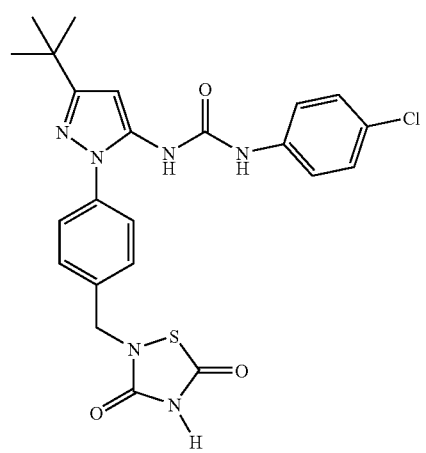
Example 8
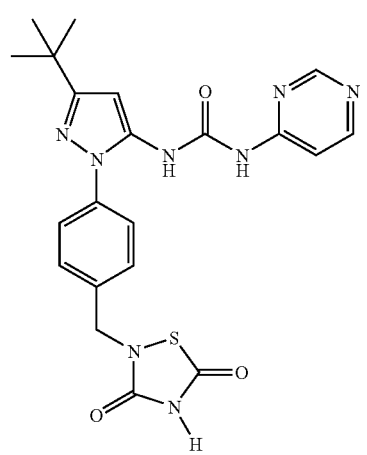
Example 9
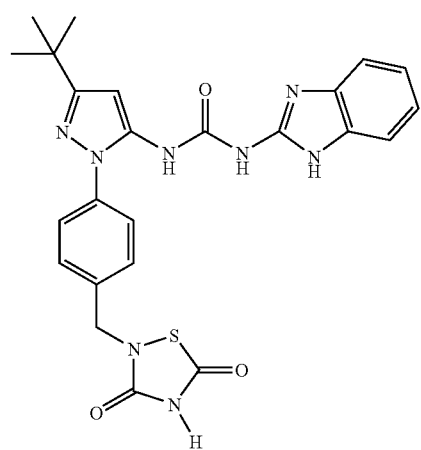

193
Example 10
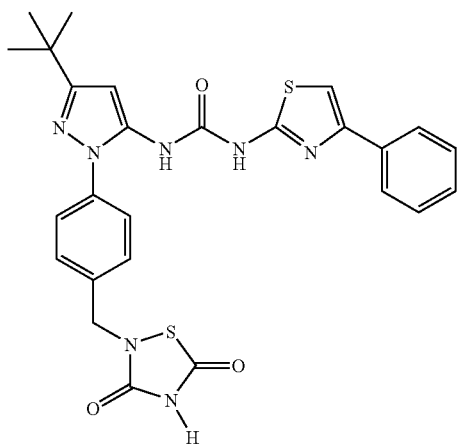
Example 11
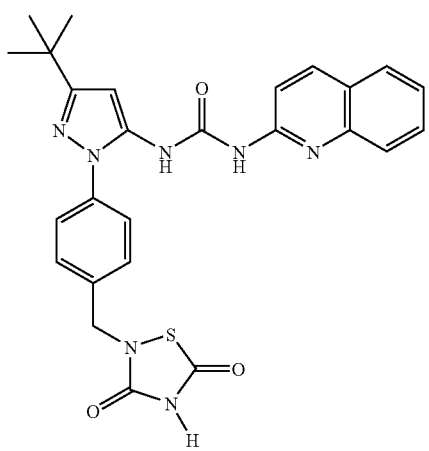
Example 12
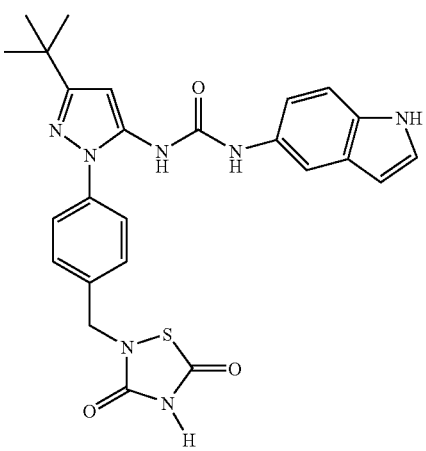
194
Example 13
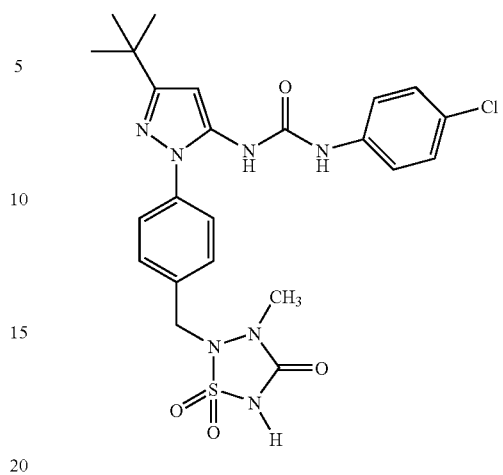
Example 14
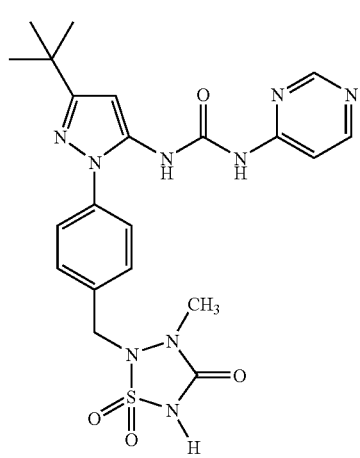
Example 15
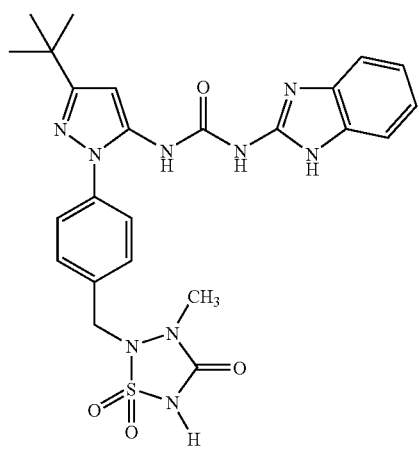

Example 16
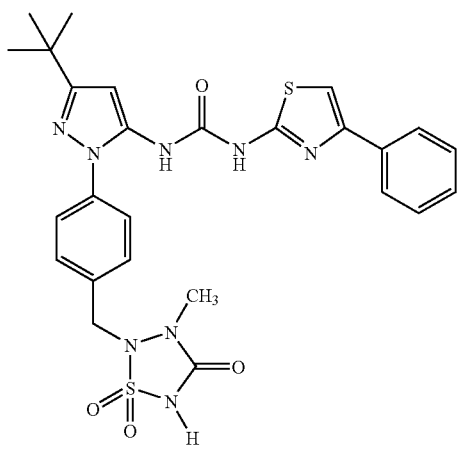
Example 17
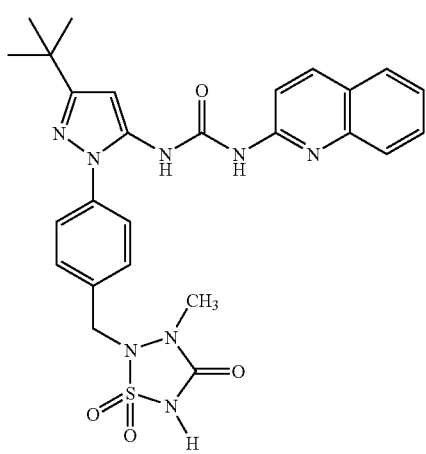
Example 18
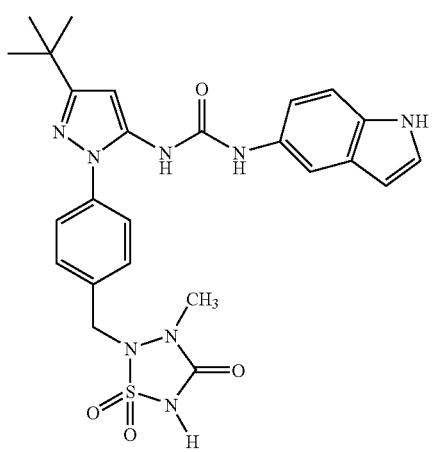
Example 19
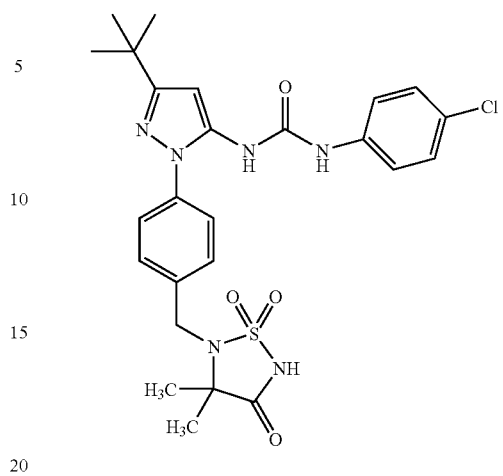
Example 20
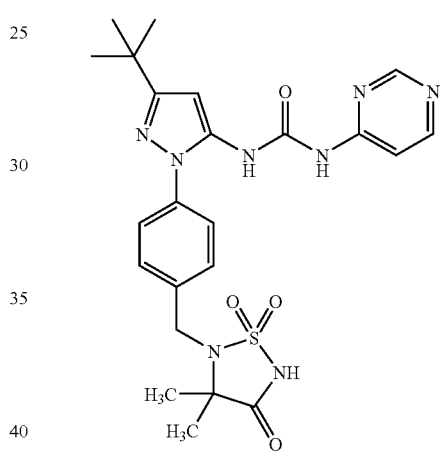
Example 21
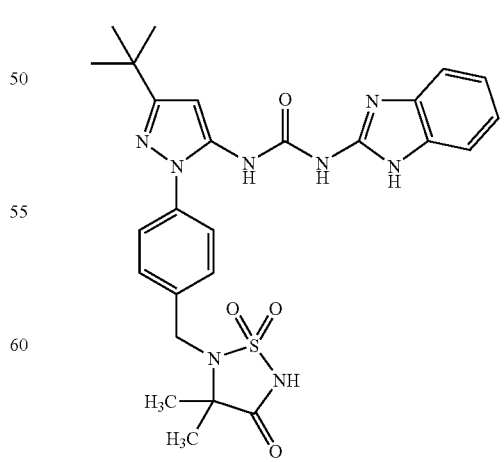

197
Example 22
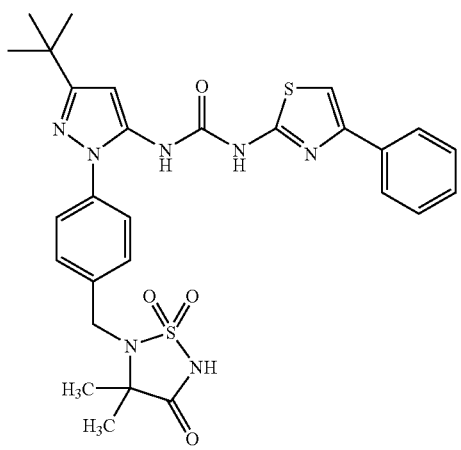
Example 23
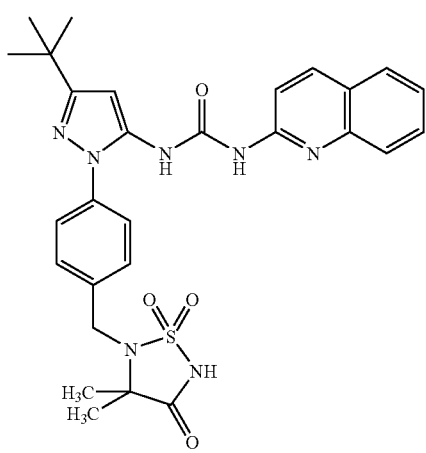
Example 24
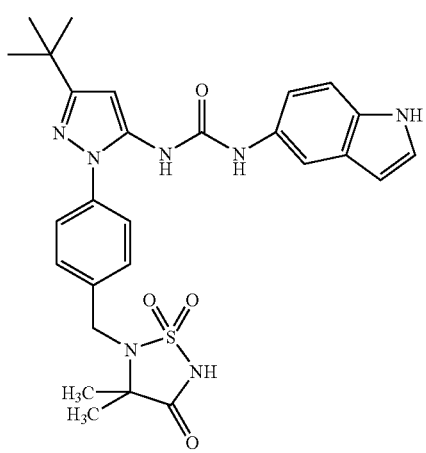
198
Example 25
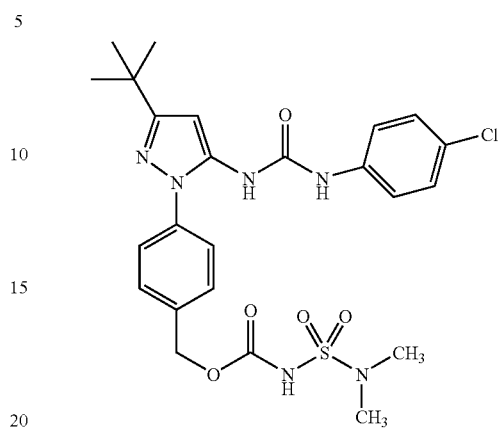
Example 26
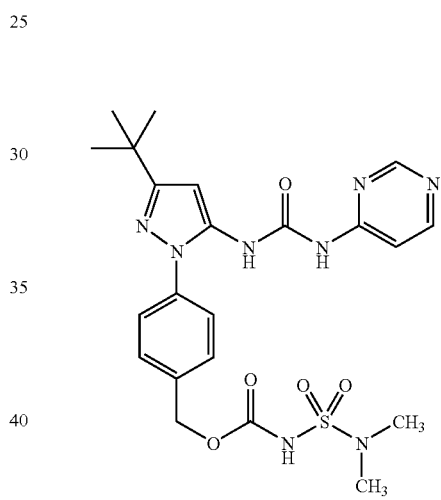
Example 27
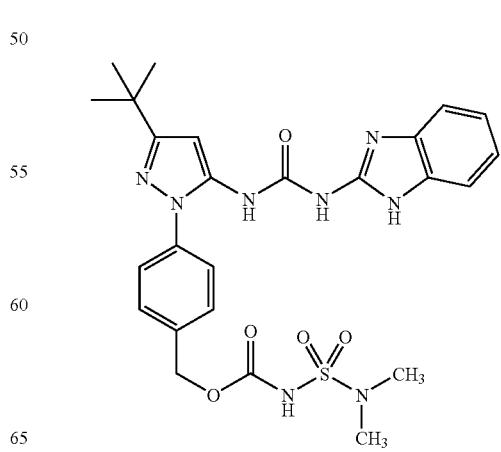

Example 28
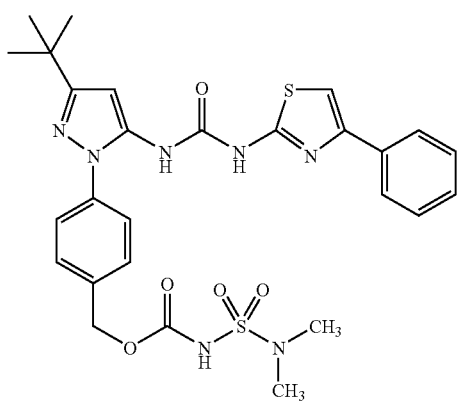
Example 29
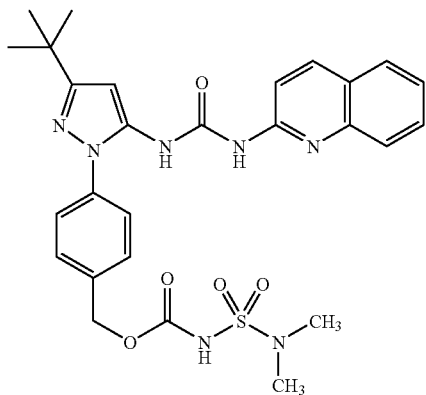
Example 30
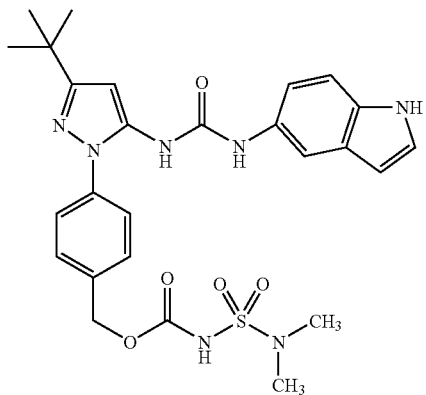
Example 31
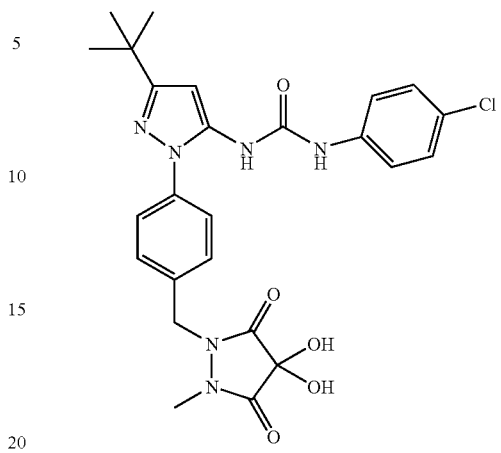
Example 32
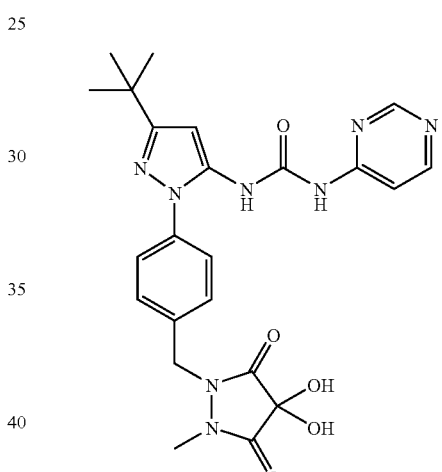
Example 33
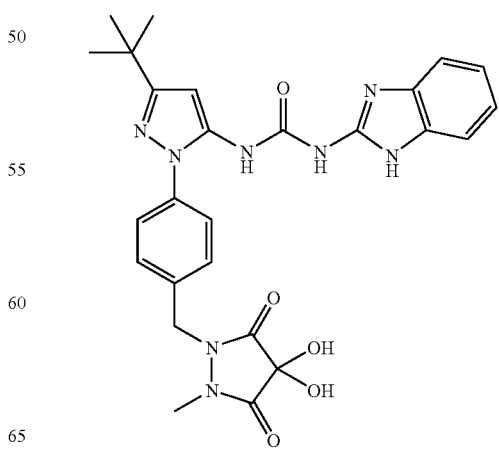

201
Example 34
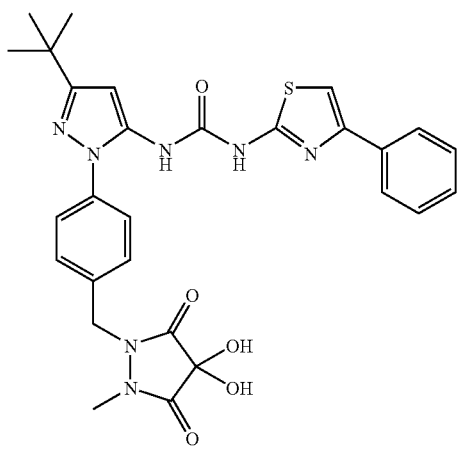
Example 35
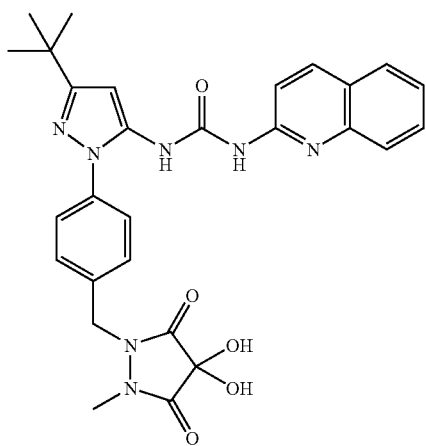
Example 36
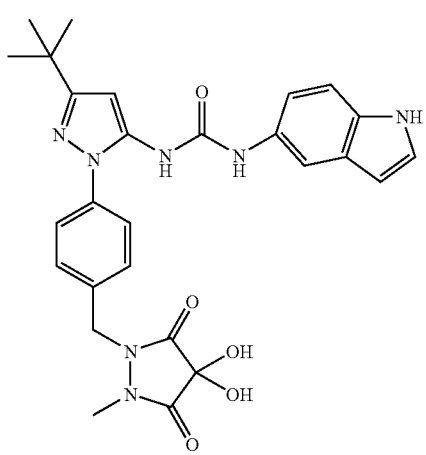
202
Example 37
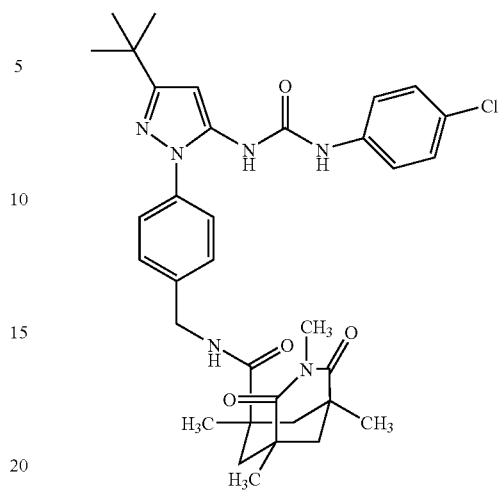
Example 38
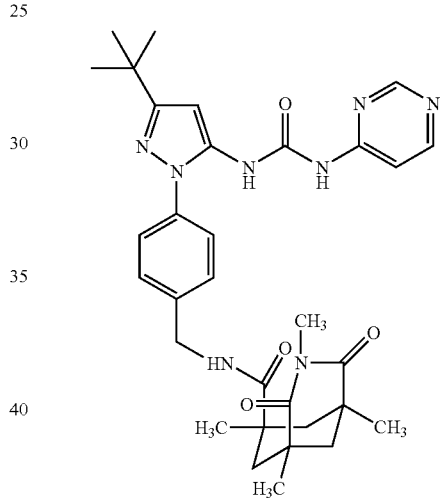
Example 39
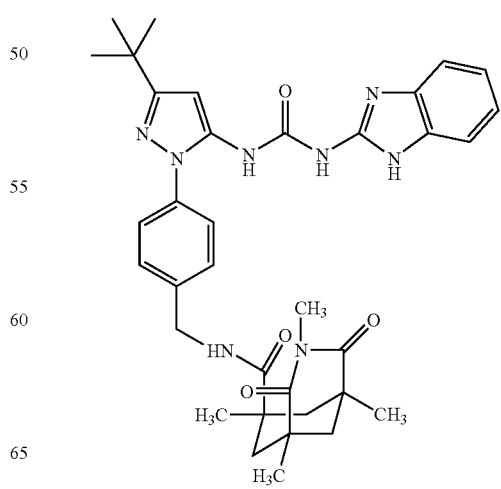

203
Example 40
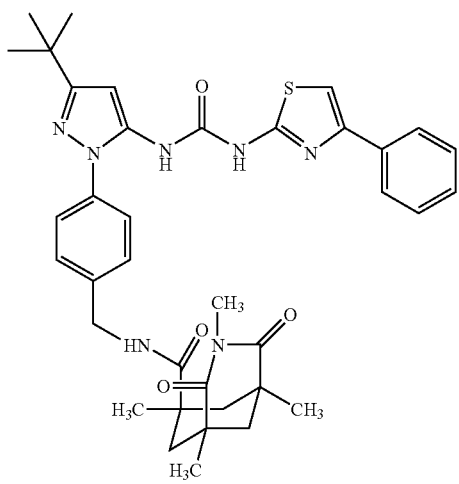
Example 41
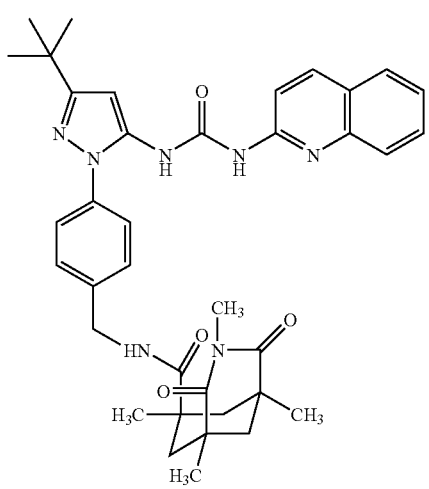
Example 42
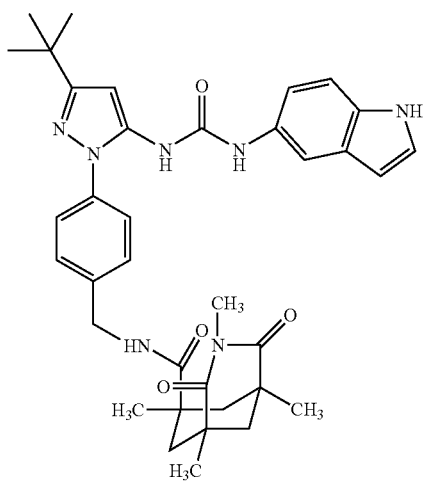
204
Example 43
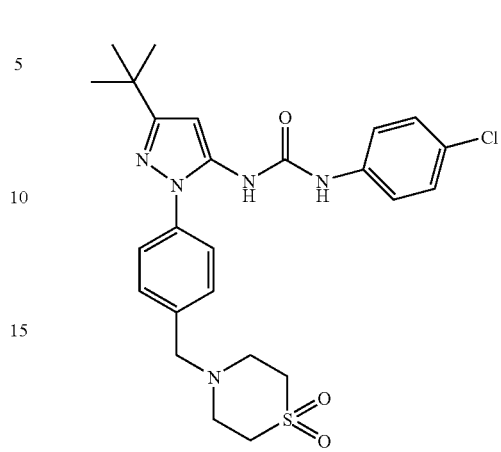
Example 44
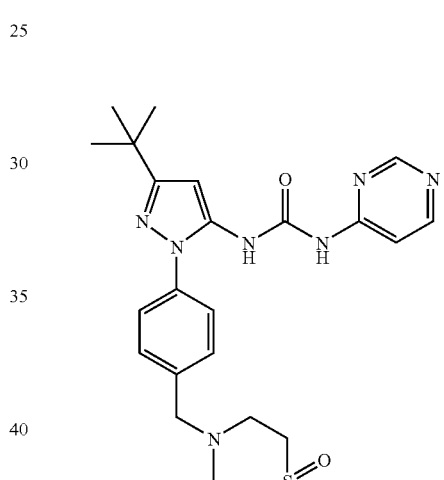
Example 45
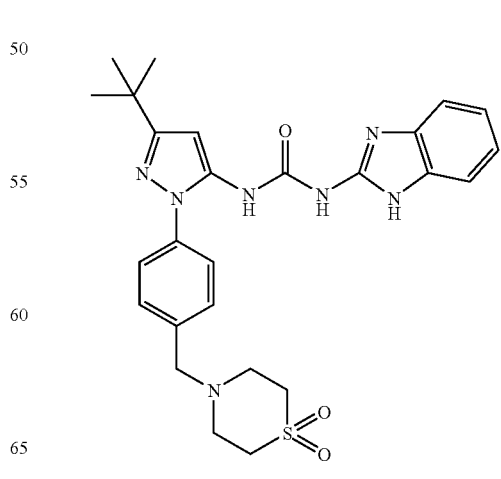

Example 46
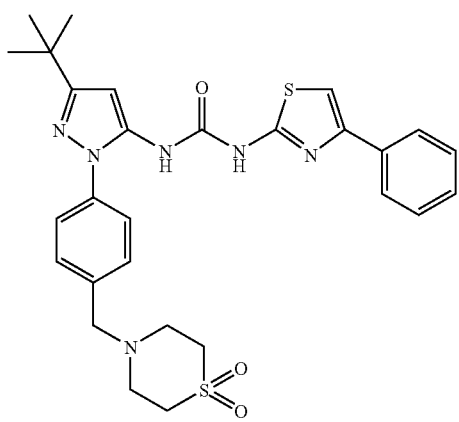
Example 47
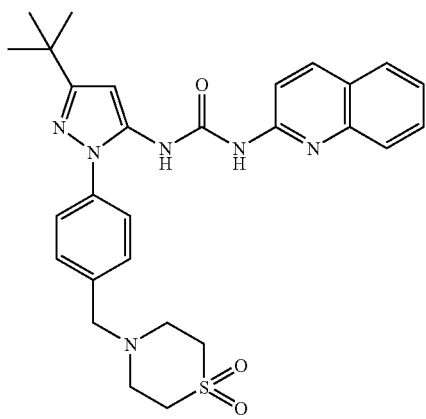
Example 48
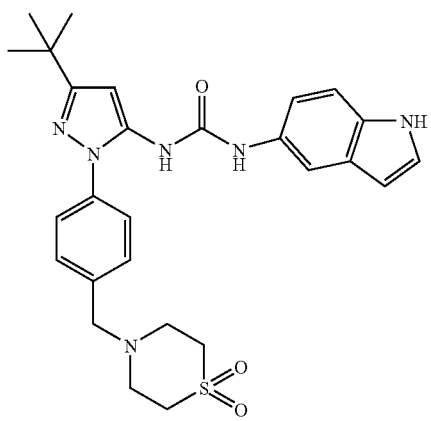
Example 49
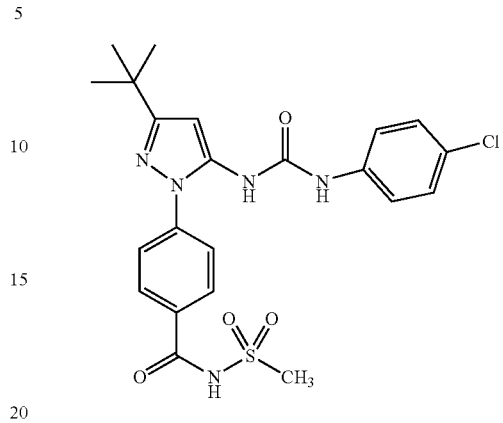
Example 50
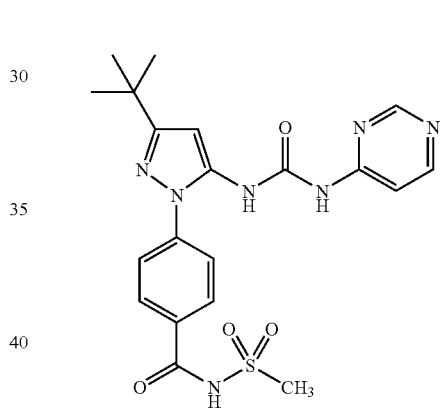
Example 51
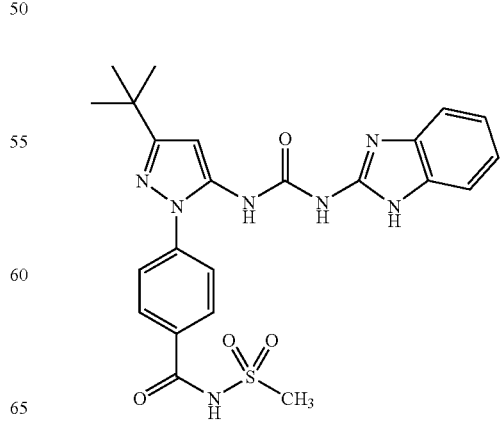

207
Example 52
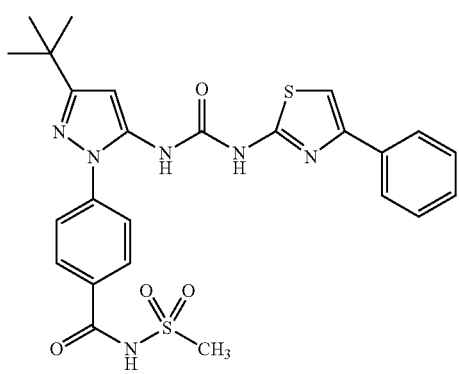
Example 53
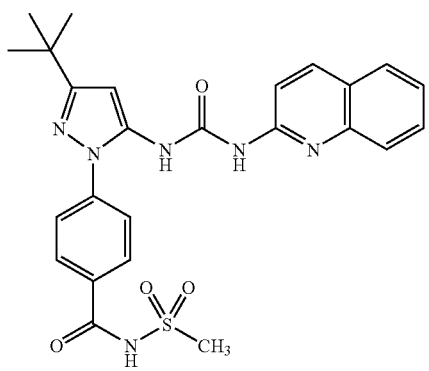
Example 54
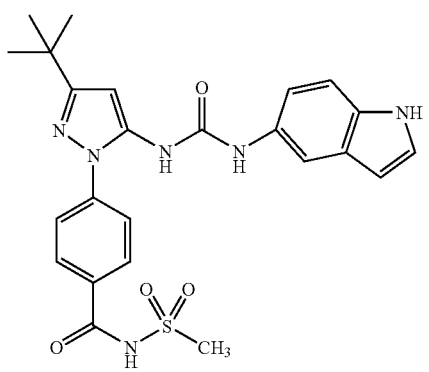
208
Example 55
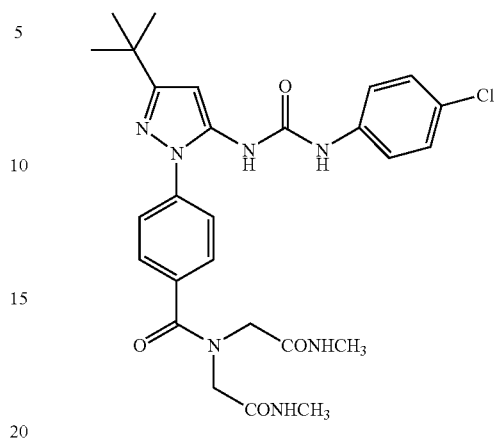
Example 56
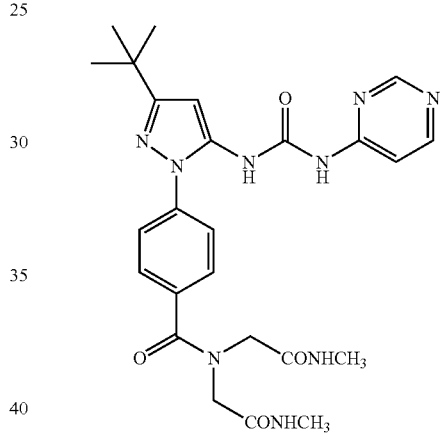
Example 57
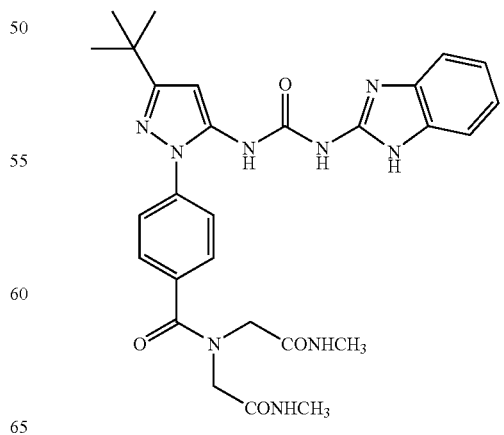

Example 58
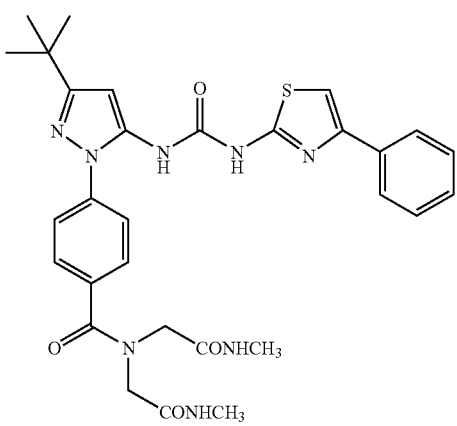
Example 59
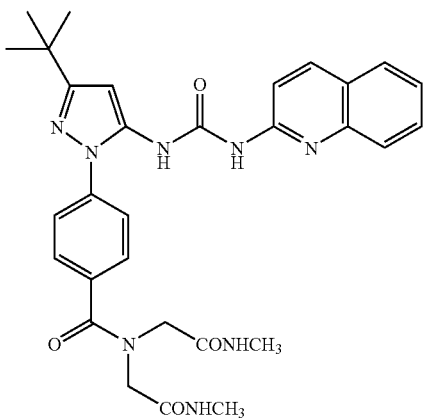
Example 60
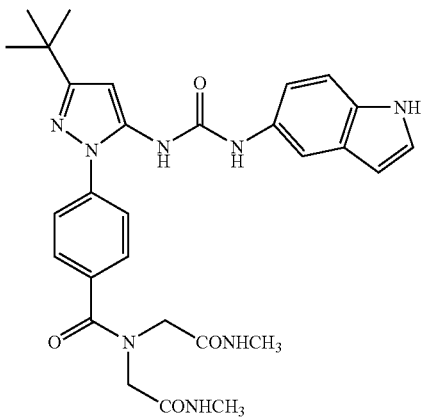
Example 61
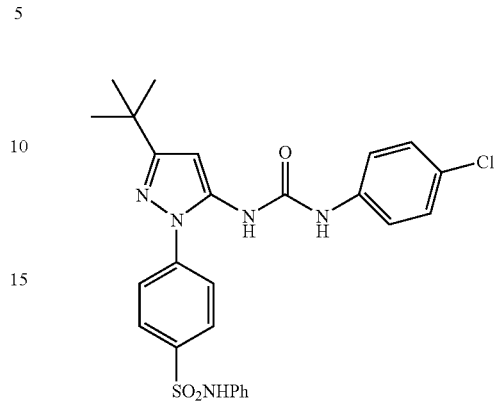
Example 62
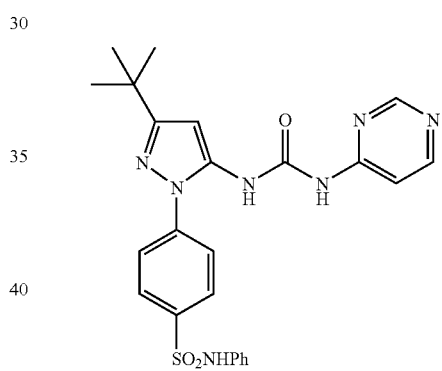
Example 63
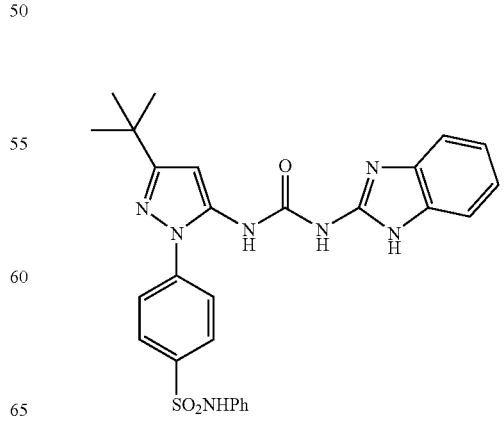

211
Example 64
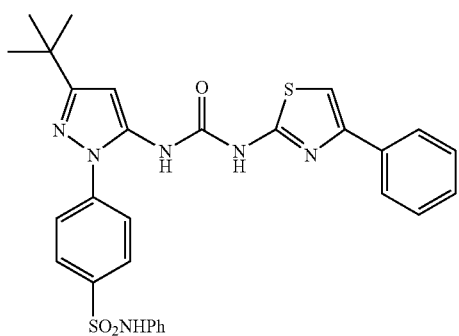
Example 65
212
Example 67
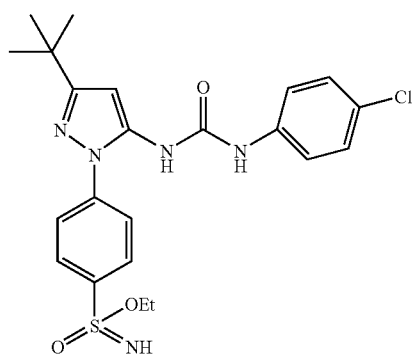
Example 68
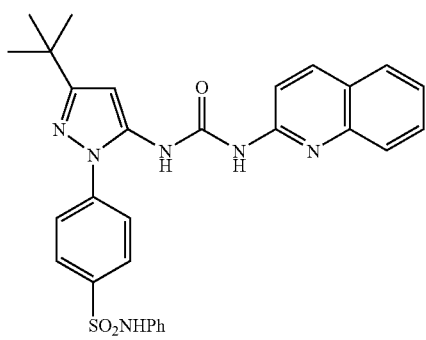
Example 66
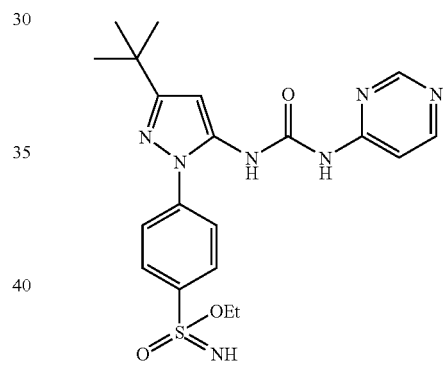
Example 69
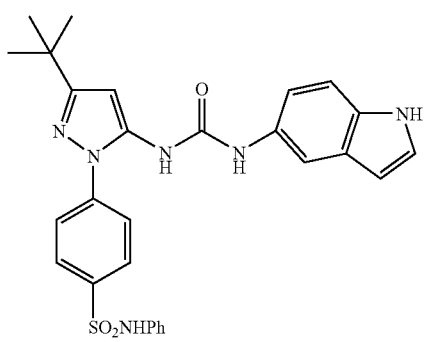
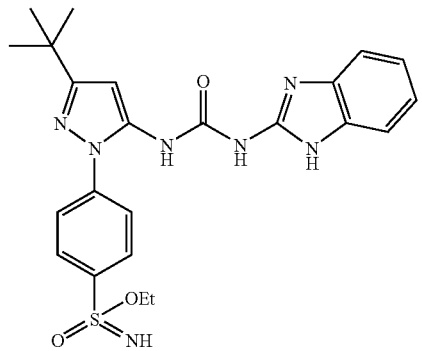

Example 70
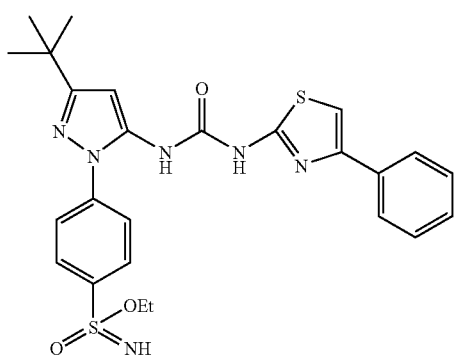
Example 71
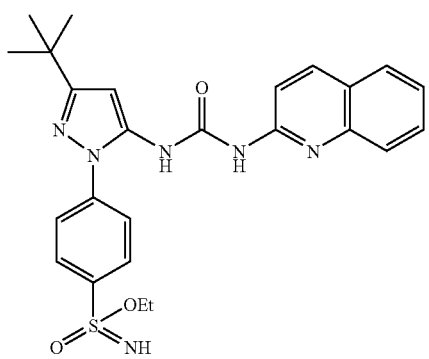
Example 72
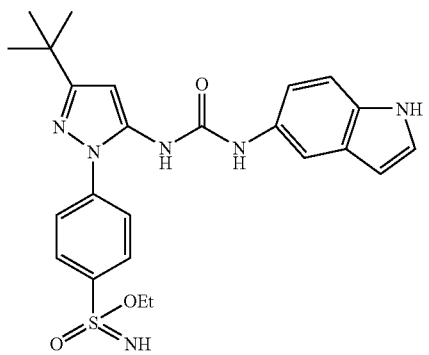
Example 73
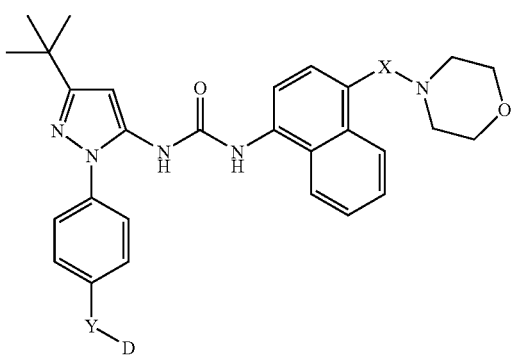
Example 74
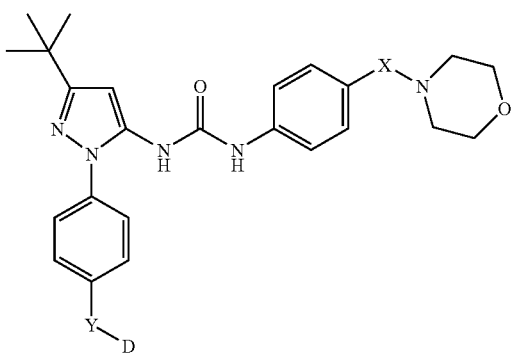
Example 75
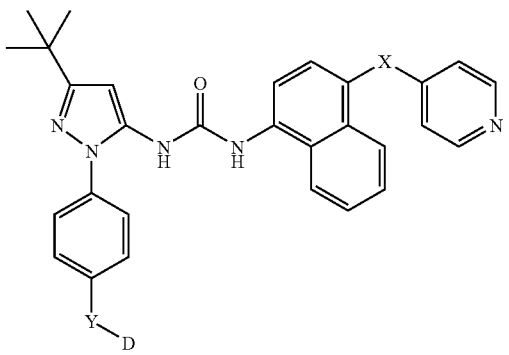

Example 76
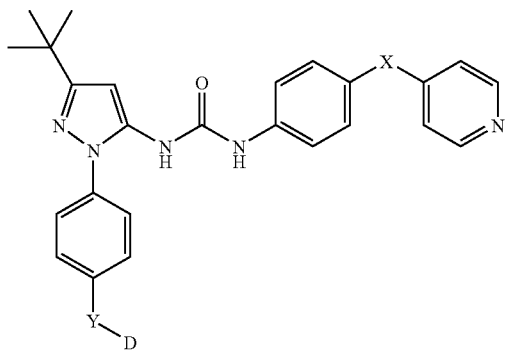
Example 77
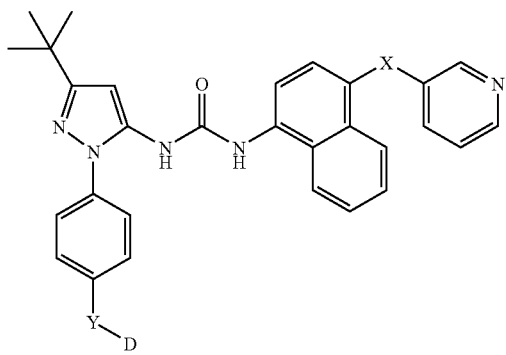
Example 78
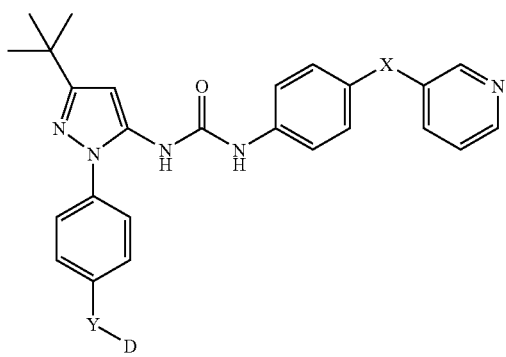
wherein X or Y is O, S, NR6, —NR6SO2-, NR6CO—, alkylene, O—(CH2)n—, NR6-(CH2)n-, wherein one of the methylene units may be substituted with an oxo group, or X or Y is a direct bond; D is taken from the groups identified in Chart I:
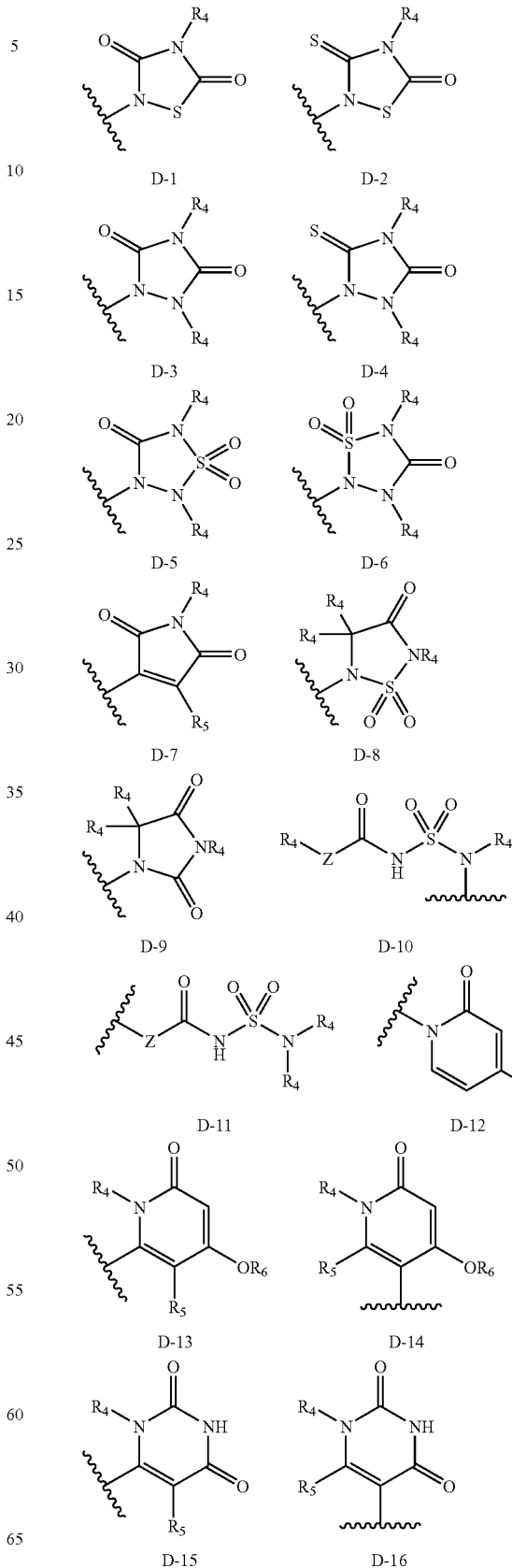
Chart 1

-continued
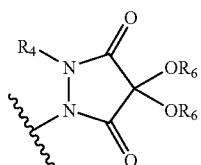
D-17
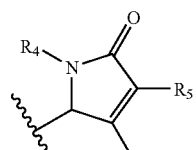
D-18
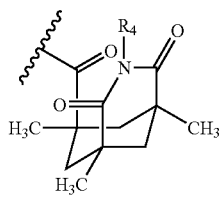
D-19
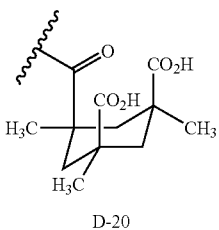
D-20
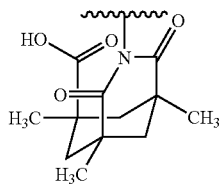
D-21
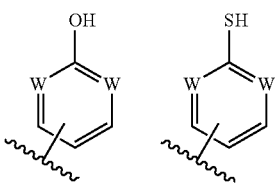
D-22    D-23
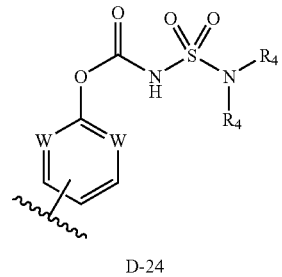
D-24
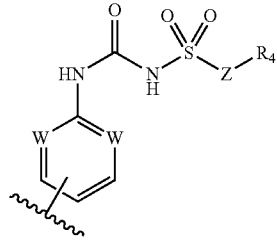
D-25    D-26
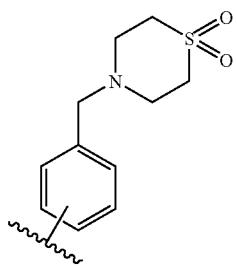
D-27    D-28
-continued
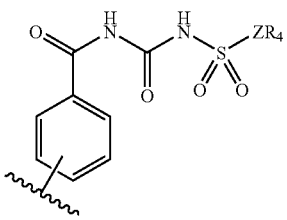
D-29
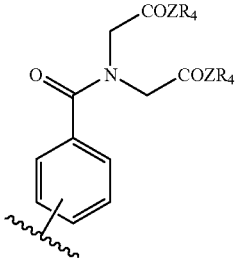 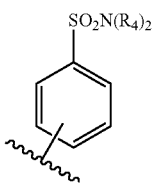
D-30    D-31
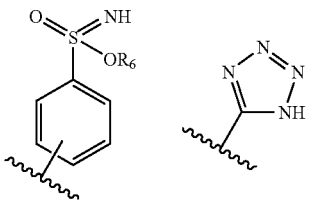 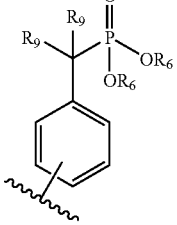
D-32    D-33    D-34
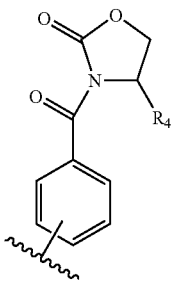 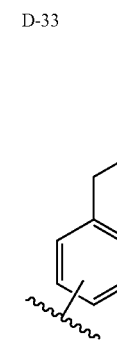
D-35    D-36
Specific examples of the present invention are illustrated by their structural formulae below:
Example 79
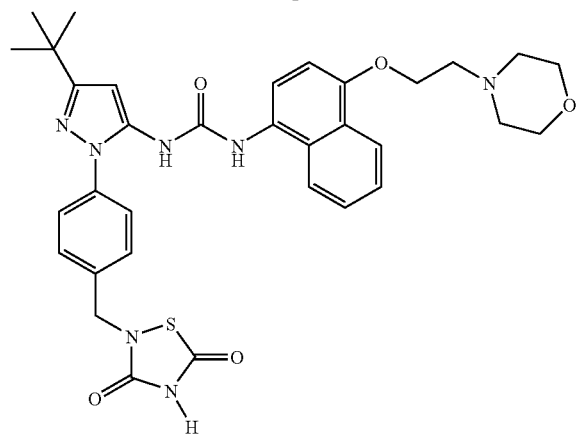

219
Example 80
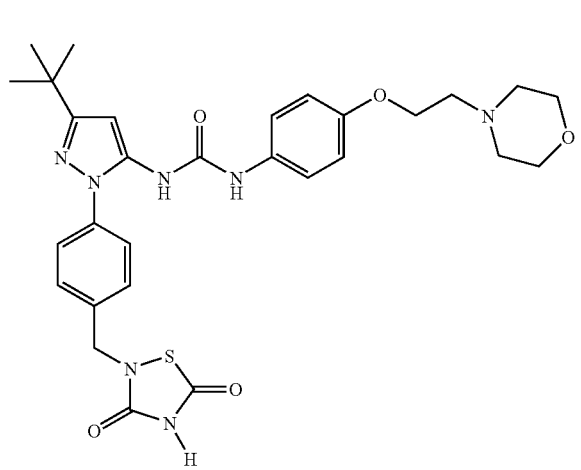
Example 81
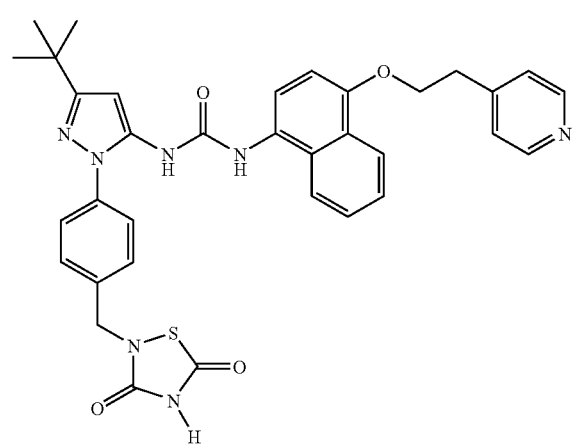
Example 82
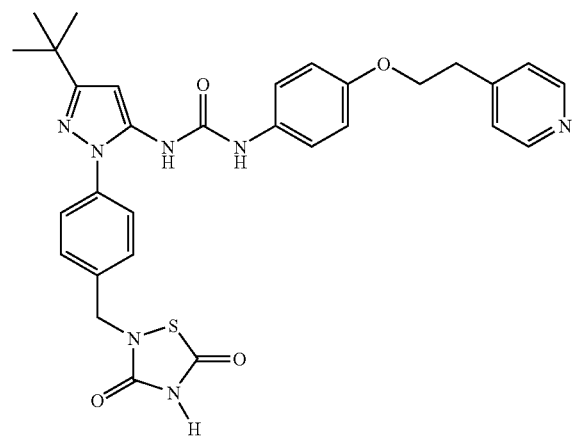
220
Example 83
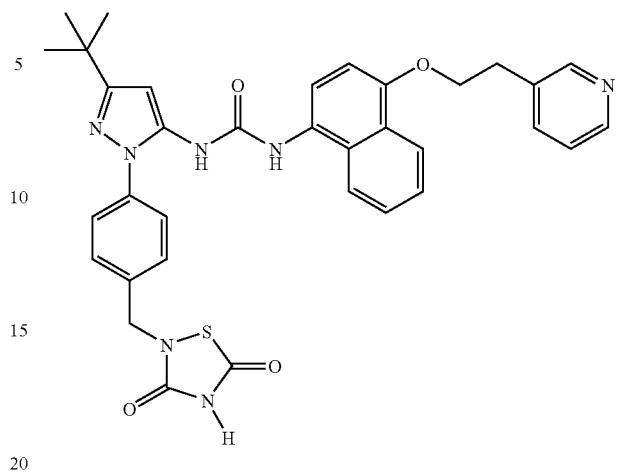
Example 84
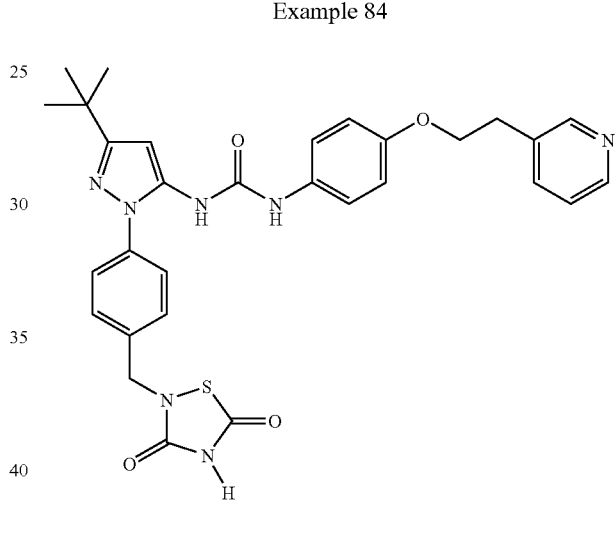
Example 85
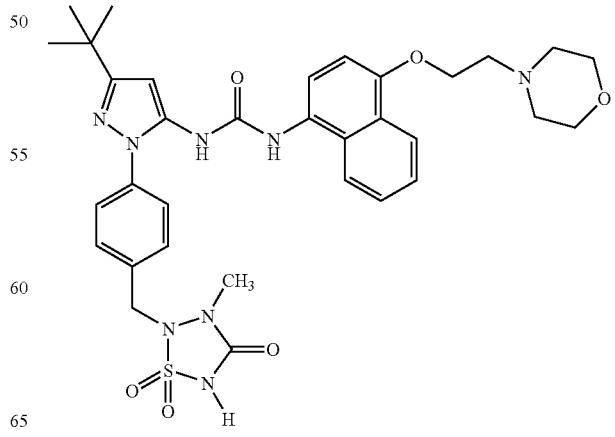

221
Example 86
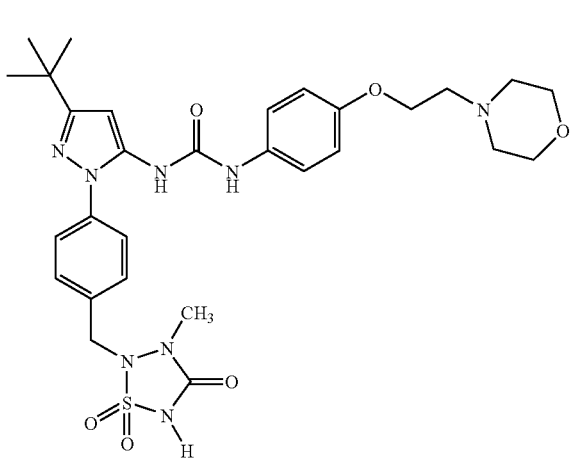
Example 87
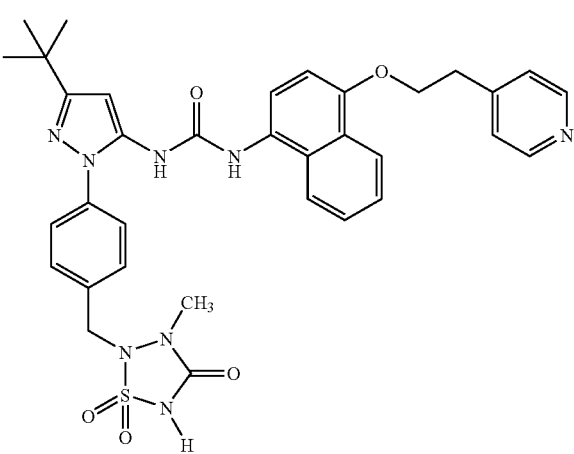
Example 88
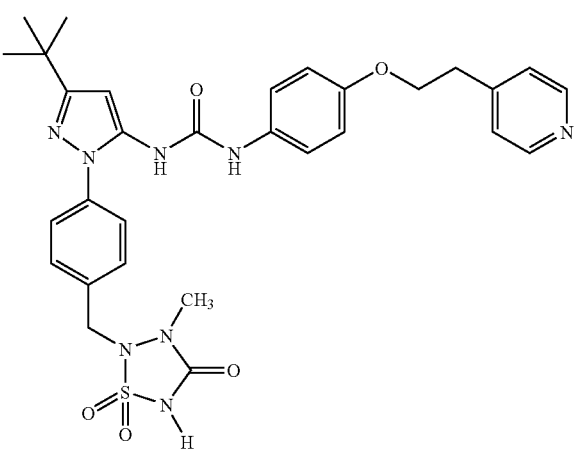
222
Example 89
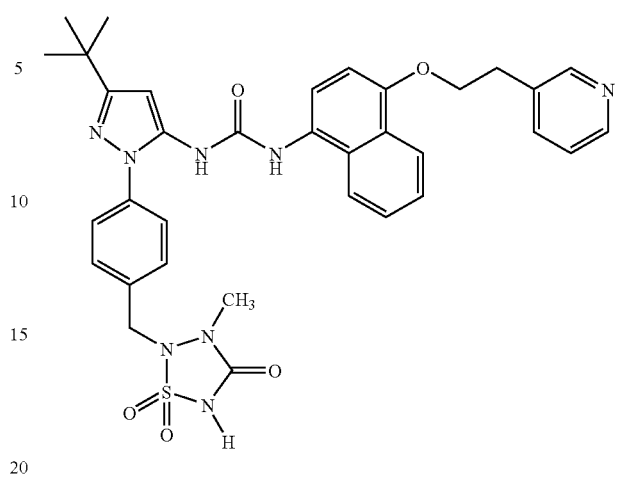
Example 90
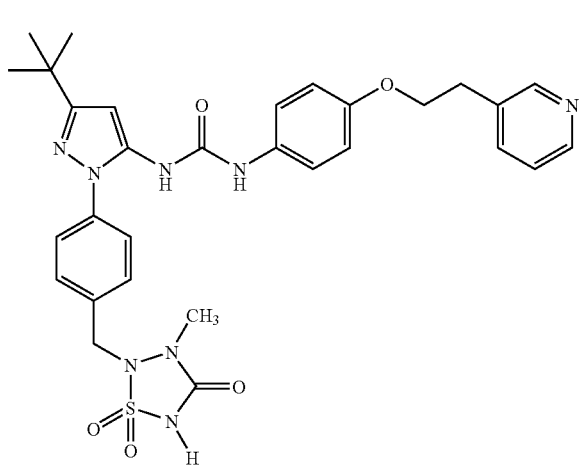
Example 91
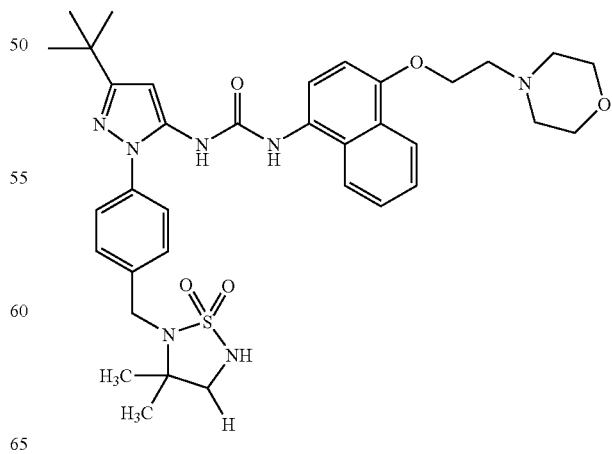

223
Example 92
224
Example 95
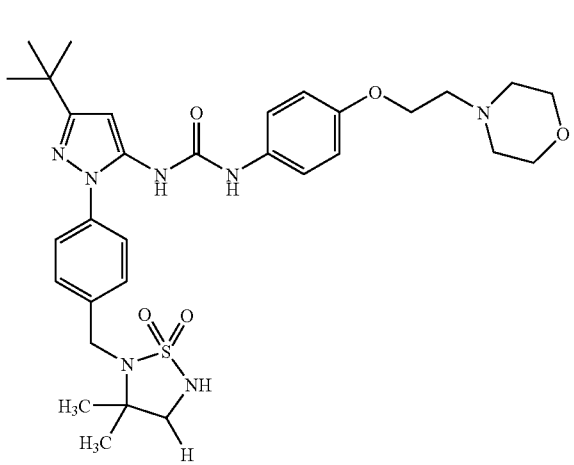
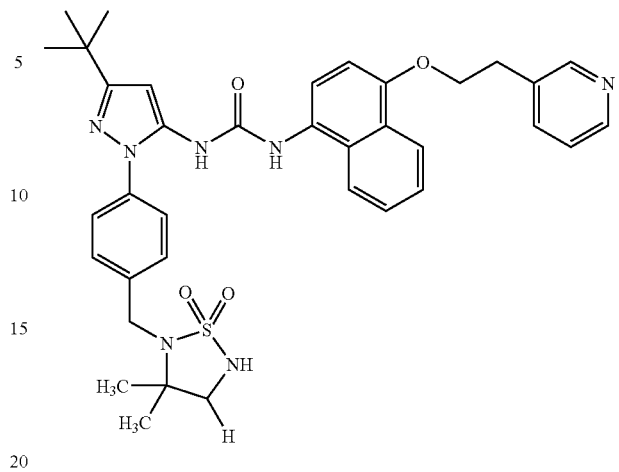
Example 93
Example 96
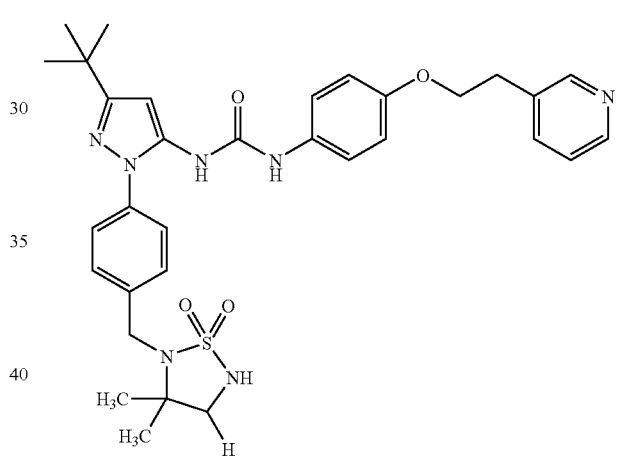
Example 94
Example 97
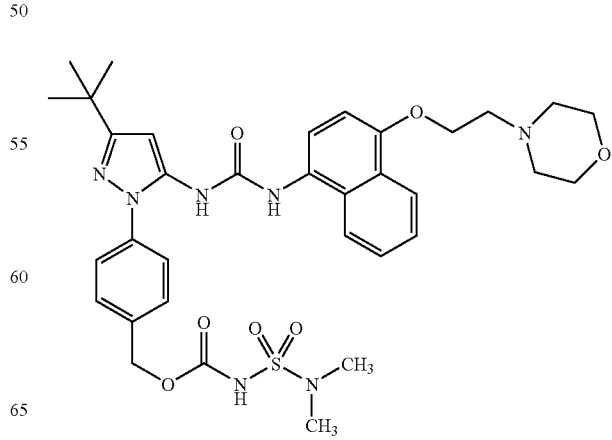

225
Example 98
226
Example 101
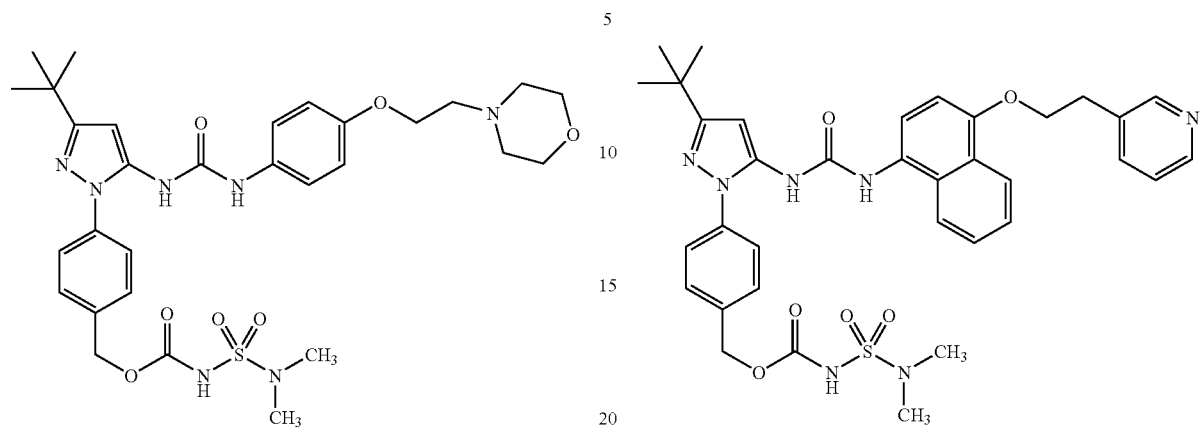
Example 99
Example 102
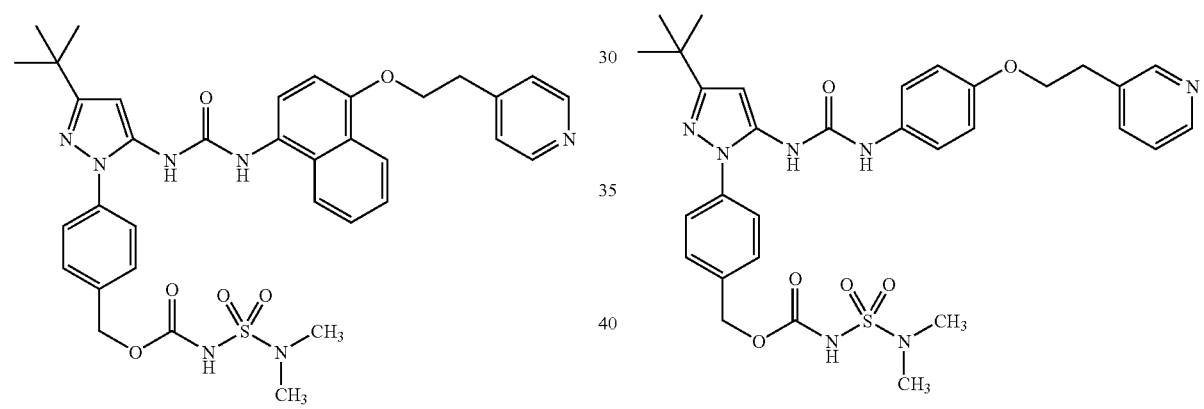
Example 100
Example 103
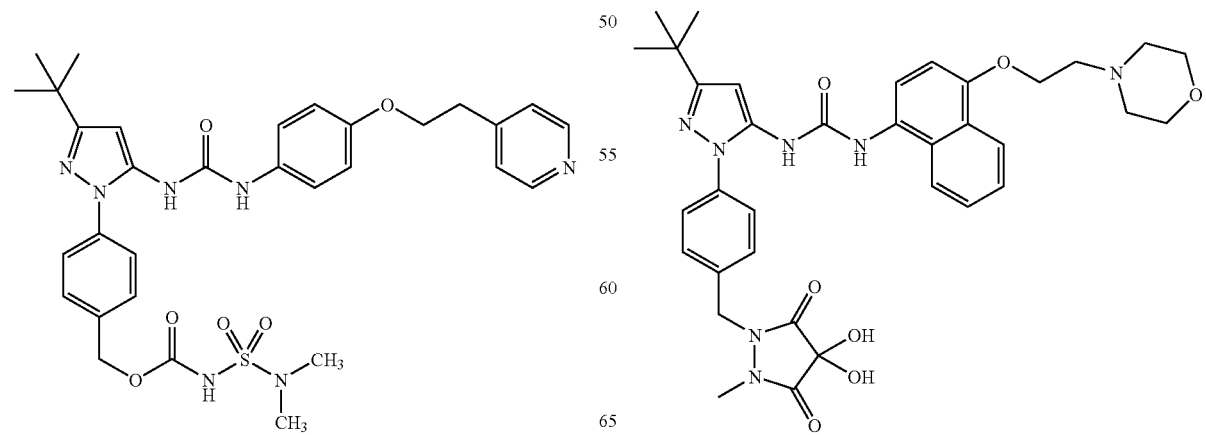

227
Example 104
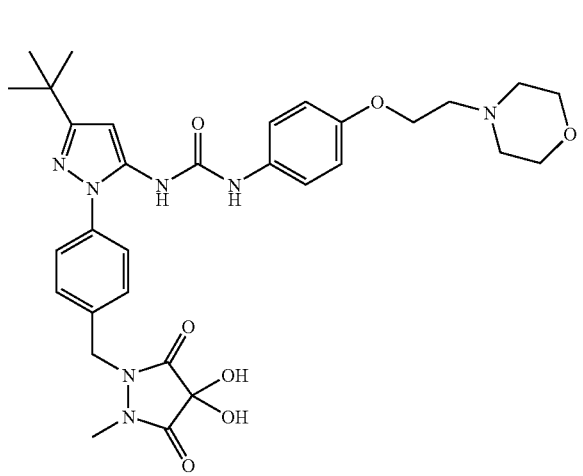
Example 105
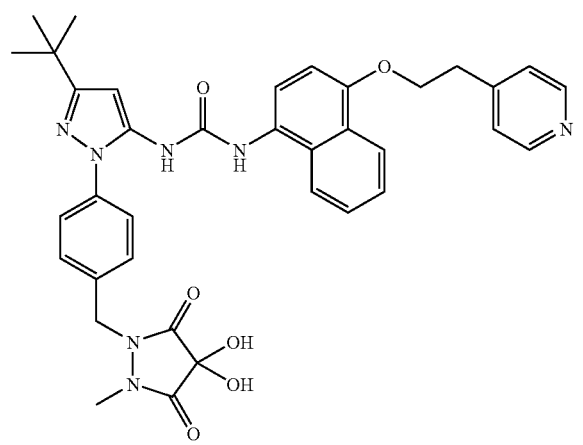
Example 106
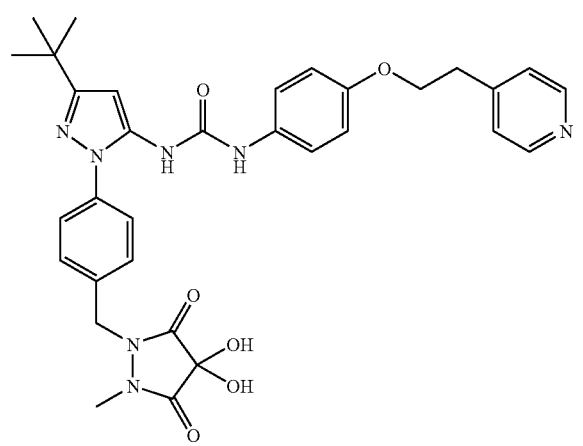
228
Example 107
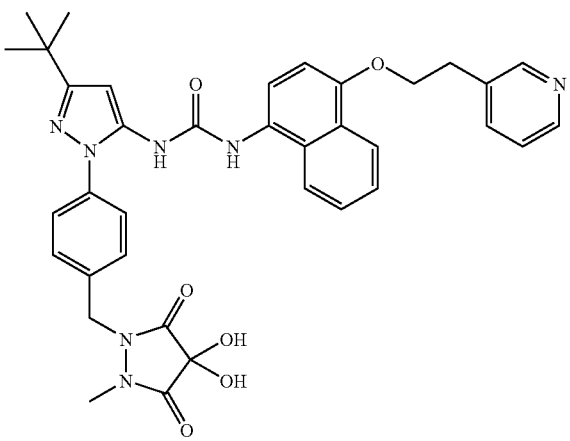
Example 108
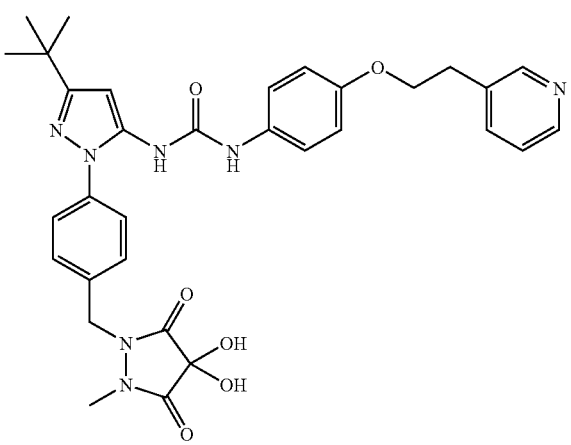
Example 109
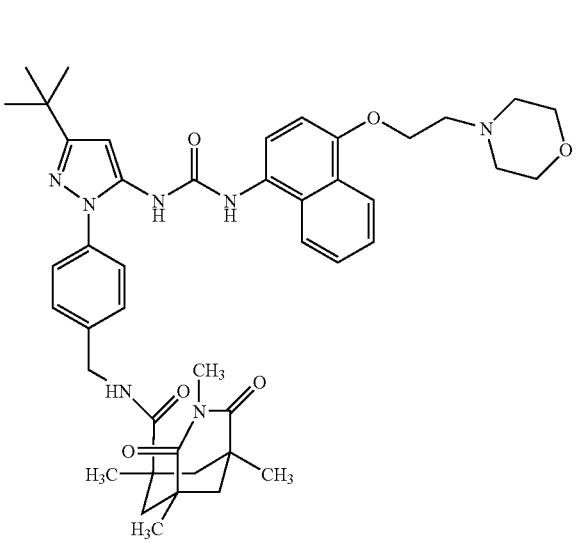

229
Example 110
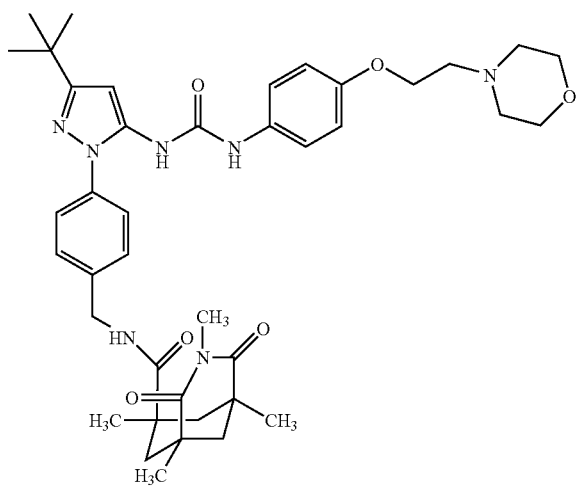
Example 111
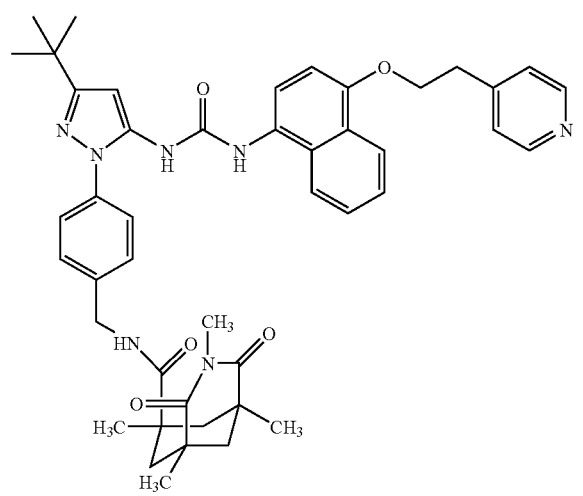
Example 112
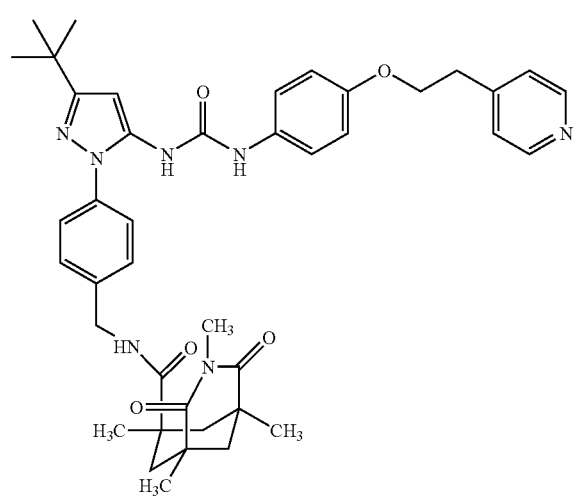
230
Example 113
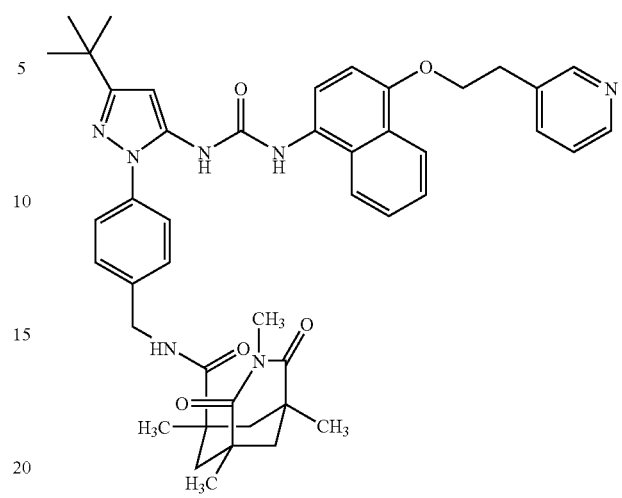
Example 114
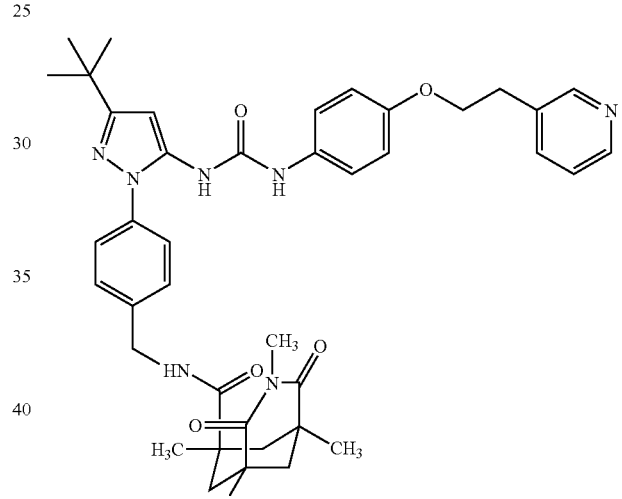
Example 115
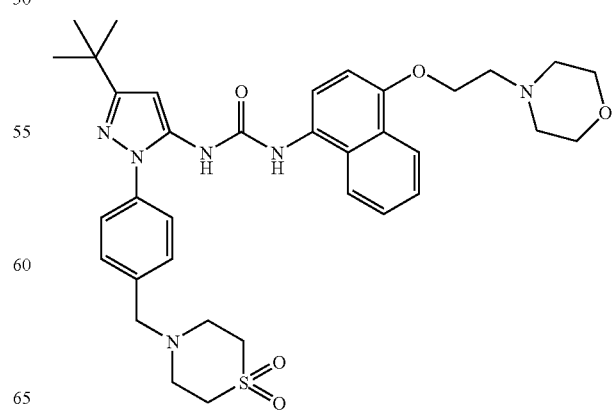

231
Example 116
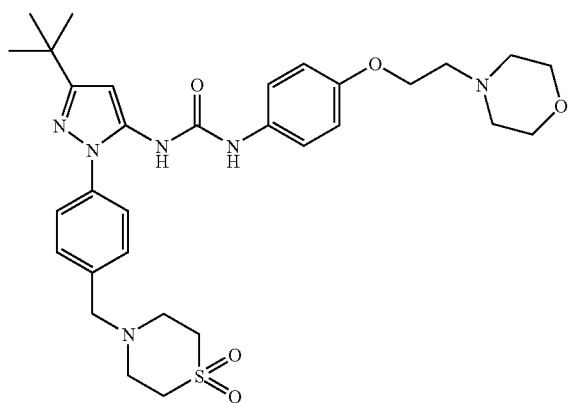
Example 117
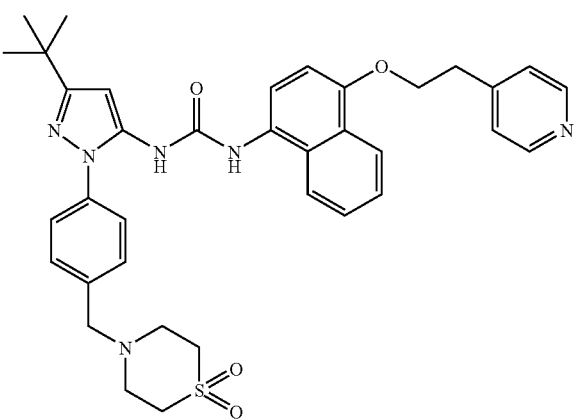
Example 118
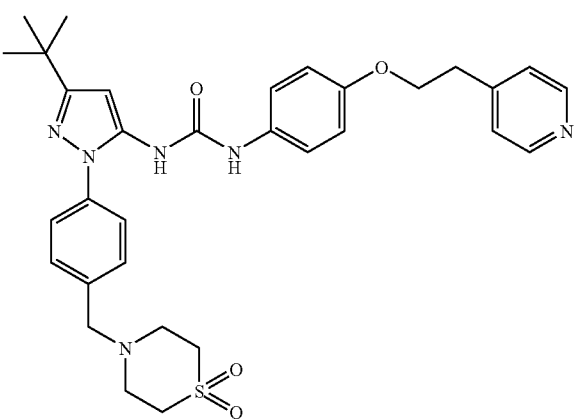
232
Example 119
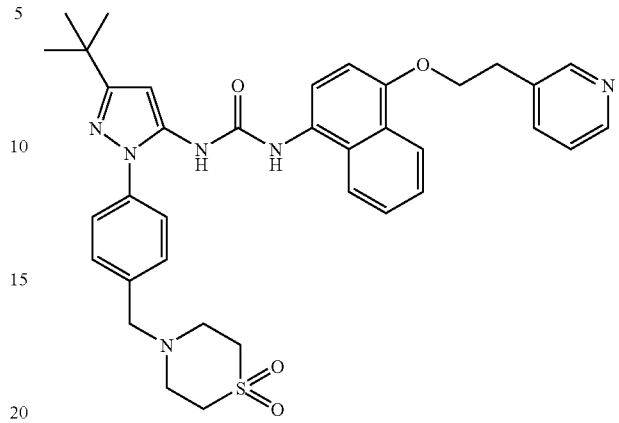
Example 120
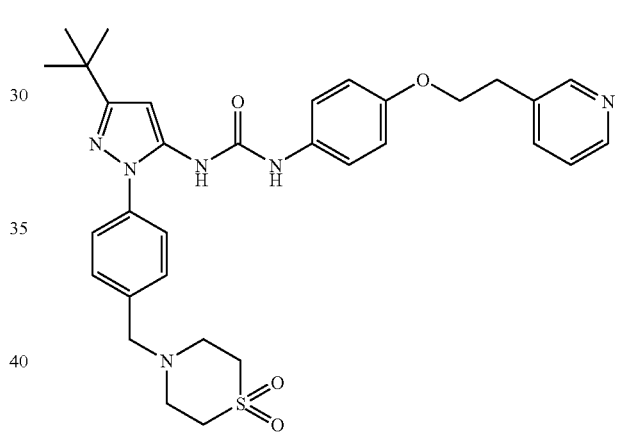
Example 121
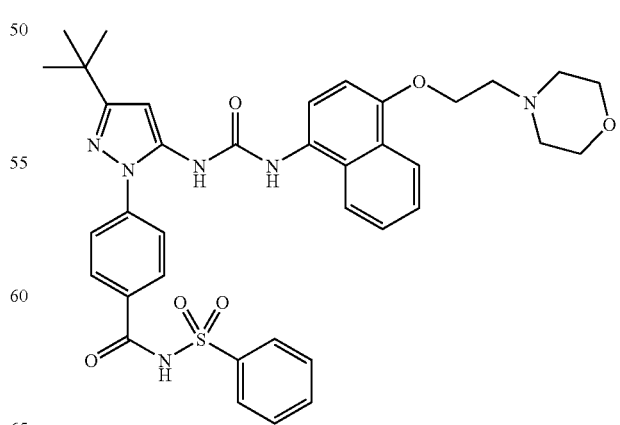

233
Example 122
234
Example 125
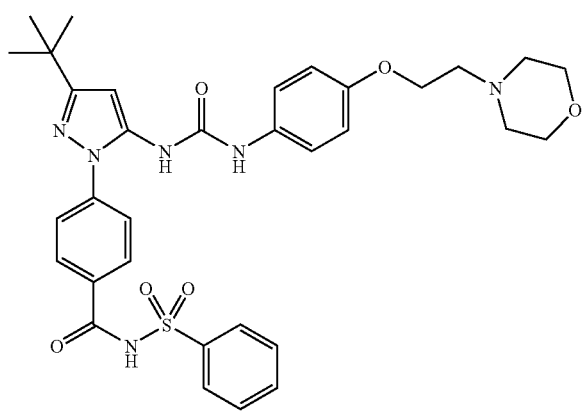
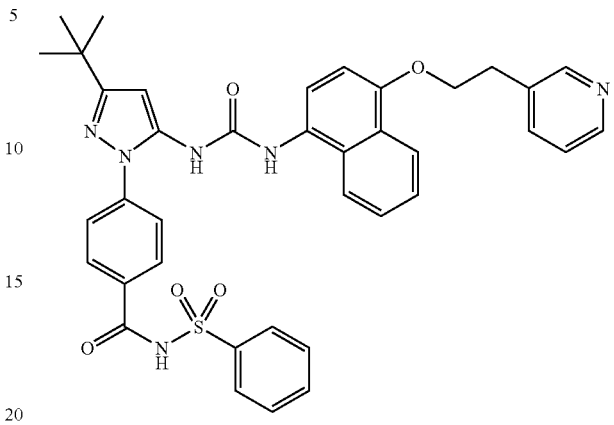
Example 123
Example 126
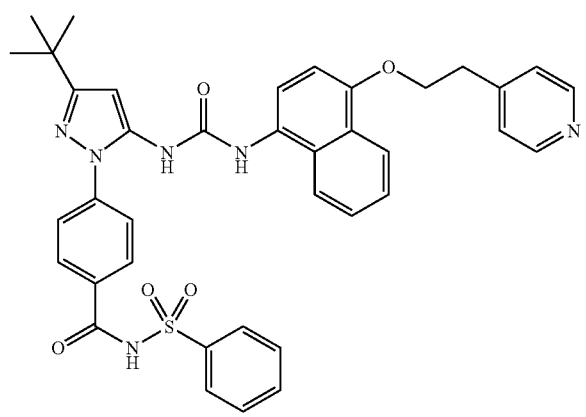
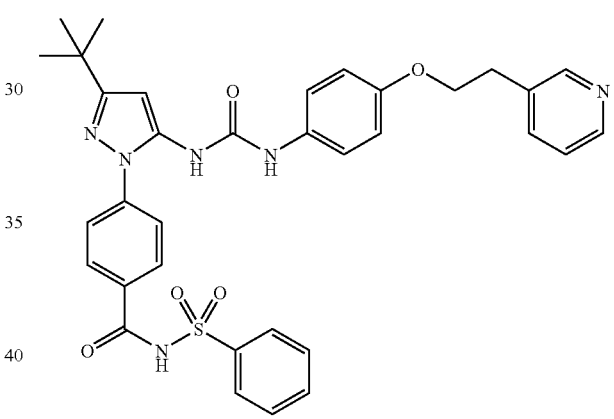
Example 124
Example 127
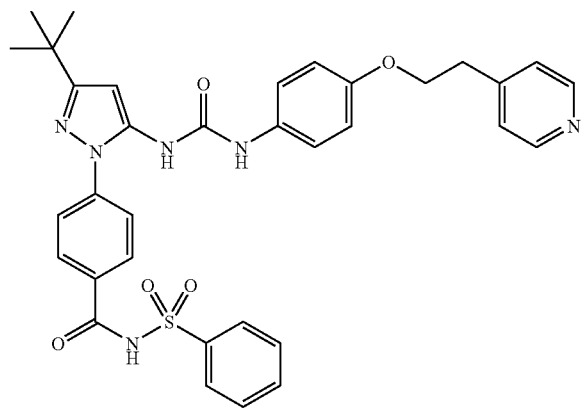
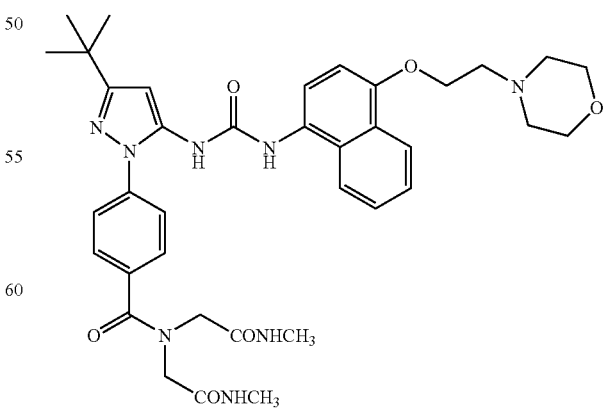

235
Example 128
236
Example 131
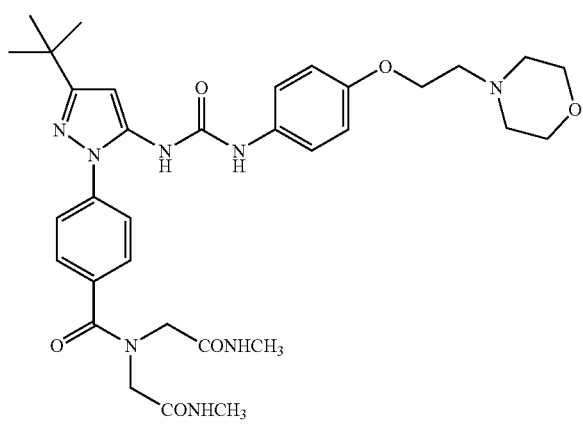
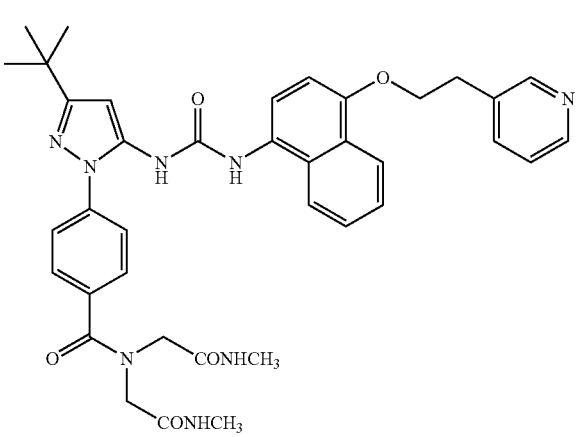
Example 129
Example 132
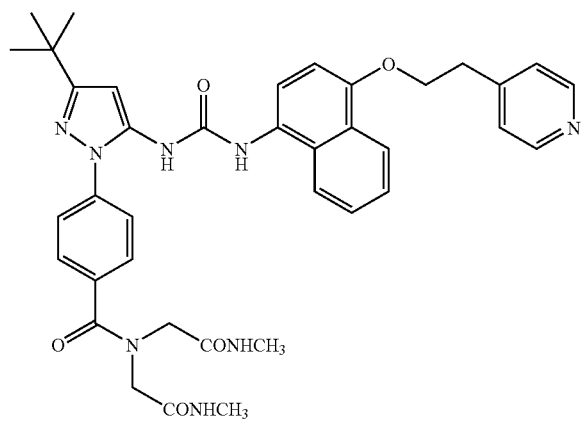
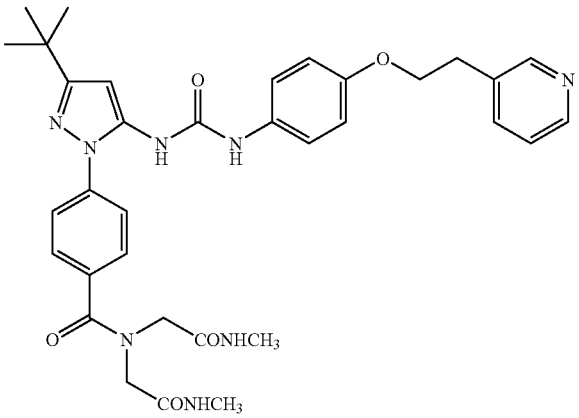
Example 130
Example 133
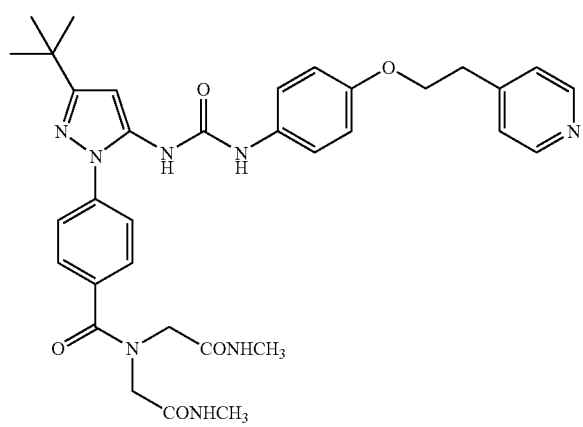
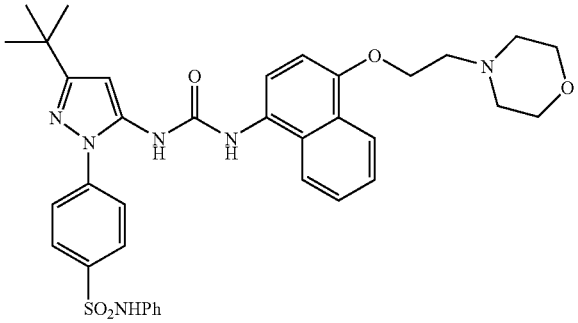

237
Example 134
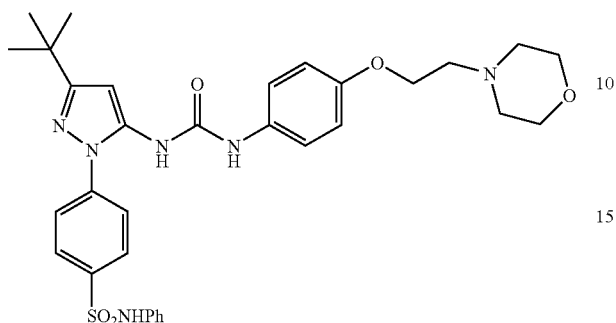
Example 135
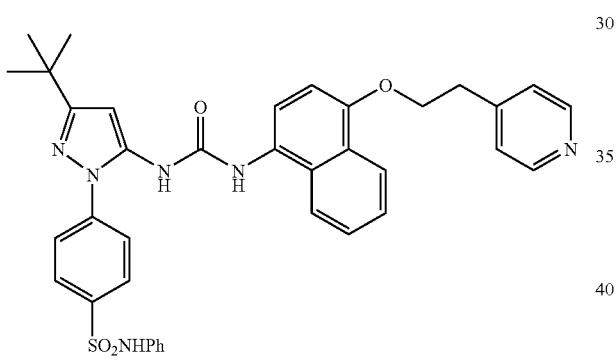
Example 136
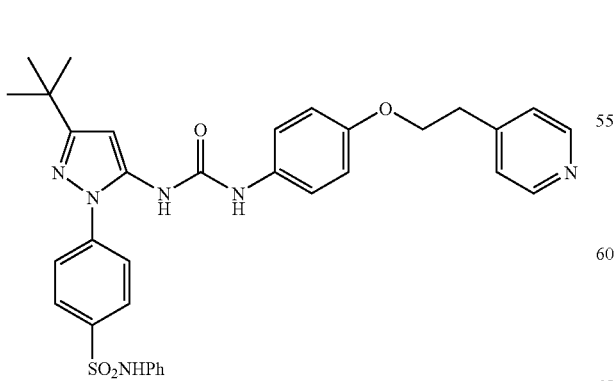
238
Example 137
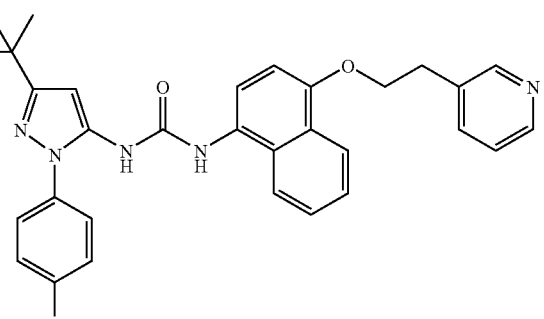
Example 138
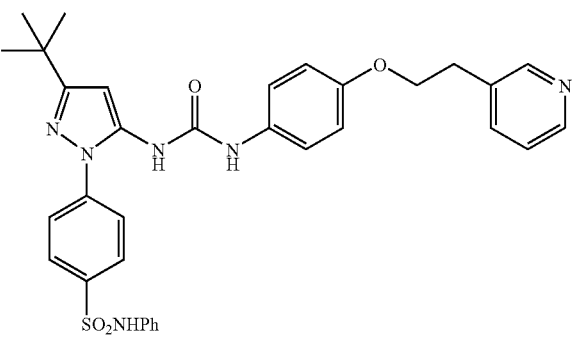
Example 139
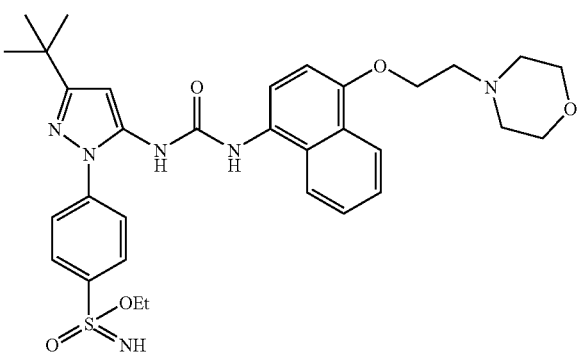

Example 140

Example 143

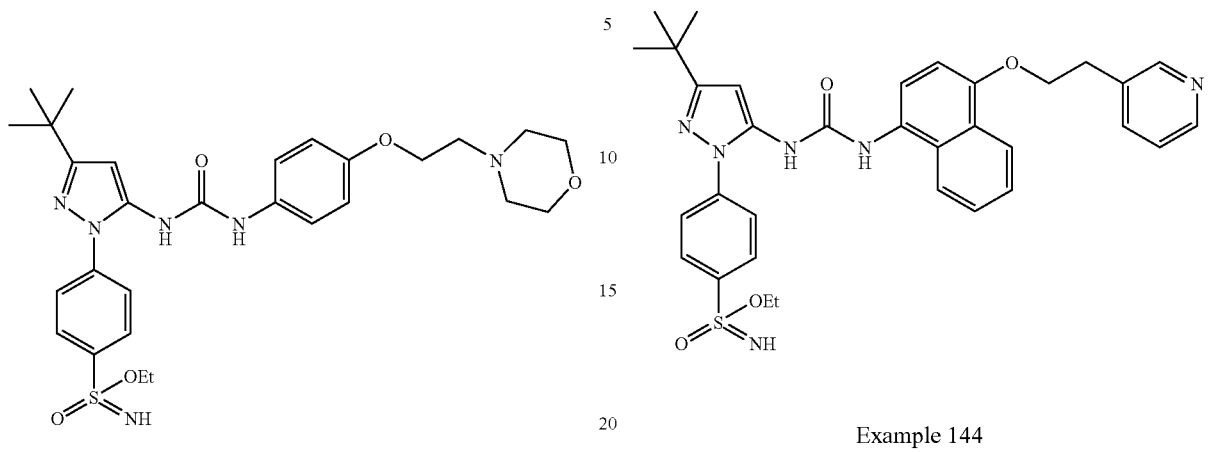

Example 144

Example 141

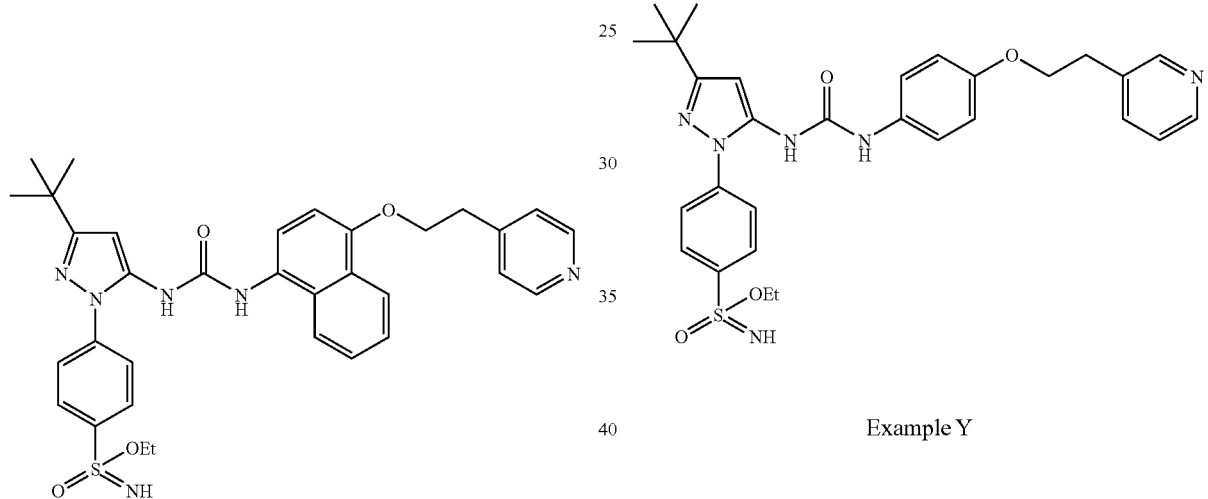

Example Y

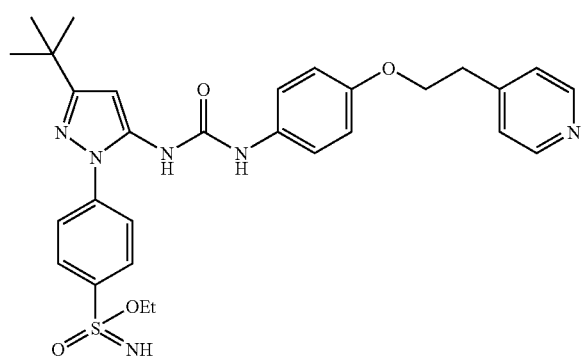

Example 142

To a solution of 3-nitro-benzaldehyde (15.1 g, 0.1 mol) in CH$_2$Cl$_2$ (200 mL) was added (triphenyl-15-phosphanylidene)-acetic acid ethyl ester (34.8 g, 0.1 mol) in CH$_2$Cl$_2$ (100 mL) dropwise at 0° C., which was stirred for 2 h. After removal the solvent under reduced pressure, the residue was purified by column chromatography to afford 3-(3-nitro-phenyl)-acrylic acid ethyl ester (16.5 g, 74.6%) $^1$H-NMR (400 MHz, CDCl$_3$): 8.42 (s, 1H), 8.23 (d, J=8.0 Hz, 1H), 7.82 (d, J=7.6 Hz, 1H), 7.72 (d, J=16.0 Hz, 1H), 7.58 (t, J=8.0 Hz, 1H), 6.56 (d, J=16.0 Hz, 1H), 4.29 (q, J=7.2 Hz, 2H), 1.36 (t, J=6.8 Hz, 3H).

A mixture of 3-(3-nitro-phenyl)-acrylic acid ethyl ester (16.5 g, 74.6 mmol) and Pd/C (1.65 g) in methanol (200 mL) was stirred under 40 psi of H$_2$ at RT for 2 h then filtered over celite. After removal the solvent, 14 g of 3-(3-amino-phenyl)- propionic acid ethyl ester was obtained and used directly without further purification. ¹H-NMR (400 MHz, CDCl₃): 7.11 (t, J=5.6 Hz, 1H), 6.67 (d, J=7.2 Hz, 1H), 6.63-6.61 (m, 2H), 4.13 (q, J=7.2 Hz, 2H), 2.87 (t, J=8.0 Hz, 2H), 2.59 (t, J=7.6 Hz, 2H), 1.34 (t, J=6.8 Hz, 3H).

To a solution of 3-(3-amino-phenyl)-propionic acid ethyl ester (14 g, 72.5 mmol) in concentrated HCl (200 mL) was added an aqueous solution (10 mL) of NaNO₂ (5 g, 72.5 mmol) at 0° C. and the resulting mixture was stirred for 1 h. A solution of SnCl₂.2H₂O (33 g, 145 mmol) in concentrated HCl (150 mL) was then added at 0° C. The reaction solution was stirred for an additional 2 h at RT. The precipitate was filtered and washed with ethanol and ether to give 3-(3-hydrazino-phenyl)-propionic acid ethyl ester as a white solid, which was used without further purification.

Example Z

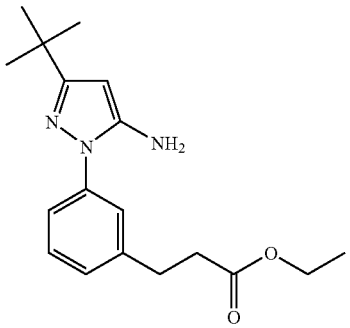

A mixture of Example Y (13 g, 53.3 mmol) and 4,4-dimethyl-3-oxo-pentanenitrile (6.9 g, 55 mol) in ethanol (150 mL) was heated to reflux overnight. The reaction solution was evaporated under reduced pressure. The residue was purified by column chromatography to give 3-[3-(5-amino-3-t-butyl-pyrazol-1-yl)-phenyl]-propionic acid ethyl ester (14.3 g, 45.4 mmol) as a white solid. ¹H NMR (DMSO-d₆): 7.39-7.32 (m, 3H), 7.11 (d, J=6.8 Hz, 1H), 5.34 (s, 1H), 5.16 (s, 2H), 4.03 (q, J=7.2 Hz, 2H), 2.88 (t, J=7.6 Hz, 2H), 2.63 (t, J=7.6 Hz, 2H), 1.19 (s, 9H), 1.15 (t, J=7.2 Hz, 3H).

Example 145

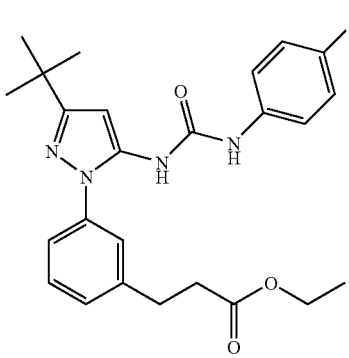

A solution of 4-fluoro-phenylamine (111 mg, 1.0 mmol) and CDI (165 mg, 1.0 mmol) in DMF (2 mL) was stirred at RT for 30 min, and was then added to a solution of Example Z (315 mg, 1.0 mmol) in DMF (2 mL). The resulting mixture was stirred at RT overnight then added to water (50 mL). The reaction mixture was extracted with ethyl acetate (3×50 mL) and the combined organic extracts were washed with brine, dried (NaSO₄) and filtered. After concentrated under reduced pressure, the residue was purified by flash chromatography to afford 3-(3-{3-t-butyl-5-[3-(4-fluoro-phenyl)-ureido]-pyrazol-1-yl}-phenyl)-propionic acid ethyl ester (150 mg, 33%). ¹H-NMR (CDCl₃): 7.91 (s, 1H), 7.42 (d, J=4.8 Hz, 1H), 7.37-7.34 (m, 2H), 7.28 (s, 1H), 7.17-7.16 (m, 2H), 6.98 (t, J=8.8 Hz, 2H), 6.59 (s, 1H), 4.04 (q, J=7.2 Hz, 2H), 3.03 (t, J=7.2 Hz, 2H), 2.77 (t, J=7.2 Hz, 2H), 1.36 (s, 9H), 1.17 (t, J=7.2 Hz, 3H); MS (ESI) m/z: 453 (M+H⁺).

Example 146

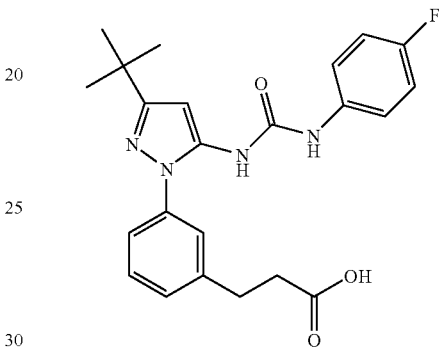

A solution of Example 145 (45 mg, 0.1 mmol) and 2N LiOH (3 mL) in MeOH (3 mL) was stirred at RT overnight. The reaction mixture was neutralized to pH=4, extracted with ethyl acetate (3×20 mL), the combined organic extracts were washed with brine, dried (NaSO₄) and filtered. The filtrate was concentrated to afford 3-(3-{3-t-butyl-5-[3-(4-fluoro-phenyl)-ureido]-pyrazol-1-yl}-phenyl)-propionic acid, (37 mg, 90%). ¹H NMR (CD₃OD): 7.63-7.62 (m, 2H), 7.56 (s, 1H), 7.53-7.48 (m, 1H), 7.41-7.38 (m, 2H), 7.04 (t, J=8.8 Hz, 2H), 5.49 (s, 1H), 3.07 (t, J=7.6 Hz, 2H), 2.72 (t, J=7.6 Hz, 2H), 1.42 (s, 9H); MS (ESI) m/z: 415 (M+H⁺).

Example 147

A mixture of 4-methoxy-phenylamine (123 mg, 1.0 mmol) and CDI (165 mg, 1.0 mmol) in DMF (2 mL) was stirred at RT for 30 min, and was then added a solution of Example Z (315 mg, 1.0 mmol) in DMF (2 mL). The resulting mixture was stirred at RT overnight then quenched with of water (50 mL).

The reaction mixture was extracted with ethyl acetate (3×50 mL) and the combined organic extracts were washed with brine, dried (NaSO$_4$), filtered, concentrated under reduced presume to yield a residue which was purified by flash chromatography to afford 3-(3-{3-t-butyl-5-[3-(4-methoxy-phenyl)-ureido]-pyrazol-1-yl}-phenyl)-propionic acid ethyl ester (210 mg, 45%). $^1$H-NMR (CD$_3$OD): 7.46 (t, J=7.6 Hz, 1H), 7.38 (s, 1H), 7.34 (d, J=7.6 Hz, 2H), 7.24 (d, J=8.4 Hz, 2H), 6.84 (d, J=8.4 Hz, 2H), 6.38 (s, 1H), 4.09 (q, J=7.2 Hz, 2H), 3.75 (s, 3H), 3.00 (t, J=7.6 Hz, 2H), 2.68 (t, J=7.6 Hz, 2H), 1.33 (s, 9H), 1.20 (t, J=7.6 Hz, 3H); MS (ESI) m/z: 465 (M+H$^+$).

Example 148

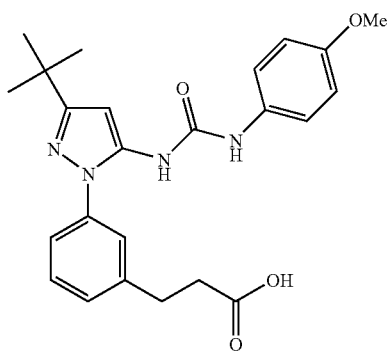

Utilizing the same synthetic procedure as for Example 61 and starting with Example 147, 3-(3-{3-t-butyl-5-[3-(4-methoxy-phenyl)-ureido]-pyrazol-1-yl}-phenyl)-propionic acid is synthesized.

Example 149

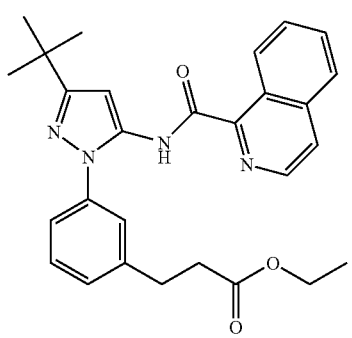

A solution of isoquinoline-1-carboxylic acid (346 mg, 2.0 mmol), Example Z (315 mg, 1.0 mmol), EDCI (394 mg, 2.0 mmol), HOBt (270 mg, 2.0 mmol), and NMM (1.0 mL) in DMF (10 mL) was stirred at RT overnight. After quenching with water (100 mL), the reaction mixture was extracted with ethyl acetate (3×100 mL). The combined organic extracts were washed with brine, dried (NaSO$_4$), filtered and concentrated under reduced pressure to yield a residue which was purified by flash chromatography to afford 3-(3-{3-t-butyl-5-[(isoquinoline-1-carbonyl)-amino]-pyrazol-1-yl}-phenyl)-propionic acid ethyl ester, (380 mg, 80%). $^1$H-NMR (DMSO-d$_6$): 8.83 (d, J=8.4 Hz, 1H), 8.85 (d, J=5.2 Hz, 1H), 8.09 (s, 1H), 8.07 (d, J=8.4 Hz, 1H), 7.82 (t, J=8.0 Hz, 1H), 7.72 (t, J=8.0 Hz, 1H), 7.52 (s, 1H), 7.44 (d, J=8.0 Hz, 1H), 7.39 (t, J=5.2 Hz, 1H), 7.22 (d, J=8.0 Hz, 1H), 6.57 (s, 1H), 3.98 (q, J=7.2 Hz, 2H), 2.84 (t, J=7.6 Hz, 2H), 2.57 (t, J=7.6 Hz, 2H), 1.32 (s, 9H), 1.10 (t, J=7.6 Hz, 1H); MS (ESI) m/z: 471 (M+H$^+$).

Example 150

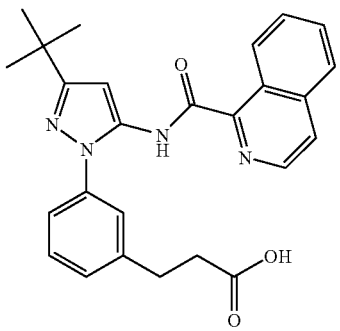

A solution of Example 149u (47 mg, 0.1 mmol) and 2N LiOH (3 mL) in MeOH (3 mL) was stirred at RT overnight. The reaction mixture was neutralized to pH=4, extracted with ethyl acetate (3×20 mL), and the combined organic extracts were washed with brine, dried (NaSO$_4$) and filtered. The filtrate was concentrated to afford 3-(3-{3-t-butyl-5-[(isoquinoline-1-carbonyl)-amino]-pyrazol-1-yl}-phenyl)-propionic acid, (39 mg, 87%). $^1$H-NMR-(DMSO-d$_6$): 10.77 (s, 1H), 9.68 (d, J=7.6 Hz, 1H), 8.44 (d, J=5.2 Hz, 1H), 7.89-7.44 (m, 2H), 7.78-7.74 (m, 2H), 7.49-7.47 (m, 3H), 7.30-7.27 (m, 3H), 6.95 (s, 1H), 3.05 (t, J=7.2 Hz, 2H), 2.75 (t, J=7.6 Hz, 2H), 1.42 (s, 9H); MS (ESI) m/z: 443 (M+H$^+$).

Example 151

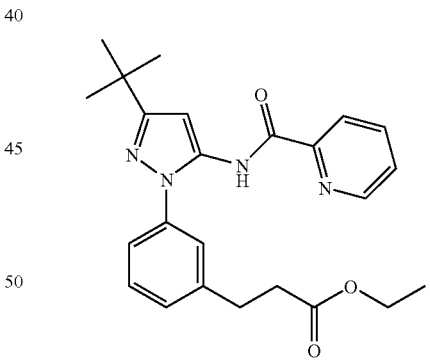

A solution of pyridine-2-carboxylic acid (246 mg, 2.0 mmol), Example Z (315 mg, 1.0 mmol), EDCI (394 mg, 2.0 mmol), HOBt (270 mg, 2.0 mmol), NMM (1.0 mL) in DMF (10 mL) was stirred at RT overnight. After quenching with water (100 mL), the reaction mixture was extracted with ethyl acetate (3×100 mL). The combined organic extracts were washed with brine, dried (NaSO$_4$), filtered and concentrated under reduced pressure to yield a residue which was purified by flash chromatography to afford 3-(3-{3-t-butyl-5-[(pyridine-2-carbonyl)-amino]-pyrazol-1-yl}-phenyl)-propionic acid ethyl ester (300 mg, 70%). $^1$H-NMR (CDCL$_3$): 8.53 (d, J=4.4 Hz, 1H), 8.26 (d, J=7.2 Hz, 1H), 7.90 (t, J=8.0 Hz, 1H), 7.48-7.43 (m, 4H), 7.27 (s, 1H), 6.87 (s, 1H), 4.13 (q, J=7.2

Hz, 2H), 3.04 (t, J=7.6 Hz, 2H), 2.71 (t, J=7.6 Hz, 2H), 1.39 (s, 9H), 1.24 (t, J=7.2 Hz, 3H); MS (ESI) m/z: 421 (M+H⁺).

Example 152

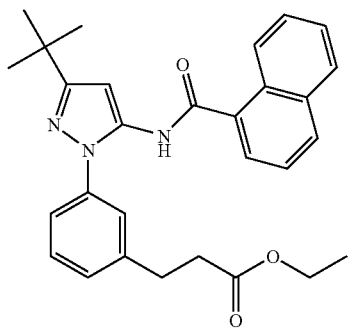

A solution of Example Z (315 mg, 1.0 mmol) and Barton's base (0.5 mL) in anhydrous CH₂Cl₂ (5 mL) under N₂ was stirred at RT for 30 min, and then added to a solution of naphthalene-1-carbonyl fluoride (348 mg, 0.2 mmol) in anhydrous CH₂Cl₂ (5 mL). The resulting mixture was stirred at RT overnight. After quenching with water (100 mL), the reaction mixture was extracted with ethyl acetate (3×100 mL). The combined organic extracts were washed with brine, dried (NaSO₄), filtered and concentrated under reduced pressure to yield a residue which was purified by flash chromatography to afford 3-(3-{3-t-butyl-5-[(naphthalene-1-carbonyl)-amino]-pyrazol-1-yl}-phenyl)-propionic acid ethyl ester, (350 mg, 74%). ¹H-NMR (CDCL₃): 8.29 (d, J=8.0 Hz, 1H), 7.98 (d, J=7.2 Hz, 2H), 7.89 (d, J=7.2 Hz, 1H), 7.62-7.57 (m, 3H), 7.49-7.28 (m, 4H), 7.03 (s, 1H), 3.94 (q, J=7.2 Hz, 2H), 2.96 (t, J=7.2 Hz, 2H), 2.58 (t, J=7.2 Hz, 2H), 1.45 (s, 9H), 1.13 (t, J=7.2 Hz, 3H); MS (ESI) m/z: 470 (M+H⁺).

Example 153

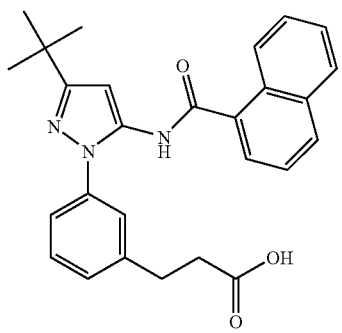

A solution of Example 152 (47 mg, 0.1 mmol) and 2N LiOH (3 mL) in MeOH (3 mL) was stirred at RT overnight. The reaction mixture was neutralized to pH=4, and extracted with ethyl acetate (3×20 mL). The combined organic extracts were washed with brine, and dried (NaSO₄) and filtered. The filtrate was concentrated to afford 3-(3-{3-t-butyl-5-[(isoquinoline-1-carbonyl)-amino]-pyrazol-1-yl}-phenyl)-propionic acid, (38 mg, 86%). ¹H NMR (DMSO-d₆): 7.99 (d, J=8.0 Hz, 1H), 7.90 (m, 2H), 7.62 (m, 1H), 7.54-7.42 (m, 6H), 7.35 (m, 1H), 6.54 (s, 1H), 2.94 (t, J=7.6 Hz, 2H), 2.57 (t, J=7.2 Hz, 2H), 1.38 (s, 9H); MS (ESI) m/z: 443 (M+H⁺).

Example 154

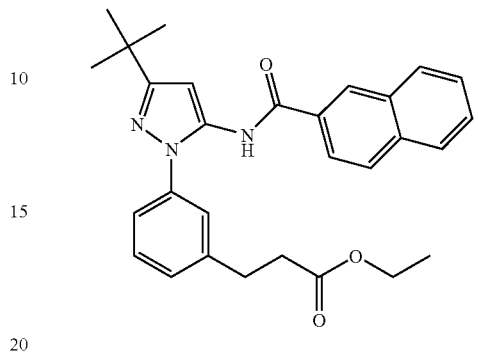

A solution of naphthalene-2-carboxylic acid (344 mg, 2.0 mmol) in SOCl₂ (10 mL) was heated to reflux for 2 h. After concentration under reduced pressure, the residue was dissolved into CH₂Cl₂ (5 mL) and was dropped into a solution of Example Z (315 mg, 1.0 mmol) in CH₂Cl₂ (10 mL) at 0° C., and was then stirred at RT overnight. After quenching with water (50 mL), the reaction mixture was extracted with CH₂Cl₂ (3×100 mL). The combined organic extracts were washed with brine, dried (NaSO₄), filtered and concentrated under reduced pressure to yield a residue which was purified by flash chromatography to afford 3-(3-{3-t-butyl-5-[(naphthalene-2-carbonyl)-amino]-pyrazol-1-yl}-phenyl)-propionic acid ethyl ester (180 mg, 38%). ¹H-NMR (CDCL₃): 8.24 (s, 1H), 8.21 (s, 1H), 7.91 (d, J=8.4 Hz, 2H), 7.88 (d, J=8.4 Hz, 1H), 7.73 (d, J=8.4 Hz, 1H), 7.63-7.49 (m, 3H), 7.45-7.26 (m, 3H), 6.94 (s, 1H), 4.02 (q, J=7.2 Hz, 2H), 3.04 (t, J=7.6 Hz, 2H), 2.67 (t, J=7.6 Hz, 2H), 1.43 (s, 9H), 1.17 (t, J=7.2 Hz, 3H); MS (ESI) m/z: 470 (M+H⁺).

Example 155

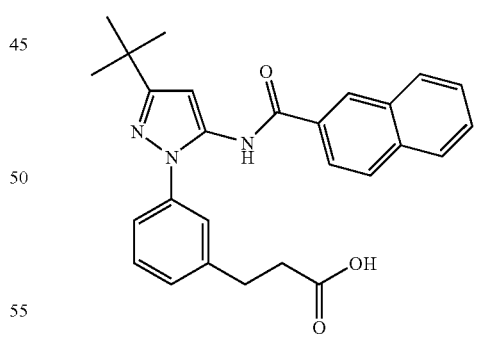

A solution of Example 154 (47 mg, 0.1 mmol) and 2N LiOH (3 mL) in MeOH (3 mL) was stirred at RT overnight. The reaction mixture was neutralized to pH=4, and extracted with ethyl acetate (3×20 mL). The combined organic extracts were washed with brine, and dried (NaSO₄) and filtered. The filtrate was concentrated to afford 3-(3-{3-t-butyl-5-[(isoquinoline-2-carbonyl)-amino]-pyrazol-1-yl}-phenyl)-propionic acid, (37 mg, 84%). ¹H-NMR (CDCL3): 8.25 (s, 1H), 8.18 (s, 1H), 7.91-7.86 (m, 3H), 7.75 (d, J=8.0 Hz, 1H), 7.59-7.55 (m, 2H), 7.48-7.39 (m, 3H), 7.28 (s, 1H), 6.81 (s, 1H), 3.02 (t, J=7.6 Hz, 2H), 2.69 (t, J=7.6 Hz, 2H), 1.42 (s, 9H); MS (ESI) m/z: 442 (M+H⁺).

Example 156

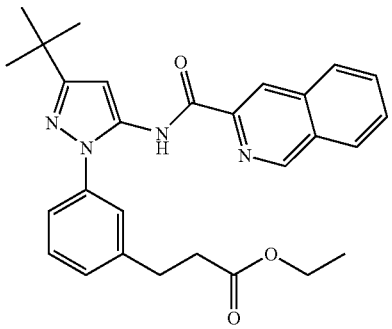

A solution of isoquinoline-3-carboxylic acid (346 mg, 2.0 mmol), example Z (315 mg, 1.0 mmol), EDCI (394 mg, 2.0 mmol), HOBt (270 mg, 2.0 mmol), and NMM (1.0 mL) in DMF (10 mL) was stirred at RT overnight. After quenching with water (50 mL), the reaction mixture was extracted with ethyl acetate (3×100 mL). The combined organic extracts were washed with brine, dried (NaSO₄) and filtered. After concentrated under reduced pressure, the residue was purified by flash chromatography to afford 3-(3-{3-t-butyl-5-[(isoquinoline-3-carbonyl)-amino]-pyrazol-1-yl}-phenyl)-propionic acid ethyl ester (250 mg, 54%). ¹H-NMR (CD₃OD): 9.24 (s, 1H), 8.63 (s, 1H), 8.17 (d, J=8.0 Hz, 1H), 8.11 (d, J=8.0 Hz, 1H), 7.88 (t, J=7.6 Hz, 1H), 7.81 (t, J=7.6 Hz, 1H), 7.50 (s, 1H), 7.48 (d, J=7.6 Hz, 1H), 7.54 (d, J=7.6 Hz, 2H), 7.36 (d, J=7.6 Hz, 1H), 6.75 (s, 1H), 4.04 (q, J=7.6 Hz, 2H), 3.01 (t, J=7.6 Hz, 2H), 2.69 (t, J=7.6 Hz, 2H), 1.39 (s, 9H), 1.14 (t, J=7.6 Hz, 3H); MS (ESI) m/z: 471 (M+H⁺).

Example 157

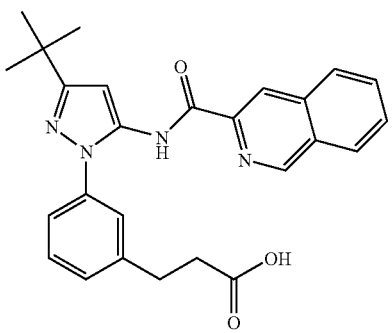

A solution of Example 156 (47 mg, 0.1 mmol) and 2N LiOH (3 mL) in MeOH (3 mL) was stirred at RT overnight. The reaction mixture was neutralized to pH=4, and extracted with ethyl acetate (3×20 mL). The combined organic extracts were washed with brine, and dried (NaSO₄) and filtered. The filtrate was concentrated to afford 3-(3-{3-t-butyl-5-[(isoquinoline-3-carbonyl)-amino]-pyrazol-1-yl}-phenyl)-propionic acid, (39 mg, 88%). ¹H NMR (CDCL3): 10.49 (s, 1H), 9.16 (s, 1H), 8.69 (s, 1H), 8.03 (d, J=7.6 Hz, 2H), 7.81 (t, J=7.2 Hz, 1H), 7.73 (t, J=7.2 Hz, 1H), 7.48-7.39 (m, 3H), 7.28 (br s, 1H), 6.94 (s, 1H), 3.02 (t, J=7.6 Hz, 2H), 2.79 (t, J=7.6 Hz, 2H), 1.42 (s, 9H); MS (ESI) m/z: 442 (M+H⁺).

Example 158

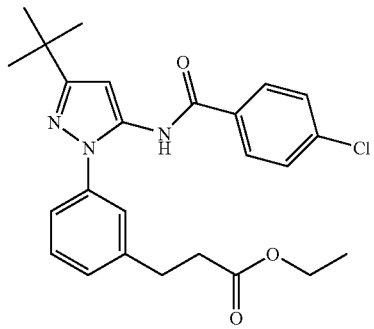

A solution of 4-chlorobenzoic acid (312 mg, 2.0 mmol) in SOCl₂ (10 mL) was heated to reflux for 2 h. After removal of the solvent, the residue was dissolved into CH₂Cl₂ (5 mL) and was dropped into a solution of Example Z (315 mg, 1.0 mmol) in CH₂Cl₂ (10 mL) at 0° C., was then stirred at RT overnight. After quenching with water (50 mL), the reaction mixture was extracted with CH₂Cl₂ (3×100 mL). The combined organic extracts were washed with brine, dried (NaSO₄) and filtered. After concentrated under reduced pressure, the residue was purified by flash chromatography to afford 3-{3-[3-t-butyl-5-(4-chloro-benzoylamino)-pyrazol-1-yl]-phenyl}-propionic acid ethyl ester (290 mg, 64%). ¹H-NMR (CDCL₃): 8.02 (s, 1H), 7.67 (d, J=8.4 Hz, 2H), 7.46 (t, J=7.6 Hz, 1H), 7.44 (d, J=8.4 Hz, 2H), 7.36 (t, J=8.4 Hz, 3H), 6.87 (s, 1H), 4.06 (q, J=7.6 Hz, 2H), 3.02 (t, J=7.6 Hz, 2H), 2.67 (t, J=7.6 Hz, 2H), 1.40 (s, 9H), 1.12 (t, J=7.6 Hz, 3H); MS (ESI) m/z: 454 (M+H⁺).

Example 159

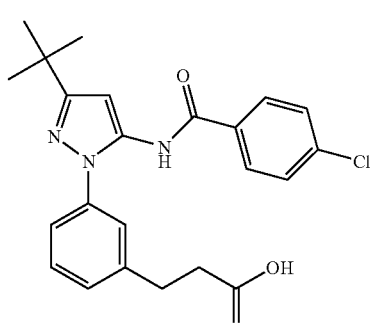

A solution of Example 158 (45 mg, 0.1 mmol) and 2N LiOH (3 mL) in MeOH (3 mL) was stirred at RT overnight. The reaction mixture was neutralized to pH=4, and extracted with ethyl acetate (3×20 mL). The combined organic extracts were washed with brine, and dried (NaSO₄) and filtered. The filtrate was concentrated to afford 3-{3-[3-t-butyl-5-(4-chloro-benzoylamino)-pyrazol-1-yl]-phenyl}-propionic acid, (38.5 mg, 87%). ¹H NMR (DMSO-d₆): 10.38 (s, 1H), 7.85 (d, J=8.4 Hz, 1H), 7.56 (d, J=8.4 Hz, 2H), 7.39 (s, 1H), 7.32 (d, J=4.8 Hz, 2H), 7.15 (t, J=4.8 Hz, 1H), 6.38 (s, 1H), 2.80 (t, J=7.6 Hz, 2H), 2.44 (t, J=7.2 Hz, 2H), 1.29 (s, 9H); MS (ESI) m/z: 426 (M+H⁺).

Example AA

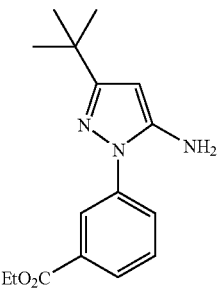

To a solution of m-aminobenzoic acid (200.0 g, 1.46 mmol) in concentrated HCl (200 mL) was added an aqueous solution (250 mL) of NaNO$_2$ (102 g, 1.46 mmol) at 0° C. and the reaction mixture was stirred for 1 h. A solution of SnCl$_2$.2H$_2$O (662 g, 2.92 mmol) in concentrated HCl (2000 mL) was then added at 0° C. The reaction solution was stirred for an additional 2 h at RT. The precipitate was filtered and washed with ethanol and ether to give 3-hydrazino-benzoic acid hydrochloride as a white solid, which was used for the next reaction without further purification. $^1$H NMR (DMSO-d$_6$): 10.85 (s, 3H), 8.46 (s, 1H), 7.53 (s, 1H), 7.48 (d, J=7.6 Hz, 1H), 7.37 (m, J=7.6 Hz, 1H), 7.21 (d, J=7.6 Hz, 1H).

A mixture of 3-hydrazino-benzoic acid hydrochloride (200 g, 1.06 mol) and 4,4-dimethyl-3-oxo-pentanenitrile (146 g, 1.167 mol) in ethanol (2 L) was heated to reflux overnight. The reaction solution was evaporated under reduced pressure. The residue was purified by column chromatography to give 3-(5-amino-3-t-butyl-pyrazol-1-yl)-benzoic acid ethyl ester (116 g, 40%) as a white solid together with 3-(5-amino-3-t-butyl-pyrazol-1-yl)-benzoic acid (93 g, 36%). 3-(5-amino-3-t-butyl-pyrazol-1-yl)-benzoic acid and ethyl ester: $^1$H NMR (DMSO-d$_6$): 8.09 (s, 1H), 8.05 (brd, J=8.0 Hz, 1H), 7.87 (br d, J=8.0 Hz, 1H), 7.71 (t, J=8.0 Hz, 1H), 5.64 (s, 1H), 4.35 (q, J=7.2 Hz, 2H), 1.34 (t, J=7.2 Hz, 3H), 1.28 (s, 9H).

Example BB

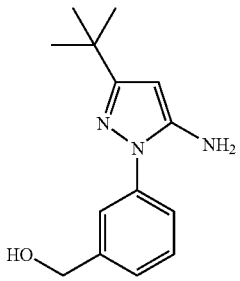

To a stirred solution of Example AA (19.5 g, 68.0 mmol) in THF (200 mL) was added LiAlH$_4$ powder (5.30 g, 0.136 mol) at −10° C. under N$_2$. The mixture was stirred for 2 h at RT and excess LiAlH$_4$ was destroyed by slow addition of ice. The reaction mixture was acidified to pH=7 with diluted HCl, the solution concentrated under reduced pressure, and the residue was extracted with ethyl acetate. The combined organic extracts were concentrated to give [3-(5-amino-3-t-butyl-pyrazol-1-yl)-phenyl]-methanol (16.35 g, 98%) as a white powder. $^1$H NMR (DMSO-d$_6$): 9.19 (s, 1H), 9.04 (s, 1H), 8.80 (s, 1H), 8.26-7.35 (m, 1H), 6.41 (s, 1H), 4.60 (s, 2H), 1.28 (s, 9H); MS (ESI) m/z: 415 (M+H$^+$).

Example CC

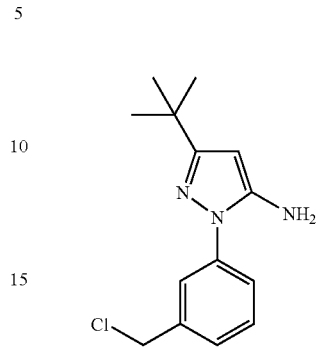

A solution of Example BB (13.8 g, 56.00 mmol) and SOCl$_2$ (8.27 mL, 0.11 mol) in THF (200 mL) was refluxed for 3 h and concentrated under reduced pressure to yield 5-t-butyl-2-(3-chloromethyl-phenyl)-2H-pyrazol-3-ylamine (14.5 g, 98%) as white powder which was used without further purification. $^1$H NMR (DMSO-d$_6$), δ 7.62 (s, 1H), 7.53 (d, J=8.0 Hz, 1H), 7.43 (t, J=8.0 Hz, 1H), 7.31 (d, J=7.2 Hz, 1H), 5.38 (s, 1H), 5.23 (br s, 2H), 4.80 (s, 2H), 1.19 (s, 9H). MS (ESI) m/z: 264 (M+H$^+$).

Example DD

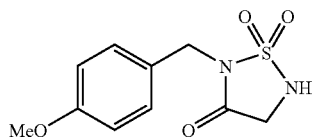

To a stirred solution of chlorosulfonyl isocyanate (1.43 g, 10.0 mmol) in CH$_2$Cl$_2$ (20 mL) at 0° C. was added 2-methyl-propan-2-ol (0.74 g, 10.0 mmol) at such a rate that the reaction solution temperature did not rise above 5° C. After being stirred for 1.5 h, a solution of glycine ethyl ester (1.45 g, 12.0 mmol) and Et$_3$N (3.2 mL, 25.0 mmol) in CH$_2$Cl$_2$ (20 mL) was added at such a rate that the reaction temperature didn't rise above 5° C. When the addition was completed, the solution was warmed to RT and stirred overnight. The reaction mixture was poured into 10% HCl and extracted with CH$_2$Cl$_2$. The organic layer was washed with saturated NaCl, dried (Mg$_2$SO$_4$) and filtered. After removal of the solvent, the crude product was washed with CH$_2$Cl$_2$ to afford ethyl 2-((N-(butyloxycarbonyl)sulfamoyl)amino)acetate (2.4 g, 85%). $^1$H-NMR (DMSO): δ 10.85 (s, 1H), 8.04 (t, J=6.0 Hz, 1H), 4.07 (q, J=5.6 Hz, 2H), 3.77 (d, J=6.0 Hz, 2H), 1.40 (s, 9H), 1.18 (t, J=7.2 Hz, 3H).

To a solution of (4-methoxyphenyl)-methanol (1.4 g, 8.5 mmol) and triphenyl-phosphane (2.6 g, 8.5 mol) in dry THF was added a solution of ethyl 2-((N-(butyloxycarbonyl)sulfamoyl)amino)acetate from the previous step (2.4 g, 8.5 mol) and DIAD (2.0 g, 8.5 mmol) in dry THF dropwise at 0° C. under N$_2$ atmosphere. The mixture was stirred at 0° C. for 2 h, warmed to RT and stirred overnight. After the solvent was removed in vacuo, the residue was purified by column chromatography to afford ethyl 2-((N-(butyloxycarbonyl)-N-(p-methoxybenzyl)sulfamoyl)amino)acetate (2.3 g, 69%) as a white solid. $^1$H-NMR (CDCl$_3$): δ 7.32 (d, J=8.8 Hz, 2H), 6.85

(d, J=8.8 Hz, 2H), 5.71 (m, 1H), 4.76 (s, 2H), 4.14 (q, J=7.2 Hz, 2H), 3.80 (s, 3H), 3.55 (d, J=5.2 Hz, 2H), 1.54 (s, 9H), 1.25 (t, J=7.2 Hz, 3H).

To a solution of HCl in methanol (2 M) was added ethyl 2-((N-(butyloxycarbonyl)-N-(p-methoxybenzyl)sulfamoyl) amino)acetate from the previous step (2.0 g, 5.0 mmol) in portions at RT and the mixture was stirred for 3 h. After the solvent was removed in vacuo, the residue was washed with diethyl ether to afford ethyl 2-((N-(p-methoxybenzyl)sulfamoyl)amino)acetate (1.0 g, 70%). $^1$H-NMR (DMSO-$d_6$): δ 7.43 (t, J=6.0 Hz, 1H), 7.287 (t, J=6.4 Hz, 1H), 7.21 (d, J=8.4 Hz, 2H), 6.86 (d, J=8.4 Hz, 2H), 3.94 (d, J=4.8 Hz, 2H), 3.71 (s, 3H), 3.64 (d, J=6.0 Hz, 2H), 3.62 (s, 3H), To a solution of ethyl 2-((N-(p-methoxybenzyl)sulfamoyl)amino)acetate from the previous step (1.0 g, 3.47 mmol) in DMF (50 mL) was added KO-t-Bu (1.56 g, 13.88 mmol) in portions under $N_2$ atmosphere at RT. The mixture was stirred overnight then quenched with HCl/methanol (2 M). After the solvent was removed in vacuo, the residue was washed with water to afford 2-(4-methoxy-benzyl)-1,1-dioxo-1$\lambda^6$-[1,2,5]thiadiazolidin-3-one (480 mg, 54%). $^1$H-NMR (CDCl$_3$): δ 7.36 (d, J=8.4 Hz, 2H), 6.87 (d, J=8.8 Hz, 2H), 4.87 (m, 1H), 4.68 (s, 2H), 4.03 (d, J=7.2 Hz, 2H), 3.80 (s, 3H).

Example EE

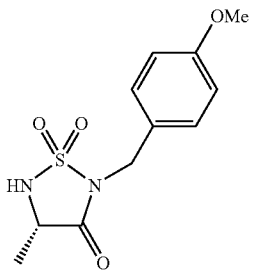

To a stirred solution of chlorosulfonyl isocyanate (1.43 g, 10.0 mmol) in CH$_2$Cl$_2$ (20 mL) at 0° C. was added benzyl alcohol (1.08 g, 10.0 mmol) at such a rate that the reaction solution temperature did not rise above 5° C. After stirring for 1.5 h, a solution of L-alanine methyl ester (1.45 g, 12.0 mmol) and Et$_3$N (3.2 mL, 25.0 mmol) in CH$_2$Cl$_2$ (20 mL) was added at such a rate that the reaction temperature didn't rise above 5° C. When the addition was completed, the reaction solution was allowed to warm up to RT and stirred overnight. The reaction mixture was poured into 10% HCl, extracted with CH$_2$Cl$_2$, the organic extracts washed with saturated NaCl, dried (Mg$_2$SO$_4$), and filtered. After removal of the solvent, the crude product was recrystallized in PE/EA (10:1) to afford the desired product (2.5 g, 79%), which was used directly in the next step. $^1$H-NMR(DMSO): δ 11.31 (s, 1H), 8.43 (d, J=8.0 Hz, 1H), 7.37-7.32 (m, 5H), 5.11 (s, 2H), 4.03 (m, 1H), 3.57 (s, 3H), 1.23 (d, J=7.2 Hz, 3H).

A mixture of material from the previous reaction (2.5 g, 12 mmol) and Pd/C (10%, 250 mg) in methanol was stirred for 4 h at 50° C. under H$_2$ atmosphere (55 psi). After the catalyst was removed by suction, the filtrate was evaporated to afford the desired compound (1.37 g, 92%) as a white solid, which was used directly in the next step. $^1$H-NMR (CDCl$_3$): δ 5.51 (d, J=5.6 Hz, 1H), 4.94 (br, 2H), 4.18 (m, 1H), 3.78 (s, 3H), 1.46 (d, J=7.2 Hz, 3H).

To a solution of 2.0 N of NaOMe in methanol (20 mL) was added a solution of compound form the previous reaction (1.2 g, 6.1 mmol) in methanol and the resulting mixture was heated to reflux overnight. After cooling down, a solution of HCl in methanol was added to acidify to pH 7. The resulted salt was filtered off and the filtrate was evaporated to dryness to afford a light yellow solid which was used directly in the next step (600 mg, 66%). $^1$H-NMR (DMSO-$d_6$): δ 6.04 (d, J=4.8 Hz, 1H), 3.60 (m, 1H), 1.11 (d, J=7.2 Hz, 3H).

A mixture of compound from the previous step (500 mg, 3.33 mmol) and 1-chloromethyl-4-methoxybenzene (156 mg, 1.0 mmol) in acetonitrile was heated to reflux overnight together with K$_2$CO$_3$ (207 mg, 1.5 mmol) and KI (250 mg, 1.5 mmol) under N$_2$ atmosphere. After cooling, the salt was filtered off and the filtrate was purified by column to afford 2-(4-methoxybenzyl)-(S)-4-methyl-1,1-dioxo-1$\lambda^6$-[1,2,5]thiadiazolidin-3-one as a white solid (200 mg), which was used without further purification.

Example 160

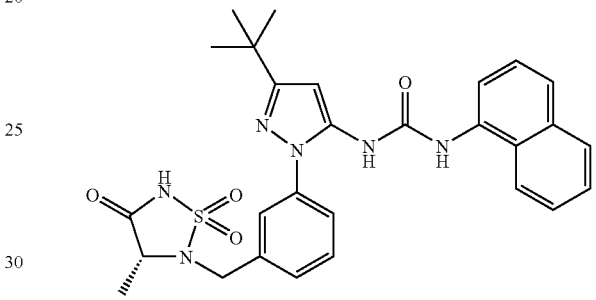

To a solution of Example EE (100 mg, 0.37 mmol) in anhydrous DMF (3 mL) was added NaH (18 mg, 0.44 mmol) at 0° C. After stirring for 0.5 h at 0° C., a solution of Example E (160 mg, 0.37 mmol) in anhydrous DMF (3 mL) was added to the reaction mixture, which was stirred overnight at RT and subsequently concentrated under reduced pressure to yield a crude solid which was used without further purification.

A solution of the crude material from the previous reaction (60 mg, 0.090 mmol) in trifluoroacetic acid (3 mL) was stirred at 50° C. for 4 h. After the solvent was removed, the residue was purified by preparative HPLC to afford 1-{5-t-butyl-2-[3-((S)-3-methyl-1,1,4-trioxo-1$\lambda^6$-[1,2,5]thiadiazolidin-2-ylmethyl)-phenyl]-2H-pyrazol-3-yl}-3-naphthalen-1-yl-urea as white powder (45 mg). $^1$H NMR (DMSO-$d_6$): 9.04 (s, 1H), 8.87 (s, 1H), 8.02 (d, J=8.0 Hz, 1H), 7.89 (d, J=7.2 Hz, 2H), 7.62 (d, J=8.0 Hz, 2H), 7.41-7.52 (m, 6H), 6.40 (s, 1H), 4.31-4.49 (dd, J=8.0 Hz, 2H), 4.03 (q, J=6.8 Hz, 1H), 1.27 (s, 9H), 1.17 (d, J=8.0 Hz, 3H). MS (ESI) m/z: 547 (M+H$^+$).

Example FF

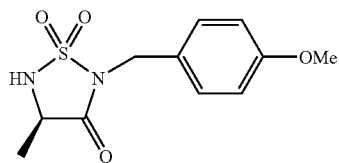

2-(4-methoxy-benzyl)-(R)-4-methyl-1,1-dioxo-1$\lambda^6$-[1,2,5]thiadiazolidin-3-one was prepared from D-alanine ethyl ester using the same procedure as Example EE.

Example 161

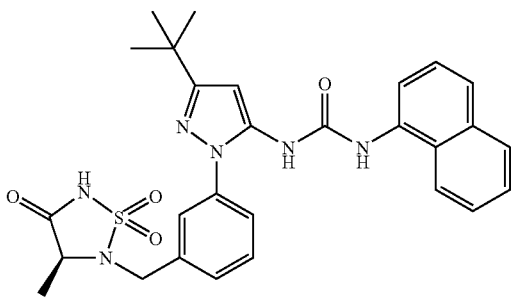

To a solution of Example FF (60 mg, 0.22 mmol) in anhydrous DMF (2 mL) was added NaH (11 mg, 0.27 mmol) at 0° C. After stirring for 0.5 h at 0° C., a solution of Example D (100 mg, 0.22 mmol) in anhydrous DMF (2 mL) was added to the reaction mixture, which was stirred overnight at RT. The crude reaction mixture was concentrated under reduced pressure and the residue by purified through preparative HPLC to yield 1-(5-t-butyl-2-{3-[5-(4-methoxy-benzyl)-(R)-3-methyl-1,1,4-trioxo-1$\lambda^6$-[1,2,5]-thiadiazolidin-2-ylmethyl]-phenyl}-2H-pyrazol-3-yl)-3-naphthalene-1-yl-urea (20 mg). $^1$H NMR (DMSO-d$_6$): 8.98 (s, 1H), 8.81 (s, 1H), 8.00 (d, J=8.0 Hz, 1H), 7.90 (d, J=7.2 Hz, 2H), 7.62 (s, 2H), 7.51-7.55 (m, 6H), 7.44 (d, J=7.6 Hz, 2H), 7.22 (d, J=8.8 Hz, 2H), 6.86 (d, J=8.8 Hz, 2H), 6.40 (s, 1H), 4.57-4.62 (dd, J=8.0 Hz, 4H), 4.53 (q, J=7.6 Hz, 1H), 3.71 (s, 3H), 1.30 (d, J=8.0 Hz, 3H), 1.27 (s, 9H). MS (ESI) m/z: 653 (M+H$^+$).

A solution of 1-(5-t-Butyl-2-{3-[5-(4-methoxy-benzyl)-(R)-3-methyl-1,1,4-trioxo-1$\lambda^6$-[1,2,5]-thiadiazolidin-2-ylmethyl]-phenyl}-2H-pyrazol-3-yl)-3-naphthalen-1-yl-urea (20 mg, 0.030 mmol) in trifluoroacetic acid (2 mL) was stirred at 50° C. for 4 h. After the solvent was removed, the residue was purified by preparative-HPLC to afford 1-{5-t-butyl-2-[3-((R)-3-methyl-1,1,4-trioxo-1$\lambda^6$-[1,2,5]thiadiazolidin-2-ylmethyl)-phenyl]-2H-pyrazol-3-yl}-3-naphthalen-1-yl-urea as a white powder (6 mg). $^1$H NMR (DMSO-d$_6$): 8.99 (s, 1H), 8.80 (s, 1H), 8.00 (d, J=7.2 Hz, 1H), 7.90 (d, J=7.2 Hz, 2H), 7.60-7.64 (m, 2H), 7.44-7.54 (m, 7H), 6.41 (s, 1H), 4.31-4.49 (dd, J=8.0 Hz, 2H), 4.03 (q, J=7.6 Hz, 1H), 1.27 (s, 9H), 1.19 (d, J=8.0 Hz, 3H). MS (ESI) m/z: 533 (M+H$^+$).

Example 162

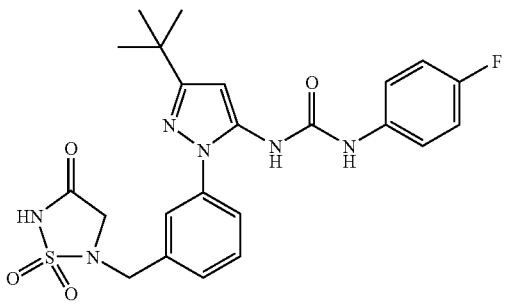

To a solution of Example CC (0.263 g, 1.0 mmol) in THF (2.0 mL) was added a solution of 1-fluoro-4-isocyanato-benzene (0.114 mL, 1.10 mmol) in THF (5.0 mL) at 0° C. The mixture was stirred at RT for 1 h then heated until all solids were dissolved. The mixture was stirred at RT for 3 h and poured into water (20 mL). The resulting precipitate was filtered, washed with diluted HCl and H$_2$O, dried under reduced pressure to yield 1-[5-t-butyl-2-(3-chloromethyl-phenyl)-2H-pyrazol-3-yl]-3-(4-fluoro-phenyl)-urea (400 mg) as a white powder. $^1$H NMR (DMSO-d$_6$): 8.99 (s, 1H), 8.38 (s, 1H), 7.59 (s, 1H), 7.44-7.51 (m, 3H), 7.38-7.40 (m, 2H), 7.08 (t, J=8.8 Hz, 2H), 6.34 (s, 1H), 4.83 (s, 2H), 1.26 (s, 9H). MS (ESI) m/z: 401 (M+H$^+$).

To a solution of 2-(4-methoxy-benzyl)-1,1-dioxo-1$\lambda^6$-[1,2,5]thiadiazolidin-3-one (64 mg, 0.25 mmol) in anhydrous DMF (2 mL) was added NaH (11 mg, 0.27 mmol) at 0° C. After stirred for 0.5 h at 0° C., a solution of 1-[5-t-butyl-2-(3-chloromethyl-phenyl)-2H-pyrazol-3-yl]-3-(4-fluoro-phenyl)-urea from the previous reaction (100 mg, 0.25 mmol) in anhydrous DMF (2 mL) was added to the reaction mixture, then was stirred overnight at RT. The crude was purified through prepared-HPLC to yield 1-(5-t-butyl-2-{3-[5-(4-methoxy-benzyl)-1,1,4-trioxo-1$\lambda^6$-[1,2,5]thiadiazolidin-2-ylmethyl]-phenyl}-2H-pyrazol-3-yl)-3-(4-fluoro-phenyl)-urea (45 mg). $^1$H NMR (DMSO-d$_6$): 8.95 (s, 1H), 8.37 (s, 1H), 7.50-7.54 (m, 3H), 7.36-7.41 (m, 3H), 7.25 (d, J=8.8 Hz, 2H), 7.07 (t, J=8.8 Hz, 2H), 6.87 (d, J=8.4 Hz, 2H), 6.35 (s, 1H), 4.64 (s, 2H), 4.47 (s, 2H), 4.19 (s, 2H), 3.75 (s, 3H), 1.26 (s, 9H). MS (ESI) m/z: 515 (M+H$^+$).

A solution of 1-(5-t-butyl-2-{3-[5-(4-methoxy-benzyl)-1,1,4-trioxo-1$\lambda^6$-[1,2,5]thiadia-zolidin-2-ylmethyl]-phenyl}-2H-pyrazol-3-yl)-3-(4-fluoro-phenyl)-urea (40 mg, 0.060 mmol) in trifluoroacetic acid (3 mL) was stirred at 50° C. for 4 h. After the solvent was removed, the residue was purified by preparative HPLC to afford 1-{5-t-butyl-2-[3-(3-(R)-methyl-1,1,4-trioxo-1$\lambda^6$-[1,2,5]thiadiazolidin-2-ylmethyl)-phenyl]-2H-pyrazol-3-yl}-3-naphthalen-1-yl-urea as a white powder (12 mg). $^1$H NMR (DMSO-d$_6$): 8.98 (s, 1H), 8.39 (s, 1H), 7.37-7.51 (m, 6H), 7.07 (t, J=8.8 Hz, 2H), 6.35 (s, 1H), 4.21 (s, 2H), 3.88 (s, 2H), 1.26 (s, 9H). MS (ESI) m/z: 501 (M+H$^+$).

Example GG

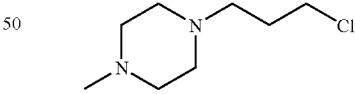

To a stirred suspension of K$_2$CO$_3$ (5.5 g, 40 mmol) and 1-bromo-3-chloro-propane (3.78 g, 24 mmol) in acetonitrile (10mL) was added a solution of N-methyl piperazine (2.0 g, 20 mmol) in acetonitrile (10 mL) dropwise at RT. After the addition was completed, the reaction mixture was stirred for 3 h then filtered. The filtrate was concentrated and dissolved in CH$_2$Cl$_2$, washed with brine, dried (NaSO$_4$) and filtered. After removal of the solvent, the residue was dissolved in ether. To the above solution was added the solution of HCl and filtered to afford the desired product (2.3 g, 65.7%). $^1$H NMR (D$_2$O): 3.61 (t, J=6.0 Hz, 2H), 3.59 (br, 8H), 3.31 (t, J=8.0 Hz, 2H), 2.92 (s, 3H), 2.15 (m, 2H).

Example 163

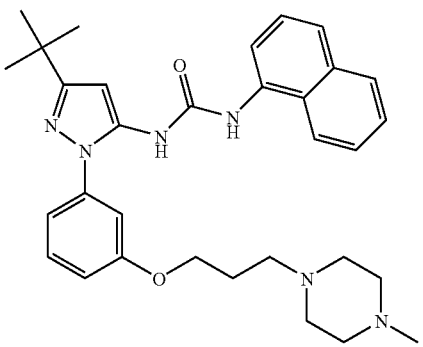

To a solution of Example 41 (100 mg, 0.25 mmol) in acetonitrile (10 mL) was added Example GG (75 mg, 0.30 mmol) and K$_2$CO$_3$ (172 mg, 1.25 mmol). The resulting mixture was stirred at 45° C. for 3 h before filtered. After the filtrate was concentrated, the residue was purified by preparative TLC to afford 1-(5-t-Butyl-2-{3-[3-(4-methyl-piperazin-1-yl)-propoxy]-phenyl}-2H-pyrazol-3-yl)-3-naphthalen-1-yl-urea (31 mg, 23%). $^1$H-NMR (CD$_3$OD): 7.93 (m, 1H), 7.88 (m, 1H), 7.71 (d, J=8.4 Hz, 1H), 7.66 (d, J=7.6 Hz, 1H), 7.43-7.50 (m, 4H), 7.14 (m, 2H), 7.05 (m, 1H), 6.43 (s, 1H), 4.10 (t, J=6.0 Hz, 2H), 3.09-3.15 (br, 4H), 2.74-2.86 (br, 6H), 2.72 (s, 3H), 1.99 (t, J=6.8 Hz, 2H), 1.35 (s, 9H). MS (ESI) m/z: 541 (M+H$^+$).

Example HH

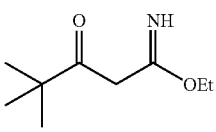

Intermediate HH was synthesized according to literature procedures starting from 4,4-dimethyl-3-oxo-pentanenitrile (10 mmole) in absolute ethanol and HCl in quantitative afford.

Example II

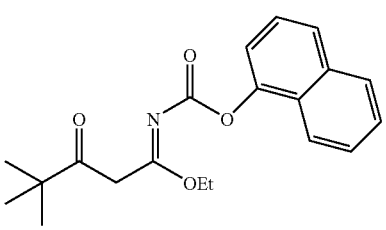

Intermediate HH (5 g, 0.0241 mol) is added to pyridine (5 mL) in CH$_2$Cl$_2$ (25 mL) and cooled in an ice bath. The suspension is stirred for 5 min and 1-napthylchloroformate is added dropwise over 5 min. The reaction mixture is stirred an additional 5 min at 0° C., and the reaction is warmed and stirred at RT for 1 h. The reaction is pour into ethyl acetate (100 mL) and water (100 ml). After shaking, the aqueous layer is removed, the organic layer washed with water, dried (MgSO$_4$) and concentrated to afford (Z)-naphthalen-1-yl 1-ethoxy-4,4-dimethyl-3-oxopentylidenecarbamate.

Example 164

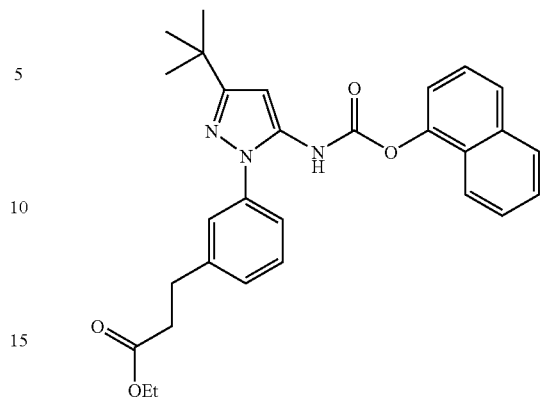

Example II (10 mmol) is dissolved in absolute EtOH (50 mL) at RT and Example Y (10.5 mmol) is added dropwise over 5 min. The reaction mixture is stirred for 30 min at RT, poured in water (100 mL) and ethyl acetate (100 mL). After shaking, the organic layer is washed with 5% HCl, water, dried (MgSO$_4$) and concentrated to afford 1-naphthyl 1-(3-(2-(ethoxycarbonyl)ethyl)phenyl)-3-t-butyl-1H-pyrazol-5-ylcarbamate.

Example 165

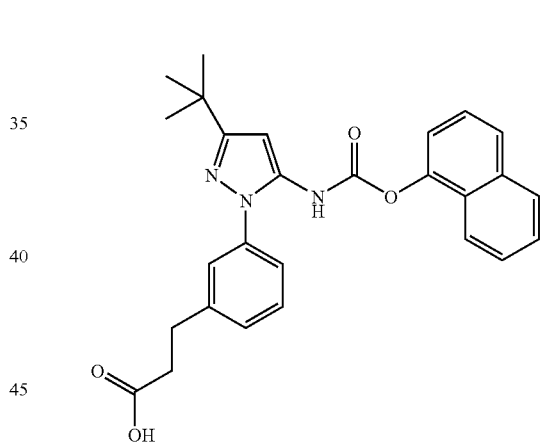

A solution of Example 164 (0.1 mmol) and 2N LiOH (3 mL) in MeOH (3 mL) is stirred at RT overnight. The reaction mixture is neutralized to pH=4, extracted with ethyl acetate (3×20 mL), the combined organic extracts are washed with brine, dried (NaSO$_4$) and filtered. The filtrate is concentrated to afford 1-napthyl 1-(3-(2-carboxyethylphenyl)-3-t-butyl-1H-pyrazol-5-ylcarbamate.

Example JJ

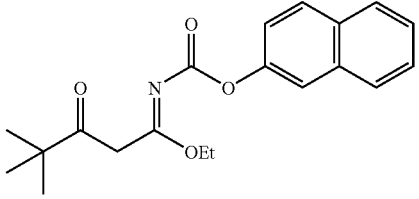

Example JJ is synthesized utilizing Example HH and 2-napthylchloroformate according to the procedure described for Example II to afford (Z)-naphthalen-2-yl-1-ethoxy-4,4-dimethyl-3-oxopentylidenecarbamate.

Example 166

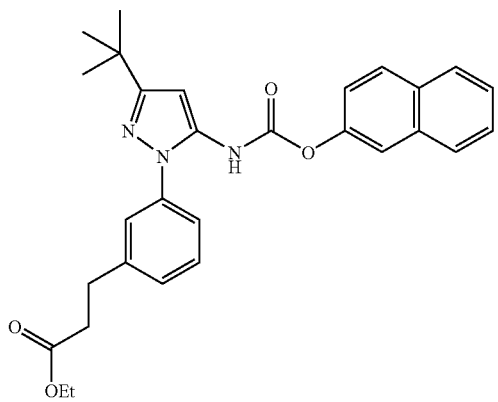

Example 166 is synthesized utilizing Example Y and Example JJ according to the procedure described for Example 79 to afford 2-naphthyl 1-(3-(2-(ethoxycarbonyl)ethyl)phenyl)-3-t-butyl-1H-pyrazol-5-ylcarbamate.

Example 167

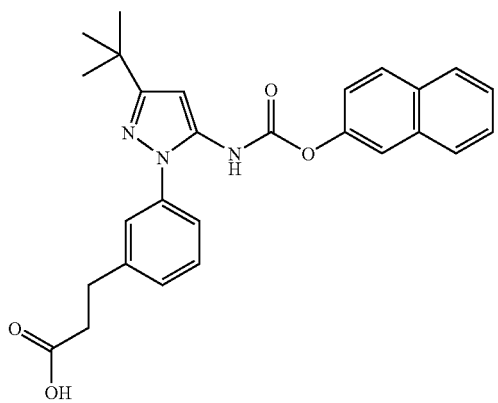

Example 167 is synthesized utilizing Example 166 according to the procedure described for Example 165 to afford 2-napthyl 1-(3-(2-carboxyethylphenyl)-3-t-butyl-1H-pyrazol-5-ylcarbamate.

Example KK

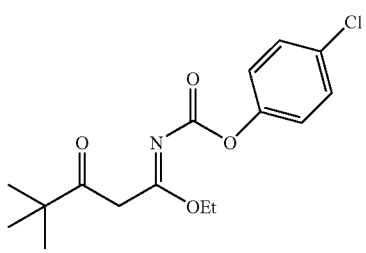

Example KK is synthesized utilizing Example HH and p-chlorophenylchloroformate according to the procedure described for Example II to afford (Z)-4-chlorophenyl 1-ethoxy-4,4-dimethyl-3-oxopentylidenecarbamate.

Example 168

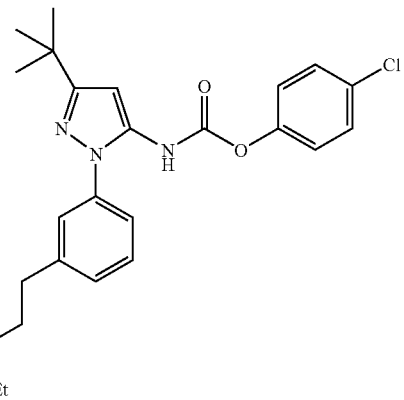

Example 168 is synthesized utilizing Example Y and Example KK according to the procedure described for Example 164 to afford 4-chlorophenyl 1-(3-(2-(ethoxycarbonyl)ethyl)phenyl)-3-t-butyl-1H-pyrazol-5-ylcarbamate.

Example 169

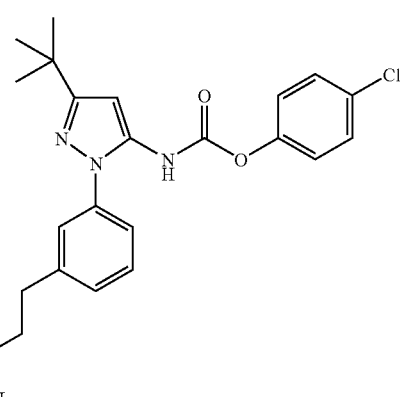

Example 169 is synthesized utilizing Example 168 according to the procedure described for Example 165 to afford 4-chlorophenyl 1-(3-(2-carboxyethylphenyl)-3-t-butyl-1H-pyrazol-5-ylcarbamate.

Example LL

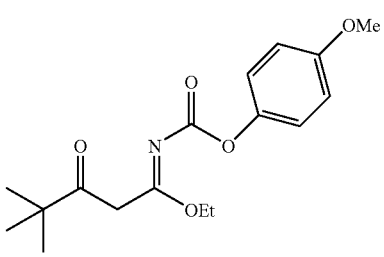

Example LL is synthesized utilizing Example HH and p-methoxyphenylchloroformate according to the procedure described for Example II to afford (Z)-4-methoxyphenyl 1-ethoxy-4,4-dimethyl-3-oxopentylidenecarbamate.

Example 170

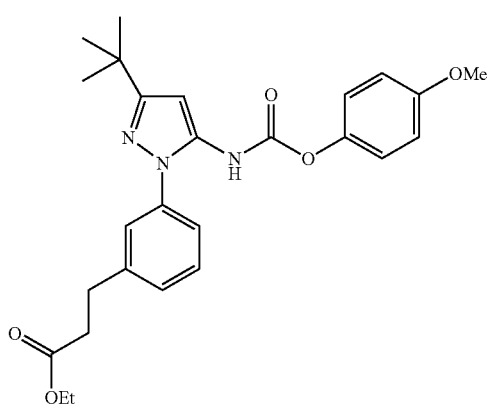

Example 170 is synthesized utilizing Example Y and Example LL according to the procedure described for Example 164 to afford 4-methoxyphenyl 1-(3-(2-(ethoxycarbonyl)ethyl)phenyl)-3-t-butyl-1H-pyrazol-5-ylcarbamate.

Example 171

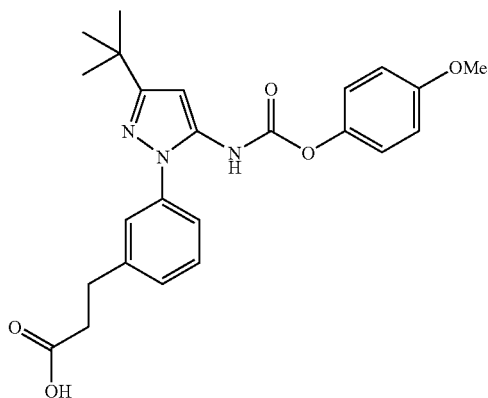

Example 171 is synthesized utilizing Example 170 according to the procedure described for Example 165 to afford 4-methoxyphenyl 1-(3-(2-carboxyethylphenyl)-3-t-butyl-1H-pyrazol-5-ylcarbamate.

Example MM

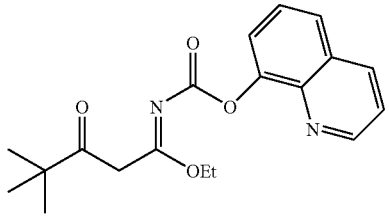

Example MM is synthesized utilizing Example HH and quinolin-8-yl-chloroformate according to the procedure described for Example II to afford (Z)-quinolin-8-yl 1-ethoxy-4,4-dimethyl-3-oxopentylidenecarbamate

Example 172

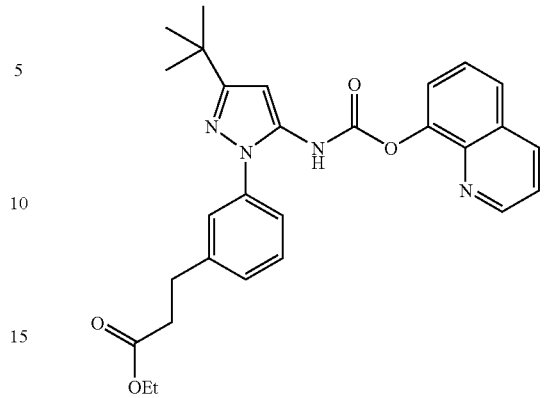

Example 172 is synthesized utilizing Example Y and Example MM according to the procedure described for Example 164 to afford quinolin-8-yl 1-(3-(2-(ethoxycarbonyl)ethyl)phenyl)-3-t-butyl-1H-pyrazol-5-ylcarbamate.

Example 173

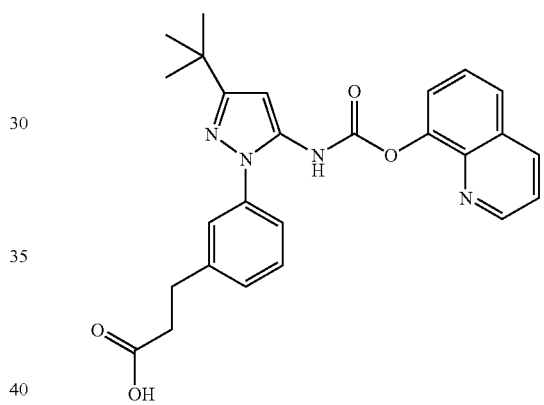

Example 173 is synthesized utilizing Example 172 according to the procedure described for Example 165 to afford quinolin-8-yl 1-(3-(2-carboxyethylphenyl)-3-t-butyl-1H-pyrazol-5-ylcarbamate.

Example 174

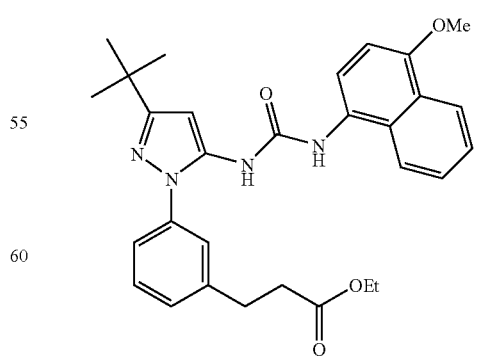

Example 174 is synthesized utilizing a mixture of 4-methoxy-1-naphthylamine and Example Z according to the procedure described for Example 147 to afford 3-(3-{3-t-butyl-5-[3-(4-methoxy-1-naphthyl)-ureido]-pyrazol-1-yl}-phenyl)-propionic acid ethyl ester.

Example 175

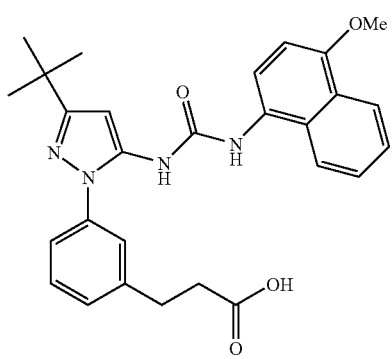

Utilizing the same synthetic procedure as for Example 146 and starting with Example 174, 3-(3-{3-t-butyl-5-[3-(4-methoxy-1-naphthyl)-ureido]-pyrazol-1-yl}-phenyl)-propionic acid is synthesized.

Example 176

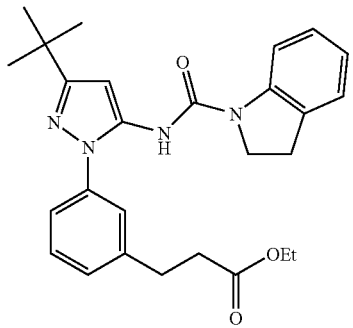

Example 176 is synthesized utilizing a mixture of indoline and Example Z according to the procedure described for Example 147 to afford ethyl 3-(3-(3-t-butyl-5-(indoline-1-carboxamido)-1H-pyrazol-1-yl)phenyl)propanoate.

Example 177

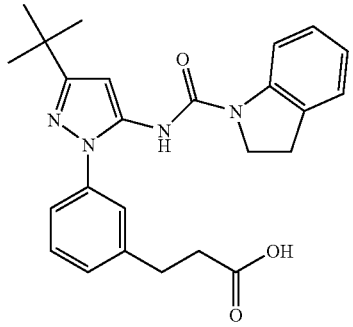

Utilizing the same synthetic procedure as for Example 146 and starting with Example 173, 3-(3-(3-t-butyl-5-(indoline-1-carboxamido)-1H-pyrazol-1-yl)phenyl)propionic acid is synthesized.

Example NN

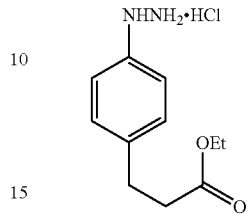

Utilizing the same synthetic procedure as for Example Y and starting with p-bromo nitrobenzene, 3-(4-hydrazino-phenyl)-propionic acid ethyl ester is synthesized.

Example 178

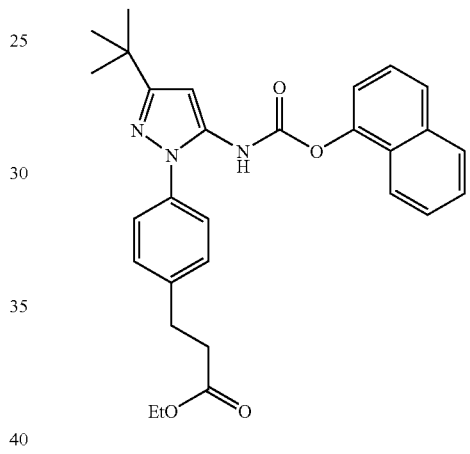

Utilizing the same synthetic procedure as for Example 164, Example II (10 mmol) and Example NN (10.5 mmol) are combined to afford 1-naphthyl 1-(4-(2-(ethoxycarbonyl)ethyl)phenyl)-3-t-butyl-1H-pyrazol-5-ylcarbamate.

Example 179

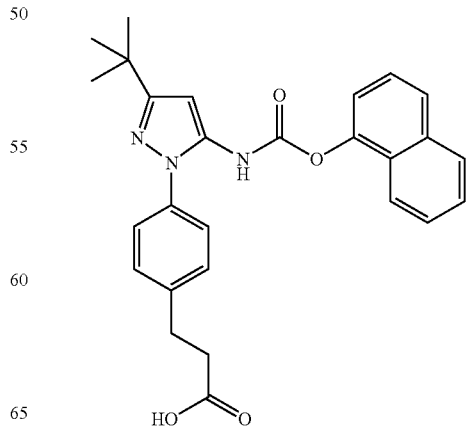

Example 179 is synthesized utilizing Example 178 according to the procedure described for Example 165 to afford 1-napthyl 1-(4-(2-carboxyethylphenyl)-3-t-butyl-1H-pyrazol-5-ylcarbamate.

Example 181 is synthesized utilizing Example 180 according to the procedure described for Example 165 to afford 2-napthyl 1-(4-(2-carboxyethylphenyl)-3-t-butyl-1H-pyrazol-5-ylcarbamate.

Example 180

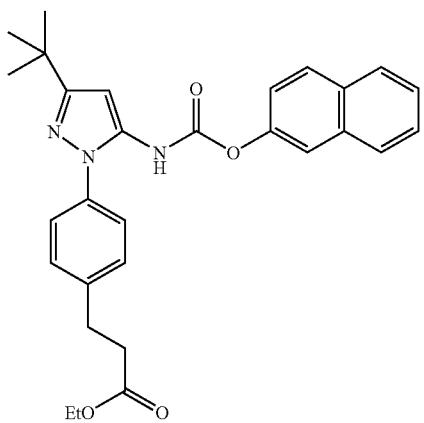

Example 182

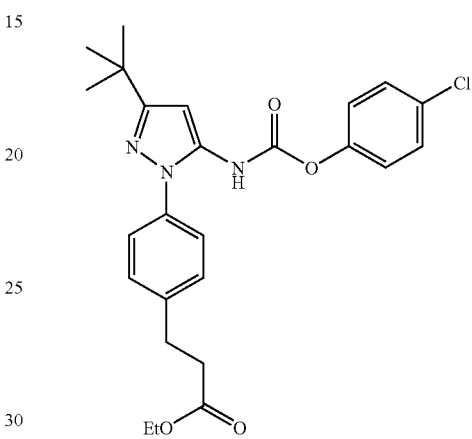

Utilizing the same synthetic procedure as for Example 164, Example JJ (10 mmol) and Example NN (10.5 mmol) are combined to afford 2-naphthyl 1-(4-(2-(ethoxycarbonyl)ethyl)phenyl)-3-t-butyl-1H-pyrazol-5-ylcarbamate.

Utilizing the same synthetic procedure as for Example 164, Example KK (10 mmol) and Example NN (10.5 mmol) are combined to afford p-chlorophenyl 1-(4-(2-(ethoxycarbonyl)ethyl)phenyl)-3-t-butyl-1H-pyrazol-5-ylcarbamate.

Example 181

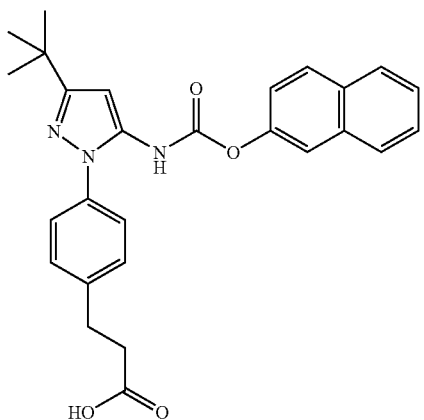

Example 183

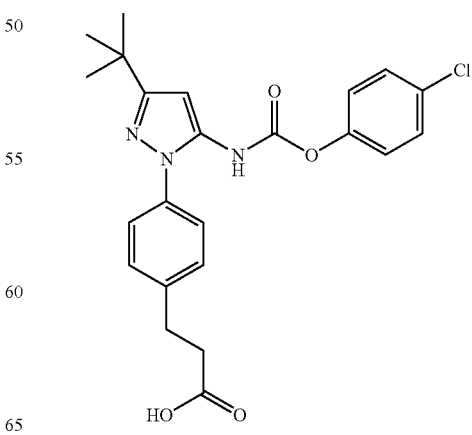

Example 183 is synthesized utilizing Example 182 according to the procedure described for Example 165 to afford 4-chlorophenyl 1-(4-(2-carboxyethylphenyl)-3-t-butyl-1H-pyrazol-5-ylcarbamate.

Example 184

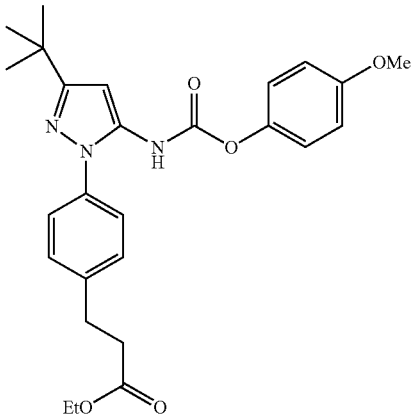

Utilizing the same synthetic procedure as for Example 164, Example LL (10 mmol) and Example NN (10.5 mmol) are combined to afford p-methoxyphenyl 1-(4-(2-(ethoxycarbonyl)ethyl)phenyl)-3-t-butyl-1H-pyrazol-5-ylcarbamate.

Example 185

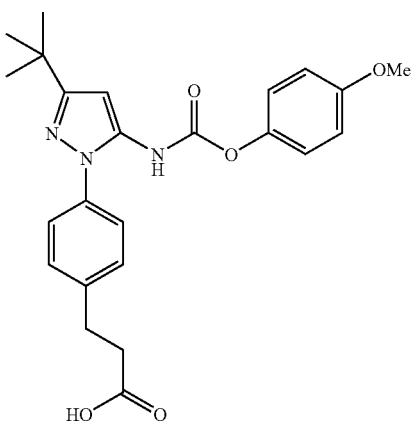

Example 185 is synthesized utilizing Example 184 according to the procedure described for Example 165 to afford p-methoxyphenyl 1-(4-(2-carboxyethylphenyl)-3-t-butyl-1H-pyrazol-5-ylcarbamate.

Example OO

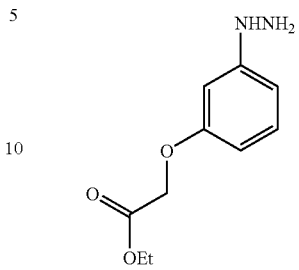

Ethyl bromoacetate is reacted with meta-nitrophenol under standard conditions to afford ethyl 2-(3-nitrophenoxy)acetate, which is elaborated to ethyl 2-(3-hydrazinophenoxy)acetate using the reduction/oxidation sequence described for Example Y.

Example PP

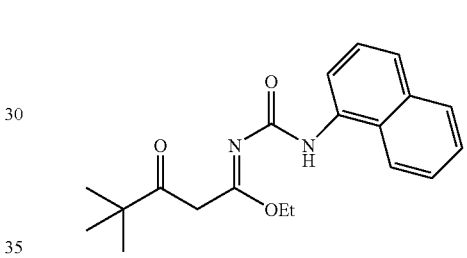

Example HH and 1-naphthylisocyanate are combined utilizing the same synthetic procedure as for Example II to afford (Z)-1-(1-ethoxy-4,4-dimethyl-3-oxopentylidene)-3-(naphthalen-1-yl)urea.

Example 186

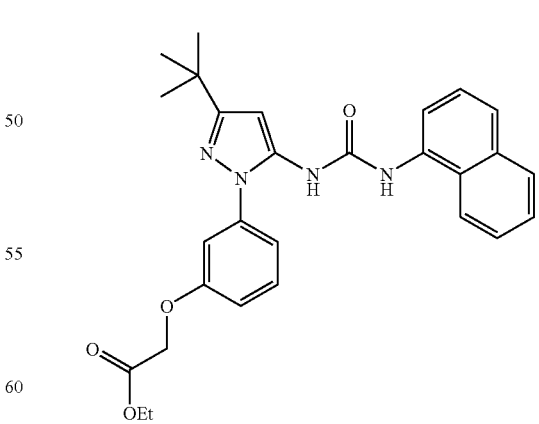

Utilizing the same synthetic procedure as for Example 164, Example PP (10 mmol) and Example OO (10.5 mmol) are combined to afford 3-(3-{3-t-butyl-5-[3-(1-naphthyl)-ureido]-pyrazol-1-yl}-phenoxy)-acetic acid ethyl ester.

Example 187

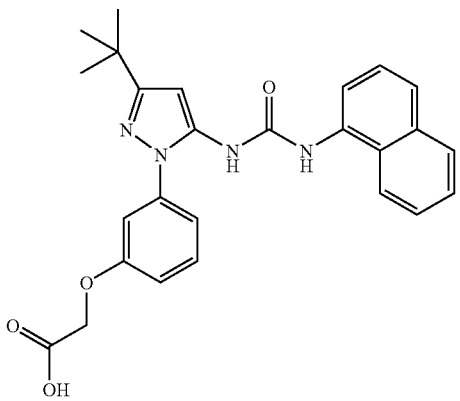

Utilizing the same synthetic procedure as for Example 146 and starting with Example 186, 3-(3-{3-t-butyl-5-[3-(1-naphthyl)-ureido]-pyrazol-1-yl}-phenoxy)-acetic acid is synthesized.

Example QQ

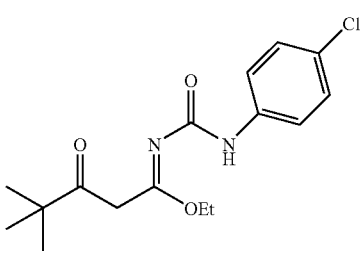

Example HH and 4-chlorophenylisocyanate are combined utilizing the same synthetic procedure as for Example II to afford (Z)-1-(4-chlorophenyl)-3-(1-ethoxy-4,4-dimethyl-3-oxopentylidene)urea

Example 188

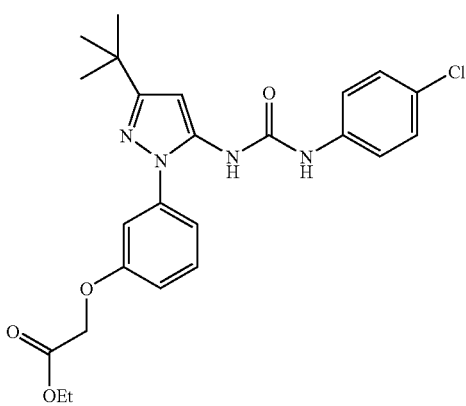

Utilizing the same synthetic procedure as for Example 164, Example QQ (10 mmol) and Example OO (10.5 mmol) are combined to afford 3-(3-{3-t-butyl-5-[3-(1-4-chlorophenyl)-ureido]-pyrazol-1-yl}-phenoxy)-acetic acid ethyl ester.

Example 189

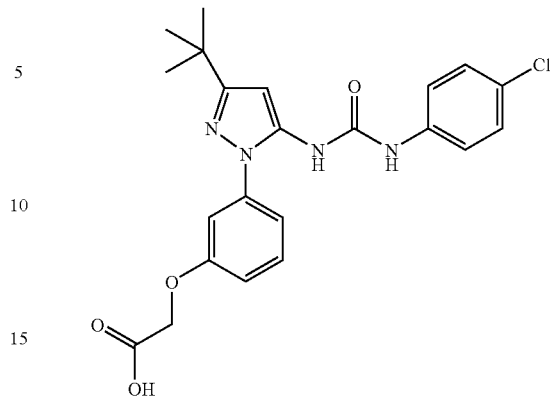

Utilizing the same synthetic procedure as for Example 146 and starting with Example 188, 3-(3-{3-t-butyl-5-[3-(14-chlorophenyl)-ureido]-pyrazol-1-yl}-phenoxy)-acetic acid is synthesized.

Example RR

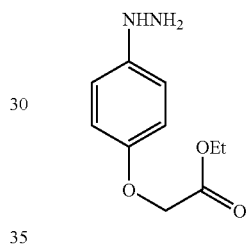

Ethyl bromoacetate is reacted with para-nitrophenol under standard conditions to afford ethyl 2-(4-nitrophenoxy)acetate, which is elaborated to ethyl 2-(4-hydrazinophenoxy)acetate using the reduction/oxidation sequence described for Example Y.

Example 190

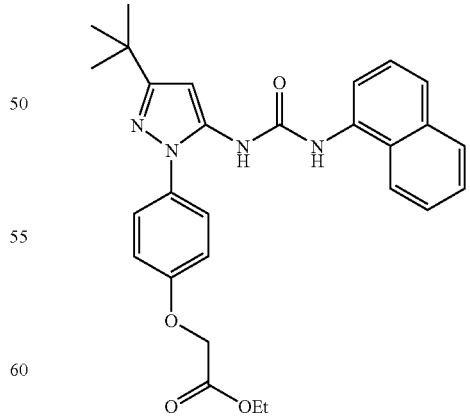

Utilizing the same synthetic procedure as for Example 164, Example PP (10 mmol) and Example RR (10.5 mmol) are combined to afford 4-(3-{3-t-butyl-5-[3-(1-naphthyl)-ureido]-pyrazol-1-yl}-phenoxy)-acetic acid ethyl ester.

Example 191

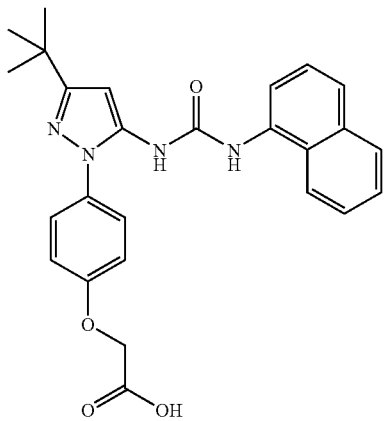

Utilizing the same synthetic procedure as for Example 146 and starting with Example 190, 4-(3-{3-t-butyl-5-[3-(1-naphthyl)-ureido]-pyrazol-1-yl}-phenoxy)-acetic acid is synthesized.

Example 192

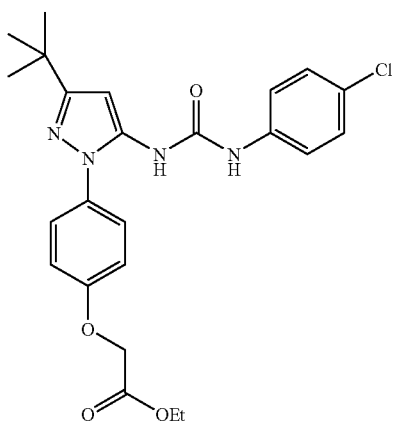

Utilizing the same synthetic procedure as for Example 164, Example QQ (10 mmol) and Example RR (10.5 mmol) are combined to afford 4-(3-{3-t-butyl-5-[3-(1-4-chlorophenyl)-ureido]-pyrazol-1-yl}-phenoxy)-acetic acid ethyl ester.

Example 193

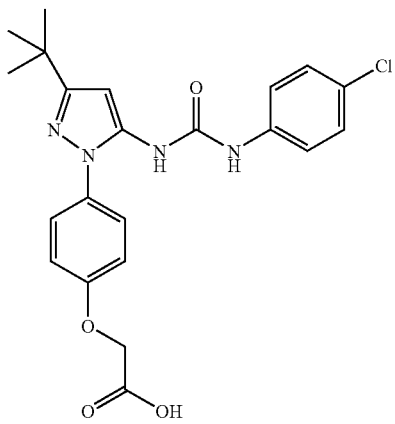

Utilizing the same synthetic procedure as for Example 146 and starting with Example 192, 4-(3-{3-t-butyl-5-[3-(14-chlorophenyl)-ureido]-pyrazol-1-yl}-phenoxy)-acetic acid is synthesized.

Example DD

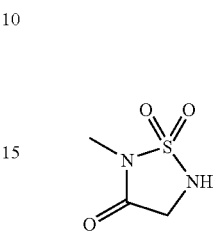

To a stirred solution of chlorosulfonyl isocyanate (1.43 g, 10.0 mmol) in $CH_2Cl_2$ (20 mL) at 0° C. was added 2-methyl-propan-2-ol (0.74 g, 10.0 mmol) at such a rate that the reaction solution temperature did not rise above 5° C. After being stirred for 1.5 h, a solution of glycine ethyl ester (1.45 g, 12.0 mmol) and $Et_3N$ (3.2 mL, 25.0 mmol) in $CH_2Cl_2$ (20 mL) was added at such a rate that the reaction temperature didn't rise above 5° C. When the addition was completed, the solution was warmed to RT and stirred overnight. The reaction mixture was poured into 10% HCl and extracted with $CH_2Cl_2$. The organic layer was washed with saturated NaCl, dried ($Mg_2SO_4$) and filtered. After removal of the solvent, the crude product was washed with $CH_2Cl_2$ to afford ethyl 2-((N-(butyloxycarbonyl)sulfamoyl)amino)acetate (2.4 g, 85%). $^1$H-NMR (DMSO): δ 10.85 (s, 1H), 8.04 (t, J=6.0 Hz, 1H), 4.07 (q, J=5.6 Hz, 2H), 3.77 (d, J=6.0 Hz, 2H), 1.40 (s, 9H), 1.18 (t, J=7.2 Hz, 3H).

To a solution of methanol (8.5 mmol) and triphenylphosphine (2.6 g, 8.5 mol) in dry THF is added a solution of ethyl 2-((N-(butyloxycarbonyl)sulfamoyl)amino)acetate from the previous step (2.4 g, 8.5 mol) and DIAD (2.0 g, 8.5 mmol) in dry THF dropwise at 0° C. under $N_2$ atmosphere. The mixture is stirred at 0° C. for 2 h, warmed to RT and is stirred overnight. After the solvent is removed in vacuo, the residue is purified by column chromatography to afford ethyl 2-((N-(butyloxycarbonyl)-N-methylsulfamoyl)amino)acetate.

To a solution of HCl in methanol (2 M) is added ethyl 2-((N-(butyloxycarbonyl)-N-methylsulfamoyl)amino)acetate from the previous step (5.0 mmol) in portions at RT and the mixture is stirred for 3 h. After the solvent is removed in vacuo, the residue is washed with diethyl ether to afford ethyl 2-((N-methylsulfamoyl)amino)acetate To a solution of ethyl 2-((N-methylsulfamoyl)amino)acetate from the previous step (3.5 mmol) in DMF (50 mL) is added KO-t-Bu (1.56 g, 13.88 mmol) in portions under $N_2$ at RT. The mixture is stirred overnight then quenched with HCl/methanol (2 M). After the solvent is removed in vacuo, the residue is washed with water to afford 2-methyl-1,1-dioxo-$1\lambda^6$-[1,2,5]thiadiazolidin-3-one (480 mg, 54%). $^1$H-NMR ($CDCl_3$): δ 7.36 (d, J=8.4 Hz, 2H), 6.87 (d, J=8.8 Hz, 2H), 4.87 (m, 1H), 4.68 (s, 2H), 4.03 (d, J=7.2 Hz, 2H), 3.80 (s, 3H).

Example 194

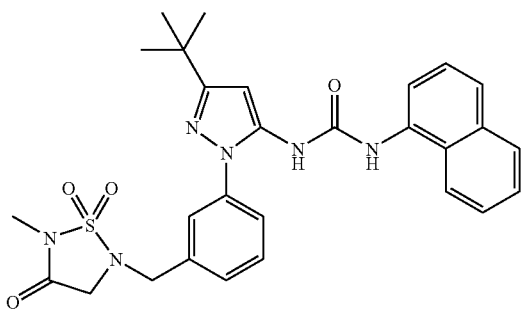

Example E and Example OO are combined utilizing the procedure for Example 160 to afford 1-(5-t-butyl-2-{3-[5-methyl-1,1,4-trioxo-1λ⁶-[1,2,5]thiadiazolidin-2-ylmethyl]-phenyl}-2H-pyrazol-3-yl)-3-naphthyl-urea.

Example 195

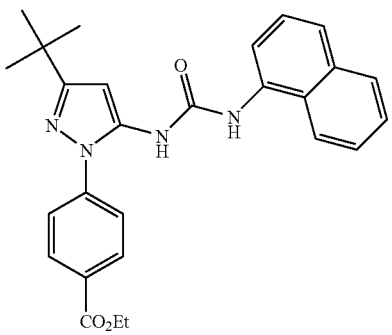

To a solution of Example X (2.9 g, 10 mmol) in THF (50 mL) was added a solution of 1-naphthyl isocyanate (1.7 g, 10 mmol) in THF (20 mL) at 0° C. The mixture was stirred at RT for 1 h and heated until all solids dissolved. The mixture was then stirred at RT for 3 h and poured into water (200 mL). The precipitate was filtered, washed with diluted HCl and H$_2$O, dried under vacuum to give 4.3 g of 4-[3-t-butyl-5-(3-naphthalen-1-yl-ureido)-pyrazol-1-yl]-benzoic acid ethyl ester, which was used without further purification.

Example 196

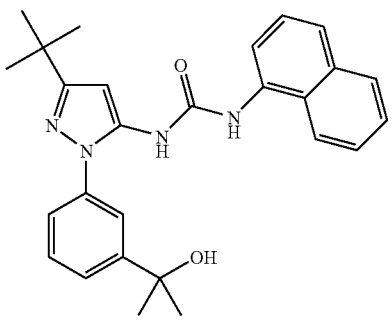

To a solution of Example B (228 mg, 0.5 mmol) in dry THF (20 mL) was added dropwise a solution of methyl magnesium bromide in toluene/THF (3.6 mL, 5.0 mmol) at −78° C. under N$_2$. After stirring for 1 h, the mixture was allowed to rise to RT and stirred for another 2 h. The reaction mixture was quenched with saturated NH$_4$Cl solution and aqueous HCl solution (10%), extracted with ethyl acetate. The combined organic extracts were washed with brine, dried (Na$_2$SO$_4$), the solvent removed in vacuo and the residue purified by column chromatography to afford 1-{5-t-butyl-2-[3-(1-hydroxy-1-methyl-ethyl)-phenyl]-2H-pyrazol-3-yl}-3-naphthalen-1-yl-urea (150 mg, 67%). $^1$H NMR (DMSO-d$_6$): 9.00 (s, 1H), 8.75 (s, 1H), 7.98 (d, J=7.6 Hz, 1H), 7.92-7.89 (m, 2H), 7.65-7.62 (m, 2H), 7.52-7.44 (m, 5H), 7.37 (d, J=6.8 Hz, 1H), 6.39 (s, 1H), 5.13 (s, 1H), 1.45 (s, 6H), 1.27 (s, 9H); MS (ESI) m/z: 443 (M+H$^+$).

Example 197

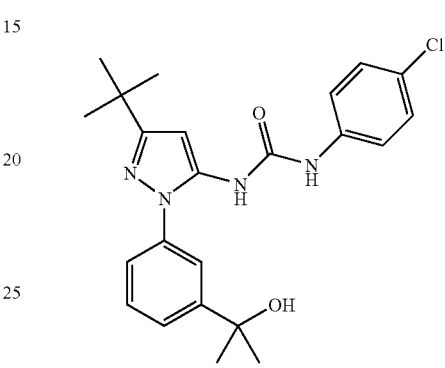

To a solution of Example C (220 mg, 0.5 mmol) in dry THF (20 mL) was added dropwise a solution of methyl magnesium bromide in toluene/THF (3.6 mL, 5.0 mmol) at −78° C. under N$_2$. After stirring for 1 h, the mixture was allowed to rise to RT and stirred for another 2 h. The reaction mixture was quenched with saturated NH$_4$Cl and aqueous HCl solution (10%), and extracted with ethyl acetate. The combined organic extracts were washed with brine, dried (Na$_2$SO$_4$), the solvent was removed in vacuo and the residue was purified by column chromatography to afford 1-{5-t-butyl-2-[3-(1-hydroxy-1-methyl-ethyl)-phenyl]-2H-pyrazol-3-yl}-3-(4-chloro-phenyl)-urea (174 mg, 81%). $^1$H NMR (DMSO-d$_6$): 9.11 (s, 1H), 8.34 (s, 1H), 7.59 (s, 1H), 7.46 (t, J=8.8 Hz, 1H), 7.43-7.40 (m, 3H), 7.31-7.28 (m, 3H), 6.34 (s, 1H), 5.13 (s, 1H), 1.42 (s, 6H), 1.27 (s, 9H); MS (ESI) m/z: 428 (M+H$^+$).

Example 198

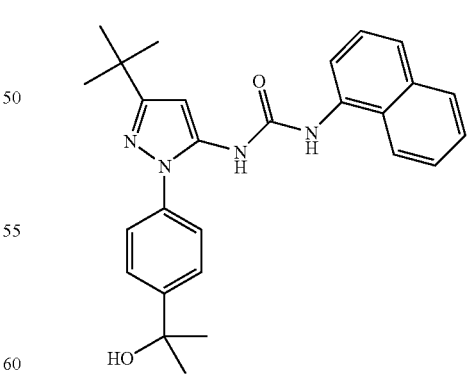

To a solution of Example 195 (228 mg, 0.5 mmol) in dry THF (20 mL) was added dropwise a solution of methylmagnesium bromide in toluene/THF (3.6 mL, 5.0 mmol) at −78° C. under N$_2$. After stirring for 1 h, the mixture was allowed to rise to RT and stirred for another 2 h. The reaction mixture was quenched with saturated NH₄Cl and aqueous HCl solution (10%), extracted with ethyl acetate. The combined organic extracts were washed with brine, dried (Na₂SO₄), the solvent was removed in vacuo and the residue purified by column chromatography to afford 1-{5-t-butyl-2-[4-(1-hydroxy-1-methyl-ethyl)-phenyl]-2H-pyrazol-3-yl}-3-naphthalen-1-yl-urea (180 mg, 81%). ¹H NMR (DMSO-$d_6$): 9.06 (s, 1H), 8.83 (s, 1H), 7.99 (d, J=8.0 Hz, 1H), 7.92 (t, J=8.0 Hz, 2H), 7.64-7.61 (m, 3H), 7.55-7.43 (m, 5H), 6.40 (s, 1H), 5.13 (s, 1H), 1.47 (s, 6H), 1.27 (s, 9H); MS (ESI) m/z: 443 (M+H⁺).

Example 199

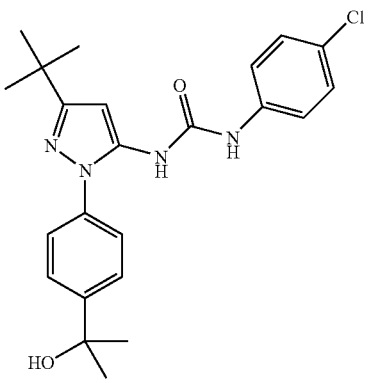

To a solution of Example 57 (220 mg, 0.5 mmol) in dry THF (20 mL) was added dropwise a solution of methyl magnesium bromide in toluene/THF (3.6 mL, 5.0 mmol) at −78° C. under N₂. After stirring for 1 h, the mixture was allowed to rise to RT and stirred for another 2 h. The reaction mixture was quenched with saturated NH₄Cl and aqueous HCl solution (10%), and extracted with ethyl acetate. The combined organic extracts were washed with brine, dried (Na₂SO₄), the solvent removed in vacuo and the residue was purified by column chromatography to afford 1-{5-t-butyl-2-[4-(1-hydroxy-1-methyl-ethyl)-phenyl]-2H-pyrazol-3-yl}-3-(4-chloro-phenyl)-urea (187 mg, 87%). ¹H-NMR (CDCl₃): 9.14 (s, 1H), 8.42 (s, 1H), 7.58 (d, J=8.4 Hz, 2H), 7.42 (d, J=5.6 Hz, 2H), 7.40 (d, J=4.8 Hz, 2H), 7.29 (d, J=8.8 Hz, H), 6.34 (s, 1H), 5.11 (s, 1H), 1.44 (s, 6H), 1.25 (s, 9H); MS (ESI) m/z: 427 (M+H⁺).

Example PP

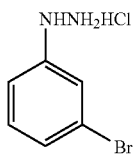

To a solution of 3-bromo-phenylamine (17 g, 0.1 mol) in concentrated HCl (200 mL) was added an aqueous solution (20 mL) of NaNO₂ (7 g, 0.1 mol) at 0° C. and the resulting mixture was stirred for 1 h. A solution of SnCl₂.2H₂O (45 g, 0.2 mmol) in concentrated HCl (500 mL) was then added at 0° C. The reaction solution was stirred for an additional 2 h at RT. The precipitate was filtered and washed with ethanol and ether to give (3-bromo-phenyl)-hydrazine as a white solid, which was used for the next reaction without further purification Example QQ

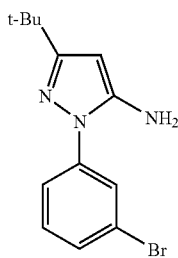

A mixture of Example PP (22.2 g, 0.1 mol) and 4,4-dimethyl-3-oxo-pentanenitrile (18.7 g, 0.15 mol) in ethanol (250 mL) was heated to reflux overnight. The reaction solution was concentrated under reduced pressure, and the residue purified by column chromatography to afford 2-(3-bromo-phenyl)-5-t-butyl-2H-pyrazol-3-ylamine as a white solid. ¹H NMR (DMSO-$d_6$): 7.85 (s, 1H), 7.68 (d, J=7.6 Hz, 1H), 7.62 (d, J=7.2 Hz, 1H), 7.50 (t, J=8.0 Hz, 1H), 5.62 (s, 1H), 1.27 (s, 9H).

Example RR

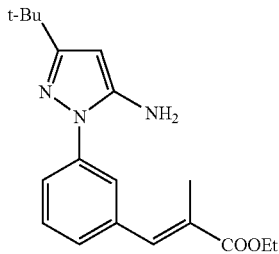

To a mixture of Example QQ (2.94 g, 10 mmol), Pd(OAc)₂ (1 mmol), PPh₃ (20 mmol), and K₂CO₃ (20 mmol) in MeCN (50 mL) was added 2-methyl-acrylic acid ethyl ester (20 mmol). The resulting mixture was heated to reflux overnight, filtered, concentrated, and the residue was purified by column chromatography to afford 1.2 g of 3-[3-(5-Amino-3-t-butyl-pyrazol-1-yl)-phenyl]-2-methyl-acrylic acid ethyl ester. ¹H NMR (CDCl₃): 7.41 (s, 1H), 7.40-7.36 (m, 2H), 7.15 (d, J=6.8 Hz, 1H), 6.24 (s, 1H), 5.51 (s, 1H), 4.27 (q, J=7.2 Hz, 2H), 2.12 (s, 3H), 1.33 (s, 9H), 1.27 (t, J=7.2 Hz, 3H).

Example SS

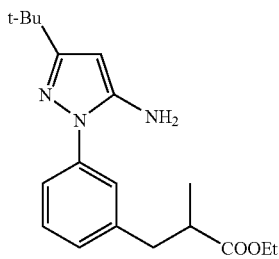

A mixture of Example RR (1.2 g) and Pd/C (120 mg, 10%) in methanol (50 mL) was stirred under 40 psi of H₂ at RT overnight, filtered. And concentrated to afford 3-[3-(5-amino-3-t-butyl-pyrazol-1-yl)-phenyl]-2-methyl-propionic acid ethyl ester as a racemate (1.1 g), which was used for the next reaction without further purification.

Example 200

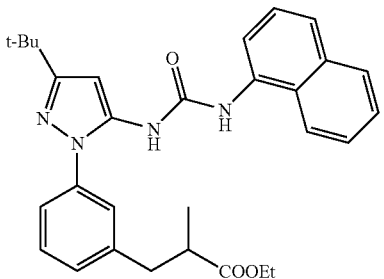

To a solution of Example SS (100 mg, 0.3 mmol) and Et₃N (60 mg, 0.6 mmol) in CH₂Cl₂ (10 mL) was added 1-isocyanato-naphthalene (77 mg, 0.45 mmol). The resulting mixture was stirred at RT overnight, added to water (50 mL), extracted with CH₂Cl₂ (3×30 mL) and the combined organic extracted were washed with brine, dried (Na₂SO₄), and filtered. After concentration under reduced pressure, the residue was purified by preparative-TLC to afford 3-(3-{3-t-butyl-5-[3-(4-fluoro-phenyl)-ureido]-pyrazol-1-yl}-phenyl)-propionic acid ethyl ester as a racemate (50 mg, 33%). $^1$H-NMR (CDCl₃): 7.99 (s, 1H), 7.91 (d, J=8.4 Hz, 1H), 7.84 (t, J=7.2 Hz, 2H), 7.67 (d, J=8.4 Hz, 1H), 7.49-7.41 (m, 3H), 7.35-7.33 (m, 3H), 7.21 (s, 1H), 7.14-7.13 (m, 1H), 6.65 (s, 1H), 3.98 (q, J=6.0 Hz, 2H), 2.92-2.88 (m, 3H), 1.36 (s, 9H), 1.24 (d, J=6.0 Hz, 3H), 1.08 (t, J=7.2 Hz, 3H); MS (ESI) m/z: 499 (M+H⁺).

Example 201

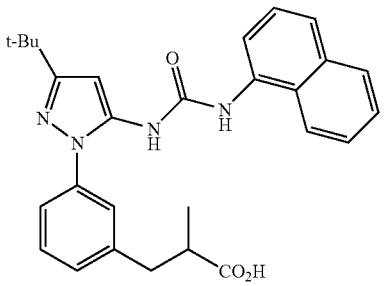

A solution of Example 200 (17 mg, mmol) and 2N LiOH (3 mL) in MeOH (3 mL) was stirred at RT over night. The reaction mixture was adjusted to pH=4, and extracted with ethyl acetate (3×20 mL). The combined organic extracts were washed with brine, dried (Na₂SO₄), and filtered. After the filtrate was concentrated, the residue was purified by preparative-TLC to afford 3-{3-[3-t-butyl-5-(3-naphthalen-1-yl-ureido)-pyrazol-1-yl]-phenyl}-2-methyl-propionic acid as a racemate (15 mg, 92%). $^1$H NMR (DMSO): 11.81 (br s, 1H), 9.58 (s, 1H), 8.56 (s, 1H), 7.95 (d, J=7.6 Hz, 1H), 7.82 (d, J=8.4 Hz, 1H), 7.55 (d, J=7.6 Hz, 1H), 7.45-7.35 (m, 5H), 7.28 (d, J=8.0 Hz, 1H), 7.14 (t, J=7.6 Hz, 1H), 6.52 (s, 1H), 3.77 (m, 1H), 2.65 (m, 1H), 2.36 (m, 1H), 1.27 (s, 9H), 1.00 (d, J=6.8 Hz, 3H); MS (ESI) m/z: 471 (M+H⁺).

Example 202

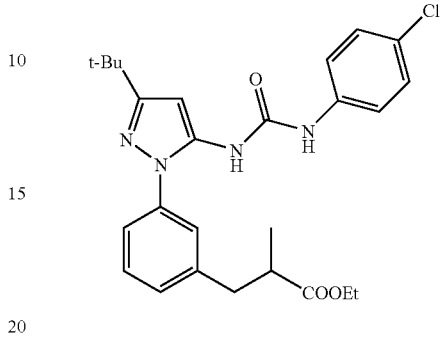

To a solution of Example SS (100 mg, 0.3 mmol) and Et₃N (60 mg, 0.6 mmol) in CH₂Cl₂ (10 mL) was added 1-chloro-4-isocyanato-benzene (77 mg, 0.45 mmol). The resulting mixture was stirred at RT overnight, and then added to water (50 mL). The solution was extracted with CH₂Cl₂ (3×30 mL) and the combined organic extracts were washed with brine, dried (Na₂SO₄), and filtered. After concentration under reduced pressure, the residue was purified by preparative-TLC to afford 3-(3-{3-t-butyl-5-[3-(4-chloro-phenyl)-ureido]-pyrazol-1-yl}-phenyl)-2-methyl-propionic acid ethyl ester as a racemate (51 mg, 35%). $^1$H-NMR (CDCl₃): 8.20 (s, 1H), 7.39 (d, J=4.4 Hz, 2H), 7.37 (d, J=8.8 Hz, 2H), 7.21 (t, J=8.4 Hz, 2H), 7.14-7.11 (m, 2H), 6.59 (s, 1H), 4.04-3.99 (m, 2H), 3.00 (m, 1H), 2.93 (m, 1H), 2.83 (m, 1H), 1.34 (s, 9H), 1.17 (d, J=6.4 Hz, 3H), 1.15 (t, J=7.2 Hz, 3H); MS (ESI) m/z: 483 (M+H⁺).

Example 203

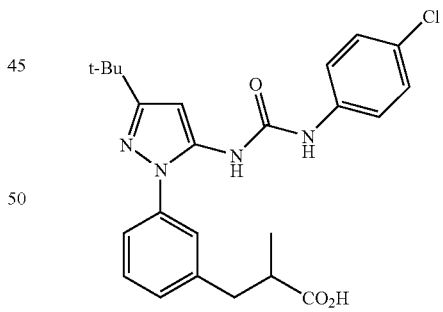

A solution of Example 202 (15 mg, mmol) and 2N LiOH (3 mL) in MeOH (3 mL) was stirred at RT overnight. The reaction mixture was adjusted to pH=4, extracted with ethyl acetate (3×20 mL), the combined organic extracts were washed with brine, dried (Na₂SO₄), and filtered. After the filtrate was concentrated, the residue was purified by preparative-TLC to afford 3-(3-{3-t-butyl-5-[3-(4-chloro-phenyl)-ureido]-pyrazol-1-yl}-phenyl)-2-methyl-propionic acid as a racemate (13 mg, 90%). $^1$H NMR (DMSO): 12.48 (br s, 1H), 9.35 (br s, 1H), 7.55 (d, J=8.8 Hz, 1H), 7.34-7.32 (m, 2H), 7.26 (d, J=8.4 Hz, 1H), 7.24 (d, J=8.8 Hz, 2H), 7.10 (d, J=7.6

Hz, 1H), 6.45 (s, 1H), 2.74 (m, 1H), 2.65 (m, 1H), 2.31 (m, 2H), 1.26 (s, 9H), 0.99 (d, J=6.8 Hz, 3H); MS (ESI) m/z: 455 (M+H⁺).

Example 204

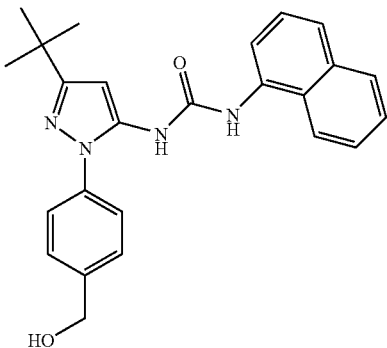

To a stirred solution of Example 195 (500 mg, 0.83 mmol) in THF (10 mL) was added LiAlH₄ powder (65 mg, 1.66 mmol) in portion at 0° C. under N₂. The mixture was stirred for 2 h at RT, excess LiAlH₄ was destroyed by a slow addition of ice, and the reaction mixture was acidified to pH=7 with dilute HCl. After the solvent was removed, the residue was extracted with ethyl acetate. The combined organic extracts were washed with brine, dried (Na₂SO₄), and filtered. After concentration in vacuo, the crude product was purified by preparative-TLC to afford 1-[2-(4-hydroxymethyl-phenyl)-5-isopropyl-2H-pyrazol-3-yl]-3-naphthalen-1-yl-urea (415 mg, 92%). ¹H NMR (DMSO-d₆): 9.04 (s, 1H), 8.78 (s, 1H), 7.98 (d, J=8.0 Hz, 1H), 7.90 (d, J=7.2 Hz, 2H), 7.63 (d, J=8.4 Hz, 1H), 7.55-7.42 (m, 7H), 6.39 (s, 1H), 5.30 (t, J=5.6 Hz, 1H), 4.56 (d, J=5.6 Hz, 2H), 1.27 (s, 9H); MS (ESI) m/z: 415 (M+H⁺).

Example 205

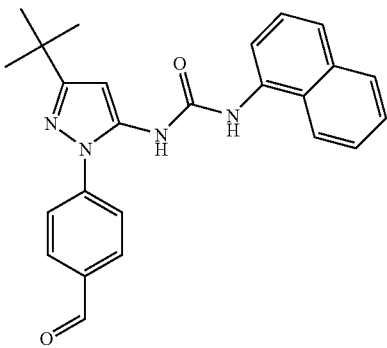

To a solution of Example 204 (200 mg) in CH₂Cl₂ (50 mL) was added MnO₂ (450 mg) at RT. The suspension was stirred for 2 h then filtered through celite. The filtrate was concentrated under reduced pressure to afford 150 mg of 1-[5-t-butyl-2-(4-formyl-phenyl)-2H-pyrazol-3-yl]-3-naphthalen-1-yl-urea, which was used without further purification.

Example 206

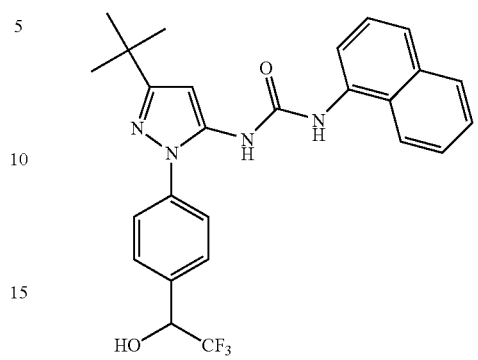

To a solution of (trifluoromethyl)trimethylsilane (77 mg) and TBAF (10 mg) in THF (10 mL) was added Example 205 (150 mg) in THF (10 mL) under N₂ atmosphere in ice-bath. The resulting mixture was stirred at 0° C. for 1 h and then warmed to RT for an additional hour. To the reaction was then added 0.5 mL of 3 NHCL, which was then stirred at RT overnight. After removal the solvent, the residue was dissolved in CH₂Cl₂ (50 mL). The organic layer was washed with saturated NaHCO₃ and brine, dried (Na₂SO₄), and filtered. After the filtrate was concentrated under reduced pressure, the residue was purified by preparative-TLC to afford the final product 1-{5-t-Butyl-2-[4-(2,2,2-trifluoro-1-hydroxy-ethyl)-phenyl]-2H-pyrazol-3-yl}-3-naphthalen-1-yl-urea (110 mg, 63%). ¹H NMR (DMSO-d₆): 9.07 (s, 1H), 8.89 (s, 1H), 8.03 (d, J=8.0 Hz, 1H), 7.90 (d, J=7.6 Hz, 2H), 7.67-7.62 (m, 5H), 7.55-7.51 (m, 2H), 7.44 (t, J=8.0 Hz, 1H), 6.95 (d, J=6.0 Hz, 1H), 6.42 (s, 1H), 5.27 (m, 1H), 1.28 (s, 9H). MS (ESI) m/z: 483 (M+H⁺).

Example 207

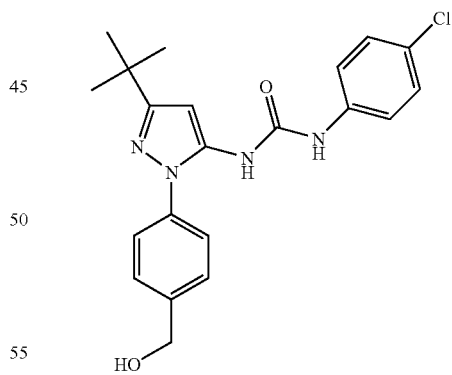

To a stirred solution of Example 57 (500 mg, 1.1 mmol) in THF (10 mL) was added LiAlH₄ powder (65 mg, 1.66 mmol) in portion at 0° C. under N₂. The mixture was stirred for 2 h at RT, excess LiAlH₄ was destroyed by a slow addition of ice, and the reaction mixture was acidified to pH=7 with diluted HCl. After the solvent removal, the residue was extracted with ethyl acetate, and the combined organic extracts were washed with brine, d dried (Na₂SO₄), and filtered, After solvent removal, the crude product was purified by preparative TLC to 1-[5-t-butyl-2-(4-hydroxymethyl-phenyl)-2H-pyrazol-3- yl]-3-(4-chloro-phenyl)-urea (380 mg, 92%) as a white powder. ¹H-NMR (CDCl₃): 8.17 (br s, 1H), 7.22 (s, 4H), 7.17 (d, J=8.0 Hz, 2H), 7.09 (d, J=8.0 Hz, 2H), 7.04 (s, H), 6.38 (s, 1H), 4.51 (s, 1H), 1.22 (s, 9H); MS (ESI) m/z: 399 (M+H⁺).

Example 208

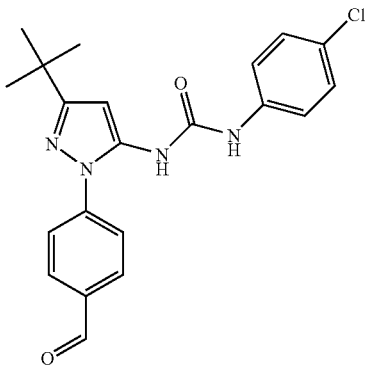

To a solution of Example 207 (200 mg) in CH₂Cl₂ (50 mL) was added MnO₂ (450 mg) at RT. The suspension was stirred for 2 h, then filtered through celite. The filtrate was concentrated to afford 160 mg of 1-[5-t-butyl-2-(4-formyl-phenyl)-2H-pyrazol-3-yl]-3-(4-chloro-phenyl)-urea, which was used without further purification.

Example 209

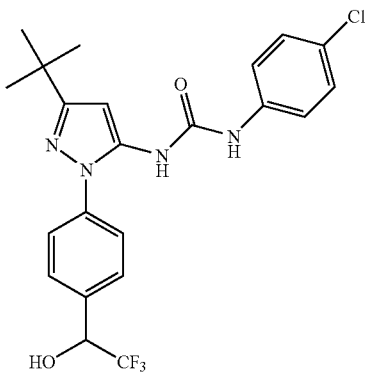

To a solution of (trifluoromethyl)trimethylsilane (86 mg) and TBAF (10 mg) in THF (10 mL) was added Example 208 (160 mg) in THF (20 mL) under N₂ atmosphere in ice-bath. The resulting mixture was stirred at 0° C. for 1 h and then warmed to RT for an additional hour. To the reaction was added 0.5 mL of 3 N HCl, which was then stirred at RT overnight. After removal of the solvent, the residue was dissolved in CH₂Cl₂ (100 mL). The organic extracts were washed with saturated NaHCO₃ and brine, dried (Na₂SO₄), and filtered. After the filtrate was concentrated under reduced pressure, the residue was purified by preparative-TLC to afford the final product 1-{5-t-butyl-2-[4-(2,2,2-trifluoro-1-hydroxy-ethyl)-phenyl]-2H-pyrazol-3-yl}-3-(4-chloro-phenyl)-urea ( 120 mg, 64%). ¹H-NMR (DMSO-d₆): 9.15 (s, 1H), 8.50 (s, 1H), 7.61 (d, J=8.4 Hz, 2H), 7.55 (d, J=8.4 Hz, 2H), 7.42 (d, J=8.8 Hz, 2H), 7.28 (d, J=8.8 Hz, 2H), 6.91 (d, J=5.6 Hz, 1H), 6.36 (s, 1H), 5.25 (m, 1H), 1.26 (s, 9H); MS (ESI) m/z: 467 (M+H⁺).

Example 210

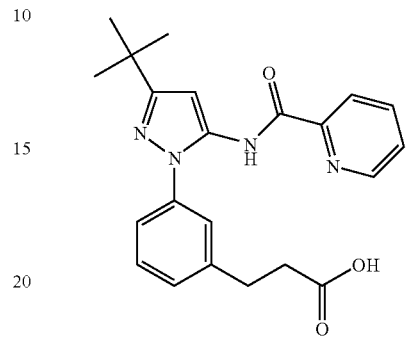

A solution of Example 151 (42 mg, 0.1 mmol) and 2N LiOH (3 mL) in MeOH (3 mL) was stirred at RT over night. The reaction mixture was neutralized to pH=4, and extracted with ethyl acetate (3×20 mL). The combined organic extracts were washed with brine, dried (Na₂SO₄), and filtered. The filtrate was concentrated to afford 3-(3-{3-t-butyl-5-[(pyridine-2-carbonyl)-amino]-pyrazol-1-yl}-phenyl)-propionic acid (30 mg, 76%). 8.45 (d, 4.0 Hz, 1H), 8.24 (d, 8.0 Hz, 1H), 7.92 (s, 1H), 7.88 (t, 7.6 Hz, 1H), 7.67 (d, 8.0 Hz, 1H), 7.36 (t, 5.6 Hz, 1H), 7.23 (t, 7.6 Hz, 1H), 6.96 (d, 6.8 Hz, 1H), 6.67 (s, 1H), 2.77 (t, 7.6 Hz, 2H), 2.22 (t, 7.6 Hz, 2H), 1.26 (s, 9H); MS (ESI) m/z: 393 (M+H⁺).

Example 211

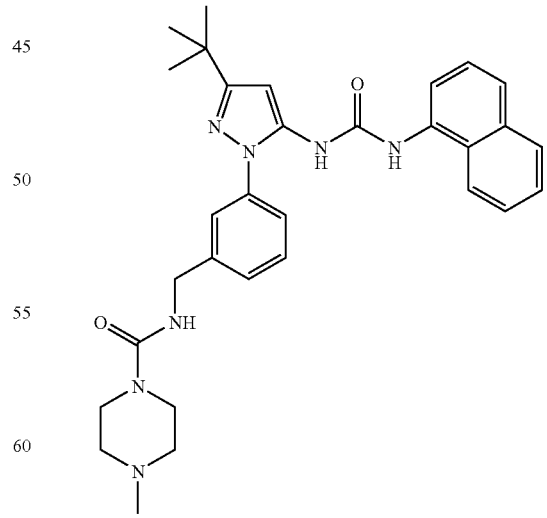

Example I is reacted with CDI and N-methyl piperazine using the procedure for Example 145 to afford the title compound.

Example 212

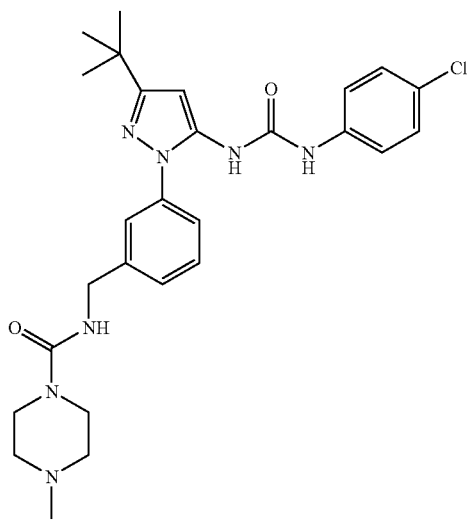

Example J is reacted with CDI and N-methyl piperazine using the procedure for Example 145 to afford the title compound.

Example 213

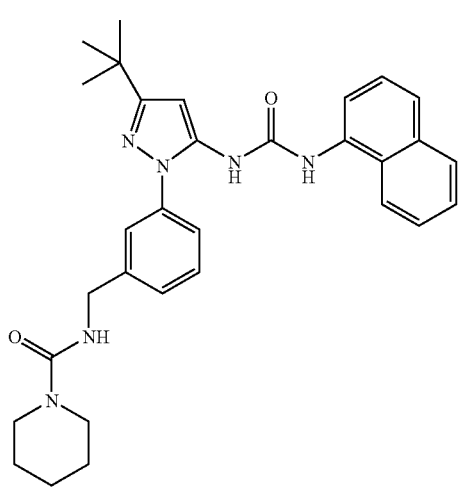

Example I is reacted with CDI and piperidine using the procedure for Example 145 to afford the title compound.

Example 214

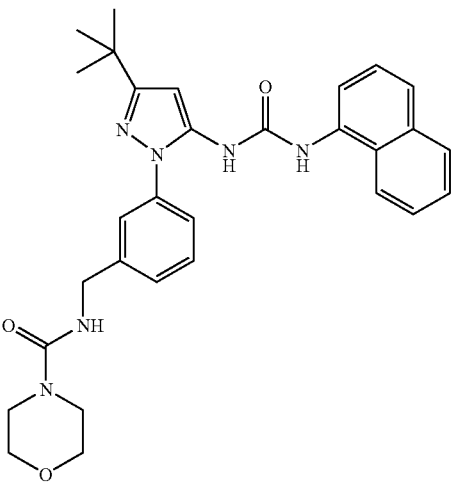

Example I is reacted with CDI and morpholine using the procedure for Example 145 to afford the title compound.

Example 215

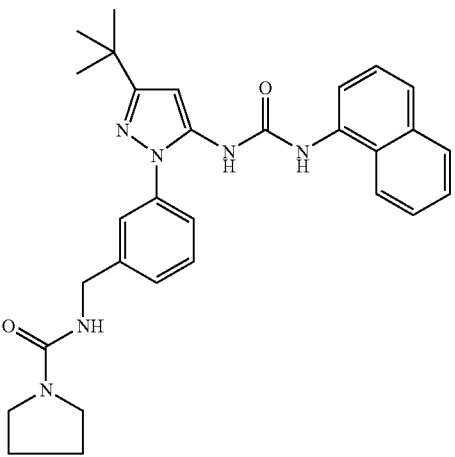

Example I is reacted with CDI and pyrrolidine using the procedure for Example 145 to afford the title compound.

Example 216

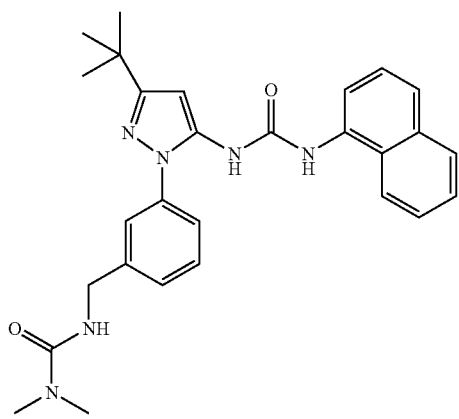

Example I is reacted with CDI and dimethylamine using the procedure for Example 145 to afford the title compound.

Example 217

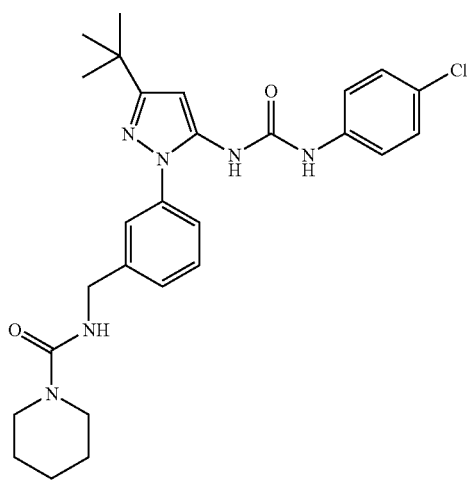

Example J is reacted with CDI and piperidine using the procedure for Example 145 to afford the title compound.

Example 218

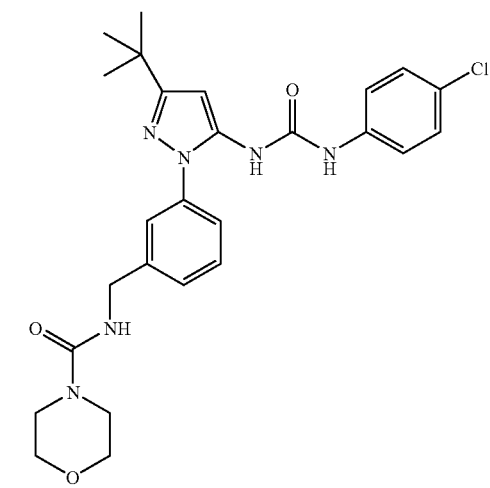

Example J is reacted with CDI and morpholine using the procedure for Example 145 to afford the title compound.

Example 219

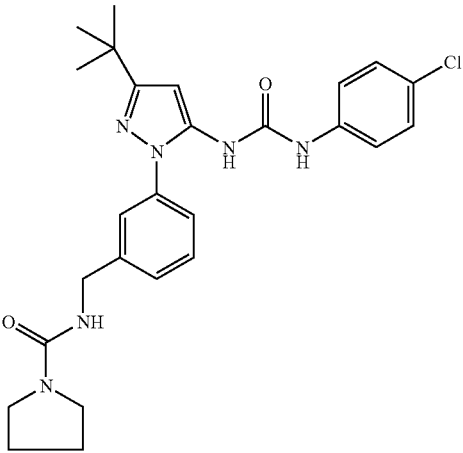

Example J is reacted with CDI and pyrrolidine using the procedure for Example 145 to afford the title compound.

Example 220

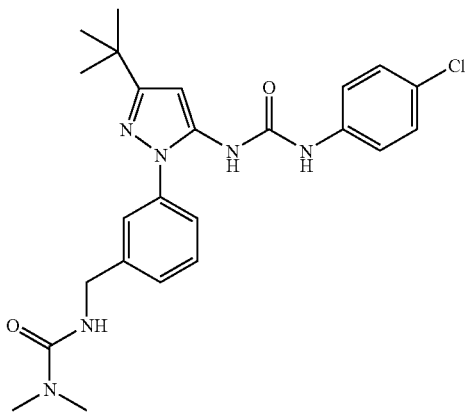

Example J is reacted with CDI and dimethylamine using the procedure for Example 145 to afford the title compound.

Example 221

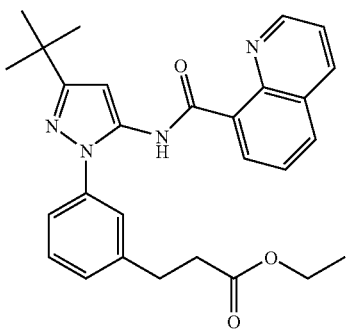

Isoquinoline-8-carboxylic acid and Example Z are reacted using the procedure for Example 149 to afford ethyl 3-(3-(3-t-butyl-5-(quinoline-8-carboxamido)-1H-pyrazol-1-yl)phenyl)propanoate.

Example 222

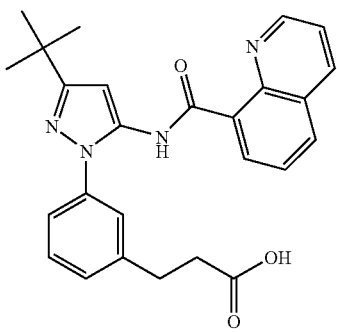

Example 222 is reacted using the procedure for Example 150 to afford 3-(3-(3-t-butyl-5-(quinoline-8-carboxamido)-1H-pyrazol-1-yl)phenyl)propanoic acid.

Example 223

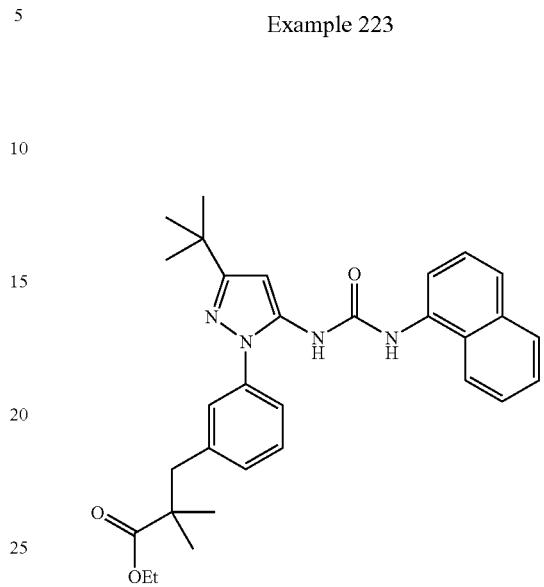

Example E is reacted with (1-ethoxy-2-methylprop-1-enyloxy)trimethylsilane under literature conditions to afford ethyl 2-(3-(3-t-butyl-5-(3-(naphthalen-1-yl)ureido)-1H-pyrazol-1-yl)benzyl)-2-methylpropanoate.

Example 224

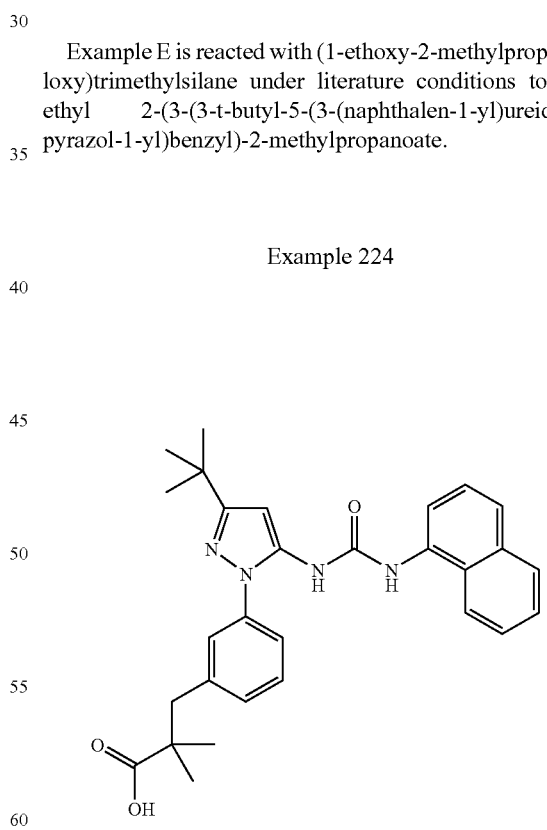

Example 224 is reacted using the procedure for Example 150 to afford 2-(3-(3-t-butyl-5-(3-(naphthalen-1-yl)ureido)-1H-pyrazol-1-yl)benzyl)-2-methylpropanoic acid

Example 225

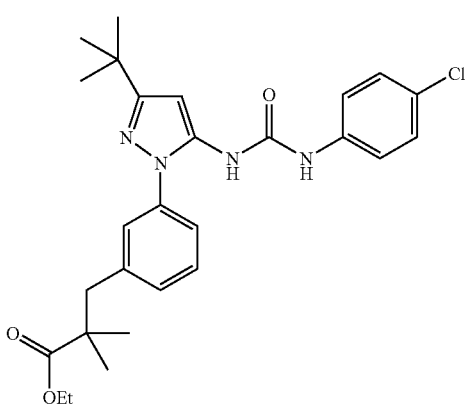

Example G is reacted with (1-ethoxy-2-methylprop-1-enyloxy)trimethylsilane under literature conditions to afford ethyl 2-(3-(3-t-butyl-5-(3-(4-chlorophenyl)ureido)-1H-pyrazol-1-yl)benzyl)-2-methylpropanoate.

Example 226

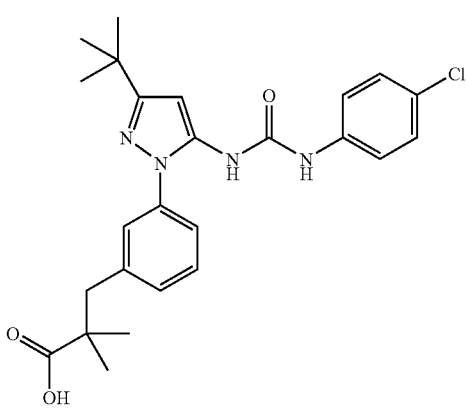

Example 226 is reacted using the procedure for Example 150 to afford 2-(3-(3-t-butyl-5-(3-(4-chlorophenyl)ureido)-1H-pyrazol-1-yl)benzyl)-2-methylpropanoic acid.

Example TT

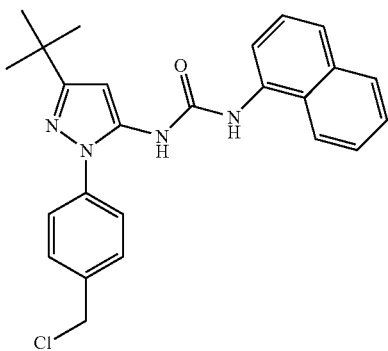

Example 204 is reacted using the procedure for Example E to afford 1-(3-t-butyl-1-(4-(chloromethyl)phenyl)-1H-pyrazol-5-yl)-3-(naphthalen-1-yl)urea

Example UU

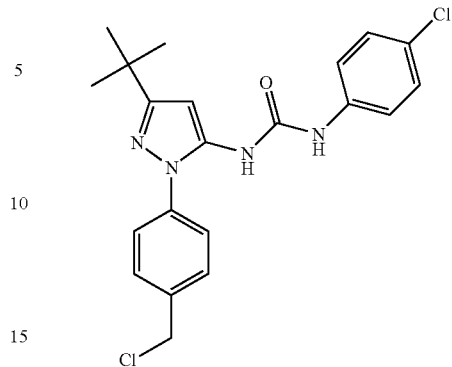

Example 122 is reacted using the procedure for Example G to afford 1-(3-t-butyl-1-(4-(chloromethyl)phenyl)-1H-pyrazol-5-yl)-3-(4-chlorophenyl)urea.

Example 227

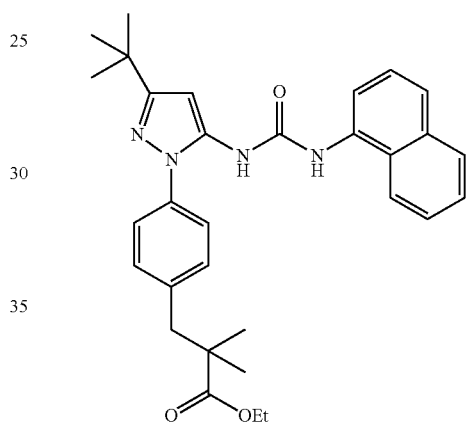

Example TT is reacted with (1-ethoxy-2-methylprop-1-enyloxy)trimethylsilane under literature conditions to afford ethyl 2-(4-(3-t-butyl-5-(3-(naphthalen-1-yl)ureido)-1H-pyrazol-1-yl)benzyl)-2-methylpropanoate.

Example 228

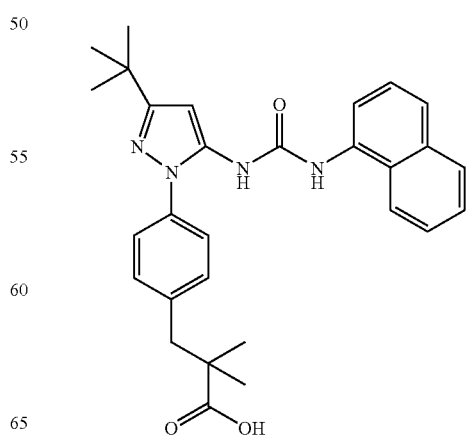

Example 227 is reacted using the procedure for Example 150 to afford 2-(4-(3-t-butyl-5-(3-(naphthalen-1-yl)ureido)-1H-pyrazol-1-yl)benzyl)-2-methylpropanoic acid.

Example 229

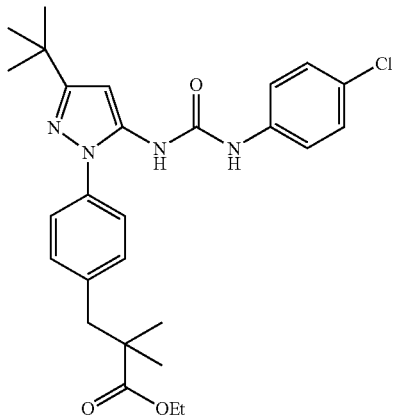

Example UU is reacted with (1-ethoxy-2-methylprop-1-enyloxy)trimethylsilane under literature conditions to afford ethyl 2-(4-(3-t-butyl-5-(3-(4-chlorophenyl)ureido)-1H-pyrazol-1-yl)benzyl)-2-methylpropanoate Example 230

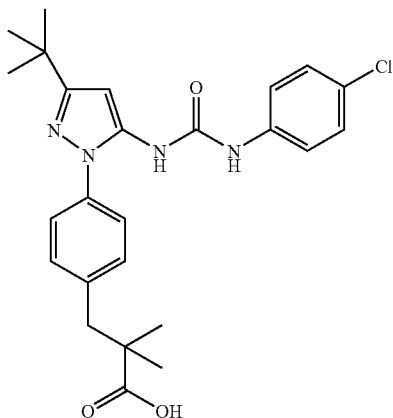

Example 144 is reacted using the procedure for Example 150 to afford 2-(4-(3-t-butyl-5-(3-(4-chlorophenyl)ureido)-1H-pyrazol-1-yl)benzyl)-2-methylpropanoic acid.

Example VV

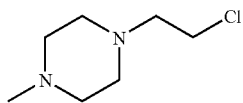

N-methyl piperazine and 1-bromo-2-chloroethane are reacted using the procedure for Example OO to afford 1-(2-chloroethyl)-4-methylpiperazine hydrochloride.

Example WW

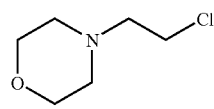

Morpholine and 1-bromo-2-chloroethane are reacted using the procedure for Example OO to afford 4-(2-chloroethyl)morpholine Example XX

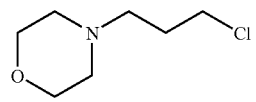

Morpholine and 1-bromo-3-chloropropane are reacted using the procedure for Example OO to afford 4-(3-chloropropyl)morpholine.

Example YY

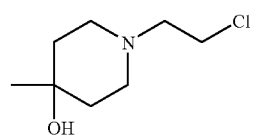

4-methylpiperidin-4-ol (made via literature methods) and 1-bromo-2-chloroethane are reacted using the procedure for Example OO to afford 1-(2-chloroethyl)-4-methylpiperidin-4-ol.

Example ZZ

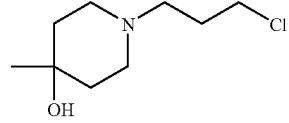

4-methylpiperidin-4-ol (made via literature methods) and 1-bromo-3-chloropropane are reacted using the procedure for Example OO to afford 1-(3-chloropropyl)-4-methylpiperidin-4-ol.

Example AAA

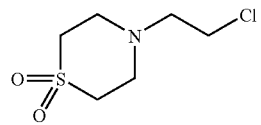

A solution of 4,4-dioxothiomorpholine and 1-bromo-2-chloroethane are reacted using the procedure for Example OO to afford 4-(2-chloroethyl)-4,4-dioxo-4-thiomorpholine.

Example BBB

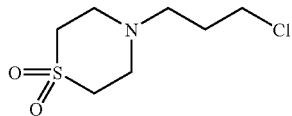

A solution of 4,4-dioxothiomorpholine and 1-bromo-3-chloropropane are reacted using the procedure for Example OO to afford 4-(3-chloropropyll)-4,4-dioxo-4-thiomorpholine.

Example CCC

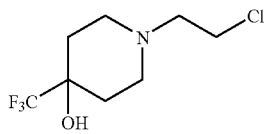

A solution of 4-(trifluoromethyl)piperidin-4-ol and 1-bromo-2-chloroethane are reacted using the procedure for Example OO to afford 1-(2-chloroethyl)-4-(trifluoromethyl)piperidin-4-ol.

Example DDD

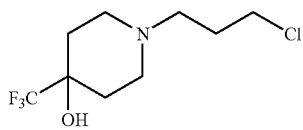

A solution of 4-(trifluoromethyl)piperidin-4-ol and 1-bromo-3-chloropropane are reacted using the procedure for Example OO to afford 1-(3-chloropropyll)-4-(trifluoromethyl)piperidin-4-ol.

Example 231

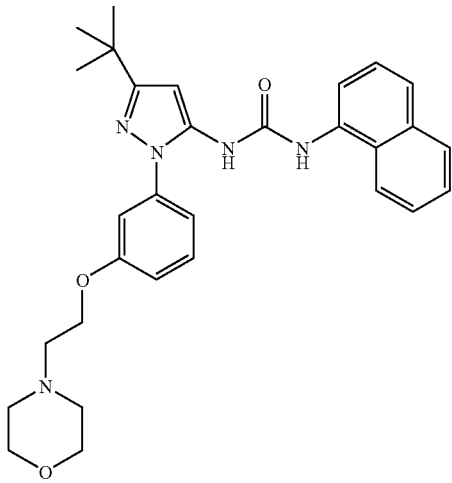

Example 41 and Example WW are reacted according to the procedure for Example 194 to afford 1-(1-(3-(2-morpholinoethoxy)phenyl)-3-t-butyl-1H-pyrazol-5-yl)-3-(naphthalen-1-yl)urea.

Example 232

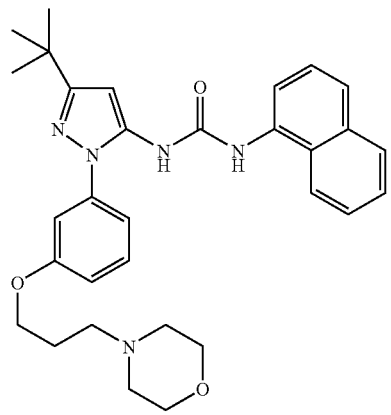

Example 41 and Example XX are reacted according to the procedure for Example to afford 1-(1-(3-(3-morpholinopropoxy)phenyl)-3-t-butyl-1H-pyrazol-5-yl)-3-(naphthalen-1-yl)urea.

Example 233

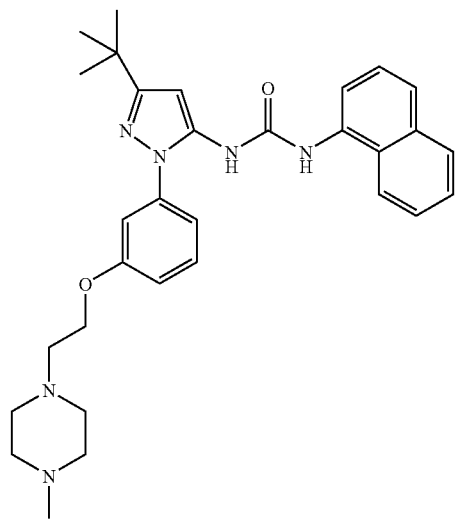

Example 41 and Example VV are reacted according to the procedure for Example 194 to afford 1-(1-(3-(2-(4-methylpiperazin-1-yl)ethoxy)phenyl)-3-t-butyl-1H-pyrazol-5-yl)-3-(naphthalen-1-yl)urea.

Example 234

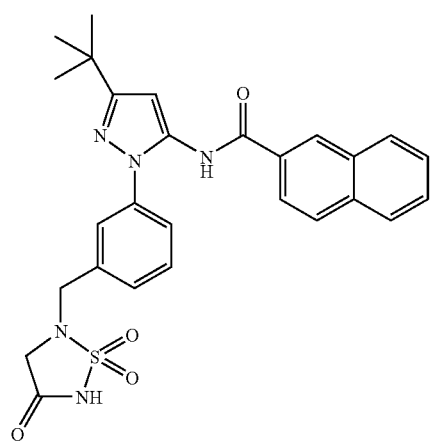

Example CC, 2-riaphthoic acid chloride and Example DD were combined utilizing the same general approach for Example 162 to yield N-(3-tert-butyl-1-(3-([5-1,1,4-trioxo-1λ⁶-[1,2,5]thiadiazolidin-2-ylmethyl]phenyl)-1H-pyrazol-5-yl)-2-naphthamide. ¹H-NMR (DMSO-d₆): 10.50 (s, 1H), 8.45 (s, 1H), 8.15-8.05 (m, 3H), 7.90 (s, 1H), 7.60 (t, J=7.2 Hz, 3H), 7.45 (s, 1H), 7.38 (t, J=8.0 Hz, 1H), 7.27 (d, J=7.2 Hz, 1H), 6.44 (s, 1H), 4.05 (s, 2H), 1.31 (s, 9H). MS (ESI) m/z: 518 (M+H⁺).

Example 235

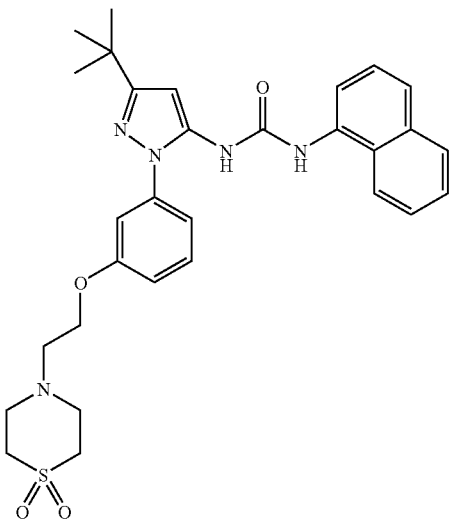

Example 41 and Example AAA are reacted according to the procedure for Example 194 to afford 1-(1-(3-(2-(4,4-dioxo-4-thio-morpholino)ethoxy)phenyl)-3-t-butyl-1H-pyrazol-5-yl)-3-(naphthalen-1-yl)urea.

Example 236

Example 41 and Example BBB are reacted according to the procedure for Example 194 to afford 1-(1-(3-(2-(4,4-dioxo-4-thio-morpholino)propoxy)phenyl)-3-t-butyl-1H-pyrazol-5-yl)-3-(naphthalen-1-yl)urea.

Example 237

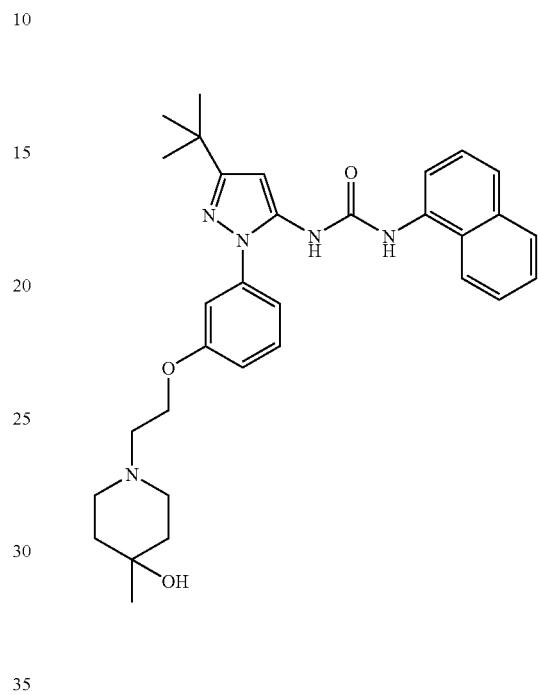

Example 41 and Example YY are reacted according to the procedure for Example 194 to afford 1-(1-(3-(2-(4-methylpiperidin-4-ol)ethoxy)phenyl)-3-t-butyl-1H-pyrazol-5-yl)-3-(naphthalen-1-yl)urea.

Example 238

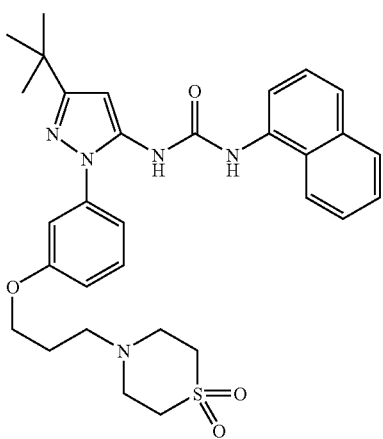

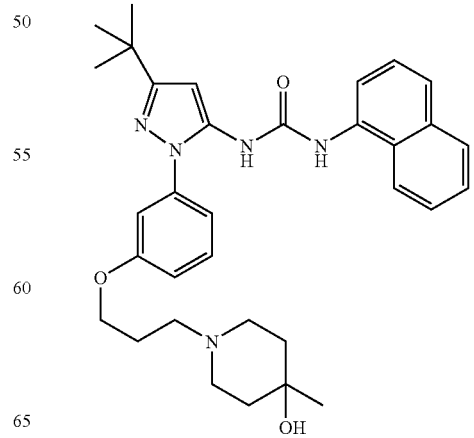

Example 41 and Example ZZ are reacted according to the procedure for Example 194 to afford 1-(1-(3-(3-(4-methylpiperidin-4-ol-)propoxy)phenyl)-3-t-butyl-1H-pyrazol-5-yl)-3-(naphthalen-1-yl)urea.

Example 239

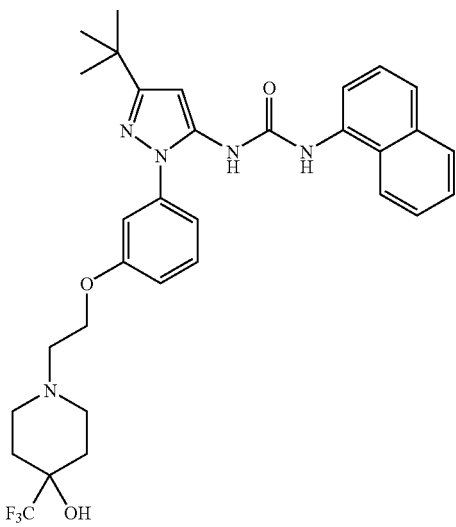

Example 41 and Example CCC are reacted according to the procedure for Example 194 to afford 1-(1-(3-(2-(4-(trifluoromethyl)piperidin-4-ol)ethoxy)phenyl)-3-t-butyl-1H-pyrazol-5-yl)-3-(naphthalen-1-yl)urea.

Example 240

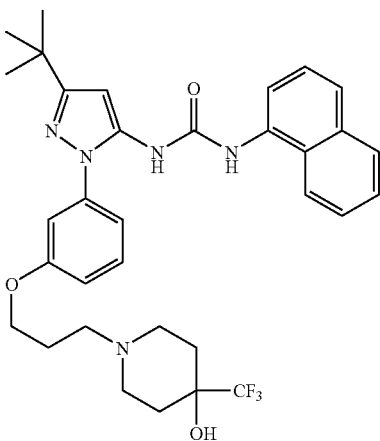

Example 41 and Example DDD are reacted according to the procedure for Example 194 to afford 1-(1-(3-(3-(4-(trifluoromethyl)piperidin-4-ol)propoxy)phenyl)-3-t-butyl-1H-pyrazol-5-yl)-3-(naphthalen-1-yl)urea.

Example 241

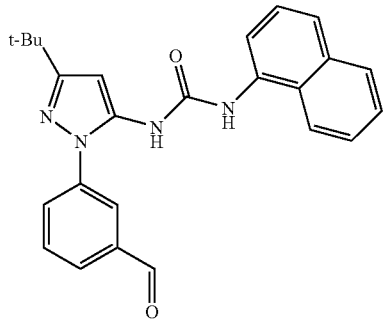

Example D is reacted using the procedure for Example 205 to afford 1-(3-t-butyl-1-(3-formylphenyl)-1H-pyrazol-5-yl)-3-(naphthalen-1-yl)urea.

Example 242

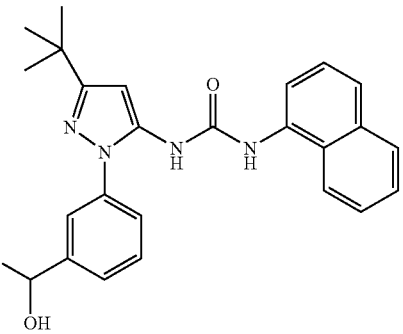

Example 242 is reacted using the procedure for Example 206 to afford 1-(3-t-butyl-1-(3-(2,2,2-trifluoro-1-hydroxyethyl)phenyl)-1H-pyrazol-5-yl)-3-(naphthalen-1-yl)urea.

Example 243

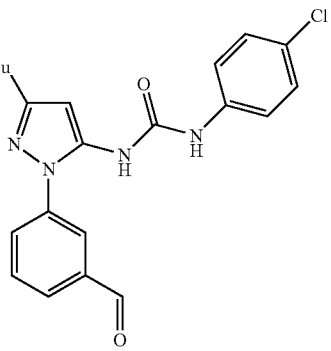

Example F is reacted using the procedure for Example 208 to afford 1-(3-t-butyl-1-(3-formylphenyl)-1H-pyrazol-5-yl)-3-(4-chlorophenyl)urea.

Example 244

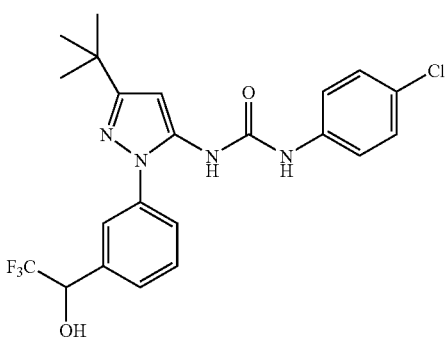

Example 244 is reacted using the procedure for Example 209 to afford 1-(3-t-butyl-1-(3-(2,2,2-trifluoro-1-hydroxyethyl)phenyl)-1H-pyrazol-5-yl)-3-(4-chlorophenyl)urea Example 245

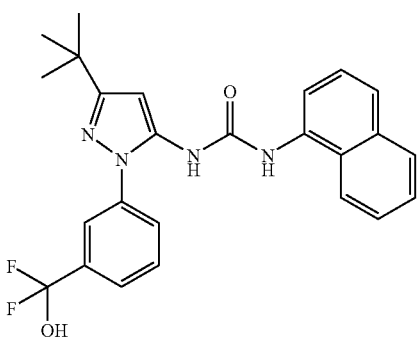

Example B is saponified using the procedure for Example 150. The resulting acid is reacted with trifluorotriazine in pyridine to afford the acid fluoride which is directly reacted with CsF and TBAF according to literature procedures (see J. Org. Chem. USSR (Engl. Transl.), 11, 1975, 315-317) to afford 1-(3-t-butyl-1-(3-(difluoro(hydroxy)methyl)phenyl)-1H-pyrazol-5-yl)-3-(naphthalen-1-yl)urea.

Example 246

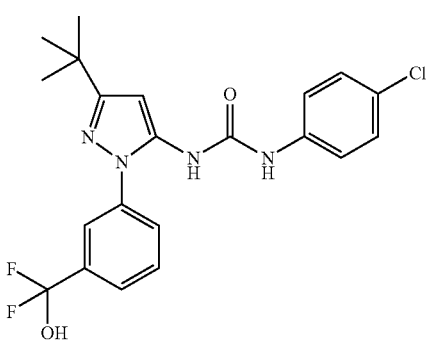

Example C is reacted according to the procedure for Example 245 to afford 1-(3-t-butyl-1-(3-(difluoro(hydroxy)methyl)phenyl)-1H-pyrazol-5-yl)-3-(4-chlorophenyl)urea.

Example 247

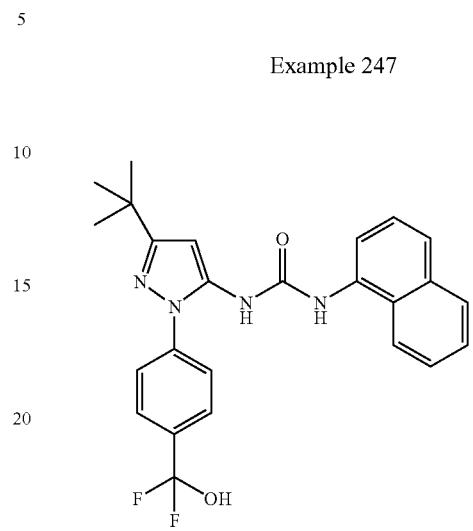

Example 205 is reacted according to the procedure for Example 245 to afford 1-(3-t-butyl-1-(4-(difluoro(hydroxy)methyl)phenyl)-1H-pyrazol-5-yl)-3-(naphthalen-1-yl)urea.

Example 248

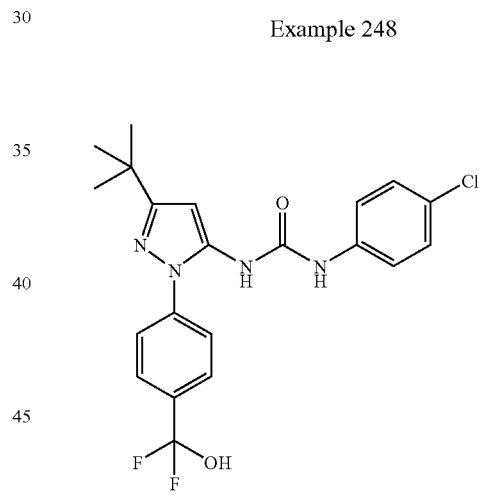

Example 57 is reacted according to the procedure for Example 245 to afford 1-(3-t-butyl-1-(4-(difluoro(hydroxy)methyl)phenyl)-1H-pyrazol-5-yl)-3-(4-chlorophenyl)urea.

Example EEE

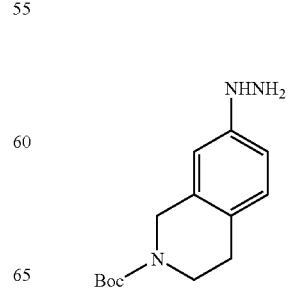

Example EEE (tert-butyl 7-hydrazinyl-3,4-dihydroisoquinoline-2(1H)-carboxylate) was synthesized according to literature procedures.

Example 249

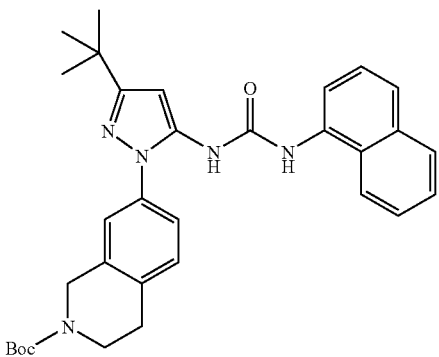

Utilizing the same synthetic procedure as for Example 164, Example EEE (10 mmol) and Example PP (10.5 mmol) are combined to afford t-butyl 7-(3-t-butyl-5-(3-(naphthalen-1-yl)ureido)-1H-pyrazol-1-yl)-3,4-dihydroisoquinoline-2 (1H)-carboxylate.

Example 250

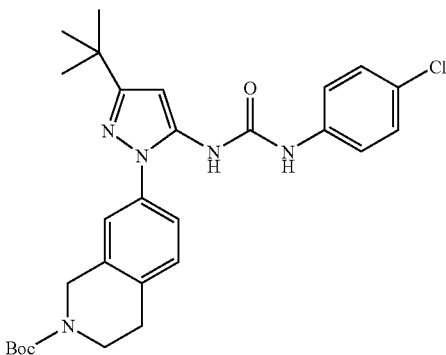

Utilizing the same synthetic procedure as for Example 164, Example EEE (10 mmol) and Example QQ (10.5 mmol) are combined to afford t-butyl 7-(3-t-butyl-5-(3-(4-chlorophenyl)ureido)-1H-pyrazol-1-yl)-3,4-dihydroisoquinoline-2 (1H)-carboxylate Example 251

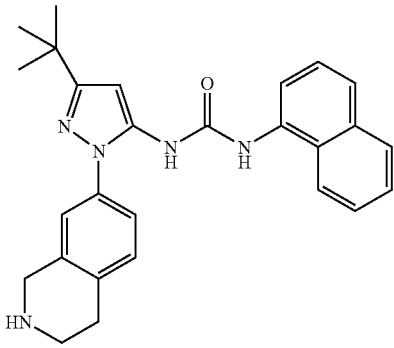

Example 249 is reacted with trifluoroacetic acid under standard conditions to afford 1-(3-t-butyl-1-(1,2,3,4-tetrahydroisoquinolin-7-yl)-1H-pyrazol-5-yl)-3-(naphthalen-1-yl) urea.

Example 252

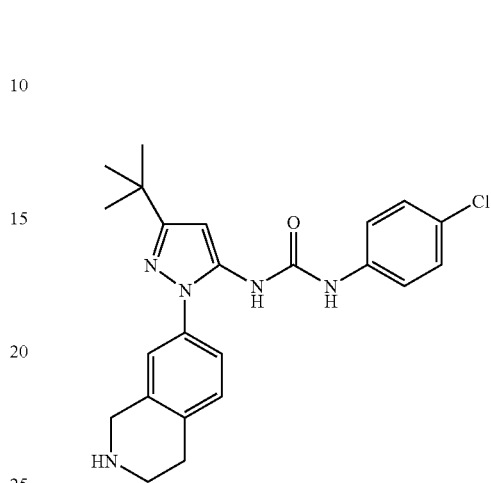

Example 250 is reacted with trifluoroacetic acid under standard conditions to afford 1-(3-t-butyl-1-(1,2,3,4-tetrahydroisoquinolin-7-yl)-1H-pyrazol-5-yl)-3-(4-chlorophenyl) urea.

Example 253

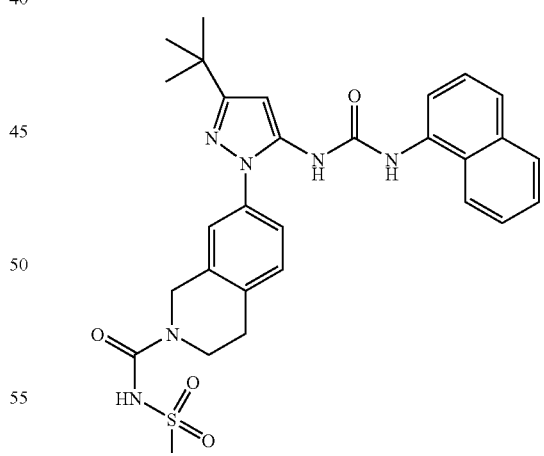

Example 251 is reacted with chlorosulfonyl isocyanate then dimethylamine according to the procedure for Example 7 to afford 1-(3-t-butyl-1-[[1-N-[[(1-dimethylaminolsulphonyl)amino]carbonyl]-1-(1,2,3,4-tetrahydroisoquinolin-7-yl)-1H-pyrazol-5-yl)-3-(naphthalen-1-yl)urea.

Example 254

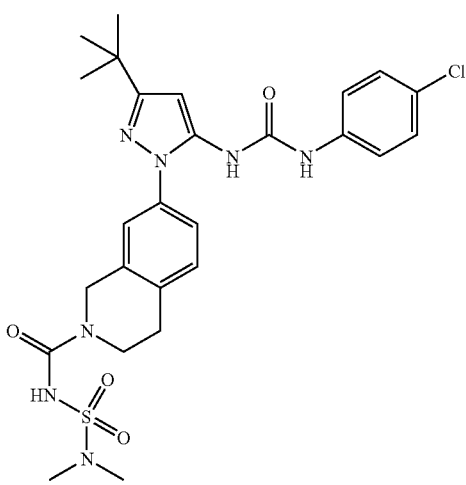

Example 252 is reacted with chlorosulfonyl isocyanate then dimethylamine according to the procedure for Example 7 to afford 1-(3-t-butyl-1-[[1-N-[[(1-dimethylaminolsulphonyl)amino]carbonyl]-1-(1,2,3,4-tetrahydroisoquinolin-7-yl)-1H-pyrazol-5-yl)-3-(4-chlorophenyl)urea.

Example 255

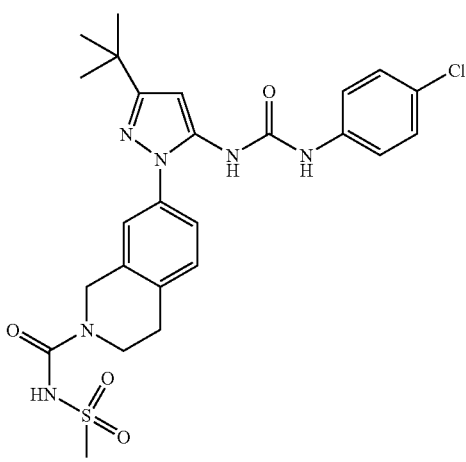

Example 252, CDI, and methanesulfonamide are reacted under standard conditions to yield 1-(3-t-butyl-1-[[1-N-[[(methanesulphonyl)amino]carbonyl]-1-(1,2,3,4-tetrahydro-isoquinolin-7-yl)-1H-pyrazol-5-yl)-3-(4-chlorophenyl)urea.

Example 256

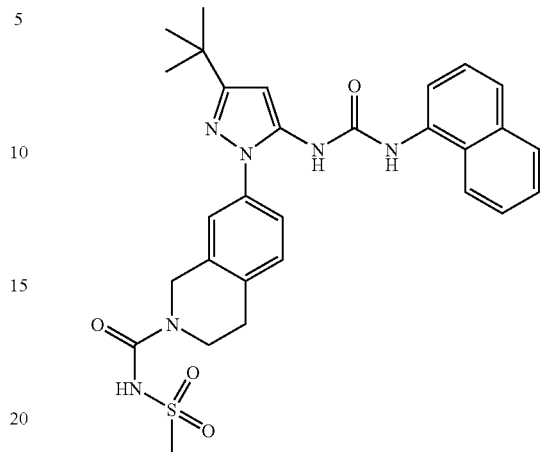

Example 251, CDI, and methanesulfonamide are reacted under standard conditions to yield 1-(3-t-butyl-1-[[1-N-[[(methanesulphonyl)amino]carbonyl]-1-(1,2,3,4-tetrahydroisoquinolin-7-yl)-1H-pyrazol-5-yl)-3-(1-naphthyl)urea.

Example FFF

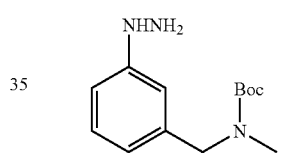

Commercially available 3-nitrobenzoic acid is reacted with methylamine and EDC under standard conditions to afford N-methyl-3-nitrobenzamide, which is reduced with LAH under standard conditions to afford N-methyl(3-nitrophenyl)methanamine, which is protected with benzylchloroformate under standard conditions to yield t-butyl 3-nitrobenzylmethylcarbamate. This material is nitrosated and reduced to yield t-butyl 3-hydrzazinobenzylmethylcarbamate.

Example 257

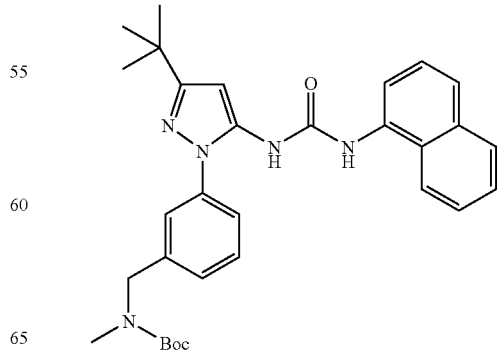

Utilizing the same synthetic procedure as for Example 164, Example FFF (10 mmol) and Example PP (10.5 mmol) are combined to afford t-butyl 3-(3-t-butyl-5-(3-(naphthalen-1-yl)ureido)-1H-pyrazol-1-yl)benzylmethylcarbamate.

Example 258

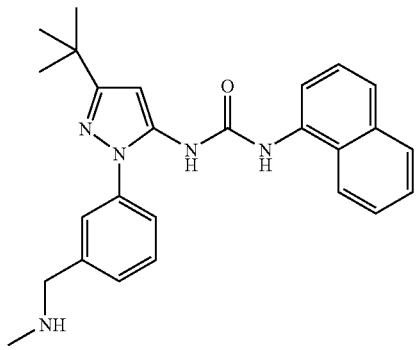

Example 257 is deprotected with trifluoroacetic acid under standard conditions to afford 1-(3-t-butyl-1-(3-((methylamino)methyl)phenyl)-1H-pyrazol-5-yl)-3-(naphthalen-1-yl)urea.

Example 259

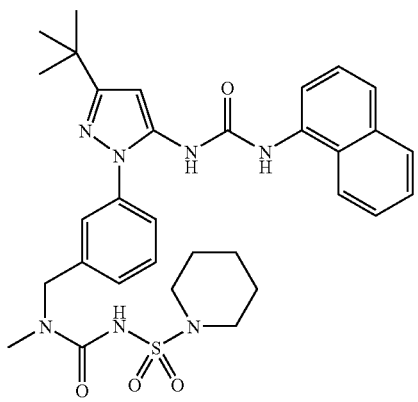

Example 258 is reacted with chlorosulfonyl isocyanate then piperidine according to the procedure for Example 7 to afford 1-(3-t-butyl-1-[[3-[[(1-piperidinylsulphonyl)amino]carbonyl]-((methylamino)methyl)phenyl)-1H-pyrazol-5-yl)-3-(naphthalen-1-yl)urea.

Example 260

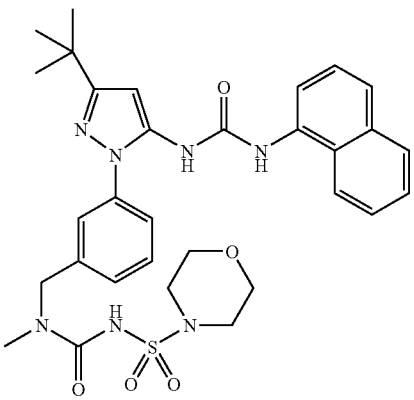

Example 258 is reacted with chlorosulfonyl isocyanate then morpholine according to the procedure for Example 7 to afford 1-(3-t-butyl-1-[[3-[[(1-morpholinyl-sulphonyl)amino]carbonyl]-((methylamino)methyl)phenyl)-1H-pyrazol-5-yl)-3-(naphthalen-1-yl)urea.

Example 261

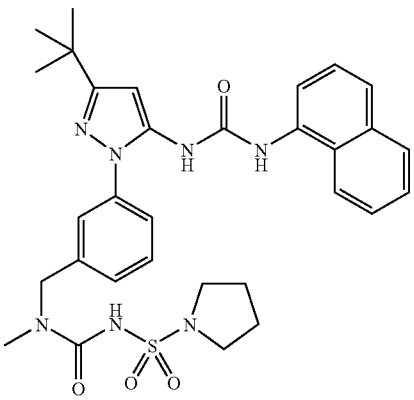

Example 258 is reacted with chlorosulfonyl isocyanate then pyrrolidine according to the procedure for Example 7 to afford 1-(3-t-butyl-1-[[3-[[(1-piperidinyl-sulphonyl)amino]carbonyl]-((methylamino)methyl)phenyl)-1H-pyrazol-5-yl)-3-(naphthalen-1-yl)urea.

Example 262

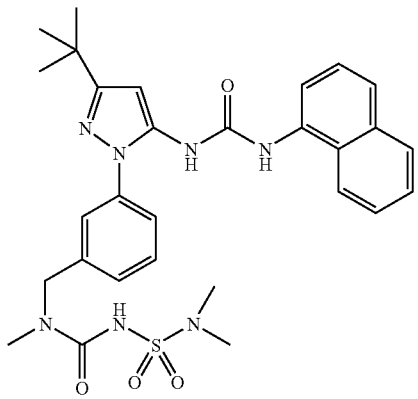

Example 258 is reacted with chlorosulfonyl isocyanate then dimethylamine according to the procedure for Example 7 to afford 1-(3-t-butyl-1-[[3-[[(1-dimethylamino-sulphonyl)amino]carbonyl]-((methylamino)methyl)phenyl)-1H-pyrazol-5-yl)-3-(naphthalen-1-yl)urea.

Example 263

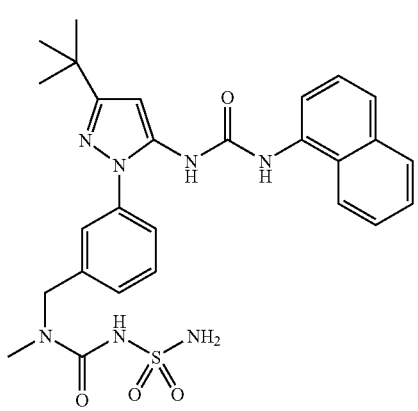

Example 258 is reacted with chlorosulfonyl isocyanate then ammonia according to the procedure for Example 7 to afford 1-(3-t-butyl-1-[[3-[[(1-aminosulphonyl)amino]carbonyl]-((methylamino)methyl)phenyl)-1H-pyrazol-5-yl)-3-(naphthalen-1-yl)urea.

Example 264

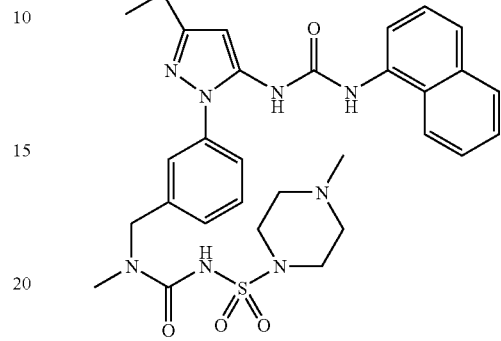

Example 258 is reacted with chlorosulfonyl isocyanate then N-methyl piperzine according to the procedure for Example 7 to afford 1-(3-t-butyl-1-[[3-[[(1-(N-methylpiperzinyl)sulphonyl)amino]carbonyl]-((methylamino)methyl)phenyl)-1H-pyrazol-5-yl)-3-(naphthalen-1-yl)urea.

Example 265

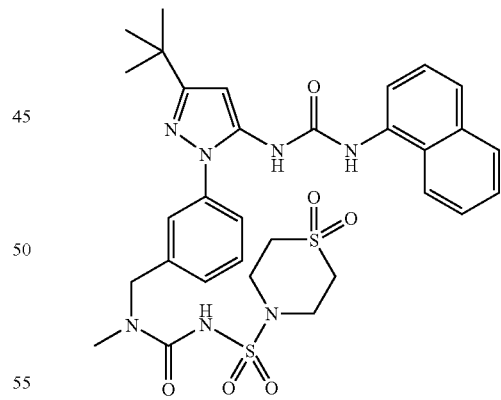

Example 258 is reacted with chlorosulfonyl isocyanate then 4,4-dioxo-4-thiomorpholine according to the procedure for Example 7 to afford 1-(3-t-butyl-1-[[3-[[(1-(4,4-dioxo-4-thiomorpholinyl)sulphonyl)amino]carbonyl]-((methylamino)methyl)phenyl)-1H-pyrazol-5-yl)-3 (naphthalen-1-yl)urea.

Example 266

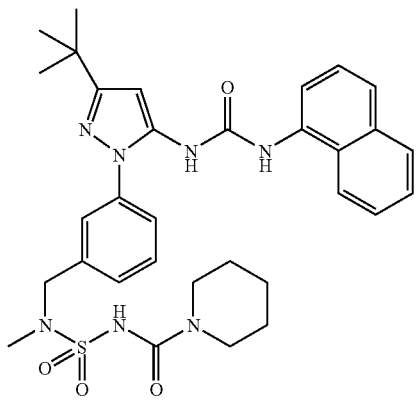

Chlorosulfonyl isocyanate, piperidine, then Example 258 are reacted according to the procedure for Example 7 to afford 1-(3-t-butyl-1-[[3-[[(1-piperidinylcarbonyl)amino]sulphonyl]-((methylamino)methyl)phenyl)-1H-pyrazol-5-yl)-3-(naphthalen-1-yl)urea.

Example 267

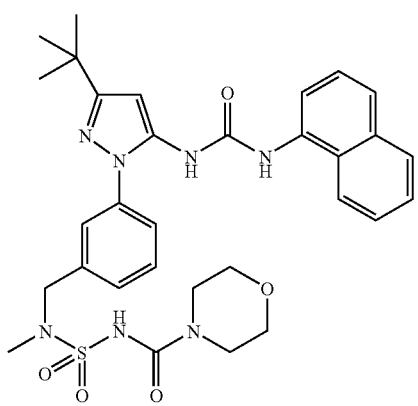

Chlorosulfonyl isocyanate, morpholine and then Example 258 are reacted according to the procedure for Example 7 to afford 1-(3-t-butyl-1-[[3-[[(1-morpholinyl-carbonyl)amino]sulphonyl]-((methylamino)methyl)phenyl)-1H-pyrazol-5-yl)-3-(naphthalen-1-yl)urea.

Example 268

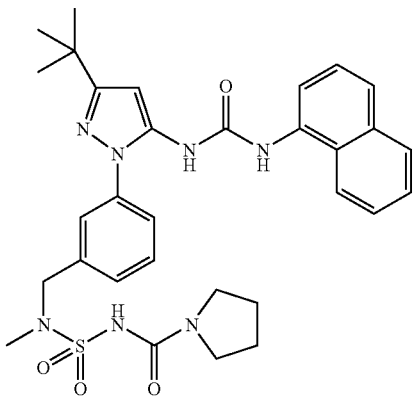

Chlorosulfonyl isocyanate, pyrrolidine and then Example 258 are reacted according to the procedure for Example 7 to afford 1-(3-t-butyl-1-[[3-[[(1-piperidinyl-carbonyl)amino]sulphonyl]-((methylamino)methyl)phenyl)-1H-pyrazol-5-yl)-3-(naphthalen-1-yl)urea.

Example 269

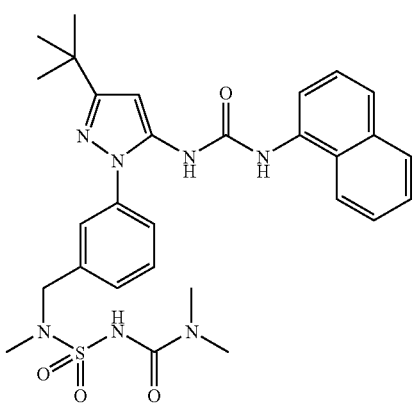

Chlorosulfonyl isocyanate, dimethylamine, then Example 258 are reacted according to the procedure for Example 7 to afford 1-(3-t-butyl-1-[[3-[[(1-dimethylamino-carbonyl)amino]sulphonyl]-((methylamino)methyl)phenyl)-1H-pyrazol-5-yl)-3-(naphthalen-1-yl)urea.

Example 270

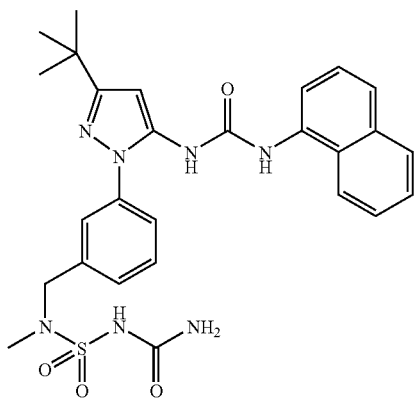

Chlorosulfonyl isocyanate, ammonia and then Example 258 are reacted according to the procedure for Example 7 to afford 1-(3-t-butyl-1-[[3-[[(1-aminocarbonyl)amino]sulphony]-((methylamino)methyl)phenyl)-1H-pyrazol-5-yl)-3-(naphthalen-1-yl)urea.

Example 271

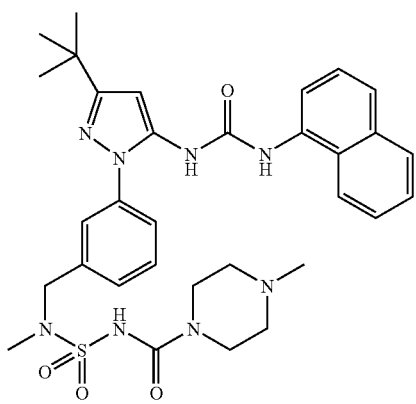

Chlorosulfonyl isocyanate, N-methyl piperzine and then Example 258 are reacted according to the procedure for Example 7 to afford 1-(3-t-butyl-1-[[3-[[(1-(N-methylpiperzinyl)carbonyl)amino]sulphonyl]-((methylamino)methyl)phenyl)-1H-pyrazol-5-yl)-3-(naphthalen-1-yl)urea.

Example 272

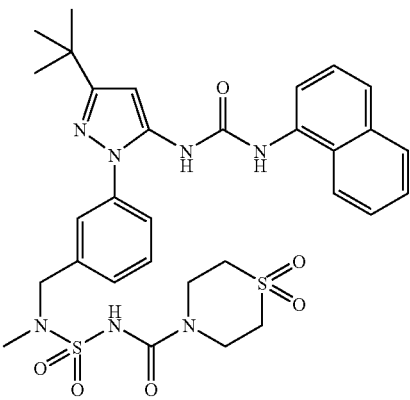

Chlorosulfonyl isocyanate, 4,4-dioxo-4-thiomorpholine and then Example 258 are reacted according to the procedure for Example 7 to afford 1-(3-t-butyl-1-[[3-[[(1-(4,4-dioxo-4-thiomorpholinyl)carbonyl)amino]sulphonyl]-((methylamino)methyl)phenyl)-1H-pyrazol-5-yl)-3-(naphthalen-1-yl)urea.

Example GGG

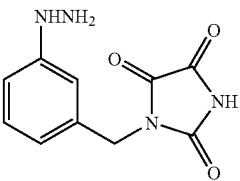

Commercially available 3-nitrobenzamide is reduced with LAH under standard conditions to afford (3-nitrophenyl)methanamine, which is reacted with 4-methoxybenzylisocyanate to afford 1-(3-nitrobenzyl)-3-(4-methoxybenzyl)urea. This material is subsequently reacted with oxalyl chloride to afford 1-(3-nitrobenzyl)-3-(4-methoxybenzyl)imidazolidine-2,4,5-trione whose nitro group is reduced and oxidized to afford 1-(3-hydrazinylbenzyl)-3-(4-methoxybenzyl)imidazolidine-2,4,5-trione. This material is deprotected with TFA under standard conditions to afford the title compound I-(3-hydrazinylbenzyl)imidazolidine-2,4,5-trione.

Example 273

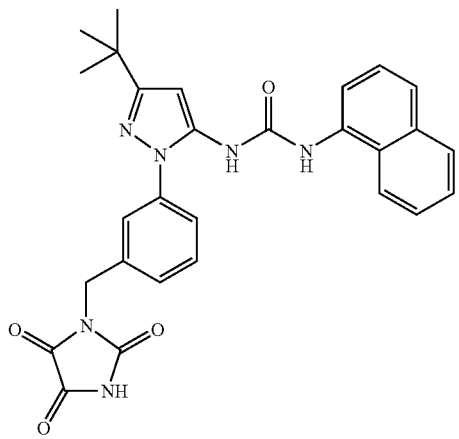

Utilizing the same synthetic procedure as for Example 164, Example GGG (10 mmol) and Example PP (10.5 mmol) are combined to afford 1-(3-t-butyl-1-(3-((2,4,5-trioxoimidazolidin-1-yl)methyl)phenyl)-1H-pyrazol-5-yl)-3-(naphthalen-1-yl)urea

Example 274

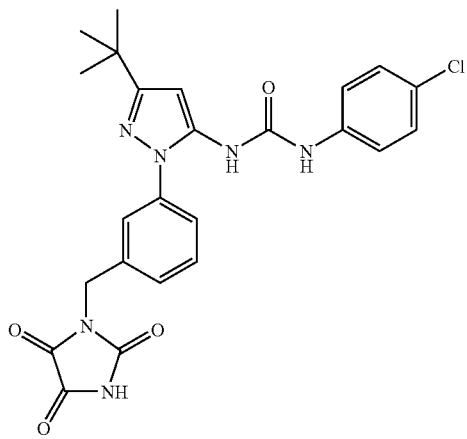

Utilizing the same synthetic procedure as for Example 164, Example GGG (10 mmol) and Example QQ (10.5 mmol) are combined to afford 1-(3-t-butyl-1-(3-((2,4,5-trioxoimidazolidin-1-yl)methyl)phenyl)-1H-pyrazol-5-yl)-3-(4-chlorophenyl)urea.

Example HHH

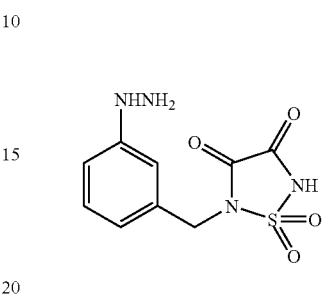

Commercially available 3-nitrobenzamide is reduced with LAH under standard conditions to afford (3-nitrophenyl)methanamine, which is reacted with N-4-methoxybenzylsulfamic acid and EDC to afford 1-(4-methoxybenzyl)-3-benzylsulfonylurea. This material is reacted with oxalyl chloride to afford 1-(3-nitrobenzyl)-3-(4-methoxybenzyl)imidazolidine-2,2-dioxo-2-thio-4,5-trione whose nitro group is reduced and oxidized to afford 1-(3-hydrazinylbenzyl)-3-(4-methoxybenzyl)imidazolidine-2,2-dioxo-2-thio-4,5-trione. This material is deprotected with TFA under standard conditions to afford the title compound I-(3-hydrazinylbenzyl)imidazolidine-2,2-dioxo-2-thio-4,5-trione.

Example 275

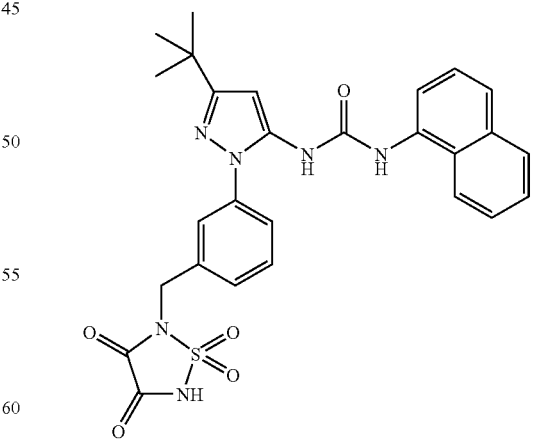

Utilizing the same synthetic procedure as for Example 164, Example HHH (10 mmol) and Example PP (10.5 mmol) are combined to afford 1-(3-t-butyl-1-(3-((2,2-dioxo-2-thio-4,5-diioxoimidazolidin-1-yl)methyl)phenyl)-1H-pyrazol-5-yl)-3-(naphthalen-1-yl)urea.

Example 276

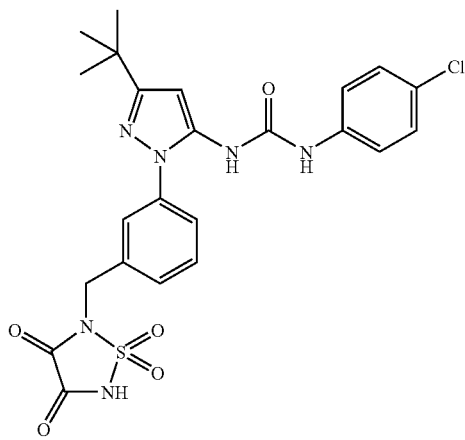

Utilizing the same synthetic procedure as for Example 164, Example HHH (10 mmol) and Example QQ (10.5 mmol) are combined to afford 1-(3-t-butyl-1-(3-((2,2-dioxo-2-thio-4,5-diioxoimidazolidin-1-yl)methyl)phenyl)-1H-pyrazol-5-yl)-3-(4-chlorophenyl)urea.

Example 277

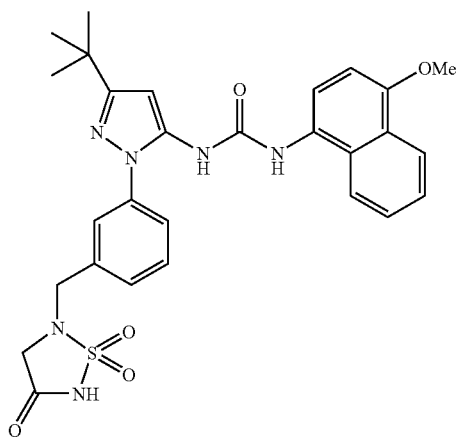

Example CC, 4-methoxy-1-aminonaphthalene and Example E are reacted using the procedure for Example 162 to afford 1-(5-t-butyl-2-{3-[1,1,4-trioxo-1$\lambda^6$-[1,2,5]thiadiazolidin-2-ylmethyl]-phenyl}-2H-pyrazol-3-yl)-3-(4-methoxynaphth-1-yl)-urea.

Example III

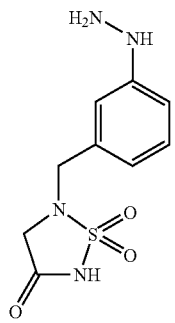

A solution of 1-(chloromethyl)-3-nitrobenzene and Example DD are combined using the procedure for Example 77 to yield 2-(4-methoxybenzyl)-5-(3-nitrophenylmethyl)-1,1-dioxo-1$\lambda^6$-[1,2,5]thiadiazolidin-3-one. This material is reduced under standard condition to yield 2-(4-methoxybenzyl)-5-(3-aminophenylmethyl)-1,1-dioxo-1$\lambda^6$-[1,2,5]thiadiazolidin-3-one, which was nitrosated and acidified to yield 5-(3-hydrazinophenylmethyl)-1,1-dioxo-1$\lambda^6$-[1,2,5]thiadiazolidin-3-one.

Example JJJ

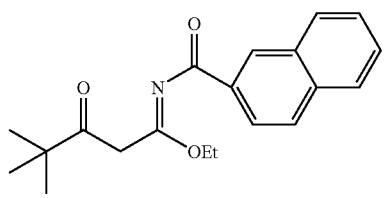

Intermediate HH (5 g, 0.0241 mol) is added to pyridine (5 mL) in $CH_2Cl_2$ (25 mL) and cooled in an ice bath. The suspension is stirred for 5 min and 2-naphthoic acid chloride is added dropwise over 5 min. The reaction mixture is stirred an additional 5 min at 0° C., and the reaction is warmed and stirred at RT for 1 h. The reaction is pour into ethyl acetate (100 mL) and water (100 ml). After shaking, the aqueous layer is removed, the organic layer washed with water, dried ($MgSO_4$) and concentrated to afford (Z)-N-(1-ethoxy-4,4-dimethyl-3-oxopentylidene)-2-naphthamide.

Example KKK

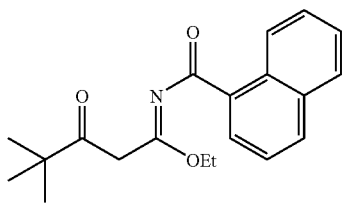

Intermediate HH (5 g, 0.0241 mol) is added to pyridine (5 mL) in CH₂Cl₂ (25 mL) and cooled in an ice bath. The suspension is stirred for 5 min and 1-naphthoic acid chloride is added dropwise over 5 min. The reaction mixture is stirred an additional 5 min at 0° C., and the reaction is warmed and stirred at RT for 1 h. The reaction is pour into ethyl acetate (100 mL) and water (100 ml). After shaking, the aqueous layer is removed, the organic layer washed with water, dried (MgSO₄) and concentrated to afford (Z)-N-(1-ethoxy-4,4-dimethyl-3-oxopentylidene)-1-naphthamide

Example LLL

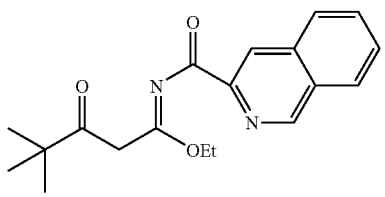

Intermediate HH (5 g, 0.0241 mol) is added to pyridine (5 mL) in CH₂Cl₂ (25 mL) and cooled in an ice bath. The suspension is stirred for 5 min and isoquinoloic acid chloride is added dropwise over 5 min. The reaction mixture is stirred an additional 5 min at 0° C., and the reaction is warmed and stirred at RT for 1 h. The reaction is pour into ethyl acetate (100 mL) and water (100 ml). After shaking, the aqueous layer is removed, the organic layer washed with water, dried (MgSO₄) and concentrated to afford (Z)-N-(1-ethoxy-4,4-dimethyl-3-oxopentylidene)isoquinoline-3-carboxamide.

Example 278

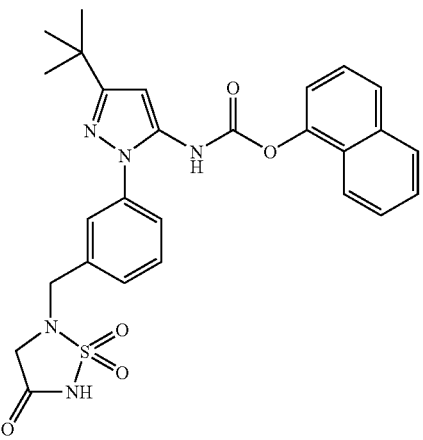

Utilizing the same synthetic procedure as for Example 164, Example III (10 mmol) and Example JJJ (10.5 mmol) are combined to afford 1-naphtyl 1-(3-t-butyl-1-(3-((2,4,5-trioxoimidazolidin-1-yl)methyl)phenyl)-1H-pyrazol-5-yl)-3-(naphthalen-1-yl)carbmate.

Example 279

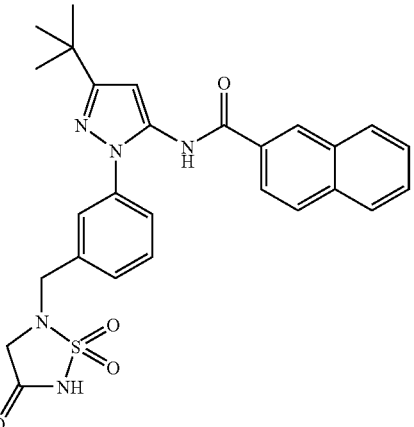

Utilizing the same synthetic procedure as for Example 164, Example III (10 mmol) and Example JJJ (10.5 mmol) are combined to afford 1-(3-t-butyl-1-(3-((2,4,5-trioxoimidazolidin-1-yl)methyl)phenyl)-1H-pyrazol-5-yl)-2-naphthamide.

Example 280

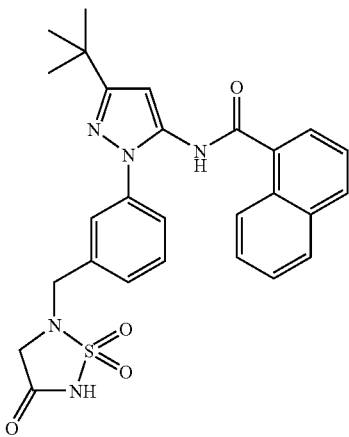

Utilizing the same synthetic procedure as for Example 164 Example III (10 mmol) and Example KKK (10.5 mmol) are combined to afford 1-(3-t-butyl-1-(3-((2,4,5-trioxoimidazolidin-1-yl)methyl)phenyl)-1H-pyrazol-5-yl)-1-naphthamide.

Example 281

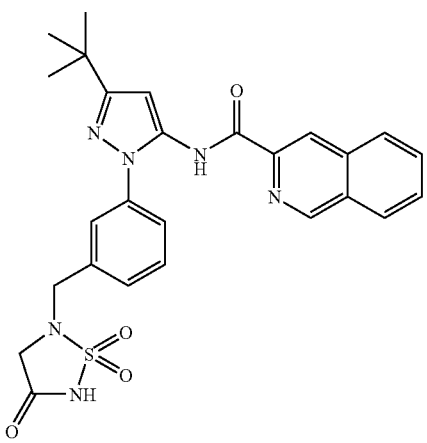

Utilizing the same synthetic procedure as for Example 149, Example III (10 mmol) and Example KKK (10.5 mmol) are combined to afford 1-(3-t-butyl-1-(3-((2,4,5-trioxoimidazolidin-1-yl)methyl)phenyl)-1H-pyrazol-5-yl)isoquinoline-3-carboxamide.

Example MMM

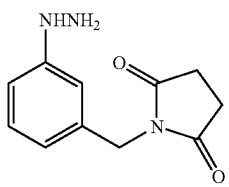

Commercially available 3-nitrobenzamide is reduced with LAH under standard conditions to afford (3-nitrophenyl)methanamine, which is reacted with succinic anhydride under standard conditions to afford 1-(3-nitrobenzyl)pyrrolidine-2,5-dione. This material is reduced at the nitro group and oxidized to afford 1-(3-hydrazinobenzyl)pyrrolidine-2,5-dione.

Example 282

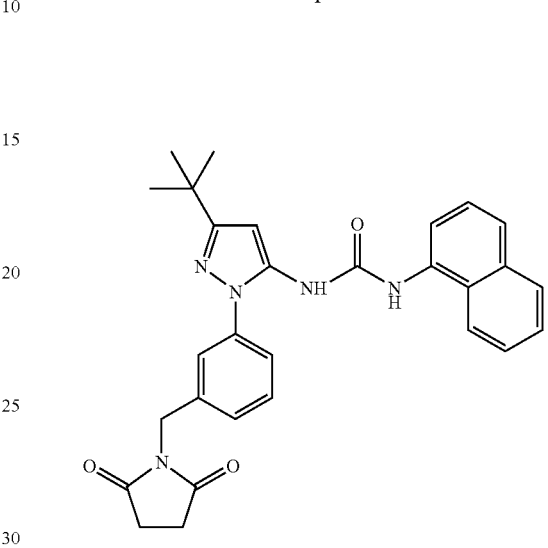

Utilizing the same synthetic procedure as for Example 164, Example MMM (10 mmol) and Example PP (10.5 mmol) are combined to afford 1-(3-t-butyl-1-(3-((2,5-dioxopyrrolidin-1-yl)methyl)phenyl)-1H-pyrazol-5-yl)-3-(naphthalen-1-yl)urea.

Example 283

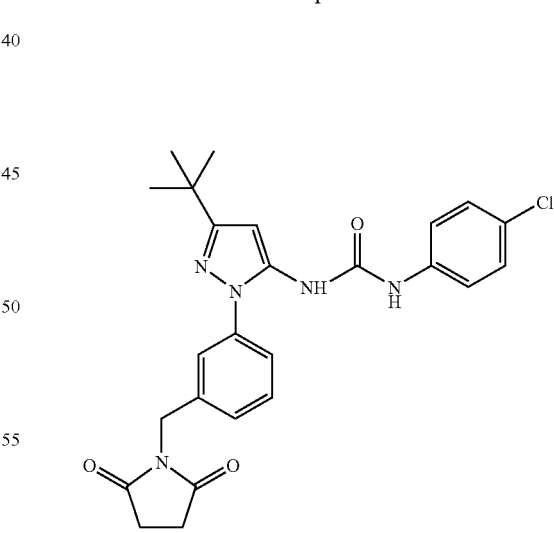

Utilizing the same synthetic procedure as for Example 164, Example MMM (10 mmol) and Example QQ (10.5 mmol) are combined to afford 1-(3-t-butyl-1-(3-((2,5-dioxopyrrolidin-1-yl)methyl)phenyl)-1H-pyrazol-5-yl)-3-(4-chlorophenyl)urea.

Example 284

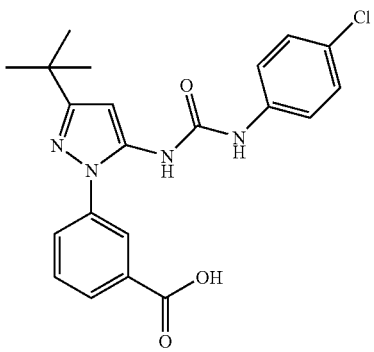

Example C was reacted with LiOH utilizing the procedure for Example 146 to yield 3-(3-t-butyl-5-(3-(4-chlorophenyl)ureido)-1H-pyrazol-1-yl)benzoic acid in 90% overall yield. $^1$H NMR (DMSO-$d_6$): 9.00 (s, 1H), 8.83 (s, 1H), 8.25-7.42 (m, 11H), 6.42 (s, 1H), 1.26 (s, 9H); MS (ESI): Expected: 412.88 Found: 413.00.

Example 285

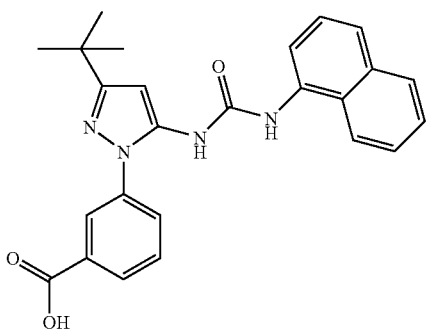

Example B was reacted with LiOH utilizing the procedure for Example 146 to yield 3-(3-t-butyl-5-(3-(naphthalen-1-yl)ureido)-1H-pyrazol-1-yl)benzoic acid in 90% overall yield. $^1$H NMR (DMSO-$d_6$): δ 9.11 (s, 1H), 8.47 (s, 1H), 8.06 (m, 1H), 7.93 (d, J=7.6 Hz, 1H), 7.81 (d, J=8.0 Hz, 1H), 7.65 (dd, J=8.0, 7.6 Hz, 1H), 7.43 (d, J=8.8 Hz, 2H), 7.30 (d, J=8.8 Hz, 2H), 6.34 (s, 1H), 1.27 (s, 9H); MS (ESI) Expected: 428.49 Found: 429.2 (M+1).

Example NNN

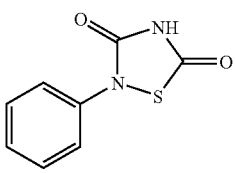

To the solution of phenyl-urea (13.0 g, 95.48 mol) in THF (100 mL) was slowly added chlorocarbonyl sulfenylchloride (13 mL, 148.85 mmol) at RT. The reaction mixture was refluxed overnight, the volatiles removed in vacuo yielded 2-phenyl-1,2,4-thiadiazolidine-3,5-dione as a white solid (4.0 g, 20%). $^1$H NMR (DMSO-$d_6$): δ 12.49 (s, 1H), 7.51 (d, J=8.0 Hz, 2H), 7.43 (t, J=7.6 Hz, 2H), 7.27 (t, J=7.2 Hz, 1H).

Example 286

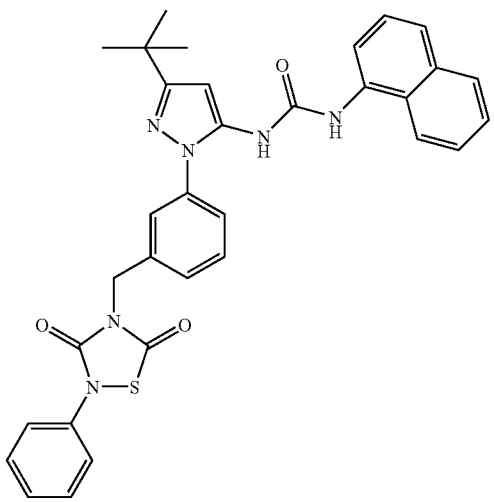

Example E and Example NNN were reacted together utilizing the same general approach as for Example 160 to afford 1-(3-t-butyl-1-(3-((3,5-dioxo-2-phenyl-1,2,4-thiadiazolidin-4-yl)methyl)phenyl)-1H-pyrazol-5-yl)-3-(naphthalen-1-yl)urea. $^1$H NMR (DMSO-$d_6$): δ 8.96 (s, 1H), 8.01-7.21 (m, 16H), 6.40 (s, 1H), 4.85 (s, 2H), 1.28 (s, 9H); MS (ESI): Expected: 590.21, Found 591.26 (M+1).

Example 287

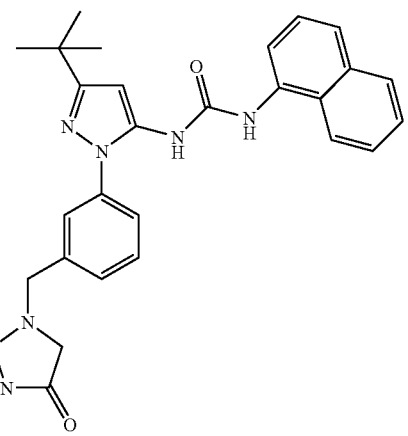

Example CC, 1-naphthylisocyanate and Example DD were combined utilizing the same general approach for Example 162 to yield 1-(5-t-butyl-2-{3-[5-1,1,4-trioxo-1$\lambda^6$-[1,2,5]thiadia-zolidin-2-ylmethyl]-phenyl}-2H-pyrazol-3-yl)-1-naphthylurea. $^1$H NMR (DMSO-$d_6$): δ 9.0 (s, 1H), 8.81 (s, 1H), 7.99-7.42 (m, 11H), 6.41 (s, 1H), 4.33 (s, 2H), 1.27 (s, 9H); MS (ESI) Exact Mass: 532.19 Found: =533.24

Example 288

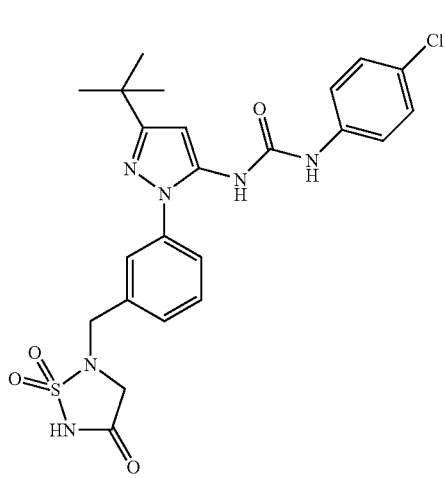

Example CC, p-chlorophenylisocyanate and Example DD were combined utilizing the same general approach for Example 162 to yield 1-(5-t-butyl-2-{3-[5-1,1,4-trioxo-1λ⁶-[1,2,5]thiadiazolidin-2-ylmethyl]-phenyl}-2H-pyrazol-3-yl)-3-(4-chloro-phenyl)-urea. ¹H NMR (DMSO-d₆): δ 9.07 (s, 1H), 8.42 (s, 1H), 7.52-7.272 (m, 8H), 6.36 (s, 1H), 4.60 (s, 2H), 1.26 (s, 9H); MS (ESI) Exact Mass: 516.13 Found: =517.1

Example 289

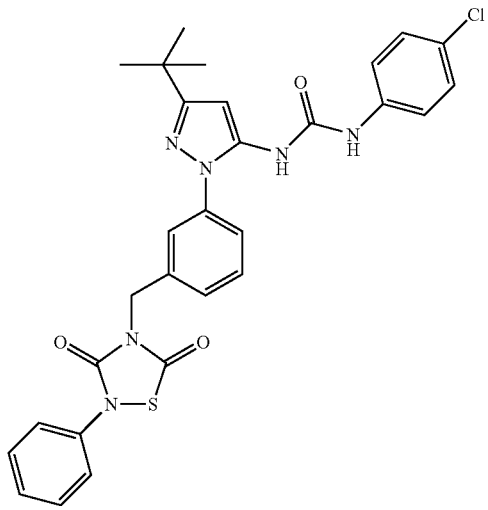

Example G and Example NNN were reacted together utilizing the same general approach as for Example 160 to afford 1-(3-t-butyl-1-(3-((3,5-dioxo-2-phenyl-1,2,4-thiadiazolidin-4-yl)methyl)phenyl)-1H-pyrazol-5-yl)-3-(4-chlorophenyl) urea. ¹H NMR (DMSO-d₆): δ 9.02 (s, 1H), 8.51 (s, 1H), 7.52-7.24 (m, 13H), 6.36 (s, 1H), 4.90 (s, 2H), 1.27 (s, 9H); MS (ESI): Expected: 574.16 Found: 575.26 (M+1)

Example 290

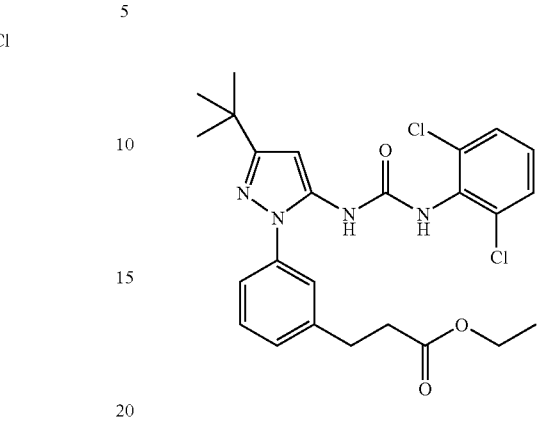

Example Z and 2,6-dichlorophenylisocyanate were reacted utilizing the same conditions as for Example 145 to yield ethyl 3-(3-(3-t-butyl-5-(3-(2,6-dichlorophenyl)ureido)-1H-pyrazol-1-yl)phenyl)propanoate. ¹H NMR (DMSO-d₆): δ 7.46-7.26 (m, 7H), 6.35 (s, 1H), 4.11 (q, J=7.2 Hz, 2H), 3.31 (t, J=5.2 Hz, 2H), 2.68 (t, J=5.6 Hz, 2H), 1.32 (s, 9H), 1.24 (t, J=7.2 Hz, 3H); MS(ESI): Expected: 502.15 Found: =503.1 (M+1).

Example 291

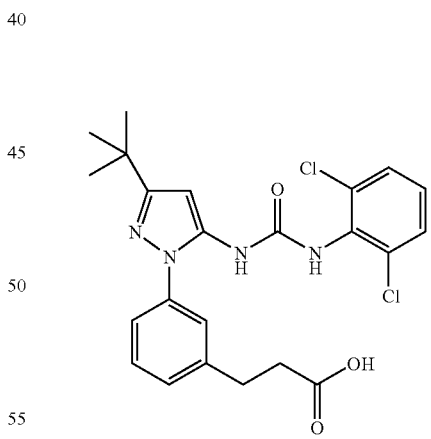

Example 290 was reacted utilizing the same condition as for Example 146 to yield 3-(3-(3-t-butyl-5-(3-(2,6-dichlorophenyl)ureido)-1H-pyrazol-1-yl)phenyl)propanoic acid in >90% yield. ¹H NMR (DMSO-d₆): δ 8.70 (s, 1H), 8.60 (s, 1H) 7.50-7.24 (m, 7H), 6.26 (s, 1H), 2.87 (t, J=5.2 Hz, 2H), 2.57 (t, J=5.6 Hz, 2H), 1.25 (s, 9H); MS(ESI): Expected: 474.12 Found: 475.18 (M+1).

Example OOO

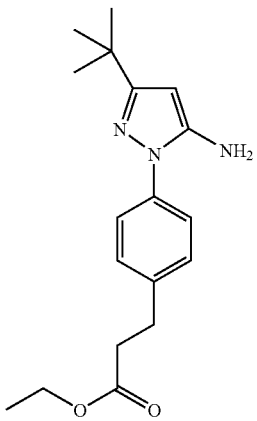

A mixture of ethyl 3-(4-aminophenyl)acrylate (1.5 g) and 10% Pd on activated carbon (0.3 g) in ethanol (20 ml) was hydrogenated at 30 psi for 18 h and filtered over Celite. Removal of the volatiles in vacuo provided ethyl 3-(4-aminophenyl)propionate (1.5 g).

A solution of the crude material from the previous reaction (1.5 g, 8.4 mmol) was dissolved in 6 N HCl (9 ml), cooled to 0° C., and vigorously stirred. Sodium nitrite (0.58 g) in water (7 ml) was added. After 1 h, tin (II) chloride dihydrate (5 g) in 6 N HCl (10 ml) was added. The reaction mixture was stirred at 0° C. for 3 h. The pH was adjusted to pH 7 to yield ethyl 3-(4-(3-t-butyl-5-amino-1H-pyrazol-1-yl)phenyl)propanoate.

Example 292

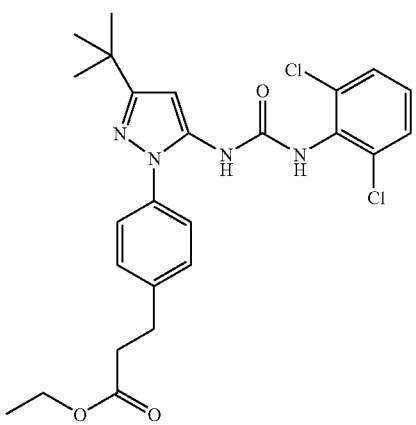

Example OOO and 2,6-dichlorophenylisocyanate were reacted utilizing the same conditions as for Example 145 to yield ethyl 3-(4-(3-t-butyl-5-(3-(2,6-dichlorophenyl)ureido)-1H-pyrazol-1-yl)phenyl)propanoate. $^1$H NMR (DMSO-d$_6$): δ 7.45-7.24 (m, 7H), 6.36 (s, 1H), 4.10 (q, J=7.2 Hz, 2H), 3.02 (t, J=5.2 Hz, 2H), 2.70 (t, J=5.6 Hz, 2H), 1.33 (s, 9H), 1.22 (t, J=7.2 Hz, 3H); MS(ESI): Expected: 502.15 Found: =503.1 (M+1).

Example 293

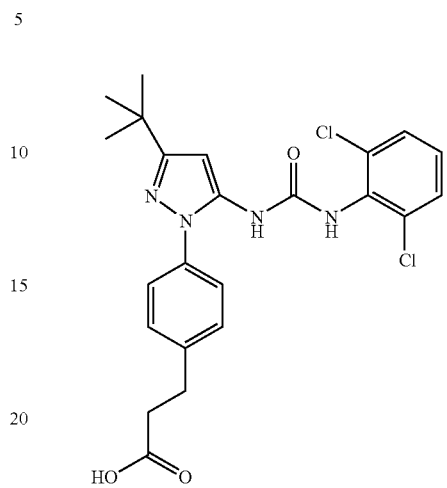

Example 292 was reacted utilizing the same condition as for Example 146 to yield 3-(3-(3-t-butyl-5-(3-(2,6-dichlorophenyl)ureido)-1H-pyrazol-1-yl)phenyl)propanoic acid in >90% yield. $^1$H NMR (DMSO-d$_6$): δ 8.66 (s, 1H), 8.58 (s, 1H) 7.50-7.28 (m, 7H), 6.27 (s, 1H), 2.85 (t, J=5.2 Hz, 2H), 2.48 (t, J=5.6 Hz, 2H), 1.24 (s, 9H); MS(ESI): Expected: 474.12 Found: 475.18 (M+1).

Example 294

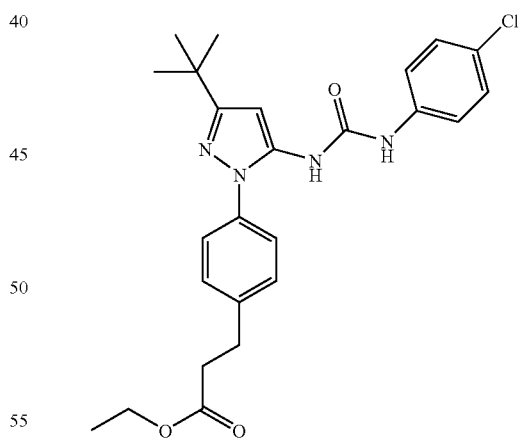

Example OOO and p-chlorophenylisocyanate were reacted utilizing the same conditions as for Example 145 to yield ethyl 3-(4-(3-tert-butyl-5-(3-(4-chlorophenyl)ureido)-1H-pyrazol-1-yl)phenyl)propanoate. $^1$H NMR (DMSO-d$_6$): δ 7.34-7.19 (m, 9H), 6.36 (s, 1H), 4.10 (q, J=7.2 Hz, 2H), 2.92 (t, J=5.2 Hz, 2H), 2.58 (t, J=5.6 Hz, 2H), 1.32 (s, 9H), 1.25 (t, J=7.2 Hz, 3H); MS(ESI): Exact Mass: 468.19 Found:=469.21 (M+1).

Example 295

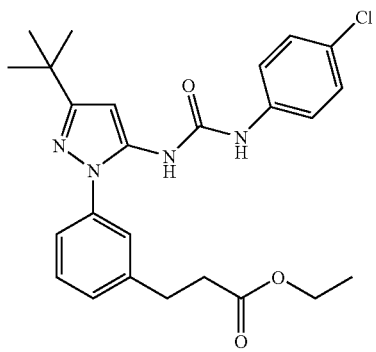

Example Z and p-chlorophenylisocyanate were reacted utilizing the same conditions as for Example 145 to yield ethyl 3-(3-(3-tert-butyl-5-(3-(4-chlorophenyl)ureido)-1H-pyrazol-1-yl)phenyl)propanoate. $^1$H NMR (DMSO-$d_6$): δ 9.12 (s, 1H), 8.37 (s, 1H), 7.41-7.27 (m, 8H), 6.34 (s, 1H), 5.73 (s, 1H), 4.01 (q, J=7.2 Hz, 2H), 2.90 (t, J=5.2 Hz, 2H), 2.62 (t, J=5.6 Hz, 2H), 1.25 (s, 9H), 1.125 (t, J=7.2 Hz, 3H); MS(ESI): Exact Mass: 468.19 Found: =469.21 (M+1).

Example 296

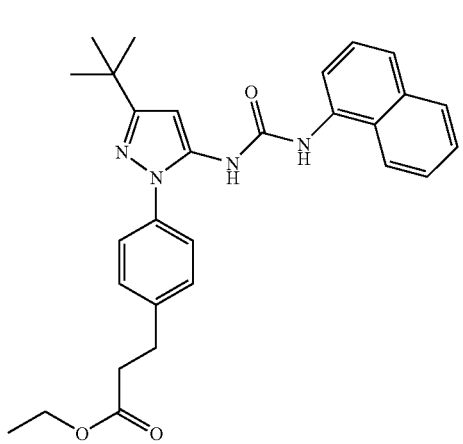

Example OOO and 1-naphthylisocyanate were reacted utilizing the same conditions as for Example 145 to yield ethyl 3-(4-(3-tert-butyl-5-(3-(naphthalen-1-yl)ureido)-1H-pyrazol-1-yl)phenyl)propanoate. δ 7.88-9.95 (m, 13H), 6.27 (s, 1H), 4.04 (q, J=7.2 Hz, 2H), 2.75 (t, J=5.2 Hz, 2H), 2.42 (t, J=5.6 Hz, 2H), 1.27 (s, 9H), 1.20 (t, J=7.2 Hz, 3H); MS(ESI): Exact Mass: 484.25 Found: =485.26 (M+1).

Example 297

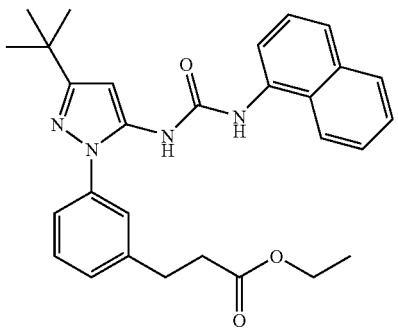

Example Z and 1-naphthylisocyanate were reacted utilizing the same conditions as for Example 145 to yield ethyl 3-(3-(3-tert-butyl-5-(3-(naphthalen-1-yl)ureido)-1H-pyrazol-1-yl)phenyl)propanoate. $^1$H NMR (DMSO-$d_6$): δ 9.01 (s, 1H), 8.80 (s, 1H), 8.0-7.27 (m, 11H), 6.41 (s, 1H), 4.01 (q, J=7.2 Hz, 2H), 2.95 (t, J=5.2 Hz, 2H), 2.72 (t, J=5.6 Hz, 2H), 1.27 (s, 9H), 1.15 (t, J=7.2 Hz, 3H); MS(ESI): Exact Mass: 484.25 Found: =485.26 (M+1).

Example 298

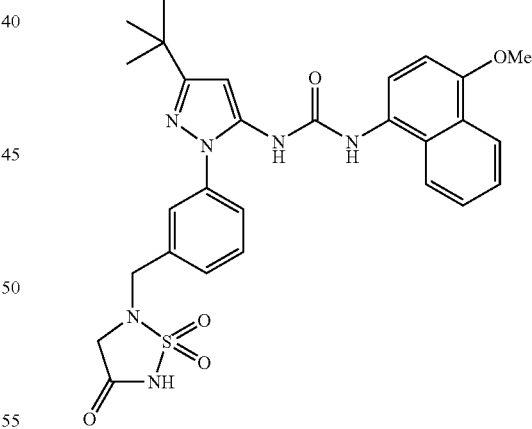

Example CC, 1-(4-methoxynaphthyl)isocyanate and Example DD were combined utilizing the same general approach for Example 162 to yield 1-(5-t-butyl-2-{3-[5-1,1,4-trioxo-1$\lambda^6$-[1,2,5]thiadiazolidin-2-ylmethyl]-phenyl}-2H-pyrazol-3-yl)-1-(4-methoxynaphthyl)urea. $^1$H NMR (DMSO-$d_6$): δ 8.69 (s, 1H), 8.61 (s, 1H), 8.15-6.90 (m, 10H), 6.36 (s, 1H), 4.37 (s, 2H), 3.93 (s, 3H), 1.22 (s, 9H); MS (ESI) Exact Mass: 562.20 Found: =563.2.

Example PPP

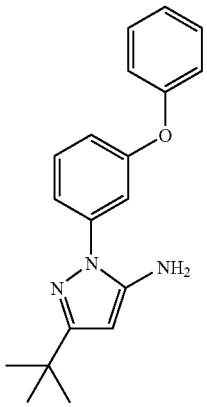

In a 250 mL Erlenmeyer flask with a magnetic stir bar, 3-phenoxyphenylamine (4.81 g, 0.026 mol) was added to 6 N HCl (40 mL) and cooled with an ice bath to 0° C. A solution of NaNO$_2$ (2.11 g, 0.0306 mol, 1.18 eq.) in water (5 mL) was added drop wise. After 30 min, SnCl$_2$2H$_2$O (52.0 g, 0.23 mol, 8.86 eq.) in 6 N HCl (100 mL) was added and the reaction mixture was allowed to stir for 3 h, and then subsequently transferred to a 500 mL round bottom flask. To this, 4,4-dimethyl-3-oxopentanenitrile (3.25 g, 0.026 mol) and EtOH (100 ml) were added and the mixture refluxed for 4 h, concentrated in vacuo and the residue extracted with EtOAc (2×100 mL) and purified by column chromatography using hexane/EtOAc/Et$_3$N (8:2:0.2) to yield 3-tert-butyl-1-(3-phenoxyphenyl)-1H-pyrazol-5-amine (1.40 g, 17%). mp: 108-110° C.; $^1$H NMR (CDCl$_3$): δ 7.3 (m, 10H), 5.7 (s, 1H), 4.9 (brs, 2H), 1.3 (s, 9H).

Example 299

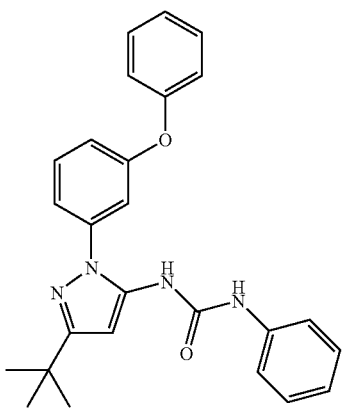

In a dry vial with a magnetic stir bar, Example PPP (0.184 g; 0.60 mmol) was dissolved in 2 mL CH$_2$Cl$_2$ (anhydrous) followed by the addition of phenylisocyanate (0.0653 mL; 0.60 mmol; 1 eq.). The reaction was kept under Ar and stirred for 18 h. Evaporation of solvent gave a crystalline mass that was recrystallized from EtOAc/hexane and then filtered washing with hexane/EtOAc (4:1) to yield 1-[3-tert-butyl-1-(3-phenoxyphenyl)-1H-pyrazol-5-yl]-3-phenylurea (0.150 g, 50%). HPLC purity: 96%; $^1$H NMR (CDCl$_3$): δ 7.5 (m, 16H), 6.8 (s, 1H), 6.5 (s, 1H), 1.4 (s, 9H).

Example QQQ

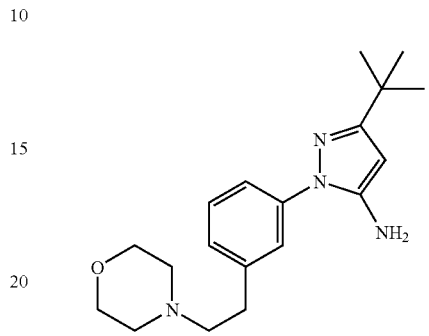

To a stirred solution of Example L (1.2 g, 3.5 mmol) in THF (6 ml) was added borane-methylsulfide (9 mmol). The mixture was heated to reflux for 90 min and cooled to RT, and 6 N HCl was added and heated to reflux for 10 min. The mixture was basified by adding sodium hydroxide, followed by extraction with ethyl acetate. The organic layer was dried (Na$_2$SO$_4$) filtered and concentrated in vacuo to yield 3-tert-butyl-1-[3-(2-morpholinoethyl)phenyl]-1H-pyrazol-5-amine (0.78 g), which was used without further purification.

Example 300

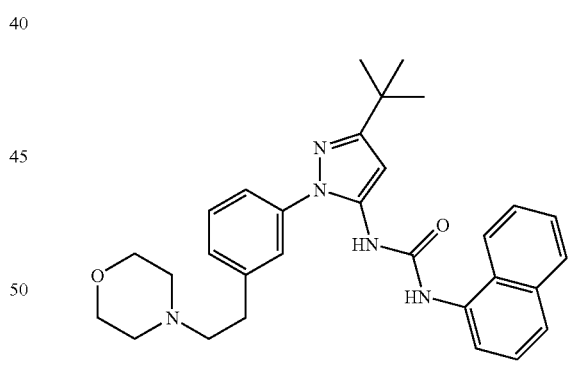

A mixture of Example QQQ (0.35 g, 1.07 mmol) and 1-naphthylisocyanate (0.18 g, 1.05 mmol) in dry CH$_2$Cl$_2$ (4 ml) was stirred at RT under N$_2$ for 18 h. The solvent was removed in vacuo and the crude product was purified by column chromatography using 5% methanol in CH$_2$Cl$_2$ (with a small amount of TEA) as the eluent (0.18 g, off-white solid) to yield 1-{3-tert-butyl-1-[3-(2-morpholinoethyl)phenyl]-1H-pyrazol-5-yl}-3-naphthalen-1-yl)urea. mp: 88-90° C.; $^1$H NMR (200 MHz, DMSO-d$_6$): δ 9.07 (s, 1H), 8.80 (s, 1H), 8.06-7.92 (m, 3H), 7.69-7.44 (m, 7H), 7.40-7.29 (m, 1H), 6.44 (s, 1H), 3.57-3.55 (m, 4H), 3.33-3.11 (m, 4H), 2.40-2.38 (m, 4H), 1.32 (s, 9H); MS

Example 301

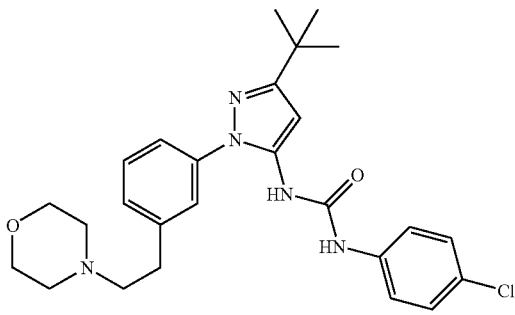

The title compound was synthesized in a manner analogous to Example 23 utilizing Example QQQ (0.35 g, 1.07 mmol) and 4-chlorophenylisocyanate (0.165 g, 1.05 mmol) to yield 1-{3-tert-butyl-1-[3-(2-morpholinoethyl)phenyl]-1H-pyrazol-5-yl}-3-(4-chlorophenyl)urea. mp: 82-84° C.; $^1$H NMR (200 MHz, DMSO-$d_6$): δ 9.18 (s, 1H, s), 8.40 (s, 1H), 7.53-7.26 (m, 8H), 6.37 (s, 1H), 3.62-3.54 (m, 4H), 2.82-2.78 (m, 4H), 2.41-2.39 (m, 4H), 1.30 (s, 9H); MS All of the references above identified are incorporated by reference herein. In addition, two simultaneously applications are also incorporated by reference, namely Modulation of Protein Functionalities, Ser. No. 10/746,545, filed Dec. 24, 2003, and Anti-Cancer Medicaments, Ser. No. 10/746,607, filed Dec. 24, 2003.

---

We claim:

1. A compound having the formula

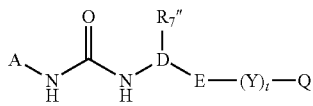

wherein:

A is selected from the group consisting of phenyl, naphthyl, pyridyl, pyrimidyl, thienyl, furyl, pyrrolyl, thiazolyl, oxazolyl, imidazolyl, indolyl, indazolyl, benzimidazolyl, benzotriazolyl, isoquinolyl, quinolyl, benzothiazolyl, benzofuranyl, benzothienyl, pyrazolylpyrimidinyl, imidazopyrimidinyl, purinyl, and

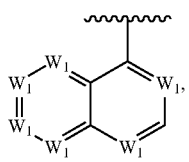

where each $W_1$ is individually selected from the group consisting of —CH— and —N—;

D is selected from the group consisting of phenyl, pyrazolyl, pyrrolyl, imidazolyl, oxazolyl, thiazolyl, furyl, oxadiazolyl, thiadiazolyl, thienyl, pyridyl, and pyrimidyl;

E is selected from the group consisting of phenyl, pyridinyl, and pyrimidinyl;

Y is selected from the group consisting of —O—, —S—, —$NR_6$—, —$NR_6SO_2$—, —$NR_6CO$—, alkynyls, alkenyls, alkylenes, —$O(CH_2)_h$—, and $NR_6(CH_{2h}$—, where h is individually selected from the group consisting of 1, 2, 3, and 4, and where for each of alkylenes, —$O(CH_2)_h$—, and —$NR_6(CH_2)_h$—, one of the methylene groups present therein may be optionally double-bonded to a side-chain oxo group except that where —$O(CH_2)_h$— the introduction of the side-chain oxo group does not form an ester moiety;

t is 0 or 1;

Q is

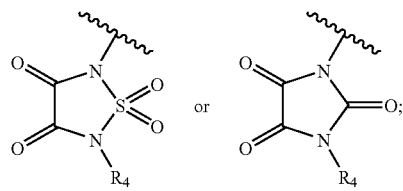

each $R_4$ group is individually selected from the group consisting of —H, alkyls, aminoalkyls, alkoxyalkyls, aryls, aralkyls, heterocyclyls, and heterocyclylalkyls except when the $R_4$ substituent places a heteroatom on an alpha-carbon directly attached to a ring nitrogen on Q;

when two $R_4$ groups are bonded with the same atom, the two $R_4$ groups optionally form an alicyclic or heterocyclic 4-7 membered ring;

each $R_6$ is individually selected from the group consisting of —H and alkyls;

$R_7''$ is selected from the group consisting of alkyls, aryls, heterocyclyls, and perfluoroalkyls;

and wherein A or Q is optionally substituted with one or more $R_7'$ substituents selected from the group consisting of —H, alkyls, aryls, heterocyclyls, alkylaminos, arylaminos, cycloalkylaminos, heterocyclylaminos, hydroxys, alkoxys, aryloxys, alkylthios, arthylthios, cyanos, halogens, nitros, alkylsulfinyls, alkylsulfonyls, aminosulfonyls, and perfluoroalkyls.

2. The compound of claim 1, wherein A is phenyl substituted by one or more $R_7'$ substituents, said $R_7'$ substituents being halogens.

3. The compound of claim 1, wherein A is an $R_7'$-substituted naphthyl.

4. The compound of claim 1, where $R_7''$ is selected from the group consisting of aryls and heterocyclyls.

5. The compound of claim 1, wherein A is an $R_7'$-substituted naphthyl.

6. The compound of claim 1, where $R_7''$ is selected from the group consisting of aryls and heterocyclyls.

7. An adduct comprising a molecule bound with a kinase, said molecule having the formula

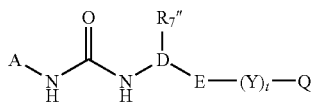

wherein:

A is selected from the group consisting of phenyl, naphthyl, pyridyl, pyrimidyl, thienyl, furyl, pyrrolyl, thiazolyl, oxazolyl, imidazolyl, indolyl, indazolyl, benzimidazolyl, benzotriazolyl, isoquinolyl, quinolyl, benzothiazolyl, benzofuranyl, benzothienyl, pyrazolylpyrimidinyl, imidazopyrimidinyl, purinyl, and

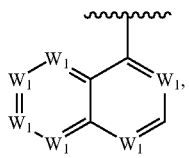

where each $W_1$ is individually selected from the group consisting of —CH— and —N—;

D is selected from the group consisting of phenyl, pyrazolyl, pyrrolyl, imidazolyl, oxazolyl, thiazolyl, furyl, oxadiazolyl, thiadiazolyl, thienyl, pyridyl, and pyrimidyl;

E is selected from the group consisting of phenyl, pyridinyl, and pyrimidinyl;

Y is selected from the group consisting of —O—, —S—, —NR$_6$—, —NR$_6$SO$_2$—, —NR$_6$CO—, alkynyls, alkenyls, alkylenes, —O(CH$_2$)$_h$—, and NR$_6$(CH$_2$)$_h$—, where h is individually selected from the group consisting of 1, 2, 3, and 4, and where for each of alkylenes, —O(CH$_2$)$_h$—, and —NR$_6$(CH$_2$)$_h$—, one of the methylene groups present therein may be optionally double-bonded to a side-chain oxo group except that where —O(CH$_2$)$_h$— the introduction of the side-chain oxo group does not form an ester moiety;

t is 0 or 1;

Q is

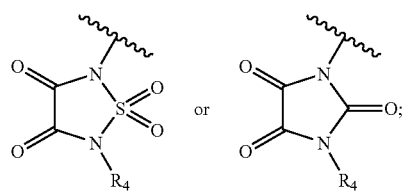

each $R_4$ group is individually selected from the group consisting of —H, alkyls, aminoalkyls, alkoxyalkyls, aryls, aralkyls, heterocyclyls, and heterocyclylalkyls except when the $R_4$ substituent places a heteroatom on an alpha-carbon directly attached to a ring nitrogen on Q;

when two $R_4$ groups are bonded with the same atom, the two $R_4$ groups optionally form an alicyclic or heterocyclic 4-7 membered ring;

each $R_6$ is individually selected from the group consisting —H and alkyls;

$R_7''$ is selected from the group consisting of alkyls, aryls, heterocyclyls, and perfluoroalkyls;

and wherein A or Q is optionally substituted with one or more $R_7'$ substituents selected from the group consisting of —H, alkyls, aryls, heterocyclyls, alkylaminos, arylaminos, cycloalkylaminos, heterocyclylaminos, hydroxys, alkoxys, aryloxys, alkylthios, arthylthios, cyanos, halogens, nitros, alkylsulfinyls, alkylsulfonyls, aminosulfonyls, and perfluoroalkyls.

8. The adduct of claim 7, wherein A is phenyl substituted by one or more $R_7'$ substituents, said $R_7'$ substituents being halogens.

9. The adduct of claim 7, wherein A is an $R_7'$-substituted naphthyl.

10. The adduct of claim 7, where $R_7''$ is selected from the group consisting of aryls and heterocyclyls.

* * * * *